US012435124B2

(12) United States Patent
Wang et al.

(10) Patent No.: US 12,435,124 B2
(45) Date of Patent: Oct. 7, 2025

(54) COMPOSITIONS AND METHODS FOR TREATING CEACAM POSITIVE CANCERS

(71) Applicant: A2 Biotherapeutics, Inc., Agoura Hills, CA (US)

(72) Inventors: Xueyin Wang, Agoura Hills, CA (US); Carl Alexander Kamb, Agoura Hills, CA (US); Han Xu, Agoura Hills, CA (US); Mark L. Sandberg, Agoura Hills, CA (US); Dora Toledo Warshaviak, Agoura Hills, CA (US)

(73) Assignee: A2 Biotherapeutics, Inc., Agoura Hills, CA (US)

( * ) Notice: Subject to any disclaimer, the term of this patent is extended or adjusted under 35 U.S.C. 154(b) by 251 days.

(21) Appl. No.: 17/814,434

(22) Filed: Jul. 22, 2022

(65) Prior Publication Data

US 2023/0172983 A1 Jun. 8, 2023

Related U.S. Application Data

(60) Division of application No. 17/517,559, filed on Nov. 2, 2021, now Pat. No. 11,433,100, which is a continuation of application No. PCT/US2021/046774, filed on Aug. 19, 2021.

(60) Provisional application No. 63/068,244, filed on Aug. 20, 2020.

(51) Int. Cl.

| | |
|---|---|
| ***C07K 14/705*** | (2006.01) |
| ***A61K 39/00*** | (2006.01) |
| ***A61K 40/11*** | (2025.01) |
| ***A61K 40/31*** | (2025.01) |
| ***A61K 40/32*** | (2025.01) |
| ***A61K 40/42*** | (2025.01) |
| ***A61P 35/00*** | (2006.01) |
| ***C07K 14/725*** | (2006.01) |

(52) U.S. Cl.
CPC ........ *C07K 14/70578* (2013.01); *A61K 40/11* (2025.01); *A61K 40/31* (2025.01); *A61K 40/32* (2025.01); *A61K 40/4266* (2025.01); *A61P 35/00* (2018.01); *C07K 14/7051* (2013.01); *C07K 14/70517* (2013.01); *C07K 14/70521* (2013.01); *A61K 2239/50* (2023.05)

(58) Field of Classification Search
None
See application file for complete search history.

(56) References Cited

U.S. PATENT DOCUMENTS

| | | | |
|---|---|---|---|
| 4,690,915 | A | 9/1987 | Rosenberg |
| 5,350,674 | A | 9/1994 | Boenisch et al. |
| 5,585,362 | A | 12/1996 | Wilson et al. |
| 5,858,358 | A | 1/1999 | June et al. |
| 5,883,223 | A | 3/1999 | Gray |
| 6,326,193 | B1 | 12/2001 | Liu et al. |
| 6,352,694 | B1 | 3/2002 | June et al. |
| 6,534,055 | B1 | 3/2003 | June et al. |
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 7,790,858 | B2 | 9/2010 | Presta |
| 8,642,742 | B2 | 2/2014 | Hofer et al. |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 9,068,008 | B2 | 6/2015 | Mossner et al. |
| 9,206,260 | B2 | 12/2015 | Hofer et al. |
| 9,745,368 | B2 | 8/2017 | Milone et al. |
| 10,040,846 | B2 | 8/2018 | Frigault et al. |
| 10,172,885 | B2 | 1/2019 | Pulé et al. |
| 10,172,886 | B2 | 1/2019 | Pulé et al. |
| 11,254,726 | B2 | 2/2022 | Kamb et al. |
| 2002/0018750 | A1 | 2/2002 | Hansen et al. |
| 2003/0091561 | A1 | 5/2003 | Van et al. |
| 2003/0170238 | A1 | 9/2003 | Gruenberg et al. |
| 2004/0101519 | A1 | 5/2004 | June et al. |
| 2005/0244858 | A1 | 11/2005 | Rossi et al. |
| 2006/0034810 | A1 | 2/2006 | Riley et al. |
| 2006/0121005 | A1 | 6/2006 | Berenson et al. |

(Continued)

FOREIGN PATENT DOCUMENTS

| | | | |
|---|---|---|---|
| BR | 112022002465 | A2 | 5/2022 |
| BR | 112022011399 | A2 | 8/2022 |

(Continued)

OTHER PUBLICATIONS

International Search Report and Written Opinion issued in International Application No. PCT/US2020/064607, mailed on Mar. 12, 2021, 11 pages.
International Search Report and Written Opinion received for PCT Application No. PCT/US2021/046774, mailed on Dec. 8, 2021, 10 pages.
International Search Report with Written Opinion corresponding to International Patent Application No. PCT/IL2017/051102, dated Jan. 14, 2018, 8 pages.
Abecasis et al. (2010) "A map of human genome variation from population-scale sequencing", Nature—1000 Genomes Project Consortium, 467(7319):1061-1073.

(Continued)

*Primary Examiner* — Ruixiang Li
(74) *Attorney, Agent, or Firm* — Mintz Levin Cohn Ferris Glovsky and Popeo, P.C.

(57) ABSTRACT

The disclosure provides immune cells comprising a first activator receptor specific to CEA, and a second inhibitory receptor, and methods of making and using same for the treatment of cancer.

19 Claims, 53 Drawing Sheets

Specification includes a Sequence Listing.

(56) References Cited

U.S. PATENT DOCUMENTS

| | | | |
|---|---|---|---|
| 2009/0053184 | A1 | 2/2009 | Morgan et al. |
| 2011/0104148 | A1 | 5/2011 | Moessner et al. |
| 2012/0009162 | A1 | 1/2012 | Yasukawa et al. |
| 2014/0068797 | A1 | 3/2014 | Doudna et al. |
| 2015/0031624 | A1 | 1/2015 | Feldman et al. |
| 2015/0376296 | A1 | 12/2015 | Fedorov et al. |
| 2016/0075795 | A1 | 3/2016 | Mössner et al. |
| 2016/0108131 | A1 | 4/2016 | Berne et al. |
| 2016/0145354 | A1 | 5/2016 | Bacac et al. |
| 2016/0229923 | A1 | 8/2016 | Hofer et al. |
| 2016/0289293 | A1 | 10/2016 | Pulé et al. |
| 2016/0289294 | A1 | 10/2016 | Pule et al. |
| 2017/0283775 | A1 | 10/2017 | June et al. |
| 2017/0296623 | A1 | 10/2017 | Juillerat et al. |
| 2017/0355781 | A1 | 12/2017 | Markel et al. |
| 2018/0044399 | A1 | 2/2018 | Rajpal et al. |
| 2018/0079827 | A1 | 3/2018 | Hofer et al. |
| 2018/0346541 | A1 | 12/2018 | Wong et al. |
| 2019/0023761 | A1 | 1/2019 | Pulé et al. |
| 2019/0185583 | A1 | 6/2019 | Hofer et al. |
| 2019/0185849 | A1 | 6/2019 | Lundberg et al. |
| 2019/0211076 | A1 | 7/2019 | Bleakley et al. |
| 2019/0248869 | A1 | 8/2019 | Gross et al. |
| 2019/0290691 | A1 | 9/2019 | Jäckel et al. |
| 2019/0359678 | A1 | 11/2019 | O'donoghue et al. |
| 2020/0016203 | A1 | 1/2020 | Pul et al. |
| 2020/0016204 | A1 | 1/2020 | Pul et al. |
| 2020/0093860 | A1 | 3/2020 | Stubenrauch et al. |
| 2020/0093861 | A1 | 3/2020 | Klein et al. |
| 2020/0123270 | A1 | 4/2020 | Doihara et al. |
| 2020/0188434 | A1 | 6/2020 | Cordoba et al. |
| 2020/0199550 | A1 | 6/2020 | Cordoba et al. |
| 2020/0261499 | A1 | 8/2020 | Gross et al. |
| 2020/0316120 | A1 | 10/2020 | Gross et al. |
| 2021/0206826 | A1 | 7/2021 | Lim et al. |
| 2021/0230247 | A1 | 7/2021 | Kamb et al. |
| 2021/0230251 | A1 | 7/2021 | Gross et al. |
| 2022/0054551 | A1 | 2/2022 | Wang et al. |
| 2022/0153807 | A1 | 5/2022 | Kamb et al. |
| 2022/0162287 | A1 | 5/2022 | Kamb et al. |

FOREIGN PATENT DOCUMENTS

| | | | |
|---|---|---|---|
| CA | 2904265 | A1 | 9/2014 |
| CN | 108219004 | A | 6/2018 |
| EP | 2681244 | B1 | 11/2017 |
| EP | 3333193 | A1 | 6/2018 |
| EP | 3632461 | A1 | 4/2020 |
| EP | 3634990 | A1 | 4/2020 |
| EP | 3688155 | A1 | 8/2020 |
| WO | 9943817 | A1 | 9/1999 |
| WO | 0129058 | A1 | 4/2001 |
| WO | 0196584 | A2 | 12/2001 |
| WO | 2012117002 | A1 | 9/2012 |
| WO | 2014145252 | A2 | 9/2014 |
| WO | 2015017214 | A1 | 2/2015 |
| WO | 2015075468 | A1 | 5/2015 |
| WO | 2015120096 | A2 | 8/2015 |
| WO | 2015142314 | A1 | 9/2015 |
| WO | 2016075612 | A1 | 5/2016 |
| WO | 2016120096 | A1 | 5/2016 |
| WO | 2016097231 | A2 | 6/2016 |
| WO | 2016126608 | A1 | 8/2016 |
| WO | 2016138034 | A1 | 9/2016 |
| WO | 2016142532 | A1 | 9/2016 |
| WO | 2016160622 | A2 | 10/2016 |
| WO | 2017011804 | A1 | 1/2017 |
| WO | 2017079705 | A1 | 5/2017 |
| WO | 2017087723 | A1 | 5/2017 |
| WO | 2017091905 | A1 | 6/2017 |
| WO | 2017156484 | A1 | 9/2017 |
| WO | 2018039247 | A1 | 3/2018 |
| WO | 2018061012 | A1 | 4/2018 |
| WO | 2018144535 | A1 | 8/2018 |
| WO | 2018148454 | A1 | 8/2018 |
| WO | 2018177967 | A1 | 10/2018 |
| WO | 2018191748 | A1 | 10/2018 |
| WO | 2018211244 | A1 | 11/2018 |
| WO | 2018211245 | A1 | 11/2018 |
| WO | 2018211246 | A1 | 11/2018 |
| WO | 2019056099 | A1 | 3/2019 |
| WO | WO-2019/056106 | A1 | 3/2019 |
| WO | 2019068007 | A1 | 4/2019 |
| WO | 2019084055 | A1 | 5/2019 |
| WO | 2019090215 | A2 | 5/2019 |
| WO | 2019192972 | A1 | 10/2019 |
| WO | 2019241549 | A1 | 12/2019 |
| WO | 2020065406 | A2 | 4/2020 |
| WO | 2020070290 | A1 | 4/2020 |
| WO | 2020172177 | A1 | 8/2020 |
| WO | 2020259550 | A1 | 12/2020 |
| WO | 2021030149 | A1 | 2/2021 |
| WO | 2021030153 | A2 | 2/2021 |
| WO | 2021030182 | A1 | 2/2021 |
| WO | 2021035093 | A1 | 2/2021 |
| WO | 2021053587 | A1 | 3/2021 |
| WO | 2021096868 | A1 | 5/2021 |
| WO | 2021110647 | A1 | 6/2021 |
| WO | 2021119489 | A1 | 6/2021 |
| WO | 2021222576 | A1 | 11/2021 |
| WO | 2021252635 | A1 | 12/2021 |
| WO | 2022036065 | A2 | 2/2022 |
| WO | 2022040470 | A1 | 2/2022 |
| WO | 2022115472 | A1 | 6/2022 |

OTHER PUBLICATIONS

Abeyweera et al. (2011) "Inhibitory signaling blocks activating receptor clustering and induces cytoskeletal retraction in natural killer cells", Journal of Cell Biology, 192(4):675-690.

Alcover et al. (Apr. 26, 2018) "Cell Biology of T Cell Receptor Expression and Regulation", Annual Review of Immunology, 36:103-125.

Altschul et al. (Oct. 5, 1990) "Basic Local Alignment Search Tool", Journal of Molecular Biology, 215(3):403-410.

Altschul et al. (Sep. 1, 1997) "Gapped BLAST and PSI-BLAST: A New Generation of Protein Database Search Programs", Nucleic Acids Research, 25(17):3389-3402.

Auton (2015) "A global reference for human genetic variation", Nature, 526(7571):68-74.

Bacac et al. (2016) "A Novel Carcinoembryonic Antigen T-Cell Bispecific Antibody (CEA TCB) for the Treatment of Solid Tumors", Clinical Cancer Research, 22(13):3286-3297.

Badran et al., Dec. 6, 2002, "Identification of Three NFAT Binding Motifs in the 5'-Upstream Region of the Human CD3γ Gene That Differentially Bind NFATc1, NFATc2, and NF-κB p50", The Journal of Biological Chemistry, 277(49):47136-47148.

Barnstable et al. (1978) "Production of Monoclonal Antibodies to Group A Erythrocytes, HLA and Other Human Cell Surface Antigens—new Tools for Genetic Analysis", Cell, 14(1):9-20.

Barrett et al. (May 1999) "Evolution of Neoplastic Cell Lineages in Barrett Oesophagus", Nature Genetics, 22(1):106-109.

Basilion et al. (Aug. 1999) "Selective Killing of Cancer Cells Based on Loss of Heterozygosity and Normal Variation in the Human Genome: A New Paradigm for Anticancer Drug Therapy", Molecular Pharmacology, 56(2):359-369.

Bausch-Fluck et al. (Apr. 20, 2015) "A Mass Spectrometric-Derived Cell Surface Protein Atlas", PloS one, 10(4): e0121314. 22 pages.

Bayle et al. (Jan. 2006) "Rapamycin analogs with differential binding specificity permit orthogonal control of protein activity", Chemistry & Biology, 13(1):99-107.

Bellon et al. (2002) "Mutational Analysis of Immunoreceptor Tyrosine-Based Inhibition Motifs of the Ig-Like Transcript 2 (CD85j) Leukocyte Receptor", Journal of Immunology, 168(7):3351-3359.

Bergbold et al. (Dec. 2013) "Emerging Role of Rhomboid Family Proteins in Mammalian Biology and Disease", Biochimica et Biophysica Acta (BBA)—Biomembranes, 1828(12):2840-2848.

Berge et al. (Dec. 1998) "Selective Expansion of a Peripheral Blood Cd8+ Memory T Cell Subset Expressing Both Granzyme B and

(56) References Cited

OTHER PUBLICATIONS

L-selectin During Primary Viral Infection in Renal Allograft Recipients", Transplantation Proceedings, 30(8):3975-3977.
Bern et al. (2019) "Inducible Down-regulation of MHC Class I Results in Natural Killer Cell Tolerance", Journal of Experimental Medicine, 216(1):99-116.
Beroukhim et al. (Feb. 18, 2010) "The Landscape of Somatic Copy-number Alteration Across Human Cancers", Nature, 463(7283):899-905(17 pages).
Binstadt et al. (Dec. 1996) "Sequential Involvement of Lck and SHP-1 With MHC-Recognizing Receptors on NK ells Inhibits FcR-initiated Tyrosine Kinase Activation", Immunity, 5(6):629-638.
Bird et al. (1988) "Single-Chain Antigen-Binding Proteins", Science, 242(4877):423-426.
Blankenstein et al. (Apr. 2015) "Targeting Cancer-specific Mutations by T Cell Receptor Gene Therapy", Current opinion in immunology, 33:112-119.
Boczkowski et al. (2000) "Induction of Tumor Immunity and Cytotoxic T Lymphocyte Responses using Dendritic Cells Transfected with Messenger RNA Amplified from Tumor Cells", Cancer Research, 60(4):1028-1034.
Boland et al. (2010) "Microsatellite Instability in Colorectal Cancer", Gastroenterology, 138(6):2073-2087 (30 pages).
Borges et al. (1997) "A family of human lymphoid and myeloid Ig-like receptors, some of which bind to MHC class I molecules", Journal of Immunology, 159(11):5192-5196.
Bryceson et al. (2008) "Line of Attack: NK Cell Specificity and Integration of Signals", Current Opinion in Immunology, 20(3):344-352 (15 pages).
Burrell et al. (2013) "The causes and consequences of genetic heterogeneity in cancer evolution", Nature, 501(7467):338-345.
Caescu et al. (Oct. 2009) "Active site determinants of substrate recognition by the metalloproteinases TACE and ADAM10", Biochemical Journal, 424(1):79-88.
Campoli et al. (Oct. 6, 2008) "HLA Antigen Changes in Malignant Cells: Epigenetic Mechanisms and Biologic Significance", Oncogene, 27(45):5869-5885.
Carney et al. (Oct. 1986) "Monoclonal Antibody Specific for an Activated RAS Protein", Proceedings of the National Academy of Sciences of the United States of America, 83(19):7485-7489.
Carpelan-Holmström et al. (1995) "Preoperative Serum Levels of CEA and CA 242 in Colorectal Cancer", British Journal of Cancer, 71(4):868-872.
Cerami et al. (May 2012) The cBio Cancer Genomics Portal: An Open Platform for Exploring Multidimensional Cancer Genomics Data, Cancer Discovery, 2(5):401-404.
Chao et al. (2006) "Isolating and Engineering Human Antibodies using Yeast Surface Display", Nature Protocols, 1(2):755-768.
Chau et al. (2004) "The Value of Routine Serum Carcino-embryonic Antigen Measurement and Computed Tomography in The Surveillance of Patients After Adjuvant Chemotherapy for Colorectal Cancer", Journal of Clinical Oncology, 22(8):1420-1429.
Chaurasiya et al. (Mar. 2017) "Viroimmunotherapy for Colorectal Cancer: Clinical Studies", Biomedicines, 5(1):11 (14 pages).
Chen et al. (Mar. 21, 2012) "Structural and Functional Distinctiveness of HLA-A2 Allelic Variants", Immunologic Research, 53:182-190.
Chess Andrew (2012) "Mechanisms and Consequences of Widespread Random Monoallelic Expression", Nature Reviews Genetics, 13(6):421-428.
Chicaybam et al. (2014) "Construction and validation of an activating and inhibitory chimeric antigen receptor (CAR) system", Cancer Research, Abstract 2797, 74(15):2 pages.
Chicaybam et al. (2015) "Construction and validation of an activating and inhibitory chimeric antigen receptor (CAR) system", Cancer Research, Abstract 3156, 75(15):2 pages.
Clarke et al. (1998) "Mice Transgenic for Human Carcinoembryonic Antigen as a Model for Immunotherapy", Cancer Research, 58(7):1469-1477.
Conaghan et al. (2008) "Targeted Killing of Colorectal Cancer Cell Lines by a Humanised LgG1 Monoclonal Antibody That Binds to Membrane-bound Carcinoembryonic Antigen", British Journal of Cancer, 98:1217-1225.
Cong et al. (Feb. 15, 2013) "Multiplex Genome Engineering Using CRISPR/Cas Systems", Science, 339(6121):819-823 (9 pages).
Cordoba et al. (May 23, 2013) "The large ectodomains of CD45 and CD148 regulate their segregation from and inhibition of ligated T-cell receptor", Blood, 121(21):4295-4302.
Da Cunha et al. (2009) "Bioinformatics construction of the human cell Surfaceome", Proceedings of the National Academy of Sciences of the United States of America, 106(39):16752-16757.
Database Genbank (Nov. 22, 2021) "*Homo sapiens* Chromosome 15, GRCh38.p14 Primary Assembly", NCBI Reference Sequence: NC_000015.10, 3 pages.
De Vree et al. (2014) "Targeted Sequencing by Proximity Ligation for Comprehensive Variant Detection and Local Haplotyping", Nature Biotechnology, 32(10):1019-1025 and 2 pages Online Methods.
Devilee et al., 2001, "Ever since Knudson", Trends in genetics, 17(10):569-573.
Doench et al. (Jan. 18, 2016) "Optimized sgRNA Design to Maximize Activity and Minimize Off-target Effects of CRISPR-Cas9", Nature Biotechnology, 34:184-191.
Dotti et al. (Jan. 2014) "Design and Development of Therapies using Chimeric Antigen Receptor-Expressing T cells", Immunological Reviews, 257(1):107-126.
Durbin et al. (May 1994) "An Epitope on Carcinoembryonic Antigen Defined by the Clinically Relevant Antibody PR1A3", Proceedings of the National Academy of Sciences of the United States of America, 91(10):4313-4317.
Eades-Perner et al. (1994) "Mice Transgenic for the Human Carcinoembryonic Antigen Gene Maintain its Spatiotemporal Expression Pattern", Cancer Research, 54(15),4169-4176.
Ebsen et al. (Oct. 9, 2013) "Differential Surface Expression of ADAM10 and ADAM17 on Human T Lymphocytes and Tumor Cells", PloS one, e76853, 8(10):16 pages.
Ellis et al. (Mar. 2000) "Frequencies of HLA-A2 Alleles in Five U.S. Population Groups: Predominance of A*02011 and Identification of HLA-A*0231", Human Immunology, 61(3):334-340.
Engelhard et al. (1991) "Influenza A—specific, HLA-A2.1-restricted cytotoxic T lymphocytes from HLA-A2.1 transgenic mice recognize fragments of the M1 protein", Journal of Immunology, 146(4):1226-1232.
Eriksson et al. (Oct. 4, 1999) "Inhibitory Receptors Alter Natural Killer Cell Interactions with Target Cells Yet Allow Simultaneous Killing of Susceptible Targets", The Journal of Experimental Medicine, 190(7):1005-1012.
Fedorov et al. (Dec. 11, 2013) "PD-1- and CTLA-4-Based Inhibitory Chimeric Antigen Receptors (iCARs) Divert Off-Target Immunotherapy Responses", Science Translational Medicine, 215ra172, 5(215):25 pages.
Feenstra et al. (1999) "HLA Class I Expression and Chromosomal Deletions at 6p and 15q in Head and Neck Squamous Cell Carcinomas", Tissue antigens, 54(3):235-245.
Finney et al. (1998) "Chimeric Receptors Providing Both Primary and Costimulatory Signaling in T Cells from a Single Gene Product", Journal of Immunology, 161(6):2791-2797.
Fu et al. (2013) "High-frequency off-target mutagenesis induced by CRISPR-Cas nucleases in human cells", Nature Biotechnology, 31(9):822-826 (13 pages).
Gao et al. (2013) "Integrative Analysis of Complex Cancer Genomics and Clinical Profiles Using the cBioPortal", Sci Signal., 6(269):1-34.
Garland et al. (Jul. 30, 1999) "The Use of Teflon Cell Culture Bags to Expand Functionally Active CD8+ Cytotoxic T Lymphocytes", Journal of Immunological Methods, 227(1-2):53-63.
Gianfrancesco et al. (2012) "A nonsynonymous TNFRSF11A variation increases NFKB activity and the severity of Paget's disease", Journal of Bone and Mineral Research, 27(2):443-452.
Gill et al. (Jan. 2015) "Going Viral: Chimeric Antigen Receptor T-Cell Therapy for Hematological Malignancies", Immunological Reviews, 263(1):68-89.

(56) References Cited

OTHER PUBLICATIONS

Gordon et al. (Jun. 22, 2015) "Mechanical Allostery: Evidence for a Force Requirement in the Proteolytic Activation of Notch", Developmental Cell, 33(6):729-736 (20 pages).
Graef et al. (1997) "Proximity and Orientation Underlie Signaling by the Non-Receptor Tyrosine Kinase ZAP70", The EMBO, 16(18):5618-5628.
Gross et al. (Dec. 1989) "Expression of Immunoglobulin-T-Cell Receptor Chimeric Molecules as Functional Receptors with Antibody-Type Specificity", Proc. Natl. Acad. Sci. USA, 86(24):10024-10028.
Gross et al. (2016) "Therapeutic Potential of T Cell Chimeric Antigen Receptors (CARs) in Cancer Treatment: Counteracting Off-Tumor Toxicities for Safe CAR T Cell Therapy", Annual Review of Pharmacology and Toxicology, 56:59-83.
GTEx Consortium (2015) "The Genotype-Tissue Expression (GTEx) Pilot Analysis: Multitissue Gene Regulation in Humans", Science, 348(6235):648-660. 33 pages.
Gustafson et al. (2017) "Immune Checkpoint Function of CD85j in CD8 T Cell Differentiation and Aging", Frontiers in Immunology, 8(692)1-12.
Haanen et al. (Nov. 1, 1999) "Selective Expansion of Cross-Reactive Cd8+ Memory T Cells by Viral Variants", Journal of Experimental Medicine, 190(9):1319-1328.
Haapasalo et al. (2011) "The Many Substrates of Presenilin/γ-Secretase", Journal of Alzheimer's disease, 25(1):3-28.
Hamburger et al. (Dec. 2020) "Engineered T cells directed at tumors with defined allelic loss", Molecular Immunology, 128:298-310.
Hanes et al. (May 1997) "In Vitro Selection and Evolution of Functional Proteins by Using Ribosome Display", Proceedings of the National Academy of Sciences, 94(10):4937-4942.
Harrer et al. (May 2018) "Chimeric Antigen Receptors in Different Cell Types: New Vehicles Join the Race", Human Gene Therapy, 29(5):547-558.
Heemskerk et al. (2013) "The Cancer Antigenome", The EMBO journal, 32(2):194-203.
Hemming et al. (Dec. 29, 2009) "Identification of β-Secretase (BACE1) Substrates Using Quantitative Proteomics", PLoS ONE, e8477, 4(12):1-14.
Hilton et al. (Apr. 2013) "Direct Binding to Antigen-Coated Beads Refines the Specificity and Cross-Reactivity of Four Monoclonal Antibodies that Recognize Polymorphic Epitopes of HLA Class I Molecules", Tissue Antigens, 81(4):212-220.
Hofmann et al. (1993) "TMbase—A Database of Membrane Spanning Proteins Segments", Journal of Biological Chemistry, 347:166 (2 pages).
Hsu et al. (2007) "Cytokine-independent growth and clonal expansion of a primary human CD8+ T-cell clone following retroviral transduction with the IL-15 gene", Blood, 109(12):5168-5177 (12 pages).
Huse et al. (2013) "Building Tolerance by Dismantling Synapses: Inhibitory Receptor Signaling in Natural Killer Cells", Immunological Reviews, 251(1):143-153.
Huston et al. (Aug. 1, 1988) "Protein Engineering of Antibody Binding Sites: Recovery of Specific Activity in an Anti-Digoxin Single-Chain Fv Analogue Produced in *Escherichia coli.*", Proceedings of the National Academy of Sciences of the United States of America, 85(16):5879-5883.
Hwang et al. (Mar. 17, 2021) "Targeting Loss of Heterozygosity for Cancer-specific Immunotherapy", Proceedings of the National Academy of Sciences of the United States of America, e2022410118, 118(12):1-10 pages.
Irles et al. (2003) "CD45 ectodomain Controls Interaction with GEMs and Lck Activity for Optimal TCR Signaling", Nature Immunology, 4:189-197.
Ji et al. (2010) "A Modified Toxicity Probability Interval Method for Dose-finding Trials", Clinical Trials, 7(6):653-663 (21 pages).
Ji et al. (2013) "Modified Toxicity Probability Interval Design: A Safer and More Reliable Method Than the 3+3 Design for Practical Phase I Trials", Journal of Clinical Oncology, 31(14):1785-1791 (12 pages).
Jimenez et al. (1999) "Chromosome Loss is the Most Frequent Mechanism Contributing to HLA Haplotype Loss in Human Tumors", International Journal of Cancer, 83(1):91-97.
Kammerer et al. (2010) "Coevolution of Activating and Inhibitory Receptors Within Mammalian Carcinoembryonic Antigen Families", BMC Biology, 8(12):1-21.
Karlin et al. (Jun. 1993) "Applications and Statistics for Multiple High-Scoring Segments in Molecular Sequences", Proceedings of the National Academy of Sciences, 90(12):5873-5877.
Karlin et al. (Mar. 1990) "Methods for Assessing the Statistical Significance of Molecular Sequence Features by Using General Scoring Schemes", Proceedings of the National Academy of Sciences of the United States of America, 87(6):2264-2268.
Katz et al. (May 2016) "Regional CAR-T Cell Infusions for Peritoneal Carcinomatosis are Superior to Systemic Delivery", Cancer Gene Therapy, 23(5):142-148 (14 pages).
Kersh et al. (1996) "Structural basis for T cell recognition of altered peptide ligands: a single T cell receptor can productively recognize a large continuum of related ligands", Journal of Experimental Medicine, 184(4):1259-1268.
Klebanoff et al. (2016) "Prospects for Gene-engineered T cell Immunotherapy for Solid Cancers", Nature medicine, 22(1):26-36 (25 pages).
Kloor et al. (2010) "Immune Evasion of Microsatellite Unstable Colorectal Cancers", International Journal of Cancer, 127:1001-1010.
Kloss et al. (2013) "Combinatorial antigen recognition with balanced signaling promotes selective tumor eradication by engineered T cells", Nature biotechnology, 31(1):71-75 (15 pages).
Knudson et al. (1971) "Mutation and cancer: statistical study of retinoblastoma", Proceedings of the National Academy of Sciences, 68(4):820-823.
Krogh et al. (Jan. 19, 2001) "Predicting Transmembrane Protein Topology with a Hidden Markov Model: Application to Complete Genomes", Journal of Molecular Biology, 305(3):567-580.
Lanitis et al. (2013) "Chimeric Antigen Receptor T Cells with Dissociated Signaling Domains Exhibit Focused Anti-Tumor Activity with Reduced Potential for Toxicity In Vivo", Cancer immunology research, 1(1):43-45 (20 pages).
Lawrence et al. (2014) "Discovery and Saturation Analysis of Cancer Genes Across 21 Tumor Types", Nature, 505(7484):495-501 (22 pages).
Lawrence et al. (2013) "Mutational heterogeneity in cancer and the search for new cancer-associated genes", Nature, 499(7457):214-218 (12 pages).
Lech et al. (Feb. 7, 2016) "Colorectal Cancer Tumour Markers and Biomarkers: Recent Therapeutic Advances", World Journal of Gastroenterology, 22(5):1745-1755.
Lee et al. (2019) "ASTCT Consensus Grading for Cytokine Release Syndrome and Neurologic Toxicity Associated with Immune Effector Cells", Biology of Blood and Marrow Transplantation, 25(4):625-638.
Lee et al. (Mar. 2003) "Distribution Analysis of Nonsynonymous Polymorphisms within the G-Protein-Coupled Receptor Gene Family", Genomics, 81(3):245-248.
Lek et al. (2016) "Analysis of Protein-Coding Genetic Variation In 60,706 Humans", Nature, 536(7616):285-291(33 pages).
Lengauer et al. (1998) "Genetic Instabilities in Human Cancers", Nature, 396(6712):643-649.
Leung et al. (2019) "Sensitive and adaptable pharmacological control of CAR T cells through extracellular receptor dimerization", JCI Insight, e124430, 4(11):19 pages.
Li et al. (2014) "A Preliminary Study of the Relationship Between Breast Cancer Metastasis and Loss of Heterozygosity by Using Exome Sequencing", Scientific Reports, 4:5460(1-6).
Li et al. (Mar. 2020) "LILRB4 ITIMs mediate the T cell suppression and infiltration of acute myeloid leukemia cells", Cellular & Molecular Immunology, 17(3):272-282.

(56) References Cited

OTHER PUBLICATIONS

Liberles et al. (Jul. 1997) "Inducible Gene Expression and Protein Translocation Using Nontoxic Ligands Identified by a Mammalian Three-hybrid Screen", Proceedings of the National Academy of Sciences, 94(15):7825-7830.
Lindblad-Toh et al. (2000) "Loss-of-heterozygosity Analysis of Small-cell Lung Carcinomas Using Single-nucleotide Polymorphism Arrays", Nature Biotechnology, 18(9):1001-1005.
Lo et al. (2008) "Comprehensive Analysis of Loss of Heterozygosity Events in Glioblastoma using the 100K SNP Mapping Arrays and Comparison with Copy No. Abnormalities Defined by BAC Array Comparative Genomic Hybridization", Genes Chromosomes Cancer, 47(3):221-237.
Long et al. (2013) "Controlling NK Cell Responses: Integration of Signals for Activation and Inhibition", Annual Review of Immunology, 31:227-258(36 pages).
MacDonald et al. (2016) "Alloantigen-specific Regulatory T Cells Generated with a Chimeric Antigen Receptor", Journal of Clinical Investigation, 126(4):1413-1424.
Maleno et al. (2004) "Distribution of HLA Class I Altered Phenotypes in Colorectal Carcinomas: High Frequency of HLA Haplotype Loss Associated with Loss of Heterozygosity in Chromosome Region 6p21", Immunogenetics, 56(4):244-253.
Maleno et al. (2010) "Frequent Loss of Heterozygosity in the B2-Microglobulin Region of Chromosome 15 in Primary Human Tumors", Immunogenetics, 63(2):65-71.
Maleno et al. (2006) "LOH at 6p21.3 Region and HLA Class Altered Phenotypes in Bladder Carcinomas", Immunogenetics, 58(7):503-510.
Maleno et al. (2002) "Multiple Mechanisms Generate HLA Class I Altered Phenotypes in Laryngeal Carcinomas: High Frequency of HLA Haplotype Loss Associated with Loss of Heterozygosity in Chromosome Region 6p21", Cancer Immunology, Immunotherapy, 51(7):389-396.
Marguerat et al. (2012) "Quantitative Analysis of Fission Yeast Transcriptomes and Proteomes in Proliferating and Quiescent Cells", Cell, 151(3):671-683.
Marinov et al. (2014) "From single-cell to cell-pool transcriptomes: stochasticity in gene expression and RNA splicing", Genome Research, 24(3):496-510.
Markowitz et al. (1995) "Inactivation of the type II TGF-beta receptor in colon cancer cells with microsatellite instability", Science, 268(5215):1336-1338.
Maude et al. (2018) "Tisagenlecleucel in Children and Young Adults with B-Cell Lymphoblastic Leukemia", The New England Journal of Medicine, 378(5):439-448.
Maus et al. (2016) "An MHC-restricted antibody-based chimeric antigen receptor requires TCR-like affinity to maintain antigen specificity", Molecular Therapy—Oncolytics, 3(16023):1-9.
McEvoy et al. (2002) "Frequency and Genetic Basis of MHC, beta-2-microglobulin and MEMO-1 Loss of Heterozygosity in Sporadic Breast Cancer", Tissue Antigens, 60(3):235-243.
McEwan et al. (2020) "Allogeneic CAR-T cell products containing 10 gene edits using CRISPR/Cas9 can retain full functionality in vivo and in vitro American Association for Cancer Research", Philadelphia, 1 page.
McGranahan et al. (2017) "Allele-Specific HLA Loss and Immune Escape in Lung Cancer Evolution", Cell, 171:1259-1271.
McGranahan et al. (2012) "Cancer Chromosomal Instability: Therapeutic and Diagnostic Challenges", EMBO reports, 13(6):528-538.
Medintz et al. (2000) "Loss of Heterozygosity Assay for Molecular Detection of Cancer Using Energy-transfer Primers and Capillary Array Electrophoresis", Genome Research, 10(8):1211-1218.
Mingoia et al. (2020) "Induction of therapeutic levels of HbF in genome-edited primary beta(0) 39-thalassaemia haematopoietic stem and progenitor cells", British Journal of Haematology, 192:395-404.
Mizuguchi et al. (2004) "Heterozygous TGFBR2 mutations in Marfan syndrome", Nature Genetics, 36(8):855-860.
Morgan et al. (2013) "Cancer regression and neurological toxicity following anti-MAGE-A3 TCR gene therapy", Journal of Immunotherapy, 36(2):133-151(38 pages).
Morgan et al. (Apr. 2010) "Case Report of a Serious Adverse Event Following the Administration of T Cells Transduced With a Chimeric Antigen Receptor Recognizing ERBB2", Molecular Therapy, 18(4):843-851.
Mori et al. (2001) "Instabilotyping: Comprehensive Identification of Frameshift Mutations Caused by Coding Region Microsatellite Instability", Cancer Research, 61:6046-6049.
Morsut et al. (Feb. 11, 2016) "Engineering Customized Cell Sensing and Response Behaviors using Synthetic Notch Receptors", Cell, 164(4):780-791.
Natali et al. (Sep. 1, 1989) Selective Changes in Expression of HLA Class I Polymorphic Determinants in Human Solid Tumors, Proceedings of the National Academy of Sciences of the United States of America, 86(17):6719-6723.
Dec. 24, 2014) A Study of R06958688 in Participants with Locally Advanced and/or Metastatic Carcinoembryonic Antigen Positive Solid Tumors, retrieved online Mar. 31, 2022, from clinicaltrials.gov/ct2/show/NCT02324257, 12 pages.
Jan. 8, 2016) A Study of the Safety, Pharmacokinetics, and Therapeutic Activity of R06958688 in Combination With Atezolizumab in Participants With Locally Advanced and/or Metastatic Carcinoembryonic Antigen (CEA)-Positive Solid Tumors, retrieved online Mar. 31, 2022, from clinicaltri als. gov/ct2/show/NCT02650713, 9 pages.
Aug. 1, 2016) CAR-T Hepatic Artery Infusions or Pancreatic Venous Infusions for CEA-Expressing Liver Metastases or Pancreas Cancer (HITM-SURE), retrieved online Mar. 31, 2022, from clinicaltrials.gov/ct2/show/NCT02850536, 8 pages.
Sep. 25, 2018) CAR-T Intraperitoneal Infusions for CEA-Expressing Adenocarcinoma Peritoneal Metastases or Malignant Ascites (IPC), retrieved online Mar. 31, 2022, from clinicaltrials.gov/ct2/show/NCT03682744, 8 pages.
Jan. 28, 2019) Phase 1b Study of CAR2Anti-CEA CAR-T Cell Hepatic Infusions for Pancreatic Carcinoma Patients With CEA+ Liver Metastases (AntiCEA_CART), retrieved online Mar. 31, 2022, from clinicaltrials.gov/ct2/show/NCT03818165, 9 pages.
Jul. 30, 2019) Study of Anti-CEA CAR-T +Chemotherapy VS Chemotherapy Alone in Patients With CEA+Pancreatic Cancer & Liver Metastases, retrieved online Mar. 31, 2022, from clinicaltrials.gov/ct2/show/NCT04037241, 14 pages.
Apr. 16, 2020) Safety and Efficacy of CEA-Targeted CAR-T Therapy for Relapsed/Refractory CEA+ Cancer, retrieved online Mar. 31, 2022, from clinicaltrials.gov/ct2/show/NCT04348643, 8 pages.
Neelapu et al. (2017) "Axicabtagene Ciloleucel CART-Cell Therapy in Refractory Large B-Cell Lymphoma", The New England Journal of Medicine, 377(26):2531-2544.
Newrzela et al. (2008) "Resistance of Mature T Cells to Oncogene Transformation", Blood, 112(6):2278-2286.
Newrzela et al. (2011) "Retroviral Insertional Mutagenesis Can Contribute to Immortalization of Mature T Lymphocytes", Molecular Medicine, 17(11-12):1223-1232.
Ng et al. (2003) "SIFT: Predicting Amino Acid Changes that Affect Protein Function", Nucleic Acids Research, 31(13):3812-3814.
Nirschl et al. (Sep. 15, 2013) "Molecular Pathways: Coexpression of Immune Checkpoint Molecules: Signaling Pathways and Implications for Cancer Immunotherapy", Clinical Cancer Research, 19(18):4917-4924.
Norell et al. (Jun. 15, 2006) "Frequent Loss of HLA-A2 Expression in Metastasizing Ovarian Carcinomas Associated with Genomic Haplotype Loss and HLA-A2-Restricted HER-2/neu-Specific Immunity", Cancer Research, 66(12):6387-6394.
Oberst et al. (Nov./Dec. 2014) "CEA/CD3 bispecific antibody MEDI-565/AMG 211 activation of T cells and subsequent killing of human tumors is independent of mutations commonly found in colorectal adenocarcinomas", MAbs, 6(6):1571-1584.
Ohgaki et al. (Oct. 1, 2004) "Genetic Pathways to Glioblastoma A Population-Based Study", Cancer Research, 64(19):6892-6899.

(56) References Cited

OTHER PUBLICATIONS

O'Keefe et al. (2010) "Copy Neutral Loss of Heterozygosity: A Novel Chromosomal Lesion in Myeloid Malignancies", Blood, 115(14):2731-2739.
Overwijk et al. (2013) "Mining the Mutanome: Developing Highly Personalized Immunotherapies Based on Mutational Analysis of Tumors", Journal for Immuno Therapy of Cancer, 1:11(1-4).
Parkhurst et al. (2009) "Characterization of Genetically Modified T-cell Receptors That Recognize the CEA:691-699 Peptide in the Context of HLA-A2.1 on Human Colorectal Cancer Cells", Clinical Cancer Research, 15(1):169-180 (23 pages).
Parkhurst et al. (2011) "T Cells Targeting Carcinoembryonic Antigen can Mediate Regression of Metastatic Colorectal Cancer but Induce Severe Transient Colitis", Molecular Therapy, 19(3):620-626.
Parsons et al. (1995) "Microsatellite Instability and Mutations of the Transforming Growth Factor Beta Type II Receptor Gene in Colorectal Cancer", Cancer Research, 55:5548-5550.
Patel et al. (2014) "Cancer CARtography: Charting Out a New Approach to Cancer Immunotherapy", Immunotherapy, 6(6):675-678(6 pages).
Patton et al. (2015) "Evaluation of the efficiency of human immune system reconstitution in NSG mice and NSG mice containing a human HLA.A2 transgene using hematopoietic stem cells purified from different sources", Journal of Immunological Methods, 422:13-21.
Priestley et al. (2019) "Pan-cancer Whole-genome Analyses of Metastatic Solid Tumours", Nature, 575(7781):210-216 (24 pages).
Qi et al. (2014) "Diversity and Clonal Selection in the Human T-cell Repertoire", Proceedings of the National Academy of Sciences of the United States of America, 111(36):13139-13144.
Qin et al. (2004) "Integrin Bi-directional Signaling: A Molecular View", PLOS Biology, 2:726-729.
Raje et al. (2019) "Anti-BCMA CART-Cell Therapy bb2121 in Relapsed or Refractory Multiple Myeloma", The New England Journal of Medicine, 380(18):1726-1737(21 pages).
Ran et al. (Sep. 12, 2013) "Double Nicking by RNA-Guided CRISPR Cas9 for Enhanced Genome Editing Specificity", Cell, 154(6):1380-1389.
Rana et al. (2001) "Genetic Variations and Polymorphisms of G Protein-coupled Receptors: Functional and Therapeutic Implications", Annual Review of Pharmacology and Toxicology, 41(1):593-624.
Rawson Robert B. (2013) "The Site-2 Protease", Biochimica et Biophysica Acta (BBA)—Biomembranes, 1828(12):2801-2807.
Restifo et al. (2012) "Adoptive Immunotherapy for Cancer: Harnessing the T Cell Response", Nature Reviews Immunology, 12(4):269-281 (30 pages).
Rosenberg et al. (2015) "Adoptive Cell Transfer as Personalized Immunotherapy for Human Cancer", Science, 348(6230):62-68.
Rosenberg Steven A. (2014) "Finding Suitable Targets is the Major Obstacle to Cancer Gene Therapy", Cancer Gene Therapy, 21:45-47.
Roybal et al. (Feb. 11, 2016) "Precision Tumor Recognition by T Cells with Combinatorial Antigen-Sensing Circuits", Cell, 164:770-779.
Sathirapongsasuti et al. (2011) "Exome Sequencing-based Copy-number Variation and Loss of Heterozygosity Detection: ExomeCNV", Bioinformatics, 27(19):2648-2654.
Savage Peter A. (2014) "Tumor Antigenicity Revealed", Trends in immunology, 35(2):47-48(3 pages).
Savova et al. (2016) "Genes with Monoallelic Expression Contribute Disproportionately to Genetic Diversity in Humans", Nature Genetics, 48(3):231-237(25 pages).
Sayós et al. (2004) "Recruitment of C-Terminal SRC Kinase by the Leukocyte Inhibitory Receptor CD85j", Biochemical and Biophysical Research Communications, 324(2):640-647.
Schumacher et al. (Apr. 3, 2015) "Neoantigens in Cancer Immunotherapy", Science, 348(6230):69-74.
Schuster et al. (2017) "The Immunopeptidomic Landscape of Ovarian Carcinomas", Proceedings of the National Academy of Sciences of the United States of America, 114(46):E9942-E9951.
Schwanhausser et al. (May 19, 2011) "Global Quantification of Mammalian Gene Expression Control", Nature, 473(7347):337-342.
Sela-Culang (Apr. 2015) "Antibody Specific Epitope Predictionemergence of a New Paradigm", Current opinion in virology, 11:98-102.
Sela-Culang et al. (Apr. 15, 2015) "PEASE: predicting B-cell epitopes utilizing antibody sequence", Bioinformatics, 31(8):1313-1315.
Shultz et al. (2010) "Generation of Functional Human T-cell Subsets with HLA-restricted Immune Responses in HLA Class I Expressing NOD/SCID/IL2r Gamma(null) Humanized Mice", Proceedings of the National Academy of Sciences of the United States of America, 107(29):13022-13027.
Skora et al. (Aug. 11, 2015) "Generation of MANAbodies Specific to HLA-Restricted Epitopes Encoded by Somatically Mutated Genes", Proceedings of the National Academy of Sciences, 112(32):9967-9972.
Skuljec et al. (Sep. 12, 2017) "Chimeric Antigen Receptor-Redirected Regulatory T Cells Suppress Experimental Allergic Airway Inflammation, a Model of Asthma", Frontiers in Immunology, Article 1125, 8:12 pages.
Smith et al. (2020) "Genome-Wide Analysis of Off-Target CRISPR/Cas9 Activity in Single-Cell-Derived Human Hematopoietic Stem and Progenitor Cell Clones", Genes, 11:1-16.
Stark et al. (Sep. 1, 1991) "Antibodies that are Specific for a Single Amino Acid Interchange in a Protein Epitope Use Structurally Distinct Variable Regions", The Journal of Experimental Medicine, 174(3):613-624.
Stark, et al. (Mar. 15, 2007) "Genome-Wide Loss of Heterozygosity and Copy Number Analysis in Melanoma using High-Density Single-Nucleotide Polymorphism Arrays", Cancer Research, 67(6):2632-2642.
Stewart et al. (1999) "Humanisation and Characterisation of PR1A3, a Monoclonal Antibody Specific for Cell-Bound Carcinoembryonic Antigen", Cancer Immunology, Immunotherapy, 47:299-306.
Strowig et al. (2009) "Priming of Protective T Cell Responses Against Virus-induced Tumors in Mice with Human Immune System Components", Journal of Experimental Medicine, 206(6):1423-1434.
Sun et al. (Jun. 11, 2014) "Construction and Evaluation of a Novel Humanized HER2-Specific Chimeric Receptor", Breast Cancer Research, 16(3): R61(10 pages).
Ta et al. (2010) "Structure-based development of a receptor activator of nuclear factor-kappaB ligand (RAN KL) inhibitor peptide and molecular basis for osteopetrosis,", Proceedings of the National Academy of Sciences of the United States of America, 107:20281-20286.
Tabernero et al. (May 20, 2017) "Phase Ia and Ib studies of the novel carcinoembryonic antigen (CEA) T-cell bispecific (CEA CD3 TCB) antibody as a single agent and in combination with atezolizumab: Preliminary efficacy and safety in patients with metastatic colorectal cancer (mCRC)", Journal of Clinical Oncology, 35(15):3002-3002 (2 pages).
Teo et al. (Nov. 1, 2012) "Statistical Challenges Associated with Detecting Copy Number Variations with Next-Generation Sequencing", Bioinformatics, 28(21):2711-2718.
Teras et al. (2016) "2016 US Lymphoid Malignancy Statistics by World Health Organization Subtypes", CA: A Cancer Journal for Clinicians, 66(6):443-459.
Thul et al. (May 26, 2017) "A Subcellular Map of the Human Proteome", Science, eaal3321, 356(6340):14 pages.
Tóth-Petróczy et al. (2011) "Slow Protein Evolutionary Rates are Dictated by Surface-core Association", Proceedings of the National Academy of Sciences of the United States of America, 108(27):11151-11156.
Treanor et al. (Jul. 3, 2006) "Microclusters of Inhibitory Killer Immunoglobulin-like Receptor Signaling at Natural Killer Cell Immunological Synapses", The Journal of cell biology, 174(1):153-161.

(56) References Cited

OTHER PUBLICATIONS

Tsai et al. (Jun. 2014) "Dimeric CRISPR RNA-Guided FokI Nucleases for Highly Specific Genome Editing", Nature Biotechnology, 32(6):569-576 (22 pages).
Uhlen et al. (Jan. 23, 2015) "Tissue-based Map of the Human Proteome", Science, 347(6220):1260419(11 pages).
Ui-Tei et al. (2000) "Sensitive Assay of RNA Interference in Drosophila and Chinese Hamster Cultured Cells Using Firefly Luciferase Gene as Target", FEBS Letters, 479:79-82.
Vakulskas et al. (2019) "Evaluation and Reduction of CRISPR Off-Target Cleavage Events", Nucleic Acid Therapeutics, 29(4):167-174.
Van Buuren et al. (May 14, 2014) "High Sensitivity of Cancer Exome-Based CD8 T Cell Neo-Antigen Identification", Oncoimmunology, e28836, 3:6 pages.
Veres et al. (Jul. 3, 2014) "Low Incidence of Off-Target Mutations in Individual CRISPR-Cas9 and TALEN Targeted Human Stem Cell Clones Detected by Whole-Genome Sequencing", Cell Stem Cell, 15:27-30.
Vincent et al. (1997) "Mutation analysis of the transforming growth factor-beta type II receptor in human cell lines resistant to growth inhibition by transforming growth factor-beta", Oncogene, 15:117-122.
Vogelstein et al. (Apr. 14, 1989) "Allelotype of Colorectal Carcinomas", Science, 244(4901):207-211.
Vogelstein et al. (Mar. 29, 2013) "Cancer Genome Landscapes", Science, 339(6127):1546-1558.
Voss et al. (Dec. 2013) "Mechanism, Specificity, and Physiology of Signal Peptide Peptidase (SPP) and SPP-like Proteases", Biochimica Et Biophysica Acta (BBA)—Biomembranes, 1828(12):2828-2839.
Vyas et al. (Oct. 15, 2001) "Spatial organization of signal transduction molecules in the NK cell immune synapses during MHC class I-regulated noncytolytic and cytolytic interactions", The Journal of immunology, 167(8):4358-4367.
Walseng et al. (Sep. 6, 2017) "A TCR-based Chimeric Antigen Receptor", Scientific Reports, 7(1):10 pages.
Wang et al. (Jan. 1, 2004) "Loss of heterozygosity and its Correlation with Expression Profiles in Subclasses of Invasive Breast Cancers", Cancer research, 64(1):64-71.
Wilkie et al. (Oct. 2012) "Dual targeting of ErbB2 and MUC1 in breast cancer using chimeric antigen receptors engineered to provide complementary signaling", Journal of Clinical Immunology, 32(5):1059-1070.
Wootton et al. (Jun. 1993) "Statistics of Local Complexity in Amino Acid Sequences and Sequence Databases", Computers & Chemistry, 17(2):149-163.
Wu et al. (Oct. 16, 2015) "Remote Control of Therapeutic T Cells Through a Small Molecule-Gated Chimeric Receptor", Science, aab4077, 350(6258):21 pages.
Xu et al. (Oct. 2020) "Structure-Function Relationships of Chimeric Antigen Receptors in Acute T Cell Responses to Antigen", Molecular Immunology, 126:56-64.
Yeung et al. (Apr. 1, 2013) "LOH in the HLA class I region at 6p21 is Associated with Shorter Survival in Newly Diagnosed Adult Glioblastoma", Clinical Cancer Research, 19(7):1816-1826.
Zhang et al. (2017) "Phase I Escalating-Dose Trial of CAR-T Therapy Targeting CEA+ Metastatic Colorectal Cancers", Molecular Therapy, 25(5):1248-1258.
Zhou et al. (2018) "Accuracy, Safety, and Reliability of Novel Phase I Trial Designs", Clinical Cancer Research, 24(18):4357-4364.
European Search Report corresponding to European Patent Application No. 17855171.9, dated Mar. 26, 2020, 8 pages.
Non-Final Office Action issued by The United States Patent and Trademark Office for U.S. Appl. No. 17/230,637, dated Aug. 31, 2021, 17 pages.
Notice of Allowance Office Action issued by The United States Patent and Trademark Office for U.S. Appl. No. 17/230,637, dated Dec. 13, 2021, 9 pages.
Notice of Allowance Office Action issued by The United States Patent and Trademark Office for U.S. Appl. No. 17/230,637, dated Dec. 28, 2021, 5 pages.
Fujiwara et al. (May 9, 2020) "Hinge and Transmembrane Domains of Chimeric Antigen Receptor Regulate Receptor Expression and Signaling Threshold", Cells, 17 pages.
Ramos et al. (Jun. 2015) "Molecular Biology Techniques for Loss of Heterozygosity Detection: The Glioma Example", Jornal Brasileiro de Patologia e Medicina Laboratorial, 51(3):189-196.
Sergeeva et al. (2008) "Direct Visualization of PR1/HLA-A2 on the Membrane of HLAA2+ CD13+CD33+ Myeloid Leukemia Blasts by a Novel Monoclonal Antibody", Blood, 112(11):2545 (2 pages).
Ashraf, S.Q. et al. (Nov. 2009). "Humanised IgG1 antibody variants targeting membrane-bound carcinoembryonic antigen by antibody-dependent cellular cytotoxicity and phagocytosis," *British Journal of Cancer* 101(10):1758-1768.
GenBank AYN55374.1, tissue factor-targeting CAR1 monomer [*Homo sapiens*], Aug. 31, 2019, located at <https://www.ncbi.nlm.nih.gov/protein/AYN55374.1> 2 pages.
GenBank ANG83989.1, 1F5-NQ-28-BB-z-2A-trCD19 [synthetic construct], May 31, 2016, 6 pages.
Hombach, A. et al. (Feb. 1999). "A chimeric receptor that selectively targets membrane-bound carcinoembryonic antigen (mCEA) in the presence of soluble CEA," *Gene Ther* 6(2):300-304.
Zhang, C. et al. (May 25, 2023). "Screening and characterization of the scFv for chimeric antigen receptor T cells targeting CEA-positive carcinoma," *Front Immunol* 14:1182409.
International Search Report and Written Opinion received for PCT Application No. PCT/US2020/045228, mailed on Dec. 21, 2020, 17 pages.
International Search Report and Written Opinion received for PCT Application No. PCT/IB2019/001108, mailed on Jun. 26, 2020, 16 pages.
International Search Report and Written Opinion received for PCT Application No. PCT/IB2020/000710, mailed on Mar. 19, 2021, 18 pages.
International Search Report and Written Opinion received for PCT Application No. PCT/US2018/053583, mailed on Feb. 25, 2019, 12 pages.
NCBI Reference Sequence: NP_000738.2, retrieved from web: Jun. 8, 2022, 3 pages.
NCBI Reference Sequence: NP_001094282.1, retrieved from web: Jun. 8, 2022, 3 pages.
NCBI Reference Sequence: NP_001278413.1, retrieved from web: Jun. 8, 2022, 8 pages.
NCBI Reference Sequence: NP_001295327.1, retrieved from web: Jun. 8, 2022, 7 pages.
NCBI Reference Sequence: NP_002199.3, retrieved from web: Jun. 8, 2022, 5 pages.
NCBI Reference Sequence: NP_003684.2, retrieved from web: Jun. 8, 2022, 4 pages.
NCBI Reference Sequence: NP_003830.1, retrieved from web: Jun. 8, 2022, 3 pages.
NCBI Reference Sequence: NP_569057.2, retrieved from web: Jun. 8, 2022, 3 pages.
An et al. (Oct. 2006) "Optimization and functional effects of stable short hairpin RNA expression in primary human lymphocytes via lentiviral vectors", Molecular Therapy, 14(4):494-504.
Betts et al. (2004) "Detection of T-Cell Degranulation: CD107a and b", Methods in Cell Biology, 75:497-512.
Brown et al. (Sep. 2004) "The LILR Family: Modulators of Innate and Adaptive Immune Pathways in Health and Disease", Tissue Antigens, Available online at: < https://onlinelibrary.wiley.com/doi/10.1111/j.0001-2815.2004.00290.x>, 64(3): 215-225.
Compagno et al. (Jun. 2009) "Mutations of Multiple Genes Cause Deregulation of NF-kappa B in Diffuse Large B-Cell Lymphoma", Nature, 459(7247):717-721(13 pages).
Diandreth et al. (2022) "The Tmod Cellular Logic Gate as a Solution for Tumor-selective Immunotherapy", Clinical Immunology, 241:109030 (8 pages).
Gerlinger et al. (2012) "Intratumor Heterogeneity and Branched Evolution Revealed by Multiregion Sequencing", New England Journal of Medicine, 366(10):883-892.

(56) References Cited

OTHER PUBLICATIONS

Guedan et al. (Mar. 15, 2019) "Engineering and Design of Chimeric Antigen Receptors", Molecular Therapy: Methods & Clinical Development, 12:145-156.
Hudecek et al. (Feb. 2015) "The Non-Signaling Extracellular Spacer Domain of Chimeric Antigen Receptors is Decisive for in Vivo Antitumor Activity", Cancer Immunology Research, 3(2):125-135.
Jayaraman et al. (2020) "CAR-T design: Elements and their Synergistic Function", EBioMedicine, 58:102931 (12 pages).
Jose et al. (Feb. 2000) "Triggering the TCR Complex Causes the Downregulation of Nonengaged Receptors by a Signal Transduction-Dependent Mechanism", Immunity, 12(2):161-170.
Katz et al. (2015) "Phase I Hepatic Immunotherapy for Metastases Study of Intra-Arterial Chimeric Antigen Receptor-Modified T-cell Therapy for CEA+ Liver Metastases", Clinical Cancer Research, 21(14):3149-3159.
Mock et al. (2022) "HLA-A?02-gated Safety Switch for Cancer Therapy Has Exquisite Specificity for Its Allelic Target Antigen", Molecular Therapy-Oncolytics, 27:157-166.
Pennisi, Elizabeth (Aug. 23, 2013) "The CRISPR Craze", Science, 341(6148):833-836.
Ren et al. (May 1, 2017) "Multiplex Genome Editing to Generate Universal Car T Cells Resistant to PD1 Inhibition", Clinical Cancer Research, 23(9):2255-2266 (21 pages).
Sandberg et al. (2022) "A Carcinoembryonic Antigen-specific Cell Therapy Selectively Targets Tumor Cells With HLA Loss of Heterozygosity in Vitro and in Vivo", Science Translational Medicine, 14(634):eabm0306 (23 pages).
Saverino et al. (Oct. 1, 2000) "The CD85/LIR-1/ILT2 Inhibitory Receptor Is Expressed by All Human T Lymphocytes and Down-Regulates Their Functions", Journal of Immunology, 165(7):3742-3755.
Spierings, E. (Aug. 31, 2008) "Minor Histocompatibility Antigens: Targets for Tumour Therapy and Transplant Tolerance", International Journal of Immunogenetics, 35(4-5):363-366.
Staub et al. (May 2004) "Systematic Identification of Immunoreceptor Tyrosine-based Inhibitory Motifs in the Human Proteome", Cellular Signalling, 16(4):435-456.
Stein et al. (May 1994) "The Cytoplasmic Domain of CD28 is Both Necessary and Sufficient for Costimulation of Interleukin-2 Secretion and Association With Phosphatidylinositol 3'-kinase.", Molecular and Cellular Biology, 14 (5):3392-3402.
Tait et al. (Mar. 31, 2001) "Clinical Relevance of the Minor Histocompatibility Antigen HA-1 in Allogeneic Bone Marrow Transplantation Between HLA Identical Siblings", Transplantation Proceedings, 33(1-2):1760-1761.
Zack et al. (Oct. 2013) "Pan-cancer Patterns of Somatic Copy No. Alteration", Nature Genetics, 45 (10):1134-1140.
Zheng et al. (May 9, 2016) "Comprehensive Pan-Genomic Characterization of Adrenocortical Carcinoma", Cell., 29(5):723-736.

FIG. 4

| Cancer (% CEA+; median >100 transcripts/cell) | Patient No. | RANK LOH Freq. | Treatable No. Range (CEA+) [MAF = 0.1 – 0.4] | NGS Dx: pass/tested [MAF = 0.1 – 0.4] |
|---|---|---|---|---|
| Rectal (100%) [30% subset of colorectal] | 15K | 0.87 | 0.8-1.6K | 2 x [0.05 – 0.11] = [1/10 – 1/5] |
| Colorectal (100%) | 53K | 0.70 | 2-5K | 2 x [0.04- 0.09] = [1/12 – 1/6] |
| Pancreatic (50%) | 43K | 0.67 | 0.8-2.0K | 2 x [0.04- 0.09] |
| Esophagael (50%) | 16K | 0.63 | 0.3-0.7K | 2 x [0.03 – 0.08] |
| Gastric (50%) | 11K | 0.47 | 0.2-0.3K | 2 x [0.03 - 0.06] |
| Lung adenocarcinoma (50%) | 109K | 0.47 | 1.5-3K | 2 x [0.03 - 0.06] = [1/20 – 1/9] |
| Head&Neck | | 0.53 | | |
| DLBCL | | 0.04 | | |
| AML | | 0.02 | | |
| All cancers | | 0.33 | | |

FIG. 9

| CANCER TYPE | DEATHS | CANCER TYPE | DEATHS |
|---|---|---|---|
| Lung and bronchus | 155,870 | Melanoma of the skin | 9,730 |
| Colorectum | 50,260 | Oral cavity and pharynx | 9,700 |
| Pancreas | 43,090 | Soft tissue (including heart) | 4,990 |
| Breast | 41,070 | Cervix | 4,210 |
| Liver and intrahepatic bile duct | 28,920 | Gallbladder and other biliary | 3,830 |
| Prostate | 26,730 | Larynx | 3,660 |
| Leukemia | 24,500 | Thyroid | 2,010 |
| Non-Hodgkin lymphoma | 20,140 | Bones and joints | 1,550 |
| Urinary bladder | 16,870 | Small intestine | 1,390 |
| Brain and other nervous system | 16,700 | Vagina and other female genital | 1,240 |
| Esophagus | 15,690 | Vulva | 1,150 |
| Kidney and renal pelvis | 14,400 | Anus, anal canal and anorectum | 1,100 |
| Ovary | 14,080 | Hodgkin lymphoma | 1,070 |
| Myeloma | 12,590 | Ureter and other urinary organs | 920 |
| Stomach | 10,960 | Testis | 410 |
| Uterine corpus | 10,920 | Penis and other male genital | 360 |

FIG. 53

| CEA CAR Tmod properties | Supporting data |
|---|---|
| High on-target, off-tumor selectivity | • CEA CAR Tmod (CEA CAR paired with an HLA-A*02-specific blocker receptor) has >10x selectivity for CEA(+)/A*02(-) tumor cells relative to CEA(+)/A*02(+) normal cells<br>• Comparable to TCR-T cells in cytotoxicity assays<br>• Selectivity confirmed in mouse xenograft experiments |
| High potency | • CEA CAR Tmod cells specifically kill a tumor cell line with native CEA and HLA-A*02 expression<br>• Similar potency to a benchmark clinical CEA TCR |
| Reversible activity | • CEA CAR Tmod cell activation is reversible in vitro, cycling between ON and OFF states |
| No inhibition from soluble CEA | • in vitro, CEA CAR Tmod cells are not inhibited by elevated levels of sCEA |
| Suitable for allogeneic or autologous | • With shRNA expression module, CEA CAR Tmod dual receptors function equivalently in HLA-A*02(+) and HLA-A*02(-) donor T cells |

COMPOSITIONS AND METHODS FOR TREATING CEACAM POSITIVE CANCERS

RELATED APPLICATIONS

This application is a divisional of U.S. application Ser. No. 17/517,559, filed Nov. 2, 2021, which is a continuation of International Application No. PCT/US2021/046774, filed on Aug. 19, 2021, which claims priority to, and benefit of, U.S. Provisional Application No. 63/068,244, filed on Aug. 20, 2020, the contents of which are incorporated by reference herein.

TECHNICAL FIELD

The disclosure relates to the fields of adoptive cell therapy and cancer therapeutics.

INCORPORATION BY REFERENCE OF SEQUENCE LISTING

This application contains a Sequence Listing which has been submitted in ASCII format via EFS-WEB and is hereby incorporated by reference in its entirety. Said ASCII copy, created on Jul. 15, 2022 is named 061250-522D01US_SeqList_ST26.xml and is 1.35 MB in size.

BACKGROUND

Cell therapy is a powerful tool for the treatment of various diseases, particularly cancers. In conventional adoptive cell therapies, immune cells are engineered to express specific receptors, for example chimeric antigen receptors (CARs) or T cell receptors (TCRs), which direct the activity of the immune cells to cellular targets via interaction of the receptor with a ligand expressed by the target cell. Identification of suitable target molecules remains challenging, as many targets are expressed in normal tissues. This expression can lead to toxicity when the transplanted cells target normal tissues expressing target molecules. There is thus a need in the art for compositions and methods useful in the treatment of disease, particularly cancers, by adoptive cell therapy.

SUMMARY

The disclosure provides compositions and methods for increasing the specificity of immune cells used in adoptive cell therapy. The disclosure provides immune cells comprising a two-receptor system that increases the specificity of the immune cells for target cells expressing a target antigen. The immune cells comprise a first, activator receptor that activates the immune cells in response to binding of the first receptor by the target antigen. The immune cells further comprise a second, inhibitory receptor specific to a non-target antigen. This second receptor inhibits activation of the immune cells when the second receptor is bound by the non-target antigen, even when the first receptor is bound by the target antigen.

The disclosure provides an immune cell comprising: (a) a first receptor, comprising an extracellular ligand binding domain specific to CEA cell adhesion molecule 5 (CEA); and (b) a second receptor, comprising an extracellular ligand binding domain specific to a non-target antigen lost in a CEA+ cancer cell, wherein the first receptor is an activator receptor responsive to CEA; and wherein the second receptor is an inhibitory receptor responsive to the non-target antigen.

In some embodiments of the immune cells of the disclosure, the non-target antigen is lost in the CEA+ cancer cell through loss of heterozygosity.

In some embodiments of the immune cells of the disclosure, the extracellular ligand binding domain of the second receptor specifically binds an allelic variant of a major histocompatibility complex (WIC) protein. In some embodiments, the extracellular ligand binding domain of the second receptor specifically binds an allelic variant of an HLA-A, HLA-B, or HLA-C protein. In some embodiments, the extracellular ligand binding domain of the second receptor specifically binds to HLA-A*01, HLA-A*02, HLA-A*03, HLA-A*11, HLA-B*07, or HLA-C*07. In some embodiments, the extracellular ligand binding domain of the second receptor specifically binds to HLA-A*02. In some embodiments, the extracellular ligand binding domain of the second receptor comprises complementarity determining regions (CDRs) CDR-L1, CDR-L2, CDR-L3, CDR-H1, CDR-H2, CDR-H3 as disclosed Table 6; or CDR sequences having at most 1, 2, or 3 substitutions, deletions, or insertions relative to the CDRs of Table 6. In some embodiments, the extracellular ligand binding domain of the second receptor comprises complementarity determining regions (CDRs) CDR-L1, CDR-L2, CDR-L3, CDR-H1, CDR-H2, CDR-H3 of SEQ ID NOS: 103-108 or of SEQ ID NOS: 109-114; or CDR sequences having at most 1, 2, or 3 substitutions, deletions, or insertions relative to the CDRs of SEQ ID NOS: 103-108 or SEQ ID NOS: 109-114. In some embodiments, the extracellular ligand binding domain of the second receptor comprises a polypeptide sequence selected from the polypeptide sequence disclosed in Table 5; or a sequence having at least 85%, at least 90%, at least 95%, at least 97% or at least 99% identity thereto. In some embodiments, the extracellular ligand binding domain of the second receptor comprises any one of SEQ ID NOS: 91-102, or a sequence having at least 85%, at least 90%, at least 95%, at least 97% or at least 99% identity thereto.

In some embodiments of the immune cells of the disclosure, the first receptor is a chimeric antigen receptor (CAR). In some embodiments, the extracellular ligand binding domain of the first receptor comprises a variable heavy (VH) portion comprising a set of heavy chain complementarity determining regions (HC-CDRs) selected from the group consisting of SEQ ID NOS: 55-58 and a variable light (VL) portion comprising a set of light chain complementarity determining regions selected from the group consisting of SEQ ID NOS: 59-63; or CDR sequences having at most 1, 2, or 3 substitutions, deletions, or insertions relative to SEQ ID NOS: 55-58 or SEQ ID NOS: 59-63. In some embodiments, the extracellular ligand binding domain of the first receptor comprises a variable heavy (VH) portion comprising a set of heavy chain complementarity determining regions (HC-CDRs) comprising SEQ ID NOS: 55-57 and a variable light (VL) portion comprising a set of light chain complementarity determining regions comprising SEQ ID NOS: 59, 61 and 63; or CDR sequences having at most 1, 2, or 3 substitutions, deletions, or insertions relative to SEQ ID NOS: 55-57 or SEQ ID NOS: 59, 61 and 63. In some embodiments, the extracellular ligand binding domain of the first receptor comprises a variable heavy (VH) portion comprising SEQ ID NO: 144 or a sequence having at least 85%, at least 90%, at least 95%, at least 97%, or at least 99% identity thereto, and a variable light (VL) portion comprising SEQ ID NO: 148 or a sequence having 85%, at least 90%, at least 95%, at least 97%, or at least 99% identity thereto. In some embodiments, the extracellular ligand binding domain of the first receptor comprises a sequence selected from the group consisting of SEQ ID NOS: 66-70, or a sequence having at least 85%, at least 90%, at least 95%, at least 97%, or at least 99% identity thereto. In some embodiments, the extracellular ligand binding domain of the first receptor comprises an scFv sequence of SEQ ID NO: 68; or a sequence having at least 85%, at least 90%, at least 95%, at least 97% or at least 99% identity thereto.

In some embodiments of the immune cells of the disclosure, the first receptor is a chimeric antigen receptor (CAR). In some embodiments, the first receptor comprises a hinge domain, a transmembrane domain and an intracellular domain. In some embodiments, the hinge domain comprises a CD8a hinge domain. In some embodiments, the CD8a hinge domain comprises a sequence of SEQ ID NO: 71, or a sequence having at least 85%, at least 90%, at least 95%, at least 97% or at least 99% identity thereto. In some embodiments, the transmembrane domain comprises a CD28 transmembrane domain. In some embodiments, the CD28 transmembrane domain comprises a sequence of SEQ ID NO: 75, or a sequence having at least 85%, at least 90%, at least 95%, at least 97% or at least 99% identity thereto. In some embodiments, the intracellular domain comprises a CD28 co-stimulatory domain, a 4-1BB co-stimulatory domain, and a CD3 activation domain. In some embodiments, the intracellular domain comprises a sequence of SEQ ID NO: 158, or a sequence having at least 85%, at least 90%, at least 95%, at least 97% or at least 99% identity thereto.

In some embodiments of the immune cells of the disclosure, the first receptor comprises a sequence of SEQ ID NO: 52, or a sequence having at least 90%, at least 95%, at least 97% or at least 99% identity thereto.

In some embodiments of the immune cells of the disclosure, the second receptor comprises a LILRB1 intracellular domain or a functional variant thereof. In some embodiments, the LILRB1 intracellular domain comprises a sequence at least 90%, at least 95%, at least 97%, at least 99%, or is identical to SEQ ID NO: 131. In some embodiments, the second receptor comprises a LILRB1 transmembrane domain or a functional variant thereof. In some embodiments, the LILRB1 transmembrane domain or a functional variant thereof comprises a sequence at least 90%, at least 95%, at least 97%, at least 99% or is identical to SEQ ID NO: 135. In some embodiments, the second receptor comprises a LILRB1 hinge domain or functional variant thereof. In some embodiments, the LILRB1 hinge domain comprises a sequence at least 90%, at least 95%, at least 97%, at least 99% or is identical to SEQ ID NO: 134. In some embodiments, the second receptor comprises a LILRB1 intracellular domain, a LILRB1 transmembrane domain, a LILRB1 hinge domain, a functional variant of any of these, or combinations thereof. In some embodiments, the LILRB1 hinge domain, LILRB1 intracellular domain and LILRB1 transmembrane domain comprises SEQ ID NO: 132 or a sequence at least 90%, at least 95%, at least 97%, at least 99% or is identical to SEQ ID NO: 132.

In some embodiments of the immune cells of the disclosure, the second receptor comprises a sequence of SEQ ID NO: 164, or a sequence having at least 90%, at least 95%, at least 97%, or at least 99% identity thereto.

In some embodiments of the immune cells of the disclosure, the CEA+ cancer cell is a pancreatic cancer cell, a colorectal cancer cell, a lung cancer cell, an esophageal cancer cell, gastric cancer cell, a head-and-neck cancer cell, a gallbladder cancer cell, a diffuse large B cell cancer cell, or acute myeloid leukemia cancer cell. In some embodiments, the CEA+ cancer cell is a lung cancer cell, a colorectal cancer cell, or a pancreatic cancer cell. In some embodiments, the CEA+ cancer cell is a CEA+/HLA-A*02− cancer cell that does not express HLA-A*02. In some embodiments, the CEA+/HLA-A*02− cancer cell is derived from a CEA+/HLA-A*02+ cell by loss of heterozygosity at HLA-A leading to loss of HLA-A*02. In some embodiments, the first receptor and the second receptor together specifically activate the immune cell in the presence of the CEA+/HLA-A*02− cancer cell having loss of heterozygosity. In some embodiments, the first receptor and the second receptor together do not specifically activate the immune cell in the presence of an CEA+ cell that has not lost HLA-A*02 by loss of heterozygosity.

In some embodiments of the immune cells of the disclosure, the immune cell is a T cell. In some embodiments, the T cell is a CD8+ CD4− T cell.

In some embodiments of the immune cells of the disclosure, expression and/or function of a MHC Class I gene has been reduced or eliminated. In some embodiments, the MHC Class I gene is beta-2-microglobulin (B2M). In some embodiments, the immune cells further comprise a polynucleotide comprising an interfering RNA, the interfering RNA comprising a sequence complementary to a sequence of a B2M mRNA. In some embodiments, the interfering RNA comprises a sequence selected from the group of sequences set forth in Table 11, or a sequence having at most 1, 2, 3, or 4 substitutions, insertions or deletions relative thereto. In some embodiments, the interfering RNA is capable of inducing RNAi-mediated degradation of the B2M mRNA. In some embodiments, the interfering RNA is a short hairpin RNA (shRNA). In some embodiments, the shRNA comprises: (a) a first sequence, having from 5' end to 3' end a sequence complementary to a sequence of the B2M mRNA; and (b) a second sequence, having from 5' end to 3' end a sequence complementary to the first sequence, wherein the first sequence and the second sequence form the shRNA. In some embodiments, the shRNA is encoded by a sequence comprising a sequence of GCACTCAAAGCTTGTTAAGATCGAAATCTTAACAAGCTTTGAGTGC (SEQ ID NO: 179) or GTTAACTTCCAATTTACATACCGAAGTATGTAAATTGGAAGTTAAC (SEQ ID NO: 180), or a sequence having at least 80%, at least 90%, or at least 95% identity thereto.

In some embodiments of the immune cells of the disclosure, expression and/or function of a MHC Class I gene has been reduced or eliminated. In some embodiments, the MHC Class I gene is beta-2-microglobulin (B2M). In some embodiments, the immune cells further comprise one or more modifications to a sequence encoding B2M, wherein the one or more modifications reduce the expression and/or eliminate the function of B2M. In some embodiments, the one or more modifications comprise one or more inactivating mutations of the endogenous gene encoding B2M. In some embodiments, the one or more inactivating mutations comprise a deletion, an insertion, a substitution, or a frameshift mutation. In some embodiments, the one or more inactivating mutations are introduced with a nucleic acid guided endonuclease in a complex with at least one guide nucleic acid (gNA) that specifically targets a sequence of the endogenous gene encoding B2M. In some embodiments, the gNA comprises a sequence selected from the group of sequences set forth in Table 10, or a sequence having at most 1, 2, 3, or 4 substitutions, insertions or deletions relative thereto.

In some embodiments of the immune cells of the disclosure, expression and/or function of a MHC Class I gene has been reduced or eliminated. In some embodiments, the MHC Class I gene is HLA-A*02. In some embodiments, the immune cells further comprise a polynucleotide comprising an interfering RNA, comprising a sequence complementary to a sequence of an HLA-A*02 mRNA. In some embodiments, the interfering RNA is capable of inducing RNA interference (RNAi)-mediated degradation of the HLA-A*02 mRNA. In some embodiments, the interfering RNA is a short hairpin RNA (shRNA) comprising: (a) a first sequence, having from 5' end to 3' end a sequence complementary to a sequence of the HLA-A*02 mRNA; and (b) a second sequence, having from 5' end to 3' end a sequence complementary to the first sequence, wherein the first sequence and the second sequence form the shRNA. In some embodiments, the shRNA comprises a sequence selected from the group of sequences set forth in Table 12.

In some embodiments of the immune cells of the disclosure, expression and/or function of a MHC Class I gene has been reduced or eliminated. In some embodiments, the MHC Class I gene is HLA-A*02. In some embodiments, the immune cells comprise one or more modifications to a sequence of an endogenous gene encoding HLA-A*02, wherein the one or modifications reduce the expression and/or eliminate the function of HLA-A*02. In some embodiments, the one or more modifications comprise one or more inactivating mutations of the endogenous gene encoding HLA-A*02. In some embodiments, the one or more inactivating mutations are introduced with a nucleic acid guided endonuclease in a complex with at least one guide nucleic acid (gNA) that specifically targets a sequence of the endogenous gene encoding HLA-A*02. In some embodiments, the gNA comprises a sequence as set forth in Table 9.

In some embodiments of the immune cells of the disclosure, the first receptor comprises a sequence of SEQ ID NO: 52, and the second receptor comprises a sequence of SEQ ID NO: 164, or sequences having at least 90%, at least 95%, at least 97% or at least 99% identity thereto. In some embodiments, the immune cells comprise an shRNA encoded by a sequence comprising GCACTCAAAGCTTGTTAAGATCGAAATCTTAACAAGCTTTGAGTGC (SEQ ID NO: 179) or a sequence having at least 80%, at least 90%, or at least 95% identity thereto. In some embodiments, the first receptor and second receptor are encoded by a single polynucleotide, and wherein the sequences encoding the first and second receptors are separated by a sequence encoding a self-cleaving polypeptide. In some embodiments, the self-cleaving polypeptide comprises a T2A self-cleaving polypeptide comprising a sequence of GSGEGRGSLLTCGDVEENPGP (SEQ ID NO: 181).

In some embodiments of the immune cells of the disclosure, the immune cells are autologous.

In some embodiments of the immune cells of the disclosure, the immune cells are allogeneic.

The disclosure provides a pharmaceutical composition, comprising a therapeutically effective amount of the immune cells of the disclosure. In some embodiments, the pharmaceutical composition further comprises a pharmaceutically acceptable carrier, diluent or excipient.

The disclosure provides a pharmaceutical composition, comprising a therapeutically effective amount of the immune cells of the disclosure for use as a medicament in the treatment of CEA+ cancer.

The disclosure provides a polynucleotide or polynucleotide system, comprising one or more polynucleotides comprising polynucleotide sequences encoding: (a) a first receptor, comprising an extracellular ligand binding domain specific to CEA cell adhesion molecule 5 positive (CEA); and (b) a second receptor, comprising an extracellular ligand binding domain specific to a non-target antigen that has been lost in the CEA+ cancer cell, wherein the first receptor is an activator receptor responsive to CEA on the CEA+ cancer cell; and wherein the second receptor is an inhibitory receptor responsive to the non-target antigen.

In some embodiments of the polynucleotide or polynucleotide system of the disclosure, the polynucleotide or polynucleotide system comprises one or more polynucleotides comprising polynucleotide sequences encoding the first receptor and the second receptor for use in generating the immune cells of the disclosure.

In some embodiments of the polynucleotide or polynucleotide system of the disclosure, the polynucleotide or polynucleotide system comprises a sequence encoding an shRNA specific to B2M. In some embodiments, the sequences encoding the first receptor, the second receptor and the shRNA specific to B2M are encoded by the same polynucleotide. In some embodiments, (a) the sequence encoding the shRNA specific to B2M comprises GCACTCAAAGCTTGTTAAGATCGAAATCTTAACAAGCTTTGAGTGC (SEQ ID NO: 179) or a sequence having at least 80%, at least 90%, or at least 95% identity thereto; (b) the sequence encoding the first receptor comprises SEQ ID NO: 143, or a sequence having at least 80%, at least 90%, or at least 95% identity thereto; and (c) the sequence encoding the second receptor comprises SEQ ID NO: 165, or a sequence having at least 80%, at least 90%, or at least 95% identity thereto.

The disclosure provides vectors comprising one or more polynucleotides of the disclosure.

The disclosure provides methods of killing CEA+ cancer cell having loss of heterozygosity at an MHC class I locus, comprising administering to the subject an effective amount of the immune cells or pharmaceutical composition of the disclosure.

The disclosure provides methods of treating CEA+ cancer in a subject having a CEA+ tumor having loss of heterozygosity at an MHC class I locus, comprising administering to the subject an effective amount of the immune cells or pharmaceutical composition of the disclosure.

The disclosure provides methods of treating a cancer in a subject comprising: (a) determining HLA-A genotype or expression of normal cells and a plurality of cancer cells of the subject; (b) optionally, determining the expression of CEA in a plurality of cancer cells of the subject; and (c) administering to the subject an effective amount of the immune cells or pharmaceutical composition of the disclosure if the normal cells express HLA-A*02 and the plurality of cancer cells do not express HLA-A*02, and the plurality of cancer cells are CEA-positive.

In some embodiments of the methods of the disclosure, the subject is a heterozygous HLA-A*02 patient with a malignancy that expresses CEA (CEA+) and has lost HLA-A*02 expression. In some embodiments, the subject is a heterozygous HLA-A*02 patient with recurrent unresectable or metastatic solid tumors that express CEA and have lost HLA-A*02 expression. In some embodiments, the cancer comprises pancreatic cancer, colorectal cancer, lung cancer, esophageal cancer, gastric cancer, head-and-neck cancer, gallbladder cancer, diffuse large B cell cancer, or acute myeloid leukemia. In some embodiments, the cancer comprises lung cancer, colorectal cancer, or pancreatic cancer.

In some embodiments of the methods of the disclosure, the cancer cells comprise CEA+/HLA-A*02− cancer cells that do not express HLA-A*02. In some embodiments, the CEA+/HLA-A*02− cancer cells are derived from a CEA+/HLA-A*02+ cell by loss of heterozygosity at HLA-A leading to loss of HLA-A*02. In some embodiments, the first receptor and the second receptor together specifically activate the immune cell in the presence of the CEA+/HLA-A*02− cancer cells. In some embodiments, the first receptor and the second receptor together do not specifically activate the immune cell in the presence of a CEA+ cell that has not lost HLA-A*02.

In some embodiments of the methods of the disclosure, administration of the immune cells or the pharmaceutical composition reduces the size of a tumor in the subject. In some embodiments, the tumor is reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In some embodiments, the tumor is eliminated. In some embodiments, administration of the immune cells or the pharmaceutical composition arrests the growth of a tumor in the subject. In some embodiments, administration of the immune cell or the pharmaceutical composition reduces the number of tumors in the subject.

In some embodiments of the methods of the disclosure, administration of the immune cells or the pharmaceutical composition results in selective killing of a cancer cell but not a normal cell in the subject. In some embodiments, at least about 60% of the cells killed are cancer cells, at least about 65% of the cells killed are cancer cells, at least about 70% of the cells killed are cancer cells, at least about 75% of the cells killed are cancer cells, at least about 80% of the cells killed are cancer cells, at least about 85% of the cells killed are cancer cells, at least about 90% of the cells killed are cancer cells, at least about 95% of the cells killed are cancer cells, or about 100% of the cells killed are cancer cells. In some embodiments, administration of the immune cell or pharmaceutical composition results in the killing of at least about 40%, about 50%, about 60%, about 70%, about 80%, about 90% or all of the cancer cells of the subject.

In some embodiments of the methods of the disclosure, administration of the immune cells or the pharmaceutical composition results in fewer side effects for the subject than administration of an otherwise equivalent immune cell comprising the first activator receptor but no second inhibitory receptor.

The disclosure provides methods of making a plurality of immune cells, comprising: (a) providing a plurality of immune cells, and (b) transforming the plurality of immune cells with the polynucleotide, polynucleotide system or vector of the disclosure.

The disclosure provides kits comprising the immune cells or pharmaceutical composition of the disclosure. In some embodiments, the kit further comprises instructions for use.

BRIEF DESCRIPTION OF THE DRAWINGS

FIG. 4 is a table showing that the addressable colorectal cancer (CRC) patient population that can be treated with a CEA TCR in combination with a RANK blocker receptor is estimated at 2,000 to 5,000 patients, depending on which RANK variant is used. In the table, the subtotal above of treatable patients is 5-11 thousand, and include the percentage of high CEA+ patients, as noted. Treated patients are calculated as: HLA-A*02 carrier freq. (0.5)×random loss (0.5)×RANK variant het freq. (0.2-0.5)×cancer RANK LOH freq.=[0.05-0.125]×LOH freq.

FIG. 9 is a table showing estimated deaths in the U.S. by cancer site, statistics taken from the American Cancer Society.

FIG. 53 is a table summarizing the properties of a dual receptor system of some embodiments described herein.

DETAILED DESCRIPTION

Figure 1:
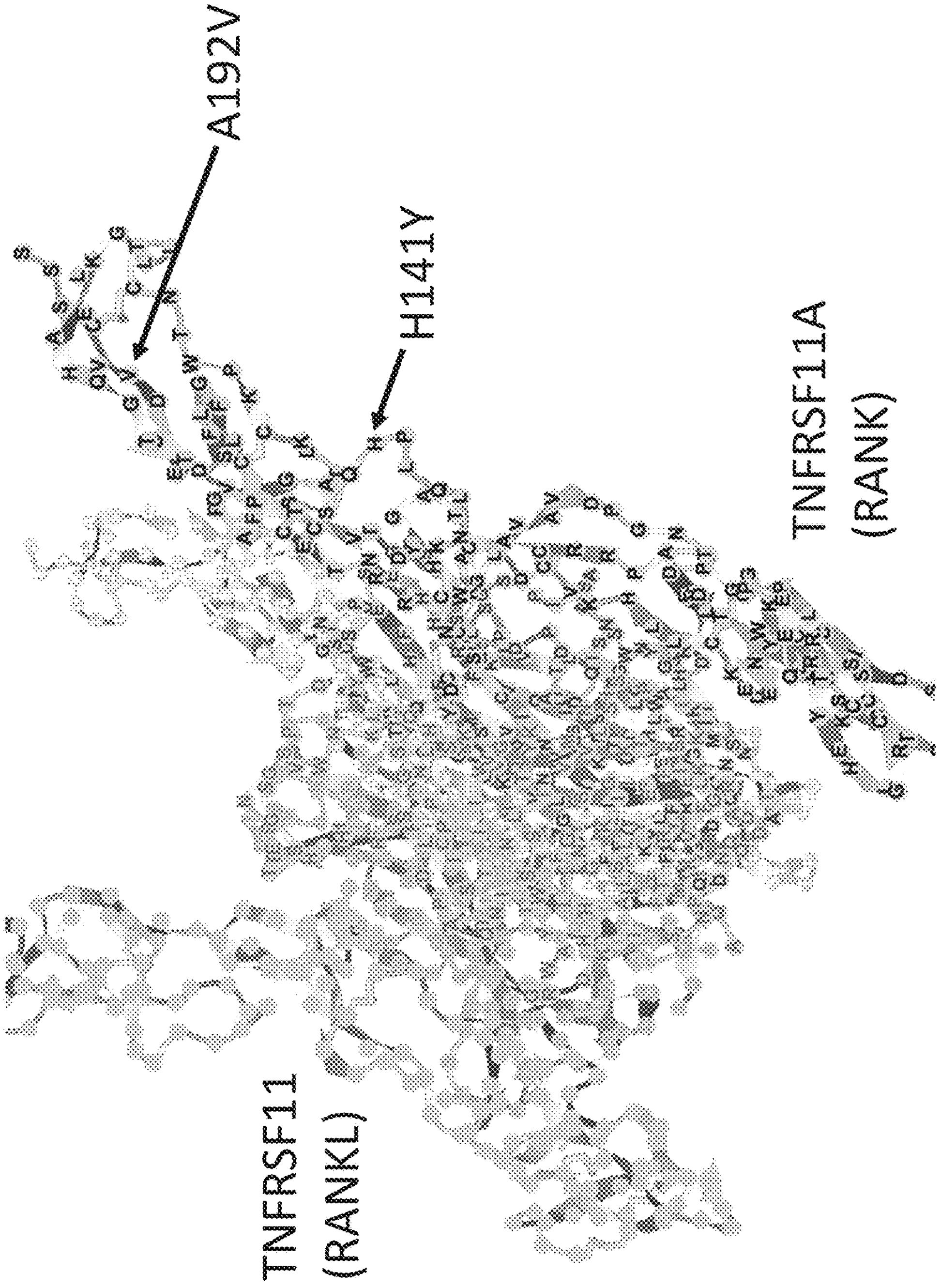
FIG. 1 is a crystal structure of TNFRSF11A (RANK) bound to TNFRS11 (RANKL), showing that the variant TNFRSF11A epitopes are on the protein surface, and presumably accessible to an antibody.
Figure 2:
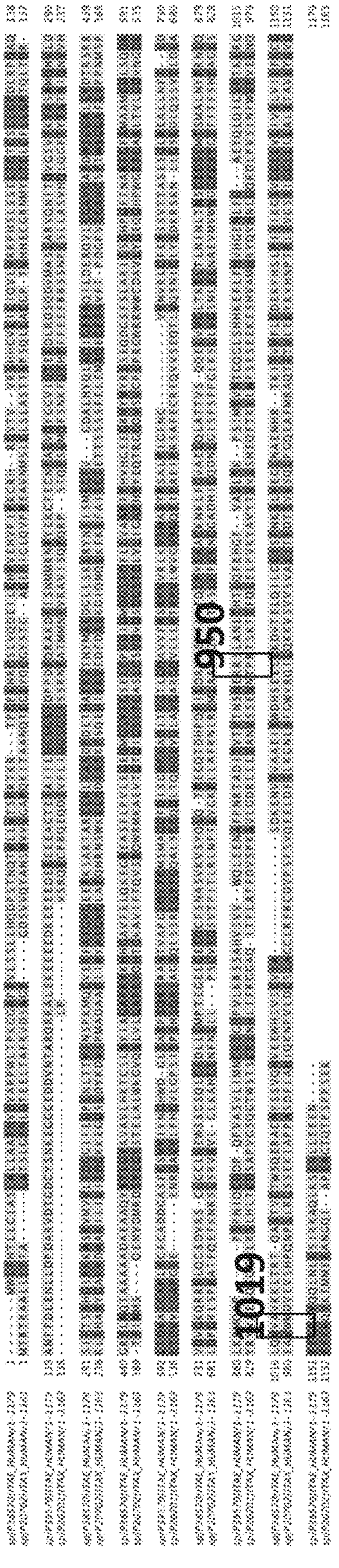
FIG. 2 shows an alignment of human Integrin alpha-E (ITGAE) (SEQ ID NO: 182) with human Integrin alpha-X (ITGAX, P20702, ITAX HUMAN) (SEQ ID NO: 183). SNP variants in ITGAE rs1716 R950W (MAF 0.2654, from the 1000 Genomes project) and rs2976230 V1019A/V1019G (MAF 0.282, from the 1000 Genomes project) are shown in boxes.
Figure 3:
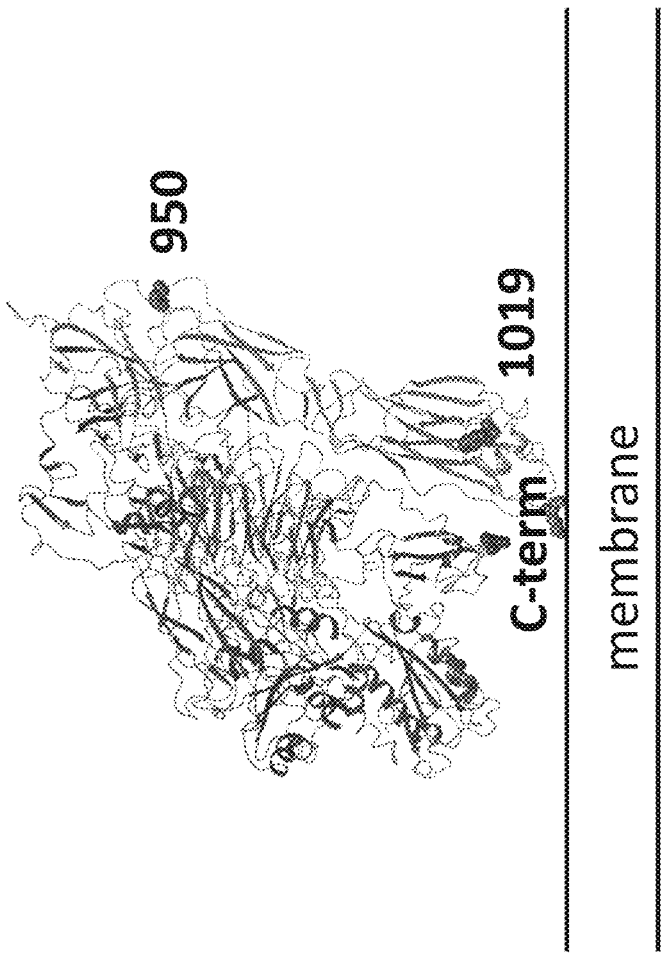
FIG. 3 is a crystal structure of the inactive conformation of ITGAX, which has 27% identity to ITGAE. The positions of the ITGAE SNPs are indicated as labeled.
Figure 5:
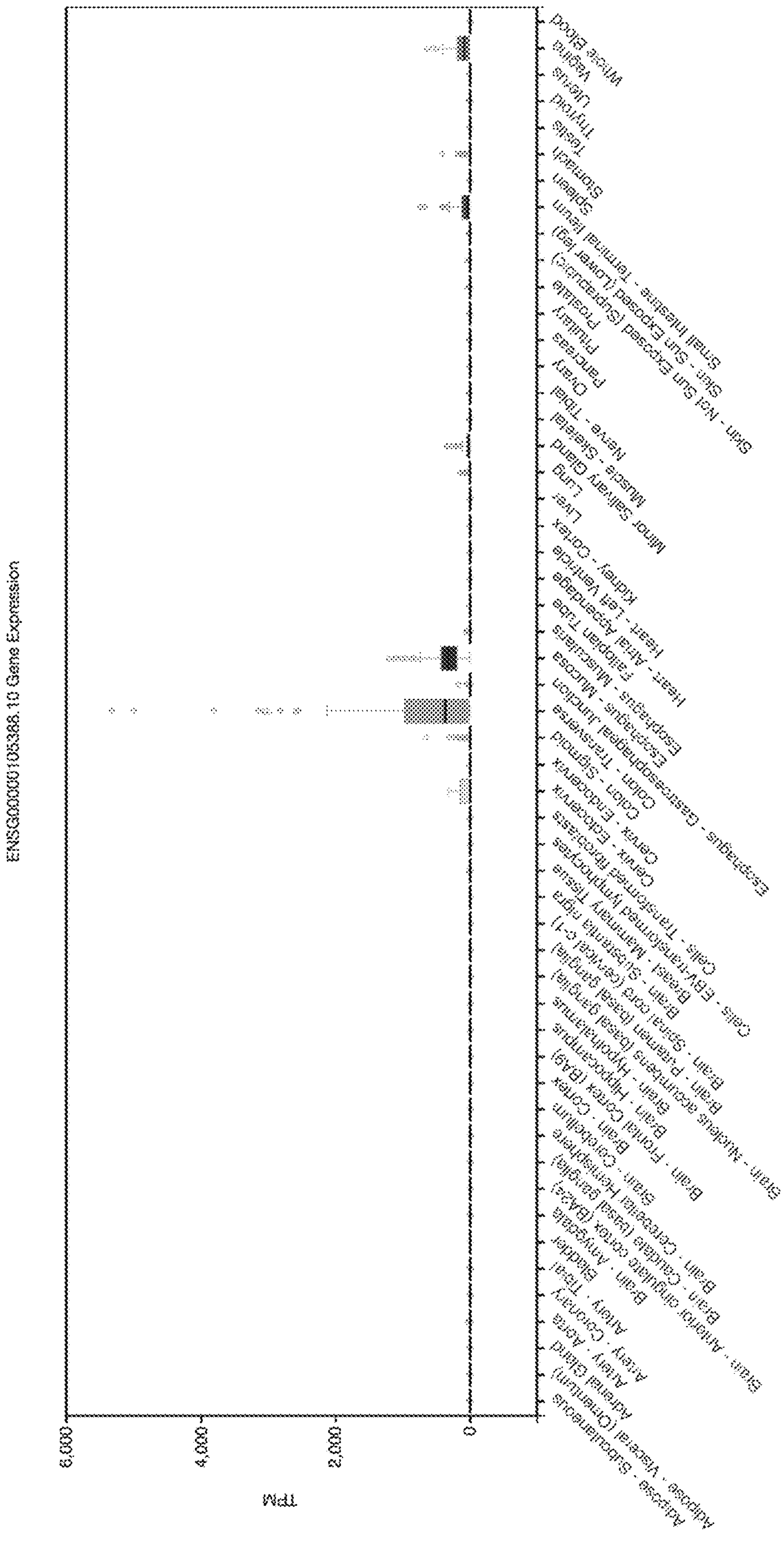
FIG. 5 shows the expression of CEA (CEACAM5) in normal tissues.
Figure 6:
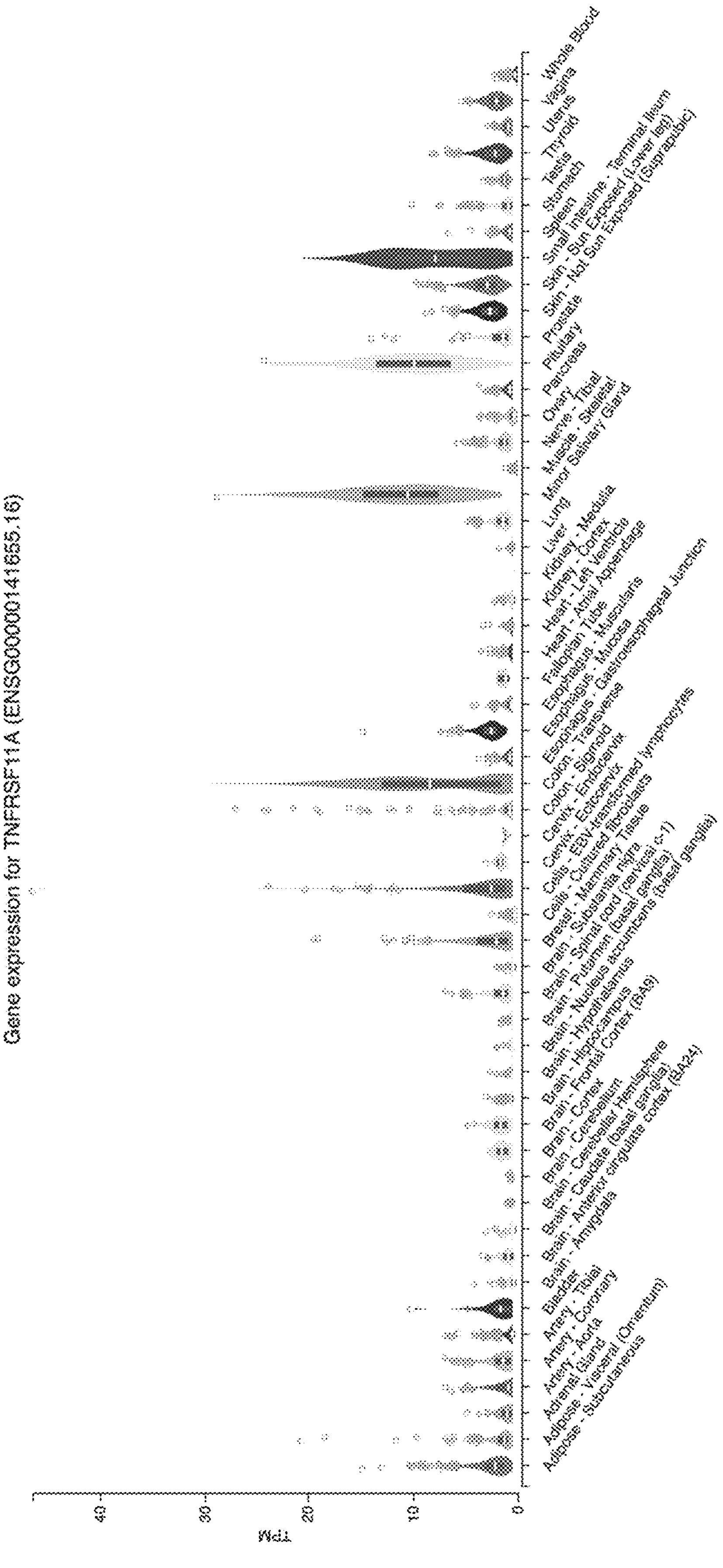
FIG. 6 shows the expression of TNFRSF11A (RANK) in normal tissues.

Provided herein are compositions and methods for treating cancers using immune cells comprising a two-receptor system responsive to differences in gene expression of a ligand between cancer and normal, wild type cells. These differences in expression can be due to loss of heterozygosity in the cancer cells. Alternatively, the differences in expression can be because the gene expression is not expressed in cancer cells, or is expressed in cancer cells at a lower level than normal cells. The two-receptor system is expressed in immune cells, for example immune cells used in adoptive cell therapy, and targets activity of these immune cells to cancer cells exhibiting loss of heterozygosity or expression differences. In this two-receptor system, the first receptor (an activator receptor, sometimes referred to herein as an A module) activates, or promotes activation of the immune cells, while the second receptor (an inhibitory receptor, sometimes referred to herein as a blocker, or inhibitor receptor, or a B module) acts to inhibit activation of the immune cells by the first receptor. Each receptor contains a ligand-binding domain (LBD) that binds a specific ligand. Signals from the two receptors upon ligand binding are integrated by the immune cell. Differential expression of ligands for the first and second receptors in cancer and normal cells, for example through loss of heterozygosity of the locus encoding the inhibitory ligand in cancer cells, or differences in transcription levels, mediates activation of immune cells by target cancer cells that express the first activator ligand but not the second inhibitory ligand.

In particular embodiments of the compositions and methods provided herein, immune cells comprising the two-receptor system described herein are used to treat CEA cell adhesion molecule 5 (CEA) positive cancers. This includes CEA-positive cancers of the gastro-intestinal (GI) tract. In the case of CEA-positive cancers, the target antigen of the activator receptor is CEA, or a peptide antigen thereof, in a complex with a major histocompatibility complex class I (MHC-I). CEA is predominantly expressed in normal adult in GI tissues as a surface protein that can be cleaved from the membrane and released in soluble form. Because of its selective expression in GI tumors, it has long been considered an attractive tumor-specific antigen that could mediate selective killing of GI tumors if CEA-positive cancer cells could be specifically targeted with an appropriate therapeutic. Moreover, the CEA gene product is an attractive target for cancer because of its high expression in virtually all colorectal tumors (and a large subset of other solid tumors) and limited expression in adult tissues. However, normal CEA expression in non-cancer (non-target) cells has prevented the effective use of CEA for targeted therapies such as adoptive cell therapies. Several therapeutics directed against CEA have been tested in the clinic and were found to induce colitis as a dose-limiting toxicity (DLT). In 2011, a clinical study with a murine TCR directed against a CEA peptide complexed with HLA-A*02 (i.e., a pMHC) was stopped in a Phase 1 study (n=3) because of localized toxicity to the colon (Parkhurst et al. Molecular Therapy 2011 19(3): P620-626; Parkhurst et al. Clin Cancer Res. 2009 Jan. 1; 15(1): 169-180). DLT occurred at a remarkably low dose of 2-4E8 cells/patient.

HLA heterozygous gene loss in a subset of tumors can be exploited to protect patients from on-target, off-tumor toxicity. By pairing an activator receptor with an inhibitory receptor, the methods provided herein increase the specificity of adoptive cell therapies and decrease harmful effects associated with these therapies, such as dose-limited toxicity. Immune cells comprising the CEA activator receptor and an HLA-A*02 specific inhibitory receptor selectively killed A*02(−) tumor cells in vitro and in vivo. These immune cells were as potent as clinically active CEA TCR-T cells, but highly selective for tumor cells that lacked HLA-A*02. The CEA CAR paired with an inhibitory receptor is a solid tumor therapeutic candidate whose activity is directed by a gene deleted in tumor cells such that normal tissue may be protected from CEA-mediated cytotoxicity.

In some embodiments, the ligand for the activator is a CEA peptide complexed with MEW class I, for example an MHC complex comprising an HLA-A*02. In the methods described herein, this CEA targeted activator receptor is paired with an inhibitory receptor, which increases the safety window of the activator by blocking its cytolytic effect on normal CEA-positive tissues. Without wishing to be bound by theory, these tissues are thought to be mostly in the gastrointestinal tract. However, the activator receptor still directs the targeted killing of tumor cells by immune cells comprising the two-receptor system, as the tumor cells do not express the ligand for the inhibitor, or blocker, receptor. The target for the second, inhibitory receptor is expressed by gastrointestinal (GI) tissues but is not expressed in cancer cells, and the inhibitory receptor recognizes this "non-target antigen" as an inhibitory stimulus. An exemplary target for the second inhibitory receptor is expressed on the surface of normal GI epithelial cells, and is lost from GI tumor cells through loss of heterozygosity (LOH) or other mechanisms, leaving a single allelic form in cancer cells that can be distinguished from other alleles via an allele-specific ligand binding domain on the inhibitory receptor. Exemplary targets of the inhibitory receptor include, but are not limited to, Major Histocompatibility Complex (MEW) proteins such as human leukocyte antigen A (HLA-A). HLA-B, HLA-C, and other HLAs. HLAs are encoding by variant genes, such as HLA-A*01, HLA-A*02, HLA-A*03, HLA-C*07, and others, which can be lost from CEA positive cancer cells through loss of heterozygosity. Alternatively, further exemplary targets of the inhibitory receptor include, but are not limited to, TNF receptor superfamily member 11a (TNFRSF11A, also called RANK), integrin subunit alpha E (ITGAE), cholinergic receptor nicotinic beta 1 subunit (ACHRB, or CHRNB), transient receptor potential cation channel subfamily V member 1 (TRPV1), and scavenger receptor class F member 1 (SREC, or SCARF). Each of these has a common nonsynonymous variant form, with the amino-acid alteration in its extracellular domain accessible to antibodies, which can be used as a B module target for a cellular integrator designed to safely treat GI cancer patients with engineered T cells activated by an activator receptor such as a CEA or CEA pMHC responsive activator receptor.

The compositions and methods of the disclosure can reduce or eliminate dose limiting toxicity (DLT) caused by expression of CEA on normal GI tissue. Without wishing to be bound by theory, it is thought that expression of CEA, while limited, is sufficiently high in the GI tract to induce adverse events of a severity that has prevented further advancement of CEA as a target for adoptive cell therapy or immunotherapy in the clinic. The disclosure provides methods of targeting CEA in cancer cells to treat CEA-positive cancers using adoptive cell therapies by adding a second inhibitory receptor that blocks activation of the adoptive immune cells in the presence of a second ligand (a ligand other than CEA, termed the non-target antigen or alternatively, blocker antigen). Using the compositions and methods described herein, tumor cells that express CEA are attacked by the adoptive immune cells expressing the two receptors because these tumor cells express only the activator ligand, CEA. In contrast, normal cells that express CEA plus the non-target antigen (alternatively termed a "blocker antigen") are protected from the adoptive immune cells. The inhibitory receptor response to the non-target antigen on normal cells prevents activation of immune cells by the CEA-targeted activator receptor. This dual-targeting approach creates the therapeutic window that will allow a CEA-directed cell therapy to be dosed safely and effectively in CEA-positive cancer patients.

The disclosure provides methods and compositions that allow the use of potent CEA CAR and TCRs that induce on-target toxicity, and renders these CEA targeted receptors useful as a therapeutic by mitigating their toxicity. None of the existing therapeutics that have been tested in the clinic, including cell and large-molecule therapies, provide a mechanism to protect normal CEA-positive tissues.

In variations, the compositions and methods described herein may be used to kill target cells and/or treat subjects in which expression of the non-target antigen is partially or completely decreased by causes other than loss of heterozygosity, including but not limited to partial gene deletion, epigenetic silencing, and point mutations or truncating mutations in the sequence encoding the non-target antigen.

Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of particular embodiments, preferred embodiments of compositions, methods and materials are described herein. For the purposes of the present disclosure, the following terms are defined below. Additional definitions are set forth throughout this disclosure.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

As used herein, the term "isolated" means material that is substantially or essentially free from components that normally accompany it in its native state. In particular embodiments, the term "obtained" or "derived" is used synonymously with isolated.

The terms "subject," "patient" and "individual" are used interchangeably herein to refer to a vertebrate, preferably a mammal, more preferably a human. Tissues, cells, and their progeny of a biological entity obtained in vivo or cultured in vitro are also encompassed. A "subject," "patient" or "individual" as used herein, includes any animal that exhibits pain that can be treated with the vectors, compositions, and methods contemplated herein. Suitable subjects (e.g., patients) include laboratory animals (such as mouse, rat, rabbit, or guinea pig), farm animals, and domestic animals or pets (such as a cat or dog). Non-human primates and, preferably, human patients, are included.

As used herein "treatment" or "treating," includes any beneficial or desirable effect, and may include even minimal improvement in symptoms. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of a symptom of disease. It also refers to delaying the onset or recurrence of a disease or condition or delaying the occurrence or recurrence of the symptoms of a disease. As used herein, "prevention" and similar words also includes reducing the intensity, effect, symptoms and/or burden of disease prior to onset or recurrence.

As used herein, the term "amount" refers to "an amount effective" or "an effective amount" of a virus to achieve a beneficial or desired prophylactic or therapeutic result, including clinical results.

A "therapeutically effective amount" of a virus or cell may vary according to factors such as the disease state, age, sex, and weight of the individual, and the ability of the virus or cell to elicit a desired response in the individual. A therapeutically effective amount is also one in which any toxic or detrimental effects of the virus or cell are outweighed by the therapeutically beneficial effects. The term "therapeutically effective amount" includes an amount that is effective to "treat" a subject (e.g., a patient).

An "increased" or "enhanced" amount of a physiological response, e.g., electrophysiological activity or cellular activity, is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the level of activity in an untreated cell.

A "decreased" or "reduced" amount of a physiological response, e.g., electrophysiological activity or cellular activity, is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the level of activity in an untreated cell.

By "maintain," or "preserve," or "maintenance," or "no change," or "no substantial change," or "no substantial decrease" refers generally to a physiological response that is comparable to a response caused by either vehicle, or a control molecule/composition. A comparable response is one that is not significantly different or measurable different from the reference response.

In general, "sequence identity" or "sequence homology" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (generally nucleotides or amino acids), divided by the total number of symbols in the shorter of the two sequences. The program may be used to determine percent identity over the entire length of the proteins being compared. Default parameters are provided to optimize searches with short query sequences in, for example, with the blastp program. The program also allows use of an SEG filter to mask-off segments of the query sequences as determined by the SEG program of Wootton and Federhen, Computers and Chemistry 17:149-163 (1993). Ranges of desired degrees of sequence identity are approximately 80% to 100% and integer values therebetween. Typically, the percent identities between a disclosed sequence and a claimed sequence are at least 80%, at least 85%, at least 90%, at least 95%, or at least 98%.

As used herein, a "polynucleotide system" refers to one or more polynucleotides. The one or more polynucleotides may be designed to work in concert for a particular application, or to produce a desired transformed cell.

The term "exogenous" is used herein to refer to any molecule, including nucleic acids, protein or peptides, small molecular compounds, and the like that originate from outside the organism. In contrast, the term "endogenous" refers to any molecule that originates from inside the organism (i.e., naturally produced by the organism).

The term "MOI" is used herein to refer to multiplicity of infection, which is the ratio of agents (e.g. viral particles) to infection targets (e.g. cells).

In the present description, any concentration range, percentage range, ratio range, or integer range is to be understood to include the value of any integer within the recited range and, when appropriate, fractions thereof (such as one tenth and one hundredth of an integer), unless otherwise indicated. The term "about", when immediately preceding a number or numeral, means that the number or numeral ranges plus or minus up to 10%.

As used herein, a "target cell" refers to cell that is targeted by an adoptive cell therapy. For example, a target cell can be cancer cell, which can be killed by the transplanted T cells of the adoptive cell therapy. Target cells of the disclosure express a target antigen, as described herein, and do not express a non-target antigen.

As used herein, a "non-target cell" refers to cell that is not targeted by an adoptive cell therapy. For example, in an adoptive cell targeting cancer cells, normal, healthy, non-cancerous cells are non-target cells. Some, or all, non-target cells in a subject may express both the target antigen and the non-target antigen. Non-target cells in a subject may express the non-target antigen irrespective of whether or not these cells also express the target antigen.

As used herein, "a non-target allelic variant" refers to an allele of a gene whose product is expressed by non-target cells, but is not expressed by target cells. For example, a non-target allelic variant is an allele of a gene that is expressed by normal, non-cancer cells of subject, but not expressed by cancer cells of the subject. The expression of the non-target allelic variant can be lost in the cancer cells by any mechanism, including, but not limited to, loss of heterozygosity, mutation, or epigenetic modification of the gene encoding the non-target allelic variant.

As used herein, "specific to" or "specifically binds to" when used with respect to a ligand binding domain, such as an antigen binding domain, refers to a ligand binding domain that has a high specificity for a named target. Antibody specificity can viewed as a measure of the goodness of fit between the ligand binding domain and the corresponding ligand, or the ability of the ligand binding domain to discriminate between similar or even dissimilar ligands. In comparison with specificity, affinity is a measure of the strength of the binding between the ligand binding domain and ligand, such that a low-affinity ligand binding domain binds weakly and high-affinity ligand binding domain binds firmly. A ligand binding domain that is specific to a target allele is one that can discriminate between different alleles of a gene. For example, a ligand binding domain that is specific to HLA-A*02 will not bind, or bind only weakly to, other HLA-A alleles such as HLA-A*01 or HLA-A*03. The person of skill in the art will appreciate that a ligand binding domain can be said to be specific to a particular target, and yet still have low levels of binding to one or more additional targets that do not affect its function in the receptor systems described herein.

As used herein, a "target antigen," whether referred to using the term antigen or the name of a specific antigen, refers to an antigen expressed by a target cell, such as a cancer cell. Expression of target antigen is not limited to target cells. Target antigens may be expressed by both cancer cells and normal, non-cancer cells in a subject.

As used herein, a "non-target antigen" (or "blocker antigen") whether referred to using the term antigen or the name of a specific antigen, refers to an antigen that is expressed by normal, non-cancer cells and is not expressed in cancer cells. This difference in expression allows the inhibitory receptor to inhibit immune cell activation in the presence of non-target cells, but not in the presence of target cells.

Polymorphism refers to the presence of two or more variants of a nucleotide sequence in a population. A polymorphism may comprise one or more base changes, an insertion, a repeat, or a deletion. A polymorphism includes e.g. a simple sequence repeat (SSR) and a single nucleotide polymorphism (SNP), which is a variation, occurring when a single nucleotide of adenine (A), thymine (T), cytosine (C) or guanine (G) is altered.

As used herein, "affinity" refers to strength of binding of a ligand to a single ligand binding site on a receptor, for example an antigen for the antigen binding domain of any of the receptors described herein. Ligand binding domains can have a weaker interaction (low affinity) with their ligand, or a stronger interaction (high affinity).

Kd, or dissociation constant, is a type of equilibrium constant that measures the propensity of a larger object to separate reversibly into smaller components, such as, for example, when a macromolecular complex comprising receptor and its cognate ligand separates into the ligand and the receptor. When the Kd is high, it means that a high concentration of ligand is need to occupy the receptor, and the affinity of the receptor for the ligand is low. Conversely, a low Kd means that the ligand has a high affinity for the receptor.

As used herein, a receptor that is "responsive" or "responsive to" refers to a receptor comprising an intracellular domain, that when bound by a ligand (i.e. antigen) generates a signal corresponding to the known function of the intracellular domain. An activator receptor bound to a target antigen can generate a signal that causes activation of an immune cell expressing the activator receptor. An inhibitory receptor bound to a non-target antigen can generate an inhibitory signal that prevents or reduces activation of an immune cell expressing the activator receptor. Responsiveness of receptors, and their ability to activate or inhibit immune cells expressing the receptors, can be assayed by any means known in the art and described herein, including, but not limited to, reporter assays and cytotoxicity assays.

As used herein, "activation" of an immune cell or an immune cell that is "activated" is an immune cell that can carry out one or more functions characteristic of an immune response. These functions include proliferation, release of cytokines, and cytotoxicity, i.e. killing of a target cell. Activated immune cells express markers that will be apparent to persons of skill in the art. For example, activated T cells can express one or more of CD69, CD71, CD25 and HLA-DR. An immune cell expressing an activator receptor (e.g. a CEA CAR) can be activated by the activator receptor when it becomes responsive to the binding of the receptor to a target antigen (e.g. CEA) expressed by the target cell. A "target antigen" can also be referred to as an "activator antigen" and may be isolated or expressed by a target cell. Activation of an immune cell expressing an inhibitory receptor can be prevented when the inhibitory receptor becomes responsive to the binding of a non-target antigen (e.g. HLA-A*02), even when the activator receptor is bound to the target activator ligand. A "non-target antigen" can also be referred to as an "inhibitory ligand" or a "blocker", and may be isolated or expressed by a target cell.

Receptor expression on an immune cell can be verified by assays that report the presence of the activator receptors and inhibitory receptors described herein. For example, a population of immune cells can be stained with a labeled molecule (e.g. a fluorophore labeled receptor-specific antibody or a fluorophore-labeled receptor-specific ligand), and quantified using fluorescence activated cell sorting (FACS) flow cytometry. This method allows a percentage of immune cells in a population of immune cells to be characterized as expressing an activator receptor, an inhibitory receptor, or both receptors. The ratio of activator receptor and inhibitory receptors expressed by the immune cells described herein can be determined by, for example, digital droplet PCR. These approaches can be used to characterize the population of cells for the production and manufacturing of the immune cells, pharmaceutical compositions, and kits described herein. For the immune cells, pharmaceutical compositions, and kits described herein, it is understood that a suitable percentage of immune cells expressing both an activator receptor and an inhibitory receptor is determined specifically for the methods described herein. For example, a suitable percentage of immune cells expressing both an activator receptor and in inhibitory receptor can be at least 50%, at least 55%, at least 60%, at least 65%, at least 70%, at least 75%, at least 80%, at least 85%, at least 90%, or at least 95%. For example, a suitable percentage of immune cells expressing both an activator receptor and an inhibitory receptor can be at most 50%, at most 55%, at most 60%, at most 65%, at most 70%, at most 75%, at most 80%, at most 85%, at most 90%, or at most 95%. For example, a suitable ratio of activator receptor and inhibitory receptor in an immune cell can be about 5:1, about 4:1, about 3:1, about 2:1, about 1:1, about 1:2, about 1:3, about 1:4, or about 1:5. It is understood that purification, enrichment, and/or depletion steps can be used on populations of immune cells to meet suitable values for the immune cells, pharmaceutical compositions, and kits described herein.

A responsive receptor expressed by the immune cells described herein can be verified by assays that measure the generation of a signal expected to be generated by the intracellular domain of the receptor. Reporter cell lines, such as Jurkat-Luciferase NFAT cells (Jurkat cells), can be used to characterize a responsive receptor. Jurkat cells are derived from T cells and comprise a stably integrated nuclear factor of activated T-cells (NFAT)-inducible luciferase reporter system. NFAT is a family of transcription factors required for immune cell activation, whose activation can be used as a signaling marker for T cell activation. Jurkat cells can be transduced or transfected with the activator receptors and/or inhibitory receptors described herein. The activator receptor is responsive to the binding of a ligand if the Jurkat cell expresses a luciferase reporter gene, and the level of responsiveness can be determined by the level of reporter gene expression. The presence of luciferase can be determined using any known luciferase detection reagent, such as luciferin. An inhibitory receptor is responsive to the binding of a ligand if, when co-expressed with an activator receptor in Jurkat cells, it prevents a normally responsive immune cell from expressing luciferase in response to the activator receptor. For example, the responsiveness of an inhibitory receptor can be determined and quantified in a Jurkat cell expressing both an activator and an inhibitor by observing the following: 1) the Jurkat cell expresses luciferase in the presence of activator receptor ligand and absence of inhibitory receptor ligand; and 2) luciferase expression in the Jurkat cell is reduced or eliminated in the presence of both an activator receptor ligand and an inhibitory receptor ligand. This approach can be used to determine the sensitivity, potency, and selectivity of activator receptors and specific pairs of activator receptors and inhibitory receptors. The sensitivity, potency, and selectivity can be quantified by EC50 or IC50 values using dose-response experiments, where an activator receptor ligand and/or inhibitory receptor ligand is titrated into a culture of Jurkat cells expressing an activator receptor or a specific pair of activator and inhibitory receptors. Alternatively, the EC50 and IC50 values can be determined in a co-culture of immune cells (e.g. Jurkat cells or primary immune cells) expressing an activator receptor or a specific pair of activator and inhibitory receptors and target cells expressing an increasing amount of an activator ligand or inhibitor ligand. An increasing amount of activator ligand or inhibitor ligand can be accomplished in the target cell by, for example, titration of activator ligand or inhibitor ligand encoding mRNA into target cells, or use of target cells that naturally express different levels of the target ligands. Exemplary suitable EC50 and IC50 values for the activator and inhibitory receptors as determined used target cells expressing varying amounts of the target and non-target ligands include an EC50 of 260 transcripts per million (TPM) or less for the activator receptor, for example an EC50 of between 10 and 260 TPM, and an IC50 of 10 TPM or less for the inhibitory receptor, for example an IC50 of 1-5 TPM.

Activation of the immune cells described herein that express an activator receptor or specific pairs of activator and inhibitory receptors can be further determined by assays that measure the viability of a target cell following co-incubation with said immune cells. The immune cells, sometimes referred to as effector cells, are co-incubated with target cells that express an activator receptor ligand, an inhibitory receptor ligand, or both an activator and inhibitory receptor ligand. Following co-incubation, viability of the target cell is measured using any method to measure viability in a cell culture. For example, viability can be determined using a mitochondrial function assay that uses a tetrazolium salt substrate to measure active mitochondrial enzymes. Viability can also be determined using imaging based methods. Target cells can express a fluorescent protein, such as green fluorescent protein or red fluorescent protein. Reduction in total cell fluorescence indicates a reduction in viability of the target cell. A reduction in viability of the target cell following incubation with immune cells expressing an activator receptor or a specific pair of activator and inhibitory receptors is interpreted as target cell-mediated activation of the immune cell. A measure of the selectivity of the immune cells can also be determined using this approach. The immune cell expressing a pair of activator and inhibitory receptors is selective if the following is observed: 1) viability is reduced in target cells expressing the activator receptor ligand but not the inhibitory receptor ligand; 2) viability is not reduced in target cells expressing both an activator receptor ligand and an inhibitory receptor ligand. From these measurements, a "specific killing" value can be derived that quantifies the percentage of immune cell activation based on the reduction in viability of target cell as a percentage of a negative control (immune cells that do not express an activator receptor). Further, from these measurements a "selectivity ratio" value can be derived that represents the ratio of the specific killing observed in target cells expressing an activator receptor ligand in the absence of inhibitory receptor ligand to the specific killing observed in target cells expressing both an activator receptor ligand and an inhibitory receptor ligand. This approach can be used to characterize the population of cells for the production and manufacturing of the immune cells, pharmaceutical compositions, and kits described herein.

A suitable specific killing value for the immune cells, pharmaceutical compositions, and kits can be, for example, the following criteria: 1) at least 40%, at least 50%, at least 60%, at least 70%, at least 80%, at least 90%, at least 95%, at least 97% or at least 99% specific killing following a 48 hour co-incubation of immune cells and target cells expressing activator receptor ligand in the absence of inhibitory receptor ligand; and 2) less than or equal to 40%, less than or equal to 35%, less than or equal to 30%, less than or equal to 25%, less than or equal to 20%, less than or equal to 15%, less than or equal to 10%, less than or equal to 5%, less than or equal to 3% or less than or equal to 1% specific killing of target cell expressing both an activator receptor ligand and an inhibitory receptor ligand.

As a further example, a suitable specific killing value for the immune cells, pharmaceutical compositions and kits can be the following criteria: 1) between 30% and 99%, between 40% and 99%, between 50% and 99%, between 55% and 95%, between 60% and 95%, between 60% and 90%, between 50% and 80%, between 50% and 70% or between 50% and 60% of target cells expressing the activator ligand but not the inhibitor ligand are killed; and 2), between 1% and 40%, between 3% and 40%, between 5% and 40%, between 5% and 30%, between 10% and 30%, between 15% and 30% or between 5% and 20% of target cells expressing the activator ligand and the inhibitor ligand are killed.

As a still further example, a suitable specific killing value for the immune cells, pharmaceutical compositions, and kits can be, for example, the following criteria: 1) at least 50% specific killing following a 48 hour co-incubation of immune cells and target cells expressing activator receptor ligand in the absence of inhibitory receptor ligand; and 2) less than or equal to 20% specific killing of target cell expressing both an activator receptor ligand and an inhibitory receptor ligand. As a further example, the immune cells are capable of killing at least 30%, at least 40%, at least 50%, at least 60%, at least 70%, at least 80%, at least 90%, at least 95%, at least 97% or at least 99% of target cells expressing the activator ligand and not the inhibitor ligand over a period of 6 hours, 12 hours, 18 hours, 24 hours, 30 hours, 36 hours, 42 hours, 48 hours, 54 hours, or 60 hours, while killing less than 40%, less than 30%, less than 20%, less than 10%, less than 5%, less than 3% or less than 1% of target cells expressing the activator and inhibitor ligands over the same time period.

A suitable specific killing value of the target cell expressing an activator ligand in the absence of an inhibitory ligand value for the immune cells, pharmaceutical compositions, and kits can be, for example, at least about 50% to at least about 95%. A suitable specific killing value of the target cell expressing an activator ligand in the absence of an inhibitory ligand value for the immune cells, pharmaceutical compositions, and kits can be, for example, at least about 50%, at least about 55%, at least about 60%, at least about 65%, at least about 70%, at least about 75%, at least about 80%, at least about 85%, at least about 90%, or at least about 95%. A suitable specific killing value of the target cell expressing an activator ligand in the absence of an inhibitory ligand value for the immune cells, pharmaceutical compositions, and kits can be, for example, at most about 50%, at most about 55%, at most about 60%, at most about 65%, at most about 70%, at most about 75%, at most about 80%, at most about 85%, at most about 90%, or at most about 95%. A suitable specific killing value of target cells expressing both an activator receptor ligand and an inhibitory receptor ligand for the immune cells, pharmaceutical compositions, and kits can be can be less than about 50%, less than about 45%, less than about 40%, less than about 35%, less than about 30%, less than about 25%, less than about 20%, less than about 15%, less than about 10%, or less than about 5%. The suitable specific killing value for the immune cells, pharmaceutical compositions, and kits can be can be determined following about 6 hours, about 12 hours, about 18 hours, about 24, about 30 hours, about 36 hours, about 42 hours, about 48 hours, about 54 hours, about 60 hours, about 66 hours, or about 72 hours of co-incubation of immune cells with target cells.

A suitable specific killing value of the target cell expressing an activator ligand in the absence of an inhibitory ligand value for the immune cells, pharmaceutical compositions, and kits can be, for example, at least about 50% to at least about 95%. A suitable specific killing value of the target cell expressing an activator ligand in the absence of an inhibitory ligand value for the immune cells, pharmaceutical compositions, and kits can be, for example, at least about 50%, at least about 55%, at least about 60%, at least about 65%, at least about 70%, at least about 75%, at least about 80%, at least about 85%, at least about 90%, or at least about 95%. A suitable specific killing value of the target cell expressing an activator ligand in the absence of an inhibitory ligand value for the immune cells, pharmaceutical compositions, and kits can be, for example, at most about 50%, at most about 55%, at most about 60%, at most about 65%, at most about 70%, at most about 75%, at most about 80%, at most about 85%, at most about 90%, or at most about 95%. A suitable specific killing value of target cells expressing both an activator receptor ligand and an inhibitory receptor ligand for the immune cells, pharmaceutical compositions, and kits can be can be less than about 50%, less than about 45%, less than about 40%, less than about 35%, less than about 30%, less than about 25%, less than about 20%, less than about 15%, less than about 10%, or less than about 5%. The suitable specific killing value for the immune cells, pharmaceutical compositions, and kits can be can be determined following about 6 hours, about 12 hours, about 18 hours, about 24, about 30 hours, about 36 hours, about 42 hours, about 48 hours, about 54 hours, about 60 hours, about 66 hours, or about 72 hours of co-incubation of immune cells with target cells.

As used herein, the term "functional variant" refers to a protein that has one or more amino-acid substitutions, insertions, or deletions as compared to a parental protein, and which retains one or more desired activities of the parental protein. A functional variant may be a fragment of the protein (i.e. a variant having N- and/or C-terminal deletions) that retain the one or more desired activities of the parental protein.

All publications and patents mentioned herein are hereby incorporated by reference in their entirety as if each individual publication or patent was specifically and individually indicated to be incorporated by reference. In case of conflict, the present application, including any definitions herein, will control. However, mention of any reference, article, publication, patent, patent publication, and patent application cited herein is not, and should not be taken as an acknowledgment, or any form of suggestion, that they constitute valid prior art or form part of the common general knowledge in any country in the world.

Activator Receptors

The disclosure provides a first receptor, comprising a first extracellular ligand binding domain specific to a target antigen comprising a cancer cell-specific antigen, or a peptide antigen thereof in a complex with a major histocompatibility complex class I (MHC-I). The first receptor is an activator receptor, and mediates activation of an immune cell expressing the first receptor upon binding of the target antigen by the extracellular ligand binding domain of the first receptor. The first receptor is responsive to a target antigen (i.e. activator ligand). For example, when a target antigen binds to or contacts the first receptor, the first receptor is responsive and activates an immune cell expressing the first receptor upon binding of the target antigen by the extracellular ligand binding domain of the first receptor. In some embodiments, the first receptor is a chimeric antigen receptor (CAR). In some embodiments, the first receptor is a T cell receptor (TCR).

In some embodiments, the first receptor is humanized. As used herein, "humanized" refers to the replacement of a sequence or a subsequence in a transgene that has been isolated or derived from a non-human species with a homologous, or functionally equivalent, human sequence. For example, a humanized antibody can be created by grafting mouse CDRs into human framework sequences, followed by back substitution of certain human framework residues for the corresponding mouse residues from the source antibody.

Activator Targets

In some embodiments, the target antigen for the first receptor is a cancer cell specific antigen. Any cell surface molecule expressed by the target cancer cells may be a suitable target antigen for the first receptor ligand binding domain. For example, a cell adhesion molecule, a cell-cell signaling molecule, an extracellular domain, a molecule involved in chemotaxis, a glycoprotein, a G protein-coupled receptor, a transmembrane, a receptor for a neurotransmitter or a voltage gated ion channel can be used as a target antigen.

In some embodiments, the target antigen is a peptide antigen of a cancer cell-specific antigen in a complex with a major histocompatibility complex class I (MHC-I). Any molecule expressed by the target cancer cells and presented by the major histocompatibility complex class I (MHC-I) on the cancer cell surface as a peptide antigen (pMHC) may be a suitable target antigen for the first receptor extracellular ligand binding domain.

In some embodiments, the cancer cell-specific antigen is CEA cell adhesion molecule 5 (CEA), or a peptide antigen thereof in a complex with a major histocompatibility complex class I (MHC-I).

The major histocompatibility complex class I (MHC-I) is a protein complex that displays antigens to cells of the immune system, triggering an immune response. The Human Leukocyte Antigens (HLAs) corresponding to MHC-I are HLA-A, HLA-B and HLA-C.

Cancer cell-specific pMHC antigens comprising any of HLA-A, HLA-B, HLA-C, HLA-E, HLA-F or HLA-G are envisaged as within the scope of the disclosure. In some embodiments, the cancer cell-specific antigen comprises HLA-A. HLA-A receptors are heterodimers comprising a heavy α chain and smaller β chain. The α chain is encoded by a variant of HLA-A, while the β chain (β2-microglobulin) is an invariant. There are several thousand variant HLA-A genes, all of which fall within the scope of the instant disclosure. In some embodiments, the MHC-I comprises a human leukocyte antigen A*02 allele (HLA-A*02).

In some embodiments, the cancer cell-specific antigen comprises HLA-B. Hundreds of versions (alleles) of the HLA-B gene are known, each of which is given a particular number (such as HLA-B27).

In some embodiments, the cancer cell-specific antigen comprises HLA-C. HLA-C belongs to the HLA class I heavy chain paralogues. This class I molecule is a heterodimer consisting of a heavy chain and a light chain (beta-2 microglobulin). Over one hundred HLA-C alleles are known in the art.

In some embodiments, the cancer cell-specific antigen is a colorectal cancer antigen. In some embodiments, the colorectal cancer antigen comprises CEA, or a peptide antigen thereof in a complex with a major histocompatibility complex class I (MHC-I).

Figure 7:
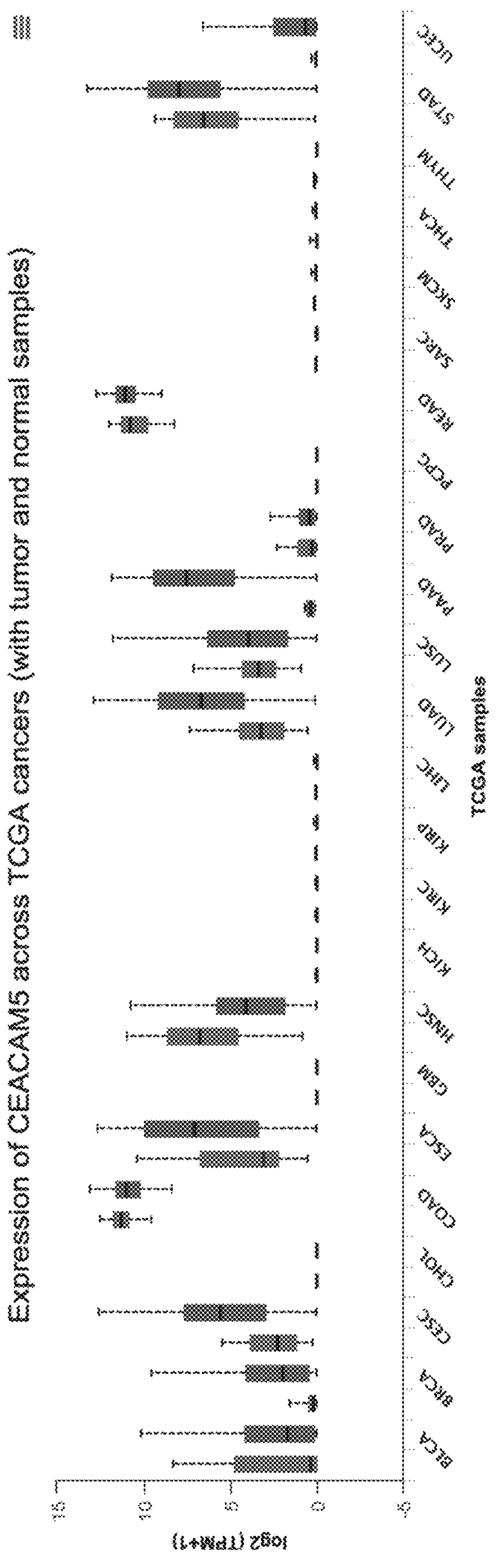
FIG. 7 shows the expression of CEA across all TCGA cancers (with tumor and normal samples. Abbreviations: BLCA (Bladder cancer), BRCA (Breast Cancer), CESC (Cervical squamous cell carcinoma and endocervical adenocarcinoma), CHOL Cholangiocarcinoma), COAD (Colon adenocarcinoma), ESCA (Esophageal carcinoma), GBM (Glioblastoma multiforme), HNSC (Head and Neck squamous cell carcinoma), KICH (Kidney Chromophobe), KIRP (Kidney renal papillary cell carcinoma), LIHC (Liver hepatocellular carcinoma), LUAD (Lung adenocarcinoma), LUSC (Lung squamous cell carcinoma), PAAD (Pancreatic adenocarcinoma), PRAD (Prostate adenocarcinoma), PCPG (Pheochromocytoma and Paraganglioma), READ (Rectum adenocarcinoma), SARC (Sarcoma), SKCM (Skin Cutaneous Melanoma), THCA (Thyroid carcinoma), THYM (Thymoma), STAD (Stomach adenocarcinoma), UCEC (Uterine Corpus Endometrial Carcinoma).
Figure 8:
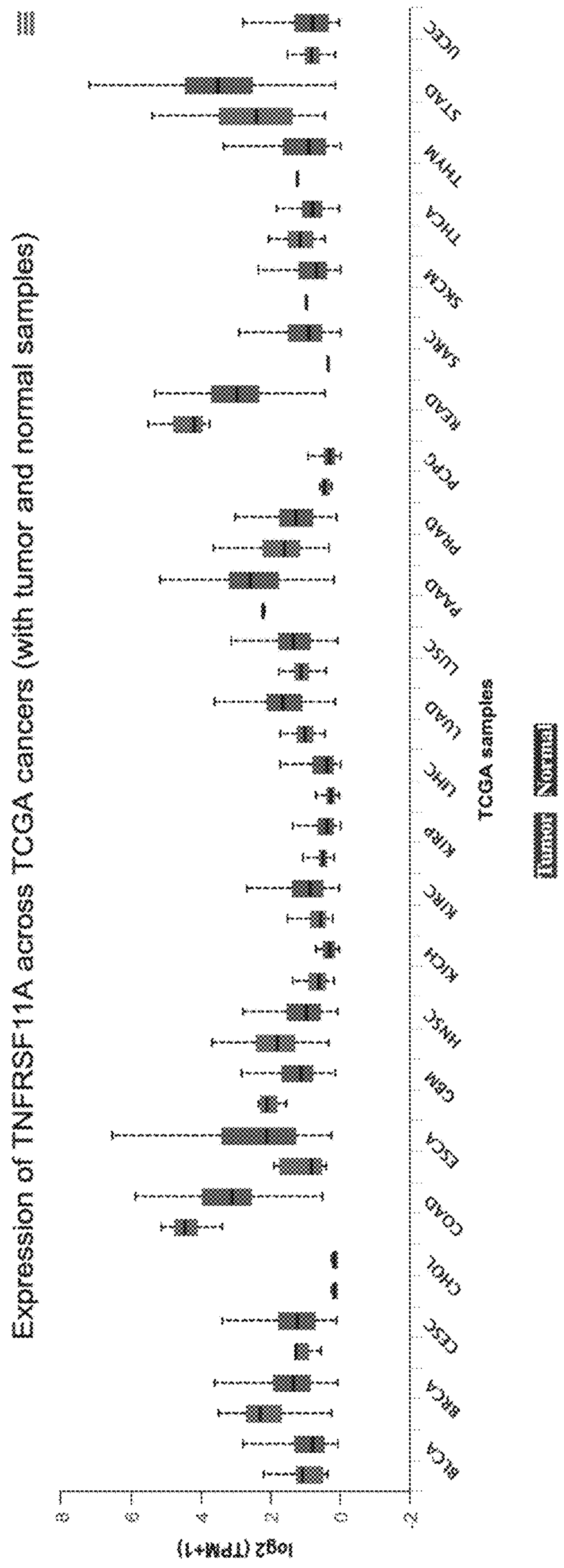
FIG. 8 shows the expression of TNFGSF11A across TCGA cancers (with tumors and normal samples).

In some embodiments, the cancer cell-specific antigen is CEA cell adhesion molecule 5 (CEA), or a peptide antigen thereof in a complex with a major histocompatibility complex class I (MHC-I). CEA is a 180-kDa glycoprotein tumor-associated protein expressed by a variety of cancer cells. CEA is a GPI-anchored adhesion molecule composed of repeated immunoglobulin domains. It is used as a biomarker in colon cancer, both as a diagnostic and as a surrogate for treatment response. Cancers that express CEA include adenocarcinomas, colorectal cancers and selected other epithelial cancers, including colorectal adenocarcinomas. However, CEA is also expressed in a variety of normal epithelial cells throughout the gastrointestinal tract, for example in the highly differentiated epithelial cells in the upper third of colonic crypts (see FIG. 7 for CEA expression).

All isoforms of CEA are envisaged as cancer cell-specific antigens of the disclosure. CEA isoform 1 is described in NCBI record number NP 001278413.1, the contents of which are incorporated by reference herein. In some embodiments, CEA comprises an amino acid sequence of:

```
                                                                    (SEQ ID NO: 1)
  1 MESPSAPPHR WCIPWQRLLL TASLLTFWNP PTTAKLTIES TPFNVAEGKE VLLLVHNLPQ

 61 HLFGYSWYKG ERVDGNRQII GYVIGTQQAT PGPAYSGREI IYPNASLLIQ NIIQNDTGFY

121 TLHVIKSDLV NEEATGQFRV YPELPKPSIS SNNSKPVEDK DAVAFTCEPE TQDATYLWWV

181 NNQSLPVSPR LQLSNGNRTL TLFNVTRNDT ASYKCETQNP VSARRSDSVI LNVLYGPDAP

241 TISPLNTSYR SGENLNLSCH AASNPPAQYS WFVNGTFQQS TQELFIPNIT VNNSGSYTCQ

301 AHNSDTGLNR TTVTTITVYA EPPKPFITSN NSNPVEDEDA VALTCEPEIQ NTTYLWWVNN

361 QSLPVSPRLQ LSNDNRTLTL LSVTRNDVGP YECGIQNELS VDHSDPVILN VLYGPDDPTI

421 SPSYTYYRPG VNLSLSCHAA SNPPAQYSWL IDGNIQQHTQ ELFISNITEK NSGLYTCQAN

481 NSASGHSRTT VKTITVSAEL PKPSISSNNS KPVEDKDAVA FTCEPEAQNT TYLWWVNGQS

541 LPVSPRLQLS NGNRTLTLFN VTRNDARAYV CGIQNSVSAN RSDPVTLDVL YGPDTPIISP

601 PDSSYLSGAN LNLSCHSASN PSPQYSWRIN GIPQQHTQVL FIAKITPNNN GTYACFVSNL

661 ATGRNNSIVK SITVSASGTS PGLSAGATVG IMIGVLVGVA LI.
```

In some embodiments, CEA comprises a sequence that shares at least 80%, at least 85%, at least 90%, at least 95%, at least 96%, at least 97%, at least 98%, or at least 99% identity to SEQ ID NO: 1. CEA isoform 2 is described in NCBI record number NP 001295327.1, the contents of which are incorporated by reference herein. In some embodiments, CEA comprises an amino acid sequence of:

(SEQ ID NO: 15)

```
  1 MESPSAPPHR WCIPWQRLLL TASLLTFWNP PTTAKLTIES TPFNVAEGKE VLLLVHNLPQ
 61 HLFGYSWYKG ERVDGNRQII GYVIGTQQAT PGPAYSGREI IYPNASLLIQ NIIQNDTGFY
121 TLHVIKSDLV NEEATGQFRV YPELPKPSIS SNNSKPVEDK DAVAFTCEPE TQDATYLWWV
181 NNQSLPVSPR LQLSNGNRTL TLFNVTRNDT ASYKCETQNP VSARRSDSVI LNVLYGPDAP
241 TISPLNTSYR SGENLNLSCH AASNPPAQYS WFVNGTFQQS TQELFIPNIT VNNSGSYTCQ
301 AHNSDTGLNR TTVTTITVYE PPKPFITSNN SNPVEDEDAV ALTCEPEIQN TTYLWWVNNQ
361 SLPVSPRLQL SNDNRTLTLL SVTRNDVGPY ECGIQNELSV DHSDPVILNV LYGPDDPTIS
421 PSYTYYRPGV NLSLSCHAAS NPPAQYSWLI DGNIQQHTQE LFISNITEKN SGLYTCQANN
481 SASGHSRTTV KTITVSAELP KPSISSNNSK PVEDKDAVAF TCEPEAQNTT YLWWVNGQSL
541 PVSPRLQLSN GNRTLTLFNV TRNDARAYVC GIQNSVSANR SDPVTLDVLY GPDTPIISPP
601 DSSYLSGANL NLSCHSASNP SPQYSWRING IPQQHTQVLF IAKITPNNNG TYACFVSNLA
661 TGRNNSIVKS ITVSASGTSP GLSAGATVGI MIGVLVGVAL I.
```

In some embodiments, CEA comprises a sequence that shares at least 80%, at least 85%, at least 90%, at least 95%, at least 96%, at least 97%, at least 98%, or at least 99% identity to SEQ ID NO: 15.

In some embodiments, the cancer cell-specific antigen is a peptide antigen derived from CEA. In some embodiments, the peptide antigen is comprises a sequence having at least 80%, at least 85%, at least 90%, at least 95%, at least 96%, at least 97%, at least 98%, or at least 99% identity to a subsequence of SEQ ID NO: 1. In some embodiments, the peptide antigen comprises a sequence identical to a subsequence of SEQ ID NO: 1. Exemplary CEA peptide antigens include amino acids 691-699 of SEQ ID NO: 1 (IMIGVLVGV), amino acids 605-613 of SEQ ID NO: 1 (YLSGANLNL), and amino acids 694-702 of SEQ ID NO: 1 (GVLVGVALI). In some embodiments the CEA peptide antigen comprises, or consists essentially of, amino acids 691-699 of SEQ ID NO: 1 (IMIGVLVGV). In some embodiments, the peptide antigen is comprises a sequence having at least 80%, at least 85%, at least 90%, at least 95%, at least 96%, at least 97%, at least 98%, or at least 99% identity to a subsequence of SEQ ID NO: 15. In some embodiments, the peptide antigen comprises a sequence identical to a subsequence of SEQ ID NO: 15. In some embodiments, the CEA peptide antigen is complexed with MHC-I. In some embodiments, the MHC-I comprises a human leukocyte antigen A*02 allele (HLA-A*02).

Extracellular Ligand Binding Domain

The disclosure provides a first receptor, comprising a first extracellular ligand binding domain specific to a target antigen. In some embodiments, the target antigen comprises a cancer cell-specific antigen.

In some embodiments, the cancer cell-specific antigen is CEA or a CEA-derived peptide antigen complexed with MHC-I, and the ligand binding domain of the first receptor recognizes and binds to the CEA antigen.

Any type of ligand binding domain that can regulate the activity of a receptor in a ligand dependent manner is envisaged as within the scope of the instant disclosure. In some embodiments, the ligand binding domain is an antigen binding domain. Exemplary antigen binding domains include, inter alia, scFv, SdAb, Vβ-only domains, and TCR antigen binding domains derived from the TCR α and β chain variable domains.

Any type of antigen binding domain is envisaged as within the scope of the instant disclosure.

For example, the first extracellular ligand binding domain may be part of a contiguous polypeptide chain including, for example, a Vβ-only domain, a single domain antibody fragment (sdAb) or heavy chain antibodies HCAb, a single chain antibody (scFv) derived from a murine, humanized or human antibodies (Harlow et al., 1999, In: Using Antibodies: A Laboratory Manual, Cold Spring Harbor Laboratory Press, N.Y.; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In some aspects, the first extracellular ligand binding domain comprises an antigen binding domain that comprises an antibody fragment. In further aspects, the first extracellular ligand binding domain comprises an antibody fragment that comprises a scFv or an sdAb.

The term "antibody," as used herein, refers to a protein, or polypeptide sequences derived from an immunoglobulin molecule, which specifically binds to an antigen. Antibodies can be intact immunoglobulins of polyclonal or monoclonal origin, or fragments thereof and can be derived from natural or from recombinant sources.

The terms "antibody fragment" or "antibody binding domain" refer to at least one portion of an antibody, or recombinant variants thereof, that contains the antigen binding domain, i.e., an antigenic determining variable region of an intact antibody, that is sufficient to confer recognition and specific binding of the antibody fragment to a target, such as an antigen and its defined epitope. Examples of antibody fragments include, but are not limited to, Fab, Fab', F(ab')2, and Fv fragments, single-chain (sc)Fv ("scFv") antibody fragments, linear antibodies, single domain antibodies (abbreviated "sdAb") (either VL or VH), camelid VHH domains, and multi-specific antibodies formed from antibody fragments.

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived.

"Heavy chain variable region" or "VH" (or, in the case of single domain antibodies, e.g., nanobodies, "VHH") with regard to an antibody refers to the fragment of the heavy chain that contains three CDRs interposed between flanking stretches known as framework regions, these framework regions are generally more highly conserved than the CDRs and form a scaffold to support the CDRs.

Unless specified, as used herein a scFv may have the VL and VH variable regions in either order, e.g., with respect to the N-terminal and C-terminal ends of the polypeptide, the scFv may comprise VL-linker-VH or may comprise VH-linker-VL.

In some embodiments, the antigen binding domain of the activator and/or inhibitory receptor comprises an scFv. In some embodiments, the scFv comprises a VL and VH region joined by a linker. In some embodiments, the linker comprises a glycine serine linker, for example GGGGSGGGGSGGGGSGG (SEQ ID NO: 146). In some embodiments, the scFv further comprises a signal sequence at the N terminus of the scFv. Exemplary signal sequences include MDMRVPAQLLGLLLLWLRGARC (SEQ ID NO: 184), which is encoded by

```
                                          (SEQ ID NO: 185)
ATGGACATGAGGGTCCCCGCTCAGCTCCTGGGGCTCCTGCTACTCTGGCT

CCGAGGTGCCAGATGT.
```

The term "antibody light chain," refers to the smaller of the two types of polypeptide chains present in antibody molecules in their naturally occurring conformations. Kappa ("K") and lambda ("λ") light chains refer to the two major antibody light chain isotypes.

The term "recombinant antibody" refers to an antibody that is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "Vβ domain", "Vβ-only domain", "β chain variable domain" or "single variable domain TCR (svd-TCR)" refers to an antigen binding domain that consists essentially of a single T Cell Receptor (TCR) beta variable domain that specifically binds to an antigen in the absence of a second TCR variable domain. The Vβ-only domain engages antigen using complementarity-determining regions (CDRs). Each Vβ-only domain contains three complement determining regions (CDR1, CDR2, and CDR3). Additional elements may be combined provided that the Vβ domain is configured to bind the epitope in the absence of a second TCR variable domain.

In some embodiments, the extracellular ligand binding domain of the first receptor comprises an antibody fragment, a single chain Fv antibody fragment (scFv), or a β chain variable domain (Vβ).

In some embodiments, the extracellular ligand binding domain of the first receptor comprises a TCR α chain variable domain and a TCR β chain variable domain.

In some embodiments, the first extracellular ligand binding domain comprises a TCR ligand binding domain that binds to a CEA antigen. In some embodiments, the CEA antigen is complexed with MHC-I, and the MHC-I comprises an HLA-A*02 allele. Exemplary TCR antigen binding domains that bind to and recognize CEA MHC-I HLA-A*02 antigens are described in Parkhurst et al. Molecular Therapy 2011 19(3): P620-626, the contents of which are incorporated herein by reference. An exemplary TCR extracellular ligand binding domain that recognizes amino acids 691-699 of SEQ ID NO: 1 (IMIGVLVGV) complexed with HLA-A*02 MHC-I comprises a TCR alpha domain of TRAV8-1*01 and TRAJ6*01, and a TCR beta domain of TRBV26*01, TRBD1*01, TRBJ2-7*01 and TRBC2.

Exemplary CDRs for that recognize a CEA MHC-I HLA-A*02 antigen comprising IMIGVLVGV (SEQ ID NO: 2) are shown in Table 1 below.

TABLE 1

CDRs for MHC-I HLA-A*02 + CEA (IMIGVLVGV (SEQ ID NO: 2))

| | A-CDR1 | A-CDR2 | A-CDR3 | B-CDR1 | B-CDR2 | B-CDR3 | Note |
|---|---|---|---|---|---|---|---|
| 1 | TSITA (SEQ ID NO: 3) | IRSNER (SEQ ID NO: 4) | ATDLTSGGNYK (SEQ ID NO: 5) | KGHPV (SEQ ID NO: 9) | FQNQEV (SEQ ID NO: 10) | ASSLGLGDYEQ (SEQ ID NO: 11) | "WT" |
| 2 | | | | | | ASSLGTGDYEQ (SEQ ID NO: 12) | BV117T |
| 3 | | | ATDFTSGGNYK (SEQ ID NO: 6) | | | ASSLGLGDYEQ (SEQ ID NO: 11) | AL-L110F |
| 4 | | | | | | ASSLGTGDYEQ (SEQ ID NO: 12) | AV-L110F/BV117T |
| 5 | | | ATDLTTGGNYK (SEQ ID NO: 7) | | | ASSLGLGDYEQ (SEQ ID NO: 11) | AV-S112T |
| 6 | | | | | | ASSLGTGDYEQ (SEQ ID NO: 12) | AV-S112T/BV117T |
| 7 | | | ATDFTTGGNYK (SEQ ID NO: 8) | | | ASSLGLGDYEQ (SEQ ID NO: 11) | AV-L110FS112T |
| 8 | | | | | | ASSLGTGDYEQ (SEQ ID NO: 12) | AV-L110FS112T/BV117T |

In some embodiments, the first extracellular ligand binding domain comprises complement determining regions (CDRs) selected from SEQ ID NOs: 3-12 or sequences having at least 85% or at least 95% identity thereto.

In some embodiments, the ligand binding domain of the first receptor comprises a TCR ligand binding domain. In some embodiments, the TCR α chain variable domain comprises a CDR-1 of TSITA (SEQ ID NO: 3), a CDR-2 of IRSNER (SEQ ID NO: 4) and a CDR-3 comprising ATDLTSGGNYK (SEQ ID NO: 5), ATDFTSGGNYK (SEQ ID NO: 6), ATDLTTGGNYK (SEQ ID NO: 7) or ATDFTTGGNYK (SEQ ID NO: 8); and the TCR β chain variable domain comprises a CDR-1 of KGHPV (SEQ ID NO: 9), a CDR-2 of FQNQEV (SEQ ID NO: 10), and a CDR-3 of ASSLGLGDYEQ (SEQ ID NO: 11) or ASSLGTGDYEQ (SEQ ID NO: 12), or sequences having at least 85% or at least 95% identity thereto. In some embodiments, the TCR α chain variable domain comprises a CDR-1 of SEQ ID NO: 9, a CDR-2 of SEQ ID NO: 10 and a CDR-3 of SEQ ID NO: 11 or SEQ ID NO: 12; and the TCR β chain variable domain comprises a CDR-1 of SEQ ID NO: 3, a CDR-2 of SEQ ID NO: 4 and a CDR-3 comprising SEQ ID NO: 5, SEQ ID NO: 6, SEQ ID NO: 7 or SEQ ID NO: 8, or sequences having at least 85% or at least 95% identity thereto.

Exemplary TCR alpha and beta chains comprising the CDRs from Table 1 are shown in Table 2 below. CDRs are underlined in the sequences in Table 2. In Table 2, the TCR alpha and TCR beta chains are separated by a P2A self-cleaving peptide (ATNFSLLKQAGDVEENPGP (SEQ ID NO: 186)) and a GSG linker.

TABLE 2

MHC-I HLA-A*02 + CEA (IMIGVLVGV (SEQ ID NO: 2)) TCR sequences

| Construct | Amino Acid Sequence | DNA Sequence |
|---|---|---|
| CT 548: pLenti 1 CEA TCR TRAV8-1*01 118P & 119T with murine constant region | MHSLLGLLMVSLWLQLTRVNSQLAEENPWALSVHEGESVTVNCSYKTSITALQWYRQKSGEGPAQLILIRSNEREKRNGRLRATLDTSSQSSSLSITATRCEDTAVYFCATDLTSGGNYKPTFGKGTSLVVHPDIQNPEPAVYQLKDPRSQDSTLCLFTDFDSQINVPKTMESGTFITDKTVLDMKAMDSKSNGAIAWSNQTSFTCQDIFKETNATYPSSDVPCDATLTEKSFETDMNLNFQNLSVMGLRILLLKVAGFNLLMTLRLWSSGSGATNFSLLKQAGDVEENPGPMATRLLCYTVLCLLGARILNSKVIQTPRYLVKGQGQKAKMRCIPEKGHPVVFWYQQNKNNEFKFLINFQNQEVLQQIDMTEKRFSAECPSNSPCSLEIQSSEAGDSALYLCASSLGLGDYEQYFGPGTRLTVLEDLRNVTPPKVSLFEPSKAEIANKQKATLVCLARGFFPDHVELSWWVNGKEVHSGVSTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 16) | (SEQ ID NO: 187) |
| CT 549: pLenti 1 CEA TCR TRAV8-1*01 118P & 119T TRBV26*01 L117T with murine constant region | MHSLLGLLMVSLWLQLTRVNSQLAEENPWALSVHEGESVTVNCSYKTSITALQWYRQKSGEGPAQLILIRSNEREKRNGRLRATLDTSSQSSSLSITATRCEDTAVYFCATDLTSGGNYKPTFGKGTSLVVHPDIQNPEPAVYQLKDPRSQDSTLCLFTDFDSQINVPKTMESGTFITDKTVLDMKAMDSKSNGAIAWSNQTSFTCQDIFKETNATYPSSDVPCDATLTEKSFETDMNLNFQNLSVMGLRILLLKVAGFNLLMTLRLWSSGSGATNFSLLKQAGDVEENPGPMATRLLCYTVLCLLGARILNSKVIQTPRYLVKGQGQKAKMRCIPEKGHPVVFWYQQNKNNEFKFLINFQNQEVLQQIDMTEKRFSAECPSNSPCSLEIQSSEAGDSALYLCASSLGTGDYEQYFGPGTRLTVLEDLRNVTPPKVSLFEPSKAEIANKQKATLVCLARGFFPDHVELSWWVNGKEVHSGVSTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 17) | (SEQ ID NO: 188) |
| CT 550: pLenti 1 CEA TCR TRAV8-1*01 118P & 119T with murine constant region | MHSLLGLLMVSLWLQLTRVNSQLAEENPWALSVHEGESVTVNCSYKTSITALQWYRQKSGEGPAQLILIRSNEREKRNGRLRATLDTSSQSSSLSITATRCEDTAVYFCATDLTSGGNYKPTFGKGTSLVVHPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSSGSGATNFSLLKQAGDVEENPGPMATRLLCYTVLCLLGARILNSKVIQTPRYLVKGQGQKAKMRCIPEKGHPVVFWYQQNKNNEFKFLINFQNQEVLQQIDMTEKRFSAECPSNSPCSLEIQSSEAGDSALYLCASSLGLGDYEQYFGPGTRLTVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 18) | (SEQ ID NO: 189) |
| CT 551: pLenti 1 CEA TCR TRAV8-1*01 L110F 118P & 119T with murine constant region | MHSLLGLLMVSLWLQLTRVNSQLAEENPWALSVHEGESVTVNCSYKTSITALQWYRQKSGEGPAQLILIRSNEREKRNGRLRATLDTSSQSSSLSITATRCEDTAVYFCATDFTSGGNYKPTFGKGTSLVVHPDIQNPEPAVYQLKDPRSQDSTLCLFTDFDSQINVPKTMESGTFITDKTVLDMKAMDSKSNGAIAWSNQTSFTCQDIFKETNATYPSSDVPCDATLTEKSFETDMNLNFQNLSVMGLRILLLKVAGFNLLMTLRLWSSGSGATNFSLLKQAGDVEENPGPMATRLLCYTVLCLLGARILNSKVIQTPRYLVKGQGQKAKMRCIPEKGHPVVFWYQQNKNNEFKFLINFQNQEVLQQIDMTEKRFSAECPSNSPCSLEIQSSEAGDSALYLCASSLGLGDYEQYFGPGTRLTVLEDLRNVTPPKVSLFEPSKAEIANKQKATLVCLARGFFPDHVELSWWVNGKEVHSGVSTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 19) | (SEQ ID NO: 190) |

TABLE 2-continued

MHC-I HLA-A*02 + CEA (IMIGVLVGV (SEQ ID NO: 2)) TCR sequences

| Construct | Amino Acid Sequence | DNA Sequence |
|---|---|---|
| CT 552: pLenti 1 CEA TCR TRAV8-1*01 S112T 118P & 119T with murine constant region | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDLTTGGNYKPTFGKGTSLVVHPDIQNPEPAVYQLKDPRSQDSTLCLFT<br>DFDSQINVPKTMESGTFITDKTVLDMKAMDSKSNGAIAWSNQTSFTCQDIFKE<br>TNATYPSSDVPCDATLTEKSFETDMNLNFQNLSVMGLRILLLKVAGFNLLMTL<br>RLWSSGSGATNFSLLKQAGDVEENPGPMATRLLCYTVLCLLGARILNSKVIQT<br>PRYLVKGQGQKAKMRCIPEKGHPVVFWYQQNKNNEFKFLINFQNQEVLQQIDM<br>TEKRFSAECPSNSPCSLEIQSSEAGDSALYLCASSLGLGDYEQYFGPGTRLTV<br>LEDLRNVTPPKVSLFEPSKAEIANKQKATLVCLARGFFPDHVELSWWVNGKEV<br>HSGVSTDPQAYKESNYSYCLSSRLRVSATFWHNPRNHFRCQVQFHGLSEEDKW<br>PEGSPKPVTQNISAEAWGRADCGITSASYQQGVLSATILYEILLGKATLYAVL<br>VSTLVVMAMVKRKNS (SEQ ID NO: 20) | (SEQ ID NO: 191) |
| CT 553: pLenti 1 CEA TCR TRAV8-1*01 L110F S112T 118P & 119T with murine constant region | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDFTTGGNYKPTFGKGTSLVVHPDIQNPEPAVYQLKDPRSQDSTLCLFT<br>DFDSQINVPKTMESGTFITDKTVLDMKAMDSKSNGAIAWSNQTSFTCQDIFKE<br>TNATYPSSDVPCDATLTEKSFETDMNLNFQNLSVMGLRILLLKVAGFNLLMTL<br>RLWSSGSGATNFSLLKQAGDVEENPGPMATRLLCYTVLCLLGARILNSKVIQT<br>PRYLVKGQGQKAKMRCIPEKGHPVVFWYQQNKNNEFKFLINFQNQEVLQQIDM<br>TEKRFSAECPSNSPCSLEIQSSEAGDSALYLCASSLGLGDYEQYFGPGTRLTV<br>LEDLRNVTPPKVSLFEPSKAEIANKQKATLVCLARGFFPDHVELSWWVNGKEV<br>HSGVSTDPQAYKESNYSYCLSSRLRVSATFWHNPRNHFRCQVQFHGLSEEDKW<br>PEGSPKPVTQNISAEAWGRADCGITSASYQQGVLSATILYEILLGKATLYAVL<br>VSTLVVMAMVKRKNS (SEQ ID NO: 21) | (SEQ ID NO: 192) |
| CT 554: pLenti 1 CEA TCR TRAV8-1*01 L110F 118P & 119T TRBV26*01 L117T with murine constant region | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDFTSGGNYKPTFGKGTSLVVHPDIQNPEPAVYQLKDPRSQDSTLCLFT<br>DFDSQINVPKTMESGTFITDKTVLDMKAMDSKSNGAIAWSNQTSFTCQDIFKE<br>TNATYPSSDVPCDATLTEKSFETDMNLNFQNLSVMGLRILLLKVAGFNLLMTL<br>RLWSSGSGATNFSLLKQAGDVEENPGPMATRLLCYTVLCLLGARILNSKVIQT<br>PRYLVKGQGQKAKMRCIPEKGHPVVFWYQQNKNNEFKFLINFQNQEVLQQIDM<br>TEKRFSAECPSNSPCSLEIQSSEAGDSALYLCASSLGTGDYEQYFGPGTRLTV<br>LEDLRNVTPPKVSLFEPSKAEIANKQKATLVCLARGFFPDHVELSWWVNGKEV<br>HSGVSTDPQAYKESNYSYCLSSRLRVSATFWHNPRNHFRCQVQFHGLSEEDKW<br>PEGSPKPVTQNISAEAWGRADCGITSASYQQGVLSATILYEILLGKATLYAVL<br>VSTLVVMAMVKRKNS (SEQ ID NO: 22) | (SEQ ID NO: 193) |
| CT 555: pLenti 1 CEA TCR TRAV8-1*01 S112T 118P & 119T TRBV26*01 L117T with murine constant region | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDLTTGGNYKPTFGKGTSLVVHPDIQNPEPAVYQLKDPRSQDSTLCLFT<br>DFDSQINVPKTMESGTFITDKTVLDMKAMDSKSNGAIAWSNQTSFTCQDIFKE<br>TNATYPSSDVPCDATLTEKSFETDMNLNFQNLSVMGLRILLLKVAGFNLLMTL<br>RLWSSGSGATNFSLLKQAGDVEENPGPMATRLLCYTVLCLLGARILNSKVIQT<br>PRYLVKGQGQKAKMRCIPEKGHPVVFWYQQNKNNEFKFLINFQNQEVLQQIDM<br>TEKRFSAECPSNSPCSLEIQSSEAGDSALYLCASSLGTGDYEQYFGPGTRLTV<br>LEDLRNVTPPKVSLFEPSKAEIANKQKATLVCLARGFFPDHVELSWWVNGKEV<br>HSGVSTDPQAYKESNYSYCLSSRLRVSATFWHNPRNHFRCQVQFHGLSEEDKW<br>PEGSPKPVTQNISAEAWGRADCGITSASYQQGVLSATILYEILLGKATLYAVL<br>VSTLVVMAMVKRKNS (SEQ ID NO: 23) | (SEQ ID NO: 194) |
| CT 556: pLenti 1 CEA TCR TRAV8-1*01 L110F S112T 118P & 119T TRBV26*01 L117T with murine constant region | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDFTTGGNYKPTFGKGTSLVVHPDIQNPEPAVYQLKDPRSQDSTLCLFT<br>DFDSQINVPKTMESGTFITDKTVLDMKAMDSKSNGAIAWSNQTSFTCQDIFKE<br>TNATYPSSDVPCDATLTEKSFETDMNLNFQNLSVMGLRILLLKVAGFNLLMTL<br>RLWSSGSGATNFSLLKQAGDVEENPGPMATRLLCYTVLCLLGARILNSKVIQT<br>PRYLVKGQGQKAKMRCIPEKGHPVVFWYQQNKNNEFKFLINFQNQEVLQQIDM<br>TEKRFSAECPSNSPCSLEIQSSEAGDSALYLCASSLGTGDYEQYFGPGTRLTV<br>LEDLRNVTPPKVSLFEPSKAEIANKQKATLVCLARGFFPDHVELSWWVNGKEV<br>HSGVSTDPQAYKESNYSYCLSSRLRVSATFWHNPRNHFRCQVQFHGLSEEDKW<br>PEGSPKPVTQNISAEAWGRADCGITSASYQQGVLSATILYEILLGKATLYAVL<br>VSTLVVMAMVKRKNS (SEQ ID NO: 24) | (SEQ ID NO: 195) |
| CT 557: pLenti 1 CEA TCR TRAV8-1*01 L110F 118P & 119T with murine constant | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDFTSGGNYKPTFGKGTSLVVHPNIQNPEPAVYQLKDPRSQDSTLCLFT<br>DFDSQINVPKTMESGTFITDKCVLDMKAMDSKSNGAIAWSNQTSFTCQDIFKE<br>TNATYPSSDVPCDATLTEKSFETDMNLNFQNLLVIVLRILLLKVAGFNLLMTL<br>RLWSSGSGATNFSLLKQAGDVEENPGPMATRLLCYTVLCLLGARILNSKVIQT<br>PRYLVKGQGQKAKMRCIPEKGHPVVFWYQQNKNNEFKFLINFQNQEVLQQIDM<br>TEKRFSAECPSNSPCSLEIQSSEAGDSALYLCASSLGLGDYEQYFGPGTRLTV<br>LEDLRNVTPPKVSLFEPSKAEIANKQKATLVCLARGFFPDHVELSWWVNGKEV | (SEQ ID NO: 196) |

TABLE 2-continued

MHC-I HLA-A*02 + CEA (IMIGVLVGV (SEQ ID NO: 2)) TCR sequences

| Construct | Amino Acid Sequence | DNA Sequence |
|---|---|---|
| region | HSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 25) | |
| CT 558: pLenti 1 CEA TCR TRAV8-1*01 S112T 118P & 119T with murine constant region | MHSLLGLLMVSLWLQLTRVNSQLAEENPWALSVHEGESVTVNCSYKTSITALQWYRQKSGEGPAQLILIRSNEREKRNGRLRATLDTSSQSSSLSITATRCEDTAVYFCATDLTTGGNYKPTFGKGTSLVVHPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSSGSGATNFSLLKQAGDVEENPGPMATRLLCYTVLCLLGARILNSKVIQTPRYLVKGQGQKAKMRCIPEKGHPVVFWYQQNKNNEFKFLINFQNQEVLQQIDMTEKRFSAECPSNSPCSLEIQSSEAGDSALYLCASSLGLGDYEQYFGPGTRLTVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 26) | (SEQ ID NO: 197) |
| CT 559: pLenti 1 CEA TCR TRAV8-1*01 L110F S112T 119T with murine constant region | MHSLLGLLMVSLWLQLTRVNSQLAEENPWALSVHEGESVTVNCSYKTSITALQWYRQKSGEGPAQLILIRSNEREKRNGRLRATLDTSSQSSSLSITATRCEDTAVYFCATDFTTGGNYKPTFGKGTSLVVHPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSSGSGATNFSLLKQAGDVEENPGPMATRLLCYTVLCLLGARILNSKVIQTPRYLVKGQGQKAKMRCIPEKGHPVVFWYQQNKNNEFKFLINFQNQEVLQQIDMTEKRFSAECPSNSPCSLEIQSSEAGDSALYLCASSLGLGDYEQYFGPGTRLTVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 27) | (SEQ ID NO: 198) |
| CT 560: pLenti 1 CEA TCR TRAV8-1*01 118P & 119T TRBV26*01 L117T with murine constant region | MHSLLGLLMVSLWLQLTRVNSQLAEENPWALSVHEGESVTVNCSYKTSITALQWYRQKSGEGPAQLILIRSNEREKRNGRLRATLDTSSQSSSLSITATRCEDTAVYFCATDLTSGGNYKPTFGKGTSLVVHPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSSGSGATNFSLLKQAGDVEENPGPMATRLLCYTVLCLLGARILNSKVIQTPRYLVKGQGQKAKMRCIPEKGHPVVFWYQQNKNNEFKFLINFQNQEVLQQIDMTEKRFSAECPSNSPCSLEIQSSEAGDSALYLCASSLGTGDYEQYFGPGTRLTVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 28) | (SEQ ID NO: 199) |
| CT 561: pLenti 1 CEA TCR TRAV8-1*01 L110F 118P & 119T TRBV26*01 L117T with murine constant region | MHSLLGLLMVSLWLQLTRVNSQLAEENPWALSVHEGESVTVNCSYKTSITALQWYRQKSGEGPAQLILIRSNEREKRNGRLRATLDTSSQSSSLSITATRCEDTAVYFCATDFTSGGNYKPTFGKGTSLVVHPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSSGSGATNFSLLKQAGDVEENPGPMATRLLCYTVLCLLGARILNSKVIQTPRYLVKGQGQKAKMRCIPEKGHPVVFWYQQNKNNEFKFLINFQNQEVLQQIDMTEKRFSAECPSNSPCSLEIQSSEAGDSALYLCASSLGTGDYEQYFGPGTRLTVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 29) | (SEQ ID NO: 200) |
| CT 562: pLenti 1 CEA TCR TRAV8-1*01 S112T 118P & 119T TRBV26*01 L117T with murine constant region | MHSLLGLLMVSLWLQLTRVNSQLAEENPWALSVHEGESVTVNCSYKTSITALQWYRQKSGEGPAQLILIRSNEREKRNGRLRATLDTSSQSSSLSITATRCEDTAVYFCATDLTTGGNYKPTFGKGTSLVVHPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSSGSGATNFSLLKQAGDVEENPGPMATRLLCYTVLCLLGARILNSKVIQTPRYLVKGQGQKAKMRCIPEKGHPVVFWYQQNKNNEFKFLINFQNQEVLQQIDMTEKRFSAECPSNSPCSLEIQSSEAGDSALYLCASSLGTGDYEQYFGPGTRLTVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 30) | (SEQ ID NO: 201) |
| CT 563: pLenti 1 CEA TCR TRAV8-1*01 L110F S112T | MHSLLGLLMVSLWLQLTRVNSQLAEENPWALSVHEGESVTVNCSYKTSITALQWYRQKSGEGPAQLILIRSNEREKRNGRLRATLDTSSQSSSLSITATRCEDTAVYFCATDFTTGGNYKPTFGKGTSLVVHPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSSGSGATNFSLLKQAGDVEENPGPMATRLLCYTVLCLLGARILNSKVIQT | (SEQ ID NO: 202) |

TABLE 2-continued

| MHC-I HLA-A*02 + CEA (IMIGVLVGV (SEQ ID NO: 2)) TCR sequences | | |
|---|---|---|
| Construct | Amino Acid Sequence | DNA Sequence |
| 118P & 119T<br>TRBV26*01<br>L117T with<br>murine<br>constant<br>region | PRYLVKGQGQKAKMRCIPEKGHPVVFWYQQNKNNEFKFLINFQNQEVLQQIDM<br>TEKRFSAECPSNSPCSLEIQSSEAGDSALYLCASSLGTGDYEQYFGPGTRLTV<br>LEDLRNVTPPKVSLFEPSKAEIANKQKATLVCLARGFFPDHVELSWWVNGKEV<br>HSGVCTDPQAYKESNYSYCLSSRLRVSATFWHNPRNHFRCQVQFHGLSEEDKW<br>PEGSPKPVTQNISAEAWGRADCGITSASYQQGVLSATILYEILLGKATLYAVL<br>VSTLVVMAMVKRKNS (SEQ ID NO: 31) | |
| CT 532:<br>pLenti 1<br>CEA TCR<br>TRAV8-<br>1*01<br>TRBV26*01<br>with<br>regular<br>murine<br>constant<br>region | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDLTSGGNYKFGKGTSLVVHPDIQNPEPAVYQLKDPRSQDSTLCLFTDF<br>DSQINVPKTMESGTFITDKTVLDMKAMDSKSNGAIAWSNQTSFTCQDIFKETN<br>ATYPSSDVPCDATLTEKSFETDMNLNFQNLSVMGLRILLLKVAGFNLLMTLRL<br>WSSGSGATNFSLLKQAGDVEENPGPMATRLLCYTVLCLLGARILNSKVIQTPR<br>YLVKGQGQKAKMRCIPEKGHPVVFWYQQNKNNEFKFLINFQNQEVLQQIDMTE<br>KRFSAECPSNSPCSLEIQSSEAGDSALYLCASSLGLGDYEQYFGPGTRLTVLE<br>DLRNVTPPKVSLFEPSKAEIANKQKATLVCLARGFFPDHVELSWWVNGKEVHS<br>GVSTDPQAYKESNYSYCLSSRLRVSATFWHNPRNHFRCQVQFHGLSEEDKWPE<br>GSPKPVTQNISAEAWGRADCGITSASYQQGVLSATILYEILLGKATLYAVLVS<br>TLVVMAMVKRKNS (SEQ ID NO: 36) | (SEQ ID NO: 203) |
| CT 533;<br>pLenti 1<br>CEA TCR<br>TRAV8-<br>1*01<br>TRBV26*01<br>L117T with<br>regular<br>murine<br>constant<br>region | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDLTSGGNYKFGKGTSLVVHPDIQNPEPAVYQLKDPRSQDSTLCLFTDF<br>DSQINVPKTMESGTFITDKTVLDMKAMDSKSNGAIAWSNQTSFTCQDIFKETN<br>ATYPSSDVPCDATLTEKSFETDMNLNFQNLSVMGLRILLLKVAGFNLLMTLRL<br>WSSGSGATNFSLLKQAGDVEENPGPMATRLLCYTVLCLLGARILNSKVIQTPR<br>YLVKGQGQKAKMRCIPEKGHPVVFWYQQNKNNEFKFLINFQNQEVLQQIDMTE<br>KRFSAECPSNSPCSLEIQSSEAGDSALYLCASSLGTGDYEQYFGPGTRLTVLE<br>DLRNVTPPKVSLFEPSKAEIANKQKATLVCLARGFFPDHVELSWWVNGKEVHS<br>GVSTDPQAYKESNYSYCLSSRLRVSATFWHNPRNHFRCQVQFHGLSEEDKWPE<br>GSPKPVTQNISAEAWGRADCGITSASYQQGVLSATILYEILLGKATLYAVLVS<br>TLVVMAMVKRKNS (SEQ ID NO: 37) | (SEQ ID NO: 204) |
| CT 534:<br>pLenti 1<br>CEA TCR<br>TRAV8-<br>1*01<br>TRBV26*01<br>murine<br>constant<br>region<br>(no PT) | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDLTSGGNYKFGKGTSLVVHPNIQNPEPAVYQLKDPRSQDSTLCLFTDF<br>DSQINVPKTMESGTFITDKTVLDMKAMDSKSNGAIAWSNQTSFTCQDIFKETN<br>ATYPSSDVPCDATLTEKSFETDMNLNFQNLLVIVLRILLLKVAGFNLLMTLRL<br>WSSGSGATNFSLLKQAGDVEENPGPMATRLLCYTVLCLLGARILNSKVIQTPR<br>YLVKGQGQKAKMRCIPEKGHPVVFWYQQNKNNEFKFLINFQNQEVLQQIDMTE<br>KRFSAECPSNSPCSLEIQSSEAGDSALYLCASSLGLGDYEQYFGPGTRLTVLE<br>DLRNVTPPKVSLFEPSKAEIANKQKATLVCLARGFFPDHVELSWWVNGKEVHS<br>GVCTDPQAYKESNYSYCLSSRLRVSATFWHNPRNHFRCQVQFHGLSEEDKWPE<br>GSPKPVTQNISAEAWGRADCGITSASYQQGVLSATILYEILLGKATLYAVLVS<br>TLVVMAMVKRKNS (SEQ ID NO: 38) | (SEQ ID NO: 205) |
| CT 535:<br>pLenti 1<br>CEA TCR<br>TRAV8-<br>1*01 L110F<br>TRBV26*01<br>with<br>regular<br>murine<br>constant<br>region | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDFTSGGNYKFGKGTSLVVHPDIQNPEPAVYQLKDPRSQDSTLCLFTDF<br>DSQINVPKTMESGTFITDKTVLDMKAMDSKSNGAIAWSNQTSFTCQDIFKETN<br>ATYPSSDVPCDATLTEKSFETDMNLNFQNLLVMGLRILLLKVAGFNLLMTLRL<br>WSSGSGATNFSLLKQAGDVEENPGPMATRLLCYTVLCLLGARILNSKVIQTPR<br>YLVKGQGQKAKMRCIPEKGHPVVFWYQQNKNNEFKFLINFQNQEVLQQIDMTE<br>KRFSAECPSNSPCSLEIQSSEAGDSALYLCASSLGLGDYEQYFGPGTRLTVLE<br>DLRNVTPPKVSLFEPSKAEIANKQKATLVCLARGFFPDHVELSWWVNGKEVHS<br>GVSTDPQAYKESNYSYCLSSRLRVSATFWHNPRNHFRCQVQFHGLSEEDKWPE<br>GSPKPVTQNISAEAWGRADCGITSASYQQGVLSATILYEILLGKATLYAVLVS<br>TLVVMAMVKRKNS (SEQ ID NO: 39) | (SEQ ID NO: 206) |
| CT 536:<br>pLenti 1<br>CEA TCR<br>TRAV8-<br>1*01 L112T<br>TRBV26*01<br>with<br>regular<br>murine<br>constant<br>region | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDLTTGGNYKFGKGTSLVVHPDIQNPEPAVYQLKDPRSQDSTLCLFTDF<br>DSQINVPKTMESGTFITDKTVLDMKAMDSKSNGAIAWSNQTSFTCQDIFKETN<br>ATYPSSDVPCDATLTEKSFETDMNLNFQNLSVMGLRILLLKVAGFNLLMTLRL<br>WSSGSGATNFSLLKQAGDVEENPGPMATRLLCYTVLCLLGARILNSKVIQTPR<br>YLVKGQGQKAKMRCIPEKGHPVVFWYQQNKNNEFKFLINFQNQEVLQQIDMTE<br>KRFSAECPSNSPCSLEIQSSEAGDSALYLCASSLGLGDYEQYFGPGTRLTVLE<br>DLRNVTPPKVSLFEPSKAEIANKQKATLVCLARGFFPDHVELSWWVNGKEVHS<br>GVSTDPQAYKESNYSYCLSSRLRVSATFWHNPRNHFRCQVQFHGLSEEDKWPE<br>GSPKPVTQNISAEAWGRADCGITSASYQQGVLSATILYEILLGKATLYAVLVS<br>TLVVMAMVKRKNS (SEQ ID NO: 40) | (SEQ ID NO: 207) |
| CT 537:<br>pLenti 1<br>CEA TCR | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDFTTGGNYKFGKGTSLVVHPDIQNPEPAVYQLKDPRSQDSTLCLFTDF | (SEQ ID NO: 208) |

TABLE 2-continued

MHC-I HLA-A*02 + CEA (IMIGVLVGV (SEQ ID NO: 2)) TCR sequences

| Construct | Amino Acid Sequence | DNA Sequence |
|---|---|---|
| TRAV8-1*01 L110F & S112T TRBV26*01 with regular murine constant region | DSQINVPKTMESGTFITDKTVLDMKAMDSKSNGAIAWSNQTSFTCQDIFKETN<br>ATYPSSDVPCDATLTEKSFETDMNLNFQNLSVMGLRILLLKVAGFNLLMTLRL<br>WSSGSGATNFSLLKQAGDVEENPGPMATRLLCYTVLCLLGARILNSKVIQTPR<br>YLVKGQGQKAKMRCIPEKGHPVVFWYQQNKNNEFKFLINFQNQEVLQQIDMTE<br>KRFSAECPSNSPCSLEIQSSEAGDSALYLCASSLGLGDYEQYFGPGTRLTVLE<br>DLRNVTPPKVSLFEPSKAEIANKQKATLVCLARGFFPDHVELSWWVNGKEVHS<br>GVSTDPQAYKESNYSYCLSSRLRVSATFWHNPRNHFRCQVQFHGLSEEDKWPE<br>GSPKPVTQNISAEAWGRADCGITSASYQQGVLSATILYEILLGKATLYAVLVS<br>TLVVMAMVKRKNS (SEQ ID NO: 41) | |
| CT 538: pLenti 1 CEA TCR TRAV8-1*01 L110F TRBV26*01 L117T with regular murine constant region | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDFTSGGNYKFGKGTSLVVHPDIQNPEPAVYQLKDPRSQDSTLCLFTDF<br>DSQINVPKTMESGTFITDKTVLDMKAMDSKSNGAIAWSNQTSFTCQDIFKETN<br>ATYPSSDVPCDATLTEKSFETDMNLNFQNLSVMGLRILLLKVAGFNLLMTLRL<br>WSSGSGATNFSLLKQAGDVEENPGPMATRLLCYTVLCLLGARILNSKVIQTPR<br>YLVKGQGQKAKMRCIPEKGHPVVFWYQQNKNNEFKFLINFQNQEVLQQIDMTE<br>KRFSAECPSNSPCSLEIQSSEAGDSALYLCASSLGTGDYEQYFGPGTRLTVLE<br>DLRNVTPPKVSLFEPSKAEIANKQKATLVCLARGFFPDHVELSWWVNGKEVHS<br>GVSTDPQAYKESNYSYCLSSRLRVSATFWHNPRNHFRCQVQFHGLSEEDKWPE<br>GSPKPVTQNISAEAWGRADCGITSASYQQGVLSATILYEILLGKATLYAVLVS<br>TLVVMAMVKRKNS (SEQ ID NO: 42) | (SEQ ID NO: 209) |
| CT 539: pLenti 1 CEA TCR TRAV8-1*01 S112T TRBV26*01 L117T with regular murine constant region | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDLTTGGNYKFGKGTSLVVHPDIQNPEPAVYQLKDPRSQDSTLCLFTDF<br>DSQINVPKTMESGTFITDKTVLDMKAMDSKSNGAIAWSNQTSFTCQDIFKETN<br>ATYPSSDVPCDATLTEKSFETDMNLNFQNLSVMGLRILLLKVAGFNLLMTLRL<br>WSSGSGATNFSLLKQAGDVEENPGPMATRLLCYTVLCLLGARILNSKVIQTPR<br>YLVKGQGQKAKMRCIPEKGHPVVFWYQQNKNNEFKFLINFQNQEVLQQIDMTE<br>KRFSAECPSNSPCSLEIQSSEAGDSALYLCASSLGTGDYEQYFGPGTRLTVLE<br>DLRNVTPPKVSLFEPSKAEIANKQKATLVCLARGFFPDHVELSWWVNGKEVHS<br>GVSTDPQAYKESNYSYCLSSRLRVSATFWHNPRNHFRCQVQFHGLSEEDKWPE<br>GSPKPVTQNISAEAWGRADCGITSASYQQGVLSATILYEILLGKATLYAVLVS<br>TLVVMAMVKRKNS (SEQ ID NO: 43) | (SEQ ID NO: 210) |
| CT 540: pLenti 1 CEA TCR TRAV8-1*01 L110F & S112T TRBV26*01 L117T with regular murine constant region | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDFTTGGNYKFGKGTSLVVHPDIQNPEPAVYQLKDPRSQDSTLCLFTDF<br>DSQINVPKTMESGTFITDKTVLDMKAMDSKSNGAIAWSNQTSFTCQDIFKETN<br>ATYPSSDVPCDATLTEKSFETDMNLNFQNLSVMGLRILLLKVAGFNLLMTLRL<br>WSSGSGATNFSLLKQAGDVEENPGPMATRLLCYTVLCLLGARILNSKVIQTPR<br>YLVKGQGQKAKMRCIPEKGHPVVFWYQQNKNNEFKFLINFQNQEVLQQIDMTE<br>KRFSAECPSNSPCSLEIQSSEAGDSALYLCASSLGTGDYEQYFGPGTRLTVLE<br>DLRNVTPPKVSLFEPSKAEIANKQKATLVCLARGFFPDHVELSWWVNGKEVHS<br>GVSTDPQAYKESNYSYCLSSRLRVSATFWHNPRNHFRCQVQFHGLSEEDKWPE<br>GSPKPVTQNISAEAWGRADCGITSASYQQGVLSATILYEILLGKATLYAVLVS<br>TLVVMAMVKRKNS (SEQ ID NO: 44) | (SEQ ID NO: 211) |
| CT 541: pLenti 1 CEA TCR TRAV8-1*01 L110F TRBV26*01 with murine constant region | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDFTSGGNYKFGKGTSLVVHPNIQNPEPAVYQLKDPRSQDSTLCLFTDF<br>DSQINVPKTMESGTFITDKCVLDMKAMDSKSNGAIAWSNQTSFTCQDIFKETN<br>ATYPSSDVPCDATLTEKSFETDMNLNFQNLLVIVLRILLLKVAGFNLLMTLRL<br>WSSGSGATNFSLLKQAGDVEENPGPMATRLLCYTVLCLLGARILNSKVIQTPR<br>YLVKGQGQKAKMRCIPEKGHPVVFWYQQNKNNEFKFLINFQNQEVLQQIDMTE<br>KRFSAECPSNSPCSLEIQSSEAGDSALYLCASSLGLGDYEQYFGPGTRLTVLE<br>DLRNVTPPKVSLFEPSKAEIANKQKATLVCLARGFFPDHVELSWWVNGKEVHS<br>GVCTDPQAYKESNYSYCLSSRLRVSATFWHNPRNHFRCQVQFHGLSEEDKWPE<br>GSPKPVTQNISAEAWGRADCGITSASYQQGVLSATILYEILLGKATLYAVLVS<br>TLVVMAMVKRKNS (SEQ ID NO: 45) | (SEQ ID NO: 212) |
| CT 542: pLenti 1 CEA TCR TRAV8-1*01 S112T TRBV26*01 with murine constant region | MHSLLGLLMVSLWLQLTRVNSQLAEENPWALSVHEGESVTVNCSYKTSITALQ<br>WYRQKSGEGPAQLILIRSNEREKRNGRLRATLDTSSQSSSLSITATRCEDTAV<br>YFCATDLTTGGNYKFGKGTSLVVHPNIQNPEPAVYQLKDPRSQDSTLCLFTDF<br>DSQINVPKTMESGTFITDKCVLDMKAMDSKSNGAIAWSNQTSFTCQDIFKETN<br>ATYPSSDVPCDATLTEKSFETDMNLNFQNLLVIVLRILLLKVAGFNLLMTLRL<br>WSSGSGATNFSLLKQAGDVEENPGPMATRLLCYTVLCLLGARILNSKVIQTPR<br>YLVKGQGQKAKMRCIPEKGHPVVFWYQQNKNNEFKFLINFQNQEVLQQIDMTE<br>KRFSAECPSNSPCSLEIQSSEAGDSALYLCASSLGLGDYEQYFGPGTRLTVLE<br>DLRNVTPPKVSLFEPSKAEIANKQKATLVCLARGFFPDHVELSWWVNGKEVHS<br>GVCTDPQAYKESNYSYCLSSRLRVSATFWHNPRNHFRCQVQFHGLSEEDKWPE<br>GSPKPVTQNISAEAWGRADCGITSASYQQGVLSATILYEILLGKATLYAVLVS<br>TLVVMAMVKRKNS (ESQ ID NO: 46) | (SEQ ID NO: 213) |

TABLE 2-continued

| MHC-I HLA-A*02 + CEA (IMIGVLVGV (SEQ ID NO: 2)) TCR sequences | | |
|---|---|---|
| Construct | Amino Acid Sequence | DNA Sequence |
| CT 543: pLenti 1 CEA TCR TRAV8-1*01 L110F & S112T TRBV26*01 with murine constant region | MHSLLGLLMVSLWLQLTRVNSQLAEENPWALSVHEGESVTVNCSYKTSITALQWYRQKSGEGPAQLILIRSNEREKRNGRLRATLDTSSQSSSLSITATRCEDTAVYFCATDFTTGGNYKFGKGTSLVVHPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSSGSGAGNFSLLKQAGDVEENPGPMATRLLCYTVLCLLGARILNSKVIQTPRYLVKGQGQKAKMRCIPEKGHPVVFWYQQNKNNEFKFLINFQNQEVLQQIDMTEKRFSAECPSNSPCSLEIQSSEAGDSALYLCASSLGLGDYEQYFGPGTRLTVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 47) | (SEQ ID NO: 214) |
| CT 544: pLenti 1 CEA TCR TRAV8-1*01 TBV26*01 L117T with murine constant region | MHSLLGLLMVSLWLQLTRVNSQLAEENPWALSVHEGESVTVNCSYKTSITALQWYRQKSGEGPAQLILIRSNEREKRNGRLRATLDTSSQSSSLSITATRCEDTAVYFCATDLTSGGNYKFGKGTSLVVHPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSSGSGATNFSLLKQAGDVEENPGPMATRLLCYTVLCLLGARILNSKVIQTPRYLVKGQGQKAKMRCIPEKGHPVVFWYQQNKNNEFKFLINFQNQEVLQQIDMTEKRFSAECPSNSPCSLEIQSSEAGDSALYLCASSLGTGDYEQYFGPGTRLTVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 48) | (SEQ ID NO: 215) |
| CT 545: pLenti 1 CEA TCR TRAV8-1*01 L110F TRBV26*01 L117T with murine constant region | MHSLLGLLMVSLWLQLTRVNSQLAEENPWALSVHEGESVTVNCSYKTSITALQWYRQKSGEGPAQLILIRSNEREKRNGRLRATLDTSSQSSSLSITATRCEDTAVYFCATDLTSGGNYKFGKGTSLVVHPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSSGSGATNFSLLKQAGDVEENPGPMATRLLCYTVLCLLGARILNSKVIQTPRYLVKGQGQKAKMRCIPEKGHPVVFWYQQNKNNEFKFLINFQNQEVLQQIDMTEKRFSAECPSNSPCSLEIQSSEAGDSALYLCASSLGTGDYEQYFGPGTRLTVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 49) | (SEQ ID NO: 216) |
| CT 546: pLenti 1 CEA TCR TRAV8-1*01 S112T TRBV26*01 L117T with murine constant region | MHSLLGLLMVSLWLQLTRVNSQLAEENPWALSVHEGESVTVNCSYKTSITALQWYRQKSGEGPAQLILIRSNEREKRNGRLRATLDTSSQSSSLSITATRCEDTAVYFCATDLTTGGNYKFGKGTSLVVHPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSSGSGATNFSLLKQAGDVEENPGPMATRLLCYTVLCLLGARILNSKVIQTPRYLVKGQGQKAKMRCIPEKGHPVVFWYQQNKNNEFKFLINFQNQEVLQQIDMTEKRFSAECPSNSPCSLEIQSSEAGDSALYLCASSLGTGDYEQYFGPGTRLTVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 50) | (SEQ ID NO: 217) |
| CT 547: pLenti 1 CEA TCR TRAV8-1*01 L110F & S112T TRBV26*01 L117T with murine constant region | MHSLLGLLMVSLWLQLTRVNSQLAEENPWALSVHEGESVTVNCSYKTSITALQWYRQKSGEGPAQLILIRSNEREKRNGRLRATLDTSSQSSSLSITATRCEDTAVYFCATDFTTGGNYKFGKGTSLVVHPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSSGSGATNFSLLKQAGDVEENPGPMATRLLCYTVLCLLGARILNSKVIQTPRYLVKGQGQKAKMRCIPEKGHPVVFWYQQNKNNEFKFLINFQNQEVLQQIDMTEKRFSAECPSNSPCSLEIQSSEAGDSALYLCASSLGTGDYEQYFGPGTRLTVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 51) | (SEQ ID NO: 218) |

In some embodiments, the first receptor comprises a sequence at least 80% identical, at least 85% identical, at least 90% identical, at least 95% identical, at least 96% identical, at least 97% identical, at least 98% identical, at least 99% identical, or at least 99.5% identical to a sequence or subsequence of any one of SEQ ID NOS: 16-31 or 36-51. In some embodiments, the first receptor comprises a sequence or subsequence of any one of SEQ ID NOS: 16-31 or 36-51.

In some embodiments, the first receptor comprises a TCR alpha chain comprising or consisting essentially of amino acids 1-270 of any one of SEQ ID NOS: 16-31, or a sequence that is at least 80% identical, at least 85% identical, at least 90% identical, at least 95% identical, at least 96% identical, at least 97% identical, at least 98% identical, at least 99% identical, or at least 99.5% identical thereto. In some embodiments, the first receptor comprises a TCR alpha chain comprising or consisting essentially of amino acids 1-270 of any one of SEQ ID NOS: 16-31.

In some embodiments, the first receptor comprises a TCR beta chain comprising or consisting essentially of amino acids 293-598 of any one of SEQ ID NOS: 16-31, or a sequence that is at least 80% identical, at least 85% identical, at least 90% identical, at least 95% identical, at least 96% identical, at least 97% identical, at least 98% identical, at least 99% identical, or at least 99.5% identical thereto. In some embodiments, the first receptor comprises a TCR beta chain comprising or consisting essentially of amino acids 293-598 of any one of SEQ ID NOS: 16-31.

In some embodiments, the first receptor comprises a TCR alpha chain comprising amino acids 1-270 of any one of SEQ ID NOS: 16-31, and a TCR beta chain comprising amino acids 293-598 of any one of SEQ ID NOS: 16-31.

In some embodiments, the first receptor comprises a TCR alpha chain comprising or consisting essentially of amino acids 1-268 of any one of SEQ ID NOS: 36-51, or a sequence that is at least 80% identical, at least 85% identical, at least 90% identical, at least 95% identical, at least 96% identical, at least 97% identical, at least 98% identical, at least 99% identical, or at least 99.5% identical thereto. In some embodiments, the first receptor comprises a TCR alpha chain comprising or consisting essentially of amino acids 1-268 of any one of SEQ ID NOS: 36-51.

In some embodiments, the first receptor comprises a TCR beta chain comprising or consisting essentially of amino acids 291-596 of any one of SEQ ID NOS: 36-51, or a sequence that is at least 80% identical, at least 85% identical, at least 90% identical, at least 95% identical, at least 96% identical, at least 97% identical, at least 98% identical, at least 99% identical, or at least 99.5% identical thereto. In some embodiments, the first receptor comprises a TCR beta chain comprising or consisting essentially of amino acids 291-596 of any one of SEQ ID NOS: 36-51.

In some embodiments, the first receptor comprises a TCR alpha chain comprising amino acids 1-268 of any one of SEQ ID NOS: 36-51, and a TCR beta chain comprising amino acids 291-596 of any one of SEQ ID NOS: 36-51.

In some embodiments, the extracellular ligand binding domain of the first receptor is an scFv. In some embodiments, the scFv domain binds to CEA. In some embodiments, the scFv is the ligand binding domain of a CAR. Exemplary CAR sequences comprising CEA targeting scFv domains are shown in Table 3 below. In Table 3, CDR sequences are underlined.

TABLE 3

Exemplary CARs with scFv that target CEA

| Protein Sequence | Nucleotide Sequence |
|---|---|
| MDMRVPAQLLGLLLLWLRG<br>ARCQVQLVQSGSELKKPGA<br>SVKVSCKASGYTFTEFGMN<br>WVRQAPGQGLEWMGWINTK<br>TGEATYVEEFKGRFVFSLD<br>TSVSTAYLQISSLKAEDTA<br>VYYCARWDFAYYVEAMDYW<br>GQGTTVTVSSGGGGSGGGG<br>SGGGGSGGDIQMTQSPSSL<br>SASVGDRVTITCKASQNVG<br>TNVAWYQQKPGKAPKLLIY<br>SASYRYSGVPSRFSGSGSG<br>TDFTLTISSLQPEDFATYY<br>CHQYYTYPLFTFGQGTKLE<br>IKTTTPAPRPPTPAPTIAS<br>QPLSLRPEACRPAAGGAVH<br>TRGLDFACDFWVLVVVGGV<br>LACYSLLVTVAFIIFWVRS<br>KRSRLLHSDYMNMTPRRPG<br>PTRKHYQPYAPPRDFAAYR<br>SKRGRKKLLYIFKQPFMRP<br>VQTTQEEDGCSCRFPEEEE<br>GGCELRVKFSRSADAPAYK<br>QGQNQLYNELNLGRREEYD<br>VLDKRRGRDPEMGGKPRRK<br>NPQEGLYNELQKDKMAEAY<br>SEIGMKGERRRGKGHDGLY<br>QGLSTATKDTYDALHMQAL<br>PPR (SEQ ID NO: 52) | ATGGACATGAGGGTCCCCGCTCAGCTCCTGGGGCTCCTGCTACTCTGGCTC<br>CGAGGTGCCAGATGTCAGGTGCAGCTGGTGCAATCTGGGTCTGAGTTGAAG<br>AAGCCTGGGGCCTCAGTGAAGGTTTCCTGCAAGGCTTCTGGATACACCTTC<br>ACTGAGTTTGGAATGAACTGGGTGCGACAGGCCCCTGGACAAGGGCTTGAG<br>TGGATGGGATGGATAAACACCAAAACTGGAGAGGCAACATATGTTGAAGAG<br>TTTAAGGGACGGTTTGTCTTCTCCTTGGACACCTCTGTCAGCACGGCATAT<br>CTGCAGATCAGCAGCCTAAAGGCTGAAGACACTGCCGTGTATTACTGTGCG<br>AGATGGGACTTCGCTTATTACGTGGAGGCTATGGACTACTGGGGCCAAGGG<br>ACCACGGTGACCGTGTCATCCGGCGGAGGTGGAAGCGGAGGGGGAGGATCT<br>GGCGGCGGAGGAAGCGGAGGCGATATCCAGATGACCCAGTCTCCATCCTCC<br>CTGTCTGCATCTGTGGGAGACAGAGTCACCATCACTTGCAAGGCCAGTCAG<br>AATGTGGGTACTAATGTTGCCTGGTATCAGCAGAAACCAGGGAAAGCACCT<br>AAGCTCCTGATCTATTCGGCATCCTACCGCTACAGTGGAGTCCCATCAAGG<br>TTCAGTGGCAGTGGATCTGGGACAGATTTCACTCTCACCATCAGCAGTCTG<br>CAACCTGAAGATTTCGCAACTTACTACTGTCACCAATATTACACCTATCCT<br>CTATTCACGTTTGGCCAGGGCACCAAGCTCGAGATCAAGACAACGACGCCA<br>GCTCCCCGCCCGCCAACCCCTGCACCTACGATTGCATCACAACCGCTGTCC<br>TGCGGCCTGAAGCTTGTCGCCCAGCCGCAGGTGGCGCCGTACATACACGGG<br>GGCTGGATTTTGCCTGTGATTTCTGGGTGCTGGTCGTTGTGGGCGGCGTGC<br>TGGCCTGCTACAGCCTGCTGGTGACAGTGGCCTTCATCATCTTTTGGGTGA<br>GGAGCAAGCGGAGTCGACTGCTGCACAGCGACTACATGAACATGACCCCCC<br>GGAGGCCTGGCCCCACCCGGAAGCACTACCAGCCCTACGCCCCTCCCAGGG<br>ATTTCGCCGCCTACCGGAGCAAACGGGGCAGAAAGAAACTCCTGTATATAT<br>TCAAACAACCATTTATGAGGCCAGTACAAACTACTCAAGAGGAAGATGGCT<br>GTAGCTGCCGATTTCCAGAAGAAGAAGAAGGAGGATGTGAACTGAGAGTGA<br>AGTTCAGCAGGAGCGCAGACGCCCCCGCGTACAAGCAGGGCCAGAACCAGC<br>TCTATAACGAGCTCAATCTAGGACGAAGAGAGGAGTACGATGTTTTGGACA<br>AGCGTAGAGGCCGGGACCCTGAGATGGGGGGAAAGCCGAGAAGGAAGAACC<br>CTCAGGAAGGCCTGTACAATGAACTGCAGAAAGATAAGATGGCGGAGGCCT<br>ACAGTGAGATTGGGATGAAAGGCGAGCGCCGGAGGGGCAAGGGGCACGATG<br>GCCTTTACCAGGGACTCAGTACAGCCACCAAGGACACCTACGACGCCCTTC<br>ACATGCAGGCCCTGCCCCCTCGCTAA (SEQ ID NO: 219) |

TABLE 3-continued

Exemplary CARs with scFv that target CEA

| Protein Sequence | Nucleotide Sequence |
|---|---|
| MDMRVPAQLLGLLLLWLRG | ATGGACATGAGGGTCCCCGCTCAGCTCCTGGGGCTCCTGCTACTCTGGCTC |
| ARCQVQLVQSGAEVKKPGA | CGAGGTGCCAGATGTCAGGTGCAGCTGGTGCAGTCTGGCGCCGAAGTGAAG |
| SVKSCKASGYTFTEFGMNW | AAACCTGGAGCTAGTGTGAAGGTGTCCTGCAAGGCCAGCGGCTACACCTTC |
| VRQAPGQGLEWMGWINTKT | ACCGAGTTCGGCATGAACTGGGTCCGACAGGCTCCAGGCCAGGGCCTCGAA |
| GEATYVEEFKGRVTFTTDT | TGGATGGGCTGGATCAACACCAAGACCGGCGAGGCCACCTACGTGGAAGAG |
| STSTAYMELRSLRSDDTAV | TTCAAGGGCAGAGTGACTTCACCACGGACACCAGCACCAGCACCGCCTACA |
| YYCARWDFAYYVEAMDYWG | TGGAACTGCGGAGCCTGAGAAGCGACGACACCGCCGTGTACTACTGCGCCA |
| QGTTVTVSSGGGGSGGGGS | GATGGGACTTCGCTTATTACGTGGAAGCCATGGACTACTGGGGCCAGGGCA |
| GGGGSGGDIQMTQSPSSLS | CCACCGTGACCGTGTCTAGCGGCGGAGGTGGAAGCGGAGGGGGAGGATCTG |
| ASVGDRVTITCKASAAVGT | GCGGCGGAGGAAGCGGAGGCGATATCCAGATGACCCAGTCTCCATCCTCCC |
| YVAWYQQKPGKAPKLLIYS | TGTCTGCATCTGTGGGAGACAGAGTCACCATCACTTGCAAGGCCAGTGCGG |
| ASYRKRGVPSRFSGSGSGT | CTGTGGGTACGTATGTTGCGTGGTATCAGCAGAAACCAGGGAAAGCACCTA |
| DFTLTISSLQPEDFATYYC | AGCTCCTGATCTATTCGGCATCCTACCGCAAAAGGGGAGTCCCATCAAGGT |
| HQYYTYPLFTFGQGTKLEI | TCAGTGGCAGTGGATCTGGGACAGATTTCACTCTCACCATCAGCAGTCTGC |
| KRTTTPAPRPPTPAPTIA | AACCTGAAGATTTCGCAACTTACTACTGTCACCAATATTACACCTATCCTC |
| SQPLSLRPEACRPAAGGAV | TATTCACGTTTGGCCAGGGCACCAAGCTCGAGATCAAGCGTACGACAACGA |
| HTRGLDFACDFWVLVVVGG | CGCCAGCTCCCCGCCCGCCAACCCCTGCACCTACGATTGCATCACAACCGC |
| VLACYSLLVTVAFIIFWVR | TGTCCTGCGGCCTGAAGCTTGTCGCCCAGCCGCAGGTGGCGCCGTACATAC |
| SKRSRLLHSDYMNMTPRRP | ACGGGGGCTGGATTTTGCCTGTGATTTCTGGGTGCTGGTCGTTGTGGGCGG |
| GPTRKHYQPYAPPRDFAAY | CGTGCTGGCCTGCTACAGCCTGCTGGTGACAGTGGCCTTCATCATCTTTTG |
| RSKRGRKKLLYIFKQPFMR | GGTGAGGAGCAAGCGGAGTCGACTGCTGCACAGCGACTACATGAACATGAC |
| PVQTTQEEDGCSCRFPEEE | CCCCCGGAGGCCTGGCCCCACCCGGAAGCACTACCAGCCCTACGCCCCTCC |
| EGGCELRVKFSRSADAPAY | CAGGGATTTCGCCGCCTACCGGAGCAAACGGGGCAGAAAGAAACTCCTGTA |
| KQGQNQLYNELNLGRREEY | TATATTCAAACAACCATTTATGAGGCCAGTACAAACTACTCAAGAGGAAGA |
| DVLDKRRGRDPEMGGKPRR | TGGCTGTAGCTGCCGATTTCCAGAAGAAGAAGAAGGAGGATGTGAACTGAG |
| KNPQEGLYNELQKDKMAEA | AGTGAAGTTCAGCAGGAGCGCAGACGCCCCCGCGTACAAGCAGGGCCAGAA |
| YSEIGMKGERRRGKGHDGL | CCAGCTCTATAACGAGCTCAATCTAGGACGAAGAGAGGAGTACGATGTTTT |
| YQGLSTATKDTYDALHMQA | GGACAAGCGTAGAGGCCGGGACCCTGAGATGGGGGGAAAGCCGAGAAGGAA |
| LPPR (SEQ ID NO: 53) | GAACCCTCAGGAAGGCCTGTACAATGAACTGCAGAAAGATAAGATGGCGGA |
| | GGCCTACAGTGAGATTGGGATGAAAGGCGAGCGCCGGAGGGGCAAGGGGCA |
| | CGATGGCCTTTACCAGGGACTCAGTACAGCCACCAAGGACACCTACGACGC |
| | CCTTCACATGCAGGCCCTGCCCCCTCGCTAG (SEQ ID NO: 220) |
| | |
| MDMRVPAQLLGLLLLWLRG | ATGGACATGAGGGTCCCCGCTCAGCTCCTGGGGCTCCTGCTACTCTGGCTC |
| ARCQVQLVQSGSELKKPGA | CGAGGTGCCAGATGTCAGGTGCAGCTGGTGCAATCTGGGTCTGAGTTGAAG |
| SVKVSCKASGYTFTEFGMN | AAGCCTGGGGCCTCAGTGAAGGTTTCCTGCAAGGCTTCTGGATACACCTTC |
| WVRQAPGQGLEWMGWINTK | ACTGAGTTTGGAATGAACTGGGTGCGACAGGCCCCTGGACAAGGGCTTGAG |
| TGEATYVEEFKGRFVFSLD | TGGATGGGATGGATAAACACCAAAACTGGAGAGGCAACATATGTTGAAGAG |
| TSVSTAYLQISSLKAEDTA | TTTAAGGGACGGTTTGTCTTCTCCTTGGACACCTCTGTCAGCACGGCATAT |
| VYYCARWDFAHYFQTMDYW | CTGCAGATCAGCAGCCTAAAGGCTGAAGACACTGCCGTGTATTACTGTGCG |
| GQGTTVTVSSGGGGSGGGG | AGATGGGACTTTGCTCATTACTTTCAGACTATGGACTACTGGGGCCAAGGG |
| SGGGGSGGDIQMTQSPSSL | ACCACGGTCACCGTCTCCTCAGGCGGAGGTGGAAGCGGAGGGGGAGGATCT |
| SASVGDRVTITCKASAAVG | GGCGGCGGAGGAAGCGGAGGCGATATCCAGATGACCCAGTCTCCATCCTCC |
| TYVAWYQQKPGKAPKLLIY | CTGTCTGCATCTGTGGGAGACAGAGTCACCATCACTTGCAAGGCCAGTGCG |
| SASYRKRGVPSRFSGSGSG | GCTGTGGGTACGTATGTTGCGTGGTATCAGCAGAAACCAGGGAAAGCACCT |
| TDFTLTISSLQPEDFATYY | AAGCTCCTGATCTATTCGGCATCCTACCGCAAAAGGGGAGTCCCATCAAGG |
| CHQYYTYPLFTFGQGTKLE | TTCAGTGGCAGTGGATCTGGGACAGATTTCACTCTCACCATCAGCAGTCTG |
| IKRTTTPAPRPPTPAPTIA | CAACCTGAAGATTTCGCAACTTACTACTGTCACCAATATTACACCTATCCT |
| SQPLSLRPEACRPAAGGAV | CTATTCACGTTTGGCCAGGGCACCAAGCTCGAGATCAAGCGTACAACGACG |
| HTRGLDFACDFWVLVVVGG | CCAGCTCCCCGCCCGCCAACCCCTGCACCTACGATTGCATCACAACCGCTG |
| VLACYSLLVTVAFIIFWVR | TCCCTGCGGCCTGAAGCTTGTCGCCCAGCCGCAGGTGGCGCCGTACATACA |
| SKRSRLLHSDYMNMTPRRP | CGGGGGCTGGATTTTGCCTGTGATTTCTGGGTGCTGGTCGTTGTGGGCGGC |
| GPTRKHYQPYAPPRDFAAY | GTGCTGGCCTGCTACAGCCTGCTGGTGACAGTGGCCTTCATCATCTTTTGG |
| RSKRGRKKLLYIFKQPFMR | GTGAGGAGCAAGCGGAGTCGACTGCTGCACAGCGACTACATGAACATGACC |
| PVQTTQEEDGCSCRFPEEE | CCCCGGAGGCCTGGCCCCACCCGGAAGCACTACCAGCCCTACGCCCCTCCC |
| EGGCELRVKFSRSADAPAY | AGGGATTTCGCCGCCTACCGGAGCAAACGGGGCAGAAAGAAACTCCTGTAT |
| KQGQNQLYNELNLGRREEY | ATATTCAAACAACCATTTATGAGGCCAGTACAAACTACTCAAGAGGAAGAT |
| DVLDKRRGRDPEMGGKPRR | GGCTGTAGCTGCCGATTTCCAGAAGAAGAAGAAGGAGGATGTGAACTGAGA |
| KNPQEGLYNELQKDKMAEA | GTGAAGTTCAGCAGGAGCGCAGACGCCCCCGCGTACAAGCAGGGCCAGAAC |
| YSEIGMKGERRRGKGHDGL | CAGCTCTATAACGAGCTCAATCTAGGACGAAGAGAGGAGTACGATGTTTTG |
| YQGLSTATKDTYDALHMQA | GACAAGCGTAGAGGCCGGGACCCTGAGATGGGGGGAAAGCCGAGAAGGAAG |
| LPPR (SEQ ID NO: 54) | AACCCTCAGGAAGGCCTGTACAATGAACTGCAGAAAGATAAGATGGCGGAG |
| | GCCTACAGTGAGATTGGGATGAAAGGCGAGCGCCGGAGGGGCAAGGGGCAC |
| | GATGGCCTTTACCAGGGACTCAGTACAGCCACCAAGGACACCTACGACGCC |
| | CTTCACATGCAGGCCCTGCCCCCTCGCTAG (SEQ ID NO: 221) |

In some embodiments, a CEA scFv comprises a CDR-H1 of EFGMN (SEQ ID NO: 55), a CDR-H2 of WINTKTGEATYVEEFKG (SEQ ID NO: 56), a CDR-H3 of WDFAYYVEAMDY (SEQ ID NO: 57) or WDFAHYFQTMDY (SEQ ID NO: 58), a CDR-L1 of KASQNVGTNVA (SEQ ID NO: 59) or KASAAVGTYVA (SEQ ID NO: 60), a CDR-L2 of SASYRYS (SEQ ID NO: 61) or SASYRKR (SEQ ID NO: 62), and a CDR-L3 of HQYYTYPLFT (SEQ ID NO: 63) or sequences having at least 85% or at least 95% identity thereto. In some embodiments, a CEA scFv comprises a CDR-H1 of EFGMN (SEQ ID NO: 55), a CDR-H2 of WINTKTGEATYVEEFKG (SEQ ID NO: 56), a CDR-H3 of WDFAYYVEAMDY (SEQ ID NO: 57) or WDFAHYFQTMDY (SEQ ID NO: 58), a CDR-L1 of KASQNVGTNVA (SEQ ID NO: 59) or KASAAVGTYVA (SEQ ID NO: 60), a CDR-L2 of SASYRYS (SEQ ID NO: 61) or SASYRKR (SEQ ID NO: 62) and a CDR-L3 of HQYYTYPLFT (SEQ ID NO: 63). In some embodiments, a CEA scFv comprises a CDR-H1 of EFGMN (SEQ ID NO: 55), a CDR-H2 of WINTKTGEATYVEEFKG (SEQ ID NO: 56), a CDR-H3 of WDFAYYVEAMDY (SEQ ID NO: 57), a CDR-L1 of KASQNVGTNVA (SEQ ID NO: 59), a CDR-L2 of SASYRYS (SEQ ID NO: 61) and a CDR-L3 of HQYYTYPLFT (SEQ ID NO: 63). In some embodiments, a CEA scFv comprises a CDR-H1 of EFGMN (SEQ ID NO: 55), a CDR-H2 of WINTKTGEATYVEEFKG (SEQ ID NO: 56), a CDR-H3 of WDFAYYVEAMDY (SEQ ID NO: 57), a CDR-L1 of KASAAVGTYVA (SEQ ID NO: 60), a CDR-L2 of SASYRKR (SEQ ID NO: 62), and a CDR-L3 of HQYYTYPLFT (SEQ ID NO: 63). In some embodiments, a CEA scFv comprises a CDR-H1 of EFGMN (SEQ ID NO: 56), a CDR-H2 of WINTKTGEATYVEEFKG (SEQ ID NO: 56), a CDR-H3 of WDFAHYFQTMDY (SEQ ID NO: 58), a CDR-L1 of KASAAVGTYVA (SEQ ID NO: 60), a CDR-L2 of SASYRKR (SEQ ID NO: 62), and a CDR-L3 of HQYYTYPLFT (SEQ ID NO: 63).

In some embodiments, the extracellular ligand binding domain of the first receptor comprises a variable heavy (VH) portion comprising a set of heavy chain complementarity determining regions (HC-CDRs) selected from the group consisting of SEQ ID NOS: 55-58 and a variable light (VL) portion comprising a set of light chain complementarity determining regions selected from the group consisting of SEQ ID NOS: 59-63; or CDR sequences having at most 1, 2, or 3 substitutions, deletions, or insertions relative to SEQ ID NOS: 55-58 or SEQ ID NOS: 59-63. In some embodiments, the extracellular ligand binding domain of the first receptor comprises a variable heavy (VH) portion comprising a set of heavy chain complementarity determining regions (HC-CDRs) comprising SEQ ID NOS: 55-57 and a variable light (VL) portion comprising a set of light chain complementarity determining regions comprising SEQ ID NOS: 59, 61 and 63; or CDR sequences having at most 1, 2, or 3 substitutions, deletions, or insertions relative to SEQ ID NOS: 55-57 or SEQ ID NOS: 59, 61 and 63. In some embodiments, the extracellular ligand binding domain of the first receptor comprises a variable heavy (VH) portion comprising a set of heavy chain complementarity determining regions (HC-CDRs) comprising SEQ ID NOS: 55-57 and a variable light (VL) portion comprising a set of light chain complementarity determining regions comprising SEQ ID NOS: 59, 61 and 63.

Exemplary scFv that recognize CEA are shown in Table 4 below. Underlining indicates CDR sequences.

TABLE 4

Exemplary scFv that target CEA

| Protein sequence | DNA sequence |
|---|---|
| QVQLQQSGAELVRSGTSVK<br>LSCTASGFNIKDSYMHWLR<br>QGPEQGLEWIGWIDPENGD<br>TEYAPKFQGKATFTTDTSS<br>NTAYLQLSSLTSEDTAVYY<br>CNEGTPTGPYYFDYWGQGT<br>TVTVSSGGGGSGGGGSGGG<br>GSGGENVLTQSPAIMSASP<br>GEKVTITCSASSSVSYMHW<br>FQQKPGTSOKLWIYSTSNL<br>ASGVPARFSGSGSGTSYSL<br>TISRMEAEDAATYYCQQRS<br>SYPLTFGAGTKLELK<br>(SEQ ID NO: 64) | CAGGTCCAGCTGCAGCAGTCTGGGGCAGAGCTTGTGAGGTCAGGGACC<br>TCAGTCAAGTTGTCCTGCACAGCTTCTGGCTTCAACATTAAAGACTCC<br>TATATGCACTGGTTGAGGCAGGGGCCTGAACAGGGCCTGGAGTGGATT<br>GGATGGATTGATCCTGAGAATGGTGATACTGAATATGCCCCGAAGTTC<br>CAGGGCAAGGCCACTTTTACTACAGACACATCCTCCAACACAGCCTAC<br>CTGCAGCTCAGCAGCCTGACATCTGAGGACACTGCCGTCTATTACTGT<br>AATGAAGGGACACCGACAGGGCCATACTATTTTGACTACTGGGGTCAA<br>GGAACCACAGTCACCGTGTCCTCAGGCGGAGGTGGAAGCGGAGGGGGA<br>GGATCTGGCGGCGGAGGAAGCGGAGGCGAGAACGTTCTCACCCAGTCT<br>CCAGCAATCATGTCTGCATCTCCAGGGGAGAAGGTCACCATAACCTGC<br>AGTGCCAGCTCAAGTGTAAGTTACATGCACTGGTTCCAGCAGAAGCCA<br>GGCACTTCTCCCAAACTCTGGATTTATAGCACATCCAACCTGGCTTCT<br>GGAGTCCCTGCTCGCTTCAGTGGCAGTGGATCTGGGACCTCTTACTCT<br>CTCACAATCAGCCGAATGGAGGCTGAAGATGCTGCCACTTATTACTGC<br>CAGCAAAGGAGTAGTTACCCGCTCACGTTCGGTGCTGGGACCAAGCTG<br>GAGCTGAAA (SEQ ID NO: 222) |
| QVQLVQSGAEVKKPGASVK<br>VSCKASGFNIKDSYMHWVR<br>QAPGQGLEWMGWIDPENGD<br>TEYAPKFQGRVTMTTDTST<br>STAYMELRSLRSDDTAVYY<br>CNEGTPTGPYYFDYWGQGT<br>TVTVSSGGGGSGGGGSGGG<br>GSGGEIVLTQSPATLSLSP<br>GERATLSCSASSSVSYMHW<br>YQQKPGLAPRLLIYSTSNL<br>ASGIPDRFSGSGSGTDFTL<br>TISRLEPEDFAVYYCQQRS<br>SYPLTFGQGTKLEIK<br>(SEQ ID NO: 65) | CAGGTCCAGCTGGTGCAGTCTGGGGCAGAGGTGAAGAAACCAGGGGCC<br>TCAGTCAAGGTGTCCTGCAAAGCTTCTGGCTTCAACATTAAAGACTCC<br>TATATGCACTGGGTGAGGCAGGCGCCTGGACAGGGCCTGGAGTGGATG<br>GGATGGATTGATCCTGAGAATGGTGATACTGAATATGCCCCGAAGTTC<br>CAGGGCAGGGTCACTATGACTACAGACACATCCACCTCCACAGCCTAC<br>ATGGAGCTCAGGAGCCTGAGATCTGACGACACTGCCGTCTATTACTGT<br>AATGAAGGGACACCGACAGGGCCATACTATTTTGACTACTGGGGTCAA<br>GGAACCACAGTCACCGTGTCTCAGGCGGAGGTGGAAGCGGAGGGGGAG<br>GATCTGGCGGCGGAGGAAGCGGAGGCGAGATCGTTCTCACCCAGTCTC<br>CAGCAACCTTGTCTCTGTCTCCAGGGGAGAGGGCCACCCTAAGCTGCA<br>GTGCCAGCTCAAGTGTAAGTTACATGCACTGGTACCAGCAGAAGCCAG<br>GCCTTGCTCCCAGACTCCTGATTTATAGCACATCCAACCTGGCTTCTG<br>GAATCCCTGATCGCTTCAGTGGCAGTGGATCTGGGACCGATTTCACTC<br>TCACAATCAGCCGACTGGAGCCTGAAGATTTCGCCGTTTATTACTGCC<br>AGCAAAGGAGTAGTTACCCGCTCACGTTCGGTCAGGGGACCAAGCTGG<br>AGATCAAA (SEQ IN NO: 223) |
| EVQLAESGGGLVQPGGSLR<br>LSCAASGFTFSSDAMSWVR<br>QAPGKGLEWVSAISGSGGS<br>TYYADSVKGRFTISRDNSK<br>NTLYLQMNSLRAEDTAVYY<br>CAKSNEFLFDYWGQGTLVT<br>VSSGGGGSGGGGSGGGGSG<br>GSSELTQDPAVSVALGQTV<br>RITCQGDSLRSSYASWYRQ | GAGGTGCAGCTGGCGGAGTCTGGGGGAGGCTTGGTACAGCCTGGGGGG<br>TCCCTGAGACTCTCCTGTGCAGCCTCTGGATTCACCTTTAGCAGCGAT<br>GCCATGAGCTGGGTCCGCCAGGCTCCAGGGAAGGGGCTGGAGTGGGTC<br>TCAGCTATTAGTGGTAGTGGTGGTAGCACATACTACGCAGACTCCGTG<br>AAGGGCCGGTTCACCATCTCCAGAGACAATTCCAAGAACACGCTGTAT<br>CTGCAAATGAACAGCCTGAGAGCCGAGGACACGGCCGTGTATTACTGT<br>GCAAAGTCTAATGAGTTTCTTTTTGACTACTGGGGCCAAGGTACCCTG<br>GTCACCGTGTCGAGTGGCGGAGGTGGAAGCGGAGGGGGAGGATCTGGC<br>GGCGGAGGAAGCGGAGGCTCTTCTGAGCTGACTCAGGACCCTGCTGTG |

TABLE 4-continued

Exemplary scFv that target CEA

| Protein sequence | DNA sequence |
|---|---|
| RPGQAPVLVIYGKNNRPSG<br>IPDRFSGSSSGNTASLTIT<br>GAQAEDEADYYWNSSYAWL<br>PYVVFGGGTKLTVLG<br>(SEQ ID NO: 66) | TCTGTGGCCTTGGGACAGACAGTCAGGATCACATGCCAAGGAGACAGC<br>CTCAGAAGCTCTTATGCAAGCTGGTACCGGCAGAGGCCAGGACAGGCC<br>CCTGTACTTGTCATCTATGGTAAAAACAACCGGCCCTCAGGGATCCCA<br>GACCGATTCTCTGGCTCCAGCTCAGGAAACACAGCTTCCTTGACCATC<br>ACTGGGGCTCAGGCGGAAGATGAGGCTGACTATTACTGGAACTCCAGC<br>TACGCTTGGCTGCCCTACGTGGTATTCGGCGGAGGGACCAAGCTGACC<br>GTCCTAGGT (SEQ ID NO: 224) |
| QVQLEQSGAGVVKPGASVK<br>LSCKASGFNIKDSYMHWLR<br>QGPGQRLEWIGWIDPENGD<br>TEYAPKFQGKATFTTDTSA<br>NTAYLGLSSLRPEDTAVYY<br>CNEGTPTGPYYFDYWGQGT<br>LVTVSSGGGGSGGGGSGGG<br>GSGGENVLTQSPSSMSVSV<br>GDRVNIACSASSSVPYMHW<br>LQQKPGKSPKLLIYLTSNL<br>ASGVPSRFSGSGSGTDYSL<br>TISSVQPEDAATYYCQQRS<br>SYPLTFGGGTKLEIK<br>(SEQ ID NO: 67) | CAGGTCCAGCTGGAGCAGTCTGGGGCAGGGGTTGTGAAGCCAGGGGCC<br>TCAGTCAAGTTGTCCTGCAAAGCTTCTGGCTTCAACATTAAAGACTCC<br>TATATGCACTGGTTGAGGCAGGGGCCTGGACAGCGCCTGGAGTGGATT<br>GGATGGATTGATCCTGAGAATGGTGATACTGAATATGCCCCGAAGTTC<br>CAGGGCAAGGCCACTTTTACTACAGACACATCCGCCAACACAGCCTAC<br>CTGGGGCTCAGCAGCCTGAGACCTGAGGACACTGCCGTCTATTACTGT<br>AATGAAGGGACACCGACAGGGCCATACTATTTTGACTACTGGGGTCAA<br>GGAACCCTAGTCACCGTGTCCTCAGGCGGAGGTGGAAGCGGAGGGGGA<br>GGATCTGGCGGCGGAGGAAGCGGAGGCGAGAACGTTCTCACCCAGTCT<br>CCAAGCTCTATGTCTGTATCTGTCGGGGACAGGGTCAACATCGCCTGC<br>AGTGCCAGCTCAAGTGTACCTTACATGCACTGGCTCCAGCAGAAGCCA<br>GGCAAATCTCCCAAACTCCTGATTTATCTCACATCCAACCTGGCTTCT<br>GGAGTCCCTAGCCGCTTCAGTGGCAGTGGATCTGGGACCGATTACTCT<br>CTCACAATCAGCTCAGTGCAGCCTGAAGATGCTGCCACTTATTACTGC<br>CAGCAAAGGAGTAGTTACCCGCTCACGTTCGGTGGTGGGACCAAGCTG<br>GAGATCAAA (SEQ ID NO: 225) |
| QVQLVQSGSELKKPGASVK<br>VSCKASGYTFTEFGMNWVR<br>QAPGQGLEWMGWINTKTGE<br>ATYVEEFKGRFVFSLDTSV<br>STAYLQISSLKAEDTAVYY<br>CARWDFAYYVEAMDYWGQG<br>TTVTVSSGGGGSGGGGSGG<br>GGSGGDIQMTQSPSSLSAS<br>VGDRVTITCKASQNVGTNV<br>AWYQQKPGKAPKLLIYSAS<br>YRYSGVPSRFSGSGSGTDF<br>TLTISSLQPEDFATYYCHQ<br>YYTYPLFTFGQGTKLEIK<br>(SEQ ID NO: 68) | CAGGTGCAGCTGGTGCAATCTGGGTCTGAGTTGAAGAAGCCTGGGGCC<br>TCAGTGAAGGTTTCCTGCAAGGCTTCTGGATACACCTTCACTGAGTTT<br>GGAATGAACTGGGTGCGACAGGCCCCTGGACAAGGGCTTGAGTGGATG<br>GGATGGATAAACACCAAAACTGGAGAGGCAACATATGTTGAAGAGTTT<br>AAGGGACGGTTTGTCTTCTCCTTGGACACCTCTGTCAGCACGGCATAT<br>CTGCAGATCAGCAGCCTAAAGGCTGAAGACACTGCCGTGTATTACTGT<br>GCGAGATGGGACTTCGCTTATTACGTGGAGGCTATGGACTACTGGGGC<br>CAAGGGACCACGGTGACCGTGTCATCCGGCGGAGGTGGAAGCGGAGGG<br>GGAGGATCTGGCGGCGGAGGAAGCGGAGGCGATATCCAGATGACCCAG<br>TCTCCATCCTCCCTGTCTGCATCTGTGGGAGACAGAGTCACCATCACT<br>TGCAAGGCCAGTCAGAATGTGGGTACTAATGTTGCCTGGTATCAGCAG<br>AAACCAGGGAAAGCACCTAAGCTCCTGATCTATTCGGCATCCTACCGC<br>TACAGTGGAGTCCCATCAAGGTTCAGTGGCAGTGGATCTGGGACAGAT<br>TTCACTCTCACCATCAGCAGTCTGCAACCTGAAGATTTCGCAACTTAC<br>TACTGTCACCAATATTACACCTATCCTCTATTCACGTTTGGCCAGGGC<br>ACCAAGCTCGAGATCAAG (SEQ ID NO: 226) |
| QVQLVQSGAEVKKPGASVK<br>VSCKASGYTKTEFGMNWVR<br>QAPGQGLEWMGWINTKTGE<br>ATYVEEFKGRVTFTTDTST<br>STAYMELRSLRSDDTAVYY<br>CARWDFAYYVEAMDYWGQG<br>TTVTVSSGGGGSGGGGSGG<br>GGSGGDIQMTQSPSSLSAS<br>VGDRVTITCKASAAVGTYV<br>AWYQQKPGKAPKLLIYSAS<br>YRKRGVPSRFSGSGSGTDF<br>TLTISSLQPEDFATYYCHQ<br>YYTYPLFTFGQGTKLEIK<br>(SEQ ID NO: 69) | CAGGTGCAGCTGGTGCAGTCTGGCGCCGAAGTGAAGAAACCTGGAGCT<br>AGTGTGAAGGTGTCCTGCAAGGCCAGCGGCTACACCTTCACCGAGTTC<br>GGCATGAACTGGGTCCGACAGGCTCCAGGCCAGGGCCTCGAATGGATG<br>GGCTGGATCAACACCAAGACCGGCGAGGCCACCTACGTGGAAGAGTTC<br>AAGGGCAGAGTGACCTTCACCACGGACACCAGCACCAGCACCGCCTAC<br>ATGGAACTGCGGAGCCTGAGAAGCGACGACACCGCCGTGTACTACTGC<br>GCRCAGATGGGACTTCGCTTATTACGTGGAAGCCATGGACTACTGGGG<br>CCAGGGCACCACCGTGACCGTGTCTAGCGGCGGAGGTGGAAGCGGAGG<br>GGGAGGATCTGGCGGCGGAGGAAGCGGAGGCGATATCCAGATGACCCA<br>GTCTCCATCCTCCCTGTCTGCATCTGTGGGAGACAGAGTCACCATCAC<br>TTGCAAGGCCAGTGCGGCTGTGGGTACGTATGTTGCGTGGTATCAGCA<br>GAAACCAGGGAAAGCACCTAAGCTCCTGATCTATTCGGCATCCTACCG<br>CAAAAGGGGAGTCCCATCAAGGTTCAGTGGCAGTGGATCTGGGACAGA<br>TTTCACTCTCACCATCAGCAGTCTGCAACCTGAAGATTTCGCAACTTA<br>CTACTGTCACCAATATTACACCTATCCTCTATTCACGTTTGGCCAGGG<br>CACCAAGCTCGAGATCAAG (SEQ ID NO: 227) |
| QVQLVQSGSELKKPGASVK<br>VSCKASGYTFTEFGMNWVR<br>QAPGQGLEWMGWINTKTGE<br>ATYVEEFKGRFVFSLDTSV<br>STAYLQISSLKAEDTAVYY<br>CARWDFAHYFQTMDYWGQG<br>TTVTVSSGGGGSGGGGSGG<br>GGSGGDIQMTQSPSSLSAS<br>VGDRVTITCKASAAVGTYV<br>AWYQQKPGKAPKLLIYSAS<br>YRKRGVPSRFSGSGSGTDF<br>TLTISSLQPEDFATYYCHQ<br>YYTYPLFTFGQGTKLEIK<br>(SEQ ID NO: 70) | CAGGTGCAGCTGGTGCAATCTGGGTCTGAGTTGAAGAAGCCTGGGGCC<br>TCAGTGAAGGTTTCCTGCAAGGCTTCTGGATACACCTTCACTGAGTTT<br>GGAATGAACTGGGTGCGACAGGCCCCTGGACAAGGGCTTGAGTGGATG<br>GGATGGATAAACACCAAAACTGGAGAGGCAACATATGTTGAAGAGTTT<br>AAGGGACGGTTTGTCTTCTCCTTGGACACCTCTGTCAGCACGGCATAT<br>CTGCAGATCAGCAGCCTAAAGGCTGAAGACACTGCCGTGTATTACTGT<br>GCGAGATGGGACTTTGCTCATTACTTTCAGACTATGGACTACTGGGGC<br>CAAGGGACCACGGTCACCGTCTCCTCAGGCGGAGGTGGAAGCGGAGGG<br>GGAGGATCTGGCGGCGGAGGAAGCGGAGGCGATATCCAGATGACCCAG<br>TCTCCATCCTCCCTGTCTGCATCTGTGGGAGACAGAGTCACCATCACT<br>TGCAAGGCCAGTGCGGCTGTGGGTACGTATGTTGCGTGGTATCAGCAG<br>AAACCAGGGAAAGCACCTAAGCTCCTGATCTATTCGGCATCCTACCGC<br>AAAAGGGGAGTCCCATCAAGGTTCAGTGGCAGTGGATCTGGGACAGAT<br>TTCACTCTCACCATCAGCAGTCTGCAACCTGAAGATTTCGCAACTTAC<br>TACTGTCACCAATATTACACCTATCCTCTATTCACGTTTGGCCAGGGC<br>ACCAAGCTCGAGATCAAG (SEQ ID NO: 228) |

In some embodiments, a CEA scFv comprises a sequence selected from the group consisting of SEQ ID NOs: 64-70, or a sequence having at least 85%, at least 90%, at least 95%, at least 97% or at least 99% identity thereto. In some embodiments, a CEA scFv comprises, or consists essentially of, a sequence selected from the group consisting of SEQ ID NOs: 64-70. Further exemplary anti-CEA antibody sequences are provided in Stewart et al. Cancer Immunol. Immunother. 47:299-306 (1999); WO 1999/043817 A1; US 2002/0018750 A1; US 2011/0104148 A1; US 2016/0108131 A1; US20160075795A1; US 2019/0185583 A1; US 2020/0123270 A1; WO 2020/259550 A1; WO 2021/053587 A1; WO 2021/110647 A1; the contents of which are incorporated by reference herein for the purpose of providing anti-CEA VH, VL, scFv, and/or ligand binding domain sequences.

In some embodiments, the extracellular ligand binding domain of the first receptor comprises a variable heavy (VH) portion comprising SEQ ID NO: 144 or a sequence having at least 85%, at least 90%, at least 95%, at least 97%, or at least 99% identity thereto, and a variable light (VL) portion comprising SEQ ID NO: 148 or a sequence having 85%, at least 90%, at least 95%, at least 97%, or at least 99% identity thereto. In some embodiments, the extracellular ligand binding domain of the first receptor comprises a variable heavy (VH) portion comprising SEQ ID NO: 144, and a variable light (VL) portion comprising SEQ ID NO: 148. In some embodiments, the extracellular ligand binding domain of the first receptor further comprises a linker between VH and VL portions.

In some embodiments, the extracellular ligand binding domain of the first receptor comprises a sequence selected from the group consisting of SEQ ID NOS: 66-70, or a sequence having at least 85%, at least 90%, at least 95%, at least 97%, or at least 99% identity thereto. In some embodiments, the extracellular ligand binding domain of the first receptor comprises an scFv sequence of SEQ ID NO: 68; or a sequence having at least 85%, at least 90%, at least 95%, at least 97% or at least 99% identity thereto. In some embodiments, the extracellular ligand binding domain of the first receptor comprises an scFv sequence of SEQ ID NO: 68.

In some embodiments, one or more (e.g., 1, 2, 3, 4, 5, or 6) amino acid residues in a CDR of the antigen binding domains provided herein are substituted with another amino acid. The substitution may be "conservative" in the sense of being a substitution within the same family of amino acids. The naturally occurring amino acids may be divided into the following four families and conservative substitutions will take place within those families: (1) amino acids with basic side chains: lysine, arginine, histidine; (2) amino acids with acidic side chains: aspartic acid, glutamic acid; (3) amino acids with uncharged polar side chains: asparagine, glutamine, serine, threonine, tyrosine; and (4) amino acids with nonpolar side chains: glycine, alanine, valine, leucine, isoleucine, proline, phenylalanine, methionine, tryptophan, cysteine. By varying the amino acid sequence of the CDRs of an antibody by addition, deletion or substitution of amino acids, various effects such as increased binding affinity for the target antigen may be obtained.

Chimeric Antigen Receptors (CARs)

The disclosure provides a first, activator receptor and immune cells comprising same. In some embodiments, the first receptor is a chimeric antigen receptor.

The term "chimeric antigen receptors (CARs)" as used herein, may refer to artificial receptors derived from T-cell receptors and encompasses engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. Exemplary CARs comprise an intracellular activation domain, a transmembrane domain, and an extracellular domain comprising a tumor associated antigen binding region. In some embodiments, CARs further comprise a hinge domain. In particular aspects, CARs comprise fusions of single-chain variable fragments (scFv) derived from monoclonal antibodies, fused to a CD3 transmembrane domain and endodomain. The specificity of other CAR designs may be derived from ligands of receptors (e.g., peptides). In certain cases, CARs comprise domains for additional co-stimulatory signaling, such as CD3, 4-1BB, FcR, CD27, CD28, CD137, DAP10, and/or OX40. In some cases, molecules can be co-expressed with the CAR, including co-stimulatory molecules, reporter genes for imaging, gene products that conditionally ablate the T cells upon addition of a pro-drug, homing receptors, cytokines, and cytokine receptors.

In some embodiments, the extracellular ligand binding domain of the first receptor is fused to the extracellular domain of a CAR.

In some embodiments, the CARs of the present disclosure comprise an extracellular hinge region. Incorporation of a hinge region can affect cytokine production from CAR-T cells and improve expansion of CAR-T cells in vivo. Exemplary hinges can be isolated or derived from IgD and CD8 domains, for example IgG1. In some embodiments, the hinge is isolated or derived from CD8a or CD28.

In some embodiments, the hinge is isolated or derived from CD8a or CD28. In some embodiments, the CD8a hinge comprises an amino acid sequence having at least 80% identity, at least 90% identity, at least 95% identity, at least 99% identity or is identical to a sequence of TTTPAPRPPTPAPTIASQPLSLRPEACRPAAGGAVHTRGLDFACD (SEQ ID NO: 71). In some embodiments, the CD8a hinge comprises SEQ ID NO: 71. In some embodiments, the CD8a hinge consists essentially of SEQ ID NO: 71. In some embodiments, the CD8a hinge is encoded by a nucleotide sequence having at least 80% identity, at least 90% identity, at least 95% identity, at least 99% identity or is identical to a sequence of (SEQ ID NO: 72)
ACCACGACGCCAGCGCCGCGACCACCAACACCGGCGCCCACCATCGCGTC

GCAGCCCCTGTCCCTGCGCCCAGAGGCGTGCCGGCCAGCGGCGGGGGGCG

CAGTGCACACGAGGGGGCTGGACTTCGCCTGTGAT.

In some embodiments, the CD8α hinge is encoded by SEQ ID NO: 72.

In some embodiments, the CD8a hinge is encoded by a nucleotide sequence having at least 80% identity, at least 90% identity, at least 95% identity, at least 99% identity or is identical to a sequence of SEQ ID NO: 156. In some embodiments, the CD8a is encoded by SEQ ID NO: 156.

In some embodiments, the CD28 hinge comprises an amino acid sequence having at least 80% identity, at least 90% identity, at least 95% identity, at least 99% identity or is identical to a sequence of CTIEVMYPPPYLDNEKSNGTIIHVKGKHLCPSPLFPGPSKP (SEQ ID NO: 73).

In some embodiments, the CD28 hinge comprises or consists essentially of SEQ ID NO: 73. In some embodiments, the CD28 hinge is encoded by a nucleotide sequence having at least 80% identity, at least 90% identity, at least 95% identity, at least 99% identity or is identical to a sequence of (SEQ ID NO: 74)
TGTACCATTGAAGTTATGTATCCTCCTCCTTACCTAGACAATGAGAAGA

GCAATGGAACCATTATCCATGTGAAAGGGAAACACCTTTGTCCAAGTCC

CCTATTTCCCGGACCTTCTAAGCCC.

In some embodiments, the CD28 hinge is encoded by SEQ ID NO: 74.

The CARs of the present disclosure can be designed to comprise a transmembrane domain that is fused to the extracellular domain of the CAR. In some embodiments, the transmembrane domain that naturally is associated with one of the domains in the CAR is used. For example, a CAR comprising a CD28 co-stimulatory domain might also use a CD28 transmembrane domain. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions may be isolated or derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, or from an immunoglobulin such as IgG4. Alternatively the transmembrane domain may be synthetic, in which case it will comprise predominantly hydrophobic residues such as leucine and valine. In some embodiments, a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In some embodiments of the CARs of the disclosure, the CARs comprise a CD28 transmembrane domain. In some embodiments, the CD28 transmembrane domain comprises an amino acid sequence having at least 80% identity, at least 90% identity, at least 95% identity, at least 99% identity or is identical to a sequence of FWVLVVVGGVLACYSLLVTVAFIIFWV (SEQ ID NO: 75). In some embodiments, the CD28 transmembrane domain comprises or consists essentially of SEQ ID NO: 75. In some embodiments, the CD28 transmembrane domain is encoded by a nucleotide sequence having at least 80% identity, at least 90% identity, at least 95% identity, at least 99% identity or is identical to a sequence of (SEQ ID NO: 76)
TTCTGGGTGCTGGTCGTTGTGGGCGGCGTGCTGGCCTGCTACAGCC

TGCTGGTGACAGTGGCCTTCATCATCTTTTGGGTG.

In some embodiments, the CD28 transmembrane domain is encoded by SEQ ID NO: 76. In some embodiments, the CD28 transmembrane domain is encoded by a nucleotide sequence having at least 80% identity, at least 90% identity, at least 95% identity, at least 99% identity or is identical to a sequence of SEQ ID NO: 157. In some embodiments, the CD28 transmembrane domain is encoded by SEQ ID NO: 157.

In some embodiments of the CARs of the disclosure, the CARs comprise an IL-2Rbeta transmembrane domain. In some embodiments, the IL-2Rbeta transmembrane domain comprises an amino acid sequence having at least 80% identity, at least 90% identity, at least 95% identity, at least 99% identity or is identical to a sequence of IPWLGHLLVGLSGAFGFIILVYLLI (SEQ ID NO: 77). In some embodiments, the IL-2Rbeta transmembrane domain comprises or consists essentially of SEQ ID NO: 77. In some embodiments, the IL-2Rbeta transmembrane domain is encoded by a nucleotide sequence having at least 80% identity, at least 90% identity, at least 95% identity, at least 99% identity or is identical to a sequence of (SEQ ID NO: 78)
ATTCCGTGGC TCGGCCACCT CCTCGTGGGC CTCAGCGGGG

CTTTTGGCTT CATCATCTTA GTGTACTTGC TGATC.

In some embodiments, the IL-2Rbeta transmembrane domain is encoded by SEQ ID NO: 78.

The cytoplasmic domain or otherwise the intracellular signaling domain of the CARs of the instant disclosure is responsible for activation of at least one of the normal effector functions of the immune cell in which the CAR has been placed. The term "effector function" refers to a specialized function of a cell. Thus the term "intracellular signaling domain" refers to the portion of a protein which transduces the effector function signal and directs the cell to perform a specialized function. While usually the entire intracellular signaling domain can be employed, in many cases it is not necessary to use the entire domain. To the extent that a truncated portion of the intracellular signaling domain is used, such truncated portion may be used in place of the intact chain as long as it transduces the effector function signal. In some cases, multiple intracellular domains can be combined to achieve the desired functions of the CAR-T cells of the instant disclosure. The term intracellular signaling domain is thus meant to include any truncated portion of one or more intracellular signaling domains sufficient to transduce the effector function signal.

Examples of intracellular signaling domains for use in the CARs of the instant disclosure include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

Accordingly, the intracellular domain of CARs of the instant disclosure comprises at least one cytoplasmic activation domain. In some embodiments, the intracellular activation domain ensures that there is T-cell receptor (TCR) signaling necessary to activate the effector functions of the CAR T-cell. In some embodiments, the at least one cytoplasmic activation is a CD247 molecule (CD3) activation domain, a stimulatory killer immunoglobulin-like receptor (KIR) KIR2DS2 activation domain, or a DNAX-activating protein of 12 kDa (DAP12) activation domain.

In some embodiments, the CD3ζ activation domain comprises an amino acid sequence having at least 80% identity, at least 90% identity, at least 95% identity, at least 99% identity or is identical to a sequence of

```
                                        (SEQ ID NO: 79)
RVKFSRSADAPAYKQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR.
```

In some embodiments, the CD3 activation domain comprises or consists essentially of SEQ ID NO: 79. In some embodiments, the CD3ζ activation domain is encoded by a nucleotide sequence having at least 80% identity, at least 90% identity, at least 95% identity, at least 99% identity or is identical to a sequence of

```
                                        (SEQ ID NO: 80)
AGAGTGAAGTTCAGCAGGAGCGCAGACGCCCCCGCGTACAAGCAGGGCCA
GAACCAGCTCTATAACGAGCTCAATCTAGGACGAAGAGAGGAGTACGATG
TTTTGGACAAGCGTAGAGGCCGGGACCCTGAGATGGGGGGAAAGCCGAGA
AGGAAGAACCCTCAGGAAGGCCTGTACAATGAACTGCAGAAAGATAAGAT
GGCGGAGGCCTACAGTGAGATTGGGATGAAAGGCGAGCGCCGGAGGGGCA
AGGGGCACGATGGCCTTTACCAGGGACTCAGTACAGCCACCAAGGACACC
TACGACGCCCTTCACATGCAGGCCCTGCCCCCTCGC.
```

In some embodiments, the CD3ζ activation domain is encoded by SEQ ID NO: 80. In some embodiments, the CD3ζ activation domain is encoded by a nucleotide sequence having at least 80% identity, at least 90% identity, at least 95% identity, at least 99% identity or is identical to a sequence of SEQ ID NO: 163. In some embodiments, the CD3ζ activation domain is encoded by SEQ ID NO: 163.

It is known that signals generated through the TCR alone are often insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. In some embodiments, the ITAM contains a tyrosine separated from a leucine or an isoleucine by any two other amino acids (YxxL/I (SEQ ID NO: 983). In some embodiments, the cytoplasmic domain contains 1, 2, 3, 4 or 5 ITAMs. An exemplary ITAM containing cytoplasmic domain is the CD3ζ activation domain. Further examples of ITAM containing primary cytoplasmic signaling sequences that can be used in the CARs of the instant disclosure include those derived from TCRζ, FcRγ, FcRβ, CD3γ, CD3δ, CD3ε, CD3ζ, CD5, CD22, CD79a, CD79b, and CD66d.

In some embodiments, the CD3ζ activation domain comprising a single ITAM comprises an amino acid sequence having at least 80% identity, at least 90% identity, at least 95% identity, at least 99% identity or is identical to a sequence of RVKFSRSADAPAYQQGQNQLYNELNLGRREEYDVLHMQALPPR (SEQ ID NO: 81). In some embodiments, the CD3ζ activation domain comprises SEQ ID NO: 81. In some embodiments, the CD3 activation domain comprising a single ITAM consists essentially of an amino acid sequence of RVKFSRSADAPAYQQGQNQLYNELNLGRREEYDVLHMQALPPR (SEQ ID NO: 81). In some embodiments, the CD3ζ activation domain comprising a single ITAM is encoded by a nucleotide sequence having at least 80% identity, at least 90% identity, at least 95% identity, at least 99% identity or is identical to a sequence of

```
                                        (SEQ ID NO: 82)
AGAGTGAAGT TCAGCAGGAG CGCAGACGCC CCCGCGTACC
AGCAGGGCCA GAACCAGGTC TATAACGAGC TCAATCTAGG
ACGAAGAGAG GAGTACGATG TTTTGCACAT GCAGGCCCTG
CCCCCTCGC
```

In some embodiments, the CD3ζ activation domain is encoded by SEQ ID NO: 82.

In some embodiments, the cytoplasmic domain of the CAR can be designed to comprise the CD3ζ signaling domain by itself or combined with any other desired cytoplasmic domain(s) useful in the context of the CAR of the instant disclosure. For example, the cytoplasmic domain of the CAR can comprise a CD3ζ chain portion and a co-stimulatory domain. The co-stimulatory domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include the co-stimulatory domain is selected from the group consisting of IL-2Rβ, Fc Receptor gamma (FcRγ), Fc Receptor beta (FcRβ), CD3g molecule gamma (CD3γ), CD3δ, CD3ε, CD5 molecule (CD5), CD22 molecule (CD22), CD79a molecule (CD79a), CD79b molecule (CD79b), carcinoembryonic antigen related cell adhesion molecule 3 (CD66d), CD27 molecule (CD27), CD28 molecule (CD28), TNF receptor superfamily member 9 (4-1BB), TNF receptor superfamily member 4 (OX40), TNF receptor superfamily member 8 (CD30), CD40 molecule (CD40), programmed cell death 1 (PD-1), inducible T cell costimulatory (ICOS), lymphocyte function-associated antigen-1 (LFA-1), CD2 molecule (CD2), CD7 molecule (CD7), TNF superfamily member 14 (LIGHT), killer cell lectin like receptor C2 (NKG2C) and CD276 molecule (B7-H3) c-stimulatory domains, or functional variants thereof. In some embodiments, the intracellular domains of CARs of the instant disclosure comprise at least one co-stimulatory domain. In some embodiments, the co-stimulatory domain is isolated or derived from CD28.

In some embodiments, the intracellular domains of CARs of the instant disclosure comprise at least one co-stimulatory domain. In some embodiments, the co-stimulatory domain is isolated or derived from CD28. In some embodiments, the CD28 co-stimulatory domain comprises an amino acid sequence having at least 80% identity, at least 90% identity, at least 95% identity, at least 99% identity or is identical to a sequence of RSKRSRLLHSDYIVINMTPRRPGPTRKHYQPYAPPRDFAAYRS (SEQ ID NO: 83). In some embodiments, the CD28 co-stimulatory domain comprises or consists essentially of SEQ ID NO: 83). In some embodiments, the CD28 co-stimulatory domain is encoded by a nucleotide sequence having at least 80% identity, at least 90% identity, at least 95% identity, at least 99% identity or is identical to a sequence of (SEQ ID NO: 84)
AGGAGCAAGCGGAGCAGACTGCTGCACAGCGACTACATGAACATGACCC

CCCGGAGGCCTGGCCCCACCCGGAAGCACTACCAGCCCTACGCCCCTCC

CAGGGATTTCGCCGCCTACCGGAGC.

In some embodiments, the CD28 co-stimulatory domain is encoded by SEQ ID NO: 84. In some embodiments, the CD28 co-stimulatory domain is encoded by a nucleotide sequence having at least 80% identity, at least 90% identity, at least 95% identity, at least 99% identity or is identical to a sequence of SEQ ID NO: 160. In some embodiments, the CD28 co-stimulatory domain is encoded by SEQ ID NO: 160.

In some embodiments, the co-stimulatory domain is isolated or derived from 4-1BB. In some embodiments, the 4-1BB co-stimulatory domain comprises an amino acid sequence having at least 80% identity, at least 90% identity, at least 95% identity, at least 99% identity or is identical to a sequence of KRGRKKLLYIFKQPFMRPVQTTQEEDGCSCRFPEEEEGGCEL (SEQ ID NO: 161). In some embodiments, the 4-1BB co-stimulatory domain comprises or consists essentially of KRGRKKLLYIFKQPFMRPVQTTQEEDGCSCRFPEEEEGGCEL (SEQ ID NO: 161). In some embodiments, the 4-1BB co-stimulatory domain s encoded by a nucleotide sequence having at least 80% identity, at least 90% identity, at least 95% identity, at least 99% identity or is identical to a sequence of (SEQ ID NO: 162)
AAACGGGGCAGAAAGAAACTCCTGTATATATTCAAACAACCATTTATGAG

GCCAGTACAAACTACTCAAGAGGAAGATGGCTGTAGCTGCCGATTTCCAG

AAGAAGAAGAAGGAGGATGTGAACTG.

In some embodiments, the intracellular domain of the CAR comprises a CD28 co-stimulatory domain, a 4-1BB costimulatory domain, and a CD3ζ activation domain. In some embodiments, the intracellular domain of the CAR comprises a sequence of (SEQ ID NO: 158)
RSKRSRLLHSDYMNMTPRRPGPTRKHYQPYAPPRDFAAYRSKRGRKKLLYF

IFKQPMRPVQTTQEEDGCSCRFPEEEEGGCELRVKFSRSADAPAYKQGQNQ

LYNELNLGRREEYDVLDKRRGRDPEMGGKPRRKNPOEGLYNELOKDKMAEA

YSEIGMKGERRRGKGHDGLYQGLSTATKDTYDALHMQALPPR, or a sequence having at least 80% identity, at least 90% identity, at least 95% identity, at least 99% identity thereto. In some embodiments, the intracellular domain of the CAR is encoded by SEQ ID NO: 159, or a sequence having at least 80% identity, at least 90% identity, at least 95% identity, at least 99% identity thereto. In some embodiments, the intracellular domain of the CAR is encoded by SEQ ID NO: 159.

The cytoplasmic domains within the cytoplasmic signaling portion of the CARs of the instant disclosure may be linked to each other in a random or specified order. Optionally, a short oligo- or polypeptide linker, for example between 2 and 10 amino acids in length may form the linkage. A glycine-serine doublet provides an example of a suitable linker. An exemplary linker comprises a sequence of GGGGSGGGGSGGGGSGG (SEQ ID NO: 146).

The cytoplasmic domains within the cytoplasmic signaling portion of the CARs of the instant disclosure may be linked to each other in a random or specified order. Optionally, a short oligo- or polypeptide linker, for example between 2 and 10 amino acids in length may form the linkage. A glycine-serine doublet provides an example of a suitable linker.

T Cell Receptors (TCRs)

The disclosure provides a first, activator receptor and immune cells comprising same. In some embodiments, the first receptor is a T cell receptor (TCR).

Exemplary TCRs comprising intracellular domains for use in the instant disclosure are described in PCT/US2020/045250 filed on Sep. 6, 2020, the contents of which are incorporated herein by reference.

As used herein, a "TCR", sometimes also called a "TCR complex" or "TCR/CD3 complex" refers to a protein complex comprising a TCR alpha chain, a TCR beta chain, and one or more of the invariant CD3 chains (zeta, gamma, delta and epsilon), sometimes referred to as subunits. The TCR alpha and beta chains can be disulfide-linked to function as a heterodimer to bind to peptide-MHC complexes. Once the TCR alpha/beta heterodimer engages peptide-MHC, conformational changes in the TCR complex in the associated invariant CD3 subunits are induced, which leads to their phosphorylation and association with downstream proteins, thereby transducing a primary stimulatory signal. In an exemplary TCR complex, the TCR alpha and TCR beta polypeptides form a heterodimer, CD3 epsilon and CD3 delta form a heterodimer, CD3 epsilon and CD3 gamma for a heterodimer, and two CD3 zeta form a homodimer.

Any suitable ligand binding domain may be fused to an extracellular domain, hinge domain or transmembrane of the TCRs described herein. For example, the ligand binding domain can be an antigen binding domain of an antibody or TCR, or comprise an antibody fragment, a Vβ only domain, a linear antibody, a single-chain variable fragment (scFv), or a single domain antibody (sdAb).

In some embodiments, the ligand binding domain is fused to one or more extracellular domains or transmembrane domains of one or more TCR subunits. The TCR subunit can be TCR alpha, TCR beta, CD3 delta, CD3 epsilon, CD3 gamma or CD3 zeta. For example, the ligand binding domain can be fused to TCR alpha, or TCR beta, or portions of the ligand binding can be fused to two subunits, for example portions of the ligand binding domain can be fused to both TCR alpha and TCR beta.

TCR subunits include TCR alpha, TCR beta, CD3 zeta, CD3 delta, CD3 gamma and CD3 epsilon. Any one or more of TCR alpha, TCR beta chain, CD3 gamma, CD3 delta, CD3 epsilon, or CD3 zeta, or fragments or derivative thereof, can be fused to one or more domains capable of providing a stimulatory signal of the disclosure, thereby enhancing TCR function and activity.

TCR transmembrane domains isolated or derived from any source are envisaged as within the scope of the disclosure. The transmembrane domain may be derived either from a natural or from a recombinant source. Where the source is natural, the domain may be derived from any membrane-bound or transmembrane protein.

In some embodiments, the transmembrane domain is capable of signaling to the intracellular domain(s) whenever the TCR complex has bound to a target. A transmembrane domain of particular use may include at least the transmembrane region(s) of e.g., the alpha, beta or zeta chain of the TCR, CD3 delta, CD3 epsilon or CD3 gamma, CD28, CD3 epsilon, CD45, CD4, CD5, CD8, CD9, CD16, CD22, CD33, CD37, CD64, CD80, CD86, CD134, CD137, CD154.

In some embodiments, the transmembrane domain can be attached to the extracellular region of a polypeptide of the TCR, e.g., the antigen binding domain of the TCR alpha or beta chain, via a hinge, e.g., a hinge from a human protein. For example, the hinge can be a human immunoglobulin (Ig) hinge, e.g., an IgG4 hinge, or a CD8a hinge. In some embodiments, the hinge is isolated or derived from CD8a or CD28.

In some embodiments, the extracellular ligand binding domain is attached to one or more transmembrane domains of the TCR. In some embodiments, the transmembrane domain comprises a TCR alpha transmembrane domain, a TCR beta transmembrane domain, or both. In some embodiments, the transmembrane comprises a CD3 zeta transmembrane domain.

A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 or up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 or up to 15 amino acids of the intracellular region).

In some embodiments, the transmembrane domain can be selected or modified by amino acid substitution to avoid binding of such domains to the transmembrane domains of the same or different surface membrane proteins, e.g., to minimize interactions with other members of the receptor complex.

When present, the transmembrane domain may be a natural TCR transmembrane domain, a natural transmembrane domain from a heterologous membrane protein, or an artificial transmembrane domain. The transmembrane domain may be a membrane anchor domain. Without limitation, a natural or artificial transmembrane domain may comprise a hydrophobic a-helix of about 20 amino acids, often with positive charges flanking the transmembrane segment. The transmembrane domain may have one transmembrane segment or more than one transmembrane segment. Prediction of transmembrane domains/segments may be made using publicly available prediction tools (e.g. TMHMM, Krogh et al. Journal of Molecular Biology 2001; 305(3):567-580; or TMpred, Hofmann & Stoffel Biol. Chem. Hoppe-Seyler 1993; 347: 166). Non-limiting examples of membrane anchor systems include platelet derived growth factor receptor (PDGFR) transmembrane domain, glycosylphosphatidylinositol (GPI) anchor (added post-translationally to a signal sequence) and the like.

In some embodiments, the transmembrane domain comprises a TCR alpha transmembrane domain. In some embodiments, the TCR alpha transmembrane domain comprises an amino acid sequence having at least 85% identity, at least 90% identity, at least 95% identity, at least 96% identity, at least 97% identity, at least 98% identity, at least 99% identity or is identical to a sequence of: VIGFRILLLKVAGFNLLMTLRLW (SEQ ID NO: 85). In some embodiments, the TCR alpha transmembrane domain comprises, or consists essentially of, SEQ ID NO: 85. In some embodiments, the TCR alpha transmembrane domain is encoded by a sequence of

```
                                        (SEQ ID NO: 86)
GTGATTGGGTTCCGAATCCTCCTCCTGAAAGTGGCCGGGTTTAATCTG

CTCATGACGCTGCGGCTGTGG.
```

In some embodiments, the transmembrane domain comprises a TCR beta transmembrane domain. In some embodiments, the TCR beta transmembrane domain comprises an amino acid sequence having at least 85% identity, at least 90% identity, at least 95% identity, at least 96% identity, at least 97% identity, at least 98% identity, at least 99% identity or is identical to a sequence of: TILYEILLGKATLYAVLVSALVL (SEQ ID NO: 87). In some embodiments, the TCR beta transmembrane domain comprises, or consists essentially of, SEQ ID NO: 87. In some embodiments, the TCR beta transmembrane domain is encoded by a sequence of

```
                                        (SEQ ID NO: 88)
ACCATCCTCTATGAGATCTTGCTAGGGAAGGCCACCTTGTATGCCGT

GCTGGTCAGTGCCCTCGTGCTG.
```

TCRs of the disclosure can comprise one or more intracellular domains. In some embodiments, the intracellular domain comprises one or more domains capable of providing a stimulatory signal to a transmembrane domain. In some embodiments, the intracellular domain comprises a first intracellular domain capable of providing a stimulatory signal and a second intracellular domain capable of providing a stimulatory signal. In other embodiments, the intracellular domain comprises a first, second and third intracellular domain capable of providing a stimulatory signal. The intracellular domains capable of providing a stimulatory signal are selected from the group consisting of a CD28 molecule (CD28) domain, a LCK proto-oncogene, Src family tyrosine kinase (Lck) domain, a TNF receptor superfamily member 9 (4-1BB) domain, a TNF receptor superfamily member 18 (GITR) domain, a CD4 molecule (CD4) domain, a CD8a molecule (CD8a) domain, a FYN proto-oncogene, Src family tyrosine kinase (Fyn) domain, a zeta chain of T cell receptor associated protein kinase 70 (ZAP70) domain, a linker for activation of T cells (LAT) domain, lymphocyte cytosolic protein 2 (SLP76) domain, (TCR) alpha, TCR beta, CD3 delta, CD3 gamma and CD3 epsilon intracellular domains.

In some embodiments, an intracellular domain comprises at least one intracellular signaling domain. An intracellular signaling domain generates a signal that promotes a function a cell, for example an immune effector function of a TCR containing cell, e.g., a TCR-expressing T-cell. In some embodiments, the intracellular domain of the first receptor of the disclosure includes at least one intracellular signaling domain. For example, the intracellular domains of CD3 gamma, delta or epsilon comprise signaling domains.

In some embodiments, the extracellular domain, transmembrane domain and intracellular domain are isolated or derived from the same protein, for example T-cell receptor (TCR) alpha, TCR beta, CD3 delta, CD3 gamma, CD3 epsilon or CD3 zeta.

Examples of intracellular domains for use in activator receptors of the disclosure include the cytoplasmic sequences of the TCR alpha, TCR beta, CD3 zeta, and 4-1BB, and the intracellular signaling co-receptors that act in concert to initiate signal transduction following antigen receptor engagement, as well as any derivative or variant of these sequences and any recombinant sequence that has the same functional capability.

In some embodiments, the intracellular signaling domain comprises a primary intracellular signaling domain. Exemplary primary intracellular signaling domains include those derived from the proteins responsible for primary stimulation, or antigen dependent stimulation.

In some embodiments, the intracellular domain comprises a CD3 delta intracellular domain, a CD3 epsilon intracellular domain, a CD3 gamma intracellular domain, a CD3 zeta intracellular domain, a TCR alpha intracellular domain or a TCR beta intracellular domain.

In some embodiments, the intracellular domain comprises a TCR alpha intracellular domain. In some embodiments, a TCR alpha intracellular domain comprises Ser-Ser. In some embodiments, a TCR alpha intracellular domain is encoded by a sequence of TCCAGC.

In some embodiments, the intracellular domain comprises a TCR beta intracellular domain. In some embodiments, the TCR beta intracellular domain comprises an amino acid sequence having at least 80% identity, at least 90% identity, or is identical to a sequence of: MAMVKRKDSR (SEQ ID NO: 89). In some embodiments, the TCR beta intracellular domain comprises, or consists essentially of SEQ ID NO: 89. In some embodiments, the TCR beta intracellular domain is encoded by a sequence of (SEQ ID NO: 90)
ATGGCCATGGTCAAGAGAAAGGATTCCAGA.

In some embodiments, the intracellular signaling domain comprises at least one stimulatory intracellular domain. In some embodiments, the intracellular signaling domain comprises a primary intracellular signaling domain, such as a CD3 delta, CD3 gamma and CD3 epsilon intracellular domain, and one additional stimulatory intracellular domain, for example a co-stimulatory domain. In some embodiments, the intracellular signaling domain comprises a primary intracellular signaling domain, such as a CD3 delta, CD3 gamma and CD3 epsilon intracellular domain, and two additional stimulatory intracellular domains.

Exemplary co-stimulatory intracellular signaling domains include those derived from proteins responsible for co-stimulatory signals, or antigen independent stimulation. Co-stimulatory molecules include, but are not limited to an MHC class I molecule, BTLA, a Toll ligand receptor, as well as DAP10, DAP12, CD30, LIGHT, OX40, CD2, CD27, CD5, ICAM-1, LFA-1 (CD11a/CD18) 4-1BB (CD137, TNF receptor superfamily member 9), and CD28 molecule (CD28). A co-stimulatory protein can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, a ligand that specifically binds with CD83, CD4, and the like. The co-stimulatory domain can comprise the entire intracellular portion, or the entire native intracellular signaling domain, of the molecule from which it is derived, or a functional variant thereof.

In some embodiments, the stimulatory domain comprises a co-stimulatory domain. In some embodiments, the co-stimulatory domain comprises a CD28 or 4-1BB co-stimulatory domain. CD28 and 4-1BB are well characterized co-stimulatory molecules required for full T cell activation and known to enhance T cell effector function. For example, CD28 and 4-1BB have been utilized in chimeric antigen receptors (CARs) to boost cytokine release, cytolytic function, and persistence over the first-generation CAR containing only the CD3 zeta signaling domain. Likewise, inclusion of co-stimulatory domains, for example CD28 and 4-1BB domains, in TCRs can increase T cell effector function and specifically allow co-stimulation in the absence of co-stimulatory ligand, which is typically down-regulated on the surface of tumor cells. In some embodiments, the stimulatory domain comprises a CD28 intracellular domain or a 4-1BB intracellular domain.

Inhibitory Receptors

The disclosure provides a second receptor, comprising an extracellular ligand binding domain specific to a non-target antigen that has been lost in a cancer cell, such as an allelic variant of a gene. The non-target allelic variant can be lost in the cancer cell through any mechanism, such as, without limitation, epigenetic changes that effect non-target allelic variant expression, mutations to the gene encoding the non-target allelic variant, disruption of cellular signaling that regulates expression of the non-target allelic variant, chromosome loss, partial or complete deletion of the genomic locus, gene silencing through modification of nucleic acids or heterochromatin, or loss of expression through other mechanisms. In variations of the compositions and methods disclosed herein, the cells or subject treated may exhibit a loss of expression of the non-target allelic variant because of non-genetic changes. Accordingly the disclosure provides compositions and methods for killing cells and/or treating subject lacking expression of the non-target antigen from any cause, including but not limited to, loss of heterozygosity.

The non-target antigen can be a protein, or an antigen peptide thereof in a complex with a major histocompatibility complex class I (MHC-I), where the non-target antigen comprises a polymorphism. Because the non-target antigen is polymorphic, loss of a single copy of the gene encoding the non-target antigen, which may occur through loss of heterozygosity in a cancer cell, yields a cancer cell that retains the other polymorphic variant of gene, but has lost the non-target antigen. For example, a subject having HLA-A*02 and HLA-A*01 alleles at the HLA locus may have a cancer in which only the HLA-A*02 allele is lost. In such a subject, the HLA-A*01 protein remains present, but is not recognized by the inhibitory receptor of immune cells encountering the cancer cell, because the inhibitor receptor is designed to be specific to the HLA-A*02 (or other non-target antigen). In normal non-malignant cells, the HLA-A*02 (or other non-target antigen) is present and inhibits activation of the engineered immune cell. In cancer cells having loss of heterozygosity, the HLA-A*02 allelic variant (or other non-target antigen) is lost. Immune cells engineered to express the inhibitory receptor do not receive an inhibitory signal from the inhibitory receptor, as the inhibitory receptor only responds to the HLA-A*02 (or other non-target antigen), which is absent on cancer cells. By this mechanism, the immune cell is selectively activated, and selectively kills, cancer cells expressing CEA but having lost HLA-A*02 (or another non-target antigen) due to loss-of-heterozygosity. HLA-A is used here as an example. Similar polymorphic variation occurs in the population at other MHC genes and in other non-MHC genes as well. Accordingly, disclosure provides a second receptor, comprising an extracellular ligand binding domain specific to a non-target antigen selected from TNFRSF11A, ACHRB, ITGAE, TRPV1, and SREC, or an antigen peptide thereof in a complex with a major histocompatibility complex class I (MHC-I), wherein the non-target antigen comprises a polymorphism, and immune cells comprising same.

In some embodiments, the second receptor is an inhibitory chimeric antigen receptor (inhibitory receptor).

In some embodiments, the second receptor is an inhibitory receptor. In some embodiments, the second receptor is humanized.

In some embodiments, the second receptor comprises SEQ ID NO: 164, or a sequence sharing at least 75%, at least 80%, at least 85%, at least 90%, at least 95%, or at least 98% identity thereto. In some embodiments, 174 or a sequence sharing at least 75%, at least 80%, at least 85%, at least 90%, at least 95%, or at least 98% identity thereto.

The disclosure provides a second receptor, which is an inhibitory receptor, comprising an extracellular ligand binding that can discriminate between single amino-acid variant alleles of a non-target antigen. This ability to discriminate between allelic variants of a non-target antigen allows the second receptor to inhibit activation of immune cells comprising the second receptor in the presence of non-target cells that express that the allele recognized by the ligand binding domain. However, activation of immune cells is not inhibited in the presence of target cells that have lost the allele, for example cancer cells that have lost one allele of a gene through loss of heterozygosity.

The disclosure provides a second receptor, which is an inhibitory receptor, comprising an extracellular ligand binding that can discriminate between different levels of expression of a non-target antigen. This allows the second receptor to inhibit activation of immune cells comprising the second receptor in the presence of non-target cells that express the ligand for the second receptor, but to allow activation of immune cells in the presence of cancer cells that express low levels, or have no expression, of the ligand for the second receptor.

Inhibitor Ligands

In some embodiments, the non-target antigen is not expressed by the target cells, and is expressed by non-target cells. In some embodiments, the non-target antigen is expressed by healthy cells, i.e. cells that are not cancer cells. In some embodiments, the target cells are a plurality of cancer cells that have lost expression of the non-target antigen through loss of heterozygosity (LOH). In some embodiments, the non-target cells are a plurality of healthy cells (i.e. non-cancer, normal, or healthy cells), that express both the target and the non-target antigen.

Any cell surface molecule expressed by the non-target cells that is not expressed by target cells may be a suitable non-target antigen for the second receptor extracellular ligand binding domain. For example, a cell adhesion molecule, a cell-cell signaling molecule, an extracellular domain, a molecule involved in chemotaxis, a glycoprotein, a G protein-coupled receptor, a transmembrane, a receptor for a neurotransmitter or a voltage gated ion channel can be used as a non-target antigen.

In some embodiments, the non-target antigen is selected from the group consisting of a polymorphic variant of TNFRSF11A, ACHRB, ITGAE, TRPV1, and SREC. In some embodiments, the non-target antigen is an antigen peptide comprising a polymorphic residue of TNFRSF11A, ACHRB, ITGAE, TRPV1, or SREC, in a complex with a major histocompatibility complex class I (MHC-I).

In some embodiments, the target antigen is a peptide antigen of a cancer cell-specific antigen in a complex with a major histocompatibility complex class I (MHC-I).

Non-target MHC-1 (pMHC) antigens comprising any of HLA-A, HLA-B, HLA-C or HLA-E are envisaged as within the scope of the disclosure.

In some embodiments, the non-target antigen comprises a Major Histocompatibility Complex (MEW) protein. In some embodiments, the MHC is MEW class I. In some embodiments, the MEW class I protein comprises a human leukocyte antigen (HLA) protein. In some embodiments, the non-target antigen comprises an allele of an HLA Class I protein selected from the group consisting of HLA-A, HLA-B, HLA-C, or HLA-E. In some embodiments, the HLA-A allele comprises HLA-A*01, HLA-A*02, HLA-A*03 or HLA-A*11. In some embodiments, the HLA-B allele comprises HLA-B*07. In some embodiments, the HLA-C allele comprises HLA-C*07.

In some embodiments, the non-target antigen comprises HLA-A. In some embodiments, the non-target antigen comprises an allele of HLA-A. in some embodiments, the allele of HLA-A comprises HLA-A*01, HLA-A*02, HLA-A*03 or HLA-A*11. In some embodiments, the non-target antigen comprises HLA-A*69.

In some embodiments, the non-target antigen comprises an allele HLA-B. In some embodiments, the allele of HLA-B comprises HLA-B*11.

In some embodiments, the non-target antigen comprises an allele of HLA-C. In some embodiments, the HLA-C allele comprises HLA-C*07.

In some embodiments, the non-target antigen is selected from the group consisting of TNFRSF11A, ACHRB, ITGAE, TRPV1, and SREC. CEA and TNFRSF11A (RANK) are low/absent in T cells, thus avoiding the in cis challenges of other ligands. LOH frequencies for the TNFRSF11A locus are extremely high (~90% in rectal cancer).

In some embodiments, the non-target antigen comprises TNFRSF11A or an antigen peptide thereof in a complex with MHC-I. Human TNFRSF11A is located on Chr18q: 35,237,593-37,208,541 and is frequently lost through LOH in colorectal cancer cells.

A wild type Human TNFRSF11A isoform 1 is described in NCBI record number NP_003830.1 the contents of which are incorporated by reference herein in their entirety. In some embodiments, TNFRSF11A comprises an amino acid sequence of:

(SEQ ID NO: 13)

```
  1 MAPRARRRRP LFALLLLCAL LARLQVALQI APPCTSEKHY EHLGRCCNKC EPGKYMSSKC

 61 TTTSDSVCLP CGPDEYLDSW NEEDKCLLHK VCDTGKALVA VVAGNSTTPR RCACTAGYHW

121 SQDCECCRRN TECAPGLGAQ HPLQLNKDTV CKPCLAGYFS DAFSSTDKCR PWTNCTFLGK

181 RVEHHGTEKS DAVCSSSLPA RKPPNEPHVY LPGLIILLLF ASVALVAAII FGVCYRKKGK

241 ALTANLWHWI NEACGRLSGD KESSGDSCVS THTANFGQQG ACEGVLLLTL EEKTFPEDMC
```

-continued

```
301 YPDQGGVCQG TCVGGGPYAQ GEDARMLSLV SKTEIEEDSF RQMPTEDEYM DRPSQPTDQL

361 LFLTEPGSKS TPPFSEPLEV GENDSLSQCF TGTQSTVGSE SCNCTEPLCR TDWTPMSSEN

421 YLQKEVDSGH CPHWAASPSP NWADVCTGCR NPPGEDCEPL VGSPKRGPLP QCAYGMGLPP

481 EEEASRTEAR DQPEDGADGR LPSSARAGAG SGSSPGGQSP ASGNVTGNSN STFISSGQVM

541 NFKGDIIVVY VSQTSQEGAA AAAEPMGRPV QEETLARRDS FAGNGPRFPD PCGGPEGLRE

601 PEKASRPVQE QGGAKA.
```

In some embodiments, TNFRSF11A comprises a sequence that shares at least 80%, at least 85%, at least 90%, at least 95%, at least 96%, at least 97%, at least 98%, or at least 99% identity to SEQ ID NO: 13. Polymorphic residues of TNFRSF11A are marked as bold and underlined in SEQ ID NO: 13.

In some embodiments, the non-target antigen comprises a polymorphism of TNFRSF11A. For example, the non-target antigen comprises a peptide derived from TNFRSF11A comprising a polymorphic residue of TNFRSF11A. Polymorphic residues of TNFRSF11A include amino acid residues 141 and 192 of SEQ ID NO: 13. In some embodiments, the non-target antigen comprises a peptide of TNFRSF11A comprising amino acid 141 (r535211496, H141Y) or 192 (r51805034, V192A) of SEQ ID NO: 13.

In some embodiments, the polymorphism of TNFRSF11A comprises an H141/A192V allele of TNFRSF11A. In some embodiments, the polymorphism of TNFRSF11A comprises a sequence of:

(polymorphic amino acids are bold and underlined)

(SEQ ID NO: 229)

1 MAPRARRRRP LFALLLLCAL LARLQVALQI APPCTSEKHY EHLGRCCNKC EPGKYMSSKC

61 TTTSDSVCLP CGPDEYLDSW NEEDKCLLHK VCDTGKALVA VVAGNSTTPR RCACTAGYHW

121 SQDCECCRRN TECAPGLGAQ <u>H</u>PLQLNKDTV CKPCLAGYFS DAFSSTDKCR PWTNCTFLGK

181 RVEHHGTEKS D<u>V</u>VCSSSLPA RKPPNEPHVY LPGLIILLLF ASVALVAAII FGVCYRKKGK

241 ALTANLWHWI NEACGRLSGD KESSGDSCVS THTANFGQQG ACEGVLLLTL EEKTFPEDMC

301 YPDQGGVCQG TCVGGGPYAQ GEDARMLSLV SKTEIEEDSF RQMPTEDEYM DRPSQPTDQL

361 LFLTEPGSKS TPPFSEPLEV GENDSLSQCF TGTQSTVGSE SCNCTEPLCR TDWTPMSSEN

421 YLQKEVDSGH CPHWAASPSP NWADVCTGCR NPPGEDCEPL VGSPKRGPLP QCAYGMGLPP

481 EEEASRTEAR DQPEDGADGR LPSSARAGAG SGSSPGGQSP ASGNVTGNSN STFISSGQVM

541 NFKGDIIVVY VSQTSQEGAA AAAEPMGRPV QEETLARRDS FAGNGPRFPD PCGGPEGLRE

601 PEKASRPVQE QGGAKA.

In some embodiments, the polymorphism of TNFRSF11A comprises an H141Y/A192 allele of TNFRSF11A. In some embodiments, the polymorphism of TNFRSF11A comprises a sequence of:

(polymorphic amino acids are bold and underlined)

(SEQ ID NO: 230)

1 MAPRARRRRP LFALLLLCAL LARLQVALQI APPCTSEKHY EHLGRCCNKC EPGKYMSSKC

61 TTTSDSVCLP CGPDEYLDSW NEEDKCLLHK VCDTGKALVA VVAGNSTTPR RCACTAGYHW

121 SQDCECCRRN TECAPGLGAQ <u>Y</u>PLQLNKDTV CKPCLAGYFS DAFSSTDKCR PWTNCTFLGK

181 RVEHHGTEKS D<u>A</u>VCSSSLPA RKPPNEPHVY LPGLIILLLF ASVALVAAII FGVCYRKKGK

241 ALTANLWHWI NEACGRLSGD KESSGDSCVS THTANFGQQG ACEGVLLLTL EEKTFPEDMC

301 YPDQGGVCQG TCVGGGPYAQ GEDARMLSLV SKTEIEEDSF RQMPTEDEYM DRPSQPTDQL

361 LFLTEPGSKS TPPFSEPLEV GENDSLSQCF TGTQSTVGSE SCNCTEPLCR TDWTPMSSEN

421 YLQKEVDSGH CPHWAASPSP NWADVCTGCR NPPGEDCEPL VGSPKRGPLP QCAYGMGLPP

481 EEEASRTEAR DQPEDGADGR LPSSARAGAG SGSSPGGQSP ASGNVTGNSN STFISSGQVM

541 NFKGDIIVVY VSQTSQEGAA AAAEPMGRPV QEETLARRDS FAGNGPRFPD PCGGPEGLRE

601 PEKASRPVQE QGGAKA.

In some embodiments, the polymorphism of TNFRSF11A comprises an H141Y/A192V allele of TNFRSF11A. In some embodiments, the polymorphism of TNFRSF11A comprises a sequence of:

```
(polymorphic amino acids are bold and underlined)
                                                  (SEQ ID NO: 231)
  1 MAPRARRRRP LFALLLLCAL LARLQVALQI APPCTSEKHY EHLGRCCNKC EPGKYMSSKC

 61 TTTSDSVCLP CGPDEYLDSW NEEDKCLLHK VCDTGKALVA VVAGNSTTPR RCACTAGYHW

121 SQDCECCRRN TECAPGLGAQ YPLQLNKDTV CKPCLAGYFS DAFSSTDKCR PWTNCTFLGK

181 RVEHHGTEKS DVVCSSSLPA RKPPNEPHVY LPGLIILLLF ASVALVAAII FGVCYRKKGK

241 ALTANLWHWI NEACGRLSGD KESSGDSCVS THTANFGQQG ACEGVLLLTL EEKTFPEDMC

301 YPDQGGVCQG TCVGGGPYAQ GEDARMLSLV SKTEIEEDSF RQMPTEDEYM DRPSQPTDQL

361 LFLTEPGSKS TPPFSEPLEV GENDSLSQCF TGTQSTVGSE SCNCTEPLCR TDWTPMSSEN

421 YLQKEVDSGH CPHWAASPSP NWADVCTGCR NPPGEDCEPL VGSPKRGPLP QCAYGMGLPP

481 EEEASRTEAR DQPEDGADGR LPSSARAGAG SGSSPGGQSP ASGNVTGNSN STFISSGQVM

541 NFKGDIIVVY VSQTSQEGAA AAAEPMGRPV QEETLARRDS FAGNGPRFPD PCGGPEGLRE

601 PEKASRPVQE QGGAKA.
```

In some embodiments, the non-target antigen comprises a TNFRSF11A polymorphism with an A at position 192 of SEQ ID NO: 13, and the second receptor comprises a ligand binding domain with a higher affinity for a TNFRSF11A ligand with an A at position 192 of SEQ ID NO: 13 than for a TNFRSF11A ligand with a V at position 192 of SEQ ID NO: 13. In some embodiments, the non-target antigen comprises a TNFRSF11A polymorphism with a V at position 192 of SEQ ID NO: 13, and the second receptor comprises a ligand binding domain with a higher affinity for a TNFRSF11A ligand with an V at position 192 of SEQ ID NO: 13 than for a TNFRSF11A ligand with an A at position 192 of SEQ ID NO: 13. In some embodiments, the non-target antigen comprises a TNFRSF11A polymorphism with an H at position 141 of SEQ ID NO: 13, and the second receptor comprises a ligand binding domain with a higher affinity for a TNFRSF11A ligand with an H at position 141 of SEQ ID NO: 13 than for a TNFRSF11A ligand with a Y at position 141 of SEQ ID NO: 13. In some embodiments, the non-target antigen comprises a TNFRSF11A polymorphism with a Y at position 141 of SEQ ID NO: 13, and the second receptor comprises a ligand binding domain with a higher affinity for a TNFRSF11A ligand with a Y at position 141 of SEQ ID NO: 13 than for a TNFRSF11A ligand with an H at position 141 of SEQ ID NO: 13.

Mouse TNFRSF11A isoform 1 is described in NCBI record number AH19185.1, the contents of which are incorporated by reference in their entirety. In some embodiments, TNFRSF11A comprises an amino acid sequence of:

```
                                                  (SEQ ID NO: 32)
  1 MAPRARRRRQ LPAPLLALCV LLVPLQVTLQ VTPPCTQERH YEHLGRCCSR CEPGKYLSSK

 61 CTPTSDSVCL PCGPDEYLDT WNEEDKCLLH KVCDAGKALV AVDPGNHTAP RRCACTAGYH

121 WNSDCECCRR NTECAPGFGA QHPLQLNKDT VCTPCLLGFF SDVFSSTDKC KPWTNCTLLG

181 KLEAHQGTTE SDVVCSSSMT LRRPPKEAQA YLPSLIVLLL FISVVVVAAI IFGVYYRKGG

241 KALTANLWNW VNDACSSLSG NKESSGDRCA GSHSATSSQQ EVCEGILLMT REEKMVPEDG

301 AGVCGPVCAA GGPWAEVRDS RTFTLVSEVE TQGDLSRKIP TEDEYTDRPS QPSTGSLLLI

361 QQGSKSIPPF QEPLEVGEND SLSQCFTGTE STVDSEGCDF TEPPSRTDSM PVSPEKHLTK

421 EIEGDSCLPW VVSSNSTDGY TGSGNTPGED HEPFPGSLKC GPLPQCAYSM GFPSEAAASM

481 AEAGVRPQDR ADEKGASGSG SSPSDQPPAS GNVTGNSNST FISSGQVMNF KGDIIVVYVS

541 QTSQEGPGSA EPESEPVGRP VQEETLAHRD SFAGTAPRFP DVCATGAGLQ EQGAPRQKDG

601 TSRPVQEQGG AQTSLHTQGS GQCAE.
```

In some embodiments, TNFRSF11A comprises a sequence that shares at least 80%, at least 85%, at least 90%, at least 95%, at least 96%, at least 97%, at least 98%, or at least 99% identity to SEQ ID NO: 32. Polymorphic residues of TNFRSF11A are marked as bold and underlined in SEQ ID NO: 32.

In some embodiments, the non-target antigen comprises a polymorphism of TNFRSF11A. Polymorphic residues of TNFRSF11A include 142 and 193 of SEQ ID NO: 32. In some embodiments, the non-target antigen comprises a peptide of TNFRSF11A comprising amino acid 142 or 193 of SEQ ID NO: 32.

In some embodiments, the non-target antigen comprises integrin Alpha-E (ITGAE) or an antigen peptide thereof in a complex with MHC-I. ITGAE comprises two polymorphisms in the extracellular domain: R950W (r51716) with a minor allele frequency (MAF) of 0.2654 and V1019A/V1019G (r52976230) with an MAF of 0.282.

Human ITGAE (R950/V10109) is described in NCBI record number NP_002199.3 the contents of which are incorporated by reference herein in their entirety. In some embodiments, ITGAE comprises an amino acid sequence of:

```
                                                              (SEQ ID NO: 14)
   1 MWLFHTLLCI ASLALLAAFN VDVARPWLTP KGGAPFVLSS LLHQDPSTNQ TWLLVTSPRT

  61 KRTPGPLHRC SLVQDEILCH PVEHVPIPKG RHRGVTVVRS HHGVLICIQV LVRRPHSLSS

 121 ELTGTCSLLG PDLRPQAQAN FFDLENLLDP DARVDTGDCY SNKEGGGEDD VNTARQRRAL

 181 EKEEEEDKEE EEDEEEEEAG TEIAIILDGS GSIDPPDFQR AKDFISNMMR NFYEKCFECN

 241 FALVQYGGVI QTEFDLRDSQ DVMASLARVQ NITQVGSVTK TASAMQHVLD SIFTSSHGSR

 301 RKASKVMVVL TDGGIFEDPL NLTTVINSPK MQGVERFAIG VGEEFKSART ARELNLIASD

 361 PDETHAFKVT NYMALDGLLS KLRYNIISME GTVGDALHYQ LAQIGFSAQI LDERQVLLGA

 421 VGAFDWSGGA LLYDTRSRRG RFLNQTAAAA ADAEAAQYSY LGYAVAVLHK TCSLSYIAGA

 481 PRYKHHGAVF ELQKEGREAS FLPVLEGEQM GSYFGSELCP VDIDMDGSTD FLLVAAPFYH

 541 VHGEEGRVYV YRLSEQDGSF SLARILSGHP GFTNARFGFA MAAMGDLSQD KLTDVAIGAP

 601 LEGFGADDGA SFGSVYIYNG HWDGLSASPS QRIRASTVAP GLQYFGMSMA GGFDISGDGL

 661 ADITVGTLGQ AVVFRSRPVV RLKVSMAFTP SALPIGFNGV VNVRLCFEIS SVTTASESGL

 721 REALLNFTLD VDVGKQRRRL QCSDVRSCLG CLREWSSGSQ LCEDLLLMPT EGELCEEDCF

 781 SNASVKVSYQ LQTPEGQTDH PQPILDRYTE PFAIFQLPYE KACKNKLFCV AELQLATTVS

 841 QQELVVGLTK ELTLNINLTN SGEDSYMTSM ALNYPRNLQL KRMQKPPSPN IQCDDPQPVA

 901 SVLIMNCRIG HPVLKRSSAH VSVVWQLEEN AFPNRTADIT VTVTNSNERR SLANETHTLQ

 961 FRHGFVAVLS KPSIMYVNTG QGLSHHKEFL FHVHGENLFG AEYQLQICVP TKLRGLQVVA

1021 VKKLTRTQAS TVCTWSQERA CAYSSVQHVE EWHSVSCVIA SDKENVTVAA EISWDHSEEL

1081 LKDVTELQIL GEISFNKSLY EGLNAENHRT KITVVFLKDE KYHSLPIIIK GSVGGLLVLI

1141 VILVILFKCG FFKRKYQQLN LESIRKAQLK SENLLEEEN.
```

In some embodiments, ITGAE comprises a sequence that shares at least 80%, at least 85%, at least 90%, at least 95%, at least 96%, at least 97%, at least 98%, or at least 99% identity to SEQ ID NO: 14. Polymorphic residues of ITGAE are marked as bold and underlined in SEQ ID NO: 14.

In some embodiments, the polymorphism of ITGAE comprises an R950W/V1019 allele of ITGAE. In some embodiments, the polymorphism of ITGAE comprises a sequence of:

```
(polymorphic amino acids are bold and underlined)
                                                             (SEQ ID NO: 232)
   1 MWLFHTLLCI ASLALLAAFN VDVARPWLTP KGGAPFVLSS LLHQDPSTNQ TWLLVTSPRT

  61 KRTPGPLHRC SLVQDEILCH PVEHVPIPKG RHRGVTVVRS HHGVLICIQV LVRRPHSLSS

 121 ELTGTCSLLG PDLRPQAQAN FFDLENLLDP DARVDTGDCY SNKEGGGEDD VNTARQRRAL

 181 EKEEEEDKEE EEDEEEEEAG TEIAIILDGS GSIDPPDFQR AKDFISNMMR NFYEKCFECN

 241 FALVQYGGVI QTEFDLRDSQ DVMASLARVQ NITQVGSVTK TASAMQHVLD SIFTSSHGSR
```

-continued

```
 301 RKASKVMVVL TDGGIFEDPL NLTTVINSPK MQGVERFAIG VGEEFKSART ARELNLIASD
 361 PDETHAFKVT NYMALDGLLS KLRYNIISME GTVGDALHYQ LAQIGFSAQI LDERQVLLGA
 421 VGAFDWSGGA LLYDTRSRRG RFLNQTAAAA ADAEAAQYSY LGYAVAVLHK TCSLSYIAGA
 481 PRYKHHGAVF ELQKEGREAS FLPVLEGEQM GSYFGSELCP VDIDMDGSTD FLLVAAPFYH
 541 VHGEEGRVYV YRLSEQDGSF SLARILSGHP GFTNARFGFA MAAMGDLSQD KLTDVAIGAP
 601 LEGFGADDGA SFGSVYIYNG HWDGLSASPS QRIRASTVAP GLQYFGMSMA GGFDISGDGL
 661 ADITVGTLGQ AVVFRSRPVV RLKVSMAFTP SALPIGFNGV VNVRLCFEIS SVTTASESGL
 721 REALLNFTLD VDVGKQRRRL QCSDVRSCLG CLREWSSGSQ LCEDLLLMPT EGELCEEDCF
 781 SNASVKVSYQ LQTPEGQTDH PQPILDRYTE PFAIFQLPYE KACKNKLFCV AELQLATTVS
 841 QQELVVGLTK ELTLNINLTN SGEDSYMTSM ALNYPRNLQL KRMQKPPSPN IQCDDPQPVA
 901 SVLIMNCRIG HPVLKRSSAH VSVVWQLEEN AFPNRTADIT VTVTNSNERW SLANETHTLQ
 961 FRHGFVAVLS KPSIMYVNTG QGLSHHKEFL FHVHGENLFG AEYQLQICVP TKLRGLQVVA
1021 VKKLTRTQAS TVCTWSQERA CAYSSVQHVE EWHSVSCVIA SDKENVTVAA EISWDHSEEL
1081 LKDVTELQIL GEISFNKSLY EGLNAENHRT KITVVFLKDE KYHSLPIIIK GSVGGLLVLI
1141 VILVILFKCG FFKRKYQQLN LESIRKAQLK SENLLEEEN.
```

In some embodiments, the polymorphism of ITGAE comprises an R950/V1019A allele of ITGAE. In some embodiments, the polymorphism of ITGAE comprises a sequence of:

(polymorphic amino acids are bold and underlined)

(SEQ ID NO: 233)

```
   1 MWLFHTLLCI ASLALLAAFN VDVARPWLTP KGGAPFVLSS LLHQDPSTNQ TWLLVTSPRT
  61 KRTPGPLHRC SLVQDEILCH PVEHVPIPKG RHRGVTVVRS HHGVLICIQV LVRRPHSLSS
 121 ELTGTCSLLG PDLRPQAQAN FFDLENLLDP DARVDTGDCY SNKEGGGEDD VNTARQRRAL
 181 EKEEEEDKEE EEDEEEEEAG TEIAIILDGS GSIDPPDFQR AKDFISNMMR NFYEKCFECN
 241 FALVQYGGVI QTEFDLRDSQ DVMASLARVQ NITQVGSVTK TASAMQHVLD SIFTSSHGSR
 301 RKASKVMVVL TDGGIFEDPL NLTTVINSPK MQGVERFAIG VGEEFKSART ARELNLIASD
 361 PDETHAFKVT NYMALDGLLS KLRYNIISME GTVGDALHYQ LAQIGFSAQI LDERQVLLGA
 421 VGAFDWSGGA LLYDTRSRRG RFLNQTAAAA ADAEAAQYSY LGYAVAVLHK TCSLSYIAGA
 481 PRYKHHGAVF ELQKEGREAS FLPVLEGEQM GSYFGSELCP VDIDMDGSTD FLLVAAPFYH
 541 VHGEEGRVYV YRLSEQDGSF SLARILSGHP GFTNARFGFA MAAMGDLSQD KLTDVAIGAP
 601 LEGFGADDGA SFGSVYIYNG HWDGLSASPS QRIRASTVAP GLQYFGMSMA GGFDISGDGL
 661 ADITVGTLGQ AVVFRSRPVV RLKVSMAFTP SALPIGFNGV VNVRLCFEIS SVTTASESGL
 721 REALLNFTLD VDVGKQRRRL QCSDVRSCLG CLREWSSGSQ LCEDLLLMPT EGELCEEDCF
 781 SNASVKVSYQ LQTPEGQTDH PQPILDRYTE PFAIFQLPYE KACKNKLFCV AELQLATTVS
 841 QQELVVGLTK ELTLNINLTN SGEDSYMTSM ALNYPRNLQL KRMQKPPSPN IQCDDPQPVA
 901 SVLIMNCRIG HPVLKRSSAH VSVVWQLEEN AFPNRTADIT VTVTNSNERR SLANETHTLQ
 961 FRHGFVAVLS KPSIMYVNTG QGLSHHKEFL FHVHGENLFG AEYQLQICVP TKLRGLQVAA
1021 VKKLTRTQAS TVCTWSQERA CAYSSVQHVE EWHSVSCVIA SDKENVTVAA EISWDHSEEL
1081 LKDVTELQIL GEISFNKSLY EGLNAENHRT KITVVFLKDE KYHSLPIIIK GSVGGLLVLI
1141 VILVILFKCG FFKRKYQQLN LESIRKAQLK SENLLEEEN.
```

In some embodiments, the polymorphism of ITGAE comprises an R950/V1019G allele of ITGAE. In some embodiments, the polymorphism of ITGAE comprises a sequence of:

(polymorphic amino acids are bold and underlined)

(SEQ ID NO: 234)

1 MWLFHTLLCI ASLALLAAFN VDVARPWLTP KGGAPFVLSS LLHQDPSTNQ TWLLVTSPRT

61 KRTPGPLHRC SLVQDEILCH PVEHVPIPKG RHRGVTVVRS HHGVLICIQV LVRRPHSLSS

121 ELTGTCSLLG PDLRPQAQAN FFDLENLLDP DARVDTGDCY SNKEGGGEDD VNTARQRRAL

181 EKEEEEDKEE EEDEEEEEAG TEIAIILDGS GSIDPPDFQR AKDFISNMMR NFYEKCFECN

241 FALVQYGGVI QTEFDLRDSQ DVMASLARVQ NITQVGSVTK TASAMQHVLD SIFTSSHGSR

301 RKASKVMVVL TDGGIFEDPL NLTTVINSPK MQGVERFAIG VGEEFKSART ARELNLIASD

361 PDETHAFKVT NYMALDGLLS KLRYNIISME GTVGDALHYQ LAQIGFSAQI LDERQVLLGA

421 VGAFDWSGGA LLYDTRSRRG RFLNQTAAAA ADAEAAQYSY LGYAVAVLHK TCSLSYIAGA

481 PRYKHHGAVF ELQKEGREAS FLPVLEGEQM GSYFGSELCP VDIDMDGSTD FLLVAAPFYH

541 VHGEEGRVYV YRLSEQDGSF SLARILSGHP GFTNARFGFA MAAMGDLSQD KLTDVAIGAP

601 LEGFGADDGA SFGSVYIYNG HWDGLSASPS QRIRASTVAP GLQYFGMSMA GGFDISGDGL

661 ADITVGTLGQ AVVFRSRPVV RLKVSMAFTP SALPIGFNGV VNVRLCFEIS SVTTASESGL

721 REALLNFTLD VDVGKQRRRL QCSDVRSCLG CLREWSSGSQ LCEDLLLMPT EGELCEEDCF

781 SNASVKVSYQ LQTPEGQTDH PQPILDRYTE PFAIFQLPYE KACKNKLFCV AELQLATTVS

841 QQELVVGLTK ELTLNINLTN SGEDSYMTSM ALNYPRNLQL KRMQKPPSPN IQCDDPQPVA

901 SVLIMNCRIG HPVLKRSSAH VSVVWQLEEN AFPNRTADIT VTVTNSNERR SLANETHTLQ

961 FRHGFVAVLS KPSIMYVNTG QGLSHHKEFL FHVHGENLFG AEYQLQICVP TKLRGLQVGA

1021 VKKLTRTQAS TVCTWSQERA CAYSSVQHVE EWHSVSCVIA SDKENVTVAA EISWDHSEEL

1081 LKDVTELQIL GEISFNKSLY EGLNAENHRT KITVVFLKDE KYHSLPIIIK GSVGGLLVLI

1141 VILVILFKCG FFKRKYQQLN LESIRKAQLK SENLLEEEN.

In some embodiments, the polymorphism of ITGAE comprises an R950W/V1019 allele of ITGAE. In some embodiments, the polymorphism of ITGAE comprises a sequence of:

(polymorphic amino acids are bold and underlined)

(SEQ ID NO: 235)

1 MWLFHTLLCI ASLALLAAFN VDVARPWLTP KGGAPFVLSS LLHQDPSTNQ TWLLVTSPRT

61 KRTPGPLHRC SLVQDEILCH PVEHVPIPKG RHRGVTVVRS HHGVLICIQV LVRRPHSLSS

121 ELTGTCSLLG PDLRPQAQAN FFDLENLLDP DARVDTGDCY SNKEGGGEDD VNTARQRRAL

181 EKEEEEDKEE EEDEEEEEAG TEIAIILDGS GSIDPPDFQR AKDFISNMMR NFYEKCFECN

241 FALVQYGGVI QTEFDLRDSQ DVMASLARVQ NITQVGSVTK TASAMQHVLD SIFTSSHGSR

301 RKASKVMVVL TDGGIFEDPL NLTTVINSPK MQGVERFAIG VGEEFKSART ARELNLIASD

361 PDETHAFKVT NYMALDGLLS KLRYNIISME GTVGDALHYQ LAQIGFSAQI LDERQVLLGA

421 VGAFDWSGGA LLYDTRSRRG RFLNQTAAAA ADAEAAQYSY LGYAVAVLHK TCSLSYIAGA

481 PRYKHHGAVF ELQKEGREAS FLPVLEGEQM GSYFGSELCP VDIDMDGSTD FLLVAAPFYH

541 VHGEEGRVYV YRLSEQDGSF SLARILSGHP GFTNARFGFA MAAMGDLSQD KLTDVAIGAP

601 LEGFGADDGA SFGSVYIYNG HWDGLSASPS QRIRASTVAP GLQYFGMSMA GGFDISGDGL

661 ADITVGTLGQ AVVFRSRPVV RLKVSMAFTP SALPIGFNGV VNVRLCFEIS SVTTASESGL

-continued

```
 721 REALLNFTLD VDVGKQRRRL QCSDVRSCLG CLREWSSGSQ LCEDLLLMPT EGELCEEDCF

 781 SNASVKVSYQ LQTPEGQTDH PQPILDRYTE PFAIFQLPYE KACKNKLFCV AELQLATTVS

 841 QQELVVGLTK ELTLNINLTN SGEDSYMTSM ALNYPRNLQL KRMQKPPSPN IQCDDPQPVA

 901 SVLIMNCRIG HPVLKRSSAH VSVVWQLEEN AFPNRTADIT VTVTNSNERW SLANETHTLQ

 961 FRHGFVAVLS KPSIMYVNTG QGLSHHKEFL FHVHGENLFG AEYQLQICVP TKLRGLQVVA

1021 VKKLTRTQAS TVCTWSQERA CAYSSVQHVE EWHSVSCVIA SDKENVTVAA EISWDHSEEL

1081 LKDVTELQIL GEISFNKSLY EGLNAENHRT KITVVFLKDE KYHSLPIIIK GSVGGLLVLI

1141 VILVILFKCG FFKRKYQQLN LESIRKAQLK SENLLEEEN.
```

In some embodiments, the polymorphism of ITGAE comprises an R950W/V1019A allele of ITGAE. In some embodiments, the polymorphism of ITGAE comprises a sequence of:

```
(polymorphic amino acids are bold and underlined)
                                                        (SEQ ID NO: 236)
   1 MWLFHTLLCI ASLALLAAFN VDVARPWLTP KGGAPFVLSS LLHQDPSTNQ TWLLVTSPRT

  61 KRTPGPLHRC SLVQDEILCH PVEHVPIPKG RHRGVTVVRS HHGVLICIQV LVRRPHSLSS

 121 ELTGTCSLLG PDLRPQAQAN FFDLENLLDP DARVDTGDCY SNKEGGGEDD VNTARQRRAL

 181 EKEEEEDKEE EEDEEEEEAG TEIAIILDGS GSIDPPDFQR AKDFISNMMR NFYEKCFECN

 241 FALVQYGGVI QTEFDLRDSQ DVMASLARVQ NITQVGSVTK TASAMQHVLD SIFTSSHGSR

 301 RKASKVMVVL TDGGIFEDPL NLTTVINSPK MQGVERFAIG VGEEFKSART ARELNLIASD

 361 PDETHAFKVT NYMALDGLLS KLRYNIISME GTVGDALHYQ LAQIGFSAQI LDERQVLLGA

 421 VGAFDWSGGA LLYDTRSRRG RFLNQTAAAA ADAEAAQYSY LGYAVAVLHK TCSLSYIAGA

 481 PRYKHHGAVF ELQKEGREAS FLPVLEGEQM GSYFGSELCP VDIDMDGSTD FLLVAAPFYH

 541 VHGEEGRVYV YRLSEQDGSF SLARILSGHP GFTNARFGFA MAAMGDLSQD KLTDVAIGAP

 601 LEGFGADDGA SFGSVYIYNG HWDGLSASPS QRIRASTVAP GLQYFGMSMA GGFDISGDGL

 661 ADITVGTLGQ AVVFRSRPVV RLKVSMAFTP SALPIGFNGV VNVRLCFEIS SVTTASESGL

 721 REALLNFTLD VDVGKQRRRL QCSDVRSCLG CLREWSSGSQ LCEDLLLMPT EGELCEEDCF

 781 SNASVKVSYQ LQTPEGQTDH PQPILDRYTE PFAIFQLPYE KACKNKLFCV AELQLATTVS

 841 QQELVVGLTK ELTLNINLTN SGEDSYMTSM ALNYPRNLQL KRMQKPPSPN IQCDDPQPVA

 901 SVLIMNCRIG HPVLKRSSAH VSVVWQLEEN AFPNRTADIT VTVTNSNERW SLANETHTLQ

 961 FRHGFVAVLS KPSIMYVNTG QGLSHHKEFL FHVHGENLFG AEYQLQICVP TKLRGLQVAA

1021 VKKLTRTQAS TVCTWSQERA CAYSSVQHVE EWHSVSCVIA SDKENVTVAA EISWDHSEEL

1081 LKDVTELQIL GEISFNKSLY EGLNAENHRT KITVVFLKDE KYHSLPIIIK GSVGGLLVLI

1141 VILVILFKCG FFKRKYQQLN LESIRKAQLK SENLLEEEN.
```

In some embodiments, the polymorphism of ITGAE comprises an R950W/V1019G allele of ITGAE. In some embodiments, the polymorphism of ITGAE comprises a sequence of:

```
(polymorphic amino acids are bold and underlined)
                                                        (SEQ ID NO: 237)
   1 MWLFHTLLCI ASLALLAAFN VDVARPWLTP KGGAPFVLSS LLHQDPSTNQ TWLLVTSPRT

  61 KRTPGPLHRC SLVQDEILCH PVEHVPIPKG RHRGVTVVRS HHGVLICIQV LVRRPHSLSS

 121 ELTGTCSLLG PDLRPQAQAN FFDLENLLDP DARVDTGDCY SNKEGGGEDD VNTARQRRAL
```

-continued

```
 181 EKEEEEDKEE EEDEEEEEAG TEIAIILDGS GSIDPPDFQR AKDFISNMMR NFYEKCFECN
 241 FALVQYGGVI QTEFDLRDSQ DVMASLARVQ NITQVGSVTK TASAMQHVLD SIFTSSHGSR
 301 RKASKVMVVL TDGGIFEDPL NLTTVINSPK MQGVERFAIG VGEEFKSART ARELNLIASD
 361 PDETHAFKVT NYMALDGLLS KLRYNIISME GTVGDALHYQ LAQIGFSAQI LDERQVLLGA
 421 VGAFDWSGGA LLYDTRSRRG RFLNQTAAAA ADAEAAQYSY LGYAVAVLHK TCSLSYIAGA
 481 PRYKHHGAVF ELQKEGREAS FLPVLEGEQM GSYFGSELCP VDIDMDGSTD FLLVAAPFYH
 541 VHGEEGRVYV YRLSEQDGSF SLARILSGHP GFTNARFGFA MAAMGDLSQD KLTDVAIGAP
 601 LEGFGADDGA SFGSVYIYNG HWDGLSASPS QRIRASTVAP GLQYFGMSMA GGFDISGDGL
 661 ADITVGTLGQ AVVFRSRPVV RLKVSMAFTP SALPIGFNGV VNVRLCFEIS SVTTASESGL
 721 REALLNFTLD VDVGKQRRRL QCSDVRSCLG CLREWSSGSQ LCEDLLLMPT EGELCEEDCF
 781 SNASVKVSYQ LQTPEGQTDH PQPILDRYTE PFAIFQLPYE KACKNKLFCV AELQLATTVS
 841 QQELVVGLTK ELTLNINLTN SGEDSYMTSM ALNYPRNLQL KRMQKPPSPN IQCDDPQPVA
 901 SVLIMNCRIG HPVLKRSSAH VSVVWQLEEN AFPNRTADIT VTVTNSNERW SLANETHTLQ
 961 FRHGFVAVLS KPSIMYVNTG QGLSHHKEFL FHVHGENLFG AEYQLQICVP TKLRGLQVGA
1021 VKKLTRTQAS TVCTWSQERA CAYSSVQHVE EWHSVSCVIA SDKENVTVAA EISWDHSEEL
1081 LKDVTELQIL GEISFNKSLY EGLNAENHRT KITVVFLKDE KYHSLPIIIK GSVGGLLVLI
1141 VILVILFKCG FFKRKYQQLN LESIRKAQLK SENLLEEEN.
```

In some embodiments, the non-target antigen comprises a polymorphism of ITGAE. For example, the non-target antigen comprises a peptide derived from ITGAE comprising a polymorphic residue of ITGAE. Polymorphic residues of ITGAE include amino acids 950 and 1019 of SEQ ID NO: 14. In some embodiments, the non-target antigen comprises a peptide of ITGAE comprising amino acid 950 or 1019 of SEQ ID NO: 14.

In some embodiments, the non-target antigen comprises a ITGAE polymorphism with a R at position 950 of SEQ ID NO: 14, and the second receptor comprises a ligand binding domain with a higher affinity for an ITGAE ligand with an R at position 950 of SEQ ID NO: 14 than for an ITGAE ligand with a W at position 950 of SEQ ID NO: 14. In some embodiments, the non-target antigen comprises a ITGAE polymorphism with a W at position 950 of SEQ ID NO: 14, and the second receptor comprises a ligand binding domain with a higher affinity for an ITGAE ligand with an W at position 950 of SEQ ID NO: 14 than for an ITGAE ligand with an R at position 950 of SEQ ID NO: 14. In some embodiments, the non-target antigen comprises a ITGAE polymorphism with a V at position 1019 of SEQ ID NO: 14, and the second receptor comprises a ligand binding domain with a higher affinity for an ITGAE ligand with a V at position 1019 of SEQ ID NO: 14 than for an ITGAE ligand with an A or G at position 1019 of SEQ ID NO: 14. In some embodiments, the non-target antigen comprises a ITGAE polymorphism with an A at position 1019 of SEQ ID NO: 14, and the second receptor comprises a ligand binding domain with a higher affinity for an ITGAE ligand with an A at position 1019 of SEQ ID NO: 14 than for an ITGAE ligand with a V or G at position 1019 of SEQ ID NO: 14. In some embodiments, the non-target antigen comprises an ITGAE polymorphism with a G at position 1019 of SEQ ID NO: 14, and the second receptor comprises a ligand binding domain with a higher affinity for an ITGAE ligand with a G at position 1019 of SEQ ID NO: 14 than for an ITGAE ligand with a V or A at position 1019 of SEQ ID NO: 14.

In some embodiments, the non-target antigen comprises ACHRB (also called CHRNB, or CHRNB1) or an antigen peptide thereof in a complex with MHC-I. Human ACHRB is described in NCBI record number NP_000738.2 the contents of which are incorporated by reference herein in their entirety. In some embodiments, ACHRB comprises an amino acid sequence of:

```
                                                           (SEQ ID NO: 33)
  1 MTPGALLMLL GALGAPLAPG VRGSEAEGRL REKLFSGYDS SVRPAREVGD RVRVSVGLIL
 61 AQLISLNEKD EEMSTKVYLD LEWTDYRLSW DPAEHDGIDS LRITAESVWL PDVVLLNNND
121 GNFDVALDIS VVVSSDGSVR WQPPGIYRSS CSIQVTYFPF DWQNCTMVFS SYSYDSSEVS
181 LQTGLGPDGQ GHQEIHIHEG TFIENGQWEI IHKPSRLIQP PGDPRGGREG QRQEVIFYLI
241 IRRKPLFYLV NVIAPCILIT LLAIFVFYLP PDAGEKMGLS IFALLTLTVF LLLLADKVPE
301 TSLSVPIIIK YLMFTMVLVT FSVILSVVVL NLHHRSPHTH QMPLWVRQIF IHKLPLYLRL
```

-continued

361 KRPKPERDLM PEPPHCSSPG SGWGRGTDEY FIRKPPSDFL FPKPNRFQPE LSAPDLRRFI

421 DGPNRAVALL PELREVVSSI SYIARQLQEQ EDHDALKEDW QFVAMVVDRL FLWTFIIFTS

481 VGTLVIFLDA TYHLPPPDPF P.

In some embodiments, ACHRB comprises a sequence that shares at least 80%, at least 85%, at least 90%, at least 95%, at least 96%, at least 97%, at least 98%, or at least 99% identity to SEQ ID NO: 33. Polymorphic residues of ACHRB are marked as bold and underlined in SEQ ID NO: 33.

In some embodiments, the non-target antigen comprises a polymorphism of ACHRB. For example, the non-target antigen comprises a peptide derived from ACHRB comprising a polymorphic residue of ACHRB. Polymorphic residues of ACHRB include 32 of SEQ ID NO: 33. In some embodiments, the non-target antigen comprises a peptide of ACHRB comprising amino acid 32 of SEQ ID NO: 33. In some embodiments, the non-target antigen comprises a peptide of ACHRB comprising an E at amino acid 32 of SEQ ID NO: 33. In some embodiments, the non-target antigen comprises a peptide of ACHRB comprising a G at amino acid 32 of SEQ ID NO: 33.

In some embodiments, the non-target antigen comprises TRPV1 or an antigen peptide thereof in a complex with MHC-I. Human TRPV1 is described in NCBI record number NP_542435.2, the contents of which are incorporated by reference herein in their entirety. In some embodiments, TRPV1 comprises an amino acid sequence of:

(SEQ ID NO: 34)

1 MKKWSSTDLG AAADPLQKDT CPDPLDGDPN SRPPPAKPQL STAKSRTRLF GKGDSEEAFP

61 VDCPHEEGEL DSCPTITVSP VITIQRPGDG PTGARLLSQD SVAASTEKTL RLYDRRSIFE

121 AVAQNNCQDL ESLLLFLQKS KKHLTDNEFK DPETGKTCLL KAMLNLHDGQ NTTIPLLLEI

181 ARQTDSLKEL VNASYTDSYY KGQTALHIAI ERRNMALVTL LVENGADVQA AAHGDFFKKT

241 KGRPGFYFGE LPLSLAACTN QLGIVKFLLQ NSWQTADISA RDSVGNTVLH ALVEVADNTA

301 DNTKFVTSMY NEILMLGAKL HPTLKLEELT NKKGMTPLAL AAGTGKIGVL AYILQREIQE

361 PECRHLSRKF TEWAYGPVHS SLYDLSCIDT CEKNSVLEVI AYSSSETPNR HDMLLVEPLN

421 RLLQDKWDRF VKRIFYFNFL VYCLYMIIFT MAAYYRPVDG LPPFKMEKTG DYFRVTGEIL

481 SVLGGVYFFF RGIQYFLQRR PSMKTLFVDS YSEMLFFLQS LFMLATVVLY FSHLKEYVAS

541 MVFSLALGWT NMLYYTRGFQ QMGIYAVMIE KMILRDLCRF MFVYIVFLFG FSTAVVTLIE

601 DGKNDSLPSE STSHRWRGPA CRPPDSSYNS LYSTCLELFK FTIGMGDLEF TENYDFKAVF

661 IILLLAYVIL TYILLLNMLI ALMGETVNKI AQESKNIWKL QRAITILDTE KSFLKCMRKA

721 FRSGKLLQVG YTPDGKDDYR WCFRVDEVNW TTWNTNVGII NEDPGNCEGV KRTLSFSLRS

781 SRVSGRHWKN FALVPLLREA SARDRQSAQP EEVYLRQFSG SLKPEDAEVF KSPAASGEK.

In some embodiments, TRPV1 comprises a sequence that shares at least 80%, at least 85%, at least 90%, at least 95%, at least 94%, at least 97%, at least 98%, or at least 99% identity to SEQ ID NO: 34. Polymorphic residues of TRPV1 are marked as bold and underlined in SEQ ID NO: 34.

In some embodiments, the non-target antigen comprises a polymorphism of TRPV1. For example, the non-target antigen comprises a peptide derived from TRPV1 comprising a polymorphic residue of TRPV1. Polymorphic residues of TRPV1 include positions 585, 459 and 469 of SEQ ID NO: 34. In some embodiments, the non-target antigen comprises a peptide of TRPV1 comprising amino acid 585, 459 or 469 of SEQ ID NO: 34. In some embodiments, the non-target antigen comprises a peptide of TRPV1 comprising an I at amino acid 585 of SEQ ID NO: 34. In some embodiments, the non-target antigen comprises a peptide of TRPV1 comprising a V at amino acid 585 of SEQ ID NO: 34.

In some embodiments, the non-target antigen comprises SREC or an antigen peptide thereof in a complex with MHC-I. Human SREC isoform 1 is described in NCBI record number NP_003684.2, the contents of which are incorporated by reference herein in their entirety. In some embodiments, SREC comprises an amino acid sequence of:

(SEQ ID NO: 35)

```
1    MGLGLLLPLL LLWTRGTQGS ELDPKGQHVC VASSPSAELQ CCAGWRQKDQ ECTIPICEGP
61   DACQKDEVCV KPGLCRCKPG FFGAHCSSRC PGQYWGPDCR ESCPCHPHGQ CEPATGACQC
121  QADRWGARCE FPCACGPHGR CDPATGVCHC EPGWWSSTCR RPCQCNTAAA RCEQATGACV
181  CKPGWWGRRC SFRCNCHGSP CEQDSGRCAC RPGWWGPECQ QQCECVRGRC SAASGECTCP
241  PGFRGARCEL PCPAGSHGVQ CAHSCGRCKH NEPCSPDTGS CESCEPGWNG TQCQQPCLPG
301  TFGESCEQQC PHCRHGEACE PDTGHCQRCD PGWLGPRCED PCPTGTFGED CGSTCPTCVQ
361  GSCDTVTGDC VCSAGYWGPS CNASCPAGFH GNNCSVPCEC PEGLCHPVSG SCQPGSGSRD
421  TALIAGSLVP LLLLFLGLAC CACCCWAPRS DLKDRPARDG ATVSRMKLQV WGTLTSLGST
481  LPCRSLSSHK LPWVTVSHHD PEVPFNHSFI EPPSAGWATD DSFSSDPESG EADEVPAYCV
541  PPQEGMVPVA QAGSSEASLA AGAFPPPEDA STPFAIPRTS SLARAKRPSV SFAEGTKFAP
601  QSRRSSGELS SPLRKPKRLS RGAQSGPEGR EAEESTGPEE AEAPESFPAA ASPGDSATGH
661  RRPPLGGRTV AEHVEAIEGS VQESSGPVTT IYMLAGKPRG SEGPVRSVFR HFGSFQKGQA
721  EAKVKRAIPK PPRQALNRKK GSPGLASGSV GQSPNSAPKA GLPGATGPMA VRPEEAVRGL
781  GAGTESSRRA QEPVSGCGSP EQDPQKQAEE ERQEEPEYEN VVPISRPPEP.
```

In some embodiments, SREC comprises a sequence that shares at least 80%, at least 85%, at least 90%, at least 95%, at least 94%, at least 97%, at least 98%, or at least 99% identity to SEQ ID NO: 35. Polymorphic residues of SREC are marked as bold and underlined in SEQ ID NO: 35.

In some embodiments, the non-target antigen comprises a polymorphism of SREC. For example, the non-target antigen comprises a peptide derived from SREC comprising a polymorphic residue of SREC. Polymorphic residues of SREC include positions 339 and 425 of SEQ ID NO: 35. In some embodiments, the non-target antigen comprises a peptide of SREC comprising amino acid 339 or 425 of SEQ ID NO: 35. In some embodiments, the non-target antigen comprises a peptide of SREC comprising an A at amino acid 425 of SEQ ID NO: 35. In some embodiments, the non-target antigen comprises a peptide of SREC comprising a V at amino acid 425 of SEQ ID NO: 35.

In some embodiments, the non-target antigen comprises C-X-C motif chemokine ligand 16 (CXCL16) or an antigen peptide thereof in a complex with MHC-I. Human CXCL16 precursor is described in NCBI record number NP_001094282.1, the contents of which are incorporated by reference herein in their entirety. In some embodiments, CXCL16 comprises an amino acid sequence of:

(SEQ ID NO: 136)

```
1    MSGSQSEVAP SPQSPRSPEM GRDLRPGSRV LLLLLLLLLV YLTQPGNGNE GSVTGSCYCG
61   KRISSDSPPS VQFMNRLRKH LRAYHRCLYY TRFQLLSWSV CGGNKDPWVQ ELMSCLDLKE
121  CGHAYSGIVA HQKHLLPTSP PISQASEGAS SDIHTPAQML LSTLQSTQRP TLPVGSLSSD
181  KELTRPNETT IHTAGHSLAA GPEAGENQKQ PEKNAGPTAR TSATVPVLCL LAIIFILTAA
241  LSYVLCKRRR GQSPQSSPDL PVHYIPVAPD SNT.
```

In some embodiments, the non-target antigen comprises a polymorphism of CXCL16. For example, the non-target antigen comprises a peptide derived from CXCL16 comprising a polymorphic residue of CXCL16. Polymorphic residues of CXCL16 include positions 142 and 200 of SEQ ID NO: 136. In some embodiments, the non-target antigen comprises a peptide of CXCL16 comprising amino acid 142 or 200 of SEQ ID NO: 136. In some embodiments, the non-target antigen comprises a peptide of CXCL16 comprising an A at amino acid 200 of SEQ ID NO: 136. In some embodiments, the non-target antigen comprises a peptide of CXCL16 comprising a V at amino acid 200 of SEQ ID NO: 136. In some embodiments, the non-target antigen comprises a peptide of CXCL16 comprising an I at amino acid 142 of SEQ ID NO: 136. In some embodiments, the non-target antigen comprises a peptide of CXCL16 comprising a T at amino acid 142 of SEQ ID NO: 136.

In some embodiments, the non-target antigen comprises collectin subfamily member 12 (COLEC12) or an antigen peptide thereof in a complex with MHC-I. Human COLEC12 is described in NCBI record number NP_569057.2, the contents of which are incorporated by reference herein in their entirety. In some embodiments, COLEC12 comprises an amino acid sequence of:

```
                                                         (SEQ ID NO: 137)
1     MKDDFAEEEE VQSFGYKRFG IQEGTQCTKC KNNWALKFSI ILLYILCALL TITVAILGYK

61    VVEKMDNVTG GMETSRQTYD DKLTAVESDL KKLGDQTGKK AISTNSELST FRSDILDLRQ

121   QLREITEKTS KNKDTLEKLQ ASGDALVDRQ SQLKETLENN SFLITTVNKT LQAYNGYVTN

181   LQQDTSVLQG NLQNQMYSHN VVIMNLNNLN LTQVQQRNLI TNLQRSVDDT SQAIQRIKND

241   FQNLQQVFLQ AKKDTDWLKE KVQSLQTLAA NNSALAKANN DTLEDMNSQL NSFTGQMENI

301   TTISQANEQN LKDLQDLHKD AENRTAIKFN QLEERFQLFE TDIVNIISNI SYTAHHLRTL

361   TSNLNEVRTT CTDTLTKHTD DLTSLNNTLA NIRLDSVSLR MQQDLMRSRL DTEVANLSVI

421   MEEMKLVDSK HGQLIKNFTI LQGPPGPRGP RGDRGSQGPP GPTGNKGQKG EKGEPGPPGP

481   AGERGPIGPA GPPGERGGKG SKGSQGPKGS RGSPGKPGPQ GSSGDPGPPG PPGKEGLPGP

541   QGPPGFQGLQ GTVGEPGVPG PRGLPGLPGV PGMPGPKGPP GPPGPSGAVV PLALQNEPTP

601   APEDNGCPPH WKNFTDKCYY FSVEKEIFED AKLFCEDKSS HLVFINTREE QQWIKKQMVG

661   RESHWIGLTD SERENEWKWL DGTSPDYKNW KAGQPDNWGH GHGPGEDCAG LIYAGQWNDF

721   QCEDVNNFIC EKDRETVLSS AL.
```

In some embodiments, COLEC12 comprises a sequence that shares at least 80%, at least 85%, at least 90%, at least 95%, at least 94%, at least 97%, at least 98%, or at least 99% identity to SEQ ID NO: 137. Polymorphic residues of COLEC12 are marked as bold and underlined in SEQ ID NO: 137.

In some embodiments, the non-target antigen comprises a polymorphism of COLEC12. For example, the non-target antigen comprises a peptide derived from COLEC12 comprising a polymorphic residue of COLEC12. Polymorphic residues of COLEC12 include position 522 of SEQ ID NO: 137. In some embodiments, the non-target antigen comprises a peptide of COLEC12 comprising amino acid 522 of SEQ ID NO: 137. In some embodiments, the non-target antigen comprises a peptide of COLEC12 comprising an S at amino acid 522 of SEQ ID NO: 137. In some embodiments, the non-target antigen comprises a peptide of COLEC12 comprising a P at amino acid 522 of SEQ ID NO: 137.

In some embodiments, the non-target antigen comprises APC down-regulated 1 (APCDD1) or an antigen peptide thereof in a complex with MHC-I. An exemplary human APCDD1 is described in UniProtKB record number Q8J025, the contents of which are incorporated by reference herein in their entirety. In some embodiments, APCDD1 comprises an amino acid sequence of:

```
                                                         (SEQ ID NO: 138)
1     MSWPRRLLLR YLFPALLLHG LGEGSALLHP DSRSHPRSLE KSAWRAFKES QCHHMLKHLH

61    NGARITVQMP PTIEGHWVST GCEVRSGPEF ITRSYRFYHN NTFKAYQFYY GSNRCTNPTY

121   TLIIRGKIRL RQASWIIRGG TEADYQLHNV QVICHTEAVA EKLGQQVNRT CPGFLADGGP

181   WVQDVAYDLW REENGCECTK AVNFAMHELQ LIRVEKQYLH HNLDHLVEEL FLGDIHTDAT

241   QRMFYRPSSY QPPLQNAKNH DHACIACRII YRSDEHHPPI LPPKADLTIG LHGEWVSQRC

301   EVRPEVLFLT RHFIFHDNNN TWEGHYYHYS DPVCKHPTFS IYARGRYSRG VLSSRVMGGT

361   EFVFKVNHMK VTPMDAATAS LLNVFNGNEC GAEGSWQVGI QQDVTHTNGC VALGIKLPHT

421   EYEIFKMEQD ARGRYLLFNG QRPSDGSSPD RPEKRATSYQ MPLVQCASSS PRAEDLAEDS

481   GSSLYGRAPG RHTWSLLLAA LACLVPLLHW NIRR.
```

In some embodiments, the non-target antigen comprises a polymorphism of APCDD1. Exemplary polymorphisms of APCDD1 include rs3748415, which can be a V, I or L at position 150 of SEQ ID NO: 138. In some embodiments, the non-target antigen comprises a peptide of APCDD1 comprising amino acid 150 of SEQ ID NO: 138. In some embodiments, the non-target antigen comprises a peptide of APCDD1 comprising an V at amino acid 150 of SEQ ID NO: 138. In some embodiments, the non-target antigen comprises a peptide of APCDD1 comprising an I at amino acid 150 of SEQ ID NO: 138. In some embodiments, the non-target antigen comprises a peptide of APCDD1 comprising an L at amino acid 150 of SEQ ID NO: 138.

A further exemplary human APCDD1 is described in UniProtKB record number V9GY82, the contents of which are incorporated by reference herein in their entirety. In some embodiments, APCDD1 comprises an amino acid sequence of:

```
                                                            (SEQ ID NO: 139)
  1    XDVAYDLWRE ENGCECTKAV NFAMHELQLI RVEKQYLHHN LDHLVEELFL GDIHTDATQR

 61    MFYRPSSYQP PLQNAKCAAE SSGSFQILPQ DSSEKEQNGL SHWCLSRPGH QKDWALCAHA

121    GPATAGCPSC LWPPAETGRK AGRTSSKTVH ACPGEAGTSS FELFYFPNCW SIETKLKISL

181    NAKLSFKPRA SAPLETGHRV KIETLSQLVF LSFIQLCCEV QSPLANK.
```

Exemplary polymorphisms of APCDD1 include rs1786683, which can be a Y or S at position 165 of SEQ ID NO: 139. In some embodiments, the non-target antigen comprises a peptide of APCDD1 comprising amino acid 165 of SEQ ID NO: 139. In some embodiments, the non-target antigen comprises a peptide of APCDD1 comprising a Y at amino acid 165 of SEQ ID NO: 139. In some embodiments, the non-target antigen comprises a peptide of APCDD1 comprising an S at amino acid 165 of SEQ ID NO: 139.

A further exemplary human APCDD1 is described in UniProt record number J3QSE3, the contents of which are incorporated by reference herein in their entirety. In some embodiments, APCDD1 comprises an amino acid sequence of:

```
                                                            (SEQ ID NO: 140)
  1    PEDVLPALQL PAPSAECQVE MGFHHVGQDG LQLPTSSDPP ALASQSAGIT GVSHRPPGRH

 61    LSNDLRTTTM PASPVGSSIG QTSTTLPSCP QRQT.
```

Exemplary polymorphisms of APCDD1 include rs9952598, which can be a Q or R at position 28 of SEQ ID NO: 140. In some embodiments, the non-target antigen comprises a peptide of APCDD1 comprising amino acid 28 of SEQ ID NO: 140. In some embodiments, the non-target antigen comprises a peptide of APCDD1 comprising a Q at amino acid 28 of SEQ ID NO: 140. In some embodiments, the non-target antigen comprises a peptide of APCDD1 comprising an R at amino acid 28 of SEQ ID NO: 140.

In some embodiments, APCDD1 comprises a sequence that shares at least 80%, at least 85%, at least 90%, at least 95%, at least 94%, at least 97%, at least 98%, or at least 99% identity to any one of SEQ ID NOs: 138-140. Polymorphic residues of APCDD1 are marked as bold and underlined in SEQ ID NOs: 138-140.

In some embodiments, the non-target antigen comprises HLA-A*01, HLA-A*02, HLA-A*03, HLA-A*11, HLA-B*07 or HLA-C*07. Various single variable domains that bind to or recognize the specified HLA alleles, for use in embodiments described herein, are described in Table 5. Such scFvs include, for example and without limitation, the following mouse and humanized scFv antibodies that bind HLA alleles in a peptide-independent way shown in Table 5 below (complementarity determining regions underlined):

TABLE 5

| HLA scFv binding domains | |
|---|---|
| HLA-A*02 antigen binding domains | |
| (mouse): | (mouse): |
| DVLMTQTPLSLPVS | GATGTTCTGATGACCCAAACTCCACTCTCCCTGCCTGTCAG |
| LGDQASISCRSSQSI | TCTTGGAGATCAAGCCTCCATCTCTTGCAGATCTAGTCAG |
| VHSNGNTYLEWYL | AGCATTGTACATAGTAATGGAAACACCTATTTAGAATGGT |
| QKPGQSPKLLIYKVS | ACCTGCAGAAGCCAGGCCAGTCTCCAAAGCTGCTCATCTA |
| NRFSGVPDRFSGSGS | CAAAGTTTCCAACCGATTTTCTGGGGTCCCAGACAGATTT |
| GTDFTLKISRVEAED | AGCGGATCTGGCTCTGGGACCGATTTCACACTCAAGATCA |
| LGVYYCFQGSHVPR | GTAGAGTGGAGGCTGAGGATCTGGGAGTTTATTACTGCTT |
| TSGGGTKLEIKGGG | TCAAGGTTCACATGTTCCTCGGACGTCCGGTGGAGGCACA |
| GSGGGGSGGGGSG | AAGCTGGAAATCAAGGGAGGTGGCGGCTCTGGAGGCGGA |
| GQVQLQQSGPELVK | GGTAGCGGAGGTGGAGGCTCTGGTGGCCAGGTCCAGCTG |
| PGASVRISCKASGYT | CAGCAGTCTGGACCTGAGCTGGTGAAGCCAGGGGCTTCAG |
| FTSYHIHWVKQRPG | TGAGGATATCCTGTAAGGCCTCTGGCTACACCTTTACAAG |
| QGLEWIGWIYPGNV | TTACCATATACATTGGGTGAAGCAGAGGCCTGGACAGGG |
| NTEYNEKFKGKATL | ACTCGAATGGATTGGATGGATTTATCCTGGAAATGTTAAT |

TABLE 5-continued

| HLA scFv binding domains | |
|---|---|
| TADKSSSTAYMHLS | ACTGAGTACAATGAGAAGTTCAAGGGCAAGGCCACACTG |
| SLTSEDSAVYFCAR | ACTGCAGACAAATCGTCCAGCACAGCCTACATGCACCTCA |
| EEITYAMDYWGQG | GCAGCCTGACCTCTGAGGACTCTGCGGTCTATTTCTGTGCC |
| TSVTVSS (SEQ ID | AGAGAGGAGATTACCTATGCTATGGATTATTGGGGTCAAG |
| NO: 91) | GAACCTCAGTCACCGTGTCCTCA (SEQ ID NO: 238) |
| | |
| (humanized): | (humanized): |
| QVQLVQSGAEVKKP | CAGGTGCAGCTGGTGCAGTCTGGGGCTGAGGTGAAGAAG |
| GSSVKVSCKASGYT | CCTGGGTCCTCAGTGAAGGTTTCCTGCAAGGCTTCTGGAT |
| FTSYHIHWVRQAPG | ACACCTTCACTAGCTATCATATACATTGGGTGCGCCAGGC |
| QGLEWMGWIYPGN | CCCCGGACAAGGGCTTGAGTGGATGGGATGGATCTACCCT |
| VNTEYNEKFKGKAT | GGCAATGTTAACACAGAATATAATGAGAAGTTCAAGGGC |
| ITADKSTSTAYMELS | AAAGCCACCATTACCGCGGACAAATCCACGAGCACAGCC |
| SLRSEDTAVYYCAR | TACATGGAGCTGAGCAGCCTGAGATCTGAAGACACGGCT |
| EEITYAMDYWGQG | GTGTATTACTGTGCGAGGGAGGAAATTACCTACGCTATGG |
| TTVTVSSGGGGSGG | ACTACTGGGGCCAGGGAACCACAGTCACCGTGTCCTCAGG |
| GGSGGGGSGGEIVL | CGGAGGTGGAAGCGGAGGGGGAGGATCTGGCGGCGGAGG |
| TQSPGTLSLSPGERA | AAGCGGAGGCGAGATTGTATTGACCCAGAGCCCAGGCAC |
| TLSCRSSQSIVHSNG | CCTGAGCCTCTCTCCAGGAGAGCGGGCCACCCTCAGTTGT |
| NTYLEWYQQKPGQ | AGATCCAGTCAGAGTATTGTACACAGTAATGGGAACACCT |
| APRLLIYKVSNRFSG | ATTTGGAATGGTATCAGCAGAAACCAGGTCAAGCCCCAA |
| IPDRFSGSGSGTDFT | GATTGCTCATCTACAAAGTCTCTAACAGATTTAGTGGTATT |
| LTISRLEPEDFAVYY | CCAGACAGGTTCAGCGGTTCCGGAAGTGGTACTGATTTCA |
| CFQGSHVPRTFGGG | CCCTCACGATCTCCAGGCTCGAGCCAGAAGATTTCGCCGT |
| TKVEIK (SEQ ID NO: | TTATTACTGTTTTCAAGGTTCACATGTGCCGCGCACATTCG |
| 92) | GTGGGGGTACTAAAGTAGAAATCAAA (SEQ ID NO: 239) |
| | |
| (humanized): | (humanized): |
| QVQLVQSGAEVKKP | CAGGTGCAGCTGGTGCAGTCTGGGGCTGAGGTGAAGAAG |
| GSSVKVSCKASGYT | CCTGGGTCCTCAGTGAAGGTTTCCTGCAAGGCTTCTGGAT |
| FTSYHIHWVRQAPG | ACACCTTCACTAGCTATCATATACATTGGGTGCGCCAGGC |
| QGLEWMGWIYPGN | CCCCGGACAAGGGCTTGAGTGGATGGGATGGATCTACCCT |
| VNTEYNEKFKGKAT | GGCAATGTTAACACAGAATATAATGAGAAGTTCAAGGGC |
| ITADKSTSTAYMELS | AAAGCCACCATTACCGCGGACAAATCCACGAGCACAGCC |
| SLRSEDTAVYYCAR | TACATGGAGCTGAGCAGCCTGAGATCTGAAGACACGGCT |
| EEITYAMDYWGQG | GTGTATTACTGTGCGAGGGAGGAAATTACCTACGCTATGG |
| TTVTVSSGGGGSGG | ACTACTGGGGCCAGGGAACCACAGTCACCGTGTCCTCAGG |
| GGSGGGGSGGDIVM | CGGAGGTGGAAGCGGAGGGGGAGGATCTGGCGGCGGAGG |
| TQTPLSLPVTPGEPA | AAGCGGAGGCGACATTGTAATGACCCAGACCCCACTCAG |
| SISCRSSQSIVHSNG | CCTGCCCGTCACTCCAGGAGAGCCGGCCAGCATCAGTTGT |
| NTYLEWYLQKPGQS | AGATCCAGTCAGAGTATTGTACACAGTAATGGGAACACCT |
| PQLLIYKVSNRFSGV | ATTTGGAATGGTATCTGCAGAAACCAGGTCAATCCCCACA |
| PDRFSGSGSGTDFTL | ATTGCTCATCTACAAAGTCTCTAACAGATTTAGTGGTGTA |
| KISRVEAEDVGVYY | CCAGACAGGTTCAGCGGTTCCGGAAGTGGTACTGATTTCA |
| CFQGSHVPRTFGGG | CCCTCAAGATCTCCAGGGTCGAGGCAGAAGATGTCGGCGT |
| TKVEIK | TTATTACTGTTTTCAAGGTTCACATGTGCCGCGCACATTCG |
| (SEQ ID NO: 93) | GTGGGGGTACTAAAGTAGAAATCAAA (SEQ ID NO: 240) |
| | |
| (humanized): | (humanized): |
| EVQLVESGGGLVKP | GAGGTGCAGCTGGTGGAGTCTGGGGGTGGGCTGGTGAAG |
| GGSLRLSCAASGYT | CCTGGGGGCTCACTGAGGCTTTCCTGCGCGGCTTCTGGAT |
| FTSYHIHWVRQAPG | ACACCTTCACTAGCTATCATATACATTGGGTGCGCCAGGC |
| KGLEWVGWIYPGN | CCCCGGAAAAGGGCTTGAGTGGGTGGGATGGATCTACCCT |
| VNTEYNEKFKGRFT | GGCAATGTTAACACAGAATATAATGAGAAGTTCAAGGGC |
| ISRDDSKNTLYLQM | AGATTCACCATTAGCAGGGACGATTCCAAGAACACACTCT |
| NSLKTEDTAVYYCA | ACCTGCAGATGAACAGCCTGAAAACTGAAGACACGGCTG |
| REEITYAMDYWGQ | TGTATTACTGTGCGAGGGAGGAAATTACCTACGCTATGGA |
| GTTVTVSSGGGGSG | CTACTGGGGCCAGGGAACCACAGTCACCGTGTCCTCAGGC |
| GGGSGGGGSGGDIQ | GGAGGTGGAAGCGGAGGGGGAGGATCTGGCGGCGGAGG |
| MTQSPSSLSASVGD | AAGCGGAGGCGACATTCAAATGACCCAGAGCCCATCCAG |
| RVTITCRSSQSIVHS | CCTGAGCGCATCTGTAGGTGACCGGGTCACCATCACTTGT |
| NGNTYLEWYQQKP | AGATCCAGTCAGAGTATTGTACACAGTAATGGGAACACCT |
| GKAPKLLIYKVSNR | ATTTGGAATGGTATCAGCAGAAACCAGGTAAAGCCCCAA |
| FSGVPSRFSGSGSGT | AATTGCTCATCTACAAAGTCTCTAACAGATTTAGTGGTGT |
| DFTLTISSLQPEDFA | ACCAAGCAGGTTCAGCGGTTCCGGAAGTGGTACTGATTTC |
| TYYCFQGSHVPRTF | ACCCTCACGATCTCCTCTCTCCAGCCAGAAGATTTCGCCA |
| GGGTKVEIK | CTTATTACTGTTTTCAAGGTTCACATGTGCCGCGCACATTC |
| (SEQ ID NO: 94) | GGTGGGGGTACTAAAGTAGAAATCAAA (SEQ ID NO: 241) |
| | |
| (humanized): | (humanized): |
| QVQLVQSGAEVKKP | CAGGTGCAGCTGGTGCAGTCTGGGGCTGAGGTGAAGAAG |
| GSSVKVSCKASGYT | CCTGGGTCCTCAGTGAAGGTTTCCTGCAAGGCTTCTGGAT |
| FTSYHIHWVRQAPG | ACACCTTCACTAGCTATCATATACATTGGGTGCGCCAGGC |
| QGLEWIGWIYPGNV | CCCCGGACAAGGGCTTGAGTGGATCGGATGGATCTACCCT |
| NTEYNEKFKGKATI | GGCAATGTTAACACAGAATATAATGAGAAGTTCAAGGGC |
| TADESTNTAYMELS | AAAGCCACCATTACCGCGGACGAATCCACGAACACAGCC |
| SLRSEDTAVYYCAR | TACATGGAGCTGAGCAGCCTGAGATCTGAAGACACGGCT |
| EEITYAMDYWGQG | GTGTATTACTGTGCGAGGGAGGAAATTACCTACGCTATGG |

TABLE 5-continued

| | |
|---|---|
| **HLA scFv binding domains** | |
| TLVTVSSGGGGSGGGGSGGGGSGGDIQMTQSPSTLSASVGDRVTITCRSSQSIVHSNGNTYLEWYQQKPGKAPKLLIYKVSNRFSGVPARFSGSGSGTEFTLTISSLQPDDFATYYCFQGSHVPRTFGQGTKVEVK (SEQ ID NO: 95) | ACTACTGGGGCCAGGGAACCCTGGTCACCGTGTCCTCAGGCGGAGGTGGAAGCGGAGGGGGAGGATCTGGCGGCGGAGGAAGCGGAGGCGACATTCAAATGACCCAGAGCCCATCCACCCTGAGCGCATCTGTAGGTGACCGGGTCACCATCACTTGTAGATCCAGTCAGAGTATTGTACACAGTAATGGGAACACCTATTTGGAATGGTATCAGCAGAAACCAGGTAAAGCCCCAAAATTGCTCATCTACAAAGTCTCTAACAGATTTAGTGGTGTACCAGCCAGGTTCAGCGGTTCCGGAAGTGGTACTGAATTCACCCTCACGATCTCCTCTCTCCAGCCAGATGATTTCGCCACTTATTACTGTTTTCAAGGTTCACATGTGCCGCGCACATTCGGTCAGGGTACTAAAGTAGAAGTCAAA (SEQ ID NO: 242) |
| (humanized): QVQLVQSGAEVKKPGSSVKVSCKASGYTFTSYHMHWVRQAPGQGLEWIGYIYPGNVNTEYNEKFKGKATLTADKSTNTAYMELSSLRSEDTAVYFCAREEITYAMDYWGQGTLVTVSSGGGGSGGGGSGGGGSGGDVQMTQSPSTLSASVGDRVTITCSSSQSIVHSNGNTYMEWYQQKPGKAPKLLIYKVSNRFSGVPDRFSGSGSGTEFTLTISSLQPDDFATYYCHQGSHVPRTFGQGTKVEVK (SEQ ID NO: 96) | (humanized): CAGGTGCAGCTGGTGCAGTCTGGGGCTGAGGTGAAGAAGCCTGGGTCCTCAGTGAAGGTTTCCTGCAAGGCTTCTGGATACACCTTCACTAGCTATCATATGCATTGGGTGCGCCAGGCCCCCGGACAAGGGCTTGAGTGGATCGGATACATCTACCCTGGCAATGTTAACACAGAATATAATGAGAAGTTCAAGGGCAAAGCCACCCTTACCGCGGACAAATCCACGAACACAGCCTACATGGAGCTGAGCAGCCTGAGATCTGAAGACACGGCTGTGTATTTCTGTGCGAGGGAGGAAATTACCTACGCTATGGACTACTGGGGCCAGGGAACCCTGGTCACCGTGTCCTCAGGCGGAGGTGGAAGCGGAGGGGGAGGATCTGGCGGCGGAGGAAGCGGAGGCGACGTTCAAATGACCCAGAGCCCATCCACCCTGAGCGCATCTGTAGGTGACCGGGTCACCATCACTTGTAGCTCCAGTCAGAGTATTGTACACAGTAATGGGAACACCTATATGGAATGGTATCAGCAGAAACCAGGTAAAGCCCCAAAATTGCTCATCTACAAAGTCTCTAACAGATTTAGTGGTGTACCAGACAGGTTCAGCGGTTCCGGAAGTGGTACTGAATTCACCCTCACGATCTCCTCTCTCCAGCCAGATGATTTCGCCACTTATTACTGTCATCAAGGTTCACATGTGCCGCGCACATTCGGTCAGGGTACTAAAGTAGAAGTCAAA (SEQ ID NO: 243) |
| **HLA-A*02 antigen binding domains** | |
| (mouse): QVQLQQSGPELVKPGASVKMSCKASGYTFTSYHIQWVKQRPGQGLEWIGWIYPGDGSTQYNEKFKGKTTLTADKSSSTAYMLLSSLTSEDSAIYFCAREGTYYAMDYWGQGTSVTVSSGGGGSGGGGSGGGGSGGDVLMTQTPLSLPVSLGDQVSISCRSSQSIVHSNGNTYLEWYLQKPGQSPKLLIYKVSNRFSGVPDRFSGSGSGTDFTLKISRVEAEDLGVYYCFQGSHVPRTFGGGTKLEIK (SEQ ID NO: 97) | (mouse): CAGGTGCAGCTGCAGCAGTCTGGGCCTGAGCTGGTGAAGCCTGGGGCCTCAGTGAAGATGTCCTGCAAGGCTTCTGGATACACCTTCACTAGCTATCATATCCAGTGGGTGAAGCAGAGGCCTGGACAAGGGCTTGAGTGGATCGGATGGATCTACCCTGGCGATGGTAGTACACAGTATAATGAGAAGTTCAAGGGCAAAACCACCCTTACCGCGGACAAATCCTCCAGCACAGCCTACATGTTGCTGAGCAGCCTGACCTCTGAAGACTCTGCTATCTATTTCTGTGCGAGGGAGGGGACCTACTACGCTATGGACTACTGGGGCCAGGGAACCTCAGTCACCGTGTCCTCAGGCGGAGGTGGAAGCGGAGGGGGAGGATCTGGCGGCGGAGGAAGCGGAGGCGATGTTTTGATGACCCAGACTCCACTCTCCCTGCCTGTCTCTCTTGGAGACCAAGTCTCCATCTCTTGTAGATCCAGTCAGAGTATTGTACACAGTAATGGGAACACCTATTTAGAATGGTATCTGCAGAAACCAGGTCAGTCTCCAAAGTTGCTCATCTACAAAGTCTCTAACAGATTTAGTGGTGTACCAGACAGGTTCAGCGGTTCCGGAAGTGGTACTGATTTCACCCTCAAGATCTCGAGAGTGGAGGCTGAGGATCTGGGAGTTTATTACTGTTTTCAAGGTTCACATGTGCCGCGCACATTCGGTGGAGGTACTAAACTGGAAATCAAA (SEQ ID NO: 244) |
| (humanized): QLQLQESGPGLVKPSETLSLTCTVSGYTFTSYHIQWIRQPPGKGLEWIGWIYPGDGSTQYNEKFKGRATISVDTSKNQFSLNLDSVSAADTAIYYCAREGTYYAMDYWGKGSTVTVSSGGGGSGGGGSGGGGSGGDIQMTQSPSSLSASVGDRVTITCRSSQSIVHSNGNTYLEWYQQKPGKAPKLLIYKVSNRFSGVPSRFSGSGSGTDFTFTISSLQPEDIATYYCFQGSHVPRTFGPGTKVDIK (SEQ ID NO: 98) | (humanized): CAGCTGCAGCTGCAGGAGTCTGGGCCCGGGCTGGTGAAGCCTTCGGAAACGCTGAGCCTCACCTGCACGGTTTCTGGATACACCTTCACCAGCTATCATATCCAGTGGATCCGACAGCCCCCTGGAAAAGGGCTTGAGTGGATCGGATGGATCTACCCTGGCGATGGTTCAACACAGTACAATGAGAAGTTCAAGGGCAGAGCCACGATTAGCGTGGACACATCCAAGAACCAATTCTCCCTGAACCTGGACAGCGTGAGTGCTGCGGACACGGCCATTTATTACTGTGCGAGAGAGGGAACTTACTACGCTATGGACTACTGGGGCAAAGGGAGCACGGTCACCGTGTCCTCAGGCGGAGGTGGAAGCGGAGGGGGAGGATCTGGCGGCGGAGGAAGCGGAGGCGACATCCAGATGACCCAGAGCCCAAGCTCCCTGAGTGCGTCCGTGGGCGACCGCGTGACCATCACTTGCAGATCCTCTCAGTCCATCGTGCACTCCAACGGCAACACGTACCTCGAGTGGTACCAGCAGAAGCCCGGGAAGGCCCCGAAACTGCTCATCTACAAGGTGAGCAACCGGTTCTCCGGCGTCCCCAGCCGCTTCTCAGGGTCCGGCTCGGGGACGGATTTCACCTTCACGATTAGCAGCTTGCAGCCCGAAGACATCGCCACGTACTACTGCTTTCAGGGAAGTCACGTGCCGCGTACCTTCGGGCCGGGCACGAAAGTGGATATTAAG (SEQ ID NO: 245) |

TABLE 5-continued

| HLA scFv binding domains | |
|---|---|
| (humanized): | (humanized): |
| EVQLVQSGAELKKP | GAGGTGCAGCTGGTGCAGTCTGGGGCCGAGCTGAAGAAG |
| GSSVKVSCKASGYT | CCTGGGTCCTCGGTGAAGGTGTCCTGCAAGGCTTCTGGAT |
| FTSYHIQWVKQAPG | ACACCTTCACCAGCTATCATATCCAGTGGGTAAAACAGGC |
| QGLEWIGWIYPGDG | CCCTGGACAAGGGCTTGAGTGGATCGGATGGATCTACCCT |
| STQYNEKFKGKATL | GGCGATGGTTCAACACAGTACAATGAGAAGTTCAAGGGC |
| TVDKSTNTAYMELS | AAAGCCACGCTTACCGTGGACAAATCCACGAACACAGCCT |
| SLRSEDTAVYYCAR | ACATGGAGCTGAGCAGCCTGAGATCTGAGGACACGGCCG |
| EGTYYAMDYWGQG | TATATTACTGTGCGAGAGAGGGAACTTACTACGCTATGGA |
| TLVTVSSGGGGSGG | CTACTGGGGCCAAGGGACCCTGGTCACCGTGTCCTCAGGC |
| GGSGGGGSGGDIQM | GGAGGTGGAAGCGGAGGGGGAGGATCTGGCGGCGGAGG |
| TQSPSTLSASVGDR | AAGCGGAGGCGACATCCAGATGACCCAGAGCCCATCCAC |
| VTITCRSSQSIVHSN | CCTGAGTGCGTCCGTGGGCGACCGCGTGACCATCACTTGC |
| GNTYLEWYQQKPG | AGATCCTCTCAGTCCATCGTGCACTCCAACGGCAACACGT |
| KAPKLLIYKVSNRFS | ACCTCGAGTGGTACCAGCAGAAGCCCGGGAAGGCCCCGA |
| GVPSRFSGSGSGTDF | AACTGCTCATCTACAAGGTGAGCAACCGGTTCTCCGGCGT |
| TLTISSLQPDDFATY | CCCCAGCCGCTTCTCAGGGTCCGGCTCGGGGACGGATTTC |
| YCFQGSHVPRTFGQ | ACCCTCACGATTAGCAGCTTGCAGCCCGATGACTTCGCCA |
| GTKVEVK (SEQ ID | CGTACTACTGCTTTCAGGGAAGTCACGTGCCGCGTACCTT |
| NO: 99) | CGGGCAGGGCACGAAAGTGGAAGTTAAG (SEQ ID NO: 246) |
| | |
| (humanized): | (humanized): |
| QVQLVQSGAEVKKP | CAGGTGCAGCTGGTGCAGTCTGGGGCCGAGGTGAAGAAG |
| GSSVKVSCKASGYT | CCTGGGTCCTCGGTGAAGGTGTCCTGCAAGGCTTCTGGAT |
| FTSYHIQWVRQAPG | ACACCTTCACCAGCTATCATATCCAGTGGGTACGACAGGC |
| QGLEWMGWIYPGD | CCCTGGACAAGGGCTTGAGTGGATGGGATGGATCTACCCT |
| GSTQYNEKFKGRVT | GGCGATGGTTCAACACAGTACAATGAGAAGTTCAAGGGC |
| ITADKSTSTAYMELS | AGAGTCACGATTACCGCGGACAAATCCACGAGCACAGCC |
| SLRSEDTAVYYCAR | TACATGGAGCTGAGCAGCCTGAGATCTGAGGACACGGCC |
| EGTYYAMDYWGQG | GTATATTACTGTGCGAGAGAGGGAACTTACTACGCTATGG |
| TTVTVSSGGGGSGG | ACTACTGGGGCCAAGGGACCACGGTCACCGTGTCCTCAGG |
| GGSGGGGSGGEIVL | CGGAGGTGGAAGCGGAGGGGGAGGATCTGGCGGCGGAGG |
| TQSPGTLSLSPGERA | AAGCGGAGGCGAGATCGTCCTGACCCAGAGCCCAGGGAC |
| TLSCRSSQSIVHSNG | CCTGAGTTTGTCCCCGGGCGAGCGCGCGACCCTCAGTTGC |
| NTYLEWYQQKPGQ | AGATCCTCTCAGTCCATCGTGCACTCCAACGGCAACACGT |
| APRLLIYKVSNRFSG | ACCTCGAGTGGTACCAGCAGAAGCCCGGGCAGGCCCCGC |
| IPDRFSGSGSGTDFT | GACTGCTCATCTACAAGGTGAGCAACCGGTTCTCCGGCAT |
| LTISRLEPEDFAVYY | CCCCGACCGCTTCTCAGGGTCCGGCTCGGGGACGGATTTC |
| CFQGSHVPRTFGGG | ACCCTCACGATTAGCCGCTTGGAGCCCGAAGACTTCGCCG |
| TKVEIK (SEQ ID NO: | TGTACTACTGCTTTCAGGGAAGTCACGTGCCGCGTACCTT |
| 100) | CGGGGGGGGCACGAAAGTGGAAATTAAG (SEQ ID NO: 247) |
| | |
| (humanized): | (humanized): |
| QVTLKQSGAEVKKP | CAGGTGACCCTGAAGCAGTCTGGGGCCGAGGTGAAGAAG |
| GSSVKVSCTASGYT | CCTGGGTCCTCGGTGAAGGTGTCCTGCACGGCTTCTGGAT |
| FTSYHVSWVRQAPG | ACACCTTCACCAGCTATCATGTCAGCTGGGTACGACAGGC |
| QGLEWLGRIYPGDG | CCCTGGACAAGGGCTTGAGTGGTTGGGAAGGATCTACCCT |
| STQYNEKFKGKVTI | GGCGATGGTTCAACACAGTACAATGAGAAGTTCAAGGGC |
| TADKSMDTSFMELT | AAAGTCACGATTACCGCGGACAAATCCATGGACACATCCT |
| SLTSEDTAVYYCAR | TCATGGAGCTGACCAGCCTGACATCTGAGGACACGGCCGT |
| EGTYYAMDLWGQG | ATATTACTGTGCGAGAGAGGGAACTTACTACGCTATGGAC |
| TLVTVSSGGGGSGG | CTCTGGGGCCAAGGGACCCTGGTCACCGTGTCCTCAGGCG |
| GGSGGGGSGGEIVL | GAGGTGGAAGCGGAGGGGGAGGATCTGGCGGCGGAGGA |
| TQSPGTLSLSPGERA | AGCGGAGGCGAGATCGTCCTGACCCAGAGCCCAGGGACC |
| TLSCRSSQSIVHSNG | CTGAGTTTGTCCCCGGGCGAGCGCGCGACCCTCAGTTGCA |
| NTYLAWYQQKPGQ | GATCCTCTCAGTCCATCGTGCACTCCAACGGCAACACGTA |
| APRLLISKVSNRFSG | CCTCGCGTGGTACCAGCAGAAGCCCGGGCAGGCCCCGCG |
| VPDRFSGSGSGTDFT | ACTGCTCATCTCCAAGGTGAGCAACCGGTTCTCCGGCGTC |
| LTISRLEPEDFAVYY | CCCGACCGCTTCTCAGGGTCCGGCTCGGGGACGGATTTCA |
| CQQGSHVPRTFGGG | CCCTCACGATTAGCCGCTTGGAGCCCGAAGACTTCGCCGT |
| TKVEIK (SEQ ID NO: | GTACTACTGCCAACAGGGAAGTCACGTGCCGCGTACCTTC |
| 101) | GGGGGGGGCACGAAAGTGGAAATTAAG (SEQ ID NO: 248) |
| | |
| (humanized): | (humanized): |
| QVQLVQSGAEVKKP | CAGGTGCAGCTGGTGCAGTCTGGGGCCGAGGTGAAGAAG |
| GASVKVSCKASGYT | CCTGGGGCCTCGGTGAAGGTGTCCTGCAAGGCTTCTGGAT |
| FTSYHMHWVRQAP | ACACCTTCACCAGCTATCATATGCACTGGGTACGACAGGC |
| GQRLEWMGWIYPG | CCCTGGACAAAGGCTTGAGTGGATGGGATGGATCTACCCT |
| DGSTQYNEKFKGKV | GGCGATGGTTCAACACAGTACAATGAGAAGTTCAAGGGC |
| TITRDTSASTAYMEL | AAAGTCACGATTACCCGGGACACATCCGCGAGCACAGCCT |
| SSLRSEDTAVYYCA | ACATGGAGCTGAGCAGCCTGAGATCTGAGGACACGGCCG |
| REGTYYAMDYWGQ | TATATTACTGTGCGAGAGAGGGAACTTACTACGCTATGGA |
| GTLVTVSSGGGGSG | CTACTGGGGCCAAGGGACCCTGGTCACCGTGTCCTCAGGC |
| GGGSGGGGSGGDIV | GGAGGTGGAAGCGGAGGGGGAGGATCTGGCGGCGGAGG |
| MTQTPLSLPVTPGEP | AAGCGGAGGCGACATCGTCATGACCCAGACCCCACTGTCC |
| ASISCRSSQSIVHSN | CTGCCTGTGACCCCGGGCGAGCCCGCGAGCATCAGTTGCA |
| GNTYLDWYLQKPG | GATCCTCTCAGTCCATCGTGCACTCCAACGGCAACACGTA |
| QSPQLLIYKVSNRFS | CCTCGACTGGTACCTGCAGAAGCCCGGGCAGTCCCCGCAA |

TABLE 5-continued

| HLA scFv binding domains | |
|---|---|
| GVPDRFSGSGSGTD FTLKISRVEAEDVG VYYCMQGSHVPRTF GGGTKVEIK (SEQ ID NO: 102) | CTGCTCATCTACAAGGTGAGCAACCGGTTCTCCGGCGTCC CCGACCGCTTCTCAGGGTCCGGCTCGGGGACGGATTTCAC CCTCAAGATTAGCCGCGTGGAGGCCGAAGACGTCGGCGT GTACTACTGCATGCAGGGAAGTCACGTGCCGCGTACCTTC GGGGGGGGCACGAAAGTGGAAATTAAG (SEQ ID NO: 249) |
| HLA-B*07 antigen binding domains | |
| 1.10_scFv | QVQLQESGPGLVKPSQTLSLTCTVSGYSITSGYSWHWIRQPP GKGLEWIGYIHFSGSTHYHPSLKSRVTISVDTSKNQFSLKLSS VTAADTAVYYCARGGVVSHYAMDCWGQGTTVTVSSGGGG SGGGGSGGGGSGGDIQMTQSPSSLSASVGDRVTITCRASENI YSNLAWYQQKPGKAPKLLIYAATYLPDGVPSRFSGSGSGTD FTLTISSLQPEDFATYYCQHFWVTPYTFGGGTKVEIK (SEQ ID NO: 250) |
| 1.9_scFv | EVQLVESGGGLVKPGGSLRLSCAASGYSITSGYSWHWVRQA PGKGLEWVSYIHFSGSTHYHPSLKSRFTISRDNAKNSLYLQM NSLRAEDTAVYYCARGGVVSHYAMDCWGQGTTVTVSSGG GGSGGGGSGGGGSGGDIQMTQSPSSVSASVGDRVTITCRASE NIYSNLAWYQQKPGKAPKLLIYAATYLPDGVPSRFSGSGSGT DFTLTISSLQPEDFATYYCQHFWVTPYTFGGGTKVEIK (SEQ ID NO: 251) |
| 1.8_scFv | EVQLVESGGGLVKPGGSLRLSCAASGYSITSGYSWHWVRQA PGKGLEWVGYIHFSGSTHYHPSLKSRFTISRDDSKNTLYLQM NSLKTEDTAVYYCARGGVVSHYAMDCWGQGTTVTVSSGG GGSGGGGSGGGGSGGEIVLTQSPATLSLSPGERATLSCRASE NIYSNLAWYQQKPGQAPRLLIYAATYLPDGIPARFSGSGSGT DFTLTISSLEPEDFAVYYCQHFWVTPYTFGGGTKVEIK (SEQ ID NO: 252) |
| 1.7_scFv | QVQLQQSGPGLVKPSQTLSLTCAISGYSITSGYSWHWIRQSPS RGLEWLGYIHFSGSTHYHPSLKSRITINPDTSKNQFSLQLNSV TPEDTAVYYCARGGVVSHYAMDCWGQGTTVTVSSGGGGS GGGGSGGGGSGGEIVLTQSPATLSLSPGERATLSCRASENIYS NLAWYQQKPGQAPRLLIYAATYLPDGIPARFSGSGSGTDFTL TISRLEPEDFAVYYCQHFWVTPYTFGGGTKVEIK (SEQ ID NO: 253) |
| 1.6_scFv | EVQLVESGGGLVKPGGSLRLSCAASGYSITSGYSWHWVRQA PGKGLEWVGYIHFSGSTHYHPSLKSRFTISRDDSKNTLYLQM NSLKTEDTAVYYCARGGVVSHYAMDCWGQGTTVTVSSGG GGSGGGGSGGGGSGGDIQMTQSPSSVSASVGDRVTITCRASE NIYSNLAWYQQKPGKAPKLLIYAATYLPDGVPSRFSGSGSGT DFTLTISSLQPEDFATYYCQHFWVTPYTFGGGTKVEIK (SEQ ID NO: 254) |
| 1.5_scFv | EVQLVESGGGLVQPGGSLRLSCAASGYSITSGYSWHWVRQA PGKGLEWVSYIHFSGSTHYHPSLKSRFTISRDNSKNTLYLQM NSLRAEDTAVYYCARGGVVSHYAMDCWGQGTTVTVSSGG GGSGGGGSGGGGSGGDIQMTQSPSSLSASVGDRVTITCRASE NIYSNLAWYQQKPGKAPKLLIYAATYLPDGVPSRFSGSGSGT DFTLTISSLQPEDFATYYCQHFWVTPYTFGGGTKVEIK (SEQ ID NO: 255) |
| 1.4_scFv | EVQLVESGGGLVKPGGSLRLSCAASGYSITSGYSWHWVRQA PGKGLEWVGYIHFSGSTHYHPSLKSRFTISRDDSKNTLYLQM NSLKTEDTAVYYCARGGVVSHYAMDCWGQGTTVTVSSGG GGSGGGGSGGGGSGGDIQMTQSPSSLSASVGDRVTITCRASE NIYSNLAWYQQKPGKAPKLLIYAATYLPDGVPSRFSGSGSGT DFTLTISSLQPEDFATYYCQHFWVTPYTFGGGTKVEIK (SEQ ID NO: 256) |
| 1.3_scFv | QVQLQQWGAGLLKPSETLSLTCAVYGYSITSGYSWHWIRQP PGKGLEWIGYIHFSGSTHYHPSLKSRVTISVDTSKNQFSLKLS SVTAADTAVYYCARGGVVSHYAMDCWGQGTTVTVSSGGG GSGGGGSGGGGSGGDIQMTQSPSSLSASVGDRVTITCRASEN IYSNLAWYQQKPGKAPKLLIYAATYLPDGVPSRFSGSGSGTD FTLTISSLQPEDFATYYCQHFWVTPYTFGGGTKVEIK (SEQ ID NO: 257) |
| 1.2_scFv | QVQLQESGPGLVKPSQTLSLTCTVSGYSITSGYSWHWIRQHP GKGLEWIGYIHFSGSTHYHPSLKSRVTISVDTSKNQFSLKLSS VTAADTAVYYCARGGVVSHYAMDCWGQGTTVTVSSGGGG SGGGGSGGGGSGGDIQMTQSPSSLSASVGDRVTITCRASENI |

TABLE 5-continued

| HLA scFv binding domains | |
|---|---|
| | YSNLAWYQQKPGKAPKLLIYAATYLPDGVPSRFSGSGSGTDFTLTISSLQPEDFATYYCQHFWVTPYTFGGGTKVEIK (SEQ ID NO: 258) |
| 1.1_scFv | QVQLQQSGPGLVKPSQTLSLTCAISGYSITSGYSWHWIRQSPSRGLEWLGYIHFSGSTHYHPSLKSRITINPDTSKNQFSLQLNSVTPEDTAVYYCARGGVVSHYAMDCWGQGTTVTVSSGGGGSGGGGSGGGGSGGDIQMTQSPSSLSASVGDRVTITCRASENIYSNLAWYQQKPGKAPKLLIYAATYLPDGVPSRFSGSGSGTDFTLTISSLQPEDFATYYCQHFWVTPYTFGGGTKVEIK (SEQ ID NO: 259) |
| **HLA-A*11 antigen binding domains** | |
| QVQLQESGPGLVKPSQTLSLTCTVSGGSISSGGYYVVSWIRQPPGKGLEWIGYIYYSGSTYYNPSLKSRVTISVDTSKNQFSLKLSSVTAADTAVYYCARHYYYYSMDVWGKGTTVTVSSGGGGSGGGGSGGGGSGGDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK (SEQ ID NO: 260) | CAGGTGCAGCTGCAGGAAAGCGGCCCTGGCCTGGTGAAACCCAGCCAGACCCTGAGCCTGACCTGCACAGTGTCCGGCGGCTCGATCAGCAGCGGCGGCTACTACTGGTCCTGGATCAGACAGCCCCCTGGCAAGGGCCTGGAATGGATCGGCTACATCTACTACAGCGGCAGCACCTACTACAACCCCAGCCTGAAGTCCAGAGTGACCATCAGCGTGGACACCAGCAAGAACCAGTTCAGCCTGAAGCTGAGCAGCGTGACAGCCGCCGACACCGCTGTGTATTACTGTGCGAGACACTACTACTACTACTCCATGGACGTCTGGGGCAAAGGGACCACGGTCACCGTGTCCTCAGGCGGAGGTGGAAGCGGAGGGGGAGGATCTGGCGGCGGAGGAAGCGGAGGCGACATCCAGATGACCCAGTCTCCATCCTCCCTGTCTGCATCTGTAGGAGACAGAGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCAACAGAGTTACAGTACCCCTCTCACTTTCGGCGGCGGAACAAAGGTGGAGATCAAG (SEQ ID NO: 261) |
| QITLKESGPTLVKPTQTLTLTCTFSGFSLSTSGVGVGWIRQPPGKALEWLALIYWNDDKRYSPSLKSRLTITKDTSKNQVVLTMTNMDPVDTATYYCAHRHMRLSCFDYWGQGTLVTVSSGGGGSGGGGSGGGGSGGDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK (SEQ ID NO: 262) | CAGATCACCCTGAAAGAGTCCGGCCCCACCCTGGTGAAACCCACCCAGACCCTGACCCTGACATGCACCTTCAGCGGCTTCAGCCTGAGCACCTCTGGCGTGGGCGTGGGCTGGATCAGACAGCCTCCCGGCAAGGCCCTGGAATGGCTGGCCCTGATCTACTGGAACGACGACAAGCGGTACAGCCCCAGCCTGAAGTCCCGGCTGACCATCACCAAGGACACCTCGAAGAACCAGGTGGTGCTGACCATGACAAACATGGACCCCGTGGACACCGCCACATATTACTGTGCACACAGACACATGCGTTTAAGCTGTTTTGACTACTGGGGCCAGGGAACCCTGGTCACCGTGTCCTCAGGCGGAGGTGGAAGCGGAGGGGGAGGATCTGGCGGCGGAGGAAGCGGAGGCGACATCCAGATGACCCAGTCTCCATCCTCCCTGTCTGCATCTGTAGGAGACAGAGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCAACAGAGTTACAGTACCCCTCTCACTTTCGGCGGCGGAACAAAGGTGGAGATCAAG (SEQ ID NO: 263) |
| QVQLVQSGAEVKKPGASVKVSCKASGYTFTSYAMHWVRQAPGQRLEWMGWINAGNGNTKYSQKFQGRVTITRDTSASTAYMELSSLRSEDTAVYYCAREGNGANPDAFDIWGQGTMVTVSSGGGGSGGGGSGGGGSGGDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK (SEQ ID NO: 264) | CAGGTGCAGCTGGTGCAGTCTGGCGCCGAAGTGAAGAAACCTGGCGCCTCCGTGAAGGTGTCCTGCAAGGCCAGCGGCTACACCTTCACCAGCTACGCCATGCACTGGGTTCGACAGGCCCCTGGCCAGAGACTGGAATGGATGGGCTGGATCAACGCCGGCAACGGCAACACCAAGTACAGCCAGAAATTCCAGGGCAGAGTGACCATCACCCGGGACACCAGCGCCAGCACCGCCTACATGGAACTGAGCAGCCTGCGGAGCGAGGACACCGCTGTGTATTACTGTGCGAGAGAAGGAAATGGTGCCAACCCTGATGCTTTTGATATCTGGGGCCAAGGGACAATGGTCACCGTGTCCTCAGGCGGAGGTGGAAGCGGAGGGGGAGGATCTGGCGGCGGAGGAAGCGGAGGCGACATCCAGATGACCCAGTCTCCATCCTCCCTGTCTGCATCTGTAGGAGACAGAGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCAACAGAGTTACAGTACCCCTCTCACTTTCGGCGGCGGAACAAAGGTGGAGATCAAG (SEQ ID NO: 265) |
| EVQLVESGGGLVQPGGSLRLSCAASGFTFSSYDMHWVRQATGKGLEWVSAIGTAGD | GAAGTGCAGCTGGTGGAAAGCGGCGGAGGCCTGGTGCAGCCTGGCGGCAGCCTGAGACTGTCTTGCGCCGCCAGCGGCTTCACCTTCAGCAGCTACGACATGCACTGGGTCCGCCAGGCCACCGGCAAGGGACTGGAATGGGTGTCCGCCATCGGCAC |

TABLE 5-continued

| HLA scFv binding domains | |
|---|---|
| TYYPGSVKGRFTISR ENAKNSLYLQMNSL RAGDTAVYYCARD LPGSYWYFDLWGR GTLVTVSSGGGGSG GGGSGGGGSGGDIQ MTQSPSSLSASVGD RVTITCRASQSISSY LNWYQQKPGKAPK LLIYAASSLQSGVPS RFSGSGSGTDFTLTI SSLQPEDFATYYCQ QSYSTPLTFGGGTK VEIK (SEQ ID NO: 266) | AGCCGGCGACACTTACTACCCCGGCAGCGTGAAGGGCCG GTTCACCATCAGCAGAGAGAACGCCAAGAACAGCCTGTA CCTGCAGATGAACAGCCTTCGAGCCGGCGATACCGCCGTG TATTACTGTGCAAGAGATCTCCCTGGTAGCTACTGGTACTT CGATCTCTGGGGCCGTGGCACCCTGGTCACTGTGTCCTCA GGCGGAGGTGGAAGCGGAGGGGGAGGATCTGGCGGCGGA GGAAGCGGAGGCGACATCCAGATGACCCAGTCTCCATCCT CCCTGTCTGCATCTGTAGGAGACAGAGTCACCATCACTTG CCGGGCAAGTCAGAGCATTAGCAGCTATTTAAATTGGTAT CAGCAGAAACCAGGGAAAGCCCCTAAGCTCCTGATCTATG CTGCATCCAGTTTGCAAAGTGGGGTCCCATCAAGGTTCAG TGGCAGTGGATCTGGGACAGATTTCACTCTCACCATCAGC AGTCTGCAACCTGAAGATTTTGCAACTTACTACTGTCAAC AGAGTTACAGTACCCCTCTCACTTTCGGCGGCGGAACAAA GGTGGAGATCAAG (SEQ ID NO: 267) |
| QVQLQESGPGLVKP SQTLSLTCTVSGGSI SSGGYYWSWIRQPP GKGLEWIGYIYYSG STYYNPSLKSRVTIS VDTSKNQFSLKLSS VTAADTAVYYCAR HYYYYYLDVWGKG TTVTVSSGGGGSGG GGSGGGGSGGDIQM TQSPSSLSASVGDRV TITCRASQSISSYLN WYQQKPGKAPKLLI YAASSLQSGVPSRFS GSGSGTDFTLTISSL QPEDFATYYCQQSY STPLTFGGGTKVEIK (SEQ ID NO: 268) | CAGGTGCAGCTGCAGGAAAGCGGCCCTGGCCTGGTGAAA CCCAGCCAGACCCTGAGCCTGACCTGCACAGTGTCCGGCG GCTCGATCAGCAGCGGCGGCTACTACTGGTCCTGGATCAG ACAGCCCCCTGGCAAGGGCCTGGAATGGATCGGCTACATC TACTACAGCGGCAGCACCTACTACAACCCCAGCCTGAAGT CCAGAGTGACCATCAGCGTGGACACCAGCAAGAACCAGT TCAGCCTGAAGCTGAGCAGCGTGACAGCCGCCGACACCG CTGTGTATTACTGTGCGAGACACTACTACTACTACTACCTG GACGTCTGGGGCAAAGGGACCACGGTCACCGTGTCCTCAG GCGGAGGTGGAAGCGGAGGGGGAGGATCTGGCGGCGGAG GAAGCGGAGGCGACATCCAGATGACCCAGTCTCCATCCTC CCTGTCTGCATCTGTAGGAGACAGAGTCACCATCACTTGC CGGGCAAGTCAGAGCATTAGCAGCTATTTAAATTGGTATC AGCAGAAACCAGGGAAAGCCCCTAAGCTCCTGATCTATGC TGCATCCAGTTTGCAAAGTGGGGTCCCATCAAGGTTCAGT GGCAGTGGATCTGGGACAGATTTCACTCTCACCATCAGCA GTCTGCAACCTGAAGATTTTGCAACTTACTACTGTCAACA GAGTTACAGTACCCCTCTCACTTTCGGCGGCGGAACAAAG GTGGAGATCAAG (SEQ ID NO: 269) |
| EVQLVESGGGLVQP GGSLRLSCAASGFTF SSYWMHWVRQAPG KGLVWVSRINSDGS STSYADSVKGRFTIS RDNAKNTLYLQMN SLRAEDTAVYYCCL GVLLYNWFDPWGQ GTLVTVSSGGGGSG GGGSGGGGSGGDIQ MTQSPSSLSASVGD RVTITCRASQSISSY LNWYQQKPGKAPK LLIYAASSLQSGVPS RFSGSGSGTDFTLTI SSLQPEDFATYYCQ QSYSTPLTFGGGTK VEIK (SEQ ID NO: 270) | GAAGTGCAGCTGGTGGAAAGCGGCGGAGGCCTGGTGCAG CCTGGCGGCAGCCTGAGACTGTCTTGCGCCGCCAGCGGCT TCACCTTCAGCAGCTACTGGATGCACTGGGTCCGCCAGGC CCCTGGCAAGGGACTGGTCTGGGTGTCTCGAATCAACAGC GACGGCAGCAGCACCAGCTACGCCGACAGCGTGAAGGGC CGGTTCACCATCAGCCGGGACAACGCCAAGAACACCCTGT ACCTGCAGATGAACAGCCTGCGGGCCGAGGACACCGCCG TGTATTACTGTTGTTTGGGTGTTTTATTATACAACTGGTTC GACCCCTGGGGCCAGGGAACCCTGGTCACCGTGTCCTCAG GCGGAGGTGGAAGCGGAGGGGGAGGATCTGGCGGCGGAG GAAGCGGAGGCGACATCCAGATGACCCAGTCTCCATCCTC CCTGTCTGCATCTGTAGGAGACAGAGTCACCATCACTTGC CGGGCAAGTCAGAGCATTAGCAGCTATTTAAATTGGTATC AGCAGAAACCAGGGAAAGCCCCTAAGCTCCTGATCTATGC TGCATCCAGTTTGCAAAGTGGGGTCCCATCAAGGTTCAGT GGCAGTGGATCTGGGACAGATTTCACTCTCACCATCAGCA GTCTGCAACCTGAAGATTTTGCAACTTACTACTGTCAACA GAGTTACAGTACCCCTCTCACTTTCGGCGGCGGAACAAAG GTGGAGATCAAG (SEQ ID NO: 271) |
| QVQLQESGPGLVKP SQTLSLTCTVSGGSI SSGGYYWSWIRQPP GKGLEWIGYIYYSG STYYNPSLKSRVTIS VDTSKNQFSLKLSS VTAADTAVYYCAR HYYYYMDVWGKG TTVTVSSGGGGSGG GGSGGGGSGGDIQM TQSPSSLSASVGDRV TITCRASQSISSYLN WYQQKPGKAPKLLI YAASSLQSGVPSRFS GSGSGTDFTLTISSL QPEDFATYYCQQSY STPLTFGGGTKVEIK (SEQ ID NO: 272) | CAGGTGCAGCTGCAGGAAAGCGGCCCTGGCCTGGTGAAA CCCAGCCAGACCCTGAGCCTGACCTGCACAGTGTCCGGCG GCTCGATCAGCAGCGGCGGCTACTACTGGTCCTGGATCAG ACAGCCCCCTGGCAAGGGCCTGGAATGGATCGGCTACATC TACTACAGCGGCAGCACCTACTACAACCCCAGCCTGAAGT CCAGAGTGACCATCAGCGTGGACACCAGCAAGAACCAGT TCAGCCTGAAGCTGAGCAGCGTGACAGCCGCCGACACCG CTGTGTATTACTGTGCGAGACACTACTACTACTACATGGA CGTCTGGGGCAAAGGGACCACGGTCACCGTGTCCTCAGGC GGAGGTGGAAGCGGAGGGGGAGGATCTGGCGGCGGAGG AAGCGGAGGCGACATCCAGATGACCCAGTCTCCATCCTCC CTGTCTGCATCTGTAGGAGACAGAGTCACCATCACTTGCC GGGCAAGTCAGAGCATTAGCAGCTATTTAAATTGGTATCA GCAGAAACCAGGGAAAGCCCCTAAGCTCCTGATCTATGCT GCATCCAGTTTGCAAAGTGGGGTCCCATCAAGGTTCAGTG GCAGTGGATCTGGGACAGATTTCACTCTCACCATCAGCAG TCTGCAACCTGAAGATTTTGCAACTTACTACTGTCAACAG AGTTACAGTACCCCTCTCACTTTCGGCGGCGGAACAAAGG TGGAGATCAAG (SEQ ID NO: 273) |
| QITLKESGPTLVKPT QTLTLTCTFSGFSLS | CAGATCACCCTGAAAGAGTCCGGCCCCACCCTGGTGAAAC CCACCCAGACCCTGACCCTGACATGCACCTTCAGCGGCTT |

TABLE 5-continued

| HLA scFv binding domains | |
|---|---|
| TSGVGVGWIRQPPG<br>KALEWLALIYWND<br>DKRYSPSLKSRLTIT<br>KDTSKNQVVLTMT<br>NMDPVDTATYYCA<br>HKTTSFYFDYWGQ<br>GTLVTVSSGGGGSG<br>GGGSGGGGSGGDIQ<br>MTQSPSSLSASVGD<br>RVTITCRASQSISSY<br>LNWYQQKPGKAPK<br>LLIYAASSLQSGVPS<br>RFSGSGSGTDFTLTI<br>SSLQPEDFATYYCQ<br>QSYSTPLTFGGGTK<br>VEIK (SEQ ID NO:<br>274) | CAGCCTGAGCACCTCTGGCGTGGGCGTGGGCTGGATCAGA<br>CAGCCTCCCGGCAAGGCCCTGGAATGGCTGGCCCTGATCT<br>ACTGGAACGACGACAAGCGGTACAGCCCCAGCCTGAAGT<br>CCCGGCTGACCATCACCAAGGACACCTCGAAGAACCAGG<br>TGGTGCTGACCATGACAAACATGGACCCCGTGGACACCGC<br>CACATATTACTGTGCACACAAAACGACGTCGTTTTACTTT<br>GACTACTGGGGCCAGGGAACCCTGGTCACCGTGTCCTCAG<br>GCGGAGGTGGAAGCGGAGGGGGAGGATCTGGCGGCGGAG<br>GAAGCGGAGGCGACATCCAGATGACCCAGTCTCCATCCTC<br>CCTGTCTGCATCTGTAGGAGACAGAGTCACCATCACTTGC<br>CGGGCAAGTCAGAGCATTAGCAGCTATTTAAATTGGTATC<br>AGCAGAAACCAGGGAAAGCCCCTAAGCTCCTGATCTATGC<br>TGCATCCAGTTTGCAAAGTGGGGTCCCATCAAGGTTCAGT<br>GGCAGTGGATCTGGGACAGATTTCACTCTCACCATCAGCA<br>GTCTGCAACCTGAAGATTTTGCAACTTACTACTGTCAACA<br>GAGTTACAGTACCCCTCTCACTTTCGGCGGCGGAACAAAG<br>GTGGAGATCAAG (SEQ ID NO: 275) |
| QVQLQESGPGLVKP<br>SQTLSLTCTVSGGSI<br>SSGGYYWSWIRQPP<br>GKGLEWIGYIYYSG<br>STYYNPSLKSRVTIS<br>VDTSKNQFSLKLSS<br>VTAADTAVYYCAR<br>HYYYYYMDVWGK<br>GTTVTVSSGGGGSG<br>GGGSGGGGSGGDIQ<br>MTQSPSSLSASVGD<br>RVTITCRASQSISSY<br>LNWYQQKPGKAPK<br>LLIYAASSLQSGVPS<br>RFSGSGSGTDFTLTI<br>SSLQPEDFATYYCQ<br>QSYSTPLTFGGGTK<br>VEIK (SEQ ID NO:<br>276) | CAGGTGCAGCTGCAGGAAAGCGGCCCTGGCCTGGTGAAA<br>CCCAGCCAGACCCTGAGCCTGACCTGCACAGTGTCCGGCG<br>GCTCGATCAGCAGCGGCGGCTACTACTGGTCCTGGATCAG<br>ACAGCCCCCTGGCAAGGGCCTGGAATGGATCGGCTACATC<br>TACTACAGCGGCAGCACCTACTACAACCCCAGCCTGAAGT<br>CCAGAGTGACCATCAGCGTGGACACCAGCAAGAACCAGT<br>TCAGCCTGAAGCTGAGCAGCGTGACAGCCGCCGACACCG<br>CTGTGTATTACTGTGCGAGACACTACTACTACTACTACAT<br>GGACGTCTGGGGCAAAGGGACCACGGTCACCGTGTCCTCA<br>GGCGGAGGTGGAAGCGGAGGGGGAGGATCTGGCGGCGGA<br>GGAAGCGGAGGCGACATCCAGATGACCCAGTCTCCATCCT<br>CCCTGTCTGCATCTGTAGGAGACAGAGTCACCATCACTTG<br>CCGGGCAAGTCAGAGCATTAGCAGCTATTTAAATTGGTAT<br>CAGCAGAAACCAGGGAAAGCCCCTAAGCTCCTGATCTATG<br>CTGCATCCAGTTTGCAAAGTGGGGTCCCATCAAGGTTCAG<br>TGGCAGTGGATCTGGGACAGATTTCACTCTCACCATCAGC<br>AGTCTGCAACCTGAAGATTTTGCAACTTACTACTGTCAAC<br>AGAGTTACAGTACCCCTCTCACTTTCGGCGGCGGAACAAA<br>GGTGGAGATCAAG (SEQ ID NO: 277) |

| HLA-C*07 antigen binding domains | |
|---|---|
| C7-45 | EVQLLESGGGLVQPGGSLRLSCAASGFTFSSYAMSWVRQAPGKGLEWVSAISGSG<br>GSTYYADSVKGRFTISRDNSKNTLYLQMNSLRAEDTAVYYCAVSFDWFDPWGQG<br>TLVTVSSGGGGSGGGGSGGGGSGGDIQMTQSPSSLSASVGDRVTITCRASQSISSY<br>LNWYQQKPGKAPKLLIYAASSLQSGVPSRFSGSGSGTDFTLTISSLQPEDFATYYCQ<br>QSYSTPLTFGGGTKVEIK (SEQ ID NO: 278) |
| C7-44 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARERSISPYYYYYMDV<br>WGKGTTVTVSSGGGGSGGGGSGGGGSGGDIQMTQSPSSLSASVGDRVTITCRAS<br>QSISSYLNWYQQKPGKAPKLLIYAASSLQSGVPSRFSGSGSGTDFTLTISSLQPEDFA<br>TYYCQQSYSTPLTFGGGTKVEIK (SEQ ID NO: 279) |
| C7-43 | QLQLQESGPGLVKPSETLSLTCTVSGGSISSSSYYWGWIRQPPGKGLEWIGSIYYSG<br>STYYNPSLKSRVTISVDTSKNQFSLKLSSVTAADTAVYYCARDSVIWYWFDPWGQG<br>TLVTVSSGGGGSGGGGSGGGGSGGQSVLTQPPSASGTPGQRVTISCSGSSSNIGS<br>NTVNWYQQLPGTAPKLLIYSNNQRPSGVPDRFSGSKSGTSASLAISGLQSEDEADY<br>YCAAWDDSLNGWVFGGGTKLTVL (SEQ ID NO: 280) |
| C7-42 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCAREEILPRLSYYYYMDV<br>WGKGTTVTVSSGGGGSGGGGSGGGGSGGDIQMTQSPSSLSASVGDRVTITCRAS<br>QSISSYLNWYQQKPGKAPKLLIYAASSLQSGVPSRFSGSGSGTDFTLTISSLQPEDFA<br>TYYCQQSYSTPLTFGGGTKVEIK (SEQ ID NO: 281) |
| C7-41 | QVQLVQSGSELKKPGASVKVSCKASGYTFTSYAMNWVRQAPGQGLEWMGWIN<br>TNTGNPTYAQGFTGRFVFSFDTSVSTAYLQICSLKAEDTAVYYCARGGRAHSSWYF<br>DLWGRGTLVTVSSGGGGSGGGGSGGGGSGGDIQMTQSPSSLSASVGDRVTITCR<br>ASQSISSYLNWYQQKPGKAPKLLIYAASSLQSGVPSRFSGSGSGTDFTLTISSLQPED<br>FATYYCQQSYSTPLTFGGGTKVEIK (SEQ ID NO: 282) |
| C7-40 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARDRIKILPRLGYYYYM<br>DVWGKGTTVIVSSGGGGSGGGGSGGGGSGGDIQMTQSPSSLSASVGDRVTITC<br>RASQSISSYLNWYQQKPGKAPKLLIYAASSLQSGVPSRFSGSGSGTDFTLTISSLQPE<br>DFATYYCQQSYSTPLTFGGGTKVEIK (SEQ ID NO: 283) |
| C7-39 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARDTVIHYYYYMDVW |

TABLE 5-continued

| | HLA scFv binding domains |
|---|---|
| | GKGTTVTVSSGGGGSGGGGSGGGGSGGDIQMTQSPSSLSASVGDRVTITCRASQ<br>SISSYLNWYQQKPGKAPKLLIYAASSLQSGVPSRFSGSGSGTDFTLTISSLQPEDFAT<br>YYCQQSYSTPLTFGGGTKVEIK (SEQ ID NO: 284) |
| C7-38 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARDVIVEVFLSYYYYMD<br>VWGKGTTVTVSSGGGGSGGGGSGGGGSGGDIQMTQSPSSLSASVGDRVTITCR<br>ASQSISSYLNWYQQKPGKAPKLLIYAASSLQSGVPSRFSGSGSGTDFTLTISSLQPED<br>FATYYCQQSYSTPLTFGGGTKVEIK (SEQ ID NO: 285) |
| C7-37 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARDIFlHYYYYMDVWG<br>KGTTVTVSSGGGGSGGGGSGGGGSGGDIQMTQSPSSLSASVGDRVTITCRASQSI<br>SSYLNWYQQKPGKAPKLLIYAASSLQSGVPSRFSGSGSGTDFTLTISSLQPEDFATYY<br>CQQSYSTPLTFGGGTKVEIK (SEQ ID NO: 286) |
| C7-36 | EVQLVESGGGLVQPGGSLRLSCAASGFTFSSYSMNWVRQAPGKGLEWVSYISSSS<br>STIYYADSVKGRFTISRDNAKNSLYLQMNSLRAEDTAVYYCARDGTFYSYSPYYFDY<br>WGQGTLVTVSSGGGGSGGGGSGGGGSGGDIQMTQSPSSLSASVGDRVTITCRA<br>SQSISSYLNWYQQKPGKAPKLLIYAASSLQSGVPSRFSGSGSGTDFTLTISSLQPEDF<br>ATYYCQQSYSTPLTFGGGTKVEIK (SEQ ID NO: 287) |
| C7-35 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCAREWIKILPRLGYYYYM<br>DVWGKGTTVTVSSGGGGSGGGGSGGGGSGGDIQMTQSPSSLSASVGDRVTITC<br>RASQSISSYLNWYQQKPGKAPKLLIYAASSLQSGVPSRFSGSGSGTDFTLTISSLQPE<br>DFATYYCQQSYSTPLTFGGGTKVEIK (SEQ ID NO: 288) |
| C7-34 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARDRSLYYYYYMDVW<br>GKGTTVTVSSGGGGSGGGGSGGGGSGGDIQMTQSPSSLSASVGDRVTITCRASQ<br>SISSYLNWYQQKPGKAPKLLIYAASSLQSGVPSRFSGSGSGTDFTLTISSLQPEDFAT<br>YYCQQSYSTPLTFGGGTKVEIK (SEQ ID NO: 289) |
| C7-33 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARDKILAPNYYYYMDV<br>WGKGTTVTVSSGGGGSGGGGSGGGGSGGDIQMTQSPSSLSASVGDRVTITCRAS<br>QSISSYLNWYQQKPGKAPKLLIYAASSLQSGVPSRFSGSGSGTDFTLTISSLQPEDFA<br>TYYCQQSYSTPLTFGGGTKVEIK (SEQ ID NO: 290) |
| C7-32 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCAREKSWKYFYYYYYYM<br>DVWGKGTTVTVSSGGGGSGGGGSGGGGSGGDIQMTQSPSSLSASVGDRVTITC<br>RASQSISSYLNWYQQKPGKAPKLLIYAASSLQSGVPSRFSGSGSGTDFTLTISSLQPE<br>DFATYYCQQSYSTPLTFGGGTKVEIK (SEQ ID NO: 291) |
| C7-31 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARENTSTIPYYYYYMDV<br>WGKGTTVTVSSGGGGSGGGGSGGGGSGGDIQMTQSPSSLSASVGDRVTITCRAS<br>QSISSYLNWYQQKPGKAPKLLIYAASSLQSGVPSRFSGSGSGTDFTLTISSLQPEDFA<br>TYYCQQSYSTPLTFGGGTKVEIK (SEQ ID NO: 292) |
| C7-30 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCAREDVDKNTSTIYYYYY<br>YMDVWGKGTTVTVSSGGGGSGGGGSGGGGSGGDIQMTQSPSSLSASVGDRVTI<br>TCRASQSISSYLNWYQQKPGKAPKLLIYAASSLQSGVPSRFSGSGSGTDFTLTISSLQ<br>PEDFATYYCQQSYSTPLTFGGGTKVEIK (SEQ ID NO: 293) |
| C7-29 | QVQLVESGGGLVKPGGSLRLSCAASGFTFSDYYMSWIRQAPGKGLEWVSYISSSG<br>STIYYADSVKGRFTISRDNAKNSLYLQMNSLRAEDTAVYYCARDGGDIVSSSAIYWY<br>FDLWGRGTLVTVSSGGGGSGGGGSGGGGSGGAIQLTQSPSSLSASVGDRVTITCR<br>ASQGISSALAWYQQKPGKAPKLLIYDASSLESGVPSRFSGSGSGTDFTLTISSLQPED<br>FATYYCQQFNSYPLTFGGGTKVEIK (SEQ ID NO: 294) |
| C7-28 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARDLILPPYYYYYMDV<br>WGKGTTVTVSSGGGGSGGGGSGGGGSGGDIQMTQSPSSLSASVGDRVTITCRAS<br>QSISSYLNWYQQKPGKAPKLLIYAASSLQSGVPSRFSGSGSGTDFTLTISSLQPEDFA<br>TYYCQQSYSTPLTFGGGTKVEIK (SEQ ID NO: 295) |
| C7-27 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARETWIKILPRYYYYYYY<br>MDVWGKGTTVTVSSGGGGSGGGGSGGGGSGGDIQMTQSPSSLSASVGDRVTIT<br>CRASQSISSYLNWYQQKPGKAPKLLIYAASSLQSGVPSRFSGSGSGTDFTLTISSLQP<br>EDFATYYCQQSYSTPLTFGGGTKVEIK (SEQ ID NO: 296) |
| C7-26 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARDLSRYYYYYMDVW |

TABLE 5-continued

| HLA scFv binding domains | |
|---|---|
| | GKGTTVTVSSGGGGSGGGGSGGGGSGGDIQMTQSPSSLSASVGDRVTITCRASQ SISSYLNWYQQKPGKAPKLLIYAASSLQSGVPSRFSGSGSGTDFTLTISSLQPEDFAT YYCQQSYSTPLTFGGGTKVEIK (SEQ ID NO: 297) |
| C7-25 | EVQLVESGGGLVQPGGSLRLSCAASGFTFSSYSMNWVRQAPGKGLEWVSYISSSS STIYYADSVKGRFTISRDNAKNSLYLQMNSLRAEDTAVYYCAREHIVLCFDYWGQG TLVTVSSGGGGSGGGGSGGGGSGGDIQMTQSPSSLSASVGDRVTITCRASQGISS WLAWYQQKPEKAPKSLIYAASSLQSGVPSRFSGSGSGTDFTLTISSLQPEDFATYYC QQYNSYPLTFGGGTKVEIK (SEQ ID NO: 298) |
| C7-24 | QVQLQESGPGLVKPSQTLSLTCTVSGGSISSGGYYWSWIRQPPGKGLEWIGYIYYS GSTYYNPSLKSRVTISVDTSKNQFSLKLSSVTAADTAVYYCARDKILPRPYYYYYMDV WGKGTTVTVSSGGGGSGGGGSGGGGSGGDIQMTQSPSSLSASVGDRVTITCRAS QSISSYLNWYQQKPGKAPKLLIYAASSLQSGVPSRFSGSGSGTDFTLTISSLQPEDFA TYYCQQSYSTPLTFGGGTKVEIK (SEQ ID NO: 299) |
| C7-23 | QVQLVQSGAEVKKPGASVKVSCKASGYTFTSYGISWVRQAPGQGLEWMGWISA YNGNTNYAQKLQGRVTMTTDTSTSTAYMELRSLRSDDTAVYYCARGSNEYFQHW GQGTLVTVSSGGGGSGGGGSGGGGSGGQSALTQPPSASGSPGQSVTISCTGTSS DVGGYNYVSWYQQHPGKAPKLMIYEVSKRPSGVPDRFSGSKSGNTASLTVSGLQ AEDEADYYCSSYAGSNNWVFGGGTKLTVL (SEQ ID NO: 300) |
| C7-22 | QVQLVQSGSELKKPGASVKVSCKASGYTFTSYAMNWVRQAPGQGLEWMGWIN TNTGNPTYAQGFTGRFVFSFDTSVSTAYLQICSLKAEDTAVYYCARGTSYWYFDLW GRGTLVTVSSGGGGSGGGGSGGGGSGGDIQMTQSPSSLSASVGDRVTITCRASQ SISSYLNWYQQKPGKAPKLLIYAASSLQSGVPSRFSGSGSGTDFTLTISSLQPEDFAT YYCQQSYSTPLTFGGGTKVEIK (SEQ ID NO: 301) |
| C7-21 | QVQLQESGPGLVKPSQTLSLTCTVSGGSISSGGYYWSWIRQPPGKGLEWIGYIYYS GSTYYNPSLKSRVTISVDTSKNQFSLKLSSVTAADTAVYYCAREEIVEVFYYYYMDV WGKGTTVTVSSGGGGSGGGGSGGGGSGGDIQMTQSPSSLSASVGDRVTITCRAS QSISSYLNWYQQKPGKAPKLLIYAASSLQSGVPSRFSGSGSGTDFTLTISSLQPEDFA TYYCQQSYSTPLTFGGGTKVEIK (SEQ ID NO: 302) |
| C7-20 | EVQLLESGGGLVQPGGSLRLSCAASGFTFSSYAMSWVRQAPGKGLEWVSAISGSG GSTYYADSVKGRFTISRDNSKNTLYLQMNSLRAEDTAVYYCAKVDDYYFDYWGQG TLVTVSSGGGGSGGGGSGGGGSGGDIQMTQSPSSLSASVGDRVTITCRASQSISSY LNWYQQKPGKAPKLLIYAASSLQSGVPSRFSGSGSGTDFTLTISSLQPEDFATYYCQ QSYSTPLTFGGGTKVEIK (SEQ ID NO: 303) |
| C7-19 | EVQLVESGGGLVQPGGSLRLSCAASGFTFSSYWMHWVRQAPGKGLVWVSRINS DGSSTSYADSVKGRFTISRDNAKNTLYLQMNSLRAEDTAVYYCAWSTNILLSYTKA FDIWGQGTMVTVSSGGGGSGGGGSGGGGSGGDIQMTQSPSSLSASVGDRVTIT CRASQSISSYLNWYQQKPGKAPKLLIYAASSLQSGVPSRFSGSGSGTDFTLTISSLQP EDFATYYCQQSYSTPLTFGGGTKVEIK (SEQ ID NO: 304) |
| C7-18 | QVQLQESGPGLVKPSQTLSLTCTVSGGSISSGGYYWSWIRQPPGKGLEWIGYIYYS GSTYYNPSLKSRVTISVDTSKNQFSLKLSSVTAADTAVYYCARDKTYYYYYYMDVW GKGTTVTVSSGGGGSGGGGSGGGGSGGDIQMTQSPSSLSASVGDRVTITCRASQ SISSYLNWYQQKPGKAPKLLIYAASSLQSGVPSRFSGSGSGTDFTLTISSLQPEDFAT YYCQQSYSTPLTFGGGTKVEIK (SEQ ID NO: 305) |
| C7-17 | QVQLQESGPGLVKPSQTLSLTCTVSGGSISSGGYYWSWIRQPPGKGLEWIGYIYYS GSTYYNPSLKSRVTISVDTSKNQFSLKLSSVTAADTAVYYCAREKYFHDKYFHDYYYY YMDVWGKGTTVTVSSGGGGSGGGGSGGGGSGGDIQMTQSPSSLSASVGDRVTI TCRASQSISSYLNWYQQKPGKAPKLLIYAASSLQSGVPSRFSGSGSGTDFTLTISSLQ PEDFATYYCQQSYSTPLTFGGGTKVEIK (SEQ ID NO: 306) |
| C7-16 | QVQLQESGPGLVKPSQTLSLTCTVSGGSISSGGYYWSWIRQPPGKGLEWIGYIYYS GSTYYNPSLKSRVTISVDTSKNQFSLKLSSVTAADTAVYYCARDTSVYYYYYMDVW GKGTTVTVSSGGGGSGGGGSGGGGSGGDIQMTQSPSSLSASVGDRVTITCRASQ SISSYLNWYQQKPGKAPKLLIYAASSLQSGVPSRFSGSGSGTDFTLTISSLQPEDFAT YYCQQSYSTPLTFGGGTKVEIK (SEQ ID NO: 307) |
| C7-15 | QVQLQESGPGLVKPSQTLSLTCTVSGGSISSGGYYWSWIRQPPGKGLEWIGYIYYS GSTYYNPSLKSRVTISVDTSKNQFSLKLSSVTAADTAVYYCAREKILPYYYYYYMDV WGKGTTVTVSSGGGGSGGGGSGGGGSGGDIQMTQSPSSLSASVGDRVTITCRAS QSISSYLNWYQQKPGKAPKLLIYAASSLQSGVPSRFSGSGSGTDFTLTISSLQPEDFA TYYCQQSYSTPLTFGGGTKVEIK (SEQ ID NO: 308) |
| C7-14 | EVQLVESGGGLVQPGGSLRLSCAASGFTFSSYSMNWVRQAPGKGLEWVSYISSSS STIYYADSVKGRFTISRDNAKNSLYLQMNSLRAEDTAVYYCAIQWIYIYINPRGFIFL HDAFDIWGQGTMVTVSSGGGGSGGGGSGGGGSGGQSVLTQPPSASGTPGQRV TISCSGSSSNIGSNTVNWYQQLPGTAPKLLIYSNNQRPSGVPDRFSGSKSGTSASLA ISGLQSEDEADYYCAAWDDSLNGWVFGGGTKLTVL (SEQ ID NO: 309) |
| C7-13 | QVQLQQSGPGLVKPSQTLSLTCAISGDSVSSNSAAWNWIRQSPSRGLEWLGRTYY RSKWYNDYAVSVKSRITINPDTSKNQFSLQLNSVTPEDTAVYYCAKEDVDFHHDAF |

TABLE 5-continued

| HLA scFv binding domains | |
|---|---|
| | DIWGQGTMVTVSSGGGGSGGGGSGGGGSGGDIQMTQSPSSLSASVGDRVTITC<br>RASQSISSYLNWYQQKPGKAPKLLIYAASSLQSGVPSRFSGSGSGTDFTLTISSLQPE<br>DFATYYCQQSYSTPLTFGGGTKVEIK (SEQ ID NO: 310) |
| C7-12 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCAREGVDKNTSTIYYYYY<br>YMDVWGKGTTVTVSSGGGGSGGGGSGGGGSGGDIQMTQSPSSLSASVGDRVTI<br>TCRASQSISSYLNWYQQKPGKAPKLLIYAASSLQSGVPSRFSGSGSGTDFTLTISSLQ<br>PEDFATYYCQQSYSTPLTFGGGTKVEIK (SEQ ID NO: 311) |
| C7-11 | EVQLVESGGGLVQPGGSLRLSCAASGFTFSSYSMNWVRQAPGKGLEWVSYISSSS<br>STIYYADSVKGRFTISRDNAKNSLYLQMNSLRAEDTAVYYCARDRRGYFDLWGRG<br>TLVTVSSGGGGSGGGGSGGGGSGGDIQMTQSPSSLSASVGDRVTITCRASQGISS<br>WLAWYQQKPEKAPKSLIYAASSLQSGVPSRFSGSGSGTDFTLTISSLQPEDFATYYC<br>QQYNSYPLTFGGGTKVEIK (SEQ ID NO: 312) |
| C7-10 | EVQLVQSGAEVKKPGATVKISCKVSGYTFTDYYMHWVQQAPGKGLEWMGLVDP<br>EDGETIYAEKFQGRVTITADTSTDTAYMELSSLRSEDTAVYYCATGIHVDIRSMED<br>WFDPWGQGTLVTVSSGGGGSGGGGSGGGGSGGDIQMTQSPSSLSASVGDRVTI<br>TCRASQSISSYLNWYQQKPGKAPKLLIYAASSLQSGVPSRFSGSGSGTDFTLTISSLQ<br>PEDFATYYCQQSYSTPLTFGGGTKVEIK (SEQ ID NO: 313) |
| C7-9 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARDIGTSYYYYMDVW<br>GKGTTVTVSSGGGGSGGGGSGGGGSGGDIQMTQSPSSLSASVGDRVTITCRASQ<br>SISSYLNWYQQKPGKAPKLLIYAASSLQSGVPSRFSGSGSGTDFTLTISSLQPEDFAT<br>YYCQQSYSTPLTFGGGTKVEIK (SEQ ID NO: 314) |
| C7-8 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCAREVVEVFLYYYYYMD<br>VWGKGTTVTVSSGGGGSGGGGSGGGGSGGDIQMTQSPSSLSASVGDRVTITCR<br>ASQSISSYLNWYQQKPGKAPKLLIYAASSLQSGVPSRFSGSGSGTDFTLTISSLQPED<br>FATYYCQQSYSTPLTFGGGTKVEIK (SEQ ID NO: 315) |
| C7-7 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARDLYYYYYYYMDVW<br>GKGTTVTVSSGGGGSGGGGSGGGGSGGDIQMTQSPSSLSASVGDRVTITCRASQ<br>SISSYLNWYQQKPGKAPKLLIYAASSLQSGVPSRFSGSGSGTDFTLTISSLQPEDFAT<br>YYCQQSYSTPLTFGGGTKVEIK (SEQ ID NO: 316) |
| C7-6 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARESWKYFYPRGS1FlH<br>YYYYMDVWGKGTTVTVSSGGGGSGGGGSGGGGSGGDIQMTQSPSSLSASVGD<br>RVTITCRASQSISSYLNWYQQKPGKAPKLLIYAASSLQSGVPSRFSGSGSGTDFTLTI<br>SSLQPEDFATYYCQQSYSTPLTFGGGTKVEIK (SEQ ID NO: 317) |
| C7-5 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARDRIVEVFYYYYMDV<br>WGKGTTVTVSSGGGGSGGGGSGGGGSGGDIQMTQSPSSLSASVGDRVTITCRAS<br>QSISSYLNWYQQKPGKAPKLLIYAASSLQSGVPSRFSGSGSGTDFTLTISSLQPEDFA<br>TYYCQQSYSTPLTFGGGTKVEIK (SEQ ID NO: 318) |
| C7-4 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCAREKYFHDWLYYYYYM<br>DVWGKGTTVIVSSGGGGSGGGGSGGGGSGGDIQMTQSPSSLSASVGDRVTITC<br>RASQSISSYLNWYQQKPGKAPKLLIYAASSLQSGVPSRFSGSGSGTDFTLTISSLQPE<br>DFATYYCQQSYSTPLTFGGGTKVEIK (SEQ ID NO: 319) |
| C7-3 | QVQLQESGPGLVKPSQTLSLTCTVSGGSISSGGYYWSWIRQPPGKGLEWIGYIYYS<br>GSTYYNPSLKSRVTISVDTSKNQFSLKLSSVTAADTAVYYCARDLVDKNTSYYYYYM<br>DVWGKGTTVIVSSGGGGSGGGGSGGGGSGGDIQMTQSPSSLSASVGDRVTITC<br>RASQSISSYLNWYQQKPGKAPKLLIYAASSLQSGVPSRFSGSGSGTDFTLTISSLQPE<br>DFATYYCQQSYSTPLTFGGGTKVEIK (SEQ ID NO: 320) |
| C7-2 | QVQLVQSGAEVKKPGASVKVSCKASGYTFTSYGISWVRQAPGQGLEWMGWISA<br>YNGNTNYAQKLQGRVTMTTDTSTSTAYMELRSLRSDDTAVYYCARVQNEYFQH<br>WGQGTLVTVSSGGGGSGGGGSGGGGSGGQSALTQPPSASGSPGQSVTISCTGTS<br>SDVGGYNYVSWYQQHPGKAPKLMIYEVSKRPSGVPDRFSGSKSGNTASLTVSGLQ<br>AEDEADYYCSSYAGSNNWVFGGGTKLTVL (SEQ ID NO: 321) |
| C7-1 | QVQLVESGGGLVKPGGSLRLSCAASGFTFSDYYMSWIRQAPGKGLEWVSYISSSG<br>STIYYADSVKGRFTISRDNAKNSLYLQMNSLRAEDTAVYYCATANWFDPWGQGTL<br>VTVSSGGGGSGGGGSGGGGSGGDIQMTQSPSSVSASVGDRVTITCRASQGISSW<br>LAWYQQKPGKAPKLLIYAASSLQSGVPSRFSGSGSGTDFTLTISSLQPEDFATYYCQ<br>QANSFPLTFGGGTKVEIK (SEQ ID NO: 322) |

TABLE 5-continued

| HLA scFv binding domains | |
|---|---|
| HLA-A*03 scFv Sequences | |
| 15 | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARERVSQRGAFDIWGQGTMVTVSSGGGGSGGGGSGGGGSGGDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK (SEQ ID NO: 323) |
| 16 | EVQLVESGGGLVQPGGSLRLSCAASGFTFSSYSMNWVRQAPGKGLEWVSYISSSSSTIYYADSVKGRFTISRDNAKNSLYLQMNSLRAEDTAVYYCARGNPDKDPFDYWGQGTLVTVSSGGGGSGGGGSGGGGSGGDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK (SEQ ID NO: 324) |
| 17 | QVQLQESGPGLVKPSETLSLTCTVSGGSVSSGSYYWSWIRQPPGKGLEWIGYIYYSGSTNYNPSLKSRVTISVDTSKNQFSLKLSSVTAADTAVYYCARDFYCTNWYFDLWGRGTLVTVSSGGGGSGGGGSGGGGSGGDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK (SEQ ID NO: 325) |
| 18 | QVQLQESGPGLVKPSETLSLTCTVSGGSISSYYWSWIRQPPGKGLEWIGYIYYSGSTNYNPSLKSRVTISVDTSKNQFSLKLSSVTAADTAVYYCARESSSGSYWYFDLWGRGTLVTVSSGGGGSGGGGSGGGGSGGDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK (SEQ ID NO: 326) |
| 19 | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARDSGYKYNLYYYYYMDVWGKGTTVTVSSGGGGSGGGGSGGGGSGGDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK (SEQ ID NO: 327) |
| 20 | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARGGDLSHYYYYMDVWGKGTTVTVSSGGGGSGGGGSGGGGSGGQTVVTQEPSLTVSPGGTVTLTCASSTGAVTSGYYPNWFQQKPGQAPRALIYSTSNKHSWTPARFSGSLLGGKAALTLSGVQPEDEAEYYCLLYYGGAQWVFGGGTKLTVL (SEQ ID NO: 328) |
| 21 | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARENRRYNSCYYFDYWGQGTLVTVSSGGGGSGGGGSGGGGSGGDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK (SEQ ID NO: 329) |
| 22 | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARGGDLSHYYYYLDVWGKGTTVTVSSGGGGSGGGGSGGGGSGGQTVVTQEPSLTVSPGGTVTLTCASSTGAVTSGYYPNWFQQKPGQAPRALIYSTSNKHSWTPARFSGSLLGGKAALTLSGVQPEDEAEYYCLLYYGGAQWVFGGGTKLTVL (SEQ ID NO: 330) |
| 23 | EVQLVESGGGLVQPGGSLRLSCAASGFTVSSNYMSWVRQAPGKGLEWVSVIYSGGSTYYADSVKGRFTISRDNSKNTLYLQMNSLRAEDTAVYYCARATLLSLSYDAFDIWGQGTMVTVSSGGGGSGGGGSGGGGSGGDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK (SEQ ID NO: 331) |
| 24 | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARGGDLSHYYYMDVWGKGTTVTVSSGGGGSGGGGSGGGGSGGQTVVTQEPSLTVSPGGTVTLTC |

TABLE 5-continued

| HLA scFv binding domains | |
|---|---|
| | ASSTGAVTSGYYPNWFQQKPGQAPRALIYSTSNKHSWTPARFSGSLLGGKAALTLSGVQPEDEAEYYCLLYYGGAQWVFGGGTKLTVL (SEQ ID NO: 332) |
| 25 | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARERDRWFDPWGQGTLVTVSSGGGGSGGGGSGGGGSGGDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK (SEQ ID NO: 333) |
| 26 | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARETPPSLGAFDIWGQGTMVTVSSGGGGSGGGGSGGGGSGGQSALTQPPSASGSPGQSVTISCTGTSSDVGGYNYVSWYQQHPGKAPKLMIYEVSKRPSGVPDRFSGSKSGNTASLTVSGLQAEDEADYYCSSYAGSNNWVFGGGTKLTVL(SEQ ID NO: 334) |
| 27 | QLQLQESGPGLVKPSETLSLTCTVSGGSISSSSYYWGWIRQPPGKGLEWIGSIYYSGSTYYNPSLKSRVTISVDTSKNQFSLKLSSVTAADTAVYYCAREAYCLSDSYWYFDLWGRGTLVTVSSGGGGSGGGGSGGGGSGGQSVLTQPPSASGTPGQRVTISCSGSSSNIGSNTVNWYQQLPGTAPKLLIYSNNQRPSGVPDRFSGSKSGTSASLAISGLQSEDEADYYCAAWDDSLNGWVFGGGTKLTVL (SEQ ID NO: 335) |
| 28 | QVQLQESGPGLVKPSQTLSLTCTVSGGSISSGGYYWSWIRQPPGKGLEWIGYIYYSGSTYYNPSLKSRVTISVDTSKNQFSLKLSSVTAADTAVYYCARESWKYFYPRGYMDVWGKGTTVTVSSGGGGSGGGGSGGGGSGGDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK (SEQ ID NO: 336) |
| **HLA-A*01 scFv Sequences** | |
| A1-9 | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARGGWTAWYYYMDVWGKGTTVTVSSGGGGSGGGGSGGGGSGGQTVVTQEPSLTVSPGGTVTLTCASSTGAVTSGYYPNWFQQKPGQAPRALIYSTSNKHSWTPARFSGSLLGGKAALTLSGVQPEDEAEYYCLLYYGGAQWVFGGGTKLTVL (SEQ ID NO: 337) |
| A1-8 | EVQLVESGGGLVQPGGSLRLSCAASGFTFSSYSMNWVRQAPGKGLEWVSYISSSSSTIYYADSVKGRFTISRDNAKNSLYLQMNSLRAEDTAVYYCARAKYYYMDVWGKGTTVTVSSGGGGSGGGGSGGGGSGGQSVLTQPPSASGTPGQRVTISCSGSSSNIGSNTVNWYQQLPGTAPKLLIYSNNQRPSGVPDRFSGSKSGTSASLAISGLQSEDEADYYCAAWDDSLNGWVFGGGTKLTVL (SEQ ID NO: 338) |
| A1-7 | QVQLQESGPGLVKPSQTLSLTCTVSGGSISSGGYYWSWIRQPPGKGLEWIGYIYYSGSTYYNPSLKSRVTISVDTSKNQFSLKLSSVTAADTAVYYCARDQVDKNTYYYYMDVWGKGTTVTVSSGGGGSGGGGSGGGGSGGDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK (SEQ ID NO: 339) |
| A1-6 | QVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARACQLAEYFQHWGQGTLVTVSSGGGGSGGGGSGGGGSGGDIQMTQSPSSVSASVGDRVTITCRASQGISSWLAWYQQKPGKAPKLLIYAASSLQSGVPSRFSGSGSGTDFTLTISSLQPEDFATYYCQQANSFPLTFGGGTKVEIK (SEQ ID NO: 340) |
| A1-5 | QVQLQESGPGLVKPSQTLSLTCTVSGGSISSGGYYWSWIRQPPGKGLEWIGYIYYSGSTYYNPSLKSRVTISVDTSKNQFSLKLSSVTAADTAVYYCARDRVDKNTSYYYMDVWGKGTTVTVSSGGGGSGGGGSGGGGSGGDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK (SEQ ID NO: 341) |

TABLE 5-continued

| HLA scFv binding domains | |
|---|---|
| A1-4 | QVQLQESGPGLVKPSDTLSLTCAVSGYSISSSNWWGWIRQPP GKGLEWIGYIYYSGSTYYNPSLKSRVTMSVDTSKNQFSLKLS SVTAVDTAVYYCARRVQLKLVHWFDPWGQGTLVTVSSGGG GSGGGGSGGGGSGGDIQMTQSPSSLSASVGDRVTITCRASQS ISSYLNWYQQKPGKAPKLLIYAASSLQSGVPSRFSGSGSGTDF TLTISSLQPEDFATYYCQQSYSTPLTFGGGTKVEIK (SEQ ID NO: 342) |
| A1-3 | QVQLVQSGAEVKKPGASVKVSCKASGYTFTSYDINWVRQA TGQGLEWMGWMNPNSGNTGYAQKFQGRVTMTRNTSISTA YMELSSLRSEDTAVYYCATYYDYVTVFYFQHWGQGTLVTV SSGGGGSGGGGSGGGGSGGDIQMTQSPSSLSASVGDRVTITC RASQSISSYLNWYQQKPGKAPKLLIYAASSLQSGVPSRFSGS GSGTDFTLTISSLQPEDFATYYCQQSYSTPLTFGGGTKVEIK (SEQ ID NO: 343) |
| A1-2 | QLQLQESGSGLVKPSQTLSLTCAVSGGSISSGGYSWSWIRQPP GKGLEWIGYIYHSGSTYYNPSLKSRVTISVDRSKNQFSLKLSS VTAADTAVYYCARESYPSFYAFDIWGQGTMVTVSSGGGGS GGGGSGGGGSGGDIQMTQSPSSLSASVGDRVTITCRASQSISS YLNWYQQKPGKAPKLLIYAASSLQSGVPSRFSGSGSGTDFTL TISSLQPEDFATYYCQQSYSTPLTFGGGTKVEIK (SEQ ID NO: 344) |
| A1-1 | QITLKESGPTLVKPTQTLTLTCTFSGFSLSTSGVGVGWIRQPP GKALEWLALIYWNDDKRYSPSLKSRLTITKDTSKNQVVLTM TNMDPVDTATYYCAHSNMWSYSLNDYYFDYWGQGTLVTV SSGGGGSGGGGSGGGGSGGDIQMTQSPSSLSASVGDRVTITC RASQSISSYLNWYQQKPGKAPKLLIYAASSLQSGVPSRFSGS GSGTDFTLTISSLQPEDFATYYCQQSYSTPLTFGGGTKVEIK (SEQ ID NO: 345) |

In some embodiments, the ligand binding domain of the second, inhibitory receptor comprises an scFv. In some embodiments, the scFv binds to HLA-A*01, HLA-A*02, HLA-A*3, HLA-A*11, HLA-B*07 or HLA-C*07, and comprises a sequence selected from the SEQ ID NOS: 91-102, 250-260, 262, 264, 266, 268, 270, 272, 274, 276, and 278-345, or the group of sequences set forth in Table 5, or a sequence having at least 80%, at least 85%, at least 90%, at least 95%, at least 97% or at least 99% identity thereto. In some embodiments, the scFv binds to HLA-A*01, HLA-A*02, HLA-A*3, HLA-A*11, HLA-B*07 or HLA-C*07, and comprises a sequence selected from the group of sequences set forth in Table 5. In some embodiments, the non-target antigen comprises HLA-A*01, and the non-target extracellular ligand binding domain of the second receptor comprises an HLA-A*01 scFv sequence comprising SEQ ID NOS: 337-345 as set forth in Table 5, or a sequence having at least 80%, at least 85%, at least 90%, at least 95%, at least 97% or at least 99% identity thereto. In some embodiments, the non-target antigen comprises HLA-A*02, and the non-target extracellular ligand binding domain of the second receptor comprises an HLA-A*02 scFv sequence comprising SEQ ID NOS: 91-102 as set forth in Table 5, or a sequence having at least 80%, at least 85%, at least 90%, at least 95%, at least 97% or at least 99% identity thereto. In some embodiments, the non-target antigen comprises HLA-A*03, and the non-target extracellular ligand binding domain of the second receptor comprises an HLA-A*03 scFv sequence comprising SEQ ID NOS: 323-336 as set forth in Table 5, or a sequence having at least 80%, at least 85%, at least 90%, at least 95%, at least 97% or at least 99% identity thereto. In some embodiments, the non-target antigen comprises HLA-A*11, and the non-target extracellular ligand binding domain of the second receptor comprises an HLA-A*11 scFv sequence comprising SEQ ID NOS: 260, 262, 264, 266, 268, 270, 272, 274 or 276 as set forth in Table 5, or a sequence having at least 80%, at least 85%, at least 90%, at least 95%, at least 97% or at least 99% identity thereto. In some embodiments, the non-target antigen comprises HLA-B*07, and the non-target extracellular ligand binding domain of the second receptor comprises an HLA-B*07 scFv sequence comprising SEQ ID NOS: 250-259 as set forth in Table 5, or a sequence having at least 80%, at least 85%, at least 90%, at least 95%, at least 97% or at least 99% identity thereto. In some embodiments, the non-target antigen comprises HLA-C*07, and the non-target extracellular ligand binding domain of the second receptor comprises an HLA-C*07 scFv sequence comprising SEQ ID NOS: 278-322 as set forth in Table 5, or a sequence having at least 80%, at least 85%, at least 90%, at least 95%, at least 97% or at least 99% identity thereto.

Exemplary heavy chain and light chain CDRs (CDR-H1, CDR-H2 and CDR-H3, or CDR-L1, CDR-L2 and CDR-L3, respectively) for HLA-A*01, HLA-A*02, HLA-A*03, HLA-A*11, HLA-B*07 and HLA-C*07 ligand binding domains are shown in table 6 below.

TABLE 6

| CDRs corresponding to HLA antigen binding domains | | | | | |
|---|---|---|---|---|---|
| CDR-L1 | CDR-L2 | CDR-L3 | CDR-H1 | CDR-H2 | CDR-H3 |
| RSSQSIVHSN GNTYLE (SEQ ID NO: 103) | KVSNRFSGVP DR (SEQ ID NO: 104) | FQGSHVPRT (SEQ ID NO: 105) | ASGYTFTSYHI H (SEQ ID NO: 106) | WIYPGNVNT EYNEKFKGK (SEQ ID NO: 107) | EEITYAMDY (SEQ ID NO: 108) |

TABLE 6-continued

| CDRs corresponding to HLA antigen binding domains | | | | | |
|---|---|---|---|---|---|
| CDR-L1 | CDR-L2 | CDR-L3 | CDR-H1 | CDR-H2 | CDR-H3 |
| RSSQSIVHSN GNTYLD (SEQ ID NO: 109) | KVSNRFSGVP DR (SEQ ID NO: 110) | MQGSHVPRT (SEQ ID NO: 111) | SGYTFTSYHM H (SEQ ID NO: 112) | WIYPGDGST QYNEKFKG (SEQ ID NO: 113) | EGTYYAMDY (SEQ ID NO: 114) |
| HLA-A*03 CDRs | | | | | |
| RASQSISSYLN (SEQ ID NO: 346) | AASSLQS (SEQ ID NO: 353) | QQSYSTPLT (SEQ ID NO: 358) | SYGIS (SEQ ID NO: 365) | WISAYNGNT NYAQKLQG (SEQ ID NO: 386) | ERVSQRGAFD I (SEQ ID NO: 405) |
| RASQSISSYLN (SEQ ID NO: 346) | AASSLQS (SEQ ID NO: 353) | QQSYSTPLT (SEQ ID NO: 358) | SYSMN (SEQ ID NO: 366) | YISSSSSTIYYA DSVKG (SEQ ID NO: 387) | GNPDKDPFD Y (SEQ ID NO: 406) |
| RASQSISSYLN (SEQ ID NO: 346) | AASSLQS (SEQ ID NO: 353) | QQSYSTPLT (SEQ ID NO: 358) | SGSYYWS (SEQ ID NO: 367) | YIYYSGSTNYN PSLKS (SEQ ID NO: 388) | DFYCTNWYF DL (SEQ ID NO: 407) |
| RASQSISSYLN (SEQ ID NO: 346) | AASSLQS (SEQ ID NO: 353) | QQSYSTPLT (SEQ ID NO: 358) | SYYWS (SEQ ID NO: 368) | YIYYSGSTNYN PSLKS (SEQ ID NO: 388) | ESSSGSYWYF DL (SEQ ID NO: 408) |
| RASQSISSYLN (SEQ ID NO: 346) | AASSLQS (SEQ ID NO: 353) | QQSYSTPLT (SEQ ID NO: 358) | SYWIG (SEQ ID NO: 369) | IIYPGDSDTRY SPSFQG (SEQ ID NO: 389) | DSGYKYNLYY YYYYMDV (SEQ ID NO: 409) |
| ASSTGAVTSG YYPN (SEQ ID NO: 347) | STSNKHS (SEQ ID NO: 354) | LLYYGGAQW V (SEQ ID NO: 359) | SYGIS (SEQ ID NO: 365) | WISAYNGNT NYAQKLQG (SEQ ID NO: 386) | GGDLSHYYYY MDV (SEQ ID NO: 410) |
| RASQSISSYLN (SEQ ID NO: 346) | AASSLQS (SEQ ID NO: 353) | QQSYSTPLT (SEQ ID NO: 358) | SYGIS (SEQ ID NO: 365) | WISAYNGNT NYAQKLQG (SEQ ID NO: 386) | ENRRYNSCYY FDY (SEQ ID NO: 411) |
| ASSTGAVTSG YYPN (SEQ ID NO: 347) | STSNKHS (SEQ ID NO: 354) | LLYYGGAQW V (SEQ ID NO: 359) | SYGIS (SEQ ID NO: 365) | WISAYNGNT NYAQKLQG (SEQ ID NO: 386) | GGDLSHYYYY LDV (SEQ ID NO: 412) |
| RASQSISSYLN (SEQ ID NO: 346) | AASSLQS (SEQ ID NO: 353) | QQSYSTPLT (SEQ ID NO: 358) | SNYMS (SEQ ID NO: 370) | VIYSGGSTYYA DSVKG (SEQ ID NO: 390) | ATLLSLSYDAF DI (SEQ ID NO: 413) |
| ASSTGAVTSG YYPN (SEQ ID NO: 347) | STSNKHS (SEQ ID NO: 354) | LLYYGGAQW V (SEQ ID NO: 359) | SYGIS (SEQ ID NO: 365) | WISAYNGNT NYAQKLQG (SEQ ID NO: 386) | GGDLSHYYY MDV (SEQ ID NO: 414) |
| RASQSISSYLN (SEQ ID NO: 346) | AASSLQS (SEQ ID NO: 353) | QQSYSTPLT (SEQ ID NO: 358) | SYWIG (SEQ ID NO: 369) | IlYPGDSDTRY SPSFQG (SEQ ID NO: 389) | ERDRWFDP (SEQ ID NO: 415) |
| TGTSSDVGGY NYVS (SEQ ID NO: 348) | EVSKRPS (SEQ ID NO: 355) | SSYAGSNNW V (SEQ ID NO: 360) | SYGIS (SEQ ID NO: 365) | WISAYNGNT NYAQKLQG (SEQ ID NO: 386) | ETPPSLGAFDI (SEQ ID NO: 416) |
| SGSSSNIGSNT VN (SEQ ID NO: 349) | SNNQRPS (SEQ ID NO: 356) | AAWDDSLNG WV (SEQ ID NO: 361) | SSSYYWG (SEQ ID NO: 371) | SIYYSGSTYYN PSLKS (SEQ ID NO: 391) | EAYCLSDSYW YFDL (SEQ ID NO: 417) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | ESWKYFYPRG YMDV (SEQ ID NO: 418) |

TABLE 6-continued

CDRs corresponding to HLA antigen binding domains

| CDR-L1 | CDR-L2 | CDR-L3 | CDR-H1 | CDR-H2 | CDR-H3 |
|---|---|---|---|---|---|
| HLA-B*07 CDRs | | | | | |
| RASENIYSNLA (SEQ ID NO: 350) | AATYLPD (SEQ ID NO: 357) | QHFWVTPYT (SEQ ID NO: 362) | SGYSWH (SEQ ID NO: 373) | YIHFSGSTHYH PSLKS (SEQ ID NO: 393) | GGVVSHYAM DC (SEQ ID NO: 419) |
| HLA-A*11 CDRs | | | | | |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | HYYYYYMDV (SEQ ID NO: 420) |
| RASQSISSYLN (SEQ ID NO: 346) | AASSLQS (SEQ ID NO: 353) | QQSYSTPLT (SEQ ID NO: 358) | TSGVGVG (SEQ ID NO: 374) | LIYWNDDKRY SPSLKS (SEQ ID NO: 394) | KTTSFYFDY (SEQ ID NO: 421) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | HYYYYMDV (SEQ ID NO: 422) |
| RASQSISSYLN (SEQ ID NO: 346) | AASSLQS (SEQ ID NO: 353) | QQSYSTPLT (SEQ ID NO: 358) | SYWMH (SEQ ID NO: 375) | RINSDGSSTSY ADSVKG (SEQ ID NO: 395) | GVLLYNWFD P (SEQ ID NO: 423) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | HYYYYYLDV (SEQ ID NO: 424) |
| RASQSISSYLN (SEQ ID NO: 346) | AASSLQS (SEQ ID NO: 353) | QQSYSTPLT (SEQ ID NO: 358) | SYDMH (SEQ ID NO: 376) | AIGTAGDTYY PGSVKG (SEQ ID NO: 396) | DLPGSYWYFD L (SEQ ID NO: 425) |
| RASQSISSYLN (SEQ ID NO: 346) | AASSLQS (SEQ ID NO: 353) | QQSYSTPLT (SEQ ID NO: 358) | SYAMH (SEQ ID NO: 377) | WINAGNGNT KYSQKFQG (SEQ ID NO: 397) | EGNGANPDA FDI (SEQ ID NO: 426) |
| RASQSISSYLN (SEQ ID NO: 346) | AASSLQS (SEQ ID NO: 353) | QQSYSTPLT (SEQ ID NO: 358) | TSGVGVG (SEQ ID NO: 374) | LIYWNDDKRY SPSLKS (SEQ ID NO: 394) | RHMRLSCFDY (SEQ ID NO: 427) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | HYYYYSMDV (SEQ ID NO: 428) |
| HLA-C*07 CDR | | | | | |
| RASQSISSYLN (SEQ ID NO: 346) | AASSLQS (SEQ ID NO: 353) | QQSYSTPLT (SEQ ID NO: 358) | SYAMS (SEQ ID NO: 378) | AISGSGGSTYY ADSVKG (SEQ ID NO: 398) | SFDWFDP (SEQ ID NO: 429) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | ERSISPYYYYY MDV (SEQ ID NO: 430) |
| SGSSSNIGSNT VN (SEQ ID NO: 349) | SNNQRPS (SEQ ID NO: 356) | AAWDDSLNG WV (SEQ ID NO: 361) | SSSYYWG (SEQ ID NO: 371) | SIYYSGSTYYN PSLKS (SEQ ID NO: 391) | DSVIWYWFD P (SEQ ID NO: 431) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | EEILPRLSYYYY MDV (SEQ ID NO: 432) |
| RASQSISSYLN (SEQ ID NO: 346) | AASSLQS (SEQ ID NO: 353) | QQSYSTPLT (SEQ ID NO: 358) | SYAMN (SEQ ID NO: 379) | WINTNTGNP TYAQGFTG (SEQ ID NO: 399) | GGRAHSSWY FDL (SEQ ID NO: 433) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DRIKILPRLGY YYYMDV (SEQ ID NO: 434) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DTVIHYYYYM DV (SEQ ID NO: 435) |

TABLE 6-continued

| CDRs corresponding to HLA antigen binding domains | | | | | |
|---|---|---|---|---|---|
| CDR-L1 | CDR-L2 | CDR-L3 | CDR-H1 | CDR-H2 | CDR-H3 |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DVIVEVFLSYY YYMDV (SEQ ID NO: 436) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DIFIHYYYYM DV (SEQ ID NO: 437) |
| RASQSISSYLN (SEQ ID NO: 346) | AASSLQS (SEQ ID NO: 353) | QQSYSTPLT (SEQ ID NO: 358) | SYSMN (SEQ ID NO: 366) | YISSSSSTIYYA DSVKG (SEQ ID NO: 387) | DGTFYSYSPYY FDY (SEQ ID NO: 438) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | EWIKILPRLGY YYYMDV (SEQ ID NO: 439) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DRSLYYYYYM DV (SEQ ID NO: 440) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DKILAPNYYYY MDV (SEQ ID NO: 441) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | EKSWKYFYYY YYYMDV (SEQ ID NO: 442) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | ENTSTIPYYYY YMDV (SEQ ID NO: 443) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | EDVDKNTSTI YYYYYYMDV (SEQ ID NO: 444) |
| RASQGISSAL A (SEQ ID NO: 351) | DASSLES (SEQ ID NO: 55) | QQFNSYPLT (SEQ ID NO: 60) | DYYMS (SEQ ID NO: 380) | YISSSGSTIYYA DSVKG (SEQ ID NO: 400) | DGGDIVSSSAI YWYFDL (SEQ ID NO: 445) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DLILPPYYYYY MDV (SEQ ID NO: 446) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | ETWIKILPRYY YYYYYMDV (SEQ ID NO: 447) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DLSRYYYYYM DV (SEQ ID NO: 448) |
| RASQGISSWL A (SEQ ID NO: 352) | AASSLQS (SEQ ID NO: 353) | QQYNSYPLT (SEQ ID NO: 363) | SYSMN (SEQ ID NO: 366) | YISSSSSTIYYA DSVKG (SEQ ID NO: 387) | EHIVLCFDY (SEQ ID NO: 449) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DKILPRPYYYY YMDV (SEQ ID NO: 450) |
| TGTSSDVGGY NYVS (SEQ ID NO: 348) | EVSKRPS (SEQ ID NO: 355) | SSYAGSNNW V (SEQ ID NO: 360) | SYGIS (SEQ ID NO: 365) | WISAYNGNT NYAQKLQG (SEQ ID NO: 386) | GSNEYFQH (SEQ ID NO: 451) |
| RASQSISSYLN (SEQ ID NO: 346) | AASSLQS (SEQ ID NO: 353) | QQSYSTPLT (SEQ ID NO: 358) | SYAMN (SEQ ID NO: 379) | WINTNTGNP TYAQGFTG (SEQ ID NO: 399) | GTSYWYFDL (SEQ ID NO: 452) |

TABLE 6-continued

CDRs corresponding to HLA antigen binding domains

| CDR-L1 | CDR-L2 | CDR-L3 | CDR-H1 | CDR-H2 | CDR-H3 |
|---|---|---|---|---|---|
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | EEIVEVFYYYY MDV (SEQ ID NO: 453) |
| RASQSISSYLN (SEQ ID NO: 346) | AASSLQS (SEQ ID NO: 353) | QQSYSTPLT (SEQ ID NO: 358) | SYAMS (SEQ ID NO: 378) | AISGSGGSTYY ADSVKG (SEQ ID NO: 398) | VDDYYFDY (SEQ ID NO: 454) |
| RASQSISSYLN (SEQ ID NO: 346) | AASSLQS (SEQ ID NO: 353) | QQSYSTPLT (SEQ ID NO: 358) | SYWMH (SEQ ID NO: 375) | RINSDGSSTSY ADSVKG (SEQ ID NO: 395) | STNILLSYTKA FDI (SEQ ID NO: 455) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DKTYYYYYYM DV (SEQ ID NO: 456) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | EKYFHDKYFH DYYYYYMDV (SEQ ID NO: 457) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DTSVYYYYYM DV (SEQ ID NO: 458) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | EKILPYYYYYY MDV (SEQ ID NO: 459) |
| SGSSSNIGSNT VN (SEQ ID NO: 349) | SNNQRPS (SEQ ID NO: 356) | AAWDDSLNG WV (SEQ ID NO: 361) | SYSMN (SEQ ID NO: 366) | YISSSSSTIYYA DSVKG (SEQ ID NO: 387) | QWIYIYINPR GFIFLHDAFDI (SEQ ID NO: 460) |
| RASQSISSYLN (SEQ ID NO: 346) | AASSLQS (SEQ ID NO: 353) | QQSYSTPLT (SEQ ID NO: 358) | SNSAAWN (SEQ ID NO: 381) | RTYYRSKWYN DYAVSVKS (SEQ ID NO: 401) | EDVDFHHDA FDI (SEQ ID NO: 461) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | EGVDKNTSTI YYYYYYMDV (SEQ ID NO: 462) |
| RASQGISSWL A (SEQ ID NO: 352) | AASSLQS (SEQ ID NO: 353) | QQYNSYPLT (SEQ ID NO: 363) | SYSMN (SEQ ID NO: 366) | YISSSSSTIYYA DSVKG (SEQ ID NO: 387) | DRRGYFDL (SEQ ID NO: 463) |
| RASQSISSYLN (SEQ ID NO: 346) | AASSLQS (SEQ ID NO: 353) | QQSYSTPLT (SEQ ID NO: 358) | DYYMH (SEQ ID NO: 382) | LVDPEDGETIY AEKFQG (SEQ ID NO: 402) | GIHVDIRSME DWFDP (SEQ ID NO: 464) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DIGTSYYYYM DV (SEQ ID NO: 465) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | EVVEVFLYYYY YMDV (SEQ ID NO: 466) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DLYYYYYYYM DV (SEQ ID NO: 467) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | ESWKYFYPRG SIFIHYYYYMD V (SEQ ID NO: 468) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DRIVEVFYYYY MDV (SEQ ID NO: 469) |

TABLE 6-continued

| CDR-L1 | CDR-L2 | CDR-L3 | CDR-H1 | CDR-H2 | CDR-H3 |
|---|---|---|---|---|---|
| CDRs corresponding to HLA antigen binding domains | | | | | |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | EKYFHDWLYY YYYMDV (SEQ ID NO: 470) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DLVDKNTSYY YYYMDV (SEQ ID NO: 471) |
| TGTSSDVGGY NYVS (SEQ ID NO: 348) | EVSKRPS (SEQ ID NO: 355) | SSYAGSNNW V (SEQ ID NO: 360) | SYGIS (SEQ ID NO: 365) | WISAYNGNT NYAQKLQG (SEQ ID NO: 386) | VQNEYFQH (SEQ ID NO: 472) |
| RASQGISSWL A (SEQ ID NO: 352) | AASSLQS (SEQ ID NO: 353) | QQANSFPLT (SEQ ID NO: 364) | DYYMS (SEQ ID NO: 380) | YISSSGSTIYYA DSVKG (SEQ ID NO: 400) | ANWFDP (SEQ ID NO: 473) |
| HLA-A*01 CDRs | | | | | |
| ASSTGAVTSG YYPN (SEQ ID NO: 347) | STSNKHS (SEQ ID NO: 354) | LLYYGGAQW V (SEQ ID NO: 359) | SYGIS (SEQ ID NO: 365) | WISAYNGNT NYAQKLQG (SEQ ID NO: 386) | GGWTAWYYY MDV (SEQ ID NO: 474) |
| SGSSSNIGSNT VN (SEQ ID NO: 349) | SNNQRPS (SEQ ID NO: 356) | AAWDDSLNG WV (SEQ ID NO: 361) | SYSMN (SEQ ID NO: 366) | YISSSSSTIYYA DSVKG (SEQ ID NO: 387) | AKYYYMDV (SEQ ID NO: 475) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DQVDKNTYYY YMDV (SEQ ID NO: 476) |
| RASQGISSWL A (SEQ ID NO: 352) | AASSLQS (SEQ ID NO: 353) | QQANSFPLT (SEQ ID NO: 364) | DYYMS (SEQ ID NO: 380) | YISSSGSTIYYA DSVKG (SEQ ID NO: 400) | ACQLAEYFQH (SEQ ID NO: 477) |
| RASQSISSYLN (SEQ ID NO: 346) | AASSLQS (SEQ ID NO: 353) | QQSYSTPLT (SEQ ID NO: 358) | SGGYYWS (SEQ ID NO: 372) | YIYYSGSTYYN PSLKS (SEQ ID NO: 392) | DRVDKNTSYY YMDV (SEQ ID NO: 478) |
| RASQSISSYLN (SEQ ID NO: 346) | AASSLQS (SEQ ID NO: 353) | QQSYSTPLT (SEQ ID NO: 358) | SSNWWG (SEQ ID NO: 383) | YIYYSGSTYYN PSLKS (SEQ ID NO: 392) | RVQLKLVHW FDP (SEQ ID NO: 479) |
| RASQSISSYLN (SEQ ID NO: 346) | AASSLQS (SEQ ID NO: 353) | QQSYSTPLT (SEQ ID NO: 358) | SYDIN (SEQ ID NO: 384) | WMNPNSGN TGYAQKFQG (SEQ ID NO: 403) | YYDYVTVFYF QH (SEQ ID NO: 480) |
| RASQSISSYLN (SEQ ID NO: 346) | AASSLQS (SEQ ID NO: 353) | QQSYSTPLT (SEQ ID NO: 358) | SGGYSWS (SEQ ID NO: 385) | YIYHSGSTYYN PSLKS (SEQ ID NO: 404) | ESYPSFYAFDI (SEQ ID NO: 481) |
| RASQSISSYLN (SEQ ID NO: 346) | AASSLQS (SEQ ID NO: 353) | QQSYSTPLT (SEQ ID NO: 358) | TSGVGVG (SEQ ID NO: 374) | LIYWNDDKRY SPSLKS (SEQ ID NO: 394) | SNMWSYSLN DYYFDY (SEQ ID NO: 482) |

In some embodiments, the non-target antigen comprises HLA-A. In some embodiments, the ligand binding domain of the second, inhibitory receptor comprises an HLA-A*01, HLA-A*02, HLA-A*03 or HLA-A*11 ligand binding domain comprising CDR sequences as set forth in Table 6.

In some embodiments, the non-target antigen comprises HLA-B. In some embodiments, the ligand binding domain of the second, inhibitory receptors comprises an HLA-B*07 ligand binding domain comprising CDR sequences as set forth in Table 6.

In some embodiments, the non-target antigen comprises HLA-C. In some embodiments, the ligand binding domain of the second, inhibitory receptors comprises an HLA-C*07 ligand binding domain comprising CDR sequences as set forth in Table 6.

In some embodiments, the extracellular ligand binding domain of the second receptor specifically binds an allelic variant of an HLA-A, HLA-B, or HLA-C protein. In some embodiments, the extracellular ligand binding domain of the second receptor specifically binds to HLA-A*01, HLA-A*02, HLA-A*03, HLA-A*11, HLA-B*07, or HLA-C*07.

In some embodiments, the extracellular ligand binding domain of the second receptor specifically binds to HLA-A*01. In some embodiments, the extracellular ligand binding domain of the second receptor comprises HLA-A*01 complementarity determining regions (CDRs) CDR-L1, CDR-L2, CDR-L3, CDR-H1, CDR-H2, CDR-H3 as disclosed Table 6; or CDR sequences having at most 1, 2, or 3 substitutions, deletions, or insertions relative to the HLA-A*01 CDRs of Table 6.

In some embodiments, the extracellular ligand binding domain of the second receptor specifically binds to HLA-A*02. In some embodiments, the extracellular ligand binding domain of the second receptor comprises HLA-A*02 complementarity determining regions (CDRs) CDR-L1, CDR-L2, CDR-L3, CDR-H1, CDR-H2, CDR-H3 as disclosed Table 6; or CDR sequences having at most 1, 2, or 3 substitutions, deletions, or insertions relative to the HLA-A*02 CDRs of Table 6.

In some embodiments, the extracellular ligand binding domain of the second receptor comprises complementarity determining regions (CDRs) CDR-L1, CDR-L2, CDR-L3, CDR-H1, CDR-H2, CDR-H3 of SEQ ID NOS: 103-108 or of SEQ ID NOS: 109-114; or CDR sequences having at most 1, 2, or 3 substitutions, deletions, or insertions relative to the CDRs of SEQ ID NOS: 103-108 or SEQ ID NOS: 109-114.

In some embodiments, the extracellular ligand binding domain of the second receptor specifically binds to HLA-A*03. In some embodiments, the extracellular ligand binding domain of the second receptor comprises HLA-A*03 complementarity determining regions (CDRs) CDR-L1, CDR-L2, CDR-L3, CDR-H1, CDR-H2, CDR-H3 as disclosed Table 6; or CDR sequences having at most 1, 2, or 3 substitutions, deletions, or insertions relative to the HLA-A*03 CDRs of Table 6.

In some embodiments, the extracellular ligand binding domain of the second receptor specifically binds to HLA-A*11. In some embodiments, the extracellular ligand binding domain of the second receptor comprises HLA-A*11 complementarity determining regions (CDRs) CDR-L1, CDR-L2, CDR-L3, CDR-H1, CDR-H2, CDR-H3 as disclosed Table 6; or CDR sequences having at most 1, 2, or 3 substitutions, deletions, or insertions relative to the HLA-A*11 CDRs of Table 6.

In some embodiments, the extracellular ligand binding domain of the second receptor specifically binds to HLA-B*07. In some embodiments, the extracellular ligand binding domain of the second receptor comprises HLA-B*07 complementarity determining regions (CDRs) CDR-L1, CDR-L2, CDR-L3, CDR-H1, CDR-H2, CDR-H3 as disclosed Table 6; or CDR sequences having at most 1, 2, or 3 substitutions, deletions, or insertions relative to the HLA-B*07 CDRs of Table 6.

In some embodiments, the extracellular ligand binding domain of the second receptor specifically binds to HLA-C*07. In some embodiments, the extracellular ligand binding domain of the second receptor comprises HLA-C*07 complementarity determining regions (CDRs) CDR-L1, CDR-L2, CDR-L3, CDR-H1, CDR-H2, CDR-H3 as disclosed Table 6; or CDR sequences having at most 1, 2, or 3 substitutions, deletions, or insertions relative to the HLA-C*07 CDRs of Table 6.

In further embodiments of any of the ligand binding domains, each CDR sequence may have 1, 2, 3 or more substitutions, insertions, or deletions. CDR sequences may tolerate substitutions, deletions, or insertions. Using sequence alignment tools, routine experimentation, and known assays, those of skill in the art may generate and test variant sequences having 1, 2, 3, or more substitutions, insertions, or deletions in CDR sequences without undue experimentation.

In some embodiments, the non-target antigen comprises HLA-A*02, and the ligand binding domain of the second receptor comprises an HLA-A*02 ligand binding domain. In some embodiments, the ligand binding domain binds HLA-A*02 independent of the peptide in a pMHC complex comprising HLA-A*02. In some embodiments, the HLA-A*02 ligand binding domain comprises an scFv domain. In some embodiments, the HLA-A*02 ligand binding domain comprises a sequence of any one of SEQ ID NOs: 91-102. In some embodiments, the HLA-A*02 ligand binding domain comprises a sequence at least 90%, at least 95% or at least 99% identical to a sequence of any one of SEQ ID NOs: 91-102.

In some embodiments, the HLA-A*02 scFv comprises the complementarity determined regions (CDRs) of any one of SEQ ID NOS: 103-114. In some embodiments, the scFv comprises a sequence at least 95% identical to any one of SEQ ID NOS: 103-114. In some embodiments, the scFv comprises a sequence identical to any one of SEQ ID NOS: 103-114. In some embodiments, the heavy chain of the antigen binding domain comprises the heavy chain CDRs of any one of SEQ ID NOS: 103-114, and wherein the light chain of the antigen binding domain comprises the light chain CDRs of any one of SEQ ID NOS: 103-114. In some embodiments, the HLA-A*02 antigen binding domain comprises a heavy chain and a light chain, and the heavy chain comprises CDRs selected from SEQ ID NOs: 106-108 and 112-14 and the light chain comprises CDRs selected from SEQ ID NOs: 103-15 and 109-111.

In some embodiments, the HLA-A*02 antigen binding domain comprises a heavy chain and a light chain, and the heavy chain comprises a sequence at least 95% identical to the heavy chain portion of any one of SEQ ID NOS: 91-102, and the light chain comprises a sequence at least 95% identical to the light chain portion of any one of SEQ ID NOS: 91-102.

In some embodiments, the heavy chain comprises a sequence identical to the heavy chain portion of any one of SEQ ID NOS: 91-102, and wherein the light chain of comprises a sequence identical to the light chain portion of any one of SEQ ID NOS: 91-102.

In some embodiments, the HLA-A*02 scFv comprises a sequence at least 95% identical, at least 96% identical, at least 97% identical, at least 98% identical, at least 99% identical or identical to any one of SEQ ID NOs: 91-102. In some embodiments, the HLA-A*02 scFv comprises a sequence identical to any one of SEQ ID NOs: 91-102.

In some embodiments, the non-target antigen comprises HLA-A*01, and the extracellular ligand binding domain of the second receptor comprises an HLA-A*01 ligand binding domain. In some embodiments, the HLA-A*1 ligand binding domain comprises an scFv domain comprising a sequence selected from the group of sequences set forth in Table 5, or a sequence at least 90%, at least 95% or at least 99% identical to thereto. In some embodiments, the HLA-A*01 scFv comprises HLA-A*1 CDR sequences as set forth in Table 6.

In some embodiments, the non-target antigen comprises HLA-A*03, and the extracellular ligand binding domain of the second receptor comprises an HLA-A*03 ligand binding domain. In some embodiments, the HLA-A*03 ligand binding domain comprises an scFv domain comprising a sequence selected from the group of sequences set forth in Table 5, or a sequence at least 90%, at least 95% or at least 99% identical to thereto. In some embodiments, the HLA-A*03 scFv comprises HLA-A*03 CDR sequences as set forth in Table 6.

In some embodiments, the non-target antigen comprises HLA-A*111, and the extracellular ligand binding domain of the second receptor comprises an HLA-A*11 ligand binding domain. In some embodiments, the HLA-A*11 ligand binding domain comprises an scFv domain comprising a sequence selected from the group of sequences set forth in Table 5, or a sequence at least 90%, at least 95% or at least 99% identical to thereto. In some embodiments, the HLA-A*11 scFv comprises HLA-A*11 CDR sequences as set forth in Table 6.

In some embodiments, the non-target antigen comprises HLA-B*07, and the extracellular ligand binding domain of the second receptor comprises an HLA-B*07 ligand binding domain. In some embodiments, the HLA-B*07 ligand binding domain comprises an scFv domain comprising a sequence selected from the group of sequences set forth in Table 5, or a sequence at least 90%, at least 95% or at least 99% identical to thereto. In some embodiments, the HLA-B*07 scFv comprises HLA-B*07 CDR sequences as set forth in Table 6.

In some embodiments, the non-target antigen comprises HLA-C*07, and the extracellular ligand binding domain of the second receptor comprises an HLA-C*07 ligand binding domain. In some embodiments, the HLA-C*07 ligand binding domain comprises an scFv domain comprising a sequence selected from the group of sequences set forth in Table 5, or a sequence at least 90%, at least 95% or at least 99% identical to thereto. In some embodiments, the HLA-C*07 scFv comprises HLA-C*07 CDR sequences as set forth in Table 6.

Inhibitory Receptors

The disclosure provides a second receptor that is an inhibitory chimeric antigen receptor. The inhibitory receptor may comprise an extracellular ligand binding domain that binds to and recognizes the non-target antigen or a peptide derivative thereof in a MHC-I complex.

Exemplary inhibitory receptors are described in PCT/US2020/045228 filed on Sep. 6, 2020, PCT/US2020/064607, filed on Dec. 11, 2020, PCT/US2021/029907, filed on Apr. 29, 2021 and PCT/US2020/059856 filed on Nov. 10, 2020, the contents of each of which are incorporated herein by reference.

The term "inhibitory receptor," as used herein refers to a ligand binding domain that is fused to an intracellular signaling domain capable of transducing an inhibitory signal that inhibits or suppresses the immune activity of an immune cell. Inhibitory receptors have immune cell inhibitory potential, and are distinct and distinguishable from CARs, which are receptors with immune cell activating potential. For example, CARs are activating receptors as they include intracellular stimulatory and/or co-stimulatory domains. Inhibitory receptors are inhibiting receptors that contain intracellular inhibitory domains.

As used herein "inhibitory signal" refers to signal transduction or changes in protein expression in an immune cell resulting in suppression of an immune response (e.g., decrease in cytokine production or reduction of immune cell activation). Inhibition or suppression of an immune cell can selective and/or reversible, or not selective and/or reversible. Inhibitory receptors are responsive to non-target antigens (e.g. HLA-A*02). For example, when a non-target antigen (e.g. HLA-A*02) binds to or contacts the inhibitory receptor, the inhibitory receptor is responsive and activates an inhibitory signal in the immune cell expressing the inhibitory receptor upon binding of the non-target antigen by the extracellular ligand binding domain of the inhibitory receptor.

Inhibitory receptors of the disclosure may comprise an extracellular ligand binding domain. Any type of ligand binding domain that can regulate the activity of a receptor in a ligand dependent manner is envisaged as within the scope of the instant disclosure.

In some embodiments, the ligand binding domain is an antigen binding domain. Exemplary antigen binding domains include, inter alia, scFv, SdAb, Vβ-only domains, and TCR antigen binding domains derived from the TCR α and β chain variable domains.

Any type of antigen binding domain is envisaged as within the scope of the instant disclosure.

In some embodiments, the extracellular ligand binding domain of the second receptor is an scFv.

In some embodiments, the extracellular ligand binding domain of the second receptor is fused to the extracellular domain of an inhibitory CAR.

In some embodiments, the inhibitory receptors of the present disclosure comprise an extracellular hinge region. Exemplary hinges can be isolated or derived from IgD and CD8 domains, for example IgG1. In some embodiments, the hinge is isolated or derived from CD8a or CD28.

The inhibitory receptors of the present disclosure can be designed to comprise a transmembrane domain that is fused to the extracellular domain of the inhibitory receptor. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions may be isolated or derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, or from an immunoglobulin such as IgG4. Alternatively the transmembrane domain may be synthetic, in which case it will comprise predominantly hydrophobic residues such as leucine and valine. In some embodiments, a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the intracellular domain of the inhibitory receptor. A glycine-serine doublet provides a particularly suitable linker.

The disclosure provides an inhibitory receptor comprising an intracellular domain. The intracellular domain of the inhibitory receptors of the instant disclosure is responsible for inhibiting activation of the immune cells comprising the inhibitory receptor, which would otherwise be activated in response to activation signals by the first receptor. In some embodiments, the inhibitory intracellular domain comprises an immunoreceptor tyrosine-based inhibitory motif (ITIM). In some embodiments, the inhibitory intracellular domain comprising an ITIM can be isolated or derived from an immune checkpoint inhibitor such as CTLA-4 and PD-1. CTLA-4 and PD-1 are immune inhibitory receptors expressed on the surface of T cells, and play a pivotal role in attenuating or terminating T cell responses.

In some embodiments, an inhibitory intracellular domain is isolated from human tumor necrosis factor related apoptosis inducing ligand (TRAIL) receptor and CD200 receptor 1. In some embodiments, the TRAIL receptor comprises TR10A, TR10B or TR10D.

In some embodiments, an inhibitory intracellular domain is isolated from phosphoprotein membrane anchor with glycosphingolipid microdomains 1 (PAG1). In some embodiments, an inhibitory intracellular domain is isolated from leukocyte immunoglobulin like receptor B1 (LILRB1).

In some embodiments, the inhibitory domain is isolated or derived from a human protein, for example a human TRAIL receptor, CTLA-4, PD-1, PAG1 or LILRB1 protein.

In some embodiments, the inhibitory domain comprises an intracellular domain, a transmembrane or a combination thereof. In some embodiments, the inhibitory domain comprises an intracellular domain, a transmembrane domain, a hinge region or a combination thereof.

In some embodiments, the inhibitory domain is isolated or derived from killer cell immunoglobulin like receptor, three Ig domains and long cytoplasmic tail 2 (KIR3DL2), killer cell immunoglobulin like receptor, three Ig domains and long cytoplasmic tail 3 (KIR3DL3), leukocyte immunoglobulin like receptor B1 (LIR1, also called LIR-1 and LILRB1), programmed cell death 1 (PD-1), Fc gamma receptor IIB (FcgRIIB), killer cell lectin like receptor K1 (NKG2D), CTLA-4, a domain containing a synthetic consensus ITIM, a ZAP70 SH2 domain (e.g., one or both of the N and C terminal SH2 domains), or ZAP70 KI_K369A (kinase inactive ZAP70).

In some embodiments, the inhibitory domain is isolated or derived from a human protein.

In some embodiments, the second, inhibitory receptor comprises an inhibitory domain. In some embodiments, the second, inhibitory receptor comprises an inhibitory intracellular domain and/or an inhibitory transmembrane domain. In some embodiments, the inhibitory intracellular domain is fused to an intracellular domain of an inhibitory receptor. In some embodiments, the inhibitory intracellular domain is fused to the transmembrane domain of an inhibitory receptor.

In some embodiments, the second, inhibitory receptor comprises a cytoplasmic domain, a transmembrane domain, and an extracellular domain or a portion thereof isolated or derived isolated or derived from the same protein, for example an ITIM containing protein. In some embodiments, the second, inhibitory receptor comprises a hinge region isolated or derived from isolated or derived from the same protein as the intracellular domain and/or transmembrane domain, for example an ITIM containing protein.

In some embodiments, the second receptor is a TCR comprising an inhibitory domain (an inhibitory TCR). In some embodiments, the inhibitory TCR comprises an inhibitory intracellular domain and/or an inhibitory transmembrane domain. In some embodiments, the inhibitory intracellular domain is fused to the intracellular domain of TCR alpha, TCR beta, CD3 delta, CD3 gamma or CD3 epsilon or a portion thereof a TCR. In some embodiments, the inhibitory intracellular domain is fused to the transmembrane domain of TCR alpha, TCR beta, CD3 delta, CD3 gamma or CD3 epsilon.

In some embodiments, the second receptor is a TCR comprising an inhibitory domain (an inhibitory TCR). In some embodiments, the inhibitory domain is isolated or derived from LILRB1.

LILRB1 Inhibitory Receptors

The disclosure provides a second, inhibitory receptor comprising a LILRB1 inhibitory domain, and optionally, a LILRB1 transmembrane and/or hinge domain, or functional variants thereof. The inclusion of the LILRB1 transmembrane domain and/or the LILRB1 hinge domain in the inhibitory receptor may increase the inhibitory signal generated by the inhibitory receptor compared to a reference inhibitory receptor having another transmembrane domain or another hinge domains. The second, inhibitory receptor comprising the LILRB1 inhibitory domain may be a CAR or TCR, as described herein. Any suitable ligand binding domain, as described herein, may be fused to the LILRB1-based second, inhibitory receptors.

Leukocyte immunoglobulin-like receptor subfamily B member 1 (LILRB1), also known as Leukocyte immunoglobulin-like receptor B1, as well as ILT2, LIRE MIR7, PIRB, CD85J, ILT-2 LIR-1, MIR-7 and PIR-B, is a member of the leukocyte immunoglobulin-like receptor (LIR) family. The LILRB1 protein belongs to the subfamily B class of LIR receptors. These receptors contain two to four extracellular immunoglobulin domains, a transmembrane domain, and two to four cytoplasmic immunoreceptor tyrosine-based inhibitory motifs (ITIMs). The LILRB1 receptor is expressed on immune cells, where it binds to MHC class I molecules on antigen-presenting cells and transduces a negative signal that inhibits stimulation of an immune response. LILRB1 is thought to regulate inflammatory responses, as well as cytotoxicity, and to play a role in limiting auto-reactivity. Multiple transcript variants encoding different isoforms of LILRB1 exist, all of which are contemplated as within the scope of the instant disclosure.

In some embodiments of the inhibitory receptors described herein, the inhibitory receptor comprises one or more domains isolated or derived from LILRB1. In some embodiments of the receptors having one or more domains isolated or derived from LILRB1, the one or more domains of LILRB1 comprise an amino acid sequence that is at least 80%, at least 90%, at least 95%, at least 96%, at least 97%, at least 98%, at least 99% or is identical to a sequence or subsequence of SEQ ID NO: 115. In some embodiments, the one or more domains of LILRB1 comprise an amino acid sequence that is identical to a sequence or subsequence of SEQ ID NO: 115. In some embodiments, the one or more domains of LILRB1 consist of an amino acid sequence that is at least 80%, at least 90%, at least 95%, at least 96%, at least 97%, at least 98%, at least 99% or is identical to a sequence or subsequence of SEQ ID NO: 115. In some embodiments, the one or more domains of LILRB1 consist of an amino acid sequence that is identical to a sequence or subsequence of SEQ ID NO: 115.

In some embodiments of the receptors having one or more domains isolated or derived from LILRB1, the one or more domains of LILRB1 are encoded by a polynucleotide sequence that is at least 80%, at least 90%, at least 95%, at least 96%, at least 97%, at least 98%, at least 99% or is identical to a sequence or subsequence of SEQ ID NO: 116.

In some embodiments of the receptors having one or more domains of LILRB1, the one or more domains of LILRB1 are encoded by a polynucleotide sequence that is identical to a sequence or subsequence of SEQ ID NO: 116.

In various embodiments, an inhibitory receptor is provided, comprising a polypeptide, wherein the polypeptide comprises one or more of: an LILRB1 hinge domain or functional variant thereof; an LILRB1 transmembrane domain or a functional variant thereof; and an LILRB1 intracellular domain or an intracellular domain comprising at least one, or at least two immunoreceptor tyrosine-based inhibitory motifs (ITIMs), wherein each ITIM is independently selected from NLYAAV (SEQ ID NO: 117), VTYAEV (SEQ ID NO: 118), VTYAQL (SEQ ID NO: 119), and SIYATL (SEQ ID NO: 120).

As used herein an "immunoreceptor tyrosine-based inhibitory motif" or "ITIM" refers to a conserved sequence of amino acids with a consensus sequence of S/I/V/LxYxxI/V/L (SEQ ID NO: 984), or the like, that is found in the cytoplasmic tails of many inhibitory receptors of the immune system. After ITIM-possessing inhibitory receptors interact with their ligand, the ITIM motif is phosphorylated, allowing the inhibitory receptor to recruit other enzymes, such as the phosphotyrosine phosphatases SHP-1 and SHP-2, or the inositol-phosphatase called SHIP.

In some embodiments, the polypeptide comprises an intracellular domain comprising at least one immunoreceptor tyrosine-based inhibitory motif (ITIM), at least two ITIMs, at least 3 ITIMs, at least 4 ITIMs, at least 5 ITIMs or at least 6 ITIMs. In some embodiments, the intracellular domain has 1, 2, 3, 4, 5, or 6 ITIMs.

In some embodiments, the polypeptide comprises an intracellular domain comprising at least one ITIM selected from the group of ITIMs consisting of NLYAAV (SEQ ID NO: 117), VTYAEV (SEQ ID NO: 118), VTYAQL (SEQ ID NO: 119), and SIYATL (SEQ ID NO: 120).

In further particular embodiments, the polypeptide comprises an intracellular domain comprising at least two immunoreceptor tyrosine-based inhibitory motifs (ITIMs), wherein each ITIM is independently selected from NLYAAV (SEQ ID NO: 117), VTYAEV (SEQ ID NO: 118), VTYAQL (SEQ ID NO: 119), and SIYATL (SEQ ID NO: 120).

In some embodiments, the intracellular domain comprises both ITIMs NLYAAV (SEQ ID NO: 117) and VTYAEV (SEQ ID NO: 118). In some embodiments, the intracellular domain comprises a sequence at least 95% identical to SEQ ID NO: 121. In some embodiments, the intracellular domain comprises or consists essentially of a sequence identical to SEQ ID NO: 121.

In some embodiments, the intracellular domain comprises both ITIMs VTYAEV (SEQ ID NO: 118) and VTYAQL (SEQ ID NO: 119). In some embodiments, the intracellular domain comprises a sequence at least 95% identical to SEQ ID NO: 122. In some embodiments, the intracellular domain comprises or consists essentially of a sequence identical to SEQ ID NO: 122.

In some embodiments, the intracellular domain comprises both ITIMs VTYAQL (SEQ ID NO: 119) and SIYATL (SEQ ID NO: 120). In some embodiments, the intracellular domain comprises a sequence at least 95% identical to SEQ ID NO: 123. In some embodiments, the intracellular domain comprises or consists essentially of a sequence identical to SEQ ID NO: 123.

In some embodiments, the intracellular domain comprises the ITIMs NLYAAV (SEQ ID NO: 117), VTYAEV (SEQ ID NO: 118), and VTYAQL (SEQ ID NO: 119). In some embodiments, the intracellular domain comprises a sequence at least 95% identical to SEQ ID NO: 124. In some embodiments, the intracellular domain comprises or consists essentially of a sequence identical to SEQ ID NO: 124.

In some embodiments, the intracellular domain comprises the ITIMs VTYAEV (SEQ ID NO: 118), VTYAQL (SEQ ID NO: 119), and SIYATL (SEQ ID NO: 120). In some embodiments, the intracellular domain comprises a sequence at least 95% identical to SEQ ID NO: 125. In some embodiments, the intracellular domain comprises or consists essentially of a sequence identical to SEQ ID NO: 125.

In some embodiments, the intracellular domain comprises the ITIMs NLYAAV (SEQ ID NO: 117), VTYAEV (SEQ ID NO: 118), VTYAQL (SEQ ID NO: 119), and SIYATL (SEQ ID NO: 120). In embodiments, the intracellular domain comprises a sequence at least 95% identical to SEQ ID NO: 126. In some embodiments, the intracellular domain comprises or consists essentially of a sequence identical to SEQ ID NO: 126.

In some embodiments, the intracellular domain comprises a sequence at least 95% identical to the LILRB1 intracellular domain (SEQ ID NO: 131). In some embodiments, the intracellular domain comprises or consists essentially of a sequence identical to the LILRB1 intracellular domain (SEQ ID NO: 131).

LILRB1 intracellular domains or functional variants thereof of the disclosure can have at least 1, at least 2, at least 4, at least 4, at least 5, at least 6, at least 7, or at least 8 ITIMs. In some embodiments, the LILRB1 intracellular domain or functional variant thereof has 2, 3, 4, 5, or 6 ITIMs.

In particular embodiments, the intracellular domain comprises two, three, four, five, or six immunoreceptor tyrosine-based inhibitory motifs (ITIMs), wherein each ITIM is independently selected from NLYAAV (SEQ ID NO: 117), VTYAEV (SEQ ID NO: 118), VTYAQL (SEQ ID NO: 119), and SIYATL (SEQ ID NO: 120).

In particular embodiments, the intracellular domain comprises at least three immunoreceptor tyrosine-based inhibitory motifs (ITIMs), wherein each ITIM is independently selected from NLYAAV (SEQ ID NO: 117), VTYAEV (SEQ ID NO: 118), VTYAQL (SEQ ID NO: 119), and SIYATL (SEQ ID NO: 120).

In particular embodiments, the intracellular domain comprises three immunoreceptor tyrosine-based inhibitory motifs (ITIMs), wherein each ITIM is independently selected from NLYAAV (SEQ ID NO: 117), VTYAEV (SEQ ID NO: 118), VTYAQL (SEQ ID NO: 119), and SIYATL (SEQ ID NO: 120).

In particular embodiments, the intracellular domain comprises four immunoreceptor tyrosine-based inhibitory motifs (ITIMs), wherein each ITIM is independently selected from NLYAAV (SEQ ID NO: 117), VTYAEV (SEQ ID NO: 118), VTYAQL (SEQ ID NO: 119), and SIYATL (SEQ ID NO: 120).

In particular embodiments, the intracellular domain comprises five immunoreceptor tyrosine-based inhibitory motifs (ITIMs), wherein each ITIM is independently selected from NLYAAV (SEQ ID NO: 117), VTYAEV (SEQ ID NO: 118), VTYAQL (SEQ ID NO: 119), and SIYATL (SEQ ID NO: 120).

In particular embodiments, the intracellular domain comprises six immunoreceptor tyrosine-based inhibitory motifs (ITIMs), wherein each ITIM is independently selected from NLYAAV (SEQ ID NO: 117), VTYAEV (SEQ ID NO: 118), VTYAQL (SEQ ID NO: 119), and SIYATL (SEQ ID NO: 120).

In particular embodiments, the intracellular domain comprises at least seven immunoreceptor tyrosine-based inhibitory motifs (ITIMs), wherein each ITIM is independently selected from NLYAAV (SEQ ID NO: 117), VTYAEV (SEQ ID NO: 118), VTYAQL (SEQ ID NO: 119), and SIYATL (SEQ ID NO: 120).

The LILRB1 protein has four immunoglobulin (Ig) like domains termed D1, D2, D3 and D4. In some embodiments, the LILRB1 hinge domain comprises an LILRB1 D3D4 domain or a functional variant thereof. In some embodiments, the LILRB1 D3D4 domain comprises a sequence at least 95%, at least 96%, at least 97%, at least 98%, at least 99% or identical to SEQ ID NO: 127. In some embodiments, the LILRB1 D3D4 domain comprises or consists essentially of SEQ ID NO: 127.

In some embodiments, the polypeptide comprises the LILRB1 hinge domain or functional variant thereof. In embodiments, the LILRB1 hinge domain or functional variant thereof comprises a sequence at least 95%, at least 96%, at least 97%, at least 98%, at least 99% identical or identical to SEQ ID NO: 134, SEQ ID NO: 127, or SEQ ID NO: 128. In embodiments, the LILRB1 hinge domain or functional variant thereof comprises a sequence at least 95% identical to SEQ ID NO: 134, SEQ ID NO: 127, or SEQ ID NO: 128.

In some embodiments, the LILRB1 hinge domain comprises a sequence identical to SEQ ID NO: 134, SEQ ID NO: 127, or SEQ ID NO: 128.

In some embodiments, the LILRB1 hinge domain consists essentially of a sequence identical to SEQ ID NO: 134, SEQ ID NO: 127, or SEQ ID NO: 128.

In some embodiments, the transmembrane domain is a LILRB1 transmembrane domain or a functional variant thereof. In some embodiments, the LILRB1 transmembrane domain or a functional variant thereof comprises a sequence at least 95% identical, at least 96% identical, at least 97% identical, at least 98% identical or at least 99% to SEQ ID NO: 135. In some embodiments, the LILRB1 transmembrane domain or a functional variant thereof comprises a sequence at least 95% identical to SEQ ID NO: 135. In some embodiments, the LILRB1 transmembrane domain comprises a sequence identical to SEQ ID NO: 135. In embodiments, the LILRB1 transmembrane domain consists essentially of a sequence identical to SEQ ID NO: 135.

In some embodiments, the transmembrane domain can be attached to the extracellular region of the second, inhibitory receptor, e.g., the antigen binding domain or ligand binding domain, via a hinge, e.g., a hinge from a human protein. For example, in some embodiments, the hinge can be a human immunoglobulin (Ig) hinge, e.g., an IgG4 hinge, a CD8a hinge or an LILRB1 hinge.

In some embodiments, the second, inhibitory receptor comprises an inhibitory domain. In some embodiments, the second, inhibitory receptor comprises an inhibitory intracellular domain and/or an inhibitory transmembrane domain. In some embodiments, the inhibitory domain is isolated or derived from LILR1B.

Inhibitory Receptors Comprising Combinations of LILRB1 Domains

In some embodiments, the LILRB1-based inhibitory receptors of the disclosure comprise more than one LILRB1 domain or functional equivalent thereof. For example, in some embodiments, the inhibitory receptor comprises an LILRB1 transmembrane domain and intracellular domain, or an LILRB1 hinge domain, transmembrane domain and intracellular domain.

In particular embodiments, the inhibitory receptor comprises an LILRB1 hinge domain or functional fragment thereof, and the LILRB1 transmembrane domain or a functional variant thereof. In some embodiments, the polypeptide comprises a sequence at least 95% identical, at least 96% identical, at least 97% identical, at least 98% identical, at least 99% identical or identical to SEQ ID NO: 129. In some embodiments, the polypeptide comprises a sequence at least 95% identical to SEQ ID NO: 129. In some embodiments, the polypeptide comprises a sequence identical to SEQ ID NO: 129.

In further embodiments, the inhibitory receptor comprises: the LILRB1 transmembrane domain or a functional variant thereof, and an LILRB1 intracellular domain and/or an intracellular domain comprising at least one immunoreceptor tyrosine-based inhibitory motif (ITIM), wherein the ITIM is selected from NLYAAV (SEQ ID NO: 117), VTYAEV (SEQ ID NO: 118), VTYAQL (SEQ ID NO: 119), and SIYATL (SEQ ID NO: 120). In some embodiments, the polypeptide comprises the LILRB1 transmembrane domain or a functional variant thereof, and an LILRB1 intracellular domain and/or an intracellular domain comprising at least two ITIM, wherein each ITIM is independently selected from NLYAAV (SEQ ID NO: 117), VTYAEV (SEQ ID NO: 118), VTYAQL (SEQ ID NO: 119), and SIYATL (SEQ ID NO: 120).

In some embodiments, the inhibitory receptor comprises a LILRB1 transmembrane domain and intracellular domain. In some embodiments, the polypeptide comprises a sequence at least 95% identical, at least 96% identical, at least 97% identical, at least 98% identical, at least 99% identical or identical to SEQ ID NO: 130. In some embodiments, the polypeptide comprises a sequence at least 95% identical to SEQ ID NO: 130. In some embodiments, the polypeptide comprises a sequence identical to SEQ ID NO: 130.

In preferred embodiments, the inhibitory receptor comprises: an LILRB1 hinge domain or functional variant thereof; an LILRB1 transmembrane domain or a functional variant thereof; and an LILRB1 intracellular domain and/or an intracellular domain comprising at least two immunoreceptor tyrosine-based inhibitory motifs (ITIMs), wherein each ITIM is independently selected from LYAAV (SEQ ID NO: 117), VTYAE (SEQ ID NO: 118), VTYAQL (SEQ ID NO: 119), and SIYATL (SEQ ID NO: 11).

In some embodiments, the inhibitory receptor comprises a sequence at least 95% identical to SEQ ID NO: 132 or SEQ ID NO: 133, or at least 99% identical to SEQ ID NO: 132 or SEQ ID NO: 133, or identical to SEQ ID NO: 132 or SEQ ID NO: 133.

In some embodiments, the polypeptide comprises a sequence at least 99% identical to SEQ ID NO: 129, or at least 99% identical to SEQ ID NO: 129, or identical to SEQ ID NO: 129.

In some embodiments, the polypeptide comprises a sequence at least 99% identical to SEQ ID NO: 130, or at least 99% identical to SEQ ID NO: 130, or identical to SEQ ID NO: 130.

TABLE 7

Polypeptide sequences for illustrative LILRB1-based inhibitory receptors

| Name | Sequence |
|---|---|
| LILRB1 | MTPILTVLICLGLSLGPRTHVQAGHLPKPTLWAEPGSVITQ GSPVTLRCQGGQETQEYRLYREKKTALWITRIPQELVKKG QFPIPSITWEHAGRYRCYYGSDTAGRSESSDPLELVVTGA YIKPTLSAQPSPVVNSGGNVILQCDSQVAFDGFSLCKEGED EHPQCLNSQPHARGSSRAIFSVGPVSPSRRWWYRCYAYDS |

TABLE 7-continued

Polypeptide sequences for illustrative LILRB1-based inhibitory receptors

| Name | Sequence |
|---|---|
| | NSPYEWSLPSDLLELLVLGVSKKPSLSVQPGPIVAPEETLT<br>LQCGSDAGYNRFVLYKDGERDFLQLAGAQPQAGLSQANF<br>TLGPVSRSYGGQYRCYGAHNLSSEWSAPSDPLDILIAGQF<br>YDRVSLSVQPGPTVASGENVTLLCQSQGWMQTFLLTKEG<br>AADDPWRLRSTYQSQKYQAEFPMGPVTSAHAGTYRC**YG**<br>**SQSSKPYLLTHPSDPLEL**VVSGPSGGPSSPTTGPTSTSGPE<br>DQPLTPTGSDPQSGLGRHLGVVIGILVAVILLLLLLLLLFLI<br>LRHRRQGKHWTSTQRKADFQHPAGAVGPEPTDRGLQWR<br>SSPAADAQEEN**LYAAV**KHTQPEDGVEMDTRSPHDEDPQA<br>**VTYAEV**KHSRPRREMASPPSPLSGEFLDTKDRQAEEDRQ<br>MDTEAAASEAPQD**VTYAQ**LHSLTLRREATEPPPSQEGPSP<br>AVP**SIYAT**LAIHPSQEGPSPAVPSIYATLAIH<br>SEQ ID NO: 115 |
| LILRB1 hinge-transmembrane-intracellular domain | **YGSQSSKPYLLTHPSDPLEL**VVSGPSGGPSSPTTGPTSTSG<br>PEDQPLTPTGSDPQSGLGRHLG**VVIGILVAVILLLLLLLLL**<br>**FLIL**RHRRQGKHWTSTQRKADFQHPAGAVGPEPTDRGLQ<br>WRSSPAADAQEENLYAAVKHTQPEDGVEMDTRSPHDEDP<br>QAVTYAEVKHSRPRREMASPPSPLSGEFLDTKDRQAEEDR<br>QMDTEAAASEAPQDVTYAQLHSLTLRREATEPPPSQEGPS<br>PAVPSIYATLAIH<br>SEQ ID NO: 132 |
| LILRB1 hinge-transmembrane-intracellular domain (w/o YGSQSSKPYLLTHPSD PLEL) | VVSGPSGGPSSPTTGPTSTSGPEDQPLTPTGSDPQSGLGRH<br>LG**VVIGILVAVILLLLLLLLLFLIL**RHRRQGKHWTSTQRK<br>ADFQHPAGAVGPEPTDRGLQWRSSPAADAQEENLYAAV<br>KHTQPEDGVEMDTRSPHDEDPQAVTYAEVKHSRPRREMA<br>SPPSPLSGEFLDTKDRQAEEDRQMDTEAAASEAPQDVTYA<br>QLHSLTLRREATEPPPSQEGPSPAVPSIYATLAIH<br>SEQ ID NO: 133 |
| LILRB1 hinge domain | **YGSQSSKPYLLTHPSDPLEL**VVSGPSGGPSSPTTGPTSTSG<br>PEDQPLTPTGSDPQSGLGRHLG<br>SEQ ID NO: 134 |
| LILRB1 transmembrane domain | **VVIGILVAVILLLLLLLLLFLIL**<br>SEQ ID NO: 135 |
| LILRB1 intracellular domain | RHRRQGKHWTSTQRKADFQHPAGAVGPEPTDRGLQWRS<br>SPAADAQEENLYAAVKHTQPEDGVEMDTRSPHDEDPQAV<br>TYAEVKHSRPRREMASPPSPLSGEFLDTKDRQAEEDRQM<br>DTEAAASEAPQDVTYAQLHSLTLRREATEPPPSQEGPSPA<br>VPSIYATLAIH<br>SEQ ID NO: 131 |
| ITIM1 | NLYAAV<br>SEQ ID NO: 117 |
| ITIM2 | VTYAEV<br>SEQ ID NO: 118 |
| ITIM3 | VTYAQL<br>SEQ ID NO: 119 |
| ITIM4 | SIYATL<br>SEQ ID NO: 120 |
| ITIM1-2 | **NLYAAV**KHTQPEDGVEMDTRSPHDEDPQA**VTYAEV**<br>SEQ ID NO: 121 |
| ITIM2-3 | **VTYAEV**KHSRPRREMASPPSPLSGEFLDTKDRQAEEDRQ<br>MDTEAAASEAPQD**VTYAQL**<br>SEQ ID NO: 122 |
| ITIM3-4 | **VTYAQL**HSLTLRREATEPPPSQEGPSPAVP**SIYATL**<br>SEQ ID NO: 123 |
| ITIM1-3 | **NLYAAV**KHTQPEDGVEMDTRSPHDEDPQA**VTYAEV**KHS<br>RPRREMASPPSPLSGEFLDTKDRQAEEDRQMDTEAAASEA<br>PQD**VTYAQL**<br>SEQ ID NO: 124 |

TABLE 7-continued

Polypeptide sequences for illustrative LILRB1-based inhibitory receptors

| Name | Sequence |
|---|---|
| ITIM2-4 | **VTYAEV**KHSRPRREMASPPSPLSGEFLDTKDRQAEEDRQMDTEAAASEAPQD**VTYAQL**HSLTLRREATEPPPSQEGPSPAVP**SIYATL**<br>SEQ ID NO: 125 |
| ITIM1-4 | **NLYAAV**KHTQPEDGVEMDTRSPHDEDPQA**VTYAEV**KHSRPRREMASPPSPLSGEFLDTKDRQAEEDRQMDTEAAASEAPQD**VTYAQL**HSLTLRREATEPPPSQEGPSPAVP**SIYATL**<br>SEQ ID NO: 126 |
| D3D4 domain | **YGSQSSKPYLLTHPSDPLEL**<br>SEQ ID NO: 127 |
| Short hinge | VVSGPSGGPSSPTTGPTSTSGPEDQPLTPTGSDPQSGLGRHLG<br>SEQ ID NO: 128 |
| Hinge (iTIM hinge) | YGSQSSKPYLLTHPSDPLELVVSGPSGGPSSPTTGPTSTSGPEDQPLTPTGSDPQSGLGRHLGV<br>SEQ ID NO: 483 |
| Short hinge 2 | VVSGPSGGPSSPTTGPTSTSGPEDQPLTPTGSDPQSGLGRHLGV<br>SEQ ID NO: 484 |
| Long hinge 1 | AGSGGSGGSGGSPVPSTPPTPSPSTPPTPSPSGGSGNSSGSGGSPVPSTPPTPSPSTPPTPSPSASV<br>SEQ ID NO: 485 |
| Long hinge 2 | AGSGGSGGSGGSPVPSTPPTNSSSTPPTPSPSPVPSTPPTNSSSTPPTPSPSPVPSTPPTNSSSTPPTPSPSASV<br>SEQ ID NO: 486 |
| 2x short hinge | VVSGPSGGPSSPTTGPTSTSGPEDQPLTPTGSDPQSGLGRHVVSGPSGGPSSPTTGPTSTSGPEDQPLTPTGSDPQSGLGRHLGV<br>SEQ ID NO: 487 |
| Hinge (truncated) | TTGPTSTSGPEDQPLTPTGSDPQSGLGRHLGV<br>SEQ ID NO: 488 |
| Hinge-transmembrane | **YGSQSSKPYLLTHPSDPLEL**VVSGPSGGPSSPTTGPTSTSGPEDQPLTPTGSDPQSGLGRHLG**VVIGILVAVILLLLLLLLLFLIL**<br>SEQ ID NO: 129 |
| Transmembrane-intracellular domain. | **VVIGILVAVILLLLLLLLLFLIL**RHRRQGKHWTSTQRKADFQHPAGAVGPEPTDRGLQWRSSPAADAQEENLYAAVKHTQPEDGVEMDTRSPHDEDPQAVTYAEVKHSRPRREMASPPSPLSGEFLDTKDRQAEEDRQMDTEAAASEAPQDVTYAQLHSLTLRREATEPPPSQEGPSPAVPSIYATLAIH<br>SEQ ID NO: 130 |

Polynucleotides and Vectors

The disclosure provides polynucleotides encoding the sequence(s) of the first and second receptors of the disclosure. The disclosure provides immune cells comprising the polynucleotides and vectors described herein.

In some embodiments, the sequence of the first and/or second receptor is operably linked to a promoter. In some embodiments, the sequence encoding the first receptor is operably linked to a first promoter, and the sequence encoding the second receptor is operably linked to a second promoter.

The disclosure provides vectors comprising the polynucleotides described herein.

In some embodiments, the first receptor is encoded by a first vector and the second receptor is encoded by a second vector. In some embodiments, both receptors are encoded by a single vector. In some embodiments, the first and/or second vector comprises an shRNA, for example a B2M shRNA.

In some embodiments, both receptors are encoded by a single vector. In some embodiments the vector comprises an shRNA, for example a B2M shRNA.

In some embodiments, the first and second receptors are encoded by a single vector. Methods of encoding multiple polypeptides using a single vector will be known to persons of ordinary skill in the art, and include, inter alia, encoding multiple polypeptides under control of different promoters, or, if a single promoter is used to control transcription of multiple polypeptides, use of sequences encoding internal ribosome entry sites (IRES) and/or self-cleaving peptides. Exemplary self-cleaving peptides include T2A, P2A, E2A and F2A self-cleaving peptides. In some embodiments, the T2A self-cleaving peptide comprises a sequence of EGRGSLLTCGDVEENPGP (SEQ ID NO: 489). In some embodiments, the P2A self-cleaving peptide comprises a sequence of ATNFSLLKQAGDVEENPGP (SEQ ID NO: 186). In some embodiments, the E2A self-cleaving peptide comprises a sequence of QCTNYALLKLAGDVESNPGP (SEQ ID NO: 490). In some embodiments, the F2A self-cleaving peptide comprises a sequence of VKQTLNFDLLKLAGDVESNPGP (SEQ ID NO: 491). In some embodiments, the T2A self-cleaving peptide comprises a sequence of EGRGSLLTCGDVEENPGP (SEQ ID NO: 489). Any of the foregoing can also include an N terminal GSG linker. For example, a T2A self-cleaving peptide can also comprise a sequence of GSGEGRGSLLTCGDVEENPGP (SEQ ID NO: 181), which can be encoded by a sequence of

```
                                        (SEQ ID NO: 492)
GGATCCGGAGAGGGCAGAGGCAGCCTGCTGACATGTGGCGACGTGGAAGA

GAACCCTGGCCCC.
```

In some embodiments, the vector is an expression vector, i.e. for the expression of the first and/or second receptor in a suitable cell.

Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

The expression of natural or synthetic nucleic acids encoding receptors is typically achieved by operably linking a nucleic acid encoding the receptor or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The polynucleotides encoding the receptors can be cloned into a number of types of vectors. For example, the polynucleotides can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to cells, such as immune cells, in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 basepairs (bp) upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1$\alpha$ (EF-1$\alpha$). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, a U6 promoter, as well as human gene promoters such as, but not limited to, the actin promoter, the myosin promoter, the hemoglobin promoter, and the creatine kinase promoter. Further, the disclosure should not be limited to the use of constitutive promoters. Inducible promoters are also contemplated as part of the disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a receptor, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected or transduced cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). One method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Regardless of the method used to introduce exogenous nucleic acids into a host cell or otherwise expose a cell to the inhibitor of the present disclosure, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the disclosure.

Immune Cells

The disclosure provides immune cells comprising the receptors, vectors and polynucleotides described herein.

In some embodiments, the immune cells comprise: (a) first receptor, comprising a first extracellular ligand binding domain specific to a target antigen selected from: (i) a cancer cell-specific antigen, or a peptide antigen thereof in a complex with a major histocompatibility complex class I (MHC-I); or (ii) CEA cell adhesion molecule 5 (CEA), or a peptide antigen thereof in a complex with a major histocompatibility complex class I (MHC-I); and (b) a second receptor, comprising a second extracellular ligand binding specific to a non-target antigen selected from TNFRSF11, ACHRB, ITGAE, TRPV1, and SREC, or an antigen peptide thereof in a complex with a major histocompatibility complex class I (MHC-I), wherein the non-target antigen comprises a polymorphism. In some embodiments, the first receptor is a CAR or TCR. In some embodiments, the second receptor is an inhibitory receptor, such as an inhibitory chimeric antigen receptor or TCR.

As used herein, the term "immune cell" refers to a cell involved in the innate or adaptive (acquired) immune systems. Exemplary innate immune cells include phagocytic cells such as neutrophils, monocytes and macrophages, Natural Killer (NK) cells, polymophonuclear leukocytes such as neutrophils eosinophils and basophils and mononuclear cells such as monocytes, macrophages and mast cells. Immune cells with roles in acquired immunity include lymphocytes such as T-cells and B-cells.

The disclosure provides immune cells comprising a first receptor comprising a sequence of SEQ ID NO: 52, and second receptor comprising a sequence of SEQ ID NO: 164, or sequences having at least 90%, at least 95%, at least 97% or at least 99% identity thereto. In some embodiments, the immune cells comprise an shRNA encoded by a sequence comprising GCACTCAAAGCTTGTTAAGATCGAAATCTTAACAAGCTTTGAGTGC (SEQ ID NO: 179) or a sequence having at least 80%, at least 90%, or at least 95% identity thereto. In some embodiments, the immune cells comprise first receptor comprising a sequence of SEQ ID NO: 52, a second receptor comprising a sequence of SEQ ID NO: 164, and a sequence encoding an shRNA comprising a sequence of SEQ ID NO: 179. In some embodiments, the first receptor and second receptor are encoded by a single polynucleotide, and wherein the sequences encoding the first and second receptors are separated by a sequence encoding a self-cleaving polypeptide. In some embodiments, the self-cleaving polypeptide comprises a T2A self-cleaving polypeptide comprising a sequence of GSGEGRGSLLTCGDVEENPGP (SEQ ID NO: 181).

The disclosure provides immune cells comprising a polypeptide comprising a sequence of SEQ ID NO: 141, or a sequence having at least 80%, at least 90%, or at least 95% identity thereto. In some embodiments, the polypeptide comprises SEQ ID NO: 141.

The disclosure provides immune cells comprising a polynucleotide comprising a sequence of SEQ ID NO: 142, or a sequence having at least 80%, at least 90%, or at least 95% identity thereto. In some embodiments, the polynucleotide comprises SEQ ID NO: 142.

As used herein, a "T-cell" refers to a type of lymphocyte that originates from a bone marrow precursor that develops in the thymus gland. There are several distinct types of T-cells which develop upon migration to the thymus, which include, helper CD4+ T-cells, cytotoxic CD8+ T cells, memory T cells, regulatory CD4+ T-cells and stem memory T-cells. Different types of T-cells can be distinguished by the ordinarily skilled artisan based on their expression of markers. Methods of distinguishing between T-cell types will be readily apparent to the ordinarily skilled artisan.

In some embodiments, the first receptor and the second receptor together specifically activate the immune cell in the presence of the target cell.

In some embodiments, the immune cell is selected form the group consisting of T cells, B cells and Natural Killer (NK) cells. In some embodiments, the immune cell is a gamma delta (γδ) T cell. In some embodiments, the immune cell is an invariant T cell. In some embodiments, the immune cell is an invariant natural killer T cell (iNKT cell). In some embodiments, the immune cell is a T cell, an NK cell or a macrophage. In some embodiments, the immune cell is a B cell. In some embodiments, the immune cell is a Natural Killer (NK) cell. In some embodiments, the immune cell is CD8−. In some embodiments, the immune cell is CD8+. In some embodiments, the immune cell is CD4+. In some embodiments, the immune cell is CD4−. In some embodiments, the immune cell is CD8−/CD4+. In some embodiments, the immune cell is a CD8+ CD4− T cell.

In some embodiments, the immune cell is non-natural. In some embodiments, the immune cell is isolated.

Methods transforming populations of immune cells, such as T cells, with the vectors of the instant disclosure will be readily apparent to the person of ordinary skill in the art. For example, CD3+ T cells can be isolated from PBMCs using a CD3+ T cell negative isolation kit (Miltenyi), according to manufacturer's instructions. T cells can be cultured at a density of 1×10^6 cells/mL in X-Vivo 15 media supplemented with 5% human AB serum and 1% Pen/strep in the presence of CD3/28 Dynabeads (1:1 cell to bead ratio) and 300 Units/mL of IL-2 (Miltenyi). After 2 days, T cells can be transduced with viral vectors, such as lentiviral vectors using methods known in the art. In some embodiments, the viral vector is transduced at a multiplicity of infection (MOI) of 5. Cells can then be cultured in IL-2 or other cytokines such as combinations of IL-7/15/21 for an additional 5 days prior to enrichment. Methods of isolating and culturing other populations of immune cells, such as B cells, or other populations of T cells, will be readily apparent to the person of ordinary skill in the art. Although this method outlines a potential approach it should be noted that these methodologies are rapidly evolving. For example excellent viral transduction of peripheral blood mononuclear cells can be achieved after 5 days of growth to generate a >99% CD3+ highly transduced cell population.

Methods of activating and culturing populations of T cells comprising the TCRs, CARs, inhibitory receptors or vectors encoding same, will be readily apparent to the person of ordinary skill in the art.

Whether prior to or after genetic modification of T cells to express a TCR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041, 10,040,846; and U.S. Pat. Appl. Pub. No. 2006/0121005.

In some embodiments, T cells of the instant disclosure are expanded and activated in vitro. Generally, the T cells of the instant disclosure are expanded in vitro by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In some embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In some embodiments, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present disclosure.

In some embodiments, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4+ T cell expansion and T cell growth is used. In some embodiments, the ratio of CD3:CD28 antibody bound to the beads ranges from 100:1 to 1:100 and all integer values there between. In one aspect of the present disclosure, more anti-CD28 antibody is bound to the particles than anti-CD3 antibody, i.e., the ratio of CD3:CD28 is less than one. In certain embodiments of the disclosure, the ratio of anti CD28 antibody to anti CD3 antibody bound to the beads is greater than 2:1.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. In some embodiments, a ratio of 1:1 cells to beads is used. One of skill in the art will appreciate that a variety of other ratios may be suitable for use in the present disclosure. In particular, ratios will vary depending on particle size and on cell size and type.

In further embodiments of the present disclosure, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached to contact the T cells. In one embodiment the cells (for example, CD4+ T cells) and beads (for example, DYNABEADS CD3/CD28 T paramagnetic beads at a ratio of 1:1) are combined in a buffer. Again, those of ordinary skill in the art can readily appreciate any cell concentration may be used. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. In some embodiments, cells that are cultured at a density of $1\times10^6$ cells/mL are used.

In some embodiments, the mixture may be cultured for several hours (about 3 hours) to about 14 days or any hourly integer value in between. In another embodiment, the beads and T cells are cultured together for 2-3 days. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. In some embodiments, the media comprises X-VIVO-15 media supplemented with 5% human AB serum, 1% penicillin/streptomycin (pen/strep) and 300 Units/ml of IL-2 (Miltenyi).

The T cells are maintained under conditions necessary to support growth, for example, an appropriate temperature (e.g., 37° C.) and atmosphere (e.g., air plus 5% CO2).

In some embodiments, the T cells comprising TCRs, CARs and inhibitory receptors of the disclosure are autologous. Prior to expansion and genetic modification, a source of T cells is obtained from a subject. Immune cells such as T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present disclosure, any number of T cell lines available in the art, may be used. In certain embodiments of the present disclosure, T cells can be obtained from a unit of blood collected from a subject using any number of techniques known to the skilled artisan, such as Ficoll™ separation.

In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In alternative embodiments, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca2+-free, Mg2+-free PBS, PlasmaLyte A, or other saline solution with or without buffer. Alternatively, the undesirable components of the apheresis sample may be removed and the cells directly resuspended in culture media.

In some embodiments, immune cells such as T cells are isolated from peripheral blood lymphocytes by lysing the red blood cells and depleting the monocytes, for example, by centrifugation through a PERCOLL™ gradient or by counterflow centrifugal elutriation. Specific subpopulations of immune cells, such as T cells, B cells, or CD4+ T cells can be further isolated by positive or negative selection techniques. For example, in one embodiment, T cells are isolated by incubation with anti-CD4-conjugated beads, for a time period sufficient for positive selection of the desired T cells.

Enrichment of an immune cell population, such as a T cell population, by negative selection can be accomplished with a combination of antibodies directed to surface markers unique to the negatively selected cells. One method is cell sorting and/or selection via negative magnetic immune-adherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD 14, CD20, CD 11b, CD 16, HLA-DR, and CD8.

For isolation of a desired population of immune cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads.

In some embodiments, the cells may be incubated on a rotator for varying lengths of time at varying speeds at either 2-10° C. or at room temperature.

T cells for stimulation, or PBMCs from which immune cells such as T cells are isolated, can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

The disclosure provides an immune cell expressing the activator and/or blocker receptors described herein, wherein the immune cell has reduced expression and/or function the major histocompatibility (MHC) class I complex.

In some embodiments, the immune cell is autologous. For example, the immune cells is isolated or derived from same subject who will receive the cell as part of a therapeutic regimen. It can be advantageous to modify autologous immune cells to have reduced expression and/or function of MEW class I with the blocker receptor is specific to an MEW class I antigen. Without wishing to be bound by theory, modification of autologous immune cells to have reduced expression and/or function of MHC class I reduces binding of the blocker receptor by MEW class I expressed by the immune cells, either in cis or in trans.

In some embodiments, the immune cell is all allogeneic. Allogeneic immune cells can be derived from a donor other than the subject to which the immune cells will be administered. Allogeneic immune cells have been commonly referred to in cell therapy as "off-the-shelf" or "universal" because of the possibility for allogeneic cells to be prepared and stored for use in subjects of a variety of genotypes.

Any suitable methods of reducing expression and/or function the MHC class I complex are envisaged as within the scope of the instant disclosure, and include, inter alia, expression of interfering RNAs that knock down one or more RNAs encoding MHC class I components, or modifications of genes encoding MHC class I components. Methods of reducing expression and/or function of the MHC class I complex described herein are suitable for use with both allogeneic and autologous immune cells.

The major histocompatibility complex (MEW) is a locus on the vertebrate genome that encodes a set of polypeptides required for the adaptive immune system. Among these are MEW class I polypeptides that include HLA-A, HLA-B, and HLA-C and alleles thereof. MHC class I alleles are highly polymorphic and expressed in all nucleated cells. MHC class I polypeptides encoded by HLA-A, HLA-B, and HLA-C and alleles thereof form heterodimers with (32 microglobulin (B2M) and present in complex with antigens on the surface of cells. As referred to herein, an MEW class I gene or polypeptide may refer to any polypeptide found in the MHC or the corresponding gene encoding said polypeptide. In some embodiments, the immune cells of the disclosure are inactivated by an inhibitor ligand comprising an MHC class I polypeptide, e.g. HLA-A, HLA-B, and HLA-C and alleles thereof. HLA-A alleles can be, for example and without limitation, HLA-A*02, HLA-A*02:01, HLA-A*02:01:01, HLA-A*02:01:01:01, and/or any gene that encodes protein identical or similar to HLA-A*02 protein. Thus, to prevent autocrine signaling/binding as described herein, it is desirable to eliminate or reduce expression of polypeptides encoded by HLA-A, HLA-B, and HLA-C and alleles thereof in the immune cells.

Immune Cells with Reduced MHC Class I Polypeptide Expression

In some embodiments, the immune cells described herein are modified to inactivate, or reduce or eliminate expression or function of an endogenous gene encoding an allele of an endogenous MHC class I polypeptide. In some embodiments, the gene encoding the MHC class I polypeptide is HLA-A, HLA-B, and/or HLA-C. HLA-A, HLA-B and HLA-C are encoded by the HLA-A, HLA-B and HLA-C loci. Each of HLA-A, HLA-B and HLA-C includes many variant alleles, all of which are envisaged as within the scope of the instant disclosure. In some embodiments, the gene encoding the MHC class I polypeptide is HLA-A. In some embodiments, the gene encoding the MHC class I polypeptide is HLA-A*02. In some embodiments, the gene encoding the MHC class I polypeptide is HLA-A*02:01. In some embodiments, the gene encoding the MHC class I polypeptide is HLA-A*02:01:01. In some embodiments, the gene encoding the MHC class I polypeptide is HLA-A*02:01:01:01.

In some embodiments, the genetically engineered immune cells described herein are modified to reduce or eliminate expression of the B2M gene product. The beta-2 microglobulin (B2M) gene encodes a protein that associates with the major histocompatibility complex (MHC) class I, i.e. MHC-I complex. The MHC-I complex is required for presentation of antigens on the cell surface. The MHC-I complex is disrupted and non-functional when the B2M is deleted (Wang D et al. Stem Cells Transl Med. 4:1234-1245 (2015)). Furthermore, the B2M gene can be disrupted with high efficiency using gene editing techniques known in the art (Ren et al. Clin. Cancer Res. 23:2255-2266 (2017)). Reducing or eliminating B2M can reduce, or eliminate functional MHC I on the surface of the immune cell.

The disclosure provides gene editing systems for editing an endogenous target gene in an immune cell. The disclosure provides interfering RNAs specific to sequences of target genes. Gene editing systems such as CRISPR/Cas systems, TALENs and zinc fingers can be used to generate double strand breaks, which, through gene repair mechanisms such as homology directed repair or non-homologous end joining (NHEJ), can be used to introduce mutations. NHEJ after resection of the ends of the break, or improper end joining, can be used to introduce deletions. In some embodiments, the target gene comprises a gene encoding a subunit of the MHC-I complex.

Target gene sequences include, but are not limited to, promoters, enhancers, introns, exons, intron/exon junctions, transcription products (pre-mRNA, mRNA, and splice variants), and/or 3' and 5' untranslated regions (UTRs). Any gene element or combination of gene elements may be targeted for the purpose of genetic editing in the immune cells described herein. Modifications to the target genes can be accomplished using any method known in the art to edit the target gene that results in altered or disrupted expression or function the target gene or gene product.

In some embodiments, modifying the gene encoding the MHC class I polypeptide comprises deleting all or a portion of the gene. In some embodiments, modifying the gene encoding the MHC class I polypeptide comprises introducing a mutation in the gene. In some embodiments, the mutation comprises a deletion, insertion, substitution, or frameshift mutation. In some embodiments, modifying the gene comprises using a nucleic acid guided endonuclease.

Gene sequences for the target genes described herein are known in the art. The sequences can be found at public databases, such as NCBI GenBank or the NCBI nucleotide database. Sequences may be found using gene identifiers, for example, the HLA-A gene has NCBI Gene ID: 3105, the HLA-B gene has NCBI Gene ID: 3106, the HLA-C gene has NCBI Gene ID: 3107, and the B2M gene has NCBI Gene ID: 567 and NCBI Reference Sequence: NC 000015.10. Gene sequences may also be found by searching public databases using keywords. For example, HLA-A alleles may be found in the NCBI nucleotide database by searching keywords, "HLA-A*02", "HLA-A*02:01", "HLA-A*02:01:01", or "HLA-A*02:01:01:01." These sequences can be used for targeting in various gene editing techniques known in the art. Table 8 provides non-limiting illustrative sequences of HLA-A allele and B2M gene sequences targeted for modification as described herein.

TABLE 8

| Exemplary Target Gene Sequences | |
|---|---|
| B2M mRNA | (SEQ ID NO: 493) |
| B2M Gene (GenBank: 567) | (SEQ ID NO: 494) |
| HLA-A*02:01:01:01 sequence encoding mRNA | (SEQ ID NO: 495) |
| HLA-A*02 (GenBank: LK021978.1) | (SEQ ID NO: 496) |

The person of ordinary skill in the art will appreciate that T can be substituted for U to convert an RNA sequence to a DNA sequence and vice versa, and both are envisaged as target gene sequences of the disclosure.

In some embodiments, a target gene is edited in the immune cells described herein using a nucleic acid guided endonuclease. Exemplary nucleic acid guided endonucleases include Class II endonucleases, such as CRISPR/Cas9.

"CRISPR" or "CRISPR gene editing" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence, knock out, or mutate a target gene. This system is a type of prokaryotic immune system that confers resistance to foreign genetic elements such as plasmids and phages and provides a form of acquired immunity. The CRISPR/Cas system has been modified for use in gene editing. This is accomplished by introducing into the eukaryotic cell a one or more specifically designed guide nucleic acids (gNAs), typically guide RNAs (gRNAs), and an appropriate Cas endonuclease which forms a ribonucleoprotein complex with the gNA. The gNA guides the gNA-endonuclease protein complex to a target genomic location, and the endonuclease introduces strand breakage at the target genomic location. This strand breakage can be repaired by cellular mechanisms such non-homologous end joining (leading to deletions) or homologous repair (which can generate insertions), thereby introducing genetic modifications into the host cell genome.

CRISPR/Cas systems are classified by class and by type. Class 2 systems currently represent a single interference protein that is categorized into three distinct types (types II, V and VI). Any class 2 CRISPR/Cas system suitable for gene editing, for example a type II, a type V or a type VI system, is envisaged as within the scope of the instant disclosure. Exemplary Class 2 type II CRISPR systems include Cas9, Csn2 and Cas4. Exemplary Class 2, type V CRISPR systems include, Cas12, Cas12a (Cpf1), Cas12b (C2c1), Cas12c (C2c3), Cas12d (CasY), Cas12e (CasX), Cas12f, Cas12g, Cas12h, Cas12i and Cas12k (C2c5). Exemplary Class 2 Type VI systems include Cas13, Cas13a (C2c2) Cas13b, Cas13c and Cas13d.

The CRISPR sequence, sometimes called a CRISPR locus, comprises alternating repeats and spacers. In a naturally-occurring CRISPR, the spacers usually comprise sequences foreign to the bacterium such as a plasmid or phage sequence. As described herein, spacer sequences may also be referred to as "targeting sequences." In CRISPR/Cas systems for a genetic engineering, the spacers are derived from the target gene sequence (the gNA).

An exemplary Class 2 type II CRISPR system relies on the protein Cas9, which is a nuclease with two active cutting sites, one for each strand of the double helix. Combining Cas9 and modified CRISPR locus RNA can be used in a system for gene editing. Pennisi (2013) Science 341: 833-836. In some embodiments, the Cas protein used to modify the immune cells is Cas9.

The CRISPR/Cas system can thus be used to edit a target gene, such as a gene targeted for editing in the immune cells described herein, by adding or deleting a base pair, or introducing a premature stop which thus decreases expression of the target. The CRISPR/Cas system can alternatively be used like RNA interference, turning off a target gene in a reversible fashion. In a mammalian cell, for example, the RNA can guide the Cas protein to a target gene promoter, sterically blocking RNA polymerases.

A Cas protein may be derived from any bacterial or archaeal Cas protein. Any suitable CRISPR/Cas system is envisaged as within the scope of the instant disclosure. In other aspects, Cas protein comprises one or more of Cas1, Cas1B, Cas2, Cas3, Cas4, Cas5, Cash, Cas7, Cas8, Cas9, Cas10, Cas12a (Cpf1), Cas13, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, CasX, CasY, homologs thereof, or modified versions thereof. In some embodiments, the Cas protein is a Cas9 protein, a Cpf1 protein, a C2c1 protein, a C2c2 protein, a C2c3 protein, Cas3, Cas3-HD, Cas 5, Cas7, Cas8, Cas10, or combinations or complexes of these. In some embodiments, the Cas protein is a Cas9 protein.

Artificial CRISPR/Cas systems can be generated which inhibit a target gene, using technology known in the art, e.g., that described in U.S. Publication No. 20140068797, and Cong (2013) Science 339: 819-823. Other artificial CRISPR/Cas systems that are known in the art may also be generated which inhibit a target gene, e.g., that described in Tsai (2014) Nature Biotechnol., 32:6 569-576, U.S. Pat. Nos. 8,871,445; 8,865,406; 8,795,965; 8,771,945; and 8,697,359. Methods of designing suitable gNAs for a particular Cas protein will be known by persons of ordinary skill in the art.

The present disclosure provides gene-targeting guide nucleic acids (gNAs) that can direct the activities of an associated polypeptide (e.g., nucleic acid guided endonuclease) to a specific target gene sequence within a target nucleic acid genome. The genome-targeting nucleic acid can be an RNA. A genome-targeting RNA is referred to as a "guide RNA" or "gRNA" herein. A guide RNA can comprise at least a targeting sequence that hybridizes to a target nucleic acid sequence of interest, and a CRISPR repeat sequence. In some Type II systems, the gRNA also comprises a second RNA called the tracrRNA sequence, also referred to herein as a "scaffold" sequence. In the Type II guide RNA (gRNA), the CRISPR repeat sequence and scaffold sequence hybridize to each other to form a duplex. In the Type V guide RNA (gRNA), the crRNA forms a duplex. In both systems, the duplex can bind a site-directed polypeptide, such that the guide RNA and site-directed polypeptide form a complex. The gene-targeting nucleic acid can provide target specificity to the complex by virtue of its association with the site-directed polypeptide. The gene-targeting nucleic acid thus can direct the activity of the site-directed polypeptide.

In some embodiments, the disclosure provides a guide RNA comprising a targeting sequence and a guide RNA scaffold sequence, wherein the targeting sequence is complementary to the sequence of a target gene.

Exemplary guide RNAs include targeting sequences of about 15-20 bases. As is understood by the person of ordinary skill in the art, each gRNA can be designed to include a targeting sequence complementary to its genomic target sequence. For example, each of the targeting sequences, e.g., the RNA version of the DNA sequences presented in Table 9, minus the three 3' nucleotides which represent that PAM site, can be put into a single RNA chimera or a crRNA.

The gene targeting nucleic acid can be a double-molecule guide RNA. The gene targeting nucleic acid can be a single-molecule guide RNA. The gene targeting nucleic acid can be any known configuration of guide RNA known in the art, such as, for example, including paired gRNA, or multiple gRNAs used in a single step. Although it is clear from genomic sequences where the coding sequences and splice junctions are, other features required for gene expression may be idiosyncratic and unclear.

A double-molecule guide RNA can comprise two strands of RNA. The first strand comprises a sequence in the 5' to 3' direction, an optional spacer extension sequence, a targeting sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) in a Type II system can comprise, in the 5' to 3' direction, an optional spacer extension sequence, a targeting sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

In some embodiments, guide RNA or single-molecule guide RNA (sgRNA) can comprise a targeting sequence and a scaffold sequence. In some embodiments, the scaffold sequence is a Cas9 gRNA sequence. In some embodiments, the scaffold sequence is encoded by a DNA sequence that comprises a sequence that shares at least 90%, at least 95%, at least 96%, at least 97%, at least 98%, or at least 99% identity to GTTTTAGAGCTAGAAATAGCAAGTTAA-AATAAGGCTA GTCCGTTATCAACTTGAAAAAGT-GGCACCGAGTCGGTGCTTTTTTT (SEQ ID NO: 497). In some embodiments, the scaffold sequence is encoded by a DNA sequence that comprise s GTTTTAGAGCT-AGAAATAGCAAGTTAAAATAAGGCTAGTCCGTTAT-CAACTTGAAA AAGTGGCACCGAGTCGGTGCTTT-TTTT (SEQ ID NO: 497).

In some embodiments, for example those embodiments where the CRISPR/Cas system is a Cas9 system, the sgRNA can comprise a 20 nucleotide targeting sequence at the 5' end of the sgRNA sequence. The sgRNA can comprise a less than a 20 nucleotide targeting sequence at the 5' end of the sgRNA sequence. The sgRNA can comprise a more than 20 nucleotide targeting sequence at the 5' end of the sgRNA sequence. The sgRNA can comprise a variable length targeting sequence with 17-30 nucleotides at the 5' end of the sgRNA sequence.

Suitable scaffold sequences, and arrangement of scaffold targeting sequences, will depend on choice of endonuclease, and will be known to persons of skill in the art.

A single-molecule guide RNA (sgRNA) in a Type II system, e.g. Cas9, can comprise, in the 5' to 3' direction, a minimum CRISPR repeat sequence and a targeting sequence.

By way of illustration, guide RNAs used in the CRISPR/Cas9 or CRISPR/Cpf1 system, or other smaller RNAs can be readily synthesized by chemical means, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

The targeting sequence of a gRNA hybridizes to a sequence in a target nucleic acid of interest. The targeting sequence of a genome-targeting nucleic acid can interact with a target nucleic acid in a sequence-specific manner via hybridization (i.e., base pairing). The nucleotide sequence of the targeting sequence can vary depending on the sequence of the target nucleic acid of interest.

In a Cas9 system described herein, the targeting sequence can be designed to hybridize to a target nucleic acid that is located 5' of the reverse complement of a PAM of the Cas9 enzyme used in the system. The targeting sequence may perfectly match the target sequence or may have mismatches. Each CRISPR/Cas system protein may have a particular PAM sequence, in a particular orientation and position, that it recognizes in a target DNA. For example, *S. pyogenes* Cas9 recognizes in a target nucleic acid a PAM that comprises the sequence 5'-NRG-3', where R comprises either A or G, where N is any nucleotide and N is immediately 3' of the target nucleic acid sequence targeted by the targeting sequence. Selection of appropriate PAM sequences will be apparent to the person of ordinary skill in the art.

The target sequence is complementary to, and hybridizes with, the targeting sequence of the gRNA. The target nucleic acid sequence can comprise 20 nucleotides. The target nucleic acid can comprise less than 20 nucleotides. The target nucleic acid can comprise more than 20 nucleotides. The target nucleic acid can comprise at least: 5, 10, 15, 16, 17, 18, 19, 20, 21, 22, 23, 24, 25, 30 or more nucleotides. In some embodiments, for example those embodiments where the CRISPR/Cas system is a Cas9 system, the target nucleic acid sequence can comprise 20 nucleotides immediately 5' of the first nucleotide of the reverse complement of the PAM sequence. This target nucleic acid sequence is often referred to as the PAM strand or a target strand, and the complementary nucleic acid sequence is often referred to the non-PAM strand or non-target strand. One of skill in the art would recognize that the targeting sequence hybridizes to the non-PAM strand of the target nucleic acid, see e.g., US20190185849A1.

In some examples, the percent complementarity between the targeting sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some examples, the percent complementarity between the targeting sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some examples, the percent complementarity between the targeting sequence and the target nucleic acid is 100% over the six contiguous 5'-most nucleotides of the target sequence of the complementary strand of the target nucleic acid. The percent complementarity between the targeting sequence and the target nucleic acid can be at least 60% over about 20 contiguous nucleotides. The length of the targeting sequence and the target nucleic acid can differ by 1 to 6 nucleotides, which may be thought of as a bulge or bulges.

The targeting sequence can be designed or chosen using computer programs known to persons of ordinary skill in the art. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, presence of SNPs, and the like. Available computer programs can take as input NCBI gene IDs, official gene symbols, Ensembl Gene IDs, genomic coordinates, or DNA sequences, and create an output file containing sgRNAs targeting the appropriate genomic regions designated as input. The computer program may also provide a summary of statistics and scores indicating on- and off-target binding of the sgRNA for the target gene (Doench et al. Nat Biotechnol. 34:184-191 (2016)). The disclosure provides guide RNAs comprising a targeting sequence. In some embodiments, the guide RNA further comprises a guide RNA scaffold sequence. In some embodiments, the targeting sequence is complementary to the sequence of a target gene selected from the group consisting of HLA-A, HLA-B, HLA-C, B2M or an allele thereof. In some embodiments, the target gene is an HLA-A gene. In some embodiments, the target gene is an HLA-B gene. In some embodiments, the target gene is an HLA-C gene. In some embodiments the target gene is HLA-A, HLA-B, HLA-C, or a combination thereof. In some embodiments, targeting sequence comprises a sequence that shares about 90%, about 95%, about 96%, about 97%, about 98%, about 99% identity to or is identical to a sequence disclosed in Table 8.

In some embodiments, the gNAs specifically target the sequence of an endogenous HLA-A locus. In some embodiments, the gNAs that specifically target the sequence of an HLA-A locus comprise a sequence that shares about 90%, about 95%, about 96%, about 97%, about 98%, or about 99% identity to a sequence selected from the sequences disclosed in Table 9. In some embodiments, the gNAs that specifically target the sequence of an HLA-A locus comprise a sequence selected from the sequences disclosed in Table 9.

In some embodiments, the gNAs specifically target a sequence of HLA-A*02 alleles. For example, the gRNAs specifically target, and hybridize to, a sequence shared by all HLA-A*02 alleles, but that is not shared by HLA-A*02 and HLA-A*03 alleles. In some embodiments, the gNAs specifically target a sequence of HLA-A*02:01 alleles. In some embodiments, the gNAs specifically target a sequence of HLA-A*02:01:01 alleles. In some embodiments, the gNAs specifically target a sequence of HLA-A*02:01:01:01 alleles. In some embodiments, the gNAs specifically target a sequence of HLA-A*02:01:01:01 alleles.

In some embodiments, the gNAs specifically target a coding DNA sequence of HLA-A*02.

In some embodiments, the gNAs specifically target a coding DNA sequence that is shared by more than 1000 HLA-A*02 alleles. In some embodiments, the gNAs that specifically target a coding DNA sequence in greater than 1000 HLA-A*02 alleles comprise a sequence that shares about 90%, about 95%, about 96%, about 97%, about 98%, about 99% identity or is identical to a sequence selected from SEQ ID NOs: 400-465.

The sequences in Tables 9-12 are presented as DNA sequences. The skilled artisan will understand that thymine (T) can be replaced with uracil (U) in any DNA sequence including those set forth in Tables 9-12, to arrive at the corresponding RNA sequence.

TABLE 9

Illustrative sequences targeting HLA-A and HLA-A alleles

| SEQ ID NO | Guide Nucleic Acid Targeting Sequences |
|---|---|
| 498 | TGGACGACACGCAGTTCGTG |
| 499 | CAGATACCTGGAGAACGGGA |
| 500 | TCCCGTTCTCCAGGTATCTG |
| 501 | CCGCCGCGGTCCAAGAGCGC |
| 502 | CCTGCGCTCTTGGACCGCGG |
| 503 | GGACCTGCGCTCTTGGACCGC |
| 504 | AAGGAGACGCTGCAGCGCACGGG |
| 505 | GAAGGAGACGCTGCAGCGCACGG |
| 506 | GCGGGCGCCGTGGATAGAGCAGG |
| 507 | TGCTCTATCCACGGCGCCCGCGG |
| 508 | CGATGAAGCGGGGCTCCCCGCGG |
| 509 | CGTGTCCCGGCCCGGCCGCGGGG |
| 510 | CGGCTCCATCCTCTGGCTCGCGG |
| 511 | GATGTAATCCTTGCCGTCGTAGG |
| 512 | ACAGCGACGCCGCGAGCCAGAGG |
| 513 | GGATGGAGCCGCGGGCGCCGTGG |
| 514 | GGCGCCGTGGATAGAGCAGGAGG |
| 515 | GCGCCGTGGATAGAGCAGGAGGG |
| 516 | CGGCTACTACAACCAGAGCGAGG |
| 517 | CTGGTTGTAGTAGCCGCGCAGGG |
| 518 | TACTACAACCAGAGCGAGGCCGG |
| 519 | CTACCTGGAGGGCACGTGCGTGG |
| 520 | CACGCACGTGCCCTCCAGGTAGG |
| 521 | GCAGGGTCCCCAGGTCCACTCGG |
| 522 | GTGGACCTGGGGACCCTGCGCGG |

TABLE 9-continued

Illustrative sequences targeting HLA-A and HLA-A alleles

| SEQ ID NO | Guide Nucleic Acid Targeting Sequences |
|---|---|
| 523 | TGGAGGGCACGTGCGTGGAGTGG |
| 524 | GTATGGCTGCGACGTGGGGTCGG |
| 525 | CTGAGCTGCCATGTCCGCCGCGG |
| 526 | GGATTACATCGCCCTGAAAGAGG |
| 527 | CAAGTGGGAGGCGGCCCATGTGG |
| 528 | GTGGGAGGCGGCCCATGTGGCGG |
| 529 | CAGTTGAGAGCCTACCTGGAGGG |
| 530 | GCAGTTGAGAGCCTACCTGGAGG |
| 531 | TACCACCAGTACGCCTACGACGG |
| 532 | TGCCGTCGTAGGCGTACTGGTGG |
| 533 | CCAGTACGCCTACGACGGCAAGG |
| 534 | GGATGTGAAGAAATACCTCATGG |
| 535 | ATTTCTTCACATCCGTGTCCCGG |
| 536 | AGGCGTACTGGTGGTACCCGCGG |
| 537 | CGTACTGGTGGTACCCGCGGAGG |
| 538 | GAGGATGTATGGCTGCGACGTGG |
| 539 | GGATGTATGGCTGCGACGTGGGG |
| 540 | CTCAGACCACCAAGCACAAGTGG |
| 541 | TCAGACCACCAAGCACAAGTGGG |
| 542 | CACCAAGCACAAGTGGGAGGCGG |
| 543 | GACCACCAAGCACAAGTGGGAGG |
| 544 | GAGCCCCGCTTCATCGCAGTGGG |
| 545 | GTAGCCCACTGCGATGAAGCGGG |
| 546 | TAGCCCACTGCGATGAAGCGGGG |
| 547 | CGTAGCCCACTGCGATGAAGCGG |
| 548 | CTTCATCGCAGTGGGCTACGTGG |
| 549 | GGAGCCCCGCTTCATCGCAGTGG |
| 550 | CGGGGAGACACGGAAAGTGAAGG |
| 551 | AGTATTGGGACGGGGAGACACGG |
| 552 | AGGGTCCGGAGTATTGGGACGGG |
| 553 | GAGGGTCCGGAGTATTGGGACGG |
| 554 | GGACCCTCCTGCTCTATCCACGG |
| 555 | GTGGATAGAGCAGGAGGGTCCGG |
| 556 | AGACTCACCGAGTGGACCTGGGG |
| 557 | CACTCGGTGAGTCTGTGAGTGGG |
| 558 | CAGACTCACCGAGTGGACCTGGG |

TABLE 9-continued

Illustrative sequences targeting HLA-A and HLA-A alleles

| SEQ ID NO | Guide Nucleic Acid Targeting Sequences |
|---|---|
| 559 | CCACTCACAGACTCACCGAGTGG |
| 560 | CCACTCGGTGAGTCTGTGAGTGG |
| 561 | TCGGACTGGCGCTTCCTCCGCGG |
| 562 | GCAGCCATACATCCTCTGGACGG |
| 563 | TCTCAACTGCTCCGCCACATGGG |
| 564 | ACCCTCATGCTGCACATGGCAGG |
| 565 | ACCTGCCATGTGCAGCATGAGGG |
| 566 | CACCTGCCATGTGCAGCATGAGG |
| 567 | GGAGGACCAGACCCAGGACACGG |
| 568 | GGATGGGGAGGACCAGACCCAGG |
| 569 | GACCTGGCAGCGGGATGGGGAGG |
| 570 | AGATCACACTGACCTGGCAGCGG |
| 571 | GATCACACTGACCTGGCAGCGGG |
| 572 | AGGTCAGTGTGATCTCCGCAGGG |
| 573 | AAGCCCCTCACCCTGAGATGGGG |
| 574 | CTGCGGAGATCACACTGACCTGG |
| 575 | CAGCAATGATGCCCACGATGGGG |
| 576 | CCAGCAATGATGCCCACGATGGG |
| 577 | GCCAGCAATGATGCCCACGATGG |
| 578 | GGATGGAACCTTCCAGAAGTGGG |
| 579 | GGGATGGAACCTTCCAGAAGTGG |
| 580 | ATGCCCACGATGGGGATGGTGGG |
| 581 | CAGCCCACCATCCCCATCGTGGG |
| 582 | CCAGCCCACCATCCCCATCGTGG |
| 583 | GATGCCCACGATGGGGATGGTGG |
| 584 | CAGGGCCCAGCACCTCAGGGTGG |
| 585 | AATGATGCCCACGATGGGGATGG |
| 586 | GGCCCTGACCCAGACCTGGGCGG |
| 587 | GACCCAGGACACGGAGCTCGTGG |
| 588 | ACACGGAGCTCGTGGAGACCAGG |
| 589 | CGTGGAGACCAGGCCTGCAGGGG |
| 590 | TCGTGGAGACCAGGCCTGCAGGG |
| 591 | AGCTGTGATCACTGGAGCTGTGG |
| 592 | AAAAGGAGGGAGCTACTCTCAGG |
| 593 | ATGTGGAGGAGGAAGAGCTCAGG |
| 594 | GTGTCTCTCACAGCTTGTAAAGG |
| 595 | GAGAGACACATCAGAGCCCTGGG |

TABLE 9-continued

Illustrative sequences targeting HLA-A and HLA-A alleles

| SEQ ID NO | Guide Nucleic Acid Targeting Sequences |
|---|---|
| 596 | CTCCGCAGGGTAGAAGCTCAGGG |
| 597 | GGCCCTGAGCTTCTACCCTGCGG |
| 598 | GCTCAGGGCCCAGCACCTCAGGG |
| 599 | TATCTCTGCTCCTGTCCAGAAGG |
| 600 | AGTAGCAGGACGAGGGTTCGGGG |
| 601 | CCCCGAGAGTAGCAGGACGAGGG |
| 602 | CCCTCGTCCTGCTACTCTCGGGG |
| 603 | CCTCGTCCTGCTACTCTCGGGGG |
| 604 | CTGTGGTCGCTGCTGTGATGTGG |
| 605 | TCGCTGCTGTGATGTGGAGGAGG |
| 606 | TGGTCGCTGCTGTGATGTGGAGG |
| 607 | CACAGCCGCCCACTTCTGGAAGG |
| 608 | CCAGAAGTGGGCGGCTGTGGTGG |
| 609 | TGGAACCTTCCAGAAGTGGGCGG |
| 610 | TCACAGCTCCAAAGAGAACCAGG |
| 611 | CTGACCATGAAGCCACCCTGAGG |
| 612 | GCAAACCCTCATGCTGCACATGG |
| 613 | TGAAGCCACCCTGAGGTGCTGGG |
| 614 | GGTGAGTCATATGCGTTTTGGGG |
| 615 | GTGAGTCATATGCGTTTTGGGGG |
| 616 | CTTCATGGTCAGAGACAGCGTGG |
| 617 | TCTGGCCCTGACCCAGACCTGGG |

The sequences disclosed in Table 9 include the corresponding genomic sequences, inclusive of the PAM sequence. The skilled artisan will understand that the targeting sequence of the gRNA does not include three 3' terminal nucleotides of the sequences in Table 9, which represent the corresponding PAM site for the gRNA.

The disclosure provides gNAs comprising a targeting sequence specific to the B2M gene. In some embodiments, the gNAs specifically target the coding sequence (CDS) sequence of the B2M gene. In some embodiments, the gNA comprises a sequence that targets the B2M gene promoter sequence.

In some embodiments the gNA comprise a targeting sequence and a gNA scaffold sequence. In some embodiments, the targeting sequence comprises a sequence set forth in Table 10, or a sequence shares about 90%, about 95%, about 96%, about 97%, about 98%, about 99% identity thereto.

In some embodiments, the targeting sequence is complementary to a sequence of the B2M gene. In some embodiments, the B2M gene comprises a sequence that shares about 90%, about 95%, about 96%, about 97%, about 98%, about 99% identity to the B2M sequence set forth in Table 8.

TABLE 10

Illustrative sequences targeting B2M

| SEQ ID NO | Sequence |
|---|---|
| 618 | CGCGAGCACAGCTAAGGCCA |
| 619 | GAGTAGCGCGAGCACAGCTA |
| 620 | AGGGTAGGAGAGACTCACGC |
| 621 | CTGAATCTTTGGAGTACCTG |
| 622 | TCACGTCATCCAGCAGAGAA |
| 623 | TCCTGAATTGCTATGTGTCT |
| 624 | AAGTCAACTTCAATGTCGGA |
| 625 | GTCTTTTTCCCGATATTCCTC |
| 626 | TGGAGTACCTGAGGAATATC |
| 627 | CAGCCCAAGATAGTTAAGTG |
| 628 | ACAAAGTCACATGGTTCACA |
| 629 | ACTCTCTCTTTCTGGCCTGG |
| 630 | TGGGCTGTGACAAAGTCACA |
| 631 | GGCCGAGATGTCTCGCTCCG |
| 632 | CAGTAAGTCAACTTCAATGT |
| 633 | ACTCACGCTGGATAGCCTCC |
| 634 | CATACTCATCTTTTTCAGTG |
| 635 | CACAGCCCAAGATAGTTAAG |
| 636 | TTCAGACTTGTCTTTCAGCA |
| 637 | AGTCACATGGTTCACACGGC |
| 638 | ATACTCATCTTTTTCAGTGG |
| 639 | GGCATACTCATCTTTTTCAG |
| 640 | ACAGCCCAAGATAGTTAAGT |
| 641 | GCTACTCTCTCTTTCTGGCC |
| 642 | TGGAGAGAGAATTGAAAAAG |
| 643 | ACTTGTCTTTCAGCAAGGAC |
| 644 | GAAGTTGACTTACTGAAGAA |
| 645 | GGCCACGGAGCGAGACATCT |
| 646 | GCATACTCATCTTTTTCAGT |
| 647 | CGTGAGTAAACCTGAATCTT |
| 648 | TTACCCCACTTAACTATCTT |
| 649 | TTGGAGTACCTGAGGAATAT |
| 650 | ACCCAGACACATAGCAATTC |
| 651 | TTTGACTTTCCATTCTCTGC |
| 652 | TTCCTGAATTGCTATGTGTC |
| 653 | CTCAGGTACTCCAAAGATTC |
| 654 | CTTACCCCACTTAACTATCT |

TABLE 10-continued

Illustrative sequences targeting B2M

| SEQ ID NO | Sequence |
|---|---|
| 655 | CTCGCGCTACTCTCTCTTTC |
| 656 | TCGATCTATGAAAAAGACAG |
| 657 | GAGACATGTAAGCAGCATCA |
| 658 | ACATGTAAGCAGCATCATGG |
| 659 | GAAGTCCTAGAATGAGCGCC |
| 660 | GAGCGCCCGGTGTCCCAAGC |
| 661 | AGCGCCCGGTGTCCCAAGCT |
| 662 | GCGCCCGGTGTCCCAAGCTG |
| 663 | CTGGGGCGCGCACCCCAGAT |
| 664 | GGGCGCGCACCCCAGATCGG |
| 665 | GGCGCGCACCCCAGATCGGA |
| 666 | CATCACGAGACTCTAAGAAA |
| 667 | TAAGAAAAGGAAACTGAAAA |
| 668 | AAGAAAAGGAAACTGAAAAC |
| 669 | GAAAGTCCCTCTCTCTAACC |
| 670 | CTAACCTGGCACTGCGTCGC |
| 671 | CTGGCACTGCGTCGCTGGCT |
| 672 | TGCGTCGCTGGCTTGGAGAC |
| 673 | GCTGGCTTGGAGACAGGTGA |
| 674 | GAGACAGGTGACGGTCCCTG |
| 675 | AGACAGGTGACGGTCCCTGC |
| 676 | CCTGCGGGCCTTGTCCTGAT |
| 677 | CGGGCCTTGTCCTGATTGGC |
| 678 | GGGCCTTGTCCTGATTGGCT |
| 679 | GGGCACGCGTTTAATATAAG |
| 680 | CACGCGTTTAATATAAGTGG |
| 681 | TATAAGTGGAGGCGTCGCGC |
| 682 | AAGTGGAGGCGTCGCGCTGG |
| 683 | AGTGGAGGCGTCGCGCTGGC |
| 684 | TTCCTGAAGCTGACAGCATT |
| 685 | TCCTGAAGCTGACAGCATTC |
| 686 | GCCCGAATGCTGTCAGCTTC |
| 687 | AAACGCGTGCCCAGCCAATC |
| 688 | GTGCCCAGCCAATCAGGACA |
| 689 | CCAATCAGGACAAGGCCCGC |
| 690 | CAATCAGGACAAGGCCCGCA |
| 691 | CAAGCCAGCGACGCAGTGCC |

TABLE 10-continued

Illustrative sequences targeting B2M

| SEQ ID NO | Sequence |
|---|---|
| 692 | CGCAGTGCCAGGTTAGAGAG |
| 693 | GCAGTGCCAGGTTAGAGAGA |
| 694 | GAGTCTCGTGATGTTTAAGA |
| 695 | TAAGAAGGCATGCACTAGAC |
| 696 | AAGAAGGCATGCACTAGACT |
| 697 | TGAGTTTGCTGTCTGTACAT |
| 698 | TACATCGGCGCCCTCCGATC |
| 699 | ACATCGGCGCCCTCCGATCT |
| 700 | CATCGGCGCCCTCCGATCTG |
| 701 | CTGGGGTGCGCGCCCCAGCT |
| 702 | TGGGGTGCGCGCCCCAGCTT |
| 703 | CGCGCCCCAGCTTGGGACAC |
| 704 | GCGCCCCAGCTTGGGACACC |
| 705 | CAAGTCACTTAGCATCTCTG |
| 706 | ACAGAAGTTCTCCTTCTGCT |
| 707 | ATTCAAAGATCTTAATCTTC |
| 708 | TTCAAAGATCTTAATCTTCT |
| 709 | TTTTCTCGAATGAAAAATGC |
| 710 | TGCAGGTCCGAGCAGTTAAC |
| 711 | GGTCCGAGCAGTTAACTGGC |
| 712 | GTCCGAGCAGTTAACTGGCT |
| 713 | TCCGAGCAGTTAACTGGCTG |
| 714 | AGCAAGTCACTTAGCATCTC |
| 715 | GCAAGTCACTTAGCATCTCT |
| 716 | TGGGGCCAGTCTGCAAAGCG |
| 717 | GGGGCCAGTCTGCAAAGCGA |
| 718 | GGGCCAGTCTGCAAAGCGAG |
| 719 | GGCCAGTCTGCAAAGCGAGG |
| 720 | GGACACCGGGCGCTCATTCT |
| 721 | GGCGCTCATTCTAGGACTTC |
| 722 | CTCATTCTAGGACTTCAGGC |
| 723 | ATTCTAGGACTTCAGGCTGG |
| 724 | TTCAGGCTGGAGGCACATTA |
| 725 | TGCCCCCTCGCTTTGCAGAC |
| 726 | GATGCTAAGTGACTTGCTAA |
| 727 | GCCCCAGCCAGTTAACTGCT |
| 728 | GCATTTTTCATTCGAGAAAA |

TABLE 10-continued

| Illustrative sequences targeting B2M | |
|---|---|
| SEQ ID NO | Sequence |
| 729 | TTTGAATGCTACCTAGCAGA |
| 730 | TTCTGTTTATAACTACAGCT |
| 731 | TCTGTTTATAACTACAGCTT |

In some embodiments, the immune cells described herein are edited using TALEN gene editing.

"TALEN" or "TALEN gene editing" refers to a transcription activator-like effector nuclease, which is an artificial nuclease used to edit a target gene.

TALENs are produced artificially by fusing a TAL effector DNA binding domain to a DNA cleavage domain. Transcription activator-like effectors (TALEs) derived from *Xanthomonas* bacteria can be engineered to bind any desired DNA sequence, including a portion of target genes such as TCR subunits, MHC class I complex components, or CD52. By combining an engineered TALE with a DNA cleavage domain, a restriction enzyme can be produced which is specific to any desired DNA sequence, including a target gene sequence. These can then be introduced into a cell, wherein they can be used for genome editing.

To produce a TALEN, a TALE protein is fused to a nuclease (N), which is a wild-type or mutated Fold endonuclease. Several mutations to FokI have been made for its use in TALENs; these, for example, improve cleavage specificity or activity.

The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity.

TALENs specific to sequences in a target gene can be constructed using any method known in the art, including various schemes using modular components.

In some embodiments, a target gene is edited in the immune cells described herein using ZFN gene editing.

"ZFN" or "Zinc Finger Nuclease" or "ZFN gene editing" refer to a zinc finger nuclease, an artificial nuclease which can be used to edit a target gene.

Like a TALEN, a ZFN comprises a Fold nuclease domain (or derivative thereof) fused to a DNA-binding domain. In the case of a ZFN, the DNA-binding domain comprises one or more zinc fingers.

A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells.

Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart.

Also like a TALEN, a ZFN can create a double-stranded break in the DNA, which can create a frame-shift mutation if improperly repaired, leading to a decrease in the expression and amount of a target gene or gene product in a cell. ZFNs can also be used with homologous recombination to mutate in a target gene.

ZFNs specific to sequences in a target gene can be constructed using any method known in the art.

In some embodiments, the expression and of function of one or more MCH-I components are reduced using RNA interference. "RNAi" or "RNA interference" refers to the process of sequence-specific post-transcriptional gene silencing, mediated by double-stranded RNA (dsRNA). Duplex RNAs such as siRNA (small interfering RNA), miRNA (micro RNA), shRNA (short hairpin RNA), ddRNA (DNA-directed RNA), piRNA (Piwi-interacting RNA), or rasiRNA (repeat associated siRNA) and modified forms thereof are all capable of mediating RNA interference. These dsRNA molecules may be commercially available or may be designed and prepared based on known sequence information. The anti-sense strand of these molecules can include RNA, DNA, PNA, or a combination thereof. DNA/RNA chimeric polynucleotides include, but are not limited to, a double-strand polynucleotide composed of DNA and RNA that inhibits the expression of a target gene. dsRNA molecules can also include one or more modified nucleotides, as described herein, which can be incorporated on either or both strands.

In RNAi gene silencing or knockdown, dsRNA comprising a first (anti-sense) strand that is complementary to a portion of a target gene and a second (sense) strand that is fully or partially complementary to the first anti-sense strand is introduced into an organism. After introduction into the organism, the target gene-specific dsRNA is processed into relatively small fragments (siRNAs) and can subsequently become distributed throughout the organism, decrease messenger RNA of target gene, leading to a phenotype that may come to closely resemble the phenotype arising from a complete or partial deletion of the target gene.

Certain dsRNAs in cells can undergo the action of Dicer enzyme, a ribonuclease III enzyme. Dicer can process the dsRNA into shorter pieces of dsRNA, i.e. siRNAs. RNAi also involves an endonuclease complex known as the RNA induced silencing complex (RISC). Following cleavage by Dicer, siRNAs enter the RISC complex and direct cleavage of a single stranded RNA target having a sequence complementary to the anti-sense strand of the siRNA duplex. The other strand of the siRNA is the passenger strand. Cleavage of the target RNA takes place in the middle of the region complementary to the anti-sense strand of the siRNA duplex. siRNAs can thus down regulate or knock down gene expression by mediating RNA interference in a sequence-specific manner.

As used herein with respect to RNA interference, "target gene" or "target sequence" refers to a gene or gene sequence whose corresponding RNA is targeted for degradation through the RNAi pathway using dsRNAs or siRNAs as described herein. Exemplary target gene sequences are shown in Table 8. To target a gene, for example using an siRNA, the siRNA comprises an anti-sense region complementary to, or substantially complementary to, at least a portion of the target gene or sequence, and sense strand complementary to the anti-sense strand. Once introduced into a cell, the siRNA directs the RISC complex to cleave an RNA comprising a target sequence, thereby degrading the RNA. The disclosure provides interfering RNAs. The double stranded RNA molecule of the disclosure may be in the form of any type of RNA interference molecule known in the art. In some embodiments, the double stranded RNA molecule is a small interfering RNA (siRNA). In other embodiments, the double stranded RNA molecule is a short hairpin RNA (shRNA) molecule. In other embodiments, the double stranded RNA molecule is a Dicer substrate that is processed in a cell to produce an siRNA. In other embodiments the double stranded RNA molecule is part of a microRNA precursor molecule.

In some embodiments, the shRNA is a length to be suitable as a Dicer substrate, which can be processed to produce a RISC active siRNA molecule. See, e.g., Rossi et al., A Dicer substrate double stranded RNA (e.g. a shRNA) can be of a length sufficient that it is processed by Dicer to produce an active siRNA, and may further include one or more of the following properties: (i) the Dicer substrate shRNA can be asymmetric, for example, having a 3' overhang on the anti-sense strand, (ii) the Dicer substrate shRNA can have a modified 3' end on the sense strand to direct orientation of Dicer binding and processing of the dsRNA to an active siRNA, for example the incorporation of one or more DNA nucleotides, and (iii) the first and second strands of the Dicer substrate ds RNA can be from 21-30 bp in length.

In some embodiments, the interfering RNAs comprise a sequence complementary to a sequence of a B2M mRNA. In some embodiments, the interfering RNA is capable of inducing RNAi-mediated degradation of the B2M mRNA. In some embodiments, the B2M mRNA sequence comprises a coding sequence. In some embodiments, the B2M mRNA sequence comprises an untranslated region.

In some embodiments, the interfering RNAs comprise a sequence complementary to a sequence of an HLA-A*02 mRNA. In some embodiments, the interfering RNA is capable of inducing RNAi-mediated degradation of the HLA-A*02 mRNA. In some embodiments, the HLA-A*02 mRNA sequence comprises a coding sequence. In some embodiments, the HLA-A*02 mRNA sequence comprises an untranslated region.

In some embodiments, the interfering RNA is a short hairpin RNA (shRNA). In some embodiments, the shRNA comprises a first sequence, having from 5' to 3' end a sequence complementary to the B2M mRNA; and a second sequence, having from 5' to 3' end a sequence complementary to the first sequence, wherein the first sequence and second sequence form the shRNA.

In some embodiments, the first sequence is 18, 19, 20, 21, or 22 nucleotides. In some embodiments, the first sequence is complementary to a sequence selected from the sequences set forth in Tables 11 and 12. In some embodiments, the first sequence has GC content greater than or equal to 25% and less than 60%. In some embodiments, the first sequence is complementary to a sequence selected from the sequences set forth in Tables 11 and 12. In some embodiments, the first sequence does not comprise four nucleotides of the same base or a run of seven C or G nucleotide bases. In some embodiments, the first sequence is 21 nucleotides.

Illustrative target B2M sequences complementary to the first sequence are shown in Table 11.

In some cases, the first sequence may have 100% identity, i.e. complete identity, homology, complementarity to the target nucleic acid sequence. In other cases, there may be one or more mismatches between the first sequence and the target nucleic acid sequence. For example, there may be 1, 2, 3, 4, 5, 6, or 7 mismatches between the sense region and the target nucleic acid sequence.

The sequences set forth in Table 11 are presented as DNA sequences. In all sequences set forth in Table 11, thymine (T) may be replaced by uracil (U) to arrive at the sequence of the target mRNA sequence.

TABLE 11

Illustrative target B2M sequences complementary to first sequence

| SEQ ID NO | Sequence |
|---|---|
| 732 | AGAGAATGGAAAGTCAAATTT |
| 733 | ATGGACATGATCTTCTTTATA |
| 734 | TGGACATGATCTTCTTTATAA |
| 735 | GGACATGATCTTCTTTATAAT |
| 736 | TGACAGGATTATTGGAAATTT |
| 737 | TTGTGGTTAATCTGGTTTATT |
| 738 | TGTGGTTAATCTGGTTTATTT |
| 739 | GCAGAGAATGGAAAGTCAAAT |
| 740 | CAGAGAATGGAAAGTCAAATT |
| 741 | GAGAATGGAAAGTCAAATTTC |
| 742 | GTCACAGCCCAAGATAGTTAA |
| 743 | TGCTTATACACTTACACTTTA |
| 744 | GCTTATACACTTACACTTTAT |
| 745 | CTTATACACTTACACTTTATG |
| 746 | ACATGGACATGATCTTCTTTA |
| 747 | CATGGACATGATCTTCTTTAT |
| 748 | ATCAACATCTTGGTCAGATTT |
| 749 | CTTGCACTCAAAGCTTGTTAA |
| 750 | AGTTAAGCGTGCATAAGTTAA |
| 751 | GCATAAGTTAACTTCCAATTT |
| 752 | TACATACTCTGCTTAGAATTT |
| 753 | ACATACTCTGCTTAGAATTTG |
| 754 | TTGACAGGATTATTGGAAATT |
| 755 | GACAGGATTATTGGAAATTTG |
| 756 | TAAGGCATGGTTGTGGTTAAT |
| 757 | GTTGTGGTTAATCTGGTTTAT |
| 758 | GTTCCACAAGTTAAATAAATC |
| 759 | TCCAGCGTACTCCAAAGATTC |
| 760 | TACTCCAAAGATTCAGGTTTA |
| 761 | ACTCCAAAGATTCAGGTTTAC |
| 762 | CACGTCATCCAGCAGAGAATG |
| 763 | GGTTTCATCCATCCGACATTG |

TABLE 11-continued

| Illustrative target B2M sequences complementary to first sequence | |
|---|---|
| SEQ ID NO | Sequence |
| 764 | CCGACATTGAAGTTGACTTAC |
| 765 | TGAAGAATGGAGAGAGAATTG |
| 766 | GAGCATTCAGACTTGTCTTTC |
| 767 | TTCAGCAAGGACTGGTCTTTC |
| 768 | GCAAGGACTGGTCTTTCTATC |
| 769 | CGTGTGAACCATGTGACTTTG |
| 770 | CTTTGTCACAGCCCAAGATAG |
| 771 | TCACAGCCCAAGATAGTTAAG |
| 772 | AGTGGGATCGAGACATGTAAG |
| 773 | AGGTTTGAAGATGCCGCATTT |
| 774 | GGTTTGAAGATGCCGCATTTG |
| 775 | TTGATATGCTTATACACTTAC |
| 776 | TGAGTGCTGTCTCCATGTTTG |
| 777 | TGTCTCCATGTTTGATGTATC |
| 778 | TCAACATCTTGGTCAGATTTG |
| 779 | TCAGATTTGAACTCTTCAATC |
| 780 | TTCAATCTCTTGCACTCAAAG |
| 781 | TTGCACTCAAAGCTTGTTAAG |
| 782 | ACTCAAAGCTTGTTAAGATAG |
| 783 | AGATAGTTAAGCGTGCATAAG |
| 784 | TGCATAAGTTAACTTCCAATT |
| 785 | GTTAACTTCCAATTTACATAC |
| 786 | ATTGACAGGATTATTGGAAAT |
| 787 | GTAAGGCATGGTTGTGGTTAA |
| 788 | GGTTGTGGTTAATCTGGTTTA |
| 789 | TTCCTGAAGCTGACAGCATTC |
| 790 | GCTATCCAGCGTACTCCAAAG |
| 791 | CATCCAGCAGAGAATGGAAAG |
| 792 | CAAATTTCCTGAATTGCTATG |
| 793 | ATTGCTATGTGTCTGGGTTTC |
| 794 | GAAGATGCCGCATTTGGATTG |
| 795 | CAATTTACATACTCTGCTTAG |
| 796 | TATCCAGCGTACTCCAAAGAT |
| 797 | ATCCAGCGTACTCCAAAGATT |
| 798 | CTCCAAAGATTCAGGTTTACT |
| 799 | TGCTATGTGTCTGGGTTTCAT |

TABLE 11-continued

| Illustrative target B2M sequences complementary to first sequence | |
|---|---|
| SEQ ID NO | Sequence |
| 800 | TTTCATCCATCCGACATTGAA |
| 801 | GAAGTTGACTTACTGAAGAAT |
| 802 | GAAGAATGGAGAGAGAATTGA |
| 803 | AGAATGGAGAGAGAATTGAAA |
| 804 | CAGCAAGGACTGGTCTTTCTA |
| 805 | AGCAAGGACTGGTCTTTCTAT |
| 806 | ACTTTGTCACAGCCCAAGATA |
| 807 | TTGTCACAGCCCAAGATAGTT |
| 808 | TGTCACAGCCCAAGATAGTTA |
| 809 | CACAGCCCAAGATAGTTAAGT |
| 810 | GCAGCATCATGGAGGTTTGAA |
| 811 | CCGCATTTGGATTGGATGAAT |
| 812 | TTGAGTGCTGTCTCCATGTTT |
| 813 | AGTGCTGTCTCCATGTTTGAT |
| 814 | CTGTCTCCATGTTTGATGTAT |
| 815 | TCTAGGAGGGCTGGCAACTTA |
| 816 | CAACATCTTGGTCAGATTTGA |
| 817 | GTCAGATTTGAACTCTTCAAT |
| 818 | TCTTGCACTCAAAGCTTGTTA |
| 819 | TGCACTCAAAGCTTGTTAAGA |
| 820 | GCACTCAAAGCTTGTTAAGAT |
| 821 | CACTCAAAGCTTGTTAAGATA |
| 822 | TCAAAGCTTGTTAAGATAGTT |
| 823 | CAAAGCTTGTTAAGATAGTTA |
| 824 | GATAGTTAAGCGTGCATAAGT |
| 825 | ATAGTTAAGCGTGCATAAGTT |
| 826 | TAGTTAAGCGTGCATAAGTTA |
| 827 | TTAAGCGTGCATAAGTTAACT |
| 828 | TAAGCGTGCATAAGTTAACTT |
| 829 | ATTTACATACTCTGCTTAGAA |
| 830 | TTTACATACTCTGCTTAGAAT |
| 831 | ACAGGATTATTGGAAATTTGT |
| 832 | CAGGATTATTGGAAATTTGTT |
| 833 | AGGCATGGTTGTGGTTAATCT |
| 834 | CAGCAGAGAATGGAAAGTCAA |
| 835 | TCCGACATTGAAGTTGACTTA |
| 836 | CTGGTCTTTCTATCTCTTGTA |

TABLE 11-continued

| Illustrative target B2M sequences complementary to first sequence | |
|---|---|
| SEQ ID NO | Sequence |
| 837 | CCGTGTGAACCATGTGACTTT |
| 838 | CCCAAGATAGTTAAGTGGGAT |
| 839 | GGTTGCTCCACAGGTAGCTCT |
| 840 | GCTCCACAGGTAGCTCTAGGA |
| 841 | GGGAGCAGAGAATTCTCTTAT |
| 842 | GGAGCAGAGAATTCTCTTATC |
| 843 | GAGCAGAGAATTCTCTTATCC |
| 844 | GAGAATTCTCTTATCCAACAT |
| 845 | GAATTCTCTTATCCAACATCA |
| 846 | AAGTGGAGCATTCAGACTTGT |
| 847 | AAGGACTGGTCTTTCTATCTC |
| 848 | AAGCTTGTTAAGATAGTTAAG |
| 849 | AAGCGTGCATAAGTTAACTTC |
| 850 | AAGATGCCGCATTTGGATTGG |
| 851 | AAGAATGGAGAGAGAATTGAA |
| 852 | AACATCAACATCTTGGTCAGA |
| 853 | AAGGCATGGTTGTGGTTAATC |
| 854 | AAGCAGCATCATGGAGGTTTG |
| 855 | AAGATGAGTATGCCTGCCGTG |
| 856 | AAGTTGACTTACTGAAGAATG |
| 857 | AAGATAGTTAAGCGTGCATAA |
| 858 | AACTTCCAATTTACATACTCT |
| 859 | AACATCTTGGTCAGATTTGAA |
| 860 | AACTCTTCAATCTCTTGCACT |
| 861 | AATTTCCTGAATTGCTATGTG |
| 862 | AATGGAAAGTCAAATTTCCTG |
| 863 | AACCATGTGACTTTGTCACAG |
| 864 | AATTGACAGGATTATTGGAAA |
| 865 | AATTCTCTTATCCAACATCAA |
| 866 | AAAGTGGAGCATTCAGACTTG |
| 867 | AAAGTCAAATTTCCTGAATTG |
| 868 | GTTGCTCCACAGGTAGCTCTA |
| 869 | AATTTACATACTCTGCTTAGA |

An exemplary sequence encoding a B2M shRNA comprises a sequence of GCACTCAAAGCTTGTTAAGATCGAAATCTTAACAAGCTTTGAGTGC (SEQ ID NO: 179), or a sequence having at least 90%, at least 95%, at least 97% or at least 99% identity thereto. A further exemplary sequence encoding a B2M shRNA comprises a sequence of GTTAACTTCCAATTTACATACCGAAGTATGTAAATTGGAAGTTAAC (SEQ ID NO: 180), or a sequence having at least 90%, at least 95%, at least 97% or at least 99% identity thereto.

In some embodiments, the interfering RNAs comprise a sequence complementary to a sequence of an HLA-A*02 mRNA. In some embodiments, the interfering RNA is capable of inducing RNAi-mediated degradation of the HLA-A*02 mRNA. In some embodiments, the HLA-A*02 mRNA sequence comprises a coding sequence. In some embodiments, the HLA-A*02 mRNA sequence comprises an untranslated region.

In some embodiments, the interfering RNA is a short hairpin RNA (shRNA). In some embodiments, the shRNA comprises a first sequence, having from 5' to 3' end a sequence complementary to the HLA-A*02 mRNA; and a second sequence, having from 5' to 3' end a sequence complementary to the first sequence, wherein the first sequence and second sequence form the shRNA Illustrative target HLA sequences complementary to the first sequence are shown in Table 12.

TABLE 12

| Illustrative target HLA sequences complementary to first sequence | |
|---|---|
| SEQ ID NO | Sequence |
| 870 | CTTCTTCCTTCCCTATTAAAA |
| 871 | TCTCACTCCATGAGGTATTTC |
| 872 | CTCTCACTCCATGAGGTATTT |
| 873 | GAGGAGGAAGAGCTCAGATAG |
| 874 | GCTCTCACTCCATGAGGTATT |
| 875 | AGGATTACATCGCCCTGAAAG |
| 876 | ACACCGTCCAGAGGATGTATG |
| 877 | AGGGTCCTTCTTCCTGGATAC |
| 878 | CCTACGACGGCAAGGATTACA |
| 879 | TCACTCCATGAGGTATTTCTT |
| 880 | CTACGACGGCAAGGATTACAT |
| 881 | CTCACTCCATGAGGTATTTCT |
| 882 | GGAGGAAGAGCTCAGATAGAA |
| 883 | CACACCGTCCAGAGGATGTAT |
| 884 | CACGCTGTCTCTGACCATGAA |
| 885 | CTGGACAGGAGCAGAGATACA |
| 886 | TGGAGGAGGAAGAGCTCAGAT |
| 887 | GGCTCTCACTCCATGAGGTAT |
| 888 | CATCTCTGTCTCAACTTCATG |
| 889 | TACGACGGCAAGGATTACATC |
| 890 | GGATTACATCGCCCTGAAAGA |
| 891 | GATTACATCGCCCTGAAAGAG |

TABLE 12-continued

| Illustrative target HLA sequences complementary to first sequence | |
|---|---|
| SEQ ID NO | Sequence |
| 892 | CTCAGACCACCAAGCACAAGT |
| 893 | TCACACCGTCCAGAGGATGTA |
| 894 | ACTCCATGAGGTATTTCTTCA |
| 895 | CACTCCATGAGGTATTTCTTC |
| 896 | CCATGAGGTATTTCTTCACAT |
| 897 | ACTTCTTCCTTCCCTATTAAA |
| 898 | GTGTCTCTCACAGCTTGTAAA |
| 899 | CTGTGTTCGTGTAGGCATAAT |
| 900 | TGTGTTCGTGTAGGCATAATG |
| 901 | TAACTTCTTCCTTCCCTATTA |
| 902 | TCTGGACAGGAGCAGAGATAC |
| 903 | TTGCTGGCCTGGTTCTCTTTG |
| 904 | TGTCTCTCACAGCTTGTAAAG |
| 905 | ACTTGAAGAACCCTGACTTTG |
| 906 | GAAGAACCCTGACTTTGTTTC |
| 907 | TCTGTGTTCGTGTAGGCATAA |
| 908 | CATGGTGCACTGAGCTGTAAC |
| 909 | GTAACTTCTTCCTTCCCTATT |
| 910 | CATGTGCAGCATGAGGGTTTG |
| 911 | TTGTTCCTGCCCTTCCCTTTG |
| 912 | ACCCAGTTCTCACTCCCATTG |
| 913 | GGGTTTCCAGAGAAGCCAATC |
| 914 | TTCTCCCTCTCCCAACCTATG |
| 915 | GTCTCTCACAGCTTGTAAAGT |
| 916 | TGTGTCTCTCACAGCTTGTAA |
| 917 | GAGGAAGAGCTCAGATAGAAA |
| 918 | TGAAGAACCCTGACTTTGTTT |
| 919 | TTGAAGAACCCTGACTTTGTT |
| 920 | GTGTTCGTGTAGGCATAATGT |
| 921 | TGGTGCACTGAGCTGTAACTT |
| 922 | CTCCCTCTCCCAACCTATGTA |
| 923 | AGGAGGAAGAGCTCAGATAGA |
| 924 | ACCTATGTAGGGTCCTTCTTC |
| 925 | GGGTCCTTCTTCCTGGATACT |
| 926 | GGTCCTTCTTCCTGGATACTC |
| 927 | GTCCTTCTTCCTGGATACTCA |
| 928 | AAGCCAATCAGTGTCGTCGCG |

TABLE 12-continued

| Illustrative target HLA sequences complementary to first sequence | |
|---|---|
| SEQ ID NO | Sequence |
| 929 | AAGAGGACCTGCGCTCTTGGA |
| 930 | AAGTGTGAGACAGCTGCCTTG |
| 931 | AAGGCACCTGCATGTGTCTGT |
| 932 | AATCATCTTTCCTGTTCCAGA |
| 933 | AAAGGCACCTGCATGTGTCTG |
| 934 | AAAGAGGACCTGCGCTCTTGG |
| 935 | AAACGCATATGACTCACCACG |
| 936 | GGAAGAGCTCAGATAGAAA |
| 937 | GGGAGACACGGAAAGTGAA |
| 938 | CACCTGCCATGTGCAGCATGA |
| 939 | GGAGATCACACTGACCTGGCA |
| 940 | GGATTACATCGCCCTGAAAG |
| 941 | GCAGGAGGGTCCGGAGTATT |
| 942 | GGACGGGGAGACACGGAAAG |
| 943 | GAAAGTGAAGGCCCACTCA |
| 944 | GATACCTGGAGAACGGGAAG |
| 945 | GCTGTGGTGGTGCCTTCTGG |
| 946 | GCTACTACAACCAGAGCGAG |
| 947 | GTGGCTCCGCAGATACCTG |
| 948 | GCCAATCAGTGTCGTCGCG |
| 949 | GAGGACCTGCGCTCTTGGA |
| 950 | GTGTGAGACAGCTGCCTTG |
| 951 | GGCACCTGCATGTGTCTGT |
| 952 | TCATCTTTCCTGTTCCAGA |
| 953 | AGGCACCTGCATGTGTCTG |
| 954 | AGAGGACCTGCGCTCTTGG |
| 955 | ACGCATATGACTCACCACG |

In some embodiments, the first sequence and second sequence are separated by a linker, sometimes referred to as a loop. In some embodiments, both the first sequence and the second sequence are encoded by one single-stranded RNA or DNA vector. In some embodiments, the loop is between the first and second sequences. In these embodiments, and the first sequence and the second sequence hybridize to form a duplex region. The first sequence and second sequence are joined by a linker sequence, forming a “hairpin” or “stem-loop” structure. The shRNA can have complementary first sequences and second sequences at opposing ends of a single stranded molecule, so that the molecule can form a duplex region with the complementary sequence portions, and the strands are linked at one end of the duplex region by a linker (i.e. loop sequence). The linker, or loop sequence, can be either a nucleotide or non-nucleotide linker. The linker can interact with the first sequence, and optionally, second sequence through covalent bonds or non-covalent interactions.

Any suitable nucleotide loop sequence is envisaged as within the scope of the disclosure. An shRNA of this disclosure may include a nucleotide, non-nucleotide, or mixed nucleotide/non-nucleotide linker that joins the first sequence of the shRNA to the second sequence of the shRNA. A nucleotide loop sequence can be >2 nucleotides in length, for example about 4, 5, 6, 7, 8, 9, 10, 11, 12, 13, 14, or 15 nucleotides in length. Illustrative loop sequences are disclosed in Table 14.

In some embodiments, the shRNA further comprises a 5' flank sequence and a 3' flank sequence. In some embodiments, wherein the 5' flank sequence is joined to the 5' end of the first sequence, and wherein the 3' flank sequence is joined to the 3' end of the second sequence.

Without wishing to be bound by theory, it is thought that flanking shRNA stem loop sequence with 5' and 3' sequences similar to those found in microRNAs can target the shRNA for processing by the endogenous microRNA processing machinery, increasing the effectiveness of shRNA processing. Alternatively, or in addition, flanking sequences may increase shRNA compatibility with polymerase II or polymerase III promoters, leading to more effective regulation of shRNA expression.

In some embodiments, the 5' flank sequence is selected from the sequences set forth in Table 13. Illustrative flank sequence are shown in Table 13.

TABLE 13

| Illustrative flank sequences | |
|---|---|
| SEQ ID NO | 5' Flank Sequence |
| 956 | GG |
| 957 | ACACCAUGUUGCCAGUCUCUAGG |
| 958 | UGAUAGCAAUGUCAGCAGUGCCU |
| 959 | UAUUGCUGUUGACAGUGAGCGAC |
| SEQ ID NO | 3' Flank Sequence |
| 960 | UGGCGUCUGGCCCAACCACAC |
| 961 | GUAAGGUUGACCAUACUCUAC |

In some embodiments, the first and second sequence are present on a single stranded polynucleotide, wherein the first sequence and second sequence are separated by 4, 5, 6, 7, 8, 9, 10, 11, 12, 13, 14, or 15 nucleotides, wherein the 4, 5, 6, 7, 8, 9, 10, 11, 12, 13, 14, or 15 nucleotides form a loop region in the shRNA. In some embodiments, the loop region comprises a sequence selected from the sequences set forth in Table 14

TABLE 14

| Illustrative loop region sequences | |
|---|---|
| SEQ ID NO | Loop Region Sequence |
| 962 | CGAA |
| 963 | UUCAAGA |
| 964 | AUAUUCA |
| 965 | UGUGCUGUC |
| 966 | CUCGAG |
| 967 | CUUCCUGUCAGA |
| 968 | CUUCCCUUUGUCAGA |
| 969 | GUGUUAUUCUUG |
| 970 | GUGUCUUAAUUG |
| 971 | GUGUUAGUCUUG |
| 972 | UCAAGAG |
| 973 | GGACAUCCAGGG |
| 974 | GUGAAGCCACAGAUG |
| 975 | GAUUCUAAAA |

shRNAs of the disclosure may be generated exogenously by chemical synthesis, by in vitro transcription, or by cleavage of longer double-stranded RNA with Dicer or another appropriate nuclease with similar activity. Chemically synthesized siRNAs, produced from protected ribonucleoside phosphoramidites using a conventional DNA/RNA synthesizer, may be obtained from commercial suppliers such as Millipore Sigma (Houston, Tex.), Ambion Inc. (Austin, Tex.). Invitrogen (Carlsbad, Calif.), or Dharmacon (Lafayette, Colo.). siRNAs can be purified by extraction with a solvent or resin, precipitation, electrophoresis, chromatography, or a combination thereof, for example. Alternatively, siRNAs may be used with little if any purification to avoid losses due to sample processing.

In some embodiments, shRNAs of the disclosure can be produced using an expression vector into which a nucleic acid encoding the double stranded RNA has been cloned, for example under control of a suitable promoter.

Pharmaceutical Compositions

The disclosure provides pharmaceutical compositions comprising immune cells comprising the first and second receptors of the disclosure and a pharmaceutically acceptable diluent, carrier or excipient.

Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; and preservatives.

In some embodiments, the immune cell expresses both the first receptor and the second receptor. In some embodiments, at least about 50%, about 55%, about 60%, about 65%, about 70%, about 75%, about 80%, about 85%, about 90%, or about 95% of the immune cells express both the first receptor and the second receptor. In some embodiments, at least 90% of the immune cells express both the first receptor and the second receptor.

Treating Cancer

Provided herein are methods of killing a plurality of cancer cells, or treating cancer, in a subject, comprising administering to the subject a therapeutically effective amount of a composition comprising immune cells comprising the first and second receptors of the disclosure. The immune cells express both receptors in the same cell.

Cancer is a disease in which abnormal cells divide without control and spread to nearby tissue. In some embodiments, the cancer comprises a liquid tumor or a solid tumor. Exemplary liquid tumors include leukemias and lymphomas. Cancers can arise in virtually an organ in the body, including epithelial tissues. Any cancer wherein a plurality of the cancer cells express the first, activator, ligand and do not express the second, inhibitor ligand is envisaged as within the scope of the instant disclosure. For example, CEA positive cancers that can be treated using the methods described herein include colorectal cancer, pancreatic cancer, esophageal cancer, gastric cancer, lung adenocarcinoma, head and neck cancer, gallbladder cancer, diffuse large B cell cancer or acute myeloid leukemia cancer.

In some embodiments, the plurality of cancer cells express the target antigen. In some embodiments, the plurality cancer cells of the subject express CEA. Any cancer whose cells express CEA, i.e. are CEA-positive, is envisaged as within the scope of the instant disclosure. Exemplary CEA-positive cancers include, but are not limited to, prostate, ovary, lung, thyroid, gastrointestinal, breast and liver cancers. Further CEA-positive cancers include colorectal cancer, pancreatic cancer, esophageal cancer, gastric cancer, lung cancer, head and neck cancer, gallbladder cancer, diffuse large B cell cancer or acute myeloid leukemia cancer. In some embodiments, the cancer comprises colon cancer, lung cancer or pancreatic cancer. In some embodiments, the CEA-positive cancer comprises lung cancer, colorectal cancer. In some embodiments, the lung cancer comprises lung adenocarcinoma, small cell lung cancer (SCLC), or non-small cell lung cancer (NSCLC). In some embodiments, the lung cancer comprises lung adenocarcinoma. The compositions and methods disclosure herein may be used to treat CEA-positive cancers that are relapsed, refractory and/or metastatic.

Provided herein are methods of treating CEA+ cancer in a subject having a CEA+ tumor, the tumor having loss of heterozygosity at an MHC class I locus. In some embodiments, the methods comprise administering to the subject an effective amount of the immune cells or pharmaceutical compositions described herein. In some embodiments, the methods comprise (a) determining HLA-A, HLA-B, or HLA-C genotype or expression of normal cells and a plurality of cancer cells of the subject; (b) determining the expression of CEA in a plurality of cancer cells of the subject; and (c) administering to the subject an effective amount of the immune cells or pharmaceutical compositions of the disclosure if the normal cells express an HLA-A, HLA-B or HLA-C non-target antigen 2 and the plurality of cancer cells do not express the HLA-A, HLA-B or HLA-C non-target antigen, and the plurality of cancer cells are also CEA-positive. In some embodiments, for example those embodiments where the cancer is known to be CEA+, the methods comprise (a) determining HLA-A, HLA-B or HLA-C genotype or expression of normal cells and a plurality of cancer cells of the subject; and (b) administering to the subject an effective amount of the immune cells or pharmaceutical compositions of the disclosure if the normal cells express an HLA-A, HLA-B or HLA-C non-target antigen and the plurality of cancer cells do not express the non-target antigen. In some embodiments, the non-target antigen comprises HLA-A*02, HLA-A*01, HLA-A*03, HLA-A*11, HLA-B*07 or HLA-C*07.

Administration of the immune cells or pharmaceutical compositions described herein can reduce the size of a tumor in the subject. In some embodiments, the size of the tumor is reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, relative to the size of the tumor before administration of the immune cells or pharmaceutical compositions. In some embodiments, the tumor is eliminated.

Administration of the immune cells or pharmaceutical compositions described herein can arrest the growth of a tumor in the subject. For example, the immune cells or pharmaceutical compositions can kill tumor cells, so that the tumor stops growing, or is reduced in size. In some cases, immune cells or pharmaceutical compositions can prevent formation of additional tumors, or reduce the total number of tumors in the subject.

Administration of the immune cells or pharmaceutical compositions described herein can result in selective killing of a cancer cell but not a wild-type cell in the subject. In some embodiments, about 60% of the cells killed are cancer cells, about 65% of the cells killed are cancer cells, about 70% of the cells killed are cancer cells, about 75% of the cells killed are cancer cells, about 80% of the cells killed are cancer cells, about 85% of the cells killed are cancer cells, about 90% of the cells killed are cancer cells, about 95% of the cells killed are cancer cells, or about 100% of the cells killed are cancer cells.

Administration of the immune cells or pharmaceutical compositions described herein can result in the killing of about 40%, about 50%, about 60%, about 70%, about 80%, about 90% or all of the cancer cells of the subject.

Administration of the immune cells or pharmaceutical compositions described herein can result in fewer side effects for the subject than administration of an otherwise equivalent immune cell comprising the first activator receptor but no second inhibitory receptor. For example, administering the immune cells or pharmaceutical compositions described herein can reduce dose limited toxicity relative to the CEA CAR, or CEA TCR administered without the second inhibitory receptor.

In some embodiments, a plurality of cancer cells do not express a polymorphic allele of TNFRSF11, ACHRB, ITGAE, TRPV1, or SREC. For example, the cancer cells have lost an allele of TNFRSF11, ACHRB, ITGAE, TRPV1, or SREC through loss of heterozygosity at that locus.

The disclosure provides methods of treating a cancer in a subject comprising: (a) determining the genotype of normal cells and a plurality of cancer cells of the subject at a polymorphic locus selected from the group consisting of rs1716 (ITGAE R950W), rs2976230 (ITGAE V1019A/V1019G), rs1805034 (TNFRSF11A V192A) and rs35211496 (TNFRSF11A H141Y); (b) determining the expression of CEA in a plurality of cancer cells; and (c) administering a plurality of immune cells to the subject if the wild-type cells are heterozygous for the polymorphic locus and the plurality of cancer cells are hemizygous for the polymorphic locus, and the plurality of cancer cells are CEA-positive, wherein the plurality of immune cells comprise: (i) a first receptor, optionally a chimeric antigen receptor (CAR) or T cell receptor (TCR), comprising an extracellular ligand binding domain specific to CEA cell adhesion molecule 5 (CEA), or a peptide antigen thereof in a complex with a major histocompatibility complex class I (MHC-I); and (ii) a second receptor, optionally an inhibitory receptor, comprising an extracellular ligand binding specific to a non-target antigen selected from TNFRSF11, ACHRB, ITGAE, TRPV1, and SREC, or an antigen peptide thereof in a complex with an a major histocompatibility complex class I (MHC-I), wherein the non-target antigen comprises a polymorphism.

Methods of genotyping cancer cells and normal cells from a subject for the presence or absence of SNPs will be readily apparent to persons of ordinary skill in the art. SNP genotyping methods include, inter alia, PCR based methods such as dual-probe TaqMan assays, array based hybridization methods and sequencing.

Methods of measuring the expression of the target antigen in cancer or wild-type cells from a subject will be readily apparent to persons of ordinary skill in the art. These include, inter alia, methods of measuring RNA expression such as RNA sequencing and reverse transcription polymerase chain reaction (RT-PCR), as well as methods of measuring protein expression such as immunohistochemistry based methods. Methods of measuring loss of heterozygosity in a plurality of cancer cells, include, inter alia, high throughput sequencing of genomic DNA extracted from cancer cells using methods known in the art.

In some embodiments, the first ligand comprises IMIGVLVGV (SEQ ID NO: 2). In some embodiments, the first ligand is complexed with a major histocompatibility complex comprising a human leukocyte antigen A*02 allele (HLA-A*02).

In some embodiments, the plurality of cancer cells comprises a TNFRSF11A 192A allele at rs1805034, and the ligand binding domain of the second receptor has a higher affinity for a TNFRSF11A ligand with an V at position 192 of SEQ ID NO: 13 than for a TNFRSF11A ligand with an A at position 192 of SEQ ID NO: 13.

In some embodiments, the plurality of cancer cells comprises a TNFRSF11A 192V allele at rs1805034, and the ligand binding domain of the second receptor has a higher affinity for a TNFRSF11A ligand with an A at position 192 of SEQ ID NO: 13 than for a TNFRSF11A ligand with an V at position 192 of SEQ ID NO: 13.

In some embodiments, the plurality of cancer cells comprises a TNFRSF11A 141H allele at rs35211496, and the ligand binding domain of the second receptor has a higher affinity for a TNFRSF11A ligand with an Y at position 141 of SEQ ID NO: 13 than for a TNFRSF11A ligand with a H at position 141 of SEQ ID NO: 13.

In some embodiments, the plurality of cancer cells comprises a TNFRSF11A 141Y allele at rs35211496, and wherein the ligand binding domain of the second receptor has a higher affinity for a TNFRSF11A ligand with a H at position 141 of SEQ ID NO: 13 than for a TNFRSF11A ligand with a Y at position 141 of SEQ ID NO: 13.

In some embodiments, the plurality of cancer cells comprises an ITGAE 950R allele at rs1716, and the ligand binding domain of the second receptor has a higher affinity for an ITGAE ligand with a W at position 950 of SEQ ID NO: 14 than for an ITGAE ligand with an R at position 950 of SEQ ID NO: 14.

In some embodiments, the plurality of cancer cells comprises an ITGAE 950W at rs1716, and the ligand binding domain of the second receptor has a higher affinity for an ITGAE ligand with an R at position 950 of SEQ ID NO: 14 than for an ITGAE ligand with a W at position 950 of SEQ ID NO: 14.

In some embodiments, the plurality of cancer cells comprises an ITGAE 1019V allele at rs2976230, and the ligand binding domain of the second receptor has a higher affinity for an ITGAE ligand with an A or G at position 1019 of SEQ ID NO: 14 than for an ITGAE ligand with an W at position 1019 of SEQ ID NO: 14.

In some embodiments, the plurality of cancer cells comprises an ITGAE 1019A allele at rs2976230, and the ligand binding domain of the second receptor has a higher affinity for an ITGAE ligand with an V or G at position 1019 of SEQ ID NO: 14 than for an ITGAE ligand with an A at position 1019 of SEQ ID NO: 14.

In some embodiments, the plurality of cancer cells comprises an ITGAE 1019G allele at rs2976230, and the ligand binding domain of the second receptor has a higher affinity for an ITGAE ligand with a V or A at position 1019 of SEQ ID NO: 14 than for an ITGAE ligand with a G at position 1019 of SEQ ID NO: 14.

In some embodiments, the immune cells are T cells.

In some embodiments, the immune cells are allogeneic or autologous.

In some embodiments, the second receptor increases the specificity of the immune cells for the CEA-positive cancer cells compared to immune cells that express the first receptor but do not express the second receptor. In some embodiments, the immune cells have reduced side effects compared to immune cells that express the first receptor but do not express the second receptor.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%.

The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present disclosure, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present disclosure, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cancer can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing cancer can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing cancer can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing cancer can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleomorphism.

Dosage and Administration

The immune cells and of the present disclosure may be administered in a number of ways depending upon whether local or systemic treatment is desired.

In general, administration may be parenteral.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al and U.S. Pat. No. 4,690,915 to Rosenberg.

The compositions of the disclosure are suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, intrasynovial injection or infusions; and kidney dialytic infusion techniques. In some embodiments, parenteral administration of the compositions of the present disclosure comprises intravenous or intraarterial administration.

The disclosure provides pharmaceutical compositions comprising a plurality of immune cells of the disclosure, and a pharmaceutically acceptable carrier, diluent or excipient.

Formulations of a pharmaceutical composition suitable for parenteral administration typically generally comprise of immune cells combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. Parenteral formulations also include aqueous solutions which may contain excipients such as salts, carbohydrates and buffering agents. Exemplary parenteral administration forms include solutions or suspensions in sterile aqueous solutions, for example, aqueous propylene glycol or dextrose solutions. Such dosage forms can be suitably buffered, if desired. Formulations for parenteral administration may be formulated to be immediate and/or modified release. Modified release formulations include delayed-, sustained-, pulsed-, controlled-, targeted and programmed release.

In some embodiments, the formulated composition comprising the immune cells is suitable for administration via injection. In some embodiments, the formulated composition comprising the immune cells is suitable for administration via infusion.

The pharmaceutical compositions of the present disclosure, which may conveniently be presented in unit dosage form, may be prepared according to conventional techniques well known in the pharmaceutical industry. Such techniques include the step of bringing into association the immune cells with the pharmaceutical carrier(s) or excipient(s), such as liquid carriers.

Aqueous suspensions may further contain substances that increase the viscosity of the suspension including, for example, sodium carboxymethylcellulose, sorbitol and/or dextran. The suspension may also contain stabilizers.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, preservatives, antioxidants, opacifiers, thickening agents and stabilizers. However, such materials, when added, should not unduly interfere with the biological activities of the immune cells of the compositions of the present disclosure.

The formulation or composition may also contain more than one active ingredient useful for the particular indication, disease, or condition being treated with the immune cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

Administration can be effected in one dose, continuously or intermittently throughout the course of treatment. Single or multiple administrations can be carried out with the dose level and pattern being selected by the treating physician.

The pharmaceutical composition in some embodiments contains the immune cells in amounts effective to treat or prevent a cancer, such as a therapeutically effective or prophylactically effective amount. Therapeutic or prophylactic efficacy in some embodiments is monitored by periodic assessment of treated subjects. For repeated administrations over days, weeks or months, depending on the condition, the treatment can be repeated until a desired suppression of cancer signs or symptoms occurs. However, other dosage regimens may be useful and can be determined. The desired dosage can be delivered by a single bolus administration or infusion of the composition or by multiple bolus administrations or infusions of the composition.

The cells or population of cells can be administrated in one or more doses. In some embodiments, an effective amount of cells can be administrated as a single dose. In some embodiments, an effective amount of cells can be administrated as more than one doses over a period time. Timing of administration is within the judgment of a managing physician and depends on the clinical condition of the patient.

The cells or population of cells may be obtained from any source, such as a blood bank or a donor, or the patient themselves.

An effective amount means an amount which provides a therapeutic or prophylactic benefit. The dosage administered will be dependent upon the age, health and weight of the recipient, kind of concurrent treatment, if any, frequency of treatment and the nature of the effect desired. In some embodiments, an effective amount of cells or composition comprising those cells are administrated parenterally. In some embodiments, administration can be an intravenous administration. In some embodiments, administration can be directly done by injection within a tumor.

For purposes of the disclosure, an assay, which comprises, for example, comparing the extent to which target cells are lysed or one or more cytokines are secreted by immune cells expressing the receptors, upon administration of a given dose of such immune cells to a mammal, among a set of mammals of which is each given a different dose of the immune cells, can be used to determine a starting dose to be administered to a mammal.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The immune cells of the disclosure are in some embodiments are co-administered with one or more additional therapeutic agents or in connection with another therapeutic intervention, either simultaneously or sequentially in any order. In some contexts, the immune cells are co-administered with another therapy sufficiently close in time such that the immune cell populations enhance the effect of one or more additional therapeutic agents, or vice versa. In some embodiments, the immune cells are administered prior to the one or more additional therapeutic agents. In some embodiments, the immune cells are administered after to the one or more additional therapeutic agents.

In embodiments, a lymphodepleting chemotherapy is administered to the subject prior to, concurrently with, or after administration (e.g., infusion) of adoptive immune cells. In an example, the lymphodepleting chemotherapy is administered to the subject prior to administration of the immune cells. For example, the lymphodepleting chemotherapy ends 1-4 days (e.g., 1, 2, 3, or 4 days) prior to adoptive cell infusion. In embodiments, multiple doses of adoptive cells are administered, e.g., as described herein. In embodiments, a lymphodepleting chemotherapy is administered to the subject prior to, concurrently with, or after administration (e.g., infusion) of the immune cells described herein. Examples of lymphodepletion include, but may not be limited to, nonmyeloablative lymphodepleting chemotherapy, myeloablative lymphodepleting chemotherapy, total body irradiation, etc. Examples of lymphodepleting agents include, but are not limited to, antithymocyte globulin, anti-CD3 antibodies, anti-CD4 antibodies, anti-CD8 antibodies, anti-CD52 antibodies, anti-CD2 antibodies, TCRαβ blockers, anti-CD20 antibodies, anti-CD19 antibodies, Bortezomib, rituximab, anti-CD 154 antibodies, rapamycin, CD3 immunotoxin, fludarabine, cyclophosphamide, busulfan, melphalan, Mabthera, Tacrolimus, alefacept, alemtuzumab, OKT3, OKT4, OKT8, OKT11, fingolimod, anti-CD40 antibodies, anti-BR3 antibodies, Campath-1H, anti-CD25 antibodies, calcineurin inhibitors, mycophenolate, and steroids, which may be used alone or in combination. As a further example, a lymphodepletion regimen can include, administration of alemtuzumab, cyclophosphamide, benduamustin, rituximab, pentostatin, and/or fludarabine. Lymphodepletion regimen can be administered in one or more cycles until the desired outcome of reduced circulating immune cells. In some embodiments, the lymphodepletion comprises administering an agent that specifically targets, and reduces or eliminates CD52+ cells in the subject, and the immune cells are modified to reduce or eliminate CD52 expression.

In some embodiments, an immune stimulating therapy is administered to the subject prior to, concurrently with, or after administration (e.g. infusion) of adoptive immune cells. In some embodiments, the immune stimulating therapy comprises homeostatic cytokines. In some embodiments, the immune stimulating therapy comprises immune-stimulatory molecules. In some embodiments, the immune stimulating therapy comprises IL-2, IL-7, IL-12, IL-15, IL-21, IL-9, or a functional fragment thereof. In some embodiments, the immune stimulating therapy comprises IL-2, IL-7, IL-12, IL-15, IL-21, IL-9, or combinations thereof. In some embodiments, the immune stimulating therapy comprises IL-2, or a functional fragment thereof.

Methods for adoptive cell therapy using autologous cells includes isolating immune cells from patient blood, performing a series of modifications on the isolated cells including transducing the cells with one or more vectors encoding the dual receptor system described herein, and administering the cells to a patient. Providing immune cells from a subject suffering from or at risk for cancer or a hematological malignancy requires isolation of immune cell from the patient's blood, and can be accomplished through methods known in the art, for example, by leukapheresis. During leukapheresis, blood from a subject is extracted and the peripheral blood mononuclear cells (PBMCs) are separated, and the remainder of the blood is returned to the subject's circulation. The PBMCs are stored either frozen or cryopreserved as a sample of immune cells and provided for further processing steps, such as, e.g. the modifications described herein.

In some embodiments, the method of treating a subject described herein comprises modifications to immune cells from the subject comprising a series of modifications comprising enrichment and/or depletion, activation, genetic modification, expansion, formulation, and cryopreservation.

The disclosure provides enrichment and/or depletion steps that can be, for example, washing and fractionating methods known in the art for preparation of subject PBMCs for downstream procedures, e.g. the modifications described herein. For example, without limitation, methods can include devices to remove gross red blood cells and platelet contaminants, systems for size-based cell fractionation for the depletion of monocytes and the isolation of lymphocytes, and/or systems that allow the enrichment of specific subsets of T cells, such as, e.g. CD4+, CD8+, CD25+, or CD62L+ T cells. Following the enrichment steps, a target sub-population of immune cells will be isolated from the subject PMBCs for further processing. Those skilled in the art will appreciate that enrichment steps, as provided herein, may also encompass any newly discovered method, device, reagent or combination thereof.

The disclosure provides activation steps that can be any method known in the art to induce activation of immune cells, e.g. T cells, required for their ex vivo expansion. Immune cell activation can be achieved, for example, by culturing the subject immune cells in the presence of dendritic cells, culturing the subject immune cells in the presence of artificial antigen-presenting cells (AAPCs), or culturing the immune cells in the presence of irradiated K562-derived AAPCs. Other methods for activating subject immune cells can be, for example, culturing the immune cells in the presence of isolated activating factors and compositions, e.g. beads, surfaces, or particles functionalized with activating factors. Activating factors can include, for example, antibodies, e.g. anti-CD3 and/or anti-CD28 antibodies. Activating factors can also be, for example, cytokines, e.g. interleukin (IL)-2 or IL-21. Activating factors can also be costimulatory molecules, such as, for example, CD40, CD40L, CD70, CD80, CD83, CD86, CD137L, ICOSL, GITRL, and CD134L. Those skilled in the art will appreciate that activating factors, as provided herein, may also encompass any newly discovered activating factor, reagent, composition, or combination thereof that can activate immune cells.

The disclosure provides genetic modification steps for modifying the subject immune cells. In some embodiments, the genetic modification comprises transducing the immune cell with a vector comprising a shRNA described herein complementary to B2M or HLA-A. In some embodiments, the genetic modification comprises modifying the genome of the immune cells to induce mutations in B2M or HLA-A using CRISPR/Cas mediated genome engineering. In some embodiments, the method comprises transducing the immune cell with one or more vectors encoding the activator and inhibitory receptors, thereby producing immune cells expressing the activator and inhibitory receptors.

The disclosure provides expansion steps for the genetically modified subject immune cells. Genetically modified subject immune cells can be expanded in any immune cell expansion system known in the art to generate therapeutic doses of immune cells for administration. For example, bioreactor bags for use in a system comprising controller pumps, and probes that allow for automatic feeding and waste removal can be used for immune cell expansion. Cell culture flasks with gas-permeable membranes at the base may be used for immune cell expansion. Any such system known in the art that enables expansion of immune cells for clinical use is encompassed by the expansion step provided herein. Immune cells are expanded in culture systems in media formulated specifically for expansion. Expansion can also be facilitated by culturing the immune cell of the disclosure in the presence of activation factors as described herein. Those skilled in the art will appreciate that expansion steps, as provided herein, may also encompass any newly discovered culture systems, media, or activating factors that can be used to expand immune cells.

The disclosure provides formulation and cryopreservation steps for the expanded genetically modified subject immune cells. Formulation steps provided include, for example, washing away excess components used in the preparation and expansion of immune cells of the methods of treatment described herein. Any pharmaceutically acceptable formulation medium or wash buffer compatible with immune cell known in the art may be used to wash, dilute/concentration immune cells, and prepare doses for administration. Formulation medium can be acceptable for administration of the immune cells, such as, for example crystalloid solutions for intravenous infusion.

Cryopreservation can optionally be used to store immune cells long-term. Cryopreservation can be achieved using known methods in the art, including for example, storing cells in a cryopreservation medium containing cryopreservation components. Cryopreservation components can include, for example, dimethyl sulfoxide or glycerol. Immune cells stored in cryopreservation medium can be cryopreserved by reducing the storage temperature to −80° C. to −196° C.

In some embodiments, the method of treatment comprises determining the HLA germline type of the subject. In some embodiments, the HLA germline type is determined in bone marrow.

In some embodiments, the method of treatment comprises determining the level of expression of CEA. In some embodiments, the level of expression of CEA is determined in tumor tissue samples from the subject. In some embodiments, the expression level of CEA is determined using next generation sequencing. In some embodiments, the expression level of CEA is determined using RNA sequencing. In some embodiments, the level of CEA is determined using immunohistochemistry.

In some embodiments, the method of treatment comprises administering a therapeutically effective dose of immune cells comprising an HLA-A*02 inhibitory receptor to a subject in need thereof, wherein the subject is determined to be HLA germline HLA-A*02 heterozygous and have cancer cells with loss of HLA-A*02. In some embodiments, the method of treatment comprises administering a therapeutically effective dose of immune cells comprising an HLA-A*01 inhibitory receptor to a subject in need thereof, wherein the subject is determined to be HLA germline HLA-A*01 heterozygous and have cancer cells with loss of HLA-A*01. In some embodiments, the method of treatment comprises administering a therapeutically effective dose of immune cells comprising an HLA-A*03 to a subject in need thereof, wherein the subject is determined to be HLA germline HLA-A*03 heterozygous and have cancer cells with loss of HLA-A*03. In some embodiments, the method of treatment comprises administering a therapeutically effective dose of immune cells comprising an HLA-A*07 inhibitory receptor to a subject in need thereof, wherein the subject is determined to be HLA germline HLA-A*07 heterozygous and have cancer cells with loss of HLA-A*07. In some embodiments, the method of treatment comprises administering a therapeutically effective dose of immune cells comprising an HLA-C*07 inhibitory receptor to a subject in need thereof, wherein the subject is determined to be HLA germline HLA-C*07 heterozygous and have cancer cells with and loss of HLA-C*07. In some embodiments, the method of treatment comprises administering a therapeutically effective dose of immune cells comprising an HLA-B*07 inhibitory receptor in a subject in need thereof, wherein the subject is determined to be HLA germline HLA-B*07 heterozygous and have cancer cells with loss of HLA-B*07.

In various embodiments, the disclosure provides method of treatment of heterozygous HLA-A*02 patients with malignancies that express CEA and have lost HLA-A*02 expression; and/or of treatment of heterozygous HLA-A*02 adult patients with recurrent unresectable or metastatic solid tumors that express CEA and have lost HLA-A*02 expression.

In some embodiments, a therapeutically effective dose of the immune cells described herein are administered. In some embodiments, the immune cells of the disclosure are administered by intravenous injection. In some embodiments, the immune cells of the disclosure are administered by intraperitoneal injection. In some embodiments, a therapeutically effective dose comprises about $0.5\times10^6$ cells, about $1\times10^6$ cells, about $2\times10^6$ cells, about $3\times10^6$ cells, $4\times10^6$ cells, about $5\times10^6$ cells, about $6\times10^6$ cells, about $7\times10^6$ cells, about $8\times10^6$ cells, about $9\times10^6$ cells, about $1\times10^7$, about $2\times10^7$, about $3\times10^7$, about $4\times10^7$, about $5\times10^7$, about $6\times10^7$, about $7\times10^7$, about $8\times10^7$, about $9\times10^7$, about $1\times10^8$ cells, about $2\times10^8$ cells, about $3\times10^8$ cells, about $4\times10^8$ cells, about $5\times10^8$ cells, about $6\times10^8$ cells, about $7\times10^8$ cells, about $8\times10^8$ cells, about $9\times10^8$ cells, about $1\times10^9$ cells, about $2\times10^9$ cells, about $3\times10^9$ cells, about $3\times10^9$ cells, about $4\times10^9$ cells, about $5\times10^9$ cells, about $5\times10^9$ cells, about $6\times10^9$ cells, about $7\times10^9$ cells, about $8\times10^9$ cells, about $9\times10^9$ cells, about $1\times10^{10}$ cells, about $2\times10^{10}$ cells, about $3\times10^{10}$ cells, about $4\times10^{10}$ cells, about $5\times10^{10}$ cells, about $6\times10^{10}$ cells, about $7\times10^{10}$ cells, about $8\times10^{10}$ cells, or about $9\times10^{10}$ cells.

In some embodiments, a therapeutically effective dose comprises about $0.5\times10^6$ cells to about $9\times10^{10}$ cells, about $1\times10^6$ cells to about $5\times10^{10}$ cells, about $2\times10^6$ cells to about $5\times10^9$ cells, about $3\times10^6$ cells to about $5\times10^9$ cells, about $4\times10^6$ cells to about $3\times10^9$ cells, about $5\times10^6$ cells to about $2\times10^9$ cells, about $6\times10^6$ cells to about $1\times10^9$ cells, $0.5\times10^6$ cells to about $6\times10^9$ cells, about $1\times10^6$ cells to about $5\times10^9$ cells, about $2\times10^6$ cells to about $5\times10^9$ cells, about $3\times10^6$ cells to about $4\times10^9$ cells, about $4\times10^6$ cells to about $3\times10^9$ cells, about $5\times10^6$ cells to about $2\times10^9$ cells, about $6\times10^6$ cells to about $1\times10^9$ cells, $0.5\times10^6$ cells to about $6\times10^8$ cells, about $1\times10^6$ cells to about $5\times10^8$ cells, about $2\times10^6$ cells to about $5\times10^8$ cells, about $3\times10^6$ cells to about $4\times10^8$ cells, about $4\times10^6$ cells to about $3\times10^8$ cells, about $5\times10^6$ cells to about $2\times10^8$ cells, about $6\times10^6$ cells to about $1\times10^8$ cells, about $7\times10^6$ cells to about $9\times10^8$ cells, about $8\times10^6$ cells to about $8\times10^8$ cells, about $9\times10^6$ cells to about $7\times10^8$ cells, about $1\times10^7$ cells to about $6\times10^8$ cells, about $2\times10^7$ cells to about $5\times10^8$ cells, about $7\times10^6$ cells to about $9\times10^7$ cells, about $8\times10^6$ cells to about $8\times10^7$ cells, about $9\times10^6$ cells to about $7\times10^7$ cells, about $1\times10^7$ cells to about $6\times10^7$ cells, or about $2\times10^7$ cells to about $5\times10^7$ cells.

In some embodiments, a therapeutically effective dose comprises about $0.5\times10^5$ cells to about $9\times10^{10}$ cells. In some embodiments, a therapeutically effective dose comprises about $0.5\times10^6$ cells to about $1\times10^{10}$ cells. In some embodiments, a therapeutically effective dose comprises about $0.5\times10^6$ cells to about $5\times10^9$ cells. In some embodiments, a therapeutically effective dose comprises about $0.5\times10^6$ cells to about $1\times10^9$ cells. In some embodiments, a therapeutically effective dose comprises about $0.5\times10^6$ cells to about $6\times10^8$ cells. In some embodiments, a therapeutically effective dose comprises about $0.5\times10^6$ cells to about $9\times10^{10}$ cells. In some embodiments, a therapeutically effective dose comprises about $0.5\times10^7$ cells to about $1\times10^{10}$ cells. In some embodiments, a therapeutically effective dose comprises about $0.5\times10^7$ cells to about $5\times10^9$ cells. In some embodiments, a therapeutically effective dose comprises about $0.5\times10^7$ cells to about $1\times10^9$ cells. In some embodiments, a therapeutically effective dose comprises about $0.5\times10^7$ cells to about $6\times10^8$ cells. In some embodiments, a therapeutically effective dose comprises about $0.5\times10^8$ cells to about $9\times10^{10}$ cells. In some embodiments, a therapeutically effective dose comprises about $0.5\times10^8$ cells to about $1\times10^{10}$ cells. In some embodiments, a therapeutically effective dose comprises about $0.5\times10^8$ cells to about $5\times10^9$ cells. In some embodiments, a therapeutically effective dose comprises about $0.5\times10^8$ cells to about $1\times10^9$ cells. The term "about" as referred to in a therapeutically dose, can be, for example, $\pm0.5\times10^6$ cells, $\pm0.5\times10^7$ cells, or $\pm0.5\times10^8$ cells.

Kits and Articles of Manufacture

The disclosure provides kits and articles of manufacture comprising the polynucleotides and vectors encoding the receptors described herein, and immune cells comprising the receptors described herein. In some embodiments, the kit comprises articles such as vials, syringes and instructions for use.

In some embodiments, the kit comprises a polynucleotide or vector comprising a sequence encoding one or more receptors of the disclosure.

In some embodiments, the kit comprises a plurality of immune cells comprising the first and second receptors as described herein. In some embodiments, the plurality of immune cells comprises a plurality of T cells.

In some embodiments, the kit further comprises instructions for use.

ENUMERATED EMBODIMENTS

The disclosure can be understood with reference to the following illustrative, enumerated embodiments:

1. An immune cell responsive to loss of heterozygosity in a cancer cell, comprising: (a) a first receptor, optionally a chimeric antigen receptor (CAR) or T cell receptor (TCR), comprising an extracellular ligand binding domain specific to a target antigen selected from: (i) a cancer cell-specific antigen, or a peptide antigen thereof in a complex with a major histocompatibility complex class I (MHC-I); or (ii) CEA cell adhesion molecule 5 (CEA), or a peptide antigen thereof in a complex with a major histocompatibility complex class I (MHC-I); and (b) a second receptor, optionally an inhibitory receptor, comprising an extracellular ligand binding domain specific to a non-target antigen selected from TNFRSF11A, ACHRB, ITGAE, TRPV1, SREC, CXCL16, COLEC12 and APCDD1, or an antigen peptide thereof in a complex with a major histocompatibility complex class I (MHC-I), wherein the non-target antigen comprises a polymorphism.

2. The immune cell of embodiment 1, wherein the target antigen is a cancer cell-specific antigen.

3. The immune cell of embodiment 1, wherein the target antigen is a peptide antigen of a cancer cell-specific antigen in a complex with a major histocompatibility complex class I (MHC-I).

4. The immune cell of embodiment 2 or embodiment 3, wherein the cancer cell is a colorectal cancer cell.

5. The immune cell of embodiment 2 or embodiment 3, wherein the cancer cell is a pancreatic cancer cell, esophageal cancer cell, gastric cancer cell, lung adenocarcinoma cell, head-and-neck cancer cell, diffuse large B cell cancer cell, or acute myeloid leukemia cancer cell.

6. The immune cell of embodiment 1, wherein the cancer cells express CEA.

7. The immune cell of embodiment 6, wherein the target antigen is CEA.

8. The immune cell of embodiment 1, wherein the target antigen is a peptide antigen of CEA in a complex with a major histocompatibility complex class I (MHC-I).

9. The immune cell of any one of embodiments 1-8, wherein the target antigen is expressed by a target cell.

10. The immune cell of any one of embodiments 1-9, wherein the non-target antigen is not expressed by the target cell.

11. The immune cell of any one of embodiments 1-9, wherein the non-target antigen is expressed by healthy cells.

12. The immune cell of any one of embodiments 1-11, wherein the healthy cells express both the target antigen and the non-target antigen.

13. The immune cell of any one of embodiments 1-12, wherein the first receptor and the second receptor together specifically activate the immune cell in the presence of the target cell.

14. The immune cell of embodiment 13, wherein the immune cell is a T cell.

15. The immune cell of embodiment 14, wherein the T cell is a CD8+ CD4− T cell.

16. The immune cell of any one of embodiments 9-15, wherein the target cell comprises a colorectal cancer cell, a pancreatic cancer cell, an esophageal cancer cell, a gastric cancer cell, a lung adenocarcinoma cell, a head and neck cancer cell, a diffuse large B cell cancer cell or an acute myeloid leukemia cancer cell.

17. The immune cell of any one of embodiments 1-16, wherein the CEA comprises a sequence that shares at least 95% identity to SEQ ID NO: 1.

18. The immune cell of any one of embodiments 1-16, wherein the peptide antigen of CEA is IMIGVLVGV (SEQ ID NO: 2).

19. The immune cell of any one of embodiments 1-18, wherein the MHC-I comprises a human leukocyte antigen A*02 allele (HLA-A*02).

20. The immune cell of any one of embodiments 1-19, wherein the first receptor is a T cell receptor (TCR).

21. The immune cell of any one of embodiments 1-19, wherein the first receptor is a chimeric antigen receptor (CAR).

22. The immune cell of embodiment 20 or 21, wherein the extracellular ligand binding domain of the first receptor comprises an antibody fragment, a single chain Fv antibody fragment (scFv), or a β chain variable domain (Vβ).

23. The immune cell of embodiment 20 or 21, wherein the extracellular ligand binding domain of the first receptor comprises a TCR α chain variable domain and a TCR β chain variable domain.

24. The immune cell of embodiment 22 or 23, wherein the extracellular ligand binding domain of the first receptor comprises complement determining regions (CDRs) selected from SEQ ID NOs: 3-12.

25. The immune cell of embodiment 23, wherein: (a) the TCR α chain variable domain comprises a CDR-1 of TSITA (SEQ ID NO: 3), a CDR-2 of IRSNER (SEQ ID NO: 4) and a CDR-3 comprising ATDLTSGGNYK (SEQ ID NO: 5), ATDFTSGGNYK (SEQ ID NO: 6), ATDLTTGGNYK (SEQ ID NO: 7) or ATDFTTGGNYK (SEQ ID NO: 8); and (b) the TCR β chain variable domain comprises a CDR-1 of KGHPV (SEQ ID NO: 9), a CDR-2 of FQNQEV (SEQ ID NO: 10), and a CDR-3 of ASSLGLGDYEQ (SEQ ID NO: 11) or ASSLGTGDYEQ (SEQ ID NO: 12).

The immune cell of embodiment 23, wherein: (a) the TCR α chain variable domain comprises a CDR-1 of SEQ ID NO: 9, a CDR-2 of SEQ ID NO: 10 and a CDR-3 of SEQ ID NO: 11 or SEQ ID NO: 12; and (b) the TCR β chain variable domain comprises a CDR-1 of SEQ ID NO: 3, a CDR-2 of SEQ ID NO: 4 and a CDR-3 comprising SEQ ID NO: 5, SEQ ID NO: 6, SEQ ID NO: 7 or SEQ ID NO: 8.

The immune cell of any one of embodiments 1-26, wherein the non-target antigen is a TNFRSF11A antigen that shares at least 95% identity to SEQ ID NO: 13 and the polymorphism is selected from: (a) A or V at position 192 of SEQ ID NO: 13, or (b) H or Y at position 141 of SEQ ID NO: 13.

The immune cell of any one of embodiments 1-26, wherein the non-target antigen is an ITGAE antigen that shares at least 95% identity to SEQ ID NO: 14 and the polymorphism is selected from (a) R or W at position 950 of SEQ ID NO: 14; or (b) V, A, or G at position 1019 of SEQ ID NO: 14.

29. An immune cell responsive to loss of heterozygosity in a cancer cell, comprising: (a) a first receptor, optionally a chimeric antigen receptor (CAR) or T cell receptor (TCR), comprising an extracellular ligand binding domain specific to CEA cell adhesion molecule 5 (CEA), or a peptide antigen thereof in a complex with a major histocompatibility complex class I (MHC-I); and (b) a second receptor, optionally an inhibitory receptor, comprising an extracellular ligand binding domain specific to a non-target antigen, wherein the non-target antigen comprises HLA-A*02.

30. The immune cell of embodiment 29, wherein the extracellular ligand binding domain of the first receptor does not recognize a CEA peptide antigen in a MHC-I complex comprising HLA-A*02.

31. The immune cell of embodiment 29 or 30, wherein the extracellular ligand binding domain of the first receptor comprises an antibody fragment, a single chain Fv antibody fragment (scFv), a β chain variable domain (Vβ), or a TCR α chain variable domain and a TCR β chain variable domain.

32. The immune cell of embodiment 29 or 30, wherein the extracellular ligand binding domain of the first receptor comprises an scFv.

33. The immune cell of embodiment 32, wherein the scFv comprises a sequence having at least 85%, at least 90%, at least 95%, at least 97% or at least 99% identity to any one of SEQ ID NOs: 64-70.

34. The immune cell of embodiment 32, wherein the scFv comprises a sequence of any one of SEQ ID NOs: 64-70.

35. The immune cell of embodiment 29-33, wherein the extracellular ligand binding domain of the first receptor comprises CDRs selected from the group consisting of SEQ ID NOs: 55-63.

36. The immune cell of any one of embodiments 29-35, wherein the extracellular ligand binding domain of the second receptor comprises an antibody fragment, a single chain Fv antibody fragment (scFv), a β chain variable domain (Vβ), or a TCR α chain variable domain and a TCR β chain variable domain.

37. The immune cell of any one of embodiments 29-35, wherein the extracellular ligand binding domain of the second receptor comprises an scFv.

38. The immune cell of embodiment 37, wherein the scFv comprises a sequence having at least 85%, at least 90%, at least 95%, at least 97% or at least 99% identity to any one of SEQ ID NOs: 91-102.

39. The immune cell of embodiment 37, wherein the scFv comprises a sequence of any one of SEQ ID NOs: 91-102.

40. The immune cell of any one of embodiments 29-39, wherein the extracellular ligand binding domain of the second receptor comprises CDRs selected from the group consisting of SEQ ID NOs: 103-114.

41. The immune cell of any one of embodiments 29-40, wherein the second receptor comprises a LILRB1 intracellular domain or a functional variant thereof.

42. The immune cell of embodiment 41, wherein the LILRB1 intracellular domain comprises a sequence at least 95% identical to SEQ ID NO: 126.

43. The immune cell of any one of embodiments 29-42, wherein the second receptor comprises a LILRB1 transmembrane domain or a functional variant thereof.

44. The immune cell of embodiment 43, wherein the LILRB1 transmembrane domain or a functional variant thereof comprises a sequence at least 95% identical to SEQ ID NO: 135.

45. The immune cell of any one of embodiments 29-44, wherein the second receptor comprises a LILRB1 hinge domain or functional variant thereof.

46. The immune cell of embodiment 45, wherein the LILRB1 hinge domain comprises a sequence at least 95% identical to SEQ ID NO: 134, SEQ ID NO: 127 or SEQ ID NO: 128.

47. The immune cell of any one of embodiments 29-46, wherein the second receptor comprises a LILRB1 intracellular domain and a LILRB1 transmembrane domain, or a functional variant thereof.

48. The immune cell of embodiment 47, wherein the LILRB1 intracellular domain and LILRB1 transmembrane domain comprises SEQ ID NO: 130 or a sequence at least 95% identical to SEQ ID NO: 130.

49. The immune cell of any one of embodiments 29-48, wherein the cancer cell is a colorectal cancer cell.

50. The immune cell of any one of embodiments 29-48, wherein the cancer cell is a pancreatic cancer cell, esophageal cancer cell, gastric cancer cell, lung adenocarcinoma cell, head-and-neck cancer cell, diffuse large B cell cancer cell, or acute myeloid leukemia cancer cell.

51. The immune cell of any one of embodiments 29-50, wherein the target antigen is expressed by a target cell.

52. The immune cell of any one of embodiments 29-51, wherein the non-target antigen is not expressed by the target cell.

53. The immune cell of embodiment 51 or 52, wherein the target cell is a colorectal cancer cell, a pancreatic cancer cell, an esophageal cancer cell, a gastric cancer cell, a lung adenocarcinoma cell, a head-and-neck cancer cell, a diffuse large B cell cancer cell, or an acute myeloid leukemia cancer cell.

54. The immune cell of any one of embodiments 29-53, wherein the non-target antigen is expressed by healthy cells.

55. The immune cell of any one of embodiments 29-54, wherein the healthy cells express both the target antigen and the non-target antigen.

56. The immune cell of any one of embodiments 29-55, wherein the first receptor and the second receptor together specifically activate the immune cell in the presence of the target cell.

57. The immune cell of embodiment 56, wherein the immune cell is a T cell.

58. The immune cell of embodiment 57, wherein the T cell is a CD8+ CD4− T cell.

59. The immune cell of any one of embodiments 29-58, wherein the CEA comprises a sequence that shares at least 95% identity to SEQ ID NO: 1.

60. The immune cell of any one of embodiments 29-59, wherein the first receptor is a chimeric antigen receptor (CAR).

61. A pharmaceutical composition, comprising a therapeutically effective amount of the immune cells of any one of embodiments 1-60.

62. The pharmaceutical composition of embodiment 61, further comprising a pharmaceutically acceptable carrier, diluent or excipient.

63. The pharmaceutical composition of embodiment 61 or 62, for use as a medicament in the treatment of cancer.

64. A polynucleotide system, comprising one or more polynucleotides comprising polynucleotide sequences encoding: (a) a first receptor, optionally a chimeric antigen receptor (CAR) or T cell receptor (TCR), comprising an extracellular ligand binding domain specific to a target antigen selected from: (i) a cancer cell-specific antigen, or a peptide antigen thereof in a complex with a major histocompatibility complex class I (MHC-I); or (ii) CEA cell adhesion molecule 5 (CEA), or a peptide antigen thereof in a complex with a major histocompatibility complex class I (MHC-I); and (b) a second receptor, optionally an inhibitory receptor, comprising an extracellular ligand binding domain specific to a non-target antigen selected from TNFRSF11A, ACHRB, ITGAE, TRPV1,SREC, CXCL16, COLEC12 and APCDD1, or an antigen peptide thereof in a complex with a major histocompatibility complex class I (MHC-I), wherein the non-target antigen comprises a polymorphism.

65. A polynucleotide system, comprising one or more polynucleotides comprising polynucleotide sequences encoding: (a) a first receptor, optionally a chimeric antigen receptor (CAR) or T cell receptor (TCR), comprising an extracellular ligand binding domain specific to CEA cell adhesion molecule 5 (CEA), or a peptide antigen thereof in a complex with a major histocompatibility complex class I (MHC-I); and (b) a second receptor, optionally an inhibitory receptor, comprising an extracellular ligand binding domain specific to a non-target antigen, wherein the non-target antigen comprises HLA-A*02.

66. A vector, comprising the one or more polynucleotides of embodiment 64 or 65.

67. A method of killing a plurality of cancer cell and/or treating cancer in a subject, comprising administering to the subject an effective amount of the immune cell of any one of embodiments 1-60 or the pharmaceutical composition of any one of embodiments 61-63.

68. The method of embodiment 67, wherein a plurality of cancer cells express the target antigen.

69. The method of embodiment 67 or 68, wherein a plurality of cancer cells do not express the non-target antigen.

70. The method of embodiment 69, wherein the plurality of cancer cells have lost the non-target antigen due to loss of heterozygosity (LOH).

71. A method of treating a cancer in a subject comprising: (a) determining the genotype of normal cells and a plurality of cancer cells of the subject at a polymorphic locus selected from the group consisting of rs1716 (ITGAE R950W), rs2976230 (ITGAE V1019A/V1019G), rs1805034 (TNFRSF11A V192A) and rs35211496 (TNFRSF11A H141Y); (b) determining the expression of CEACAM5 in a plurality of cancer cells; and (c) administering a plurality of immune cells to the subject if the normal cells are heterozygous for the polymorphic locus and the plurality of cancer cells are hemizygous for the polymorphic locus, and the plurality of cancer cells are CEA-positive, wherein the plurality of immune cells comprise: (i) a first receptor, optionally a chimeric antigen receptor (CAR) or T cell receptor (TCR), comprising an extracellular ligand binding domain specific to CEA cell adhesion molecule 5 (CEA), or a peptide antigen thereof in a complex with a major histocompatibility complex class I (MHC-I); and (ii) a second receptor, optionally an inhibitory receptor, comprising an extracellular ligand binding domain specific to a non-target antigen selected from TNFRSF11A, ACHRB, ITGAE, TRPV1, and SREC, or an antigen peptide thereof in a complex with an a major histocompatibility complex class I (MHC-I), wherein the non-target antigen comprises a polymorphism.

72. A method of treating a cancer in a subject comprising: (a) determining HLA-A genotype or expression for normal cells and a plurality of cancer cells of the subject; (b) determining the expression of CEA in a plurality of cancer cells; and (c) administering a plurality of immune cells to the subject if the normal cells express HLA-A*02 and the plurality of cancer cells do not express HLA-A*02, and the plurality of cancer cells are CEA-positive, wherein the plurality of immune cells comprise: (i) a first receptor, optionally a chimeric antigen receptor (CAR) or T cell receptor (TCR), comprising an extracellular ligand binding domain specific to CEA cell adhesion molecule 5 (CEA), or a peptide antigen thereof in a complex with a major histocompatibility complex class I (MHC-I); and (ii) a second receptor, optionally an inhibitory receptor, comprising an extracellular ligand binding domain specific to a non-target antigen, wherein the non-target antigen comprises HLA-A*02.

73. A method of making a plurality of immune cells, comprising: (a) providing a plurality of immune cells, and (b) transforming the plurality of immune cells with the polynucleotide system of embodiment 64 or 65, or the vector of embodiment 66.

74. A kit comprising the immune cell of any one of embodiments 1-60 or the pharmaceutical composition of any one of embodiments 61-63.

75. The kit of embodiment 74, further comprising instructions for use.

76. A TCR comprising: (1) a TCR alpha chain comprising or consisting essentially of amino acids 1-270 of any one of SEQ ID NOS: 16-31, or a sequence at least 95% identical thereto; and (2) a TCR beta chain comprising or consisting essentially of amino acids 293-598 of any one of SEQ ID NOS: 16-31, or a sequence at least 95% identical thereto.

77. A TCR comprising: (a) a TCR alpha chain comprising amino acids 1-270 of SEQ ID NO: 16 and a TCR beta chain comprising amino acids 293-598 of SEQ ID NO: 16; (b) a TCR alpha chain comprising amino acids 1-270 of SEQ ID NO: 17 and a TCR beta chain comprising amino acids 293-598 of SEQ ID NO: 17; (c) a TCR alpha chain comprising amino acids 1-270 of SEQ ID NO: 18 and a TCR beta chain comprising amino acids 293-598 of SEQ ID NO: 18; (d) a TCR alpha chain comprising amino acids 1-270 of SEQ ID NO: 19 and a TCR beta chain comprising amino acids 293-598 of SEQ ID NO: 19; (e) a TCR alpha chain comprising amino acids 1-270 of SEQ ID NO: 20 and a TCR beta chain comprising amino acids 293-598 of SEQ ID NO: 20; (f) a TCR alpha chain comprising amino acids 1-270 of SEQ ID NO: 21 and a TCR beta chain comprising amino acids 293-598 of SEQ ID NO: 21; (g) a TCR alpha chain comprising amino acids 1-270 of SEQ ID NO: 22 and a TCR beta chain comprising amino acids 293-598 of SEQ ID NO: 22; (h) a TCR alpha chain comprising amino acids 1-270 of SEQ ID NO: 23 and a TCR beta chain comprising amino acids 293-598 of SEQ ID NO: 23; (i) a TCR alpha chain comprising amino acids 1-270 of SEQ ID NO: 24 and a TCR beta chain comprising amino acids 293-598 of SEQ ID NO: 24; (j) a TCR alpha chain comprising amino acids 1-270 of SEQ ID NO: 25 and a TCR beta chain comprising amino acids 293-598 of SEQ ID NO: 25; (k) a TCR alpha chain comprising amino acids 1-270 of SEQ ID NO: 26 and a TCR beta chain comprising amino acids 293-598 of SEQ ID NO: 26; (l) a TCR alpha chain comprising amino acids 1-270 of SEQ ID NO: 27 and a TCR beta chain comprising amino acids 293-598 of SEQ ID NO: 27; (m) a TCR alpha chain comprising amino acids 1-270 of SEQ ID NO: 28 and a TCR beta chain comprising amino acids 293-598 of SEQ ID NO: 28; (n) a TCR alpha chain comprising amino acids 1-270 of SEQ ID NO: 29 and a TCR beta chain comprising amino acids 293-598 of SEQ ID NO: 29; (o) a TCR alpha chain comprising amino acids 1-270 of SEQ ID NO: 30 and a TCR beta chain comprising amino acids 293-598 of SEQ ID NO: 30; or (p) a TCR alpha chain comprising amino acids 1-270 of SEQ ID NO: 31 and a TCR beta chain comprising amino acids 293-598 of SEQ ID NO: 31.

78. An immune cell, comprising the TCR of embodiment 76 or 77.

79. The immune cell of embodiment 78, further comprising a second receptor, optionally an inhibitory receptor, comprising an extracellular ligand binding domain specific to a non-target antigen selected from TNFRSF11A, ACHRB, ITGAE, TRPV1, SREC, CXCL16, COLEC12 and APCDD1, or an antigen peptide thereof in a complex with an a major histocompatibility complex class I (MHC-I), wherein the non-target antigen comprises a polymorphism.

EXAMPLES

The following Examples are intended for illustration only and do not limit the scope of the invention. Throughout the examples, the term “blocker antigen” is used to describe embodiments of a non-target antigen.

Example 1: Identification of TNFRS11A as a Blocker

The GISTIC TCGA database was searched to identify regions lost due to loss of heterozygosity in colorectal cancers. Chr18q: 35,237,593-37,208,54 was identified as the regions that was most frequently lost due to loss of heterozygosity in colorectal cancers. Surface proteins encoded on Chr. 18q were filtered for those expressed by normal colon cells.

These surface proteins were searched for nonsynonymous SNPS in the extracellular domains of the proteins using the following process:

- The NCBI dbSNP database for common variants was downloaded (Note, for NCBI the “common” category is based on germline origin and a minor allele frequency (MAF) of >=0.01 in at least one major population, with at least two unrelated individuals having the minor allele)
- This database was analyzed only variants in chromosome 18 and chromosome 17
- Variants with MAF<0.1 were removed
- VEP (Variant Effect Predictor) was run, and only missense variants that were in protein coding regions were kept
- The following genes were removed:
  - genes without transmembrane domains
  - genes located in Golgi, ER, mitochondria, endosome, nucleus membrane
  - genes that are not highly expressed in colon (GTEx expression level <5 TPM)
  - genes that are amplified as opposed to deleted
- loss of heterozygosity of candidate genes was checked in the TCGA Copy Number Portal
- Candidate genes were checked for other variants in Ensembl Genome Browser
  - If there are variants, the location of the variation was checked (is it in the extracellular domain?)

An overview of the filtering pipeline is shown in Table 15 below.

TABLE 15

Identification of candidate blocker targets on Chromosome 17 and 18.

| No. of genes (total) | TM genes | MAF > 0.1 chr18q OR chr17p | Expression in Colon-Transverse > 5 TPM | Genes after removal of CNA amplifications, only HOMDEL shown | VEP (protein-coding, missense variants) | Not in Golgi, ER, mitochondria, endosome, nucleus membrane | In ECD |
|---|---|---|---|---|---|---|---|
| 20,365 | 5177 | 255 | 132 | 72 | 23 | 13 | 5 |

CNA: Copy number amplification

TPM: Transcripts per Kilobase Million (The Genotype-Tissue Expression, GTEx project, gtexportal.org/home)

Five candidate genes passed all filters. A summary of these five genes is shown in Tables 16-19 below.

TABLE 16

Expression.

| | | Expression (RPKM) GTEx-Normal | | Expression (RPKM) CCLE Colorectal Cancer Cell Line | | |
|---|---|---|---|---|---|---|
| Entry name | Gene names | Colon-Sigmoid | Colon-Transverse | HS255T_FIBROBLAST (ACH-000199) | HS675T_FIBROBLAST (ACH-000214) | HS698T_FIBROBLAST (ACH-000850) |
| TNR11_HUMAN | TNFRSF11A RANK | 0.7953 | 9.33 | 0.02581 | 0.00609 | 0.04472 |
| ACHB_HUMAN | CHRNB1 ACHRB CHRNB | 5.172 | 4.861 | 2.55857 | 4.50562 | 1.21823 |
| ITAE_HUMAN | ITGAE | 7.72 | 6.5555 | 7.73753 | 5.3983 | 4.82732 |
| TRPV1_HUMAN | TRPV1 VR1 | 6.978 | 8.0955 | 0.0613 | 0 | 0.04903 |
| SREC_HUMAN | SCARF1 KIAA0149 SREC | 8.325 | 11.15 | 0.22201 | 0.24929 | 0.07219 |

TABLE 17

Position, Characteristics and Variation

| Entry name | Cytoband | Freq of del. | Result | Impact | Biotype | Protein Pos. | Amino Acids | Codons | MAF | ECD |
|---|---|---|---|---|---|---|---|---|---|---|
| TNR11_HUMAN | 18q21.33 | 0.026 | MS | Mod. | PC | 192 | A/V | gCg/ gTg | 0.5942 | yes |
| ACHB_HUMAN | 17p13.1 | 0.013 | MS | Mod. | PC | 32 | E/G | gAg/ gGg | 0.1206 | yes |
| ITAE_HUMAN | 17p13.2 | 0.01 | MS | Mod. | PC | 950*, 1019 | R/W | Cgg/ Tgg | 0.2654 | yes |
| TRPV1_HUMAN | 17p13.2 | 0.01 | MS | Mod. | PC | 585*, 469, 459 | I/V | Atc/ Gtc | 0.3177 | yes |
| SREC_HUMAN | 17p1.3 | 0.008 | MS | Mod. | PC | 425*, 339 | A/V | gCg/ gTg | 0.333 | yes |

MS: missense variant

Mod.: Moderate

PC: Protein Coding

Pos.: Position

*indicate protein positions with the indicated amino acids and codons

MAF: minor allele frequency

TABLE 18

| Copy Number | | |
|---|---|---|
| Entry name | Frequency of deletion, overall | Uniprot ECD residue range |
| TNR11_HUMAN | 0.6786 | 30-212 |
| ACHB_HUMAN | 0.5607 | 24-244 |
| ITAE_HUMAN | 0.5248 | 19-1124 |
| TRPV1_HUMAN | 0.5231 | 455-471 |
| SREC_HUMAN | 0.5162 | 20-421 |

Results in Table 18 are from the TCGA Copy Number Portal.

The crystal structures were examined to verify the accessibility of the extracellular domain SNPs to an antibody.

Using these methods, TNFRS11A (RANK) was identified as a target for a blocker receptor to pair with a CEA TCR or CAR activator. The TNFRSF11A (RANK) receptor is expressed in a wide range of normal tissues, including the gut. Gut expression includes expression in the colon, wherein the median normal TNFRSF11A colon expression is 23 transcripts/cell. Maximum CRC CEA expression in the colon is 8,780 transcripts/cell. TNFRSF11A is also expressed in the esophagus. The median normal esophagus TNFRSF11A expression is 2 transcripts/cell. Maximum EsCa CEA expression in the esophagus is 6,208 transcripts/cell. TNFRSF11A encodes a 616-residue protein that binds RANKL (the target of denosumab). It includes a 28 amino acid signal peptide, a 184 amino acid extracellular domain, a 21 amino acid transmembrane domain and a 383 amino acid intracellular domain. TNFRSF11A contains two common nonsynonymous variants, rs1805034 (V192A) which has an MAF of 0.4, and rs35211496 (H141Y) which has MAF of about 0.2.

Example 2: CEA CAR Mediated Activation of Jurkat Cells is Blocked by an HLA-A*2 Inhibitory Receptor Cell Culture Jurkat cells encoding an NFAT Luciferase reporter were obtained from BPS Bioscience. In culture, Jurkat cells were maintained in RPMI media supplemented with 10% FBS, 1% Pen/Strep and 0.4 mg/mL G418/Geneticin. HeLa cells were maintained as suggested by ATCC.

Jurkat Cell Transfection

Jurkat cells were transiently transfected via 100 uL format 4D-Nucleofactor™ (Lonza) according to manufacturer's protocol using the settings for Jurkat cells. Cotransfection was performed with 1-3 ug of activator construct and 1-3 ug of blocker constructs or empty vector per 1e6 cells and recovered in RPMI media supplemented with 20% heat-inactivated FBS and 0.1% Pen/Strep.

Jurkat-NFAT-Luciferase Activation Studies

Figure 10:
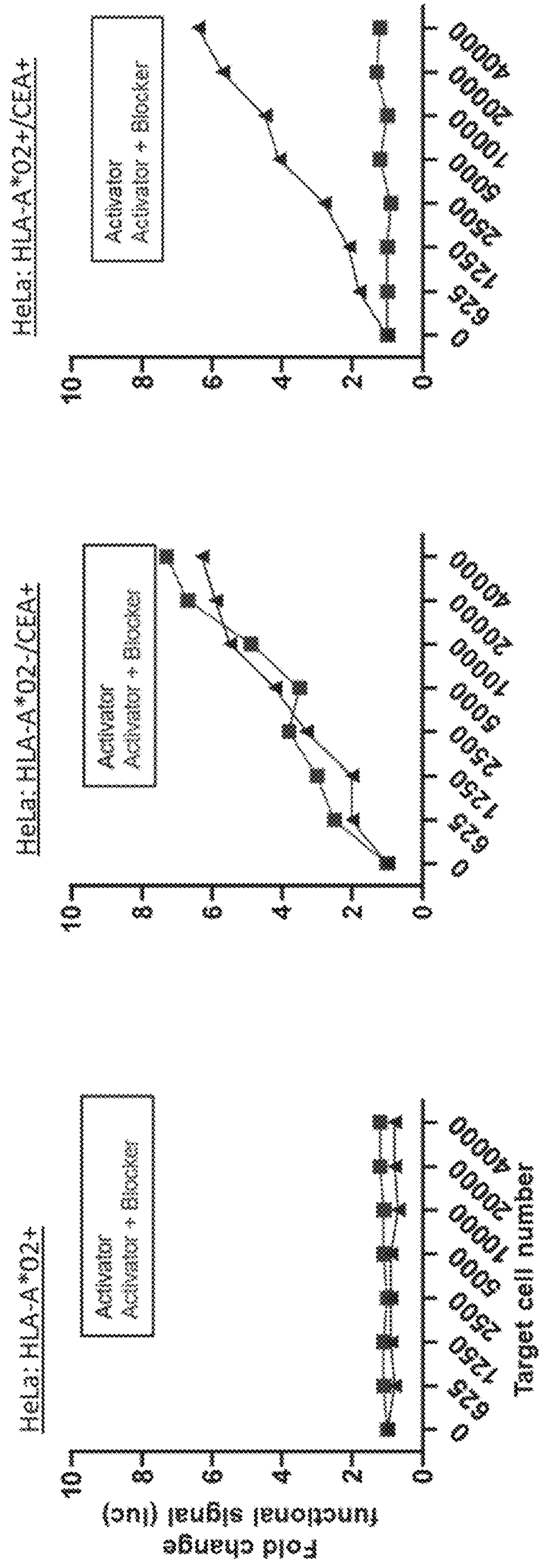
FIG. 10 is a series of plots showing that an HLA-A*02 inhibitory receptor can block activation of Jurkat cells by a CEA CAR.

HeLa cells expressing HLA-A*02, CEA or both, were co-cultured with Jurkat cells, and Jurkat cell activation was assayed using the NFAT-luciferase reporter system. The ability of a blocker receptor with an HLA-A-A*02 antigen binding domain and a LIR-1 ICD (C1765) to block activation of Jurkat cells expressing an activator CAR with an CEA scFv (CT618) was assayed. HeLa cells were transduced with polynucleotides encoding HLA-A*02+ and/or CEA+ to generate HLA-A*02+/CEA-HeLa cells, HLA-A*02−/CEA+ HeLa cells and CEA+/HLA-A*02+ HeLa cells to use as target cells for Jurkat cell activation assays. These HeLa cells were co-cultured with Jurkat cells, and Jurkat cell activation was assayed using the NFAT Luciferase reporter system. The results are shown in FIG. 10. As can be seen in FIG. 10, an HLA-A*02 LIR1 blocker can inhibit Jurkat cell activation by a CEA scFv CAR when Jurkat cells are cultured with CEA+/HLA-A*02+ target cells.

Example 3: Identification of Additional Blocker Target Antigens

Figure 11:
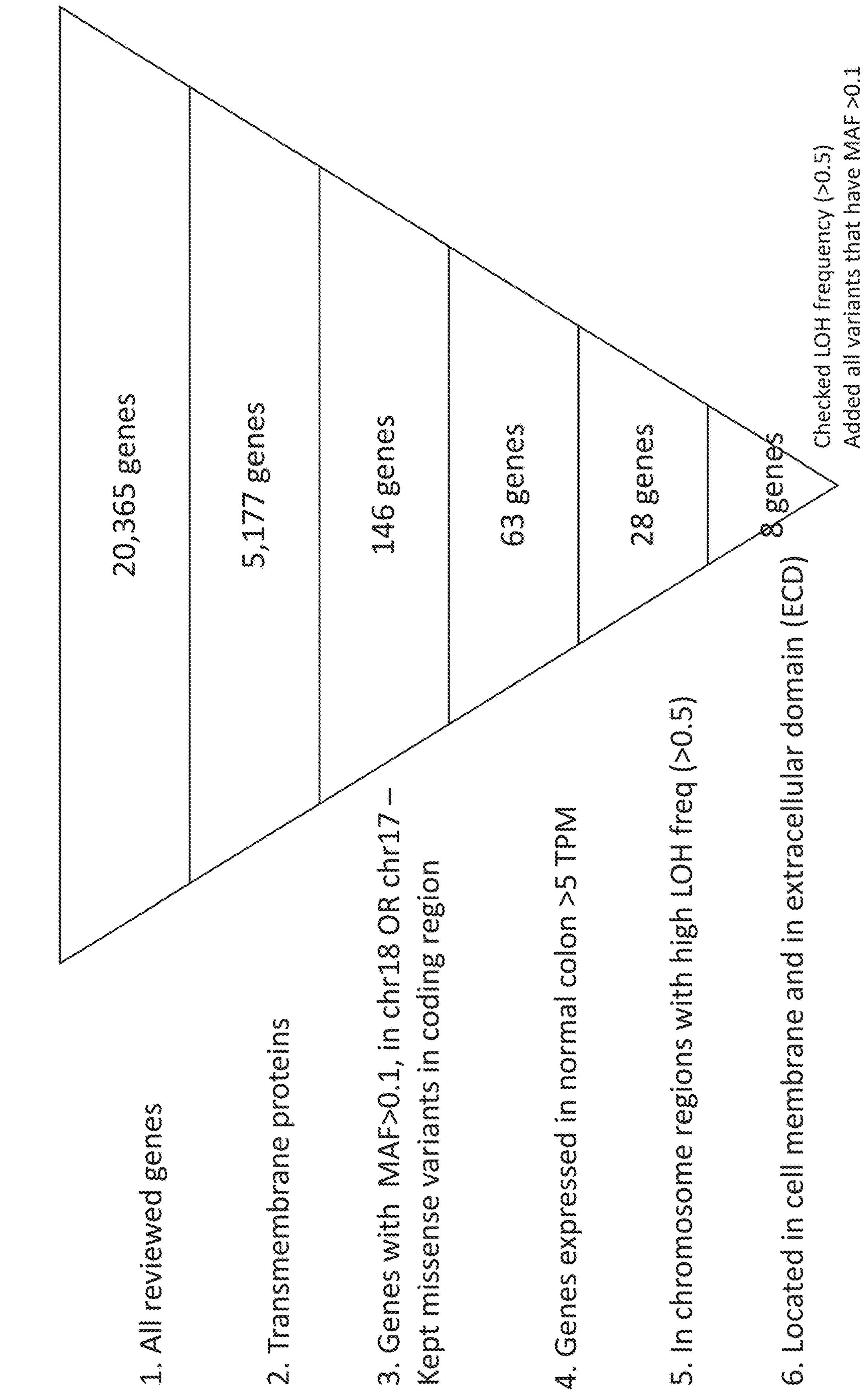
FIG. 11 is a diagram showing the bioinformatics search process used to identify potential non-target antigen (blocker) candidate genes.
Figure 12:
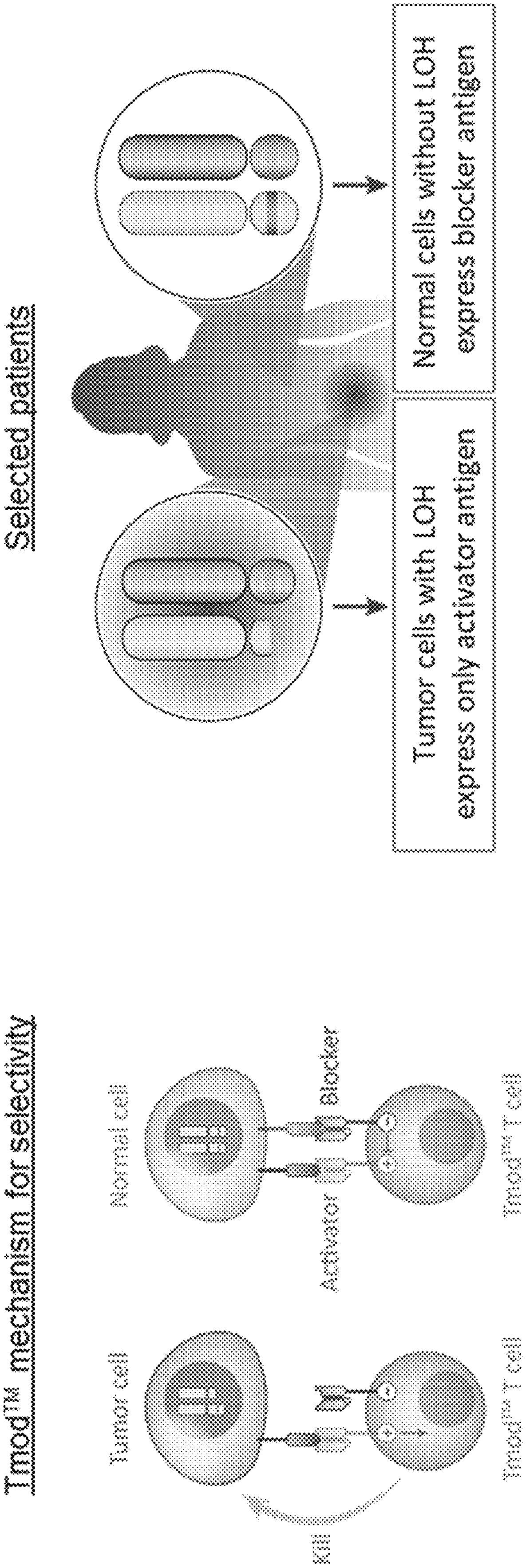
FIG. 12 is a pair of diagrams showing discrimination between tumor and normal tissue using loss of heterozygosity (LOH). Engineered immune cells kill tumors but spare normal cells. In the case of an exemplary embodiment, immune cells express CEA CAR, the activator antigen is CEA, and the blocker antigen is HLA-A*02. Patients with germline heterozygosity of HLA-A*02 and clonal LOH of HLA-A*02 in tumors are selected.

A bioinformatics pipeline similar to the one used to identify TNFRSF11A in Example 1 was used to identify additional candidate blocker targets. The set of human genes was searched for genes with common nonsynonymous variants in extracellular domains that have high loss of heterozygosity (greater than 0.5) in colorectal cancers. Genes with nonsynonymous variants were searched in dbSNP, a database of single nucleotide polymorphisms, that also includes. small-scale insertions and deletions along with publication, population frequency, molecular consequence, and genomic mapping information. Common variations were defined as having a minor allele frequency (MAF) of greater than or equal to 0.01 in at least one major population and with at least two unrelated individuals having the minor allele in NCBI. MAF of greater than or equal to 0.1 as criterion for common variations. The focus was on chromosomes 17 and 18, as these chromosomes have high LOH in colorectal cancers. Genes were filtered for membrane proteins, colon expression, and common nonsynonymous variants in the extracellular domain, as described above. A summary of the search process is shown in FIG. 11.

Additional databases used in this analysis include the following: Uniprot (The Universal Protein Resource), which was used resource for protein sequence and annotation data hosted by EMBL-EBI, SIB and PIR. GTEx (The Genotype-Tissue Expression) was use as a public resource for tissue-specific gene expression and regulation. It contains samples from 54 non-diseased tissue sites across nearly 1000 individuals. TCGA (The Cancer Genome Atlas) was used as a resource for over 20,000 primary cancer and matched normal samples spanning 33 cancer types. The TCGA-COADREAD dataset is a Colon Adenocarcinoma and Rectum Adenocarcinoma dataset. CCLE (Cancer cell line Encyclopedia) contains information on 57 Colorectal Cancer (CRC) cell lines.

RNASeqDB is database of processed data from the GTEx and TCGA using the same pipeline which allows comparative studies from Memorial Sloan Kettering Cancer Center. 372 TCGA-COADREAD samples and 339 normal colon samples from GTEx were analyzed.

COLEC12, CXCL16 and APCDD1 were identified using these methods as potential blocker targets. Table 19 summarizes the expression data for these genes in colorectal cancers. Expression data from UCSC Xena browser (for TCGA) and CCLE samples.

TABLE 19

| Expression | | | | |
|---|---|---|---|---|
| Gene name | TCGA-Colorectal Adenocarcenoma (Median-FPKM (383 samples) | Median expression_ CCLE_ colorectal_ RPKM (57 cell lines) | Colon-Sigmoid | Colon-Transverse |
| CXCL16 | 5.7509 | 25.88884 | 11.51 | 15.44 |
| COLEC12 | −0.6416 | 0.01964 | 27.25 | 11.24 |
| APCDD1 | 4.1498 | 0.58982 | 12.26 | 11.22 |

Table 20 summarizes the variants and minor allele frequencies.

TABLE 20

| Position, Characteristics and Variation | | | | | |
|---|---|---|---|---|---|
| Gene names | All variants | TCGA-Colorectal Adenocarcenoma_Frequency of heterozygous deletion (score = −1) | Protein position of Amino Acid Change | Amino acid Change | MAF |
| CXCL16 | rs2277680, rs1050998 | 0.569805195 | 1.200, 2.142 | 1. A/V, 2. I/T | 1. 0.4615, 2. 0.4633 |
| COLEC12 | rs2305025 | 0.584415584 | 522 | S/P | 0.6252 |
| APCDD1 | rs1786683 | 0.600649351 | 165 | Y/S | 0.2496 |

TABLE 21

| LOH Frequencies in Various Cancers | | | |
|---|---|---|---|
| | | LOH Freq | |
| | COLEC12 | CXCL16 | APCDD1 |
| All cancers | 0.23 | 0.36 | 0.23 |
| CRC | 0.59 | 0.58 | 0.6 |
| Lung | 0.3 | 0.58 | 0.29 |
| Pancreatic | 0.3 | 0.48 | 0.28 |
| Ovarian | 0.39 | 0.74 | 0.36 |
| DBCL | 0.15 | 0.23 | 0.13 |
| Blood | 0.06 | 0.11 | 0.05 |
| variant | S/P | I/T | Y/S |
| MAF | 0.63 | 0.46 | 0.25 |

Example 4: Identification of Antigen Binding Domains Specific to Blocker Target Antigens Publicly available antibodies to candidate blocker antigens are sequenced, if CDR sequences are unknown. If no antibodies to candidate blocker targets are available, these antibodies are generated by immunization of mice, rats, or rabbits with purified protein (e.g., COLEC12, CXCL16, TNFRS11A and other targets described in the Examples). Sera from immunized animals is used to screen for mAbs for binding to blocker targets. Antibodies to blocker targets are also generated using the huTARG system. Antibodies with the desired specificity are then isolated and sequenced to determine CDR sequences.

CDR sequence from antibodies to blocker targets are used to generate scFv using standard molecular biology techniques. Candidate scFv are fused to inhibitory receptor hinge or transmembrane domains to generate inhibitory receptors using standard molecular biology techniques. Candidate scFv are also fused to activator receptor hinge or transmembrane domains (e.g., CAR) to generate full length activator receptors to use as a positive control for scFv binding to target antigens. The ability of candidate scFv to work in the context of an inhibitory receptor is assayed in Jurkat cells using the NFAT-luciferase reporter assay.

Example 5: Methods for Examples 6-11

Cell Line Generation

Target cell lines were grown per vendor instructions. Genetic modifications to construct CEA(−) HLA-A*02(−) cell lines as shown in Table 25 used CRIPSR/Cas9. Guide RNAs were purchased from Synthego and/or IDT (Integrated DNA Technologies) and the targeting sequences are listed in Table 22. To form RNP complexes S.p. HiFi Cas9 protein (IDT) was mixed with sgRNAs at 1:3 molar ratios before electroporation with settings tailored for each cell line using the 4D Nucleofector (Lonza).

To generate CEA(+) HLA-A*02(+) and CEA(+) HLA-A*02(−) HeLa cell lines, pLenti plasmid encoding CEA with or without a plasmid encoding HLA-A*02 was transfected into HeLa cells. Stable pools expressing CEA and/or HLA-A*02 were enriched by FACS and expanded afterwards.

To establish HLA-A*02(+) K562 and Colo668 lines, lentivirus encoding HLA-A*02 heavy chain was transduced to create stable pools. To generate CEA(+) target cells, all CEA(−) target cells, except for Colo668 and H508, were transfected with CEA mRNA (see below) using 4D Nucleofector, and assayed within 1-3 days post transfection. Lentivirus encoding *Renilla* luciferase and RFP (in cis) was purchased from Biosettia and transduced to establish stable pools of RFP-expressing target cells. The target knockout or over-expressing cell lines were enriched for target-negative or -positive pools by FACS using an HLA-A*02 antibody (BV421, BioLegend, Cat #343326), or CEA antibody (R&D systems, MAB41281). RFP-expressing pools of target cell lines were selected by FACS.

CEA CAR with or without the A*02 blocker was stably expressed in luciferase-reporter Jurkat cells by lentiviral transduction.

In Vitro Transcription of mRNAs mRNA was synthesized in 25 ul of 1× reaction buffer containing 40 mM Tris-HCL, 10 mM dithiothreitol, 2 mM spermidine, 0.002% Triton X-100, 27 mM magnesium acetate, 5 mM CleanCap Cap 1 AG trimer (TriLink), and 5 mM each of ATP, CTP, GTP, and pseudo-uridine triphosphate (NEB). The reaction proceeded 2 hours at 37° C. with final concentrations of 8 U/μL T7 RNA polymerase (NEB, M0460T), 0.002 U/μL inorganic pyrophosphatase (NEB, M2403L), 1 U/μL murine RNase inhibitor (NEB, M0314L), and 0.025 μg/μL linearized-T7-template. 0.4 U/μL DNase I (NEB, M0303L) was added at the end of the reaction at 37° C. for 15 min in 1× DNase I buffer to remove template. poly(A) tailing of RNAs was performed per manufacturer's protocols with *E. coli* poly (A) polymerase (NEB, M0276) and RNAs were purified by a supplier's cleanup kit (NEB, T2040L). RNAs were treated with 0.2 U/μg Antarctic phosphatase (NEB, M0289L) in 1× Antarctic phosphatase buffer for 1 hour and repurified by (NEB, T2040L). RNA concentrations were measured by Nanodrop and examined on 1% Agarose gels.

Flow Cytometry for Probe Binding and Receptor Expression

The expression of CARs and TCRs were assessed via flow cytometry using biotinylated protein L (ThermoFisher #29997) followed by fluorescently labeled streptavidin (for CARs), or fluorescently labeled anti-murine TRBV antibody (for TCRs; Biolegend Cl:H57-597). Blocker-antigen binding was determined by staining Tmod-expressing Jurkat cells with biotinylated-pMHCs probes, tetramerized and prelabeled with streptavidin conjugated to an appropriate fluorochrome (Biolegend). After staining at 4° C., median fluorescence intensity (MFI) was determined using a FACS Canto II flow cytometer (BD Biosciences).

Jurkat Cell Functional Assay

Target cells expressing activator and blocker antigen natively, recombinantly, or transiently by mRNA transfection were used in this study. If mRNA transfection was used, each pair of target cells (HLA-A*02(−) and HLA-A*02(+)) were electroporated using 4D Nucleofactor (Lonza) with variable amounts of CEA mRNA, starting from 2 mRNA in a 9-fold dilution series for a total of 6-16 points. Electroporated cells or cells natively/stably expressing the target antigen were seeded and grown under normal tissue culture conditions at a density of 10,000 cells/well in 384-well plates (Corning, Cat #3570) for 18-20 hours. 12,000 Jurkat cells, wild type or expressing CEA CAR or CEA Tmod constructs, were added to target cell wells and co-cultured for 6 hours before luciferin substrate was added to measure the luciferase signal using a Tecan Infinite M1000.

To quantify CEA expression, target cells from each CEA mRNA titration point were seeded in a 96-well plate (Corning, Cat #3610) and grown for 18-20 hours before cell collection. CEA expression was quantified using CEA antibody (R&D systems, MAB41281) and QIFIKIT (Agilent, K007811-8) according to the manufacturer's protocol to determine surface CEA molecule numbers. Standard curves were generated for cell surface number vs. mRNA (see below).

Conversion of EC50 and IC50 Molecules/Cell Value into TPM

To generate protein molecules/cell vs. TPM standard curves, the surface expression of CEA or HLA-A*02 on multiple cell lines was either determined in-house as described above or taken from previously published results. The TPM values were from DepMap portal (depmap.org/portal/). The slope (k) was determined by fitting molecules/cell=k*TPM, and used to convert EC50 and IC50 in molecules/cell to TPM for comparison to tissue and cell line antigen expression values.

Primary T Cell Generation and Characterization

Informed-consent for primary T cells and donor collection protocols were approved by an Institutional Review Board (IRB) at Allcells®. Allcells® followed HIPAA compliance and approved protocols (www.allcells.com/cell-tissue-procurement/donor-facilities/). PBMCs were purified from Leukopaks purchased from Allcells®. LymphoONE™ media (Takara WK552) was supplemented with 1% human AB Serum (GeminiBio 100-512) unless otherwise stated. Human PBMCs were grown in LymphoONE™ and supplemented with TransAct™ (Miltenyi 130-111-160) following the manufacturers guidelines (1:100 dilution) for 24 hours before transduction with CEA CAR-alone and CEA Tmod-encoding lentivirus. Additional LymphoONE™ supplemented with IL-2 (300 IU/ml) was added 24 hours after transduction to transduced cells which were cultured for 3 days before transfer to a 24-well G-Rex plate (Wilson Wolf 80192M). Fresh IL-2 (300 IU/ml) was added every 48 hours with media change every 7 days during expansion in G-Rex plates. Expression and antigen binding of transduced CARs or Tmod components in primary T cells were confirmed by flow cytometry as described above.

For in vivo studies, CEA CAR and CEA Tmod were generated as described above with the use of G-Rex 10 (Wilson Wolf 80040S) or G-Rex100 (Wilson Wolf 80500) to accommodate the larger quantity of cells beginning on day 3. T cells were counted, and media was exchanged every other day starting on day 3. Enrichment of CAR- and Tmod-expressing cells was performed on day 9.

To enrich CAR- or Tmod dual receptor-expressing population, cells were labeled with protein L-biotin (Thermo Scientific Cat #29997) streptavidin-PE or probe-biotin/streptavidin-PE, followed by anti-PE microbeads (Miltenyi 130-048-801) according to the manufacturer's protocol, and subsequently enriched using AutoMACS® Pro Separator (Miltenyi). Enriched cells were grown in G-Rex plates as before harvest.

Primary T Cell Functional Assay (Acute)

Target cell line pairs (HLA-A*02(−) and HLA-A*02(+)), expressing either GFP or RFP, were electroporated with CEA mRNA at stated amounts using 4D Nucleofector and cultured as described above, except that 384-well PDL-coated plates (Greiner bio-one, Cat #781091) were used for cell imaging. If needed, identical cell numbers were seeded in parallel in another 384-well plate (Corning, Cat #3570) for cell density determination. On the next day, target cell seeding density was measured by cell-titer glow (Promega, G7570) per manufacturer's instruction. Percentages of CEA CAR-positive and CEA CAR/A*02 blocker double-positive T cells were determined by flow cytometry before co-culture. If needed, untransduced T cells were mixed with CEA CAR-positive pools to match the percentage of positive CEA CAR cells to the double-positive population. Target cells and T cells were co-cultured for up to 48 hours. Whole-well fluorescence signal was monitored on IncuCyte S3 or ImageXpress® Micro Confocal imager (Molecule Device Corporation) with a 4× objective during co-culture, and total fluorescence area or intensity was recorded over time. Reduction of fluorescence signal in CAR or Tmod co-cultures compared to wells without T cells or co-cultured with untransduced T cells allowed comparisons of cytotoxicity of CEA activator and CEA Tmod constructs. CEA expression on target cells was determined using the QIFIKIT as described above.

When mixed target cells were used, normal CEA(+)A*02(+) target cells with GFP-*renilla* luciferase and tumor CEA(+)A*02(−) target cells engineered with RFP-firefly luciferase were mixed at 1:1 ratios and co-cultured with enriched primary T cells as described above. Cytotoxicity was determined by monitoring GFP and RFP signal loss on IncuCyte S3.

Reversibility Cytotoxicity Assays

Target cell lines were co-cultured with T cells in LymphoneONE™ plus 1% human serum and 1×P/S. Briefly, target cells were plated at 500,000 cells/well in 6-well plates for bulk co-cultures intended for serial-transfer experiments. In 384-well imaging plates, target cells were seeded at 5,000 cells/well and incubated overnight. The next day, T cells were added to co-culture wells at a nominal effector-to-target (E:T) ratio of 3:1 (1,500,000 cells/well in the 6-well format; 15,000 cells/well in the 384-well format). Incubation/imaging was performed on the IncuCyte® S3 platform (Sartorius), with imaging every 2 hours for 48 hours (spanning each round of serial co-culture); 6-well plates were incubated offline at 37° C. At the end of each 48-hour cycle, T cells were separated from target cells and collected from 6-well co-cultures; these T cells were counted and resuspended at a uniform density in fresh media for transfer to (i) a new well of bulk target cells for the next co-culture in the indicated series, and (ii) a new set of imaging wells (384-well format) to collect data for the next co-culture in the series. In the second round, 12-well plates were used for bulk co-cultures containing 750,000 T cells and 250,000 target cells (E:T ratio remained constant throughout the series; imaging plate co-cultures were used throughout the study in the 384-well format at a nominal 15,000:5,000 E:T ratio). The result was a series of co-cultures in which enriched primary T cells were alternately cultured with normal (CEA(+) HLA-A*02(+)) then tumor (CEA(+) HLA-A*02(−)) target cells, or vice versa. Data were presented as specific killing (%), reflecting the percent loss of the target-cell GFP signal in transduced populations compared to donor-matched untransduced T cells.

Xenograft Study

In vivo experiments were conducted by Explora BioLabs under Institutional Animal Care and Use Committee (IACUC)-approved protocols. 5-6 week-old female NSG (NOD.Cg-Prkdc$^{scid}$Il2rg$^{tmlWjl}$/SzJ), JAX stock No. 005557 mice were purchased from The Jackson Labs. Animals were acclimated to the housing environment for at least 3 days prior to the initiation of the study.

After acclimation to the housing environment, animals were injected with tumor cells, as determined in a pilot study that established the proper cell number. The H508 xenograft model was established using the wildtype or isogenic HLA-A*02(−) cell lines engineered with a firefly luciferase reporter (see above). 2E7 H508 cells in 50% were injected subcutaneously into the flanks of NSG mice. “Normal” cells were injected subcutaneously into the right flank, and tumor cells into the left flank of each mouse. Tumor growth was monitored via caliper measurements. When tumors reach an average size of ~100-200 mm$^3$, animals were randomized into groups and T cells administered via the tail vein. Post T-cell injection, tumor measurements were performed 3 times per week until total tumor burden in mice reaches 2,000 mm$^3$. Bioluminescence quantification was performed on a subset of 5 mice from each cohort of 7. In brief, each mouse received a 100 ul subcutaneous injection of XenoLight D-luciferin potassium salt (PerkinElmer 122799) and then were imaged 15 minutes later on their dorsal side using an IVIS® Spectrum In Vivo Imaging System (Perkin Elmer). Animals were monitored for general health via clinical observations and effects on body weight at regular intervals throughout the study.

Blood and serum collected on days=−1, 2, 9, 16, 30 post T cell injection and at termination of the study. Staining for T cells in the blood and spleen was performed after red blood cell lysis on a BD FACSCanto II. Mouse cells were excluded by staining with antibodies to mouse CD45 and Ter119. Human T cells were stained with antibodies to human CD3, CD4 and CD8. The source of all antibodies is listed in Supplementary Table 23.

TABLE 22 gRNA targeting sequences used for CRISPR/Cas9 generated knockout of CEA and HLA-A

| gRNA | CEA | HLA-A |
|---|---|---|
| 1 | GATCTGACTTTATGACGTGT (SEQ ID NO: 976) | CCTTCACATTCCGTGTCTCC (SEQ ID NO: 977) |
| 2 | N/A | ACAGCGACGCCGCGAGCCAG (SEQ ID NO: 978) |
| 3 | N/A | TTCACATCCGTGTCCCGGCC (SEQ ID NO: 979) |

TABLE 23

Summary of Antibodies and recombinant proteins used in Examples 7-11

| Antibody | Name | Vendor | Cat # |
|---|---|---|---|
| 1 | Brilliant Violet 421 ™ anti-human HLA-A2 Antibody | BioLegend | 343326 |
| 2 | Streptavidin-PE | ThermoFisher Scientific | 12-4317-87 |
| 3 | Protein L | Thermo Scientific | 29997 |
| 4 | Streptavidin-APC | BioLegend | 405243 |
| 5 | F(ab')2-Goat anti-Mouse IgG (H + L) Cross-Adsorbed Secondary Antibody, Alexa Fluor 647 | ThermoFisher Scientific | A-21237 |
| 6 | Brilliant Violet 421 ™ anti-mouse TCR β chain Antibody | BioLegend | 109230 |
| 7 | Purified anti-human HLA-A2 Antibody | BioLegend | 343302 |
| 8 | Human CEACAM-5 Antibody | R&D Systems | MAB41281 |
| 9 | Soluble CEA (sCEA) | R&D Systems | 4128-CM-050 |
| 10 | APC anti-mouse TER-119/ Erythroid Cells Antibody | Biolegend | 116212 |
| 11 | APC anti-mouse CD45 Antibody | Biolegend | 103112 |
| 12 | Brilliant Violet 510 ™ anti-human CD3 Antibody | Biolegend | 300448 |
| 13 | Alexa Fluor ® 488 anti-human CD4 Antibody | Biolegend | 317420 |
| 14 | PE anti-human CD8 Antibody | Biolegend | 344706 |
| 15 | PE anti-mouse TCR β chain Antibody | Biolegend | 109208 |

Figure 13:
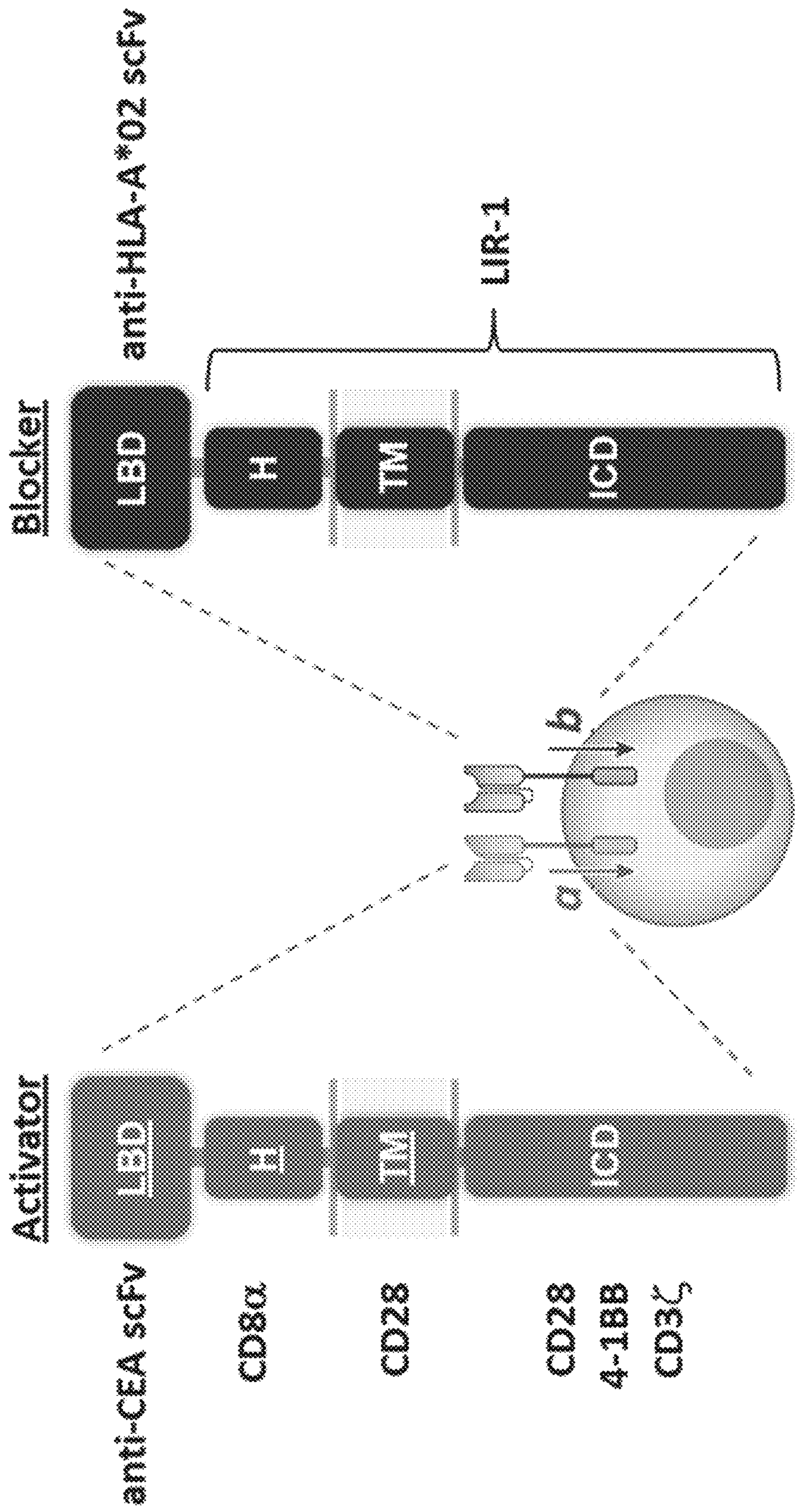
FIG. 13 is a diagram showing the molecular composition of an exemplary dual receptor system of the disclosure, comprising a CEA CAR and an HLA-A*02 scFv LILRB1 inhibitory receptor.

Example 6: Design and Activity of a CEA Chimeric Antigen Receptor and LILRB1 Inhibitory Receptor Pair A humanized scFv based on a mouse mAb that binds an extracellular epitope in the membrane-proximal CEA B3 domain was generated. The original mAb was thought to bind an epitope that is absent from the shed form of the protein, thereby avoiding the risk of receptor inhibition by soluble CEA. The CEA scFv was fused to a generation 3 CAR, which included a CD8a hinge, a CD28 transmembrane domain, and 4-1BB, and CD3ζ intracellular domains (FIG. 13). The sequences are shown in Table 24 below.

Figure 14:
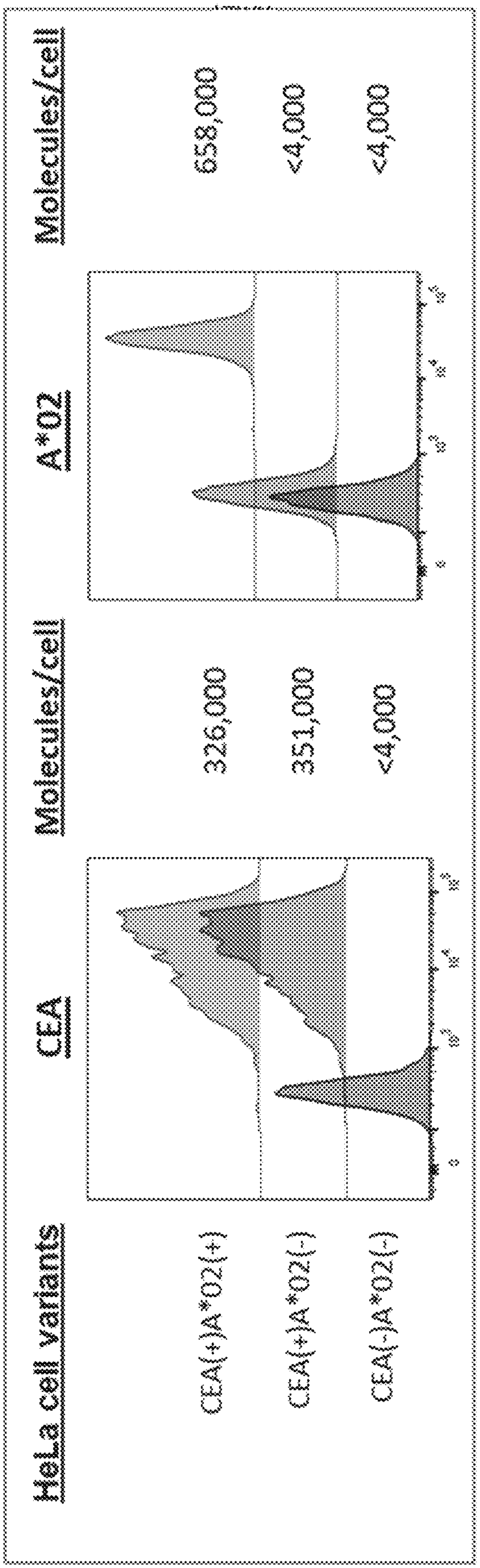
FIG. 14 shows the expression of CEA and HLA-A*02 antigens in HeLa cells. A*02: HLA-A*02.

After confirming activity of the CAR activator alone, the CEA CAR was co-expressed with the HLA-A*02 inhibitory receptor, a construct that contains an HLA-A*02-specific scFv fused to the hinge, transmembrane and signaling domains of the LILRB1 gene product (LIR-1). LIR-1 is a member of the immune inhibitory receptor family and contains 4 ITIMs in its signaling domain. The CAR and LIR-1 inhibitory receptors expressed well on the surface of Jurkat and primary T cells, and both receptors functioned in a largely ligand-dependent fashion using HeLa target cells engineered to express CEA, HLA-A*02 or both (FIGS. 14-17). CEA and HLA-A*02 were stably expressed in HeLa cells, which were stained with labeled mAbs and analyzed by flow cytometry. The surface antigen density of each antigen was determined using QIFIKIT (FIG. 14). Expression and enrichment of both receptors in transfected Jurkat cells and transduced primary T effector cells was confirmed using fluorescence activated flow cytometry (FACS).

Figure 15:
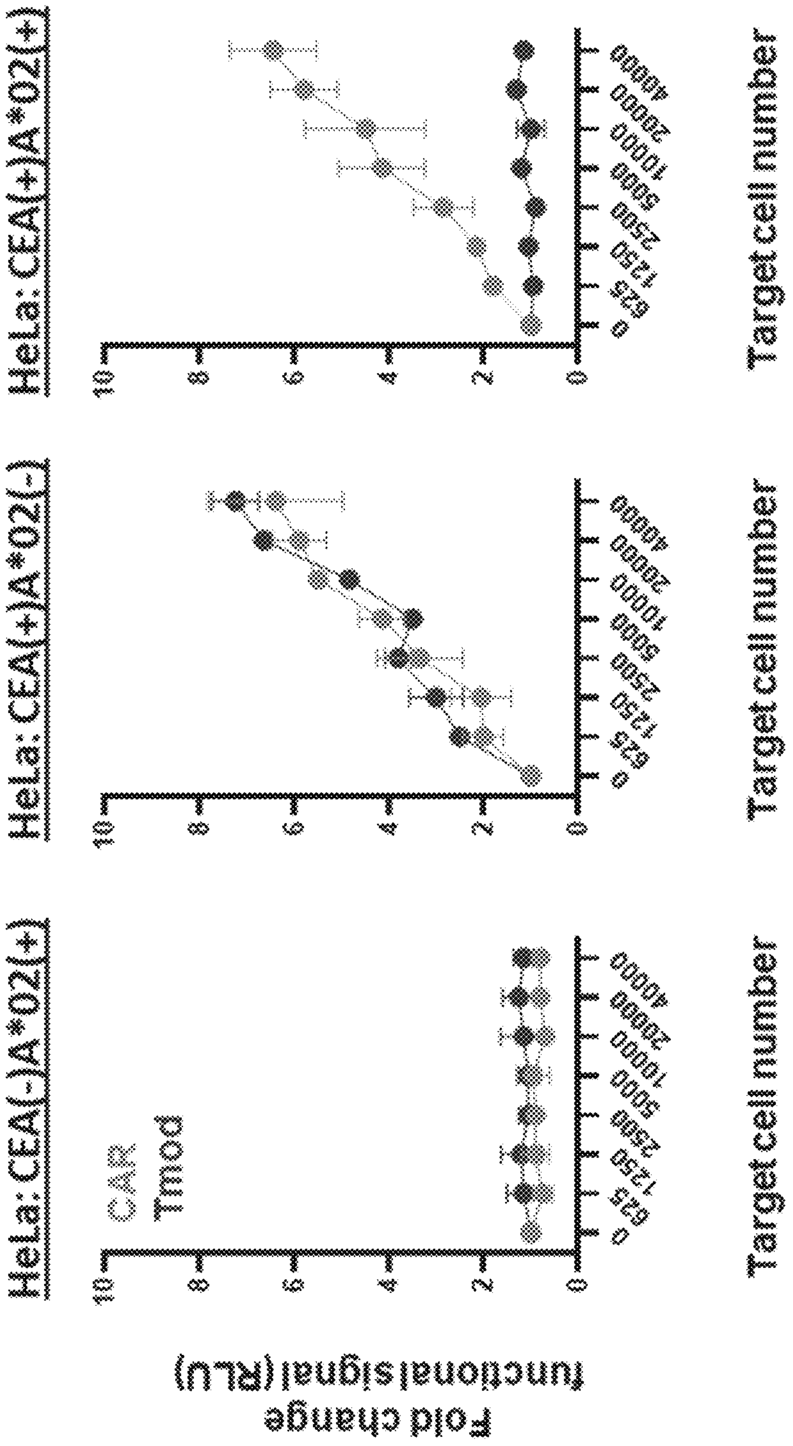
FIG. 15 shows that the CEA activator and HLA-A*02 LILRB1 inhibitory receptor function in Jurkat cells using engineered HeLa cells as targets for cytotoxicity. A*02: HLA-A*02; Tmod: the cells express the CEA CAR and the HLA-A*02 inhibitory receptor; CAR: cells express the CEA CAR only.

Except where noted, a single vector construct with both receptor modules encoded by a single fusion gene containing a cleavable T2A linker and an shRNA expression cassette to reduce $\beta_2$ microglobulin (B2M) expression was used to transfect Jurkat cells, or transduce primary effector T cells In FIG. 15, the CEA CAR is specifically blocked in Jurkat cells co-cultured with HeLa target cells that express both CEA and HLA-A*02. Jurkat cells that contain an NFAT-luciferase reporter were engineered to stably express activator and blocker from two separate constructs.

Figure 16:
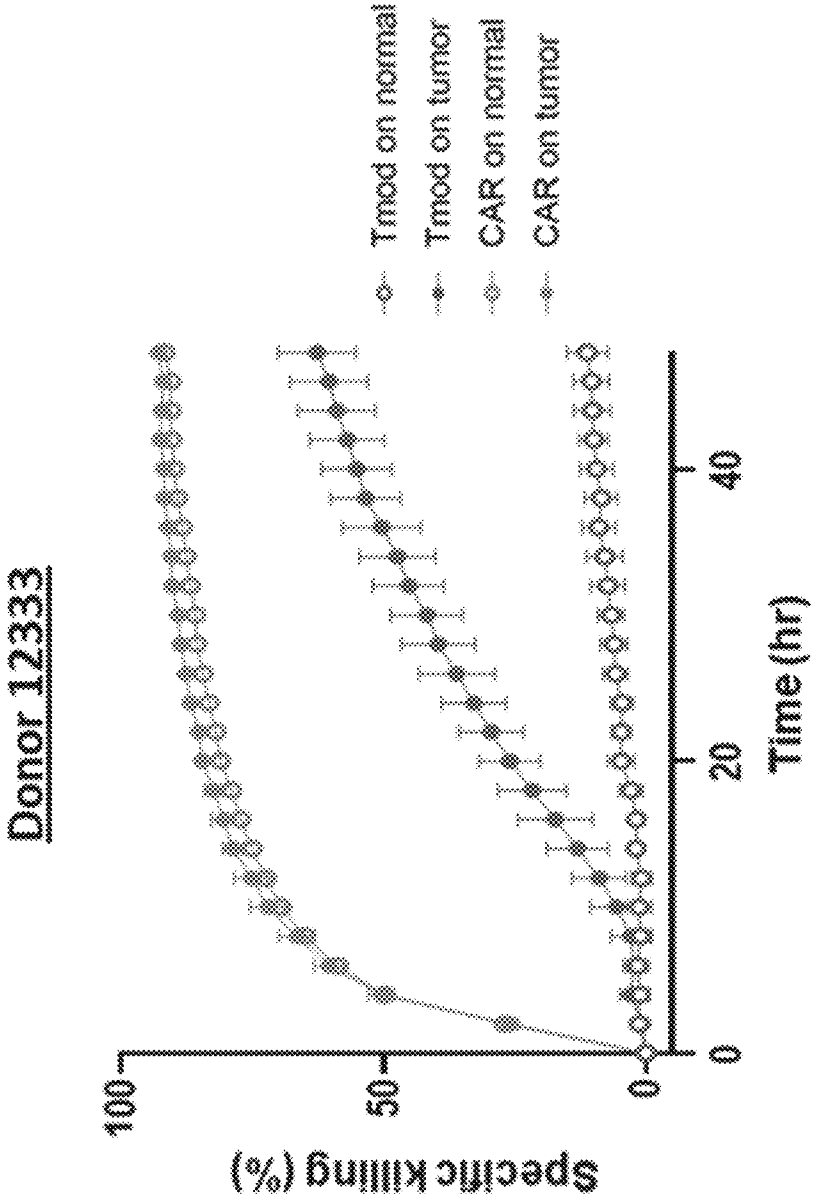
FIG. 16 shows that the CEA activator and HLA-A*02 LILRB1 inhibitory receptor function in donor T cells from a single donor on HeLa cells. Tmod: the cells express the CEA CAR and the HLA-A*02 inhibitory receptor; CAR: cells express the CEA CAR only.
Figure 17:
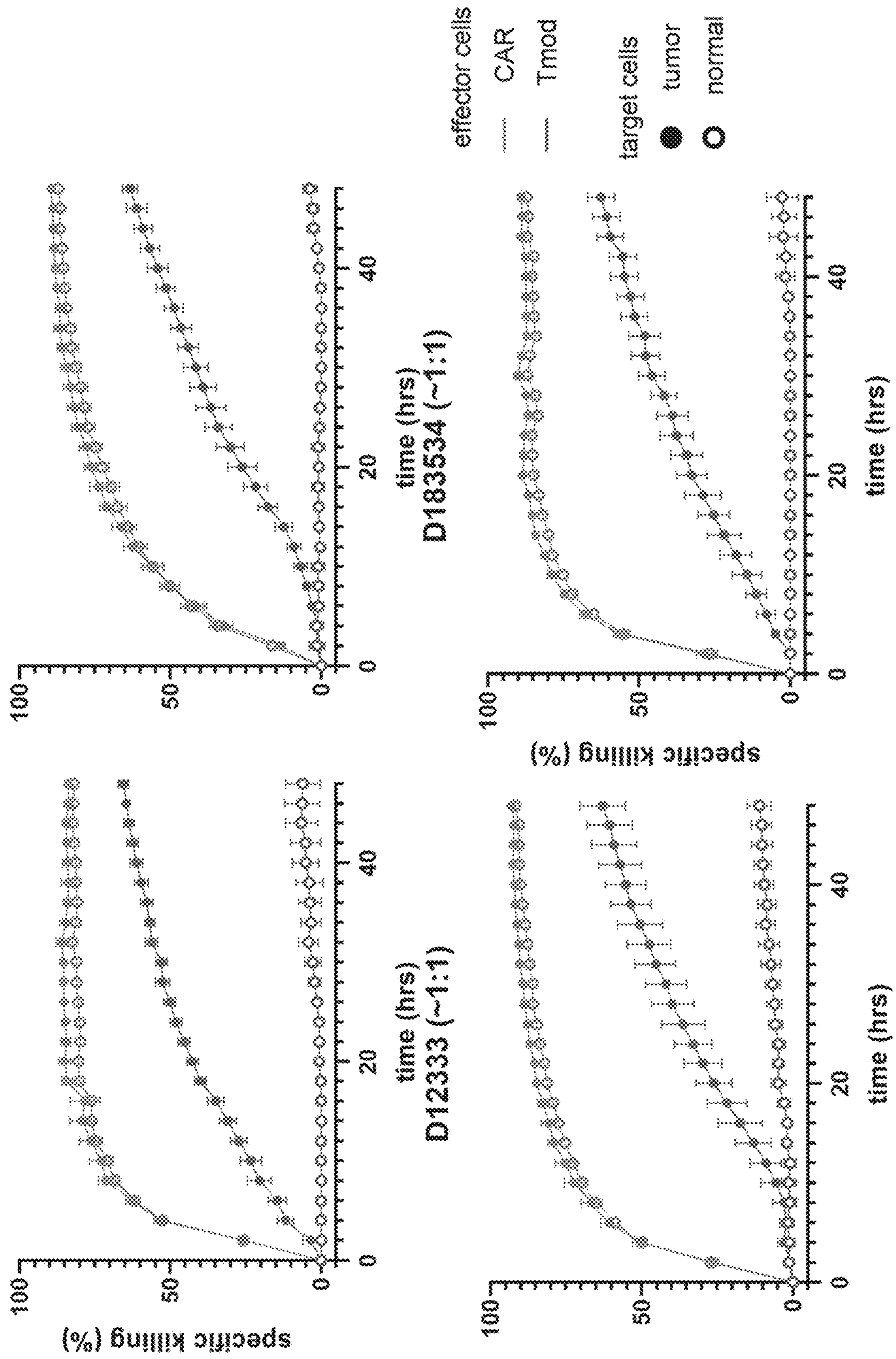
FIG. 17 shows that the CEA activator and HLA-A*02 LILRB1 inhibitory receptor function in T cells from four donors on HeLa cells. Tmod: the cells express the CEA CAR and the HLA-A*02 inhibitory receptor; CAR: cells express the CEA CAR only. Target cells are HeLa cells expressing CEA only or CEA and HLA-A*02.

In FIGS. 16 and 17, cytotoxicity in primary T cells expressing the two receptors was assayed with engineered HeLa cell targets. In FIG. 16, a single lentiviral vector encoding both receptors was used for transduction of HLA-A*02(+) donor T cells, which were enriched for blocker-positive cells prior to assay. One donor (who was HL-A*02 (+)) is shown in FIG. 16, while four donors are shown in FIG. 17.

Results for T cells from additional donors are shown in FIG. 17. Engineered HeLa cells were again used a targets for cytotoxicity, and primary T cells were transduced with a single lentiviral vector encoding both receptors. Enrichment was performed using the blocker ligand (HLAA*02 pMHC) and protein L, prior to assay. The donors were A*02(+), except D183534, who was HLA-A*02(−).

TABLE 24

Sequences of CEA CAR and LILRB1 Inhibitory Receptor

| Name | Protein Sequence | DNA Sequence |
|---|---|---|
| | Activator receptor | |
| CEA | MDMRVPAQLLGLLL | ATGGATATGAGAGTGCCTGCCCAGCTGCTCGGACTGCTCCTTC |
| CAR- | LWLRGARCDVLMTQ | TGTGGTTGAGAGGAGCTCGGTGCGATGTTCTGATGACCCAAAC |
| T2A- | TPLSLPVSLGDQAS | TCCACTCTCCCTGCCTGTCAGTCTTGGAGATCAAGCCTCCATC |
| HLA- | ISCRSSQSIVHSNG | TCTTGCAGATCTAGTCAGAGCATTGTACATAGTAATGGAAACA |
| A*02 | NTYLEWYLQKPGQS | CCTATTTAGAATGGTACCTGCAGAAGCCAGGCCAGTCTCCAAA |
| inhibitory | PKLLIYKVSNRFSG | GCTGCTCATCTACAAAGTTTCCAACCGATTTTCTGGGGTCCCA |
| Receptor | VPDRFSGSGSGTDF | GACAGATTTAGCGGATCTGGCTCTGGGACCGATTTCACACTCA |
| | TLKISRVEAEDLGV | AGATCAGTAGAGTGGAGGCTGAGGATCTGGGAGTTTATTACTG |
| | YYCFQGSHVPRTSG | CTTTCAAGGTTCACATGTTCCTCGGACGTCCGGTGGAGGCACA |
| | GGTKLEIKGGGGSG | AAGCTGGAAATCAAGGGAGGTGGCGGCTCTGGAGGCGGAGGTA |
| | GGGSGGGGSGGQVQ | GCGGAGGTGGAGGCTCTGGTGGCCAGGTCCAGCTGCAGCAGTC |
| | LQQSGPELVKPGAS | TGGACCTGAGCTGGTGAAGCCAGGGGCTTCAGTGAGGATATCC |
| | VRISCKASGYTFTS | TGTAAGGCCTCTGGCTACACCTTTACAAGTTACCATATACATT |
| | YHIHWVKQRPGQGL | GGGTGAAGCAGAGGCCTGGACAGGGACTCGAATGGATTGGATG |
| | EWIGWIYPGNVNTE | GATTTATCCTGGAAATGTTAATACTGAGTACAATGAGAAGTTC |
| | YNEKFKGKATLTAD | AAGGGCAAGGCCACACTGACTGCAGACAAATCGTCCAGCACAG |
| | KSSSTAYMHLSSLT | CCTACATGCACCTCAGCAGCCTGACCTCTGAGGACTCTGCGGT |
| | SEDSAVYFCAREEI | CTATTTCTGTGCCAGAGAGGAGATTACCTATGCTATGGATTAT |
| | TYAMDYWGQGTSVT | TGGGGTCAAGGAACCTCAGTCACCGTGTCCTCATACGGCTCAC |
| | VSSYGSQSSKPYLL | AGAGCTCCAAACCCTACCTGCTGACTCACCCTAGTGATCCTCT |
| | THPSDPLELVVSGP | GGAGCTCGTGGTCTCAGGACCGTCTGGAGGCCCAAGCTCTCCG |
| | SGGPSSPTTGPTST | ACAACAGGCCCCACCTCCACATCTGGCCCTGAGGACCAGCCCC |
| | SGPEDQPLTPTGSD | TCACACCCACCGGGTCGGATCCTCAGAGTGGTCTGGGAAGACA |
| | PQSGLGRHLGVVIG | CCTGGGAGTTGTGATCGGCATCTTGGTGGCCGTCATCCTACTG |
| | ILVAVILLLLLLLL | CTCCTCCTCCTGCTCCTGCTCTTCCTCATCCTCCGACATCGAC |
| | LFLILRHRRQGKHW | GTCAGGGCAAACACTGGACATCGACCCAGAGAAAGGCTGATTT |
| | TSTQRKADFQHPAG | CCAACATCCTGCAGGGGCTGTGGGGCCAGAGCCCACAGACAGA |
| | AVGPEPTDRGLQWR | GGCCTGCAGTGGAGGTCCAGCCCAGCTGCCGATGCCCAGGAAG |
| | SSPAADAQEENLYA | AAAACCTCTATGCTGCCGTGAAGCACACACAGCCTGAGGATGG |
| | AVKHTQPEDGVEMD | GGTGGAGATGGATACTCGGAGCCCACACGATGAAGATCCACAG |
| | TRSPHDEDPQAVTY | GCAGTGACGTATGCCGAGGTGAAACACTCCAGACCTAGAAGGG |
| | AEVKHSRPRREMAS | AAATGGCCTCTCCTCCTTCCCCACTGTCTGGAGAGTTCCTGGA |
| | PPSPLSGEFLDTKD | CACAAAGGACAGACAGGCGGAAGAGGACAGGCAGATGGACACT |
| | RQAEEDRQMDTEAA | GAGGCTGCTGCATCTGAAGCTCCTCAGGATGTGACCTACGCCC |
| | ASEAPQDVTYAQLH | AGCTGCACAGCTTGACCCTCAGACGGGAGGCAACTGAGCCTCC |
| | SLTLRREATEPPPS | TCCATCCCAGGAAGGGCCCTCTCCAGCTGTGCCCAGCATCTAC |
| | QEGPSPAVPSIYAT | GCCACTCTGGCCATCCACGGATCCGGAGAGGGCAGAGGCAGCC |
| | LAIHGSGEGRGSLL | TGCTGACATGTGGCGACGTGGAAGAGAACCCTGGCCCCATGGA |
| | TCGDVEENPGPMDM | CATGAGGGTCCCCGCTCAGCTCCTGGGGCTCCTGCTACTCTGG |
| | RVPAQLLGLLLLWL | CTCCGAGGTGCCAGATGTCAGGTGCAGCTGGTGCAATCTGGGT |
| | RGARCQVQLVQSGS | CTGAGTTGAAGAAGCCTGGGGCCTCAGTGAAGGTTTCCTGCAA |
| | ELKKPGASVKVSCK | GGCTTCTGGATACACCTTCACTGAGTTTGGAATGAACTGGGTG |
| | ASGYTFTEFGMNWV | CGACAGGCCCCTGGACAAGGGCTTGAGTGGATGGGATGGATAA |
| | RQAPGQGLEWMGWI | ACACCAAAACTGGAGAGGCAACATATGTTGAAGAGTTTAAGGG |
| | NTKTGEATYVEEFK | ACGGTTTGTCTTCTCCTTGGACACCTCTGTCAGCACGGCATAT |
| | GRFVFSLDTSVSTA | CTGCAGATCAGCAGCCTAAAGGCTGAAGACACTGCCGTGTATT |
| | YLQISSLKAEDTAV | ACTGTGCGAGATGGGACTTCGCTTATTACGTGGAGGCTATGGA |
| | YYCARWDFAYYVEA | CTACTGGGGCCAAGGGACCACGGTGACCGTGTCATCCGGCGGA |
| | MDYWGQGTTVTVSS | GGTGGAAGCGGAGGGGGAGGATCTGGCGGCGGAGGAAGCGGAG |
| | GGGGSGGGGSGGGG | GCGATATCCAGATGACCCAGTCTCCATCCTCCCTGTCTGCATC |
| | SGGDIQMTQSPSSL | TGTGGGAGACAGAGTCACCATCACTTGCAAGGCCAGTCAGAAT |
| | SASVGDRVTITCKA | GTGGGTACTAATGTTGCCTGGTATCAGCAGAAACCAGGGAAAG |
| | SQNVGTNVAWYQQK | CACCTAAGCTCCTGATCTATTCGGCATCCTACCGCTACAGTGG |
| | PGKAPKLLIYSASY | AGTCCCATCAAGGTTCAGTGGCAGTGGATCTGGGACAGATTTC |
| | RYSGVPSRFSGSGS | ACTCTCACCATCAGCAGTCTGCAACCTGAAGATTTCGCAACTT |
| | GTDFTLTISSLQPE | ACTACTGTCACCAATATTACACCTATCCTCTATTCACGTTTGG |
| | DFATYYCHQYYTYP | CCAGGGCACCAAGCTCGAGATCAAGACAACGACGCCAGCTCCC |
| | LFTFGQGTKLEIKT | CGCCCGCCAACCCCTGCACCTACGATTGCATCACAACCGCTGT |
| | TTPAPRPPTPAPTI | CCCTGCGGCCTGAAGCTTGTCGCCCAGCCGCAGGTGGCGCCGT |
| | ASQPLSLRPEACRP | ACATACACGGGGGCTGGATTTTGCCTGTGATTTCTGGGTGCTG |
| | AAGGAVHTRGLDFA | GTCGTTGTGGGCGGCGTGCTGGCCTGCTACAGCCTGCTGGTGA |

TABLE 24-continued

Sequences of CEA CAR and LILRB1 Inhibitory Receptor

| Name | Protein Sequence | DNA Sequence |
|---|---|---|
| | CDFWVLVVVGGVLA<br>CYSLLVTVAFIIFW<br>VRSKRSRLLHSDYM<br>NMTPRRPGPTRKHY<br>QPYAPPRDFAAYRS<br>KRGRKKLLYIFKQP<br>FMRPVQTTQEEDGC<br>SCRFPEEEEGGCEL<br>RVKFSRSADAPAYK<br>QGQNQLYNELNLGR<br>REEYDVLDKRRGRD<br>PEMGGKPRRKNPQE<br>GLYNELQKDKMAEA<br>YSEIGMKGERRRGK<br>GHDGLYQGLSTATK<br>DTYDALHMQALPPR<br>(SEQ ID NO:<br>141) | CAGTGGCCTTCATCATCTTTTGGGTGAGGAGCAAGCGGAGTCG<br>ACTGCTGCACAGCGACTACATGAACATGACCCCCCGGAGGCCT<br>GGCCCCACCCGGAAGCACTACCAGCCCTACGCCCCTCCCAGGG<br>ATTTCGCCGCCTACCGGAGCAAACGGGGCAGAAAGAAACTCCT<br>GTATATATTCAAACAACCATTTATGAGGCCAGTACAAACTACT<br>CAAGAGGAAGATGGCTGTAGCTGCCGATTTCCAGAAGAAGAAG<br>AAGGAGGATGTGAACTGAGAGTGAAGTTCAGCAGGAGCGCAGA<br>CGCCCCCGCGTACAAGCAGGGCCAGAACCAGCTCTATAACGAG<br>CTCAATCTAGGACGAAGAGAGGAGTACGATGTTTTGGACAAGC<br>GTAGAGGCCGGGACCCTGAGATGGGGGGAAAGCCGAGAAGGAA<br>GAACCCTCAGGAAGGCCTGTACAATGAACTGCAGAAAGATAAG<br>ATGGCGGAGGCCTACAGTGAGATTGGGATGAAAGGCGAGCGCC<br>GGAGGGGCAAGGGGCACGATGGCCTTTACCAGGGACTCAGTAC<br>AGCCACCAAGGACACCTACGACGCCCTTCACATGCAGGCCCTG<br>CCCCCTCGCTAA (SEQ ID NO: 142) |
| CEA CAR | MDMRVPAQLLGLLL<br>LWLRGARCQVQLVQ<br>SGSELKKPGASVKV<br>SCKASGYTFTEFGM<br>NWVRQAPGQGLEWM<br>GWINTKTGEATYVE<br>EFKGRFVFSLDTSV<br>STAYLQISSLKAED<br>TAVYYCARWDFAYY<br>VEAMDYWGQGTTVT<br>VSSGGGGSGGGGSG<br>GGGSGGDIQMTQSP<br>SSLSASVGDRVTIT<br>CKASQNVGTNVAWY<br>QQKPGKAPKLLIYS<br>ASYRYSGVPSRFSG<br>SGSGTDFTLTISSL<br>QPEDFATYYCHQYY<br>TYPLFTFGQGTKLE<br>IKTTTPAPRPPTPA<br>PTIASQPLSLRPEA<br>CRPAAGGAVHTRGL<br>DFACDFWVLVVVGG<br>VLACYSLLVTVAFI<br>IFWVRSKRSRLLHS<br>DYMNMTPRRPGPTR<br>KHYQPYAPPRDFAA<br>YRSKRGRKKLLYIF<br>KQPFMRPVQTTQEE<br>DGCSCRFPEEEEGG<br>CELRVKFSRSADAP<br>AYKQGQNQLYNELN<br>LGRREEYDVLDKRR<br>GRDPEMGGKPRRKN<br>PQEGLYNELQKDKM<br>AEAYSEIGMKGERR<br>RGKGHDGLYQGLST<br>ATKDTYDALHMQAL<br>PPR (SEQ ID<br>NO: 52) | ATGGACATGAGGGTCCCCGCTCAGCTCCTGGGGCTCCTGCTAC<br>TCTGGCTCCGAGGTGCCAGATGTCAGGTGCAGCTGGTGCAATC<br>TGGGTCTGAGTTGAAGAAGCCTGGGGCCTCAGTGAAGGTTTCC<br>TGCAAGGCTTCTGGATACACCTTCACTGAGTTTGGAATGAACT<br>GGGTGCGACAGGCCCCTGGACAAGGGCTTGAGTGGATGGGATG<br>GATAAACACCAAAACTGGAGAGGCAACATATGTTGAAGAGTTT<br>AAGGGACGGTTTGTCTTCTCCTTGGACACCTCTGTCAGCACGG<br>CATATCTGCAGATCAGCAGCCTAAAGGCTGAAGACACTGCCGT<br>GTATTACTGTGCGAGATGGGACTTCGCTTATTACGTGGAGGCT<br>ATGGACTACTGGGGCCAAGGGACCACGGTGACCGTGTCATCCG<br>GCGGAGGTGGAAGCGGAGGGGGAGGATCTGGCGGCGGAGGAAG<br>CGGAGGCGATATCCAGATGACCCAGTCTCCATCCTCCCTGTCT<br>GCATCTGTGGGAGACAGAGTCACCATCACTTGCAAGGCCAGTC<br>AGAATGTGGGTACTAATGTTGCCTGGTATCAGCAGAAACCAGG<br>GAAAGCACCTAAGCTCCTGATCTATTCGGCATCCTACCGCTAC<br>AGTGGAGTCCCATCAAGGTTCAGTGGCAGTGGATCTGGGACAG<br>ATTTCACTCTCACCATCAGCAGTCTGCAACCTGAAGATTTCGC<br>AACTTACTACTGTCACCAATATTACACCTATCCTCTATTCACG<br>TTTGGCCAGGGCACCAAGCTCGAGATCAAGACAACGACGCCAG<br>CTCCCCGCCCGCCAACCCCTGCACCTACGATTGCATCACAACC<br>GCTGTCCCTGCGGCCTGAAGCTTGTCGCCCAGCCGCAGGTGGC<br>GCCGTACATACACGGGGGCTGGATTTTGCCTGTGATTTCTGGG<br>TGCTGGTCGTTGTGGGCGGCGTGCTGGCCTGCTACAGCCTGCT<br>GGTGACAGTGGCCTTCATCATCTTTTGGGTGAGGAGCAAGCGG<br>AGTCGACTGCTGCACAGCGACTACATGAACATGACCCCCCGGA<br>GGCCTGGCCCCACCCGGAAGCACTACCAGCCCTACGCCCCTCC<br>CAGGGATTTCGCCGCCTACCGGAGCAAACGGGGCAGAAAGAAA<br>CTCCTGTATATATTCAAACAACCATTTATGAGGCCAGTACAAA<br>CTACTCAAGAGGAAGATGGCTGTAGCTGCCGATTTCCAGAAGA<br>AGAAGAAGGAGGATGTGAACTGAGAGTGAAGTTCAGCAGGAGC<br>GCAGACGCCCCCGCGTACAAGCAGGGCCAGAACCAGCTCTATA<br>ACGAGCTCAATCTAGGACGAAGAGAGGAGTACGATGTTTTGGA<br>CAAGCGTAGAGGCCGGGACCCTGAGATGGGGGGAAAGCCGAGA<br>AGGAAGAACCCTCAGGAAGGCCTGTACAATGAACTGCAGAAAG<br>ATAAGATGGCGGAGGCCTACAGTGAGATTGGGATGAAAGGCGA<br>GCGCCGGAGGGGCAAGGGGCACGATGGCCTTTACCAGGGACTC<br>AGTACAGCCACCAAGGACACCTACGACGCCCTTCACATGCAGG<br>CCCTGCCCCCTCGC (SEQ ID NO: 143) |
| CEA CAR VH region | QVQLVQSGSELKKP<br>GASVKVSCKASGYT<br>FTEFGMNWVRQAPG<br>QGLEWMGWINTKTG<br>EATYVEEFKGRFVF<br>SLDTSVSTAYLQIS<br>SLKAEDTAVYYCAR<br>WDFAYYVEAMDYWG<br>QGTTVTVSS (SEQ<br>ID NO: 144) | CAGGTGCAGCTGGTGCAATCTGGGTCTGAGTTGAAGAAGCCTG<br>GGGCCTCAGTGAAGGTTTCCTGCAAGGCTTCTGGATACACCTT<br>CACTGAGTTTGGAATGAACTGGGTGCGACAGGCCCCTGGACAA<br>GGGCTTGAGTGGATGGGATGGATAAACACCAAAACTGGAGAGG<br>CAACATATGTTGAAGAGTTTAAGGGACGGTTTGTCTTCTCCTT<br>GGACACCTCTGTCAGCACGGCATATCTGCAGATCAGCAGCCTA<br>AAGGCTGAAGACACTGCCGTGTATTACTGTGCGAGATGGGACT<br>TCGCTTATTACGTGGAGGCTATGGACTACTGGGGCCAAGGGAC<br>CACGGTGACCGTGTCATCC (SEQ ID NO: 145) |
| Linker | GGGGSGGGGSGGGG<br>SGG (SEQ ID<br>NO: 146) | GGCGGAGGTGGAAGCGGAGGGGGAGGATCTGGCGGCGGAGGAA<br>GCGGAGGC (SEQ ID NO: 147) |

TABLE 24-continued

Sequences of CEA CAR and LILRB1 Inhibitory Receptor

| Name | Protein Sequence | DNA Sequence |
|---|---|---|
| CEA CAR VL region | DIQMTQSPSSLSASVGDRVTITCKASQNVGTNVAWYQQKPGKAPKLLIYSASYRYSGVPSRFSGSGSGTDFTLTISSLQPEDFATYYCHQYYTYPLFTFGQGTKLEIK (SEQ ID NO: 148) | GATATCCAGATGACCCAGTCTCCATCCTCCCTGTCTGCATCTGTGGGAGACAGAGTCACCATCACTTGCAAGGCCAGTCAGAATGTGGGTACTAATGTTGCCTGGTATCAGCAGAAACCAGGGAAAGCACCTAAGCTCCTGATCTATTCGGCATCCTACCGCTACAGTGGAGTCCCATCAAGGTTCAGTGGCAGTGGATCTGGGACAGATTTCACTCTCACCATCAGCAGTCTGCAACCTGAAGATTTCGCAACTTACTACTGTCACCAATATTACACCTATCCTCTATTCACGTTTGGCCAGGGCACCAAGCTCGAGATCAAG (SEQ ID NO: 149) |
| CDR-H1 | EFGMN (SEQ ID NO: 55) | GAGTTTGGAATGAAC (SEQ ID NO: 150) |
| CDR-H2 | WINTKTGEATYVEEFKG (SEQ ID NO: 56) | TGGATAAACACCAAAACTGGAGAGGCAACATATGTTGAAGAGTTTAAGGGA (SEQ ID NO: 151) |
| CDR-H3 | WDFAYYVEAMDY (SEQ ID NO: 57) | TGGGACTTCGCTTATTACGTGGAGGCTATGGACTAC(SEQ ID NO: 152) |
| CDR-L1 | KASQNVGTNVA (SEQ ID NO: 59) | AAGGCCAGTCAGAATGTGGGTACTAATGTTGCC (SEQ ID NO: 153) |
| CDR-L2 | SASYRYS (SEQ ID NO: 61 | TCGGCATCCTACCGCTACAGT (SEQ ID NO: 154) |
| CDR-L3 | HQYYTYPLFT (SEQ ID NO: 63 | CACCAATATTACACCTATCCTCTATTCACG (SEQ ID NO: 155) |
| CD8α hinge | TTTPAPRPPTPAPTIASQPLSLRPEACRPAAGGAVHTRGLDFACD (SEQ ID NO: 71) | ACAACGACGCCAGCTCCCCGCCCGCCAACCCCTGCACCTACGATTGCATCACAACCGCTGTCCCTGCGGCCTGAAGCTTGTCGCCCAGCCGCAGGTGGCGCCGTACATACACGGGGGCTGGATTTTGCCTGTGAT (SEQ ID NO: 156) |
| CD28 trans-mem-brane domain | FWVLVVVGGVLACYSLLVTVAFIIFWV (SEQ ID NO: 75) | TTCTGGGTGCTGGTCGTTGTGGGCGGCGTGCTGGCCTGCTACAGCCTGCTGGTGACAGTGGCCTTCATCATCTTTTGGGTG (SEQ ID NO: 157) |
| CD28-41BB-CD3ζ intracel-lular domain | RSKRSRLLHSDYMNMTPRRPGPTRKHYQPYAPPRDFAAYRSKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (SEQ ID NO: 158) | AGGAGCAAGCGGAGTCGACTGCTGCACAGCGACTACATGAACATGACCCCCCGGAGGCCTGGCCCCACCCGGAAGCACTACCAGCCCTACGCCCCTCCCAGGGATTTCGCCGCCTACCGGAGCAAACGGGGCAGAAAGAAACTCCTGTATATATTCAAACAACCATTTATGAGGCCAGTACAAACTACTCAAGAGGAAGATGGCTGTAGCTGCCGATTTCCAGAAGAAGAAGAAGGAGGATGTGAACTGAGAGTGAAGTTCAGCAGGAGCGCAGACGCCCCCGCGTACAAGCAGGGCCAGAACCAGCTCTATAACGAGCTCAATCTAGGACGAAGAGAGGAGTACGATGTTTTGGACAAGCGTAGAGGCCGGGACCCTGAGATGGGGGGAAAGCCGAGAAGGAAGAACCCTCAGGAAGGCCTGTACAATGAACTGCAGAAAGATAAGATGGCGGAGGCCTACAGTGAGATTGGGATGAAAGGCGAGCGCCGGAGGGGCAAGGGGCACGATGGCCTTTACCAGGGACTCAGTACAGCCACCAAGGACACCTACGACGCCCTTCACATGCAGGCCCTGCCCCCTCGC (SEQ ID NO: 159) |
| CD28 co-stimula-tory domain | RSKRSRLLHSDYMNMTPRRPGPTRKHYQPYAPPRDFAAYRS (SEQ ID NO: 83) | AGGAGCAAGCGGAGTCGACTGCTGCACAGCGACTACATGAACATGACCCCCCGGAGGCCTGGCCCCACCCGGAAGCACTACCAGCCCTACGCCCCTCCCAGGGATTTCGCCGCCTACCGGAGC (SEQ ID NO: 160) |
| 4-1BB | KRGRKKLLYIFKQPFMRPVQTTQEEDGCSCRFPEEEEGGCEL (SEQ ID NO: 161) | AAACGGGGCAGAAAGAAACTCCTGTATATATTCAAACAACCATTTATGAGGCCAGTACAAACTACTCAAGAGGAAGATGGCTGTAGCTGCCGATTTCCAGAAGAAGAAGAAGGAGGATGTGAACTG (SEQ ID NO: 162) |

TABLE 24-continued

Sequences of CEA CAR and LILRB1 Inhibitory Receptor

| Name | Protein Sequence | DNA Sequence |
|---|---|---|
| CD3ζ | RVKFSRSADAPAYK QGQNQLYNELNLGR REEYDVLDKRRGRD PEMGGKPRRKNPQE GLYNELQKDKMAEA YSEIGMKGERRRGK GHDGLYQGLSTATK DTYDALHMQALPPR (SEQ ID NO: 79) | AGAGTGAAGTTCAGCAGGAGCGCAGACGCCCCCGCGTACAAGC AGGGCCAGAACCAGCTCTATAACGAGCTCAATCTAGGACGAAG AGAGGAGTACGATGTTTTGGACAAGCGTAGAGGCCGGGACCCT GAGATGGGGGGAAAGCCGAGAAGGAAGAACCCTCAGGAAGGCC TGTACAATGAACTGCAGAAAGATAAGATGGCGGAGGCCTACAG TGAGATTGGGATGAAAGGCGAGCGCCGGAGGGGCAAGGGGCAC GATGGCCTTTACCAGGGACTCAGTACAGCCACCAAGGACACCT ACGACGCCCTTCACATGCAGGCCCTGCCCCCTCGC (SEQ ID NO: 163) |
| Inhibitory Receptor | | |
| anti-HLA-A*02 scFv-LILRB1 hinge, TM and ICD | MDMRVPAQLLGLLL LWLRGARCDVLMTQ TPLSLPVSLGDQAS ISCRSSQSIVHSNG NTYLEWYLQKPGQS PKLLIYKVSNRFSG VPDRFSGSGSGTDF TLKISRVEAEDLGV YYCFQGSHVPRTSG GGTKLEIKGGGGSG GGGSGGGGSGGQVQ LQQSGPELVKPGAS VRISCKASGYTFTS YHIHWVKQRPGQGL EWIGWIYPGNVNTE YNEKFKGKATLTAD KSSSTAYMHLSSLT SEDSAVYFCAREEI TYAMDYWGQGTSVT VSSYGSQSSKPYLL THPSDPLELVVSGP SGGPSSPTTGPTST SGPEDQPLTPTGSD PQSGLGRHLGVVIG ILVAVILLLLLLLL LFLILRHRRQGKHW TSTQRKADFQHPAG AVGPEPTDRGLQWR SSPAADAQEENLYA AVKHTQPEDGVEMD TRSPHDEDPQAVTY AEVKHSRPRREMAS PPSPLSGEFLDTKD RQAEEDRQMDTEAA ASEAPQDVTYAQLH SLTLRREATEPPPS QEGPSPAVPSIYAT LATH (SEQ ID NO: 164) | ATGGATATGAGAGTGCCTGCCCAGCTGCTCGGACTGCTCCTTC TGTGGTTGAGAGGAGCTCGGTGCGATGTTCTGATGACCCAAAC TCCACTCTCCCTGCCTGTCAGTCTTGGAGATCAAGCCTCCATC TCTTGCAGATCTAGTCAGAGCATTGTACATAGTAATGGAAACA CCTATTTAGAATGGTACCTGCAGAAGCCAGGCCAGTCTCCAAA GCTGCTCATCTACAAAGTTTCCAACCGATTTTCTGGGGTCCCA GACAGATTTAGCGGATCTGGCTCTGGGACCGATTTCACACTCA AGATCAGTAGAGTGGAGGCTGAGGATCTGGGAGTTTATTACTG CTTTCAAGGTTCACATGTTCCTCGGACGTCCGGTGGAGGCACA AAGCTGGAAATCAAGGGAGGTGGCGGCTCTGGAGGCGGAGGTA GCGGAGGTGGAGGCTCTGGTGGCCAGGTCCAGCTGCAGCAGTC TGGACCTGAGCTGGTGAAGCCAGGGGCTTCAGTGAGGATATCC TGTAAGGCCTCTGGCTACACCTTTACAAGTTACCATATACATT GGGTGAAGCAGAGGCCTGGACAGGGACTCGAATGGATTGGATG GATTTATCCTGGAAATGTTAATACTGAGTACAATGAGAAGTTC AAGGGCAAGGCCACACTGACTGCAGACAAATCGTCCAGCACAG CCTACATGCACCTCAGCAGCCTGACCTCTGAGGACTCTGCGGT CTATTTCTGTGCCAGAGAGGAGATTACCTATGCTATGGATTAT TGGGGTCAAGGAACCTCAGTCACCGTGTCCTCATACGGCTCAC AGAGCTCCAAACCCTACCTGCTGACTCACCCTAGTGATCCTCT GGAGCTCGTGGTCTCAGGACCGTCTGGAGGCCCAAGCTCTCCG ACAACAGGCCCCACCTCCACATCTGGCCCTGAGGACCAGCCCC TCACACCCACCGGGTCGGATCCTCAGAGTGGTCTGGGAAGACA CCTGGGAGTTGTGATCGGCATCTTGGTGGCCGTCATCCTACTG CTCCTCCTCCTGCTCCTGCTCTTCCTCATCCTCCGACATCGAC GTCAGGGCAAACACTGGACATCGACCCAGAGAAAGGCTGATTT CCAACATCCTGCAGGGGCTGTGGGGCCAGAGCCCACAGACAGA GGCCTGCAGTGGAGGTCCAGCCCAGCTGCCGATGCCCAGGAAG AAAACCTCTATGCTGCCGTGAAGCACACACAGCCTGAGGATGG GGTGGAGATGGATACTCGGAGCCCACACGATGAAGATCCACAG GCAGTGACGTATGCCGAGGTGAAACACTCCAGACCTAGAAGGG AAATGGCCTCTCCTCCTTCCCCACTGTCTGGAGAGTTCCTGGA CACAAAGGACAGACAGGCGGAAGAGGACAGGCAGATGGACACT GAGGCTGCTGCATCTGAAGCTCCTCAGGATGTGACCTACGCCC AGCTGCACAGCTTGACCCTCAGACGGGAGGCAACTGAGCCTCC TCCATCCCAGGAAGGGCCCTCTCCAGCTGTGCCCAGCATCTAC GCCACTCTGGCCATCCAC (SEQ ID NO: 165) |
| VL | DVLMTQTPLSLPVS LGDQASISCRSSQS IVHSNGNTYLEWYL QKPGQSPKLLIYKV SNRFSGVPDRFSGS GSGTDFTLKISRVE AEDLGVYYCFQGSH VPRTSGGGTKLEIK (SEQ ID NO: 166) | GATGTTCTGATGACCCAAACTCCACTCTCCCTGCCTGTCAGTC TTGGAGATCAAGCCTCCATCTCTTGCAGATCTAGTCAGAGCAT TGTACATAGTAATGGAAACACCTATTTAGAATGGTACCTGCAG AAGCCAGGCCAGTCTCCAAAGCTGCTCATCTACAAAGTTTCCA ACCGATTTTCTGGGGTCCCAGACAGATTTAGCGGATCTGGCTC TGGGACCGATTTCACACTCAAGATCAGTAGAGTGGAGGCTGAG GATCTGGGAGTTTATTACTGCTTTCAAGGTTCACATGTTCCTC GGACGTCCGGTGGAGGCACAAAGCTGGAAATCAAG (SEQ ID NO: 167) |
| linker | GGGGSGGGGSGGGG SGG (SEQ ID NO: 146) | GGAGGTGGCGGCTCTGGAGGCGGAGGTAGCGGAGGTGGAGGCT CTGGTGGC (SEQ ID NO: 980) |
| VH | QVQLQQSGPELVKP GASVRISCKASGYT FTSYHIHWVKQRPG QGLEWIGWIYPGNV NTEYNEKFKGKATL | CAGGTCCAGCTGCAGCAGTCTGGACCTGAGCTGGTGAAGCCAG GGGCTTCAGTGAGGATATCCTGTAAGGCCTCTGGCTACACCTT TACAAGTTACCATATACATTGGGTGAAGCAGAGGCCTGGACAG GGACTCGAATGGATTGGATGGATTTATCCTGGAAATGTTAATA CTGAGTACAATGAGAAGTTCAAGGGCAAGGCCACACTGACTGC |

TABLE 24-continued

Sequences of CEA CAR and LILRB1 Inhibitory Receptor

| Name | Protein Sequence | DNA Sequence |
|---|---|---|
| | TADKSSSTAYMHLS SLTSEDSAVYFCAR EEITYAMDYWGQGT SVTVSS (SEQ ID NO: 981) | AGACAAATCGTCCAGCACAGCCTACATGCACCTCAGCAGCCTG ACCTCTGAGGACTCTGCGGTCTATTTCTGTGCCAGAGAGGAGA TTACCTATGCTATGGATTATTGGGGTCAAGGAACCTCAGTCAC CGTGTCCTCA (SEQ ID NO: 982) |
| CDR-L1 | RSSQSIVHSNGNTY LE (SEQ ID NO: 103) | AGATCTAGTCAGAGCATTGTACATAGTAATGGAAACACCTATT TAGAA (SEQ ID NO: 169) |
| CDR-L2 | KVSNRFSGVPDR (SEQ ID NO: 104) | AAAGTTTCCAACCGATTTTCTGGGGTCCCAGACAGA (SEQ ID NO: 170) |
| CDR-L3 | FQGSHVPRT (SEQ ID NO: 105) | TTTCAAGGTTCACATGTTCCTCGGACG (SEQ ID NO: 171) |
| CDR-H1 | ASGYTFTSYHIH (SEQ ID NO: 106) | GCCTCTGGCTACACCTTTACAAGTTACCATATACAT (SEQ ID NO: 172) |
| CDR-H2 | WIYPGNVNTEYNEK FKGK (SEQ ID NO: 107) | TGGATTTATCCTGGAAATGTTAATACTGAGTACAATGAGAAGT TCAAGGGCAAG (SEQ ID NO: 173) |
| CDR-H3 | EEITYAMDY (SEQ ID NO: 108) | GAGGAGATTACCTATGCTATGGATTAT (SEQ ID NO: 174) |
| LILR1B hinge, TM and ICD | YGSQSSKPYLLTHP SDPLELVVSGPSGG PSSPTTGPTSTSGP EDQPLTPTGSDPQS GLGRHLGVVIGILV AVILLLLLLLLLFL ILRHRRQGKHWTST QRKADFQHPAGAVG PEPTDRGLQWRSSP AADAQEENLYAAVK HTQPEDGVEMDTRS PHDEDPQAVTYAEV KHSRPRREMASPPS PLSGEFLDTKDRQA EEDRQMDTEAAASE APQDVTYAQLHSLT LRREATEPPPSQEG PSPAVPSIYATLAI H (SEQ ID NO: 132) | TACGGCTCACAGAGCTCCAAACCCTACCTGCTGACTCACCCTA GTGATCCTCTGGAGCTCGTGGTCTCAGGACCGTCTGGAGGCCC AAGCTCTCCGACAACAGGCCCCACCTCCACATCTGGCCCTGAG GACCAGCCCCTCACACCCACCGGGTCGGATCCTCAGAGTGGTC TGGGAAGACACCTGGGAGTTGTGATCGGCATCTTGGTGGCCGT CATCCTACTGCTCCTCCTCCTGCTCCTGCTCTTCCTCATCCTC CGACATCGACGTCAGGGCAAACACTGGACATCGACCCAGAGAA AGGCTGATTTCCAACATCCTGCAGGGGCTGTGGGGCCAGAGCC CACAGACAGAGGCCTGCAGTGGAGGTCCAGCCCAGCTGCCGAT GCCCAGGAAGAAAACCTCTATGCTGCCGTGAAGCACACACAGC CTGAGGATGGGGTGGAGATGGATACTCGGAGCCCACACGATGA AGATCCACAGGCAGTGACGTATGCCGAGGTGAAACACTCCAGA CCTAGAAGGGAAATGGCCTCTCCTCCTTCCCCACTGTCTGGAG AGTTCCTGGACACAAAGGACAGACAGGCGGAAGAGGACAGGCA GATGGACACTGAGGCTGCTGCATCTGAAGCTCCTCAGGATGTG ACCTACGCCCAGCTGCACAGCTTGACCCTCAGACGGGAGGCAA CTGAGCCTCCTCCATCCCAGGAAGGGCCCTCTCCAGCTGTGCC CAGCATCTACGCCACTCTGGCCATCCAC (SEQ ID NO: 175) |
| LILRB1 hinge | YGSQSSKPYLLTHP SDPLELVVSGPSGG PSSPTTGPTSTSGP EDQPLTPTGSDPQS GLGRHLG (SEQ ID NO: 134) | TACGGCTCACAGAGCTCCAAACCCTACCTGCTGACTCACCCTA GTGATCCTCTGGAGCTCGTGGTCTCAGGACCGTCTGGAGGCCC AAGCTCTCCGACAACAGGCCCCACCTCCACATCTGGCCCTGAG GACCAGCCCCTCACACCCACCGGGTCGGATCCTCAGAGTGGTC TGGGAAGACACCTGGGA (SEQ ID NO: 176) |
| LILRB1 TM | VVIGILVAVILLLL LLLLLFLIL (SEQ ID NO: 135) | GTTGTGATCGGCATCTTGGTGGCCGTCATCCTACTGCTCCTCC TCCTGCTCCTGCTCTTCCTCATCCTC (SEQ ID NO: 177) |
| LILRB1 ICD | RHRRQGKHWTSTQR KADFQHPAGAVGPE PTDRGLQWRSSPAA DAQEENLYAAVKHT QPEDGVEMDTRSPH DEDPQAVTYAEVKH SRPRREMASPPSPL SGEFLDTKDRQAEE DRQMDTEAAASEAP QDVTYAQLHSLTLR REATEPPPSQEGPS PAVPSIYATLAIH (SEQ ID NO: 131) | CGACATCGACGTCAGGGCAAACACTGGACATCGACCCAGAGAA AGGCTGATTTCCAACATCCTGCAGGGGCTGTGGGGCCAGAGCC CACAGACAGAGGCCTGCAGTGGAGGTCCAGCCCAGCTGCCGAT GCCCAGGAAGAAAACCTCTATGCTGCCGTGAAGCACACACAGC CTGAGGATGGGGTGGAGATGGATACTCGGAGCCCACACGATGA AGATCCACAGGCAGTGACGTATGCCGAGGTGAAACACTCCAGA CCTAGAAGGGAAATGGCCTCTCCTCCTTCCCCACTGTCTGGAG AGTTCCTGGACACAAAGGACAGACAGGCGGAAGAGGACAGGCA GATGGACACTGAGGCTGCTGCATCTGAAGCTCCTCAGGATGTG ACCTACGCCCAGCTGCACAGCTTGACCCTCAGACGGGAGGCAA CTGAGCCTCCTCCATCCCAGGAAGGGCCCTCTCCAGCTGTGCC CAGCATCTACGCCACTCTGGCCATCCAC (SEQ ID NO: 178) |

TABLE 24-continued

| Sequences of CEA CAR and LILRB1 Inhibitory Receptor | | |
|---|---|---|
| Name | Protein Sequence | DNA Sequence |
| | | shRNA |
| B2M shRNA | Not Relevant | GCACTCAAAGCTTGTTAAGATCGAAATCTTAACAAGCTTTGAG TGC (SEQ ID NO: 179) |

Example 7: Sensitivity and Selectivity of a CEA CAR and LILRB1 Inhibitory Receptor Pair The $EC_{50}$ of the CEA activator and IC50 of the HLA-A*02 LILRB1 blocker receptor were quantified. These values can be compared with target antigen expression values of human tumor and normal tissues.

Figure 18:
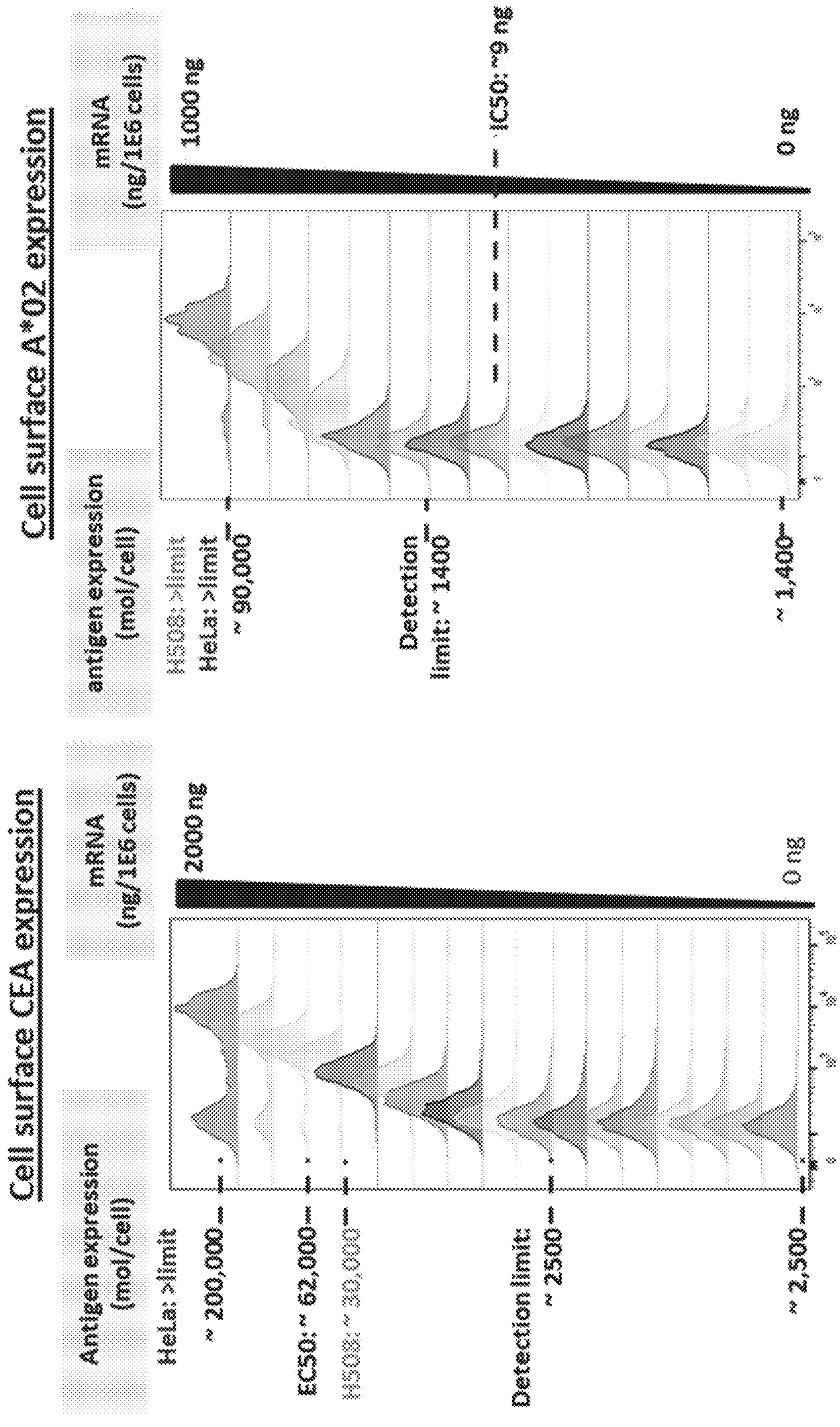
FIG. 18 shows the cell-surface expression of CEA and HLA-A*02 by mRNA titration in HeLa cells. A*02: HLA-A*02.
Figure 19:
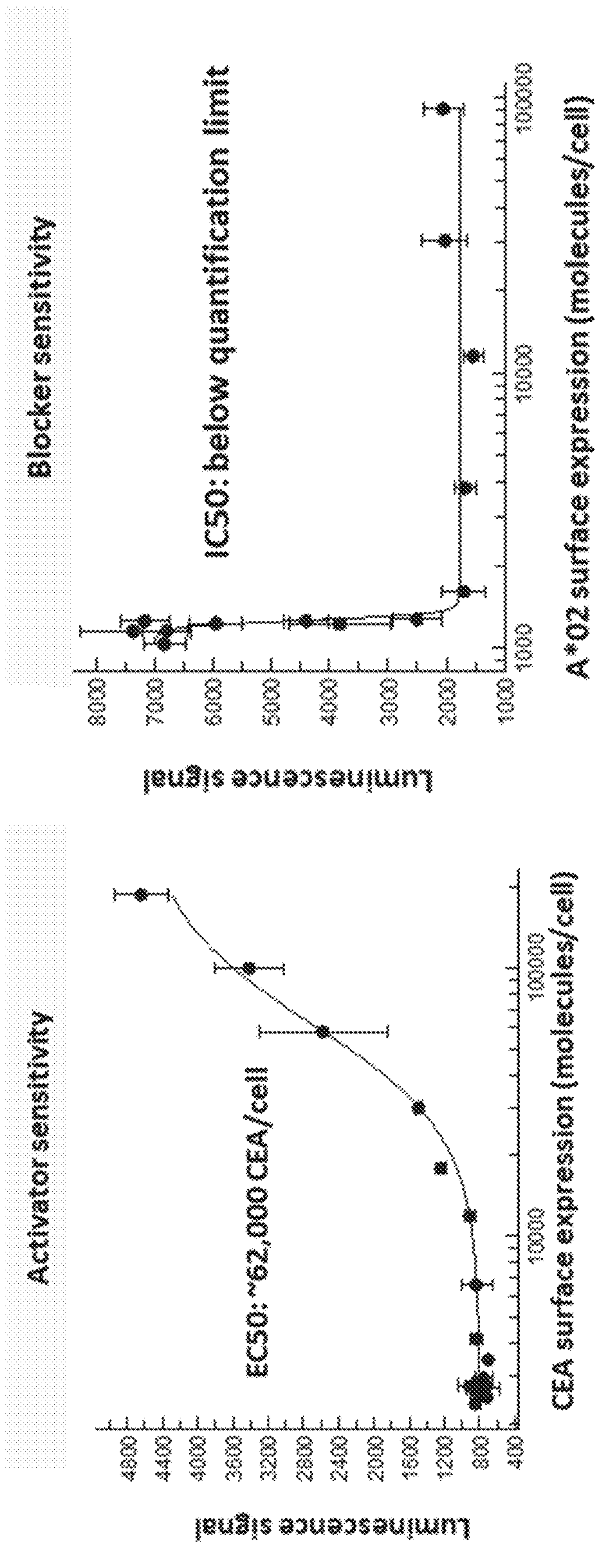
FIG. 19 shows CEA CAR activator and HLA-A*02 LILRB1 blocker sensitivity measured as a function of the number of CEA surface molecules in HeLa cells using Jurkat effector cells with stably expressed CEA activator and HLA-A*02 blocker receptors.
Figure 20:
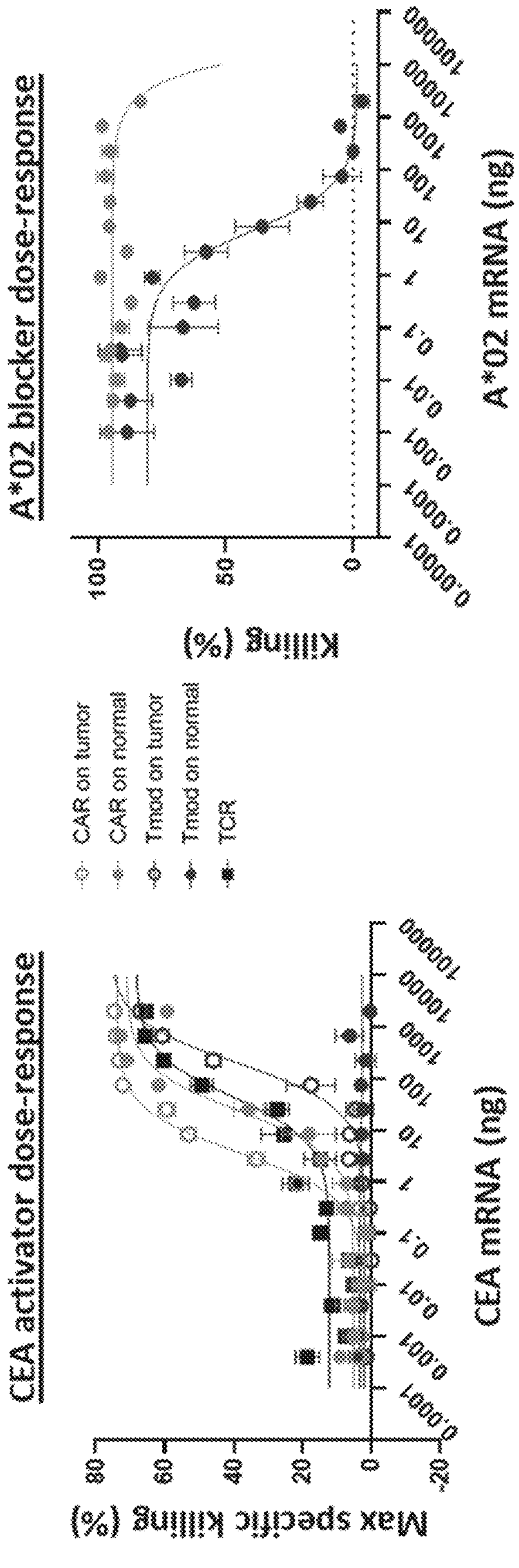
FIG. 20 shows sensitivity of activator and blocker of primary T cells expressing CEA CAR Tmod (both the CEA CAR and HLA-A*02 and LILRB1 inhibitory receptors), CAR-only, and CEA TCR. The dose response curve for the activator (right) is shown for the CEA CAR, CEA CAR with the HLA-A*02 blocker (Tmod), and the CEA TCR, while the dose response curve for the inhibitory receptor (blocker) is only for the CEA CAR and the CEA CAR with the HLA-A*02 blocker (Tmod). A*02: HLA-A*02.

Synthetic mRNA was to control surface levels of CEA and HLA-A*02 antigens on HeLa target cells and variants, coupled with functional measurements in Jurkat cells (FIGS. 18-19). A similar experiments using primary T cell cytotoxicity assays was conducted, and included an HLA-A*02-restricted CEA TCR for comparison (FIG. 20). The CEA TCR is described in CEA TCR is described in Parkhurst et al. (2009). Clin Cancer Res 15, 169-180. This TCR was shown by Rosenberg and colleagues to be active in the clinic, but terminated because of colitis (Parkhurst et al., 2011, Mol Ther 19, 620-626).

Figure 22:
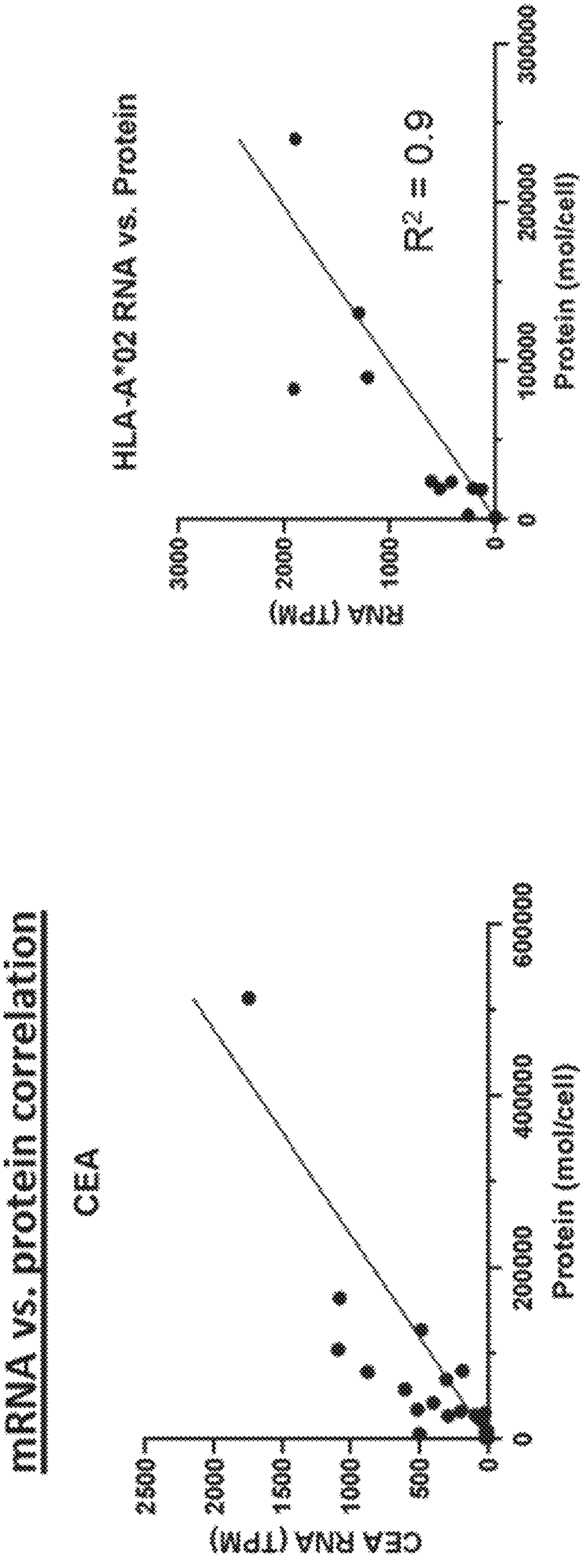
FIG. 22 shows standard curves used to convert molecules/cell to TPM values. Data in the CEA standard curve (left) show CEA cell surface expression from Bacac et al. 2016, Clin Cancer Res 22, 3286-3297 plotted against mRNA (TPM) from the GTEx database. TPM: transcripts per million.

In FIG. 20, the HLA-A*02(+) donor T cells with both receptors were co-cultured with HeLa target cells. For EC50 estimation, different amounts of CEA mRNA were transfected into CEA(−) HLA-A*02(−) or CEA(−) HLA-A*02 (+) HeLa cells before co-culture. To create matched surrogate “normal” cells, 1 μg A*02 mRNA were co-transfected. Maximum killing (Kmax; normalized to total target cell number) was plotted against CEA mRNA amount. The EC50s calculated as mRNA amount and molecules/cell are listed in Table 25. The TCR EC50 is given in CEA surface antigens/cell, but the actual target is a CEA pMHC. For IC50, different amounts of HLA-A*02 mRNA were co-transfected with 125 ng CEA mRNA into cells before co-culture. Killing was monitored for 48 hours. The decrease in killing, normalized to Kmax, was plotted against A*02 mRNA amount. The IC50 of HLA-A*02 blocking CEA Tmod is ~6.8 ng of mRNA and ~100K molecules/cell using standard curves in FIG. 22. Standard curves were used to relate mRNA levels (see FIG. 18) to surface protein molecules, and the results are shown in FIG. 19. These experiments demonstrated that EC50 and IC50 measured in Jurkat cell assays were comparable to the equivalent sensitivity parameters derived from T cell cytotoxicity assays.

Figure 21:
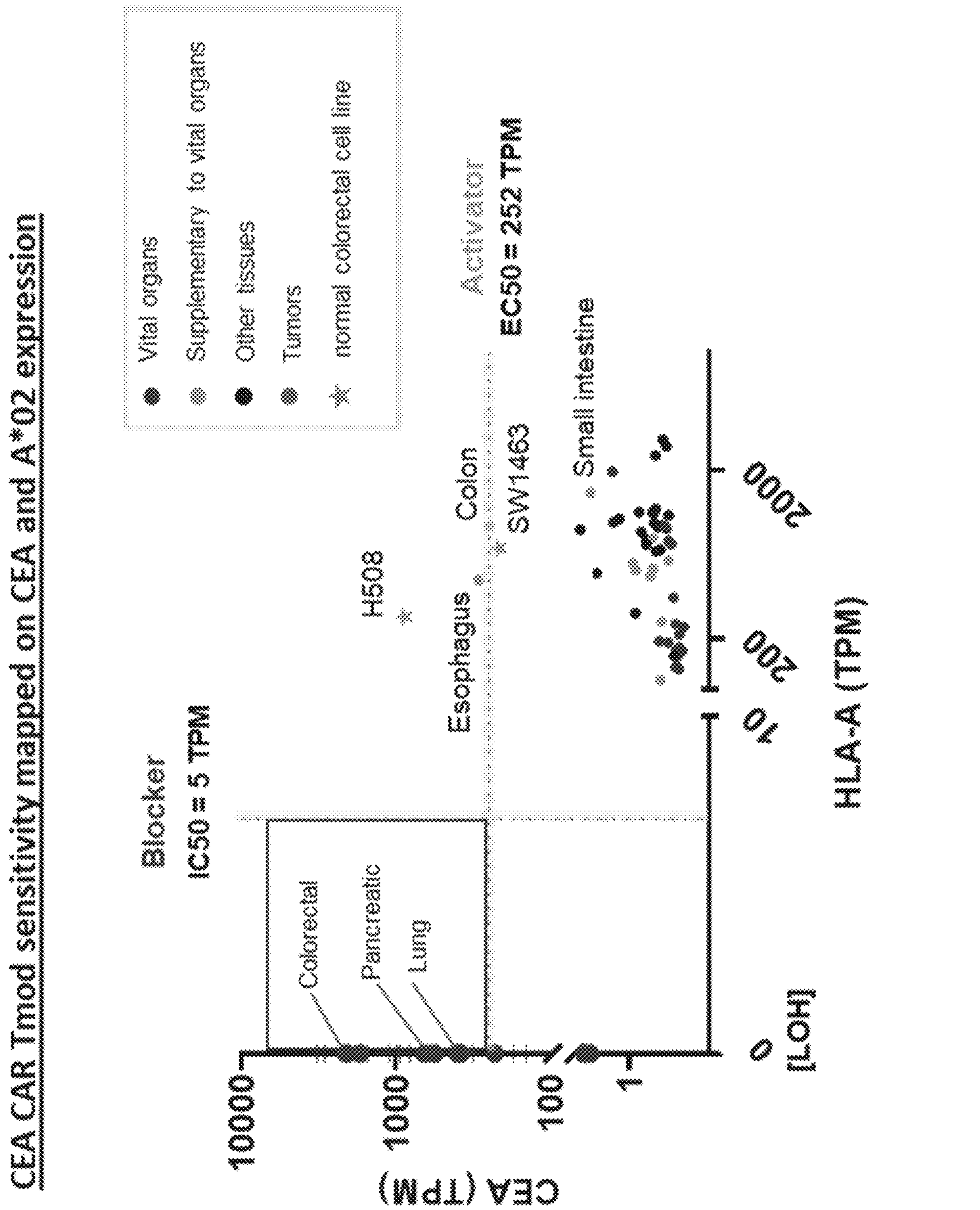
FIG. 21 shows that the combination of CEA CAR and HLA-A*02 inhibitory receptor is predicted to kill tumors while protecting normal tissues. TPM: transcripts per million; A*02: HLA-A*02; LOH: loss of heterozygosity.

FIG. 21 shows the CEA CAR and HLA-A*02 inhibitory receptor EC50 and IC50 on a graph with the tumor and normal expression values for the CEA and A*02 antigens. In FIG. 21, data in CEA standard curve replotted from Bacac, M. et al. (2016) Clin Cancer Res 22, 3286-3297. EC50 and IC50 values were determined. Tumor types had HLA-A expression set at 0 TPM to account for selection of HLA-A*02(−) tumors by LOH. Tumor data was from the TCGA database and normal tissue data was from GTEx database.

Most normal tissues express CEA well below the EC50 of the two-receptor combination. The exceptions are colon and esophagus, which fall in the quadrant above the CEA EC50 in FIG. 21. However, all normal tissues, including colon and esophagus, have expression levels of HL-A*02 well above the blocker receptor IC50 and are thought to be safe from CEA-directed killing by immune cells expressing the receptor combination. Many solid tumors, notably colorectal, pancreatic, and lung, express CEA levels above the EC50. These malignant tissues are expected to activate CEA CAR in immune cells expressing the two receptors in the absence of HLA-A*02 expression (i.e., when selected for LOH).

Figure 23:
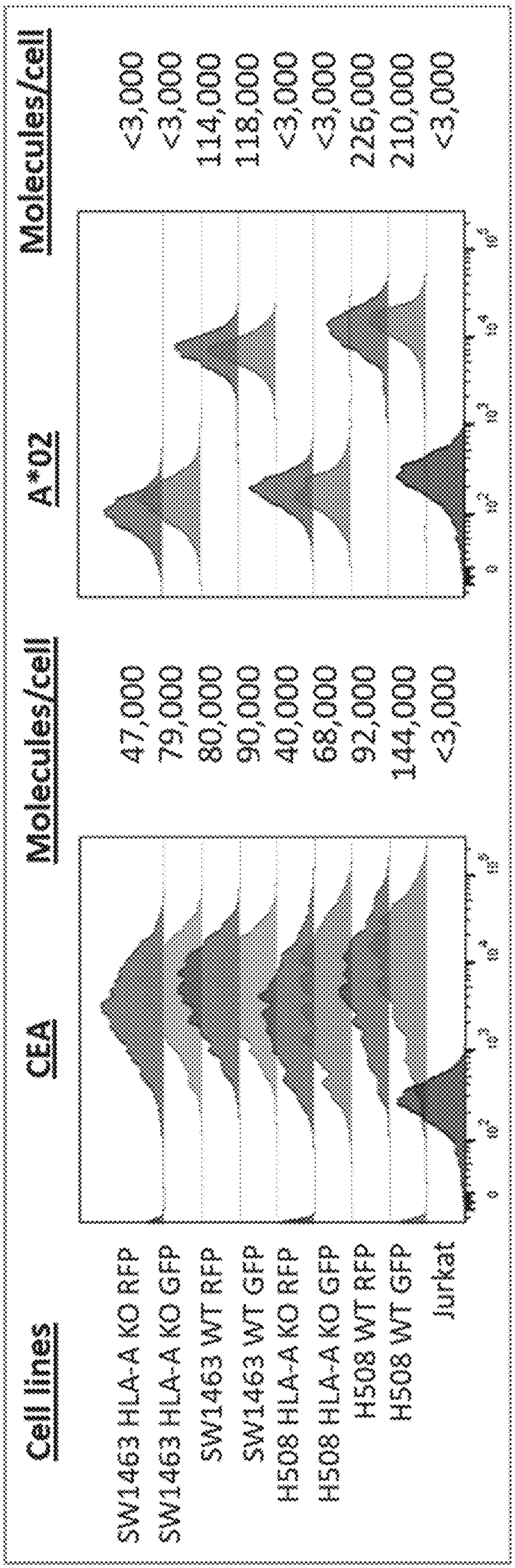
FIG. 23 shows surface expression of CEA and HLA-A*02 on H508 and SW1463 cell lines. WT: wild type; KO: indicated gene is knocked out.

A variety of colon cancer cell lines were characterized to identify lines representative of native levels of antigen expression in normal colon. Colon cancer lines H508 and SW1463 were selected (Table 26). Both are heterozygous for HLA-A*02 and express CEA. Comparison of RNA-Seq datasets showed that these lines express CEA and HLA-A at levels that reflect expression of these genes in normal colon. To create target cell lines to use as target-related controls, gene knockout versions of H508 and SW1463 that lacked either HLA-A*02 or CEA expression were generated (FIG. 23). As shown in FIG. 23, the H508 and SW1463 lines prior to genetic manipulation have antigen numbers and HLA-A*02:CEA expression ratios similar to normal colon tissue. To make variants for testing, stable pools of HLA-A*02-deficient cells were derived from CRISPR knockout and analyzed here by flow cytometry after staining with CEA or HLA-A*02 mAbs. All cell lines were from fresh thaws of early passage vials.

Figure 24:
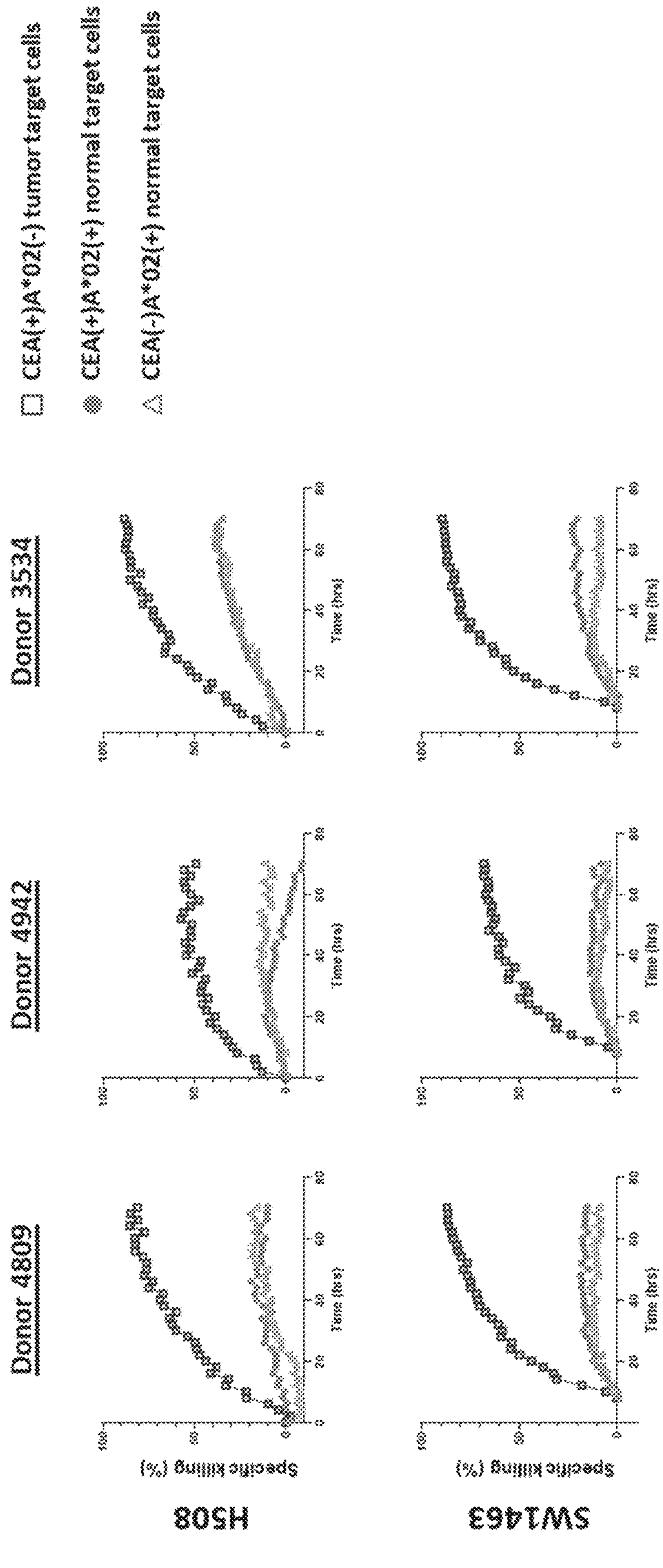
FIG. 24 shows cytotoxicity data of CEA Tmod expressing cells (cells expressing both the CEA CAR and HLA-A*02 scFv inhibitory receptor) derived from three HLA-A*02(−) donors, which were assayed with colorectal cell lines as targets. A*02: HLA-A*02.

The selective response of CEA CAR Tmod cells (cells expressing the dual CEA CAR and HLA-A*02 scFv LILRB1 inhibitory receptor system) to H508 and SW1463 colorectal cancer lines with endogenous antigen expression was confirmed in primary T cell cytotoxicity assays (FIG. 24). In FIG. 24, raw data were plotted without background subtraction. A time course using background (CEA(−) HLA-A*02(+) cells, in triangles) was also carried out. Tumor and normal target cells were H508 and SW1463 with or without genetic modifications, as shown in the key at right. Two separate vectors (one for the activator receptor and one for the blocker receptor) were used to transduce donor T cells, without an shRNA to knock down B2M. All donors were HLA-A*02(−).

FIG. 24 shows an example of how the Tmod dual receptor system enables the selective killing of H508 target cells. In FIG. 24, three NCI-H508-RFP target cell lines were used: CEA+HLA-A*02(+) (normal, filled circles), CEA-HLA-A*02(+) (normal, triangles) and CEA+HLA-A*02(−) (tumor, squares). Cytotoxic assay was performed at a 3:1 effector-to-target ratio. Specific killing was determined based on the total pixel area of RFP or GFP signal present in the transduced T-cell co-culture and expressed as percent relative to the untransduced T-cell co-culture control.

Figure 25:
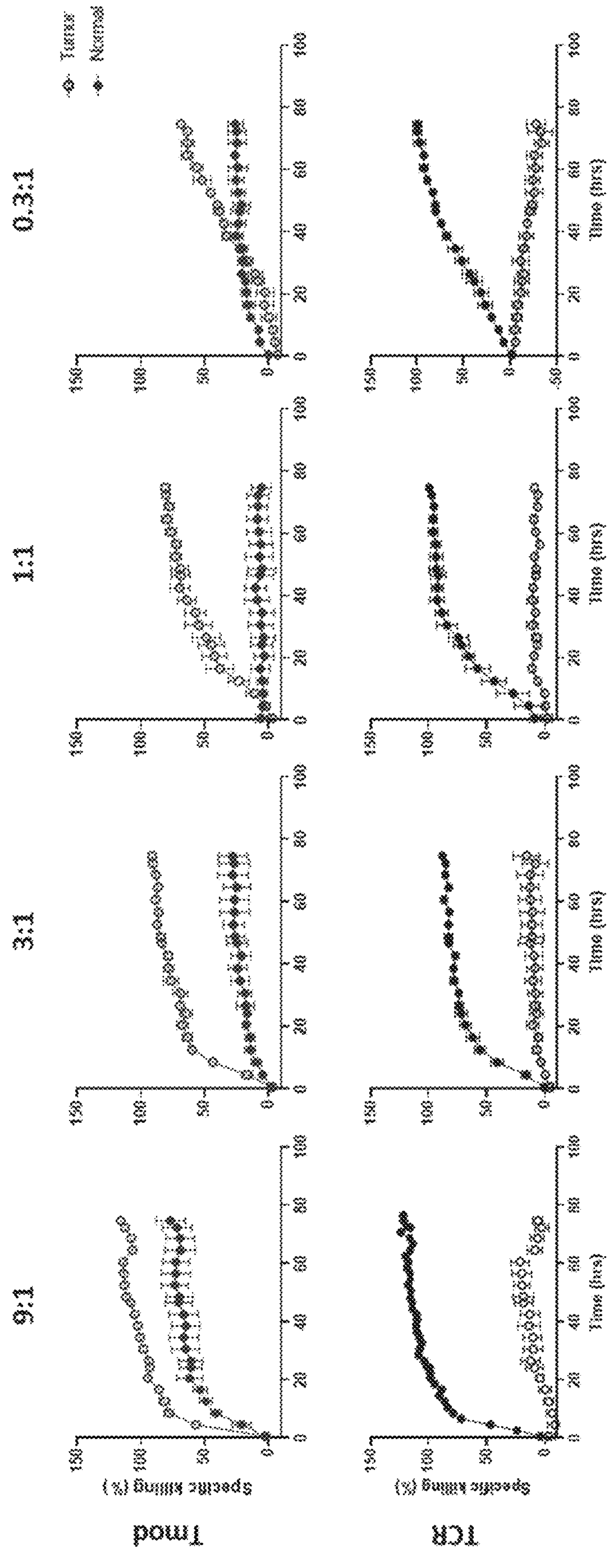
FIG. 25 shows a time course of CEA CAR Tmod and TCR T killing of tumor and normal cells at different E:T ratios using HLA-A*02(+) donor T cells transduced with the CEA TCR or the Tmod dual receptor system.
Figure 32:
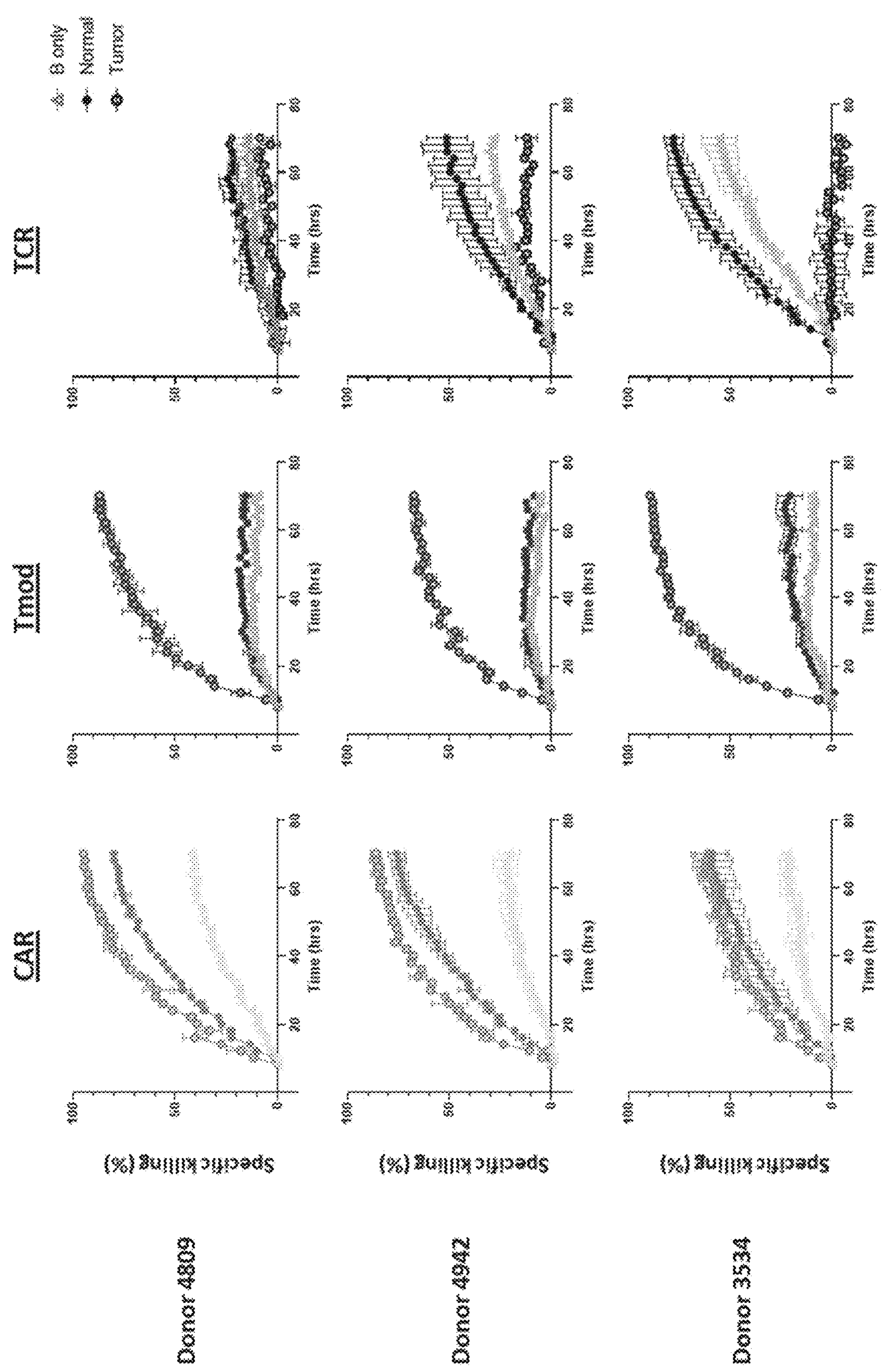
FIG. 32 shows cytotoxicity assays with effector T cells expressing the CEA CAR Tmod dual receptors and CEA(+) target cell lines. E:T was 3:1 for target cell co-cultures, H508 target cells were used. B only refers to CEA(−) HLA-A*02 (+) target cells.
Figure 33:
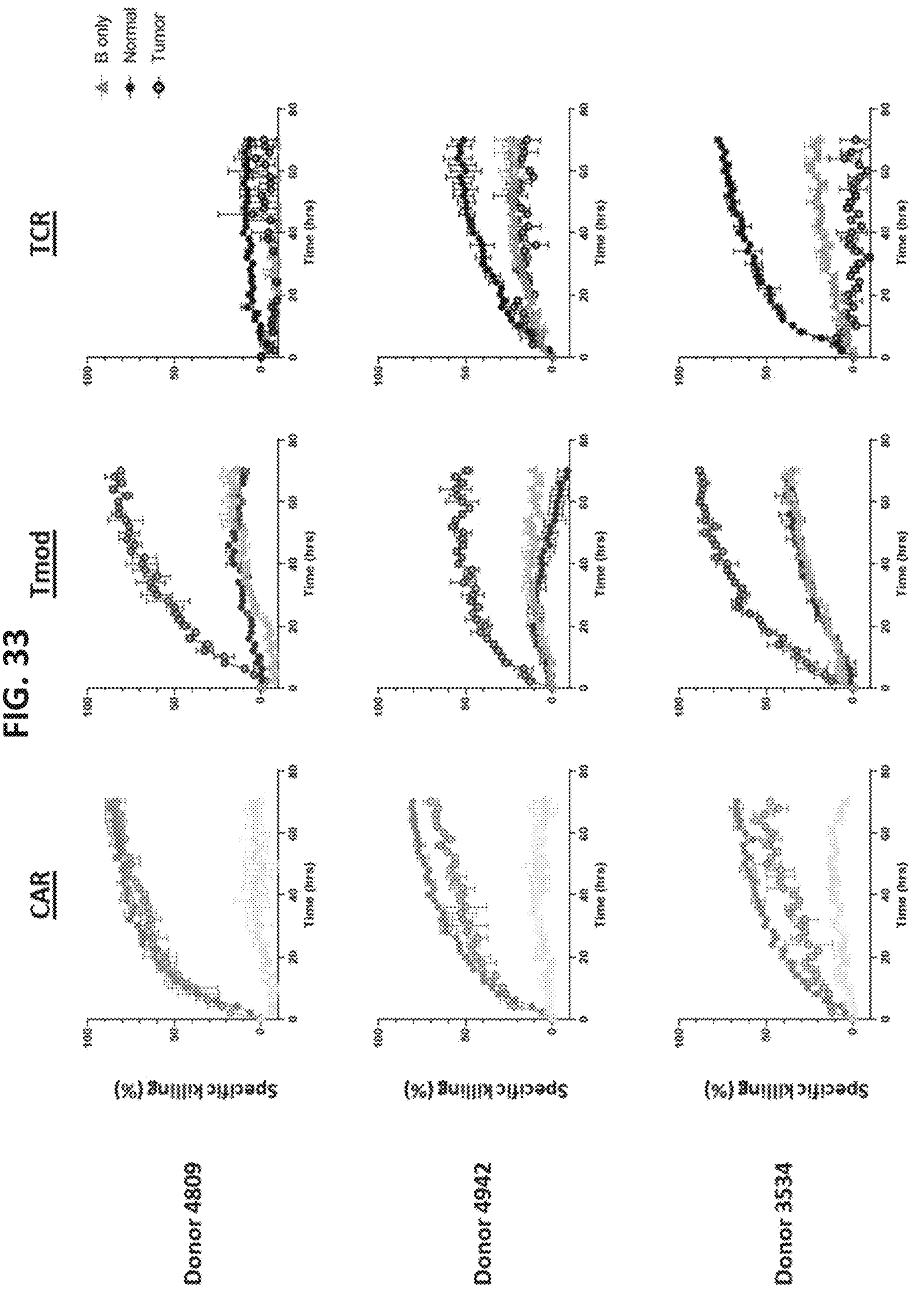
FIG. 33 shows cytotoxicity assays with effector T cells expressing the CEA CAR Tmod dual receptors and CEA(+) target cell lines. E:T was 3:1 for target cell co-cultures, SW1463 target cells were used. B only, CEA(−) HLA-A*02 (+) target cells.
Figure 34:
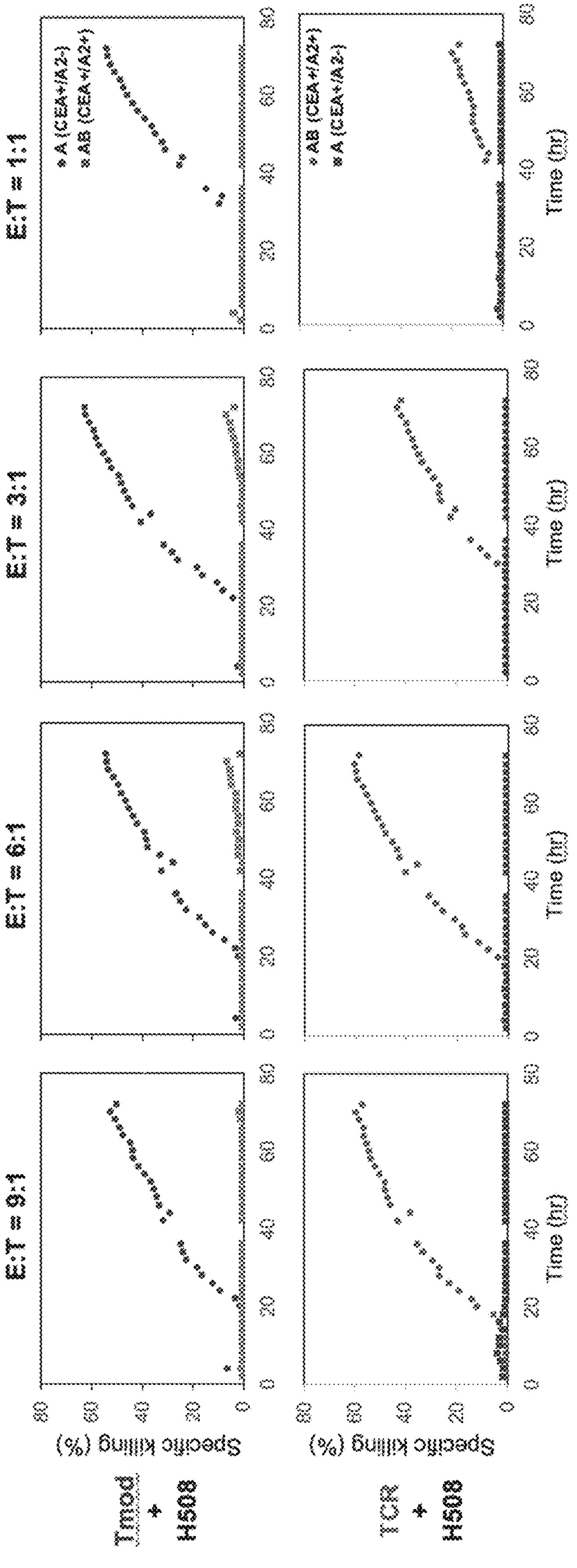
FIG. 34 shows that effector T cells expressing the CEA Tmod dual receptors (cells were transduced using separate activator and blocker lentiviral vectors) enables selective killing of tumor vs. normal cells in the colorectal cancer cell line H508. T cells expressing the Tmod receptors were as sensitive, but more selective, for normal cells than the benchmark CEA TCR. T cells were derived from an HLA-A*02(−) donor (D4809).

Both the CEA CAR Tmod expressing cells and the benchmark TCR demonstrated comparable target-selective cytotoxicity at low E:T ratios (FIG. 25). In FIG. 25, background killing of CEA(−) HLA-A*02(+) target cells was subtracted from specific killing. In the absence of a functional HLA-A*02 gene, the TCR was inactive even at E:T=9:1. At this ratio, the CEA CAR Tmod expressing cells demonstrated reduced selectivity for HLA-A*02(−) target cells. This difference between the Tmod expressing and TCR expressing cells may be partly related to the donor haplotype, as it was not seen in HLA-A*02(−) donors (FIGS. 32-34) and/or the extreme difference in absolute antigen levels of their respective targets: a pMHC for the TCR and CEA surface antigen for the CEA CAR construct.

Figure 26:
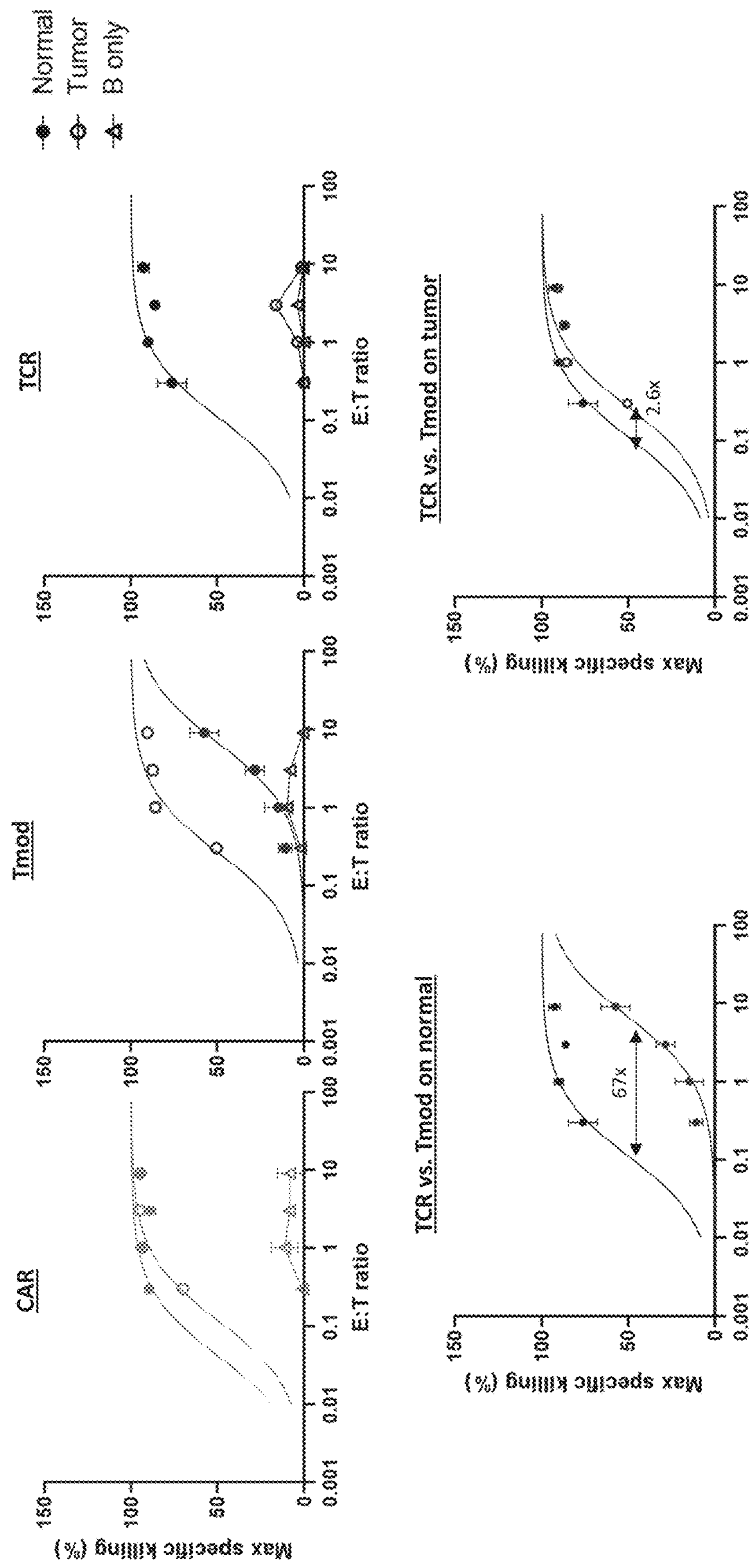
FIG. 26 shows that effector cells expressing the CEA CAR Tmod dual receptor system kill tumor cells similarly to cells expressing the CEA TCR, but are ~70× less active in killing CEA(+) HLA-A*02(+) normal H508 target cells. tumor: CEA(+) HLA-A*02(−) target cells; B only: target cells express HLA-A*02 only; normal: CEA(+) HLA-A*02 (+) target cells.

Unlike the TCR expressing cells, CEA CAR Tmod expressing cells were able to distinguish CEA(+) HLA-A*02(−) tumor cells from CEA(+) HLA-A*02(+) normal cells based solely on expression of the blocker antigen, displaying ~70× shift in response vs. E:T ratio (FIG. 26). In contrast, the TCR was nonselective against the normal cells, consistent with its clinical profile.

TABLE 25

CEA(+) target cell lines compared to normal colon expression of CEA and A*02 antigens

| | CEA | | HLA-A*02 | | HLA-A*02/CEA | |
|---|---|---|---|---|---|---|
| Cell line | Mol./cell | TPM | Mol./cell | TPM | Mol. | TPM |
| Jurkat [CEA(−)A*02( )] (negative control) | 20 | NA | 8 | NA | | |
| H508 [CEA(+)A*02(+)] | 92-144k | 527 | 210-220k | 389 | ~2 | 1.5 |
| H508 [CEA(+)A*02(−)] | 40-68k | | <3k | ND | | |
| SW1463 [CEA(+)A*02(+)] | 80-90k | 216 | ~110k | 344 | ~1.2 | 3.2 |
| SW1463 [CEA(+)A*02(−)] | 47-79k | | <3k | ND | | |
| HeLa [CEA(+)/A*02(+)] | 330k | N/D | 660k | ND | ~2 | |
| HeLa [CEA(+)/A*02(−)] | 350K | | <3.5k | | | |
| Normal colon | ND | ~250 | ND | ~930 | ND | 3.7 |

In Table 25, H508 and SW1463 are colorectal cancer cell lines with native CEA and HLA-A*02 expression. HeLa is a cervical cancer cell line that is CEA(−) and HLA-A*02(−). HeLa cells were genetically engineered to express CEA and HLA-A*02. Cells were stained and molecules/cell calculated as described above. TPM are for HLA-A. MFI, median fluorescence intensity; TPM, transcripts per million; NA: not applicable; ND, not done.

TABLE 26

Expression of CEA and A*02 (TPM) in 14 cell lines

| | | | | Gene modification to generate CEA(−) HLA-A*02(−) cells | | Gene modification to generate CEA(−) HLA0A*02(+) cells | |
|---|---|---|---|---|---|---|---|
| Cell line | Tissue origin | CEA (TPM) | HLA-A*02 (TPM, corrected by heterozygosity) | CEA | HLA-A*02 | CEA | HLA-A*02 |
| NIHOVCAR3 | ovary | 0 | 40 | — | KO | — | — |
| SW982 | soft tissue | 0 | 533 | — | KO | — | — |
| COLO668 | lung | 180 | 0 | KO | | KO | Overexpression |
| HEPG2 | liver | 0 | 245 | — | KO | — | — |
| U2OS | bone | 0 | 54 | — | KO | — | — |
| K562 | haematopoietic and lymphoid tissue | 0 | 0 | — | | — | Overexpression |
| NCIH508 | Large intestine | 527 | 389 | KO | KO | KO | — |
| RAJI | haematopoietic and lymphoid tissue | 0 | 0 | | | | Overexpression |
| SHP77 | lung | 30 | 130 | KO | KO | KO | — |
| MS751 | cervix | 0 | 78 | — | KO | — | — |
| LNCAP_CLONE_FGC | prostate | 0 | 58 | — | KO | — | — |
| SW480 | large intestine | 0 | 205 | — | KO | — | — |
| A375 | skin | 0 | 110 | — | KO | — | — |
| A498 | kidney | 0 | 617 | — | KO | | — |

Gene expression information was obtained from DepMap. The 14 cell lines were obtained from commercial sources. CEA(−) HLA-A*02(−) and CEA(−) HLA-A*02(+) isogenic cell lines were generated by knockout (KO) of CEA and/or HL-A*02 using CRISPR gene-editing and, in the cell lines lacking A*02, cells were transduced with lentiviral vector expressing A*02.

Figure 27:
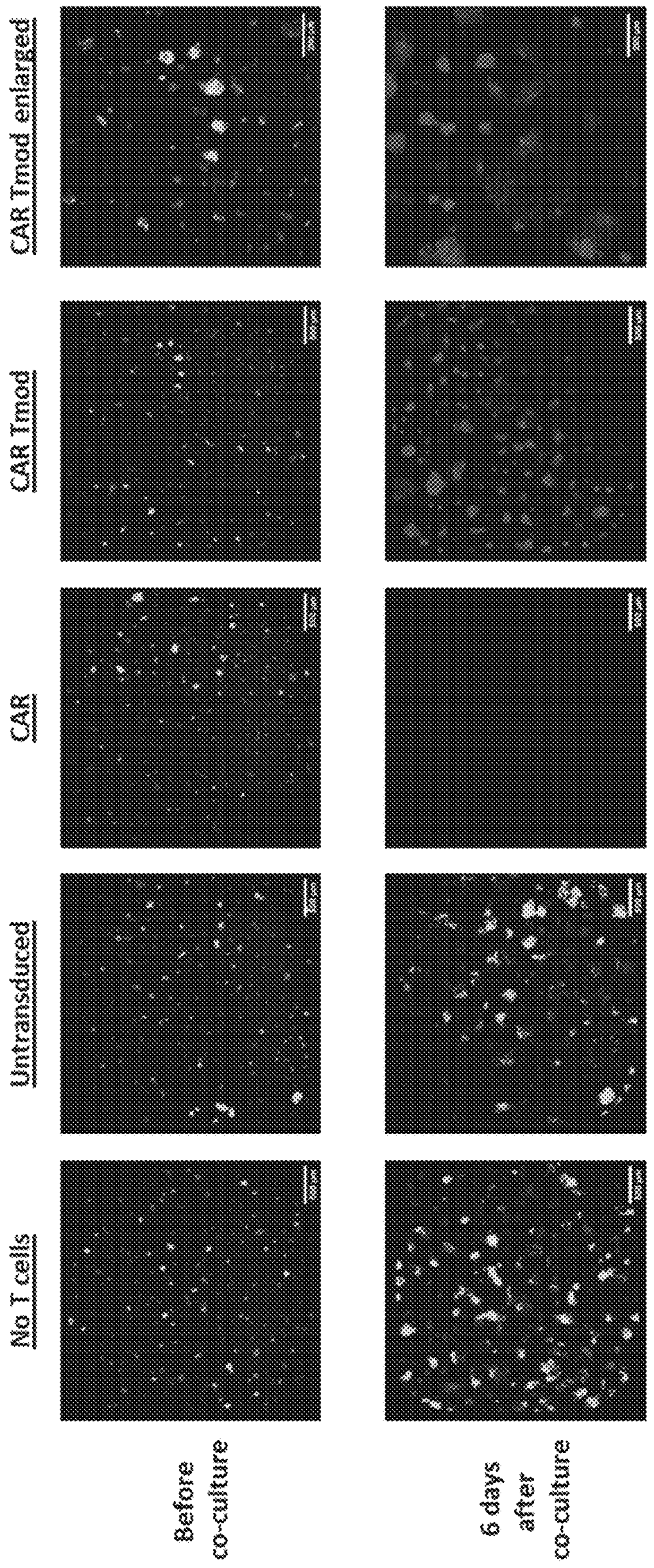
FIG. 27 shows selective cytotoxicity of effector cells expressing the CEA CAR Tmod dual receptors when presented with mixed tumor and normal cell cultures at a 1:1 ratio. The tumor cells were H508 CEA(+) HLA-A*02(−) cells that stably expressed GFP (green). Normal cells were H508 CEA(+) HLA-A*02(+) cells that stably expressed RFP (red). T cells were from HLA-A*02(+) donor D12333. Scale bar is 500 microns.
Figure 28:
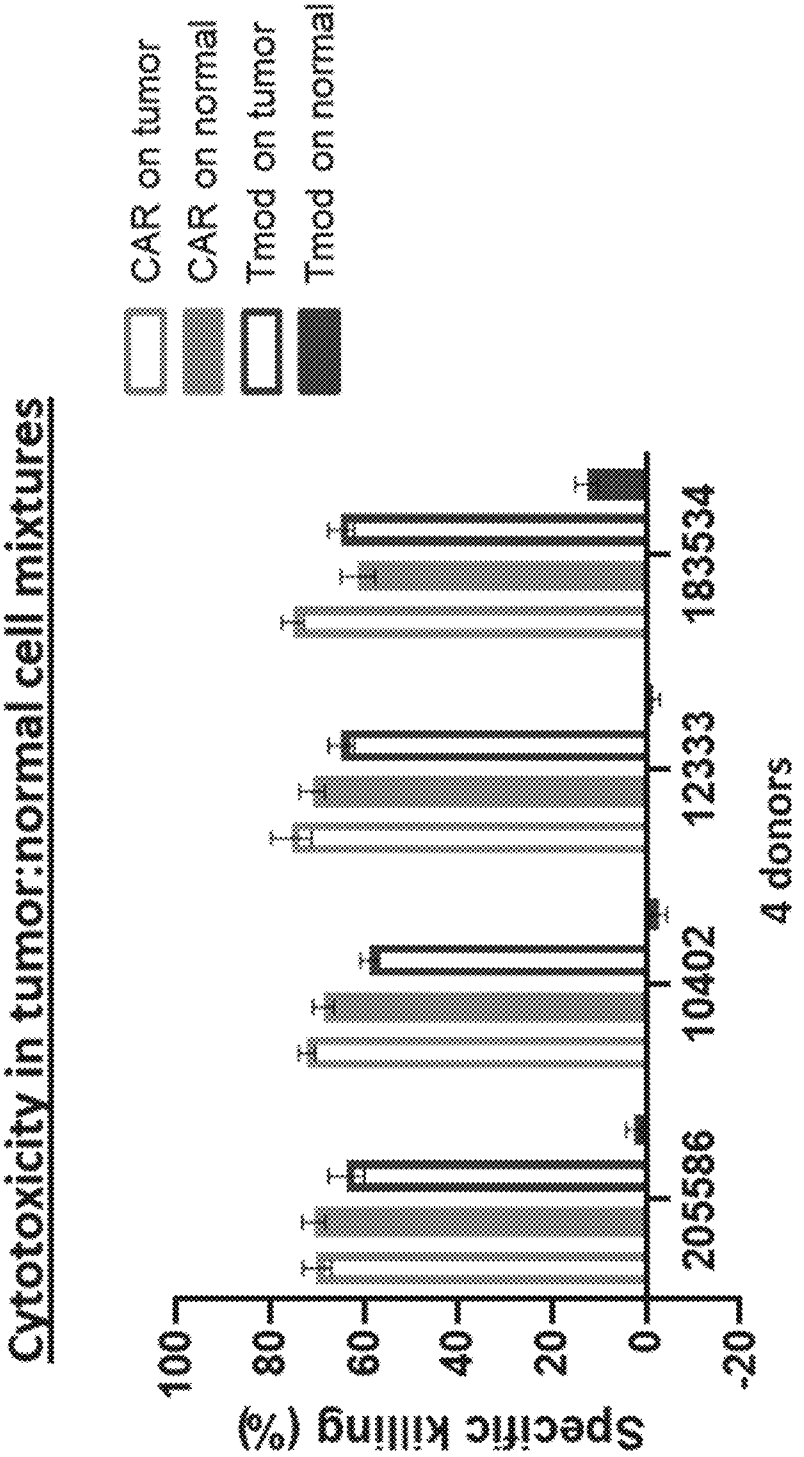
FIG. 28 shows a summary of specific killing effector cells expressing the CEA CAR and HLA-A*02 inhibitory receptor (Tmod) in 1:1 mixtures of tumor:normal target cells. H508 target cells genotypes were as in FIG. 26, and no IL-2 was added. Donor T cells were HLA-A*02(+) except for donor 183534.

Example 8: Tumor Discrimination and Reversible Activation in Mixed and Serial Cultures A series of experiments to test the function of cells expressing the CEA CAR Tmod dual receptor system (CEA CAR and HLA-A*02 scFv LILRB1 inhibitory receptor) in more challenging in vitro functional assays. First, the ability of cells expressing the two receptors to distinguish tumor from normal cells in mixed cell cultures was tested. Wild-type H508 cells were labeled with RFP to simulate normal cells and HLA-A*02 knockout (KO) isogenic cells were labeled with GFP and used to simulate tumor cells. The colored proteins provided a convenient readout for cell survival in vitro. The two labeled cell lines were mixed at a 1:1 ratio and co-cultured with effector T cells expressing the two Tmod receptors. Afterward, the target cells were visualized by microscopy. While T cells expressing the CEA CAR alone killed both tumor and normal lines completely, T cells expressing the CEA CAR and the inhibitory receptor killed only the tumor cells (FIGS. 27-28).

Figure 29:
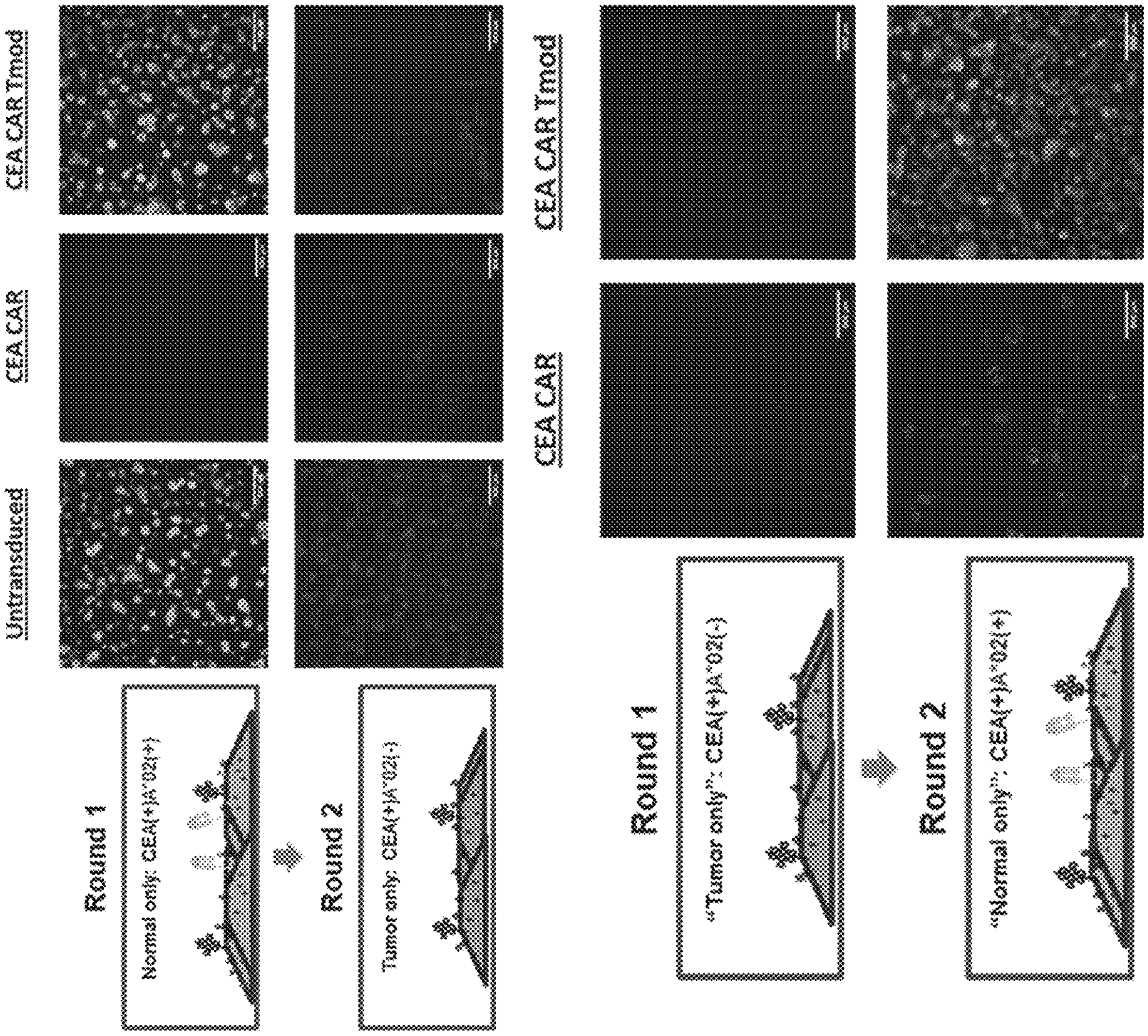
FIG. 29 shows image of targets cells co-cultured serially. For cytotoxicity assays T cells were transduced, enriched for blocker antigen, and transferred from one specific type of target cell to the next. Both normal and tumor cells are labeled with GFP but red pseudo-color is used to visualize tumor cells and green is used for normal cells. Scale bars indicate 500 microns.
Figure 30:
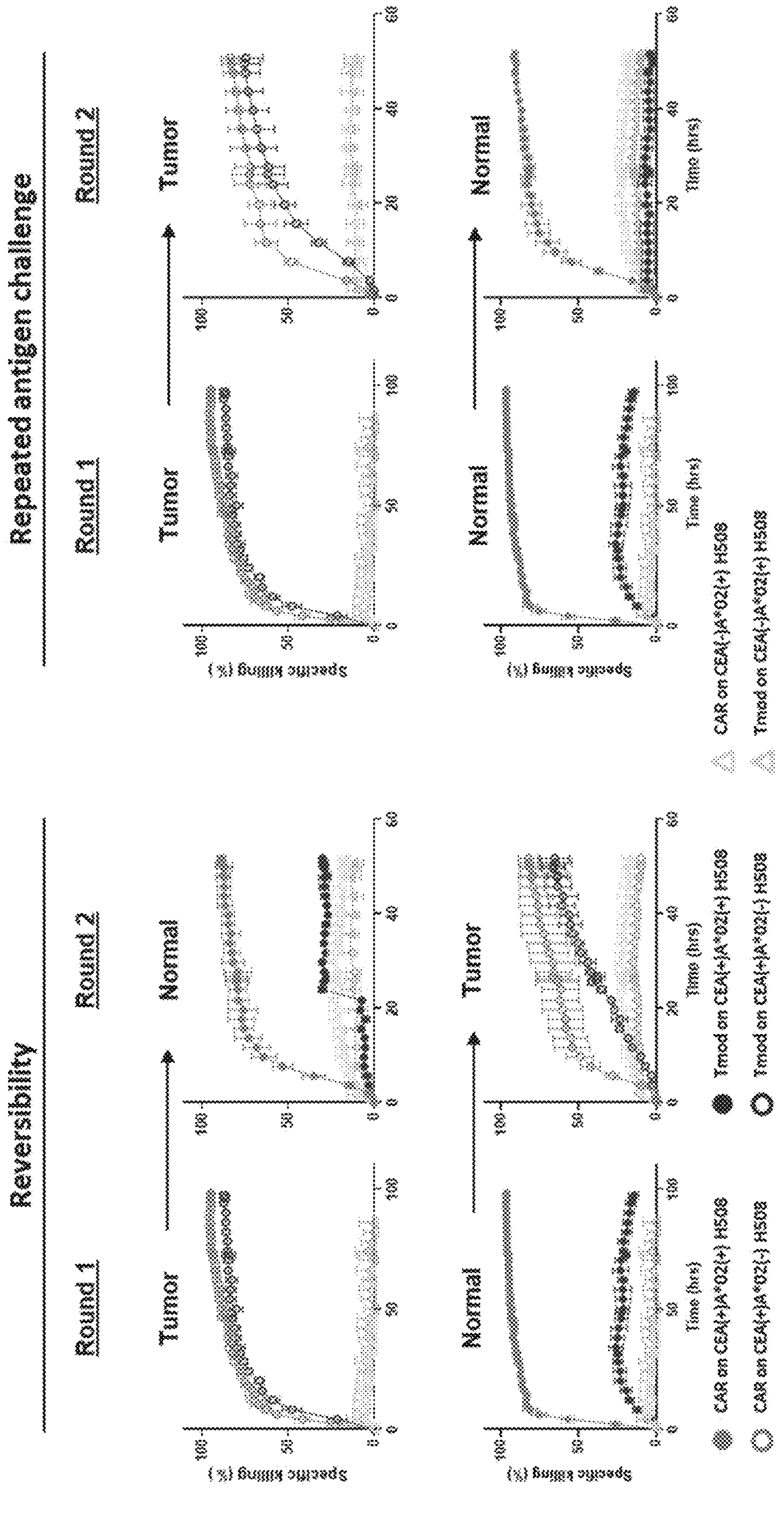
FIG. 30 shows a time course of CEA CAR Tmod expressing cells and CEA CAR expressing cells in a repeated antigen challenge. Horizontal arrows show the transfers from target cell type (tumor or normal H508). Donor T cells transduced with CEA CAR, or the Tmod dual receptors were HLA-A*02(+) (D12333).
Figure 35:
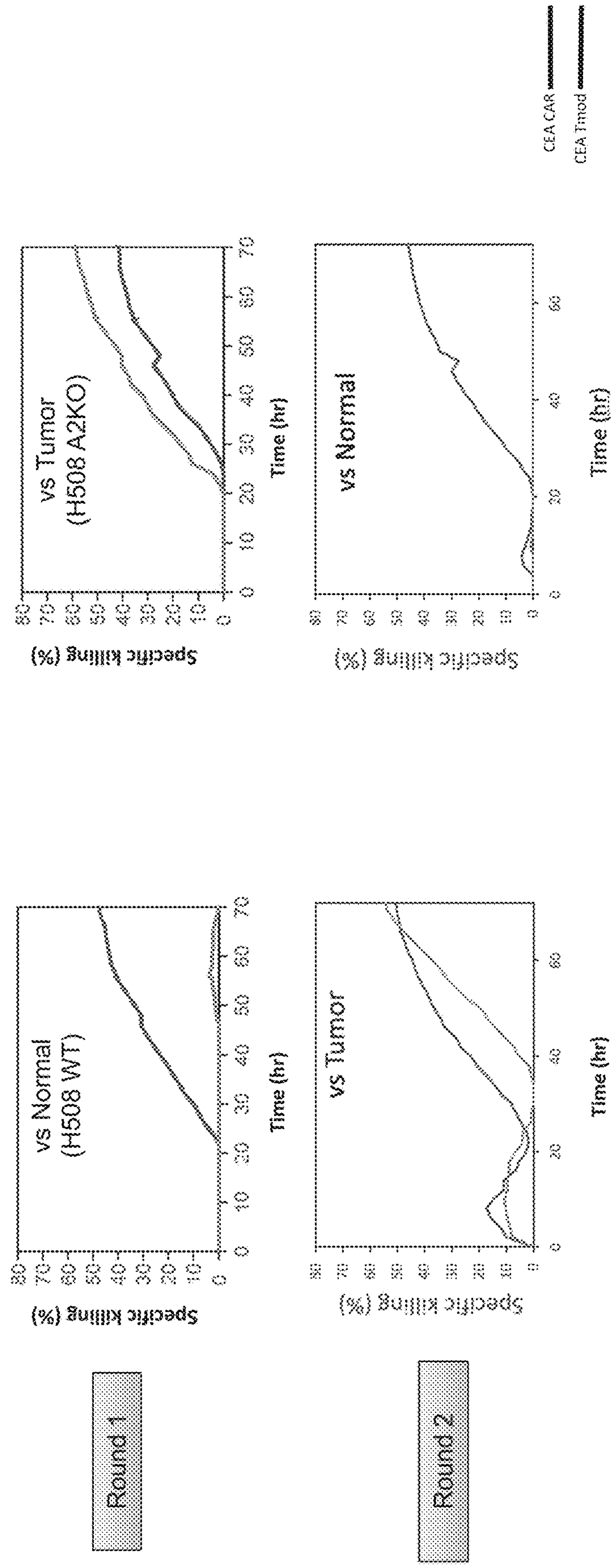
FIG. 35 shows quantification of reversible cytotoxicity by effector T cells expressing the CEA Tmod dual receptors (which were delivered via 2 separate lentiviral vectors), in HLA-A*02(−) donor cells (D4809). T cells were exposed first to either tumor or normal cells in round 1, then normal or tumor cells, respectively, in round 2 and selective tumor vs. normal cell killing was measured. WT: wild type; A2KO: HLA-A*02 knock out.

Next, the capacity of the CEA CAR Tmod dual receptors to mediate reversible activation, another property of a solid-tumor cell therapy, was assayed. Effector T cells expressing the CEA CAR Tmod receptors were cultured serially in the presence of different target cells, i.e. from tumor to normal or from normal to tumor, in order to simulate the experience of T cells in the body moving through a heterogeneous environment. The effector T cells expressing the Tmod dual receptors were able to switch sequentially between activated (ON) and blocked (OFF) states in both directions (FIGS. 29-30, FIG. 35).

Figure 31:
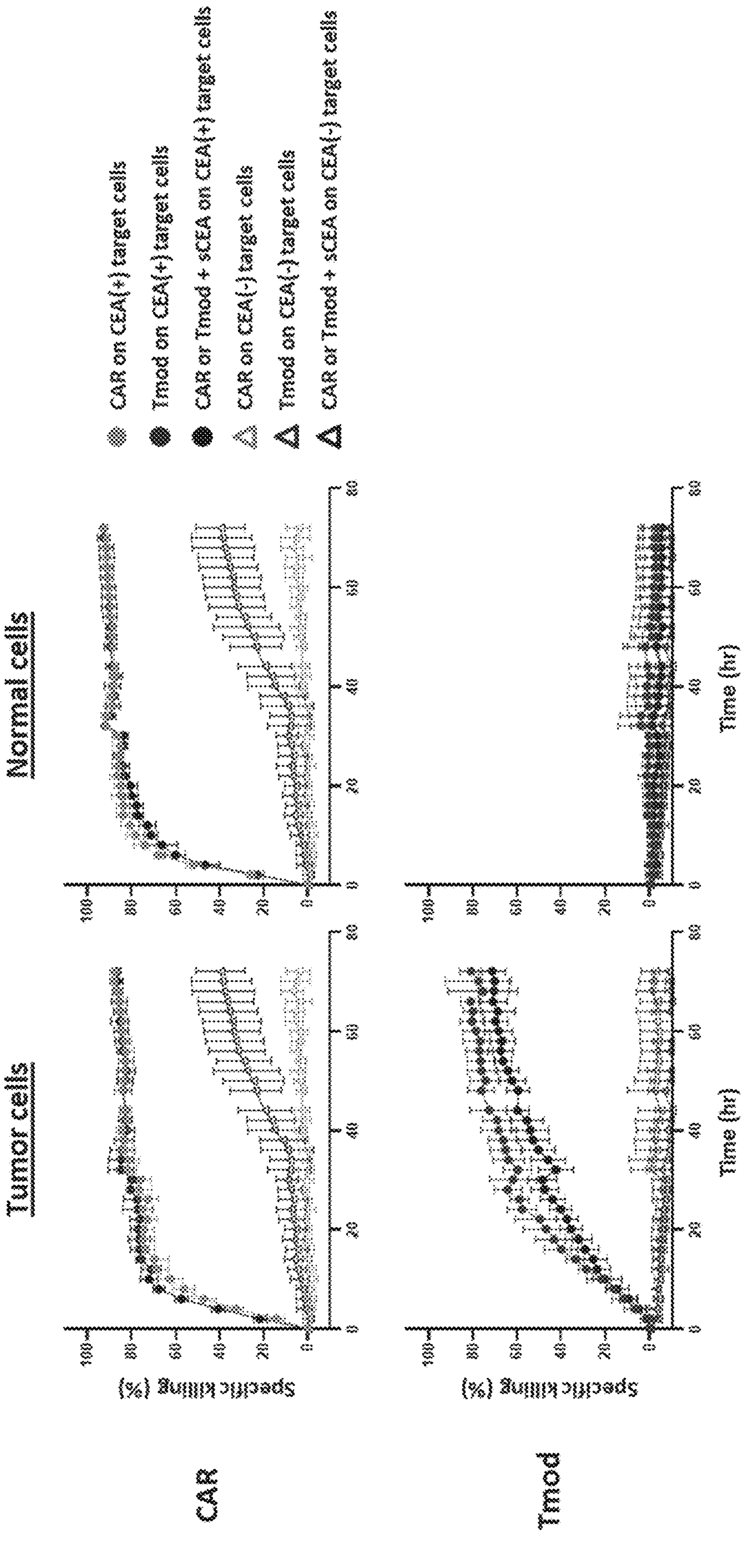
FIG. 31 shows that the presence of soluble CEA (sCEA; 10 ug/mL) does not significantly affect CEA CAR Tmod cytotoxicity in H508 cells. Genotypes of tumor, normal, and B as follows: tumor: CEA(+) HLA-A*02(−) target cells; normal: CEA(+) HLA-A*02(+) target cells; B: CEA(−) HLA-A*02(+) target cells.

Finally, the sensitivity of effector T cells expressing the two receptors was not affected by exogenous soluble CEA (sCEA), even at the highest levels detected in patients' blood (FIG. 31). Representative data from one HLA-A*02(+) donor (D12333) is shown in FIG. 31, and T cells from four donors were tested. sCEA activated the CEA CAR in T cells from all 4 donors at longer time points. The presence of sCEA (10 ug/mL) did not significantly influence cytotoxicity of effector T cells expressing both Tmod receptors across multiple donors. Interestingly, the CEA CAR appeared to react to sCEA at longer time points. This activation, possibly derived from CEA aggregated on the cell surface, was not detected in cells expressing both Tmod receptors.

Example 9: Off Target Reactivity Against Cell Lines that do not Express CEA

One consideration for all cell therapeutics, including this one, is off-target reactivity. Therefore, a process to test for functional off-target reactivity beyond the target-specific cell selectivity arising from activator- and blocker-antigen expression was established. It is worth noting that for the dual receptor system described here, clinical on-target safety (tumor vs. normal cells), is primarily achieved not by the activator receptor but by the blocker receptor, which responds to the presence or absence of its cognate blocker antigen. Normal cells that ubiquitously express the blocker antigen, HLA-A*02, are protected from cytotoxicity, reducing the on-target, off-tumor risk. This safety mechanism also protects patients from off-target reactivity. Activation by any potential engagement of the activator receptor with off-target molecules will be inhibited by the ubiquitous presence of HLA-A*02 protein which engages the blocker receptor.

Figure 36:
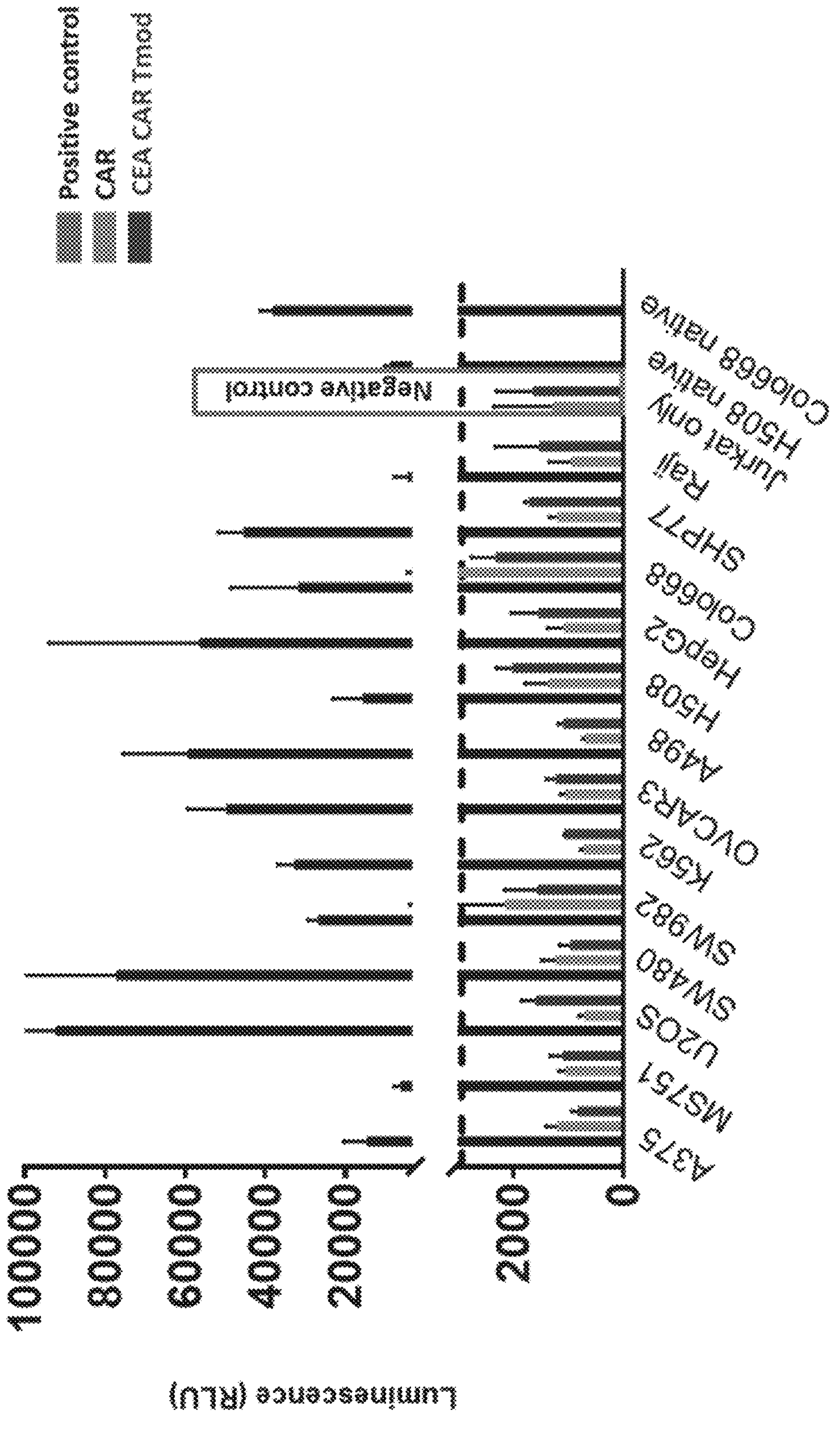
FIG. 36 shows Jurkat cell assays of CEA CAR Tmod dual receptor off-target selectivity using a cell line panel chosen to represent greater than 90% of human adult tissue gene expression. Jurkat effector cells expressing the Tmod receptors were co-cultured with individual target cell lines described in Table 26. Positive control cell lines, which represent tumor cells, were transfected with 2 ug of CEA mRNA or natively expressed CEA. Normal cells are CEA(−) HLA-A*02(+). The horizontal dashed line is placed at the mean+2× the standard deviation (SD) of data from Jurkat cells (expressing the Tmod receptors) alone. Co-cultures were of 10,000 (10K) Jurkat cells and 10K target cells in each well. Left bars: Jurkat cells expressing the Tmod dual receptors with CEA+HLA-A*02(−) cells; Middle bars: CAR expressing Jurkat cells with CEA(−) target cells; right bars, Jurkat cells expressing both receptors with CEA(−) HLA-A*02(+) target cells. Negative controls are in the grey box.

Human cell lines were used as surrogates for normal tissues in the body, and diverse cell-line panel that represents ~90% of adult gene expression at the level of >0.5 transcripts/cell was assembled (Table 26). A combination of transgenic and gene-knockout lines were used to generate both positive and negative controls. None of the target cell lines that were CEA-triggered a significant response above background level in Jurkat effector cells (hat expressed CEA CAR Tmod receptor constructs (FIG. 36). COLO 668 cells stimulated response in CEA CAR expressing Jurkat cells but not in CEA CAR Tmod Jurkat cells expressing both receptors. However, this response was not observed for either the CAR alone, or the CAR in combination with the inhibitory receptor, in primary T cells. These findings suggest that CEA CAR Tmod expressing cells have a low probability of off-target functional activity based on Jurkat cell assays.

Figure 37:
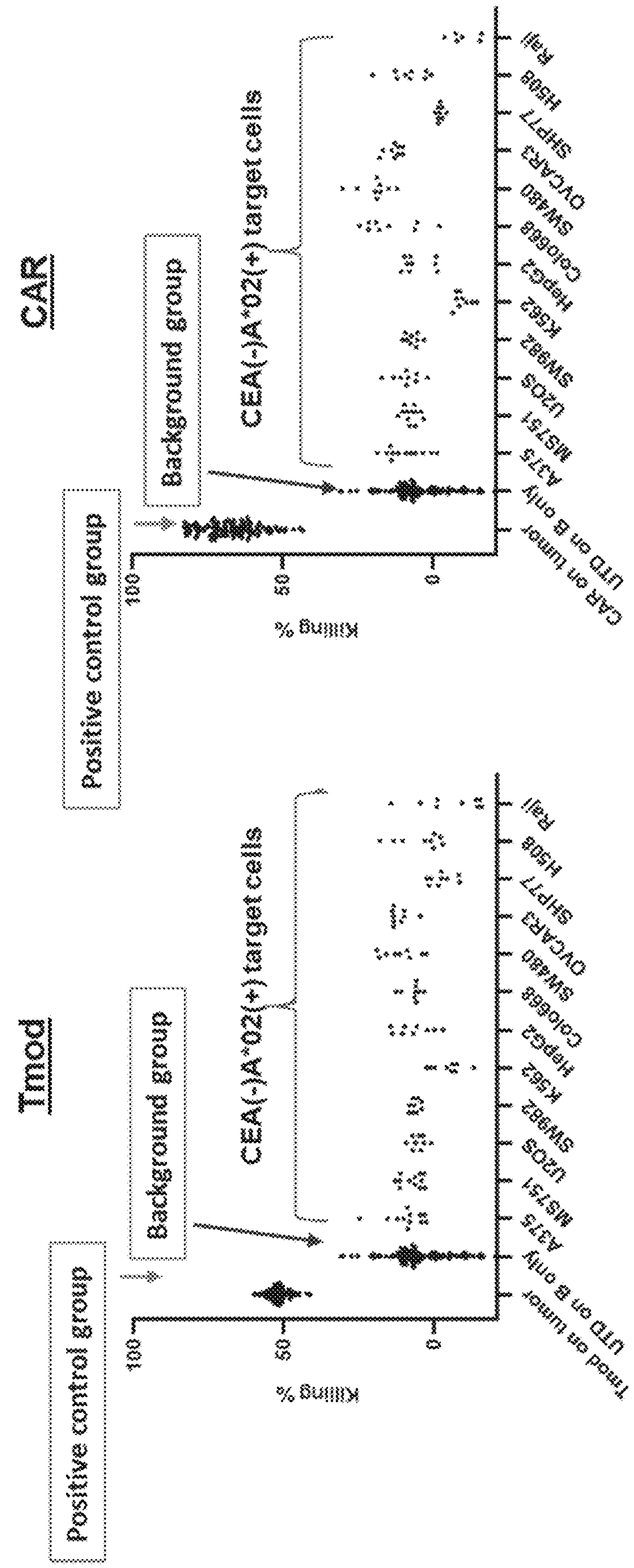
FIG. 37 shows a summary of cytotoxicity data for effector T cells expressing the CEA CAR Tmod dual receptors derived from 3 HLA-A*02(+) donors. UTD, untransduced.
Figure 38:
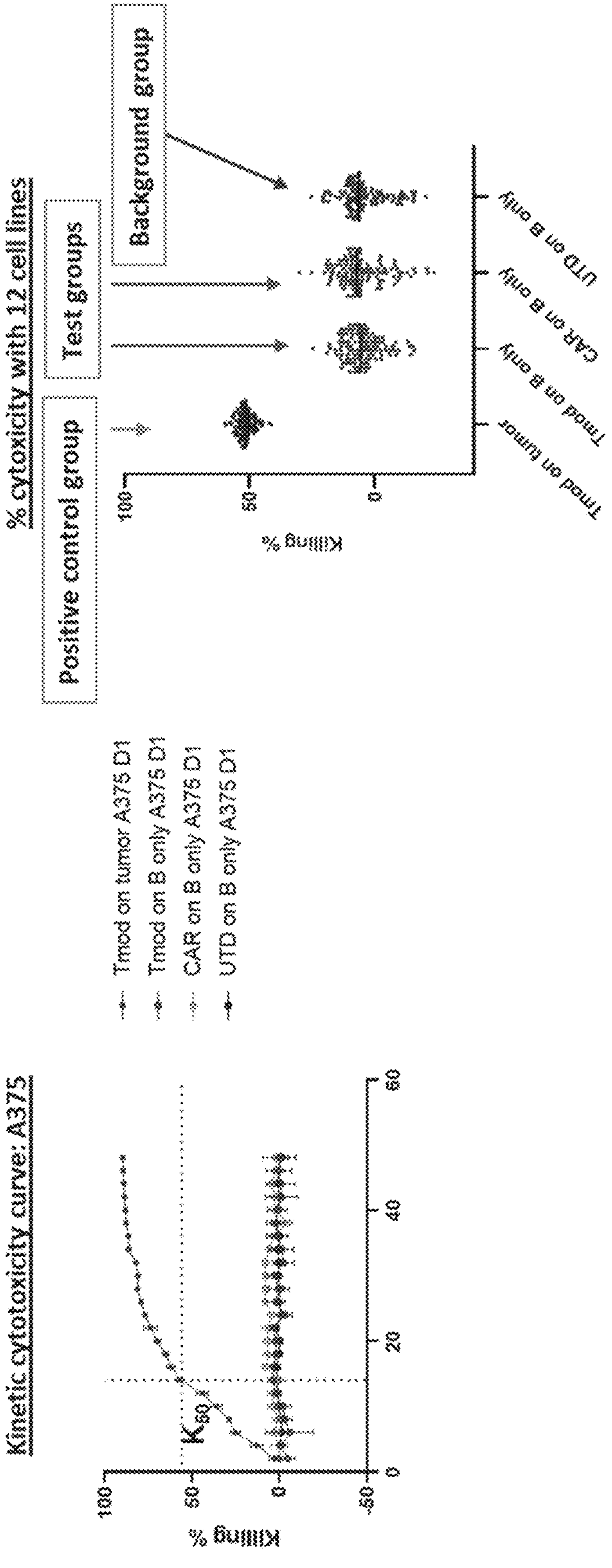
FIG. 38 shows a summary of selectivity data using primary T effector cells.

The same approach was used to test cytotoxicity of primary T cells expressing the CEA CAR Tmod receptors. Time points where the CEA CAR Tmod expressing cells killed ~50% of the CEA mRNA-transfected positive-control cell lines were selected (K50;

FIGS. 37-38). In FIG. 37, T cells were tested against the cell line panel described in Table 26. One HLA-A*02(−) donor was tested on A375 and MS751 cells. The E:T ratio used was 3:1. The time at which the Tmod dual receptor expressing cells reached greater than or equal to 50% killing on tumor cells (tK50) was chosen to compare % killing by the T cells expressing CEA CAR alone, both CEA CAR Tmod receptors, and untransduced T cells. As negative control, CEA(−) cell lines were co-cultured with untransduced T cells. The mean 50% target-cell killing (K50) of T cells expressing the CEA CAR Tmod dual receptors with tumor cells as targets, i.e. CEA(+) HLA-A*02(−) target cells, was ~6× above the background mean of the untransduced T cell co-cultures.

In FIG. 38, all killing in % was normalized against the growth of target cells only (no T cells). An example of kinetic data from one cell line (A375) is shown at the left. The cell line was transfected with 1 ug of CEA mRNA. All data are from E:T 3:1 experiments. The time at which Tmod cells reached greater than or equal to 50% killing on tumor cells was chosen to compare % killing by the CEA CAR, CEA CAR Tmod and untransduced T cells. All donor measurements (3-4 donors) on 12 different target cell lines were pooled for the right graph. The high end of dynamic range (positive controls) at Tmod T cells with tumor target cells [CEA(+)A*02(−)] at K50, was estimated using the highest transfected CAR mRNA level. Background was estimated from untransduced T cells with CEA(−) target cells. Cross reactivity was estimated from the individual cell line means from the Tmod and CAR expressing Jurkat cells with the target cells (test groups).

Wild-type CEA(+) H508 triggered a strong response from CEA CAR-T cells. No significant off-target responses were detected with CEA CAR Tmod cells and CEA(−) target cells. Thus, the primary T cell cytotoxicity assay yielded no evidence of off-target activation by the CEA CAR Tmod construct. Notably, both Jurkat and primary T cell assays can detect functional target interactions at levels <100 molecules/cell, at least 1,000× lower than CEA is estimated to be present on the surface of H508 cells and normal colon epithelium.

Example 10: Tumor-Specific Efficacy in a Mouse Model

Figure 39:
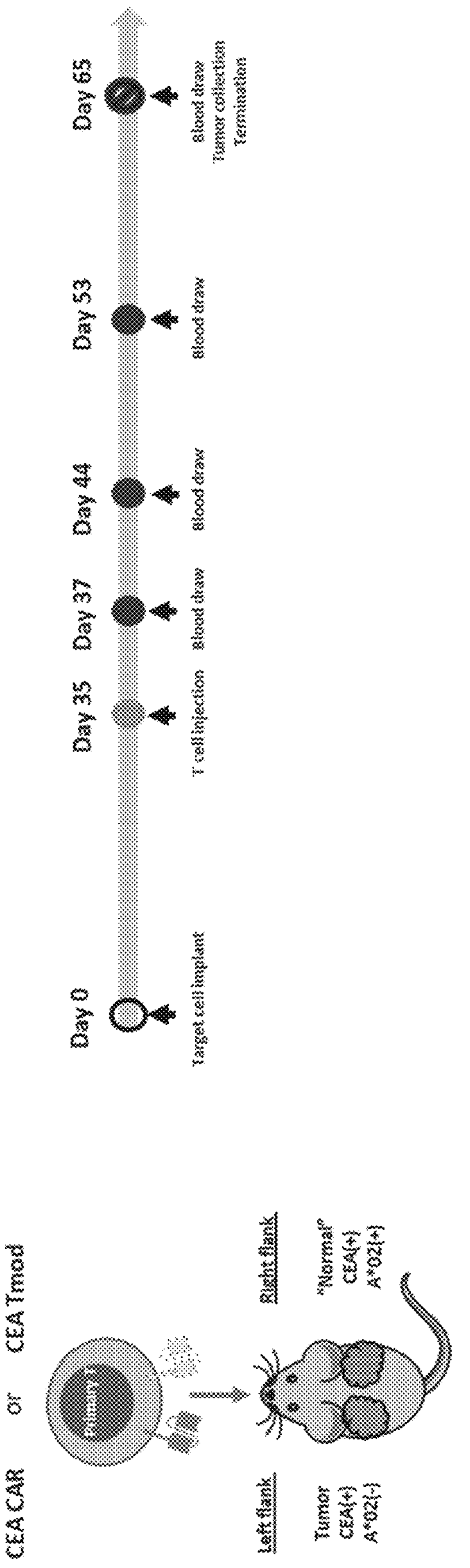
FIG. 39 shows the design of a mouse xenograft study with human T cells expressing CEA CAR or the CEA Tmod dual receptors. Xenograft experimental design and tumor volume vs. time are shown.

In vivo experiments were used confirm function of T cells expressing the CEA CAR Tmod dual receptors in mouse xenografts (FIG. 39). A single lentiviral vector encoding either the CEA CAR, or the dual receptor system, was used to transduce T cells from an HLA-A*02(−) donor, without a B2M shRNA. Donor T cells were HLA-A*02(−) (D4809). The cell line H508 chosen for the xenograft study, to reflect normal expression levels of CEA and HLA-A*02. Two dose levels of CEA CART or CEA CAR Tmod cells (from an HLA-A*02(−) donor) were used: 5E6 and 2E7 cells per mouse. After scaling up T cell production with IL-2, the enriched lentivirus-transduced primary T cells were infused via the tail vein of mice harboring two types of H508 tumor, one on each flank: one from CEA(+) HLA-A*02(+) normal cells to model normal colon epithelium and one from CEA(+) HLA-A*02(−) cells to model tumor.

Figure 40:
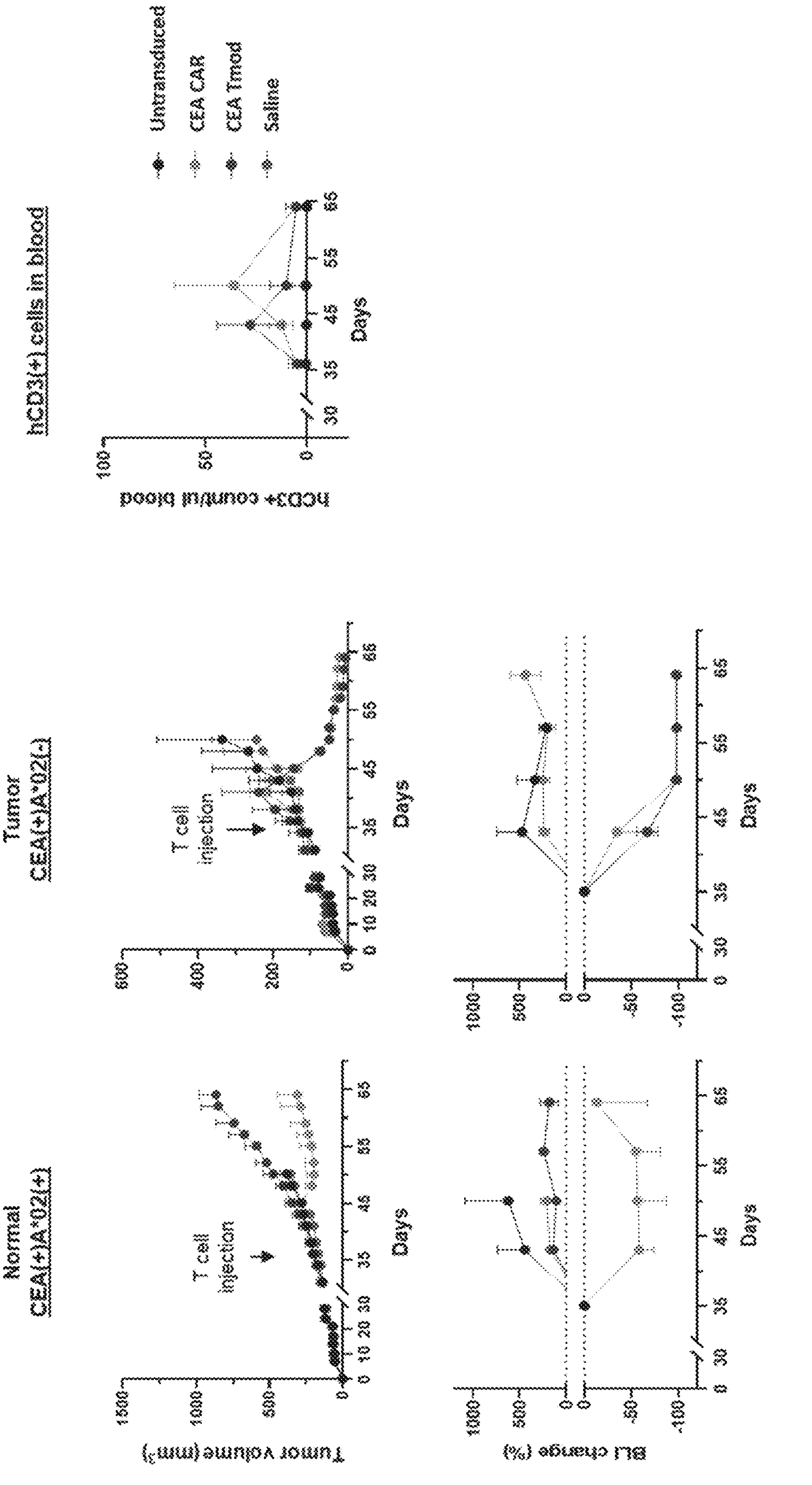
FIG. 40 shows tumor volume measured by caliper in the mouse xenograft study. Error bars are SEM. N=7 mice/group (5 in Saline and UTD, or untransduced, groups); xenograft=H508 colon cancer cell line that express firefly luciferase; dose=2E7 human T cells/mouse via tail vein injection. BLI % change=100×(BLI day t−BLI day 35)/(BLI day 35). −100% on the y-axis at the lower right indicates zero bioluminescence signal; i.e., no evidence of any residual tumor cells. Human T cells in mouse blood were detected with an hCD3 mAb.
Figure 41:
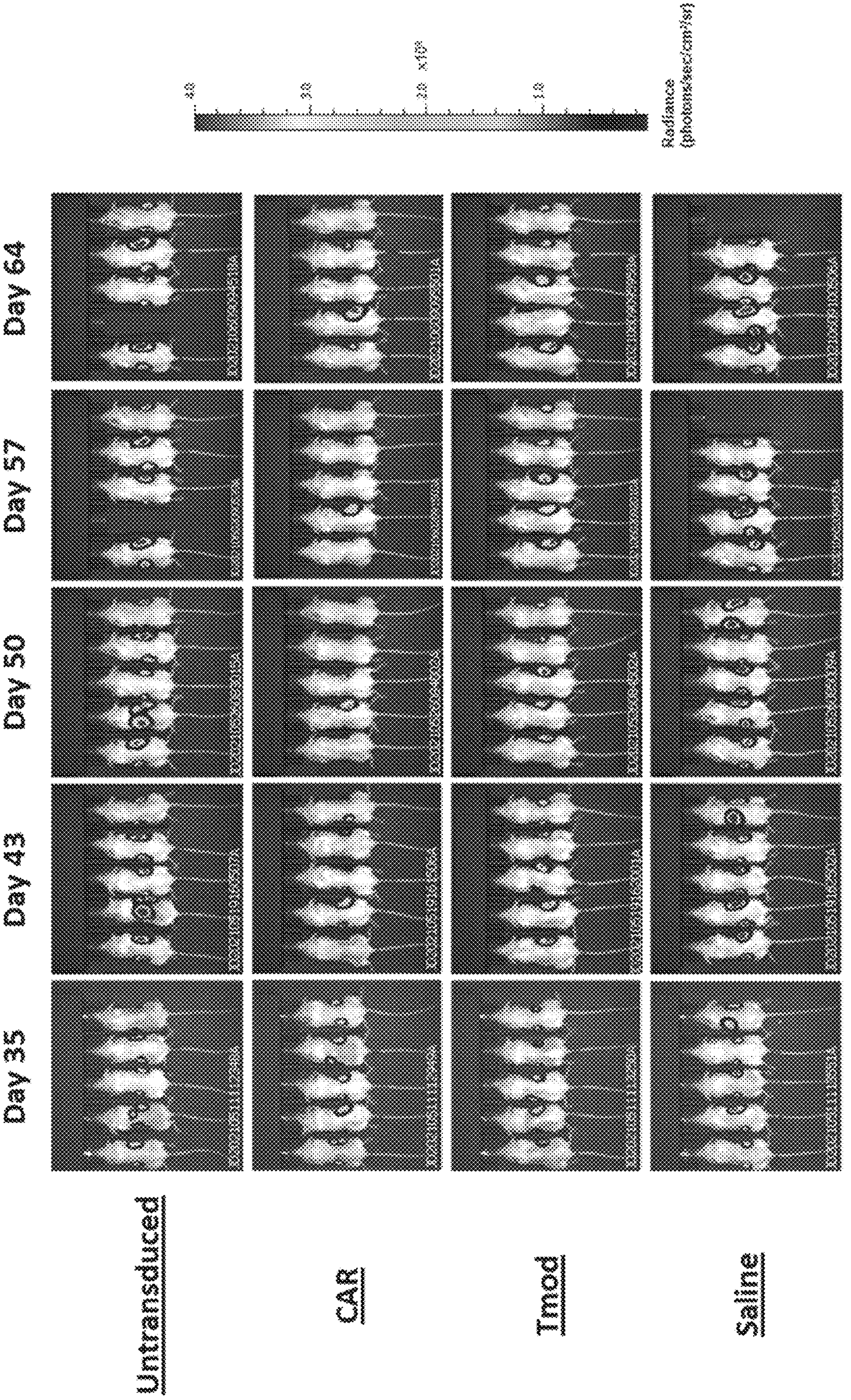
FIG. 41 shows images of five mice from each group (a subset of those in FIG. 40) which were used to measure bioluminescence (lucerifase) over time. One Tmod mouse ($2^{nd}$ from the left, day 64) did not receive BLI substrate by mistake.
Figure 42:
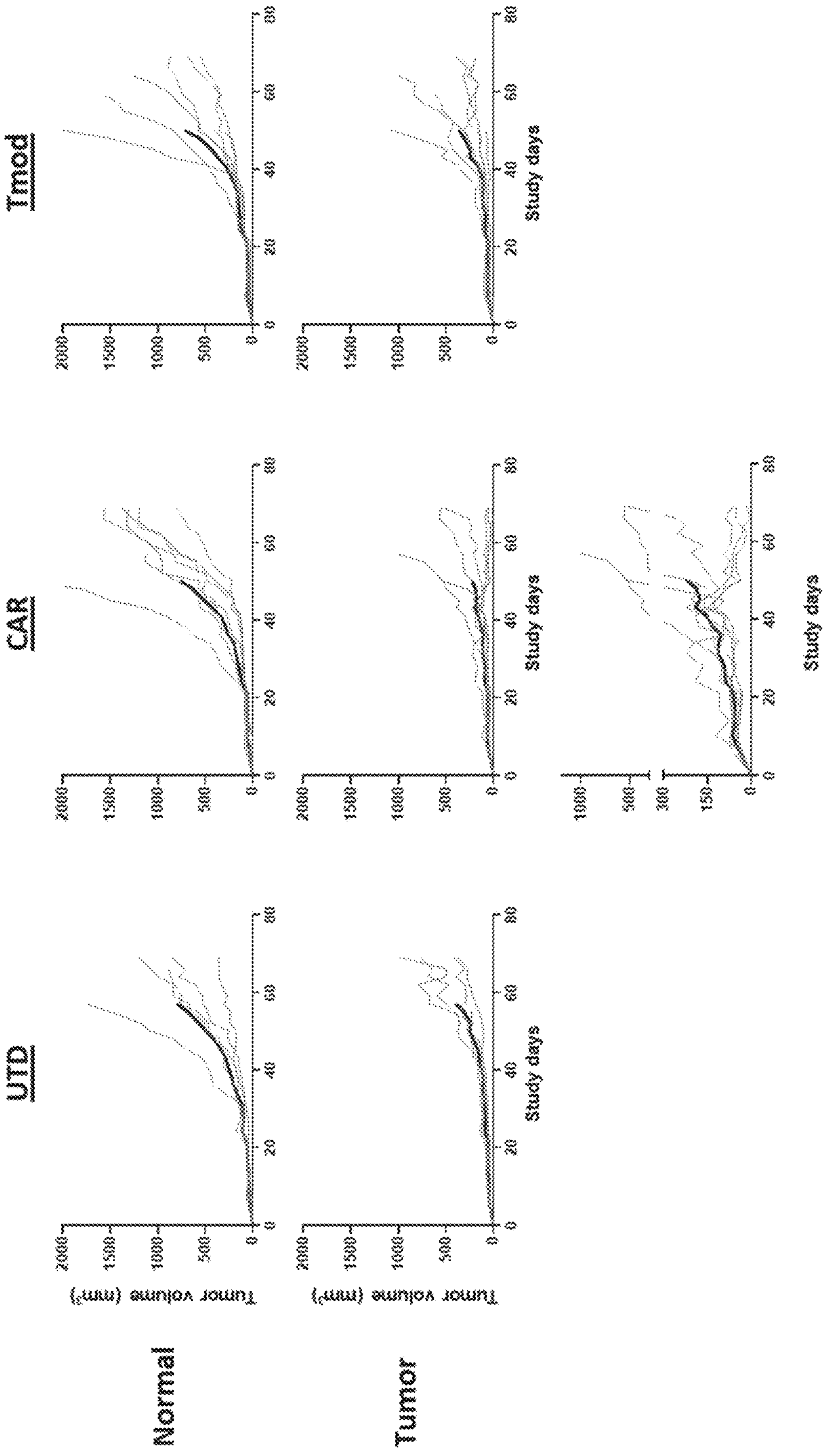
FIG. 42 shows xenograft study results for the T cell dose of 5E6 T cells per mouse. The center bottom panel shows replotted data from the panel above, to show tumor volumes at higher resolution. UTD: untransduced; CAR, T cell transduced with CEA CAR alone; Tmod, T cells transduced with CEA CAR and HLA-A*02 scFv LILRB1 inhibitory receptor.

The 5E6 dose demonstrated small and inconsistent effects for the CAR and Tmod constructs (FIG. 42). However, the 2E7 dose showed dramatic differences (FIGS. 40-41). In FIG. 40, 7 mice/group were used (except that 5 were in the saline and UTD, or untransduced, groups). The xenograft was from an H508 colon cancer cell line that was engineered to express firefly luciferase. Mice were injected with CEA CAR or CEA CAR Tmod dual receptor expressing cells at a dose of 2E7 human T cells per mouse via tail vein injection. Data points in FIG. 40 are shown for each cohort up to the time when individual mice in the cohort had large tumor volumes (>2000 $mm^3$ total volume). One-direction error bars are used for some curves to avoid crowding. Error bars are standard error of the mean. All mice in the cohort injected with T cells expressing the Tmod dual receptors showed no tumor growth over ~20 additional days, suggesting a curative effect. One mouse in the CAR/normal graft cohort escaped and grew, causing the average to increase.

Figure 43:
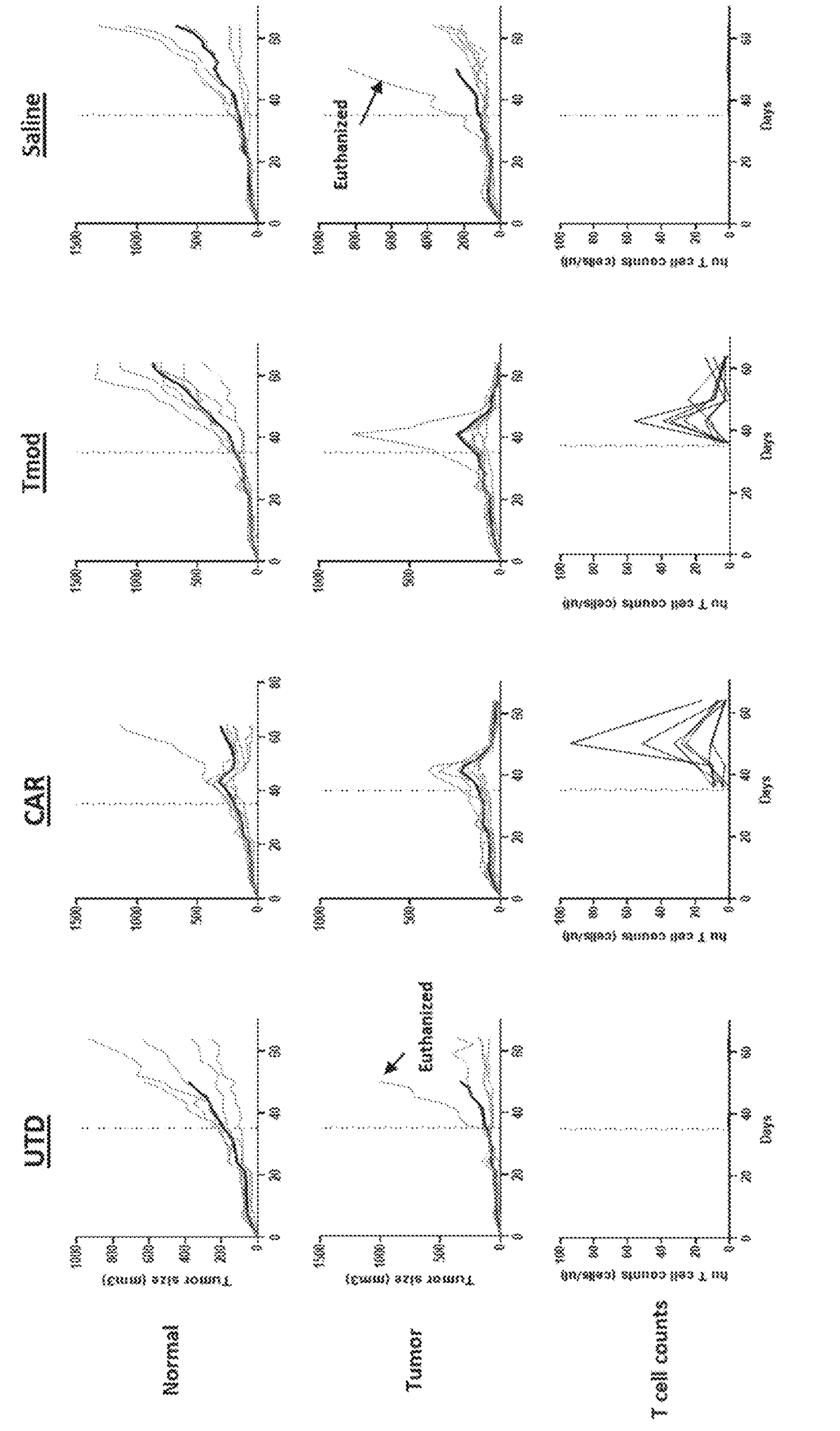
FIG. 43 shows individual tumor data from the mouse xenograft study. Light gray thin lines: individual mouse; black thick lines: average; dotted vertical line: T cell injection day (Day 35). UTD, untransduced T cells; CAR, T cells transduced with CEA CAR, Tmod, T cells transduced with both CEA CAR and HLA-A*02 ScFv LILRB1 inhibitory receptor; saline, mice injected with saline control.

FIGS. 42-43 for individual tumor data. As seen in FIG. 43, one CAR-T-treated animal, the tumor responded, but then resumed growth. This may be attributable to the larger tumor volume in that animal at T cell infusion. The normal grafts were slightly larger than the tumor grafts on average, and the CAR-T cells did not eradicate tumors completely. Both animals treated with cells expressing the CEA CAR and the CEA CAR in combination with the HLA-A*02 inhibitory receptor (Tmod cells) showed a reduction in CD3+ T cells. However, animals treated with the Tmod cells started to reduce the level of CD3+ T cells at an earlier time point. The reduction of T cell count at the end of the assay in the cohort injected with T cells expressing the Tmod dual receptors is likely attributable to the complete elimination of the tumor on one flank and the effective blocking of antigen by the graft on the other flank, resulting in the cessation of effective activator signaling.

Figure 44:
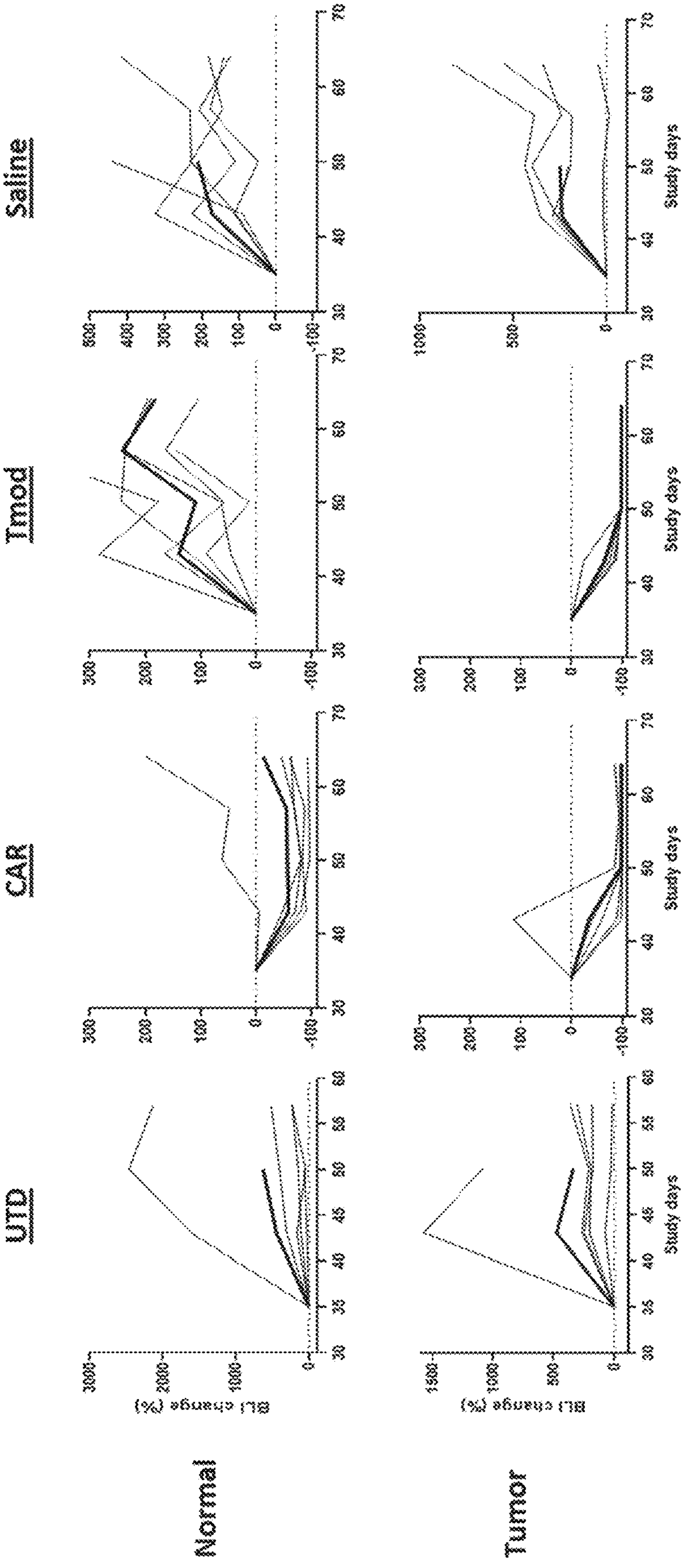
FIG. 44 shows bioluminescence (BLI) in individual mice in the xenograft study. % BLI was determined as described for FIG. 40. UTD, untransduced T cells; CAR, T cells transduced with CEA CAR, Tmod, T cells transduced with both CEA CAR and HLA-A*02 ScFv LILRB1 inhibitory receptor; saline, mice injected with saline control.

Whereas cells expressing the CEA CAR alone killed both tumor and normal grafts, the Tmod-engineered T cells only killed the HLA-A*02(−) tumor. Normal HLA-A*02 (+) H508 cells grew in the mice similar to saline-treated controls. The caliper measurements of tumor size were confirmed by bioluminescence, with no signal detected on the flanks of the Tmod-treated mice which had harbored tumors (FIGS. 40-41). For unknown reasons, the xenografts on the right flank were on average slightly larger than the tumors on the left flank. This resulted in a subtle apparent efficacy difference between the tumor and normal H508 cells treated by T cells expressing the CEA CAR and T cells expressing the Tmod dual receptors. CAR and Tmod treated mice showed very similar activity on the left flank. Although the Tmod T cell treated cohort appeared to be tumor-free, the CAR-T cohort had residual average tumor volume on the right flank bearing the normal graft, including one escaper that initially responded and then resumed growth (FIGS. 43-44). One tumor in the Tmod Tcell injected cohort was nearly 1 cc before being eliminated like the others in the cohort. These results suggest that CEA CAR Tmod T cells function in vivo in the same potent, tumor-selective manner as in vitro.

Figure 45:
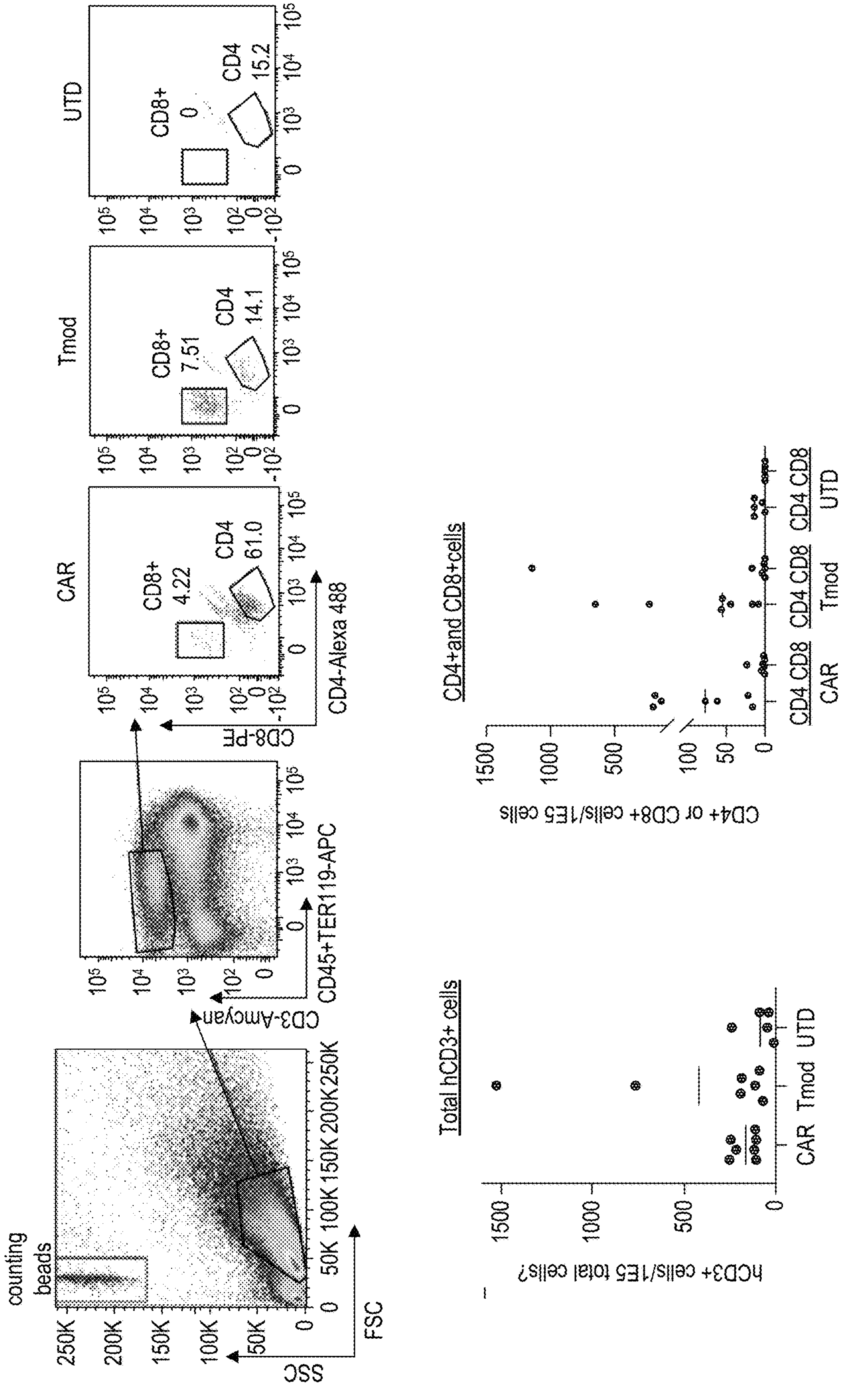
FIG. 45 shows cell analysis from spleens of mice from the xenograft study. Cells were harvested 30 days post T cell injection.

A variety of other parameters, including blood counts of the infused T cells were also measured. Two days post infusion, T cells from all cohorts were present at a level 1/10,000 of the concentration expected if they survived and remained in the blood (FIG. 40). However, in the cohorts treated with the CEA CAR and CEA CAR Tmod T cells, the T cell count increased over time. Ultimately the CEA CAR Tmod T cells declined, paralleling tumor elimination. The CAR-T cells remained longer, presumably because residual CEA(+) HLA-A*02(+) graft cells were present to provide antigen stimulation. By 30 days post infusion they had declined to baseline. In the Tmod T cell cohort, xenografts continued to grow on the right flank of the mice, but these expressed the HLA-A*02 blocker antigen, effectively preventing activator-antigen stimulation of the Tmod cells. Several other analyses were conducted on the cells, tissues and organs of the mice (FIG. 45). FIG. 45 shows that the majority of mice had higher CD4 counts than CD8 counts. The presence of CD3(+) human T cells was observed in spleens of two mice in the CEA Tmod group 30 days post T cell injection. The mice were generally healthy and maintained body weight similar to that of the saline and control untransduced T cell group.

Example 11: HLA-A*02 Cis Binding and Autologous Therapy

Figure 46:
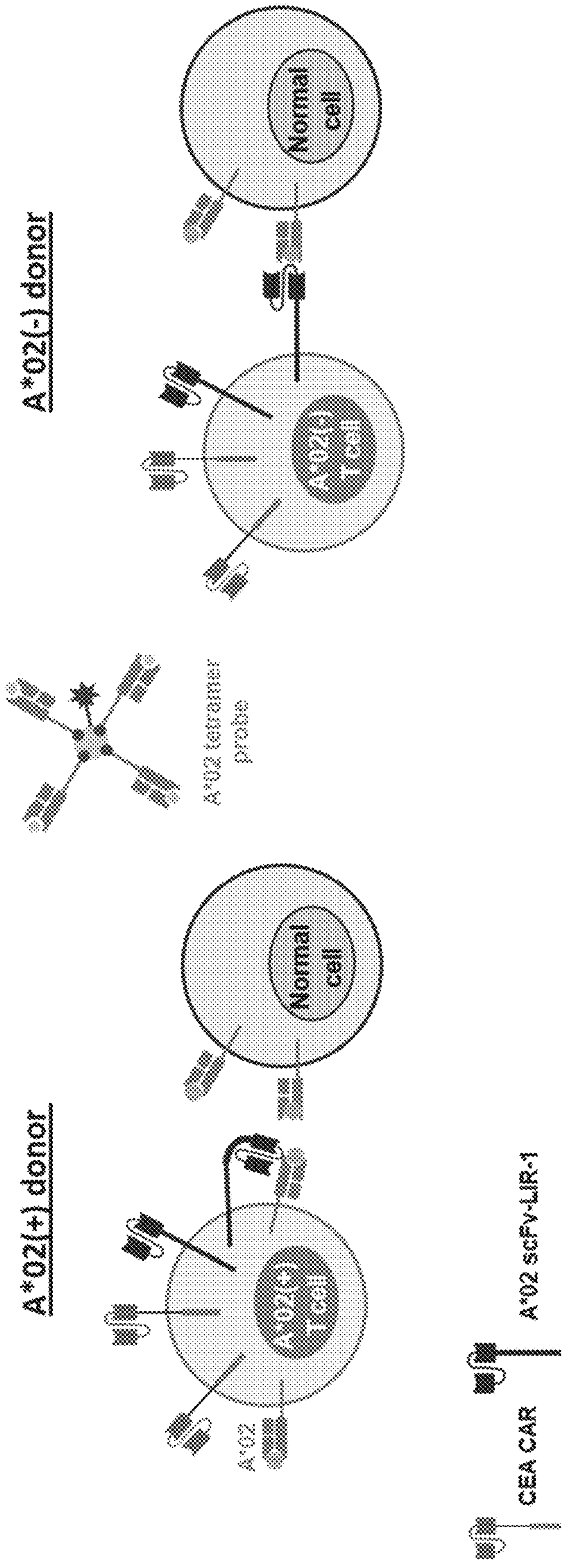
FIG. 46 is a diagram showing how HLA-A*02 antigen can bind to the HLA-A*02 Tmod blocker receptor in cis in HLA-A*02(+) T cells to hinder blocker receptor binding/function in trans with respect to normal cells. This effect can be detected via labeled HLA-A*02 tetramer and by functional assays.
Figure 50:
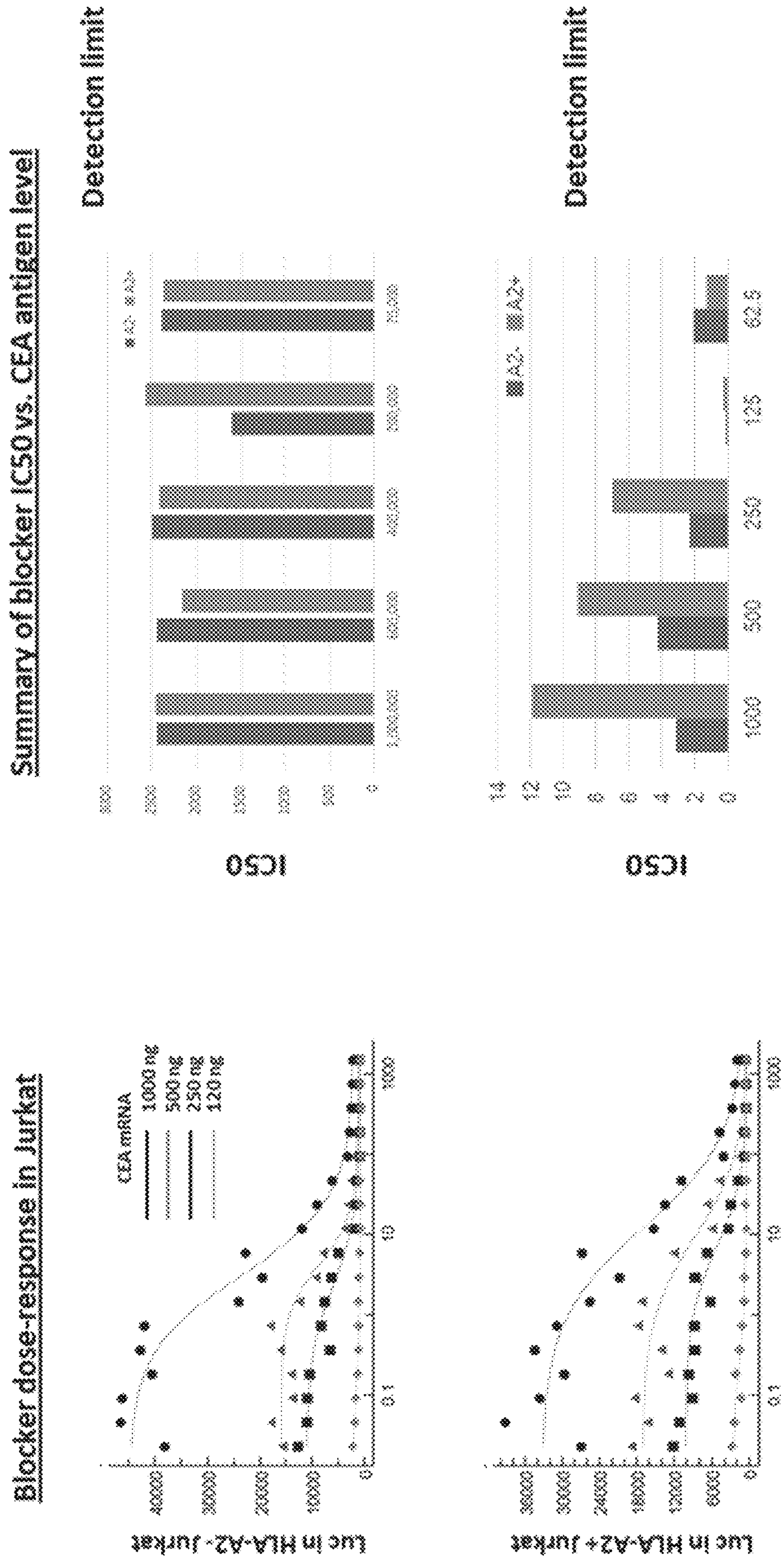
FIG. 50 shows that the HLA-A*02 LILRB1 inhibitory receptor is equally sensitive in HLA-A*02(+) and HLA-A*02(−) Jurkat cells when assayed using HeLa target cells.

An HLA-A*02 blocker receptor could in principle be impacted in cis by endogenous A*02 in autologous T cells (FIG. 46). Responses in parental Jurkat cells were therefore compared with a Jurkat line engineered to express HLA-A*02. Little difference was seen in blocker receptor surface expression level was detected between the HLA-A*02(+) transgenic Jurkat line compared to the wild-type HLA-A*02 (−) parental line (FIG. 50). The IC50 of the blocker was also similar in HLA-A*02(+) and HLA-A*02(−) Jurkat cells.

Figure 47:
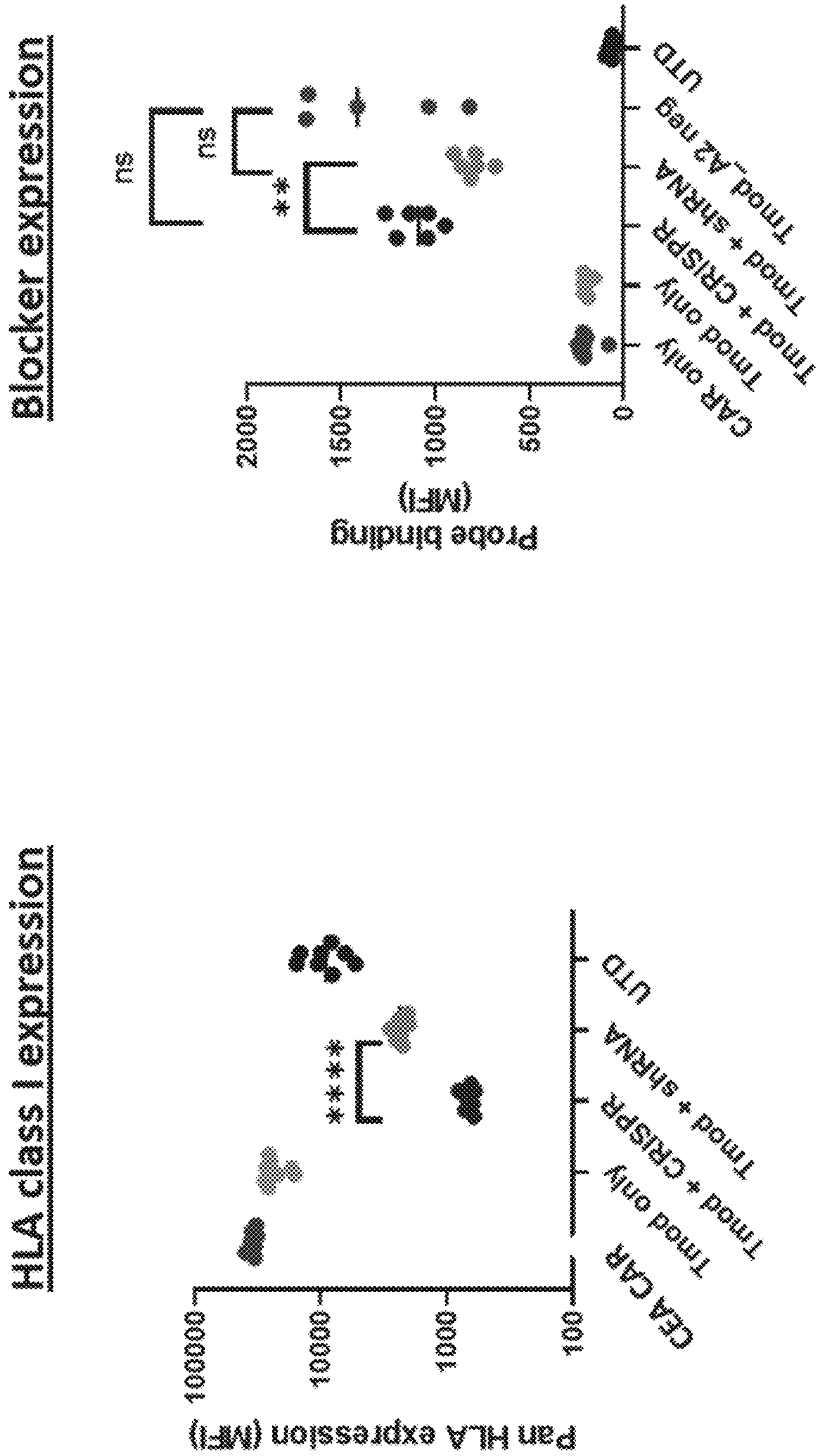
FIG. 47 shows that CRISPR using a guide RNA (gRNA) to B2M and a B2M shRNA reduce HLA expression on cell surface and increase blocker receptor availability in HLA-A*02(+) T cells.
Figure 51:
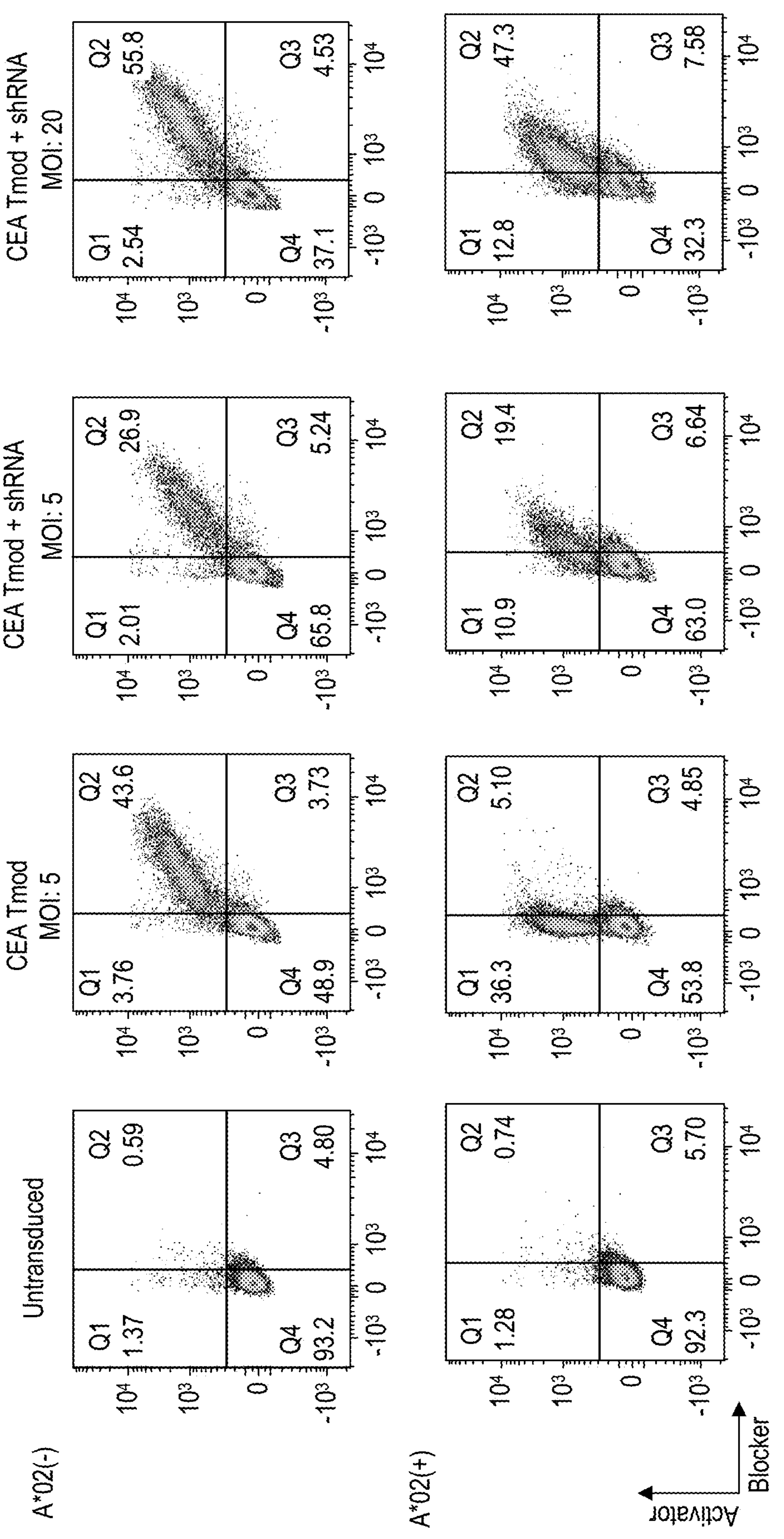
FIG. 51 shows that co-expression of a B2M shRNA in T cells expressing the HLA-A*02 scFv LILRB1 inhibitory receptor frees the receptor to bind probe on primary T cells.

However, results were different in primary T cells. T cells from HLA-A*02(+) donors expressed less blocker receptor on their surface compared to HLA-A*02(−) donors (FIG. 47). To address this difference, an shRNA module that targets B2M was developed. B2M is the common light chain of HLA class I molecules and is required for their expression on the cell surface. The HLA-A*02 tetramer binding difference between HLA-A*02(+) and HLA-A*02(−) donor cells transduced with CEA CAR Tmod receptors was substantially reduced, with binding levels close to those seen with CRISPR-treated T cells (FIGS. 47 and 51). As seen in FIG. 47, the B2M shRNA partially restored probe binding. B2M knockout via CRISPR/Cas9 similarly restored probe binding to the same level as seen in HLA-A*02(−) cells. HLA class I was detected by pan HLA-I mAb W6/32, and blocker receptor expression was detected by A*02 tetramer. Individual dots in FIG. 47 represent different donors. In total, 8 donors were used: 6 donors who were HLA-A*02(+) and 2 donors who were HLA-A*02(−). All were tested in triplicate and the average was plotted as a single dot. The group labeled Tmod_A2 neg contains data from the 2 HLA-A*02 (−) donors with the 3 conditions/constructs to its immediate left (Tmod only, Tmod+CRISPR, Tmod+shRNA plotted together). One T cell population from this experiment died and was excluded here and in FIG. 48.

Levels of B2M in T cells from three donors are shown in Table 27 below. Total RNA from 3 donors of untransduced T cells and Tmod transduced T cells (including the B2M shRNA) was extracted and reverse transcribed into complementary DNA. Droplet digital polymerase chain reaction reactions were set up to assess B2M expression levels in the untransduced T cells and A2B530. B2M mRNA expression level was normalized to beta actin gene expression.

TABLE 27

| Relative mRNA Expression Level of B2M Between Tmod transduced and Untransduced T cells | | |
|---|---|---|
| HLA-A* | B2M Expression Level | |
| 02(+) Donor | UTD | Transduced with Tmod+ B2M shRNA |
| 1 | 100% | 34% ± 1.5% |
| 2 | 100% | 18% ± 1.1% |
| 3 | 100% | 24% ± 1.1% |

Figure 48:
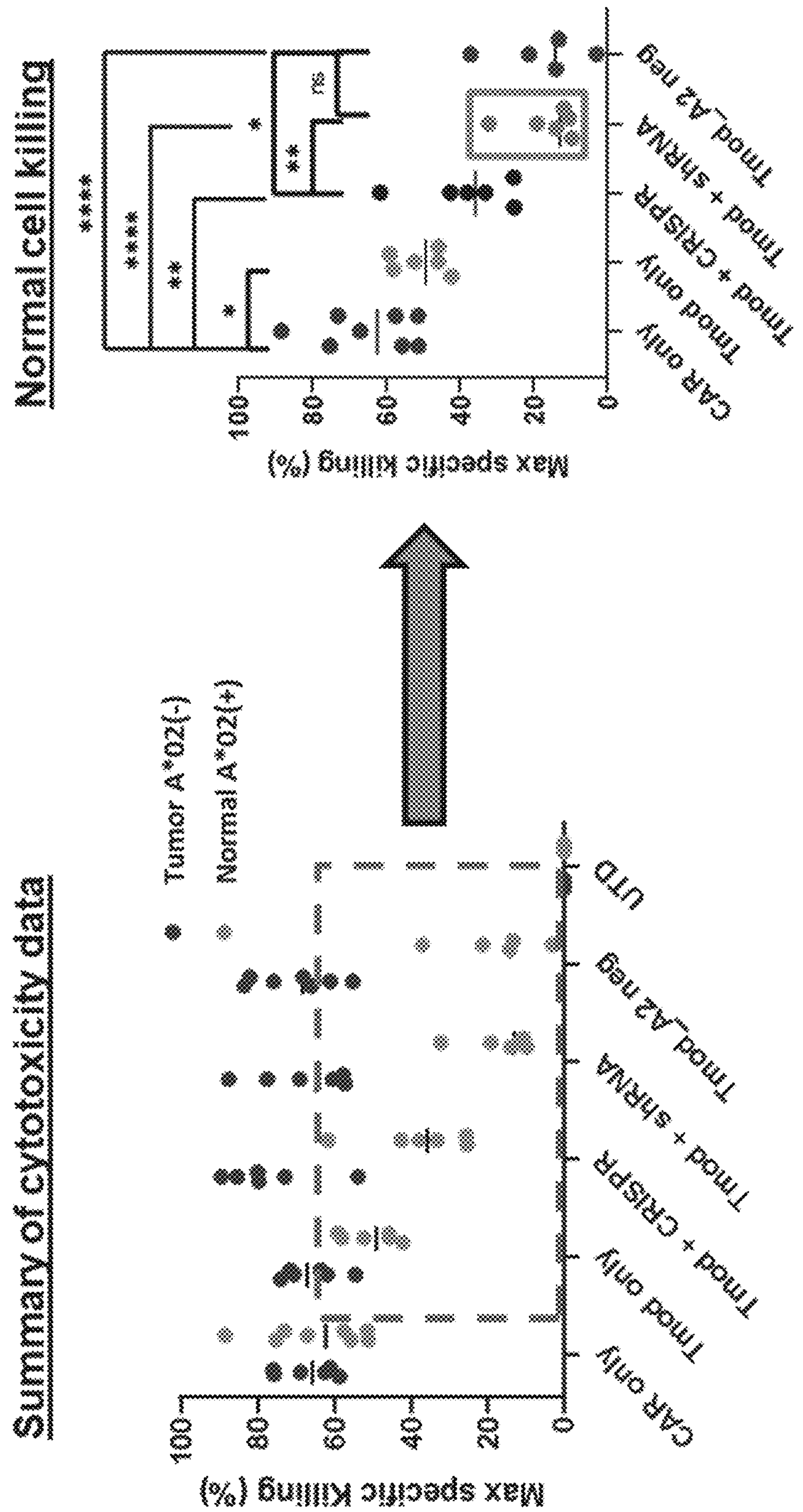
FIG. 48 shows the effect of a B2M shRNA construct on cis binding for the 1st generation autologous T cells expressing the CEA CAR and HLA-A*02 scFvLILRB1 inhibitory receptor (Tmod).
Figure 49:
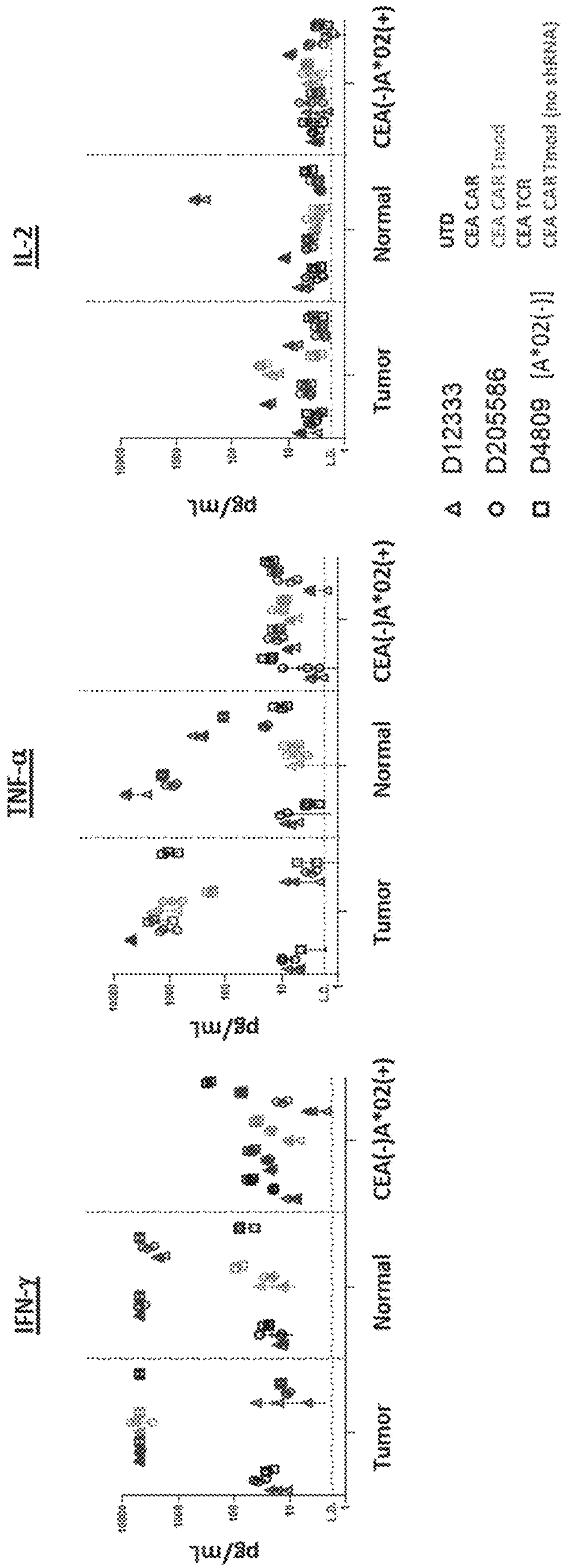
FIG. 49 shows cytokine secretion in acute cytotoxicity assays. Tumor cells were CEA(+) HLA-A*02(−) H508 cells; normal cells were CEA(+) HLA-A*02(+) H508 cells; L.D., limit of detection=background+3× standard deviation for each assay.
Figure 52:
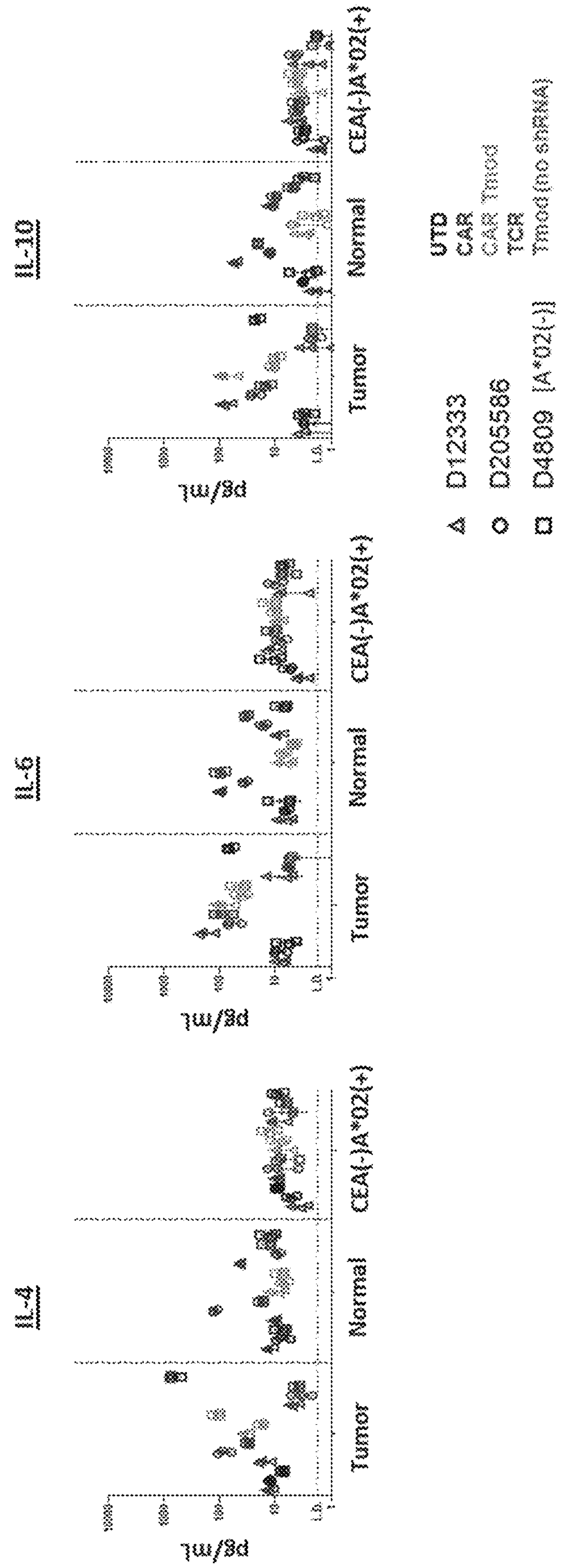
FIG. 52 shows cytokine secretion in acute cytotoxicity assays. Tumor, CEA(+) HLA-A*02(−) H508 cells; normal CEA(+) HLA-A*02(+) H508 cells; L.D., limit of detection=background+3× standard deviation for each assay.

In cytotoxicity assays using H508 target cells, the CEA CAR Tmod construct killed and blocked as effectively in A*02(+) donors (n=6) as in A*02(−) donors (n=2) (FIG. 48). These data correlated with cytokine release (FIGS. 49 and 52). Thus, the CEA CAR Tmod construct that contains a B2M shRNA module may be suitable as an autologous T cell therapy for a subset of A*02 heterozygous solid-tumor patients whose tumor contain HLA-A LOH.

In FIG. 48, the functions of Tmod with a B2M shRNA module in HLA-A*02(+) donors is indistinguishable from its function in HLA-A*02(−) donors. Normal indicates H508 target cells with native CEA and HLA-A*02 expression; while tumor indicates H508 target cells with HLA-A*02 deleted. The assay was carried out after 48 hours with an E:T of 3:1. The graph on the right contains only the normal target cell data replotted from the dashed-line box in the left graph.

In FIG. 49, cytokine expression from CEA CAR Tmod expressing cells was compared to CEA CAR expressing cells and cells expressing the benchmark TCR. Donors D123333 and D205586 were HLA-A*02(+), while donor D4809 was HLA-A*02(−). This dataset included and a test of the CEA Tmod receptors with and without the B2M shRNA. The IFN-g assay saturated at 10K pg/mL.

Additional cytokines are shown in FIG. 52. Cells expressing the CEA CAR Tmod receptors were compared against CEA CAR expressing cells and cells expressing the benchmark TCR. Donors 1 and 2 were HLA-A*02(+); donor 3 was HLA-A*02(−). The data includes a test of the CEA Tmod receptors without a B2M shRNA.

What is claimed is:

1. A polynucleotide comprising one or more polynucleotide sequences encoding:

a. a first receptor polypeptide, comprising an extracellular ligand binding domain specific to CEA cell adhesion molecule 5 (CEA); and b. a second receptor polypeptide, comprising an extracellular ligand binding domain specific to HLA-A*02, wherein the first receptor is an activator receptor responsive to CEA; and wherein the second receptor is an inhibitory receptor responsive to HLA-A*02;

wherein the extracellular ligand binding domain of the first receptor comprises a variable heavy (VH) portion comprising complementarity determining regions (CDRs) CDR-H1, CDR-H2, and CDR-H3 of SEQ ID NOS: 55, 56, and 57, respectively, and a variable light (VL) portion comprising CDRs CDR-L1, CDR-L2, and CDR-L3 of SEQ ID NOS: 59, 61, and 63, respectively; and wherein the extracellular ligand binding domain of the second receptor comprises a VH portion comprising CDRs CDR-H1, CDR-H2, and CDR-H3 of SEQ ID NOS: 106, 107, and 108, respectively, and a VL portion comprising CDRs CDR-L1, CDR-L2, and CDR-L3 of SEQ ID NOS: 103, 104, and 105, respectively.

2. The polynucleotide of claim 1, wherein the extracellular ligand binding domain of the first receptor comprises a VH portion comprising SEQ ID NO: 144 or a sequence having at least 85%, at least 90%, at least 95%, at least 97%, or at least 99% identity thereto, and a VL portion comprising SEQ ID NO: 148 or a sequence having 85%, at least 90%, at least 95%, at least 97%, or at least 99% identity thereto.

3. The polynucleotide of claim 1, wherein the extracellular ligand binding domain of the second receptor comprises a VH portion comprising SEQ ID NO: 981 or a sequence having at least 85%, at least 90%, at least 95%, at least 97%, or at least 99% identity thereto, and a VL portion comprising SEQ ID NO: 166 or a sequence having 85%, at least 90%, at least 95%, at least 97%, or at least 99% identity thereto.

4. The polynucleotide of claim 1, wherein the extracellular ligand binding domain of the first receptor comprises an scFv sequence of SEQ ID NO: 68 or a sequence having at least 85%, at least 90%, at least 95%, at least 97% or at least 99% identity thereto.

5. The polynucleotide of claim 1, wherein the extracellular ligand binding domain of the second receptor comprises an scFv sequence of SEQ ID NO: 91 or a sequence having at least 85%, at least 90%, at least 95%, at least 97% or at least 99% identity thereto.

6. The polynucleotide of claim 1, wherein the first receptor is a chimeric antigen receptor (CAR) comprising a hinge domain, a transmembrane domain and an intracellular domain.

7. The polynucleotide of claim 1, wherein the first receptor comprises a sequence of SEQ ID NO: 52, or a sequence having at least 90%, at least 95%, at least 97% or at least 99% identity thereto.

8. The polynucleotide of claim 1, wherein the second receptor comprises a LILRB1 intracellular domain or a functional variant thereof.

9. The polynucleotide of claim 8, wherein the LILRB1 intracellular domain comprises a sequence at least 90%, at least 95%, at least 97%, at least 99%, or is identical to SEQ ID NO: 131.

10. The polynucleotide of claim 1, wherein the second receptor comprises a LILRB1 transmembrane domain comprising a sequence at least 90%, at least 95%, at least 97%, at least 99% or is identical to SEQ ID NO: 135.

11. The polynucleotide of claim 1, wherein the second receptor comprises a LILRB1 hinge domain comprising a sequence at least 90%, at least 95%, at least 97%, at least 99% or is identical to SEQ ID NO: 134.

12. The polynucleotide of claim 1, wherein the second receptor comprises a sequence of SEQ ID NO: 164, or a sequence having at least 90%, at least 95%, at least 97%, or at least 99% identity thereto.

13. A pharmaceutical composition, comprising a therapeutically effective amount of the polynucleotide of claim 1 and a pharmaceutically acceptable carrier, diluent or excipient.

14. The polynucleotide of claim 1, wherein the second receptor comprises a LILRB1 intracellular domain, a LILRB1 transmembrane domain, a LILRB1 hinge domain, a functional variant of any of these, or combinations thereof.

15. The polynucleotide of claim 1, wherein the second receptor comprises a LILRB1 intracellular domain, a LILRB1 transmembrane domain, and a LILRB1 hinge domain.

16. The polynucleotide of claim 15, wherein the second receptor comprises a sequence of SEQ ID NO: 164.

17. A polynucleotide system, comprising one or more polynucleotide sequences comprising:

a. a first polynucleotide encoding a first receptor polypeptide, comprising an extracellular ligand binding domain specific to CEA cell adhesion molecule 5 positive (CEA); and b. a second polynucleotide encoding a second receptor polypeptide, comprising an extracellular ligand binding domain specific to HLA-A*02, wherein the first receptor is an activator receptor responsive to CEA on the CEA+ cancer cell; and wherein the second receptor is an inhibitory receptor responsive to HLA-A*02;

wherein the extracellular ligand binding domain of the first receptor comprises a variable heavy (VH) portion comprising complementarity determining regions (CDRs) CDR-H1, CDR-H2, and CDR-H3 of SEQ ID NOS: 55, 56, and 57, respectively, and a variable light (VL) portion comprising CDRs CDR-L1, CDR-L2, and CDR-L3 of SEQ ID NOS: 59, 61, and 63, respectively; and wherein the extracellular ligand binding domain of the second receptor comprises a VH portion comprising CDRs CDR-H1, CDR-H2, and CDR-H3 of SEQ ID NOS: 106, 107, and 108, respectively, and a VL portion comprising CDRs CDR-L1, CDR-L2, and CDR-L3 of SEQ ID NOS: 103, 104, and 105, respectively.

18. A vector comprising the polynucleotide system of claim 17.

19. The vector of claim 18, wherein the vector is a lentiviral vector.

* * * * *

SEQUENCE LISTING

```
Sequence total quantity: 984
SEQ ID NO: 1            moltype = AA  length = 702
FEATURE                 Location/Qualifiers
source                  1..702
                        mol_type = protein
                        organism = Homo sapiens
SEQUENCE: 1
MESPSAPPHR WCIPWQRLLL TASLLTFWNP PTTAKLTIES TPFNVAEGKE VLLLVHNLPQ  60
HLFGYSWYKG ERVDGNRQII GYVIGTQQAT PGPAYSGREI IYPNASLLIQ NIIQNDTGFY  120
TLHVIKSDLV NEEATGQFRV YPELPKPSIS SNNSKPVEDK DAVAFTCEPE TQDATYLWWV  180
NNQSLPVSPR LQLSNGNRTL TLFNVTRNDT ASYKCETQNP VSARRSDSVI LNVLYGPDAP  240
TISPLNTSYR SGENLNLSCH AASNPPAQYS WFVNGTFQQS TQELFIPNIT VNNSGSYTCQ  300
AHNSDTGLNR TTVTTITVYA EPPKPFITSN NSNPVEDEDA VALTCEPEIQ NTTYLWWVNN  360
QSLPVSPRLQ LSNDNRTLTL LSVTRNDVGP YECGIQNELS VDHSDPVILN VLYGPDDPTI  420
SPSYTYYRPG VNLSLSCHAA SNPPAQYSWL IDGNIQQHTQ ELFISNITEK NSGLYTCQAN  480
NSASGHSRTT VKTITVSAEL PKPSISSNNS KPVEDKDAVA FTCEPEAQNT TYLWWVNGQS  540
LPVSPRLQLS NGNRTLTLFN VTRNDARAYV CGIQNSVSAN RSDPVTLDVL YGPDTPIISP  600
PDSSYLSGAN LNLSCHSASN PSPQYSWRIN GIPQQHTQVL FIAKITPNNN GTYACFVSNL  660
ATGRNNSIVK SITVSASGTS PGLSAGATVG IMIGVLVGVA LI                    702

SEQ ID NO: 2            moltype = AA  length = 9
FEATURE                 Location/Qualifiers
source                  1..9
                        mol_type = protein
                        organism = Homo sapiens
SEQUENCE: 2
IMIGVLVGV                                                         9

SEQ ID NO: 3            moltype = AA  length = 5
FEATURE                 Location/Qualifiers
REGION                  1..5
                        note = anti-MHC-I HLA-A*02 + CEA (IMIGVLVGV) A-CDR1
source                  1..5
                        mol_type = protein
                        organism = synthetic construct
SEQUENCE: 3
TSITA                                                             5

SEQ ID NO: 4            moltype = AA  length = 6
FEATURE                 Location/Qualifiers
REGION                  1..6
                        note = anti-MHC-I HLA-A*02 + CEA (IMIGVLVGV) A-CDR2
source                  1..6
                        mol_type = protein
                        organism = synthetic construct
SEQUENCE: 4
IRSNER                                                            6

SEQ ID NO: 5            moltype = AA  length = 11
FEATURE                 Location/Qualifiers
```

```
REGION                  1..11
                        note = anti-MHC-I HLA-A*02 + CEA (IMIGVLVGV) A-CDR3
source                  1..11
                        mol_type = protein
                        organism = synthetic construct
SEQUENCE: 5
ATDLTSGGNY K                                                                11

SEQ ID NO: 6            moltype = AA  length = 11
FEATURE                 Location/Qualifiers
REGION                  1..11
                        note = anti-MHC-I HLA-A*02 + CEA (IMIGVLVGV) A-CDR3
source                  1..11
                        mol_type = protein
                        organism = synthetic construct
SEQUENCE: 6
ATDFTSGGNY K                                                                11

SEQ ID NO: 7            moltype = AA  length = 11
FEATURE                 Location/Qualifiers
REGION                  1..11
                        note = anti-MHC-I HLA-A*02 + CEA (IMIGVLVGV) A-CDR3
source                  1..11
                        mol_type = protein
                        organism = synthetic construct
SEQUENCE: 7
ATDLTTGGNY K                                                                11

SEQ ID NO: 8            moltype = AA  length = 11
FEATURE                 Location/Qualifiers
REGION                  1..11
                        note = anti-MHC-I HLA-A*02 + CEA (IMIGVLVGV) A-CDR3
source                  1..11
                        mol_type = protein
                        organism = synthetic construct
SEQUENCE: 8
ATDFTTGGNY K                                                                11

SEQ ID NO: 9            moltype = AA  length = 5
FEATURE                 Location/Qualifiers
REGION                  1..5
                        note = anti-MHC-I HLA-A*02 + CEA (IMIGVLVGV) B-CDR1
source                  1..5
                        mol_type = protein
                        organism = synthetic construct
SEQUENCE: 9
KGHPV                                                                       5

SEQ ID NO: 10           moltype = AA  length = 6
FEATURE                 Location/Qualifiers
REGION                  1..6
                        note = anti-MHC-I HLA-A*02 + CEA (IMIGVLVGV) B-CDR2
source                  1..6
                        mol_type = protein
                        organism = synthetic construct
SEQUENCE: 10
FQNQEV                                                                      6

SEQ ID NO: 11           moltype = AA  length = 11
FEATURE                 Location/Qualifiers
REGION                  1..11
                        note = anti-MHC-I HLA-A*02 + CEA (IMIGVLVGV) B-CDR3
source                  1..11
                        mol_type = protein
                        organism = synthetic construct
SEQUENCE: 11
ASSLGLGDYE Q                                                                11

SEQ ID NO: 12           moltype = AA  length = 11
FEATURE                 Location/Qualifiers
REGION                  1..11
                        note = anti-MHC-I HLA-A*02 + CEA (IMIGVLVGV) B-CDR3
source                  1..11
                        mol_type = protein
                        organism = synthetic construct
SEQUENCE: 12
ASSLGTGDYE Q                                                                11

SEQ ID NO: 13           moltype = AA  length = 616
```

```
FEATURE                 Location/Qualifiers
source                  1..616
                        mol_type = protein
                        organism = Homo sapiens
SEQUENCE: 13
MAPRARRRRP LFALLLLCAL LARLQVALQI APPCTSEKHY EHLGRCCNKC EPGKYMSSKC  60
TTTSDSVCLP CGPDEYLDSW NEEDKCLLHK VCDTGKALVA VVAGNSTTPR RCACTAGYHW  120
SQDCECCRRN TECAPGLGAQ HPLQLNKDTV CKPCLAGYFS DAFSSTDKCR PWTNCTFLGK  180
RVEHHGTEKS DAVCSSSLPA RKPPNEPHVY LPGLIILLLF ASVALVAAII FGVCYRKKGK  240
ALTANLWHWI NEACGRLSGD KESSGDSCVS THTANFGQQG ACEGVLLLTL EEKTFPEDMC  300
YPDQGGVCQG TCVGGGPYAQ GEDARMLSLV SKTEIEEDSF RQMPTEDEYM DRPSQPTDQL  360
LFLTEPGSKS TPPFSEPLEV GENDSLSQCF TGTQSTVGSE SCNCTEPLCR TDWTPMSSEN  420
YLQKEVDSGH CPHWAASPSP NWADVCTGCR NPPGEDCEPL VGSPKRGPLP QCAYGMGLPP  480
EEEASRTEAR DQPEDGADGR LPSSARAGAG SGSSPGGQSP ASGNVTGNSN STFISSGQVM  540
NFKGDIIVVY VSQTSQEGAA AAAEPMGRPV QEETLARRDS FAGNGPRFPD PCGGPEGLRE  600
PEKASRPVQE QGGAKA                                                616

SEQ ID NO: 14           moltype = AA  length = 1179
FEATURE                 Location/Qualifiers
source                  1..1179
                        mol_type = protein
                        organism = Homo sapiens
SEQUENCE: 14
MWLFHTLLCI ASLALLAAFN VDVARPWLTP KGGAPFVLSS LLHQDPSTNQ TWLLVTSPRT  60
KRTPGPLHRC SLVQDEILCH PVEHVPIPKG RHRGVTVVRS HHGVLICIQV LVRRPHSLSS  120
ELTGTCSLLG PDLRPQAQAN FFDLENLLDP DARVDTGDCY SNKEGGGEDD VNTARQRRAL  180
EKEEEEDKEE EEDEEEEEAG TEIAIILDGS GSIDPPDFQR AKDFISNMMR NFYEKCFECN  240
FALVQYGGVI QTEFDLRDSQ DVMASLARVQ NITQVGSVTK TASAMQHVLD SIFTSSHGSR  300
RKASKVMVVL TDGGIFEDPL NLTTVINSPK MQGVERFAIG VGEEFKSART ARELNLIASD  360
PDETHAFKVT NYMALDGLLS KLRYNIISME GTVGDALHYQ LAQIGFSAQI LDERQVLLGA  420
VGAFDWSGGA LLYDTRSRRG RFLNQTAAAA ADAEAAQYSY LGYAVAVLHK TCSLSYIAGA  480
PRYKHHGAVF ELQKEGREAS FLPVLEGEQM GSYFGSELCP VDIDMDGSTD FLLVAAPFYH  540
VHGEEGRVYV YRLSEQDGSF SLARILSGHP GFTNARFGFA MAAMGDLSQD KLTDVAIGAP  600
LEGFGADDGA SFGSVYIYNG HWDGLSASPS QRIRASTVAP GLQYFGMSMA GGFDISGDGL  660
ADITVGTLGQ AVVFRSRPVV RLKVSMAFTP SALPIGFNGV VNVRLCFEIS SVTTASESGL  720
REALLNFTLD VDVGKQRRRL QCSDVRSCLG CLREWSSGSQ LCEDLLLMPT EGELCEEDCF  780
SNASVKVSYQ LQTPEGQTDH PQPILDRYTE PFAIFQLPYE KACKNKLFCV AELQLATTVS  840
QQELVVGLTK ELTLNINLTN SGEDSYMTSM ALNYPRNLQL KRMQKPPSPN IQCDDPQPVA  900
SVLIMNCRIG HPVLKRSSAH VSVVWQLEEN AFPNRTADIT VTVTNSNERR SLANETHTLQ  960
FRHGFVAVLS KPSIMYVNTG QGLSHHKEFL FHVHGENLFG AEYQLQICVP TKLRGLQVVA  1020
VKKLTRTQAS TVCTWSQERA CAYSSVQHVE EWHSVSCVIA SDKENVTVAA EISWDHSEEL  1080
LKDVTELQIL GEISFNKSLY EGLNAENHRT KITVVFLKDE KYHSLPIIIK GSVGGLLVLI  1140
VILVILFKCG FFKRKYQQLN LESIRKAQLK SENLLEEEN                       1179

SEQ ID NO: 15           moltype = AA  length = 701
FEATURE                 Location/Qualifiers
source                  1..701
                        mol_type = protein
                        organism = Homo sapiens
SEQUENCE: 15
MESPSAPPHR WCIPWQRLLL TASLLTFWNP PTTAKLTIES TPFNVAEGKE VLLLVHNLPQ  60
HLFGYSWYKG ERVDGNRQII GYVIGTQQAT PGPAYSGREI IYPNASLLIQ NIIQNDTGFY  120
TLHVIKSDLV NEEATGQFRV YPELPKPSIS SNNSKPVEDK DAVAFTCEPE TQDATYLWWV  180
NNQSLPVSPR LQLSNGNRTL TLFNVTRNDT ASYKCETQNP VSARRSDSVI LNVLYGPDAP  240
TISPLNTSYR SGENLNLSCH AASNPPAQYS WFVNGTFQQS TQELFIPNIT VNNSGSYTCQ  300
AHNSDTGLNR TTVTTITVYE PPKPFITSNN SNPVEDEDAV ALTCEPEIQN TTYLWWVNNQ  360
SLPVSPRLQL SNDNRTLTLL SVTRNDVGPY ECGIQNELSV DHSDPVILNV LYGPDDPTIS  420
PSYTYYRPGV NLSLSCHAAS NPPAQYSWLI DGNIQQHTQE LFISNITEKN SGLYTCQANN  480
SASGHSRTTV KTITVSAELP KPSISSNNSK PVEDKDAVAF TCEPEAQNTT YLWWVNGQSL  540
PVSPRLQLSN GNRTLTLFNV TRNDARAYVC GIQNSVSANR SDPVTLDVLY GPDTPIISPP  600
DSSYLSGANL NLSCHSASNP SPQYSWRING IPQQHTQVLF IAKITPNNNG TYACFVSNLA  660
TGRNNSIVKS ITVSASGTSP GLSAGATVGI MIGVLVGVAL I                    701

SEQ ID NO: 16           moltype = AA  length = 598
FEATURE                 Location/Qualifiers
REGION                  1..598
                        note = CT 548: pLenti 1 CEA TCR TRAV8-1*01 118P & 119T with
                         murineconstant region
source                  1..598
                        mol_type = protein
                        organism = synthetic construct
SEQUENCE: 16
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTSGGNYK  120
PTFGKGTSLV VHPDIQNPEP AVYQLKDPRS QDSTLCLFTD FDSQINVPKT MESGTFITDK  180
TVLDMKAMDS KSNGAIAWSN QTSFTCQDIF KETNATYPSS DVPCDATLTE KSFETDMNLN  240
FQNLSVMGLR ILLLKVAGFN LLMTLRLWSS GSGATNFSLL KQAGDVEENP GPMATRLLCY  300
TVLCLLGARI LNSKVIQTPR YLVKGQGQKA KMRCIPEKGH PVVFWYQQNK NNEFKFLINF  360
QNQEVLQQID MTEKRFSAEC PSNSPCSLEI QSSEAGDSAL YLCASSLGLG DYEQYFGPGT  420
```

```
RLTVLEDLRN VTPPKVSLFE PSKAEIANKQ KATLVCLARG FFPDHVELSW WVNGKEVHSG  480
VSTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 17          moltype = AA  length = 598
FEATURE                Location/Qualifiers
REGION                 1..598
                       note = CT 549: pLenti 1 CEA TCR TRAV8-1*01 118P & 119T
                        TRBV26*01 L117Twith murine constant region
source                 1..598
                       mol_type = protein
                       organism = synthetic construct
SEQUENCE: 17
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTSGGNYK  120
PTFGKGTSLV VHPDIQNPEP AVYQLKDPRS QDSTLCLFTD FDSQINVPKT MESGTFITDK  180
TVLDMKAMDS KSNGAIAWSN QTSFTCQDIF KETNATYPSS DVPCDATLTE KSFETDMNLN  240
FQNLSVMGLR ILLLKVAGFN LLMTLRLWSS GSGATNFSLL KQAGDVEENP GPMATRLLCY  300
TVLCLLGARI LNSKVIQTPR YLVKGQGQKA KMRCIPEKGH PVVFWYQQNK NNEFKFLINF  360
QNQEVLQQID MTEKRFSAEC PSNSPCSLEI QSSEAGDSAL YLCASSLGTG DYEQYFGPGT  420
RLTVLEDLRN VTPPKVSLFE PSKAEIANKQ KATLVCLARG FFPDHVELSW WVNGKEVHSG  480
VSTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 18          moltype = AA  length = 598
FEATURE                Location/Qualifiers
REGION                 1..598
                       note = CT 550: pLenti 1 CEA TCR TRAV8-1*01 118P & 119T with
                        murineconstant region
source                 1..598
                       mol_type = protein
                       organism = synthetic construct
SEQUENCE: 18
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTSGGNYK  120
PTFGKGTSLV VHPNIQNPEP AVYQLKDPRS QDSTLCLFTD FDSQINVPKT MESGTFITDK  180
CVLDMKAMDS KSNGAIAWSN QTSFTCQDIF KETNATYPSS DVPCDATLTE KSFETDMNLN  240
FQNLLVIVLR ILLLKVAGFN LLMTLRLWSS GSGATNFSLL KQAGDVEENP GPMATRLLCY  300
TVLCLLGARI LNSKVIQTPR YLVKGQGQKA KMRCIPEKGH PVVFWYQQNK NNEFKFLINF  360
QNQEVLQQID MTEKRFSAEC PSNSPCSLEI QSSEAGDSAL YLCASSLGLG DYEQYFGPGT  420
RLTVLEDLRN VTPPKVSLFE PSKAEIANKQ KATLVCLARG FFPDHVELSW WVNGKEVHSG  480
VCTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 19          moltype = AA  length = 598
FEATURE                Location/Qualifiers
REGION                 1..598
                       note = CT 551: pLenti 1 CEA TCR TRAV8-1*01 L110F 118P &
                        119T with murineconstant region
source                 1..598
                       mol_type = protein
                       organism = synthetic construct
SEQUENCE: 19
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDFTSGGNYK  120
PTFGKGTSLV VHPDIQNPEP AVYQLKDPRS QDSTLCLFTD FDSQINVPKT MESGTFITDK  180
TVLDMKAMDS KSNGAIAWSN QTSFTCQDIF KETNATYPSS DVPCDATLTE KSFETDMNLN  240
FQNLSVMGLR ILLLKVAGFN LLMTLRLWSS GSGATNFSLL KQAGDVEENP GPMATRLLCY  300
TVLCLLGARI LNSKVIQTPR YLVKGQGQKA KMRCIPEKGH PVVFWYQQNK NNEFKFLINF  360
QNQEVLQQID MTEKRFSAEC PSNSPCSLEI QSSEAGDSAL YLCASSLGLG DYEQYFGPGT  420
RLTVLEDLRN VTPPKVSLFE PSKAEIANKQ KATLVCLARG FFPDHVELSW WVNGKEVHSG  480
VSTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 20          moltype = AA  length = 598
FEATURE                Location/Qualifiers
REGION                 1..598
                       note = CT 552: pLenti 1 CEA TCR TRAV8-1*01 S112T 118P &
                        119T with murineconstant region
source                 1..598
                       mol_type = protein
                       organism = synthetic construct
SEQUENCE: 20
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTTGGNYK  120
PTFGKGTSLV VHPDIQNPEP AVYQLKDPRS QDSTLCLFTD FDSQINVPKT MESGTFITDK  180
TVLDMKAMDS KSNGAIAWSN QTSFTCQDIF KETNATYPSS DVPCDATLTE KSFETDMNLN  240
FQNLSVMGLR ILLLKVAGFN LLMTLRLWSS GSGATNFSLL KQAGDVEENP GPMATRLLCY  300
TVLCLLGARI LNSKVIQTPR YLVKGQGQKA KMRCIPEKGH PVVFWYQQNK NNEFKFLINF  360
```

```
QNQEVLQQID MTEKRFSAEC PSNSPCSLEI QSSEAGDSAL YLCASSLGLG DYEQYFGPGT  420
RLTVLEDLRN VTPPKVSLFE PSKAEIANKQ KATLVCLARG FFPDHVELSW WVNGKEVHSG  480
VSTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 21           moltype = AA  length = 598
FEATURE                 Location/Qualifiers
REGION                  1..598
                        note = CT 553: pLenti 1 CEA TCR TRAV8-1*01 L110F S112T 118P
                         & 119T withmurine constant region
source                  1..598
                        mol_type = protein
                        organism = synthetic construct
SEQUENCE: 21
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDFTTGGNYK  120
PTFGKGTSLV VHPDIQNPEP AVYQLKDPRS QDSTLCLFTD FDSQINVPKT MESGTFITDK  180
TVLDMKAMDS KSNGAIAWSN QTSFTCQDIF KETNATYPSS DVPCDATLTE KSFETDMNLN  240
FQNLSVMGLR ILLLKVAGFN LLMTLRLWSS GSGATNFSLL KQAGDVEENP GPMATRLLCY  300
TVLCLLGARI LNSKVIQTPR YLVKGQGQKA KMRCIPEKGH PVVFWYQQNK NNEFKFLINF  360
QNQEVLQQID MTEKRFSAEC PSNSPCSLEI QSSEAGDSAL YLCASSLGLG DYEQYFGPGT  420
RLTVLEDLRN VTPPKVSLFE PSKAEIANKQ KATLVCLARG FFPDHVELSW WVNGKEVHSG  480
VSTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 22           moltype = AA  length = 598
FEATURE                 Location/Qualifiers
REGION                  1..598
                        note = CT 554: pLenti 1 CEA TCR TRAV8-1*01 L110F 118P &
                         119T TRBV26*01L117T with murine constant region
source                  1..598
                        mol_type = protein
                        organism = synthetic construct
SEQUENCE: 22
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDFTSGGNYK  120
PTFGKGTSLV VHPDIQNPEP AVYQLKDPRS QDSTLCLFTD FDSQINVPKT MESGTFITDK  180
TVLDMKAMDS KSNGAIAWSN QTSFTCQDIF KETNATYPSS DVPCDATLTE KSFETDMNLN  240
FQNLSVMGLR ILLLKVAGFN LLMTLRLWSS GSGATNFSLL KQAGDVEENP GPMATRLLCY  300
TVLCLLGARI LNSKVIQTPR YLVKGQGQKA KMRCIPEKGH PVVFWYQQNK NNEFKFLINF  360
QNQEVLQQID MTEKRFSAEC PSNSPCSLEI QSSEAGDSAL YLCASSLGTG DYEQYFGPGT  420
RLTVLEDLRN VTPPKVSLFE PSKAEIANKQ KATLVCLARG FFPDHVELSW WVNGKEVHSG  480
VSTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 23           moltype = AA  length = 598
FEATURE                 Location/Qualifiers
REGION                  1..598
                        note = CT 555: pLenti 1 CEA TCR TRAV8-1*01 S112T 118P &
                         119T TRBV26*01L117T with murine constant region
source                  1..598
                        mol_type = protein
                        organism = synthetic construct
SEQUENCE: 23
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTTGGNYK  120
PTFGKGTSLV VHPDIQNPEP AVYQLKDPRS QDSTLCLFTD FDSQINVPKT MESGTFITDK  180
TVLDMKAMDS KSNGAIAWSN QTSFTCQDIF KETNATYPSS DVPCDATLTE KSFETDMNLN  240
FQNLSVMGLR ILLLKVAGFN LLMTLRLWSS GSGATNFSLL KQAGDVEENP GPMATRLLCY  300
TVLCLLGARI LNSKVIQTPR YLVKGQGQKA KMRCIPEKGH PVVFWYQQNK NNEFKFLINF  360
QNQEVLQQID MTEKRFSAEC PSNSPCSLEI QSSEAGDSAL YLCASSLGTG DYEQYFGPGT  420
RLTVLEDLRN VTPPKVSLFE PSKAEIANKQ KATLVCLARG FFPDHVELSW WVNGKEVHSG  480
VSTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 24           moltype = AA  length = 598
FEATURE                 Location/Qualifiers
REGION                  1..598
                        note = CT 556: pLenti 1 CEA TCR TRAV8-1*01 L110F S112T 118P
                         & 119TTRBV26*01 L117T with murine constant region
source                  1..598
                        mol_type = protein
                        organism = synthetic construct
SEQUENCE: 24
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDFTTGGNYK  120
PTFGKGTSLV VHPDIQNPEP AVYQLKDPRS QDSTLCLFTD FDSQINVPKT MESGTFITDK  180
TVLDMKAMDS KSNGAIAWSN QTSFTCQDIF KETNATYPSS DVPCDATLTE KSFETDMNLN  240
FQNLSVMGLR ILLLKVAGFN LLMTLRLWSS GSGATNFSLL KQAGDVEENP GPMATRLLCY  300
```

```
TVLCLLGARI LNSKVIQTPR YLVKGQGQKA KMRCIPEKGH PVVFWYQQNK NNEFKFLINF  360
QNQEVLQQID MTEKRFSAEC PSNSPCSLEI QSSEAGDSAL YLCASSLGTG DYEQYFGPGT  420
RLTVLEDLRN VTPPKVSLFE PSKAEIANKQ KATLVCLARG FFPDHVELSW WVNGKEVHSG  480
VSTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 25          moltype = AA  length = 598
FEATURE                Location/Qualifiers
REGION                 1..598
                       note = CT 557: pLenti 1 CEA TCR TRAV8-1*01 L110F 118P &
                        119T with murineconstant region
source                 1..598
                       mol_type = protein
                       organism = synthetic construct
SEQUENCE: 25
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDFTSGGNYK  120
PTFGKGTSLV VHPNIQNPEP AVYQLKDPRS QDSTLCLFTD FDSQINVPKT MESGTFITDK  180
CVLDMKAMDS KSNGAIAWSN QTSFTCQDIF KETNATYPSS DVPCDATLTE KSFETDMNLN  240
FQNLLVIVLR ILLLKVAGFN LLMTLRLWSS GSGATNFSLL KQAGDVEENP GPMATRLLCY  300
TVLCLLGARI LNSKVIQTPR YLVKGQGQKA KMRCIPEKGH PVVFWYQQNK NNEFKFLINF  360
QNQEVLQQID MTEKRFSAEC PSNSPCSLEI QSSEAGDSAL YLCASSLGLG DYEQYFGPGT  420
RLTVLEDLRN VTPPKVSLFE PSKAEIANKQ KATLVCLARG FFPDHVELSW WVNGKEVHSG  480
VCTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 26          moltype = AA  length = 598
FEATURE                Location/Qualifiers
REGION                 1..598
                       note = CT 558: pLenti 1 CEA TCR TRAV8-1*01 S112T 118P &
                        119T with murineconstant region
source                 1..598
                       mol_type = protein
                       organism = synthetic construct
SEQUENCE: 26
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTTGGNYK  120
PTFGKGTSLV VHPNIQNPEP AVYQLKDPRS QDSTLCLFTD FDSQINVPKT MESGTFITDK  180
CVLDMKAMDS KSNGAIAWSN QTSFTCQDIF KETNATYPSS DVPCDATLTE KSFETDMNLN  240
FQNLLVIVLR ILLLKVAGFN LLMTLRLWSS GSGATNFSLL KQAGDVEENP GPMATRLLCY  300
TVLCLLGARI LNSKVIQTPR YLVKGQGQKA KMRCIPEKGH PVVFWYQQNK NNEFKFLINF  360
QNQEVLQQID MTEKRFSAEC PSNSPCSLEI QSSEAGDSAL YLCASSLGLG DYEQYFGPGT  420
RLTVLEDLRN VTPPKVSLFE PSKAEIANKQ KATLVCLARG FFPDHVELSW WVNGKEVHSG  480
VCTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 27          moltype = AA  length = 598
FEATURE                Location/Qualifiers
REGION                 1..598
                       note = CT 559: pLenti 1 CEA TCR TRAV8-1*01 L110F S112T 118P
                        & 119T withmurine constant region
source                 1..598
                       mol_type = protein
                       organism = synthetic construct
SEQUENCE: 27
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDFTTGGNYK  120
PTFGKGTSLV VHPNIQNPEP AVYQLKDPRS QDSTLCLFTD FDSQINVPKT MESGTFITDK  180
CVLDMKAMDS KSNGAIAWSN QTSFTCQDIF KETNATYPSS DVPCDATLTE KSFETDMNLN  240
FQNLLVIVLR ILLLKVAGFN LLMTLRLWSS GSGATNFSLL KQAGDVEENP GPMATRLLCY  300
TVLCLLGARI LNSKVIQTPR YLVKGQGQKA KMRCIPEKGH PVVFWYQQNK NNEFKFLINF  360
QNQEVLQQID MTEKRFSAEC PSNSPCSLEI QSSEAGDSAL YLCASSLGLG DYEQYFGPGT  420
RLTVLEDLRN VTPPKVSLFE PSKAEIANKQ KATLVCLARG FFPDHVELSW WVNGKEVHSG  480
VCTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 28          moltype = AA  length = 598
FEATURE                Location/Qualifiers
REGION                 1..598
                       note = CT 560: pLenti 1 CEA TCR TRAV8-1*01 118P & 119T
                        TRBV26*01 L117Twith murine constant region
source                 1..598
                       mol_type = protein
                       organism = synthetic construct
SEQUENCE: 28
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTSGGNYK  120
PTFGKGTSLV VHPNIQNPEP AVYQLKDPRS QDSTLCLFTD FDSQINVPKT MESGTFITDK  180
CVLDMKAMDS KSNGAIAWSN QTSFTCQDIF KETNATYPSS DVPCDATLTE KSFETDMNLN  240
```

```
FQNLLVIVLR ILLLKVAGFN LLMTLRLWSS GSGATNFSLL KQAGDVEENP GPMATRLLCY  300
TVLCLLGARI LNSKVIQTPR YLVKGQGQKA KMRCIPEKGH PVVFWYQQNK NNEFKFLINF  360
QNQEVLQQID MTEKRFSAEC PSNSPCSLEI QSSEAGDSAL YLCASSLGTG DYEQYFGPGT  420
RLTVLEDLRN VTPPKVSLFE PSKAEIANKQ KATLVCLARG FFPDHVELSW WVNGKEVHSG  480
VCTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 29          moltype = AA  length = 598
FEATURE                Location/Qualifiers
REGION                 1..598
                       note = CT 561: pLenti 1 CEA TCR TRAV8-1*01 L110F 118P &
                        119T TRBV26*01L117T with murine constant region
source                 1..598
                       mol_type = protein
                       organism = synthetic construct
SEQUENCE: 29
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTTGGNYK  120
PTFGKGTSLV VHPNIQNPEP AVYQLKDPRS QDSTLCLFTD FDSQINVPKT MESGTFITDK  180
CVLDMKAMDS KSNGAIAWSN QTSFTCQDIF KETNATYPSS DVPCDATLTE KSFETDMNLN  240
FQNLLVIVLR ILLLKVAGFN LLMTLRLWSS GSGATNFSLL KQAGDVEENP GPMATRLLCY  300
TVLCLLGARI LNSKVIQTPR YLVKGQGQKA KMRCIPEKGH PVVFWYQQNK NNEFKFLINF  360
QNQEVLQQID MTEKRFSAEC PSNSPCSLEI QSSEAGDSAL YLCASSLGTG DYEQYFGPGT  420
RLTVLEDLRN VTPPKVSLFE PSKAEIANKQ KATLVCLARG FFPDHVELSW WVNGKEVHSG  480
VCTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 30          moltype = AA  length = 598
FEATURE                Location/Qualifiers
REGION                 1..598
                       note = CT 562: pLenti 1 CEA TCR TRAV8-1*01 S112T 118P &
                        119T TRBV26*01L117T with murine constant region
source                 1..598
                       mol_type = protein
                       organism = synthetic construct
SEQUENCE: 30
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTTGGNYK  120
PTFGKGTSLV VHPNIQNPEP AVYQLKDPRS QDSTLCLFTD FDSQINVPKT MESGTFITDK  180
CVLDMKAMDS KSNGAIAWSN QTSFTCQDIF KETNATYPSS DVPCDATLTE KSFETDMNLN  240
FQNLLVIVLR ILLLKVAGFN LLMTLRLWSS GSGATNFSLL KQAGDVEENP GPMATRLLCY  300
TVLCLLGARI LNSKVIQTPR YLVKGQGQKA KMRCIPEKGH PVVFWYQQNK NNEFKFLINF  360
QNQEVLQQID MTEKRFSAEC PSNSPCSLEI QSSEAGDSAL YLCASSLGTG DYEQYFGPGT  420
RLTVLEDLRN VTPPKVSLFE PSKAEIANKQ KATLVCLARG FFPDHVELSW WVNGKEVHSG  480
VCTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 31          moltype = AA  length = 598
FEATURE                Location/Qualifiers
REGION                 1..598
                       note = CT 563: pLenti 1 CEA TCR TRAV8-1*01 L110F S112T 118P
                        & 119TTRBV26*01 L117T with murine constant region
source                 1..598
                       mol_type = protein
                       organism = synthetic construct
SEQUENCE: 31
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDFTTGGNYK  120
PTFGKGTSLV VHPNIQNPEP AVYQLKDPRS QDSTLCLFTD FDSQINVPKT MESGTFITDK  180
CVLDMKAMDS KSNGAIAWSN QTSFTCQDIF KETNATYPSS DVPCDATLTE KSFETDMNLN  240
FQNLLVIVLR ILLLKVAGFN LLMTLRLWSS GSGATNFSLL KQAGDVEENP GPMATRLLCY  300
TVLCLLGARI LNSKVIQTPR YLVKGQGQKA KMRCIPEKGH PVVFWYQQNK NNEFKFLINF  360
QNQEVLQQID MTEKRFSAEC PSNSPCSLEI QSSEAGDSAL YLCASSLGTG DYEQYFGPGT  420
RLTVLEDLRN VTPPKVSLFE PSKAEIANKQ KATLVCLARG FFPDHVELSW WVNGKEVHSG  480
VCTDPQAYKE SNYSYCLSSR LRVSATFWHN PRNHFRCQVQ FHGLSEEDKW PEGSPKPVTQ  540
NISAEAWGRA DCGITSASYQ QGVLSATILY EILLGKATLY AVLVSTLVVM AMVKRKNS    598

SEQ ID NO: 32          moltype = AA  length = 625
FEATURE                Location/Qualifiers
source                 1..625
                       mol_type = protein
                       organism = Mus musculus
SEQUENCE: 32
MAPRARRRRQ LPAPLLALCV LLVPLQVTLQ VTPPCTQERH YEHLGRCCSR CEPGKYLSSK  60
CTPTSDSVCL PCGPDEYLDT WNEEDKCLLH KVCDAGKALV AVDPGNHTAP RRCACTAGYH  120
WNSDCECCRR NTECAPGFGA QHPLQLNKDT VCTPCLLGFF SDVFSSTDKC KPWTNCTLLG  180
KLEAHQGTTE SDVVCSSSMT LRRPPKEAQA YLPSLIVLLL FISVVVVAAI IFGVYYRKGG  240
KALTANLWNW VNDACSSLSG NKESSGDRCA GSHSATSSQQ EVCEGILLMT REEKMVPEDG  300
AGVCGPVCAA GGPWAEVRDS RTFTLVSEVE TQGDLSRKIP TEDEYTDRPS QPSTGSLLLI  360
```

```
QQGSKSIPPF QEPLEVGEND SLSQCFTGTE STVDSEGCDF TEPPSRTDSM PVSPEKHLTK  420
EIEGDSCLPW VVSSNSTDGY TGSGNTPGED HEPFPGSLKC GPLPQCAYSM GFPSEAAASM  480
AEAGVRPQDR ADEKGASGSG SSPSDQPPAS GNVTGNSNST FISSGQVMNF KGDIIVVYVS  540
QTSQEGPGSA EPESEPVGRP VQEETLAHRD SFAGTAPRFP DVCATGAGLQ EQGAPRQKDG  600
TSRPVQEQGG AQTSLHTQGS GQCAE                                       625

SEQ ID NO: 33          moltype = AA  length = 501
FEATURE                Location/Qualifiers
source                 1..501
                       mol_type = protein
                       organism = Homo sapiens
SEQUENCE: 33
MTPGALLMLL GALGAPLAPG VRGSEAEGRL REKLFSGYDS SVRPAREVGD RVRVSVGLIL  60
AQLISLNEKD EEMSTKVYLD LEWTDYRLSW DPAEHDGIDS LRITAESVWL PDVVLLNNND  120
GNFDVALDIS VVVSSDGSVR WQPPGIYRSS CSIQVTYFPF DWQNCTMVFS SYSYDSSEVS  180
LQTGLGPDGQ GHQEIHIHEG TFIENGQWEI IHKPSRLIQP PGDPRGGREG QRQEVIFYLI  240
IRRKPLFYLV NVIAPCILIT LLAIFVFYLP PDAGEKMGLS IFALLTLTVF LLLLADKVPE  300
TSLSVPIIIK YLMFTMVLVT FSVILSVVVL NLHHRSPHTH QMPLWVRQIF IHKLPLYLRL  360
KRPKPERDLM PEPPHCSSPG SGWGRGTDEY FIRKPPSDFL FPKPNRFQPE LSAPDLRRFI  420
DGPNRAVALL PELREVVSSI SYIARQLQEQ EDHDALKEDW QFVAMVVDRL FLWTFIIFTS  480
VGTLVIFLDA TYHLPPPDPF P                                           501

SEQ ID NO: 34          moltype = AA  length = 839
FEATURE                Location/Qualifiers
source                 1..839
                       mol_type = protein
                       organism = Homo sapiens
SEQUENCE: 34
MKKWSSTDLG AAADPLQKDT CPDPLDGDPN SRPPPAKPQL STAKSRTRLF GKGDSEEAFP  60
VDCPHEEGEL DSCPTITVSP VITIQRPGDG PTGARLLSQD SVAASTEKTL RLYDRRSIFE  120
AVAQNNCQDL ESLLLFLQKS KKHLTDNEFK DPETGKTCLL KAMLNLHDGQ NTTIPLLLEI  180
ARQTDSLKEL VNASYTDSYY KGQTALHIAI ERRNMALVTL LVENGADVQA AAHGDFFKKT  240
KGRPGFYFGE LPLSLAACTN QLGIVKFLLQ NSWQTADISA RDSVGNTVLH ALVEVADNTA  300
DNTKFVTSMY NEILMLGAKL HPTLKLEELT NKKGMTPLAL AAGTGKIGVL AYILQREIQE  360
PECRHLSRKF TEWAYGPVHS SLYDLSCIDT CEKNSVLEVI AYSSSETPNR HDMLLVEPLN  420
RLLQDKWDRF VKRIFYFNFL VYCLYMIIFT MAAYYRPVDG LPPFKMEKTG DYFRVTGEIL  480
SVLGGVYFFF RGIQYFLQRR PSMKTLFVDS YSEMLFFLQS LFMLATVVLY FSHLKEYVAS  540
MVFSLALGWT NMLYYTRGFQ QMGIYAVMIE KMILRDLCRF MFVYIVFLFG FSTAVVTLIE  600
DGKNDSLPSE STSHRWRGPA CRPPDSSYNS LYSTCLELFK FTIGMGDLEF TENYDFKAVF  660
IILLLAYVIL TYILLLNMLI ALMGETVNKI AQESKNIWKL QRAITILDTE KSFLKCMRKA  720
FRSGKLLQVG YTPDGKDDYR WCFRVDEVNW TTWNTNVGII NEDPGNCEGV KRTLSFSLRS  780
SRVSGRHWKN FALVPLLREA SARDRQSAQP EEVYLRQFSG SLKPEDAEVF KSPAASGEK   839

SEQ ID NO: 35          moltype = AA  length = 830
FEATURE                Location/Qualifiers
source                 1..830
                       mol_type = protein
                       organism = Homo sapiens
SEQUENCE: 35
MGLGLLLPLL LLWTRGTQGS ELDPKGQHVC VASSPSAELQ CCAGWRQKDQ ECTIPICEGP  60
DACQKDEVCV KPGLCRCKPG FFGAHCSSRC PGQYWGPDCR ESCPCHPHGQ CEPATGACQC  120
QADRWGARCE FPCACGPHGR CDPATGVCHC EPGWWSSTCR RPCQCNTAAA RCEQATGACV  180
CKPGWWGRRC SFRCNCHGSP CEQDSGRCAC RPGWWGPECQ QQCECVRGRC SAASGECTCP  240
PGFRGARCEL PCPAGSHGVQ CAHSCGRCKH NEPCSPDTGS CESCEPGWNG TQCQQPCLPG  300
TFGESCEQQC PHCRHGEACE PDTGHCQRCD PGWLGPRCED PCPTGTFGED CGSTCPTCVQ  360
GSCDTVTGDC VCSAGYWGPS CNASCPAGFH GNNCSVPCEC PEGLCHPVSG SCQPGSGSRD  420
TALIAGSLVP LLLLFLGLAC CACCCWAPRS DLKDRPARDG ATVSRMKLQV WGTLTSLGST  480
LPCRSLSSHK LPWVTVSHHD PEVPFNHSFI EPPSAGWATD DSFSSDPESG EADEVPAYCV  540
PPQEGMVPVA QAGSSEASLA AGAFPPPEDA STPFAIPRTS SLARAKRPSV SFAEGTKFAP  600
QSRRSSGELS SPLRKPKRLS RGAQSGPEGR EAEESTGPEE AEAPESFPAA ASPGDSATGH  660
RRPPLGGRTV AEHVEAIEGS VQESSGPVTT IYMLAGKPRG SEGPVRSVFR HFGSFQKGQA  720
EAKVKRAIPK PPRQALNRKK GSPGLASGSV GQSPNSAPKA GLPGATGPMA VRPEEAVRGL  780
GAGTESSRRA QEPVSGCGSP EQDPQKQAEE ERQEEPEYEN VVPISRPPEP            830

SEQ ID NO: 36          moltype = AA  length = 596
FEATURE                Location/Qualifiers
REGION                 1..596
                       note = CT 532: pLenti 1 CEA TCR TRAV8-1*01 TRBV26*01 with
                        regular murineconstant region
source                 1..596
                       mol_type = protein
                       organism = synthetic construct
SEQUENCE: 36
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTSGGNYK  120
FGKGTSLVVH PDIQNPEPAV YQLKDPRSQD STLCLFTDFD SQINVPKTME SGTFITDKTV  180
LDMKAMDSKS NGAIAWSNQT SFTCQDIFKE TNATYPSSDV PCDATLTEKS FETDMNLNFQ  240
NLSVMGLRIL LLKVAGFNLL MTLRLWSSGS GATNFSLLKQ AGDVEENPGP MATRLLCYTV  300
LCLLGARILN SKVIQTPRYL VKGQGQKAKM RCIPEKGHPV VFWYQQNKNN EFKFLINFQN  360
```

```
QEVLQQIDMT EKRFSAECPS NSPCSLEIQS SEAGDSALYL CASSLGLGDY EQYFGPGTRL  420
TVLEDLRNVT PPKVSLFEPS KAEIANKQKA TLVCLARGFF PDHVELSWWV NGKEVHSGVS  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 37           moltype = AA  length = 596
FEATURE                 Location/Qualifiers
REGION                  1..596
                        note = CT 533: pLenti 1 CEA TCR TRAV8-1*01 TRBV26*01 L117T
                         with regularmurine constant region
source                  1..596
                        mol_type = protein
                        organism = synthetic construct
SEQUENCE: 37
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTSGGNYK  120
FGKGTSLVVH PDIQNPEPAV YQLKDPRSQD STLCLFTDFD SQINVPKTME SGTFITDKTV  180
LDMKAMDSKS NGAIAWSNQT SFTCQDIFKE TNATYPSSDV PCDATLTEKS FETDMNLNFQ  240
NLSVMGLRIL LLKVAGFNLL MTLRLWSSGS GATNFSLLKQ AGDVEENPGP MATRLLCYTV  300
LCLLGARILN SKVIQTPRYL VKGQGQKAKM RCIPEKGHPV VFWYQQNKNN EFKFLINFQN  360
QEVLQQIDMT EKRFSAECPS NSPCSLEIQS SEAGDSALYL CASSLGTGDY EQYFGPGTRL  420
TVLEDLRNVT PPKVSLFEPS KAEIANKQKA TLVCLARGFF PDHVELSWWV NGKEVHSGVS  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 38           moltype = AA  length = 596
FEATURE                 Location/Qualifiers
REGION                  1..596
                        note = CT 534: pLenti 1 CEA TCR TRAV8-1*01 TRBV26*01 murine
                         constantregion (no PT)
source                  1..596
                        mol_type = protein
                        organism = synthetic construct
SEQUENCE: 38
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTSGGNYK  120
FGKGTSLVVH PNIQNPEPAV YQLKDPRSQD STLCLFTDFD SQINVPKTME SGTFITDKCV  180
LDMKAMDSKS NGAIAWSNQT SFTCQDIFKE TNATYPSSDV PCDATLTEKS FETDMNLNFQ  240
NLLVIVLRIL LLKVAGFNLL MTLRLWSSGS GATNFSLLKQ AGDVEENPGP MATRLLCYTV  300
LCLLGARILN SKVIQTPRYL VKGQGQKAKM RCIPEKGHPV VFWYQQNKNN EFKFLINFQN  360
QEVLQQIDMT EKRFSAECPS NSPCSLEIQS SEAGDSALYL CASSLGLGDY EQYFGPGTRL  420
TVLEDLRNVT PPKVSLFEPS KAEIANKQKA TLVCLARGFF PDHVELSWWV NGKEVHSGVC  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 39           moltype = AA  length = 596
FEATURE                 Location/Qualifiers
REGION                  1..596
                        note = CT 535: pLenti 1 CEA TCR TRAV8-1*01 L110F TRBV26*01
                         with regularmurine constant region
source                  1..596
                        mol_type = protein
                        organism = synthetic construct
SEQUENCE: 39
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDFTSGGNYK  120
FGKGTSLVVH PDIQNPEPAV YQLKDPRSQD STLCLFTDFD SQINVPKTME SGTFITDKTV  180
LDMKAMDSKS NGAIAWSNQT SFTCQDIFKE TNATYPSSDV PCDATLTEKS FETDMNLNFQ  240
NLSVMGLRIL LLKVAGFNLL MTLRLWSSGS GATNFSLLKQ AGDVEENPGP MATRLLCYTV  300
LCLLGARILN SKVIQTPRYL VKGQGQKAKM RCIPEKGHPV VFWYQQNKNN EFKFLINFQN  360
QEVLQQIDMT EKRFSAECPS NSPCSLEIQS SEAGDSALYL CASSLGLGDY EQYFGPGTRL  420
TVLEDLRNVT PPKVSLFEPS KAEIANKQKA TLVCLARGFF PDHVELSWWV NGKEVHSGVS  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 40           moltype = AA  length = 596
FEATURE                 Location/Qualifiers
REGION                  1..596
                        note = CT 536: pLenti 1 CEA TCR TRAV8-1*01 S112TTRBV26*01
                         with regularmurine constant region
source                  1..596
                        mol_type = protein
                        organism = synthetic construct
SEQUENCE: 40
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTTGGNYK  120
FGKGTSLVVH PDIQNPEPAV YQLKDPRSQD STLCLFTDFD SQINVPKTME SGTFITDKTV  180
LDMKAMDSKS NGAIAWSNQT SFTCQDIFKE TNATYPSSDV PCDATLTEKS FETDMNLNFQ  240
NLSVMGLRIL LLKVAGFNLL MTLRLWSSGS GATNFSLLKQ AGDVEENPGP MATRLLCYTV  300
```

```
LCLLGARILN SKVIQTPRYL VKGQGQKAKM RCIPEKGHPV VFWYQQNKNN EFKFLINFQN  360
QEVLQQIDMT EKRFSAECPS NSPCSLEIQS SEAGDSALYL CASSLGLGDY EQYFGPGTRL  420
TVLEDLRNVT PPKVSLFEPS KAEIANKQKA TLVCLARGFF PDHVELSWWV NGKEVHSGVS  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 41          moltype = AA  length = 596
FEATURE                Location/Qualifiers
REGION                 1..596
                       note = CT 537: pLenti 1 CEA TCR TRAV8-1*01 L110F & S112T
                        TRBV26*01 withregular murine constant region
source                 1..596
                       mol_type = protein
                       organism = synthetic construct
SEQUENCE: 41
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDFTTGGNYK  120
FGKGTSLVVH PDIQNPEPAV YQLKDPRSQD STLCLFTDFD SQINVPKTME SGTFITDKTV  180
LDMKAMDSKS NGAIAWSNQT SFTCQDIFKE TNATYPSSDV PCDATLTEKS FETDMNLNFQ  240
NLSVMGLRIL LLKVAGFNLL MTLRLWSSGS GATNFSLLKQ AGDVEENPGP MATRLLCYTV  300
LCLLGARILN SKVIQTPRYL VKGQGQKAKM RCIPEKGHPV VFWYQQNKNN EFKFLINFQN  360
QEVLQQIDMT EKRFSAECPS NSPCSLEIQS SEAGDSALYL CASSLGLGDY EQYFGPGTRL  420
TVLEDLRNVT PPKVSLFEPS KAEIANKQKA TLVCLARGFF PDHVELSWWV NGKEVHSGVS  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 42          moltype = AA  length = 596
FEATURE                Location/Qualifiers
REGION                 1..596
                       note = CT 538: pLenti 1 CEA TCR TRAV8-1*01 L110F TRBV26*01
                        L117T withregular murine constant region
source                 1..596
                       mol_type = protein
                       organism = synthetic construct
SEQUENCE: 42
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDFTSGGNYK  120
FGKGTSLVVH PDIQNPEPAV YQLKDPRSQD STLCLFTDFD SQINVPKTME SGTFITDKTV  180
LDMKAMDSKS NGAIAWSNQT SFTCQDIFKE TNATYPSSDV PCDATLTEKS FETDMNLNFQ  240
NLSVMGLRIL LLKVAGFNLL MTLRLWSSGS GATNFSLLKQ AGDVEENPGP MATRLLCYTV  300
LCLLGARILN SKVIQTPRYL VKGQGQKAKM RCIPEKGHPV VFWYQQNKNN EFKFLINFQN  360
QEVLQQIDMT EKRFSAECPS NSPCSLEIQS SEAGDSALYL CASSLGTGDY EQYFGPGTRL  420
TVLEDLRNVT PPKVSLFEPS KAEIANKQKA TLVCLARGFF PDHVELSWWV NGKEVHSGVS  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 43          moltype = AA  length = 596
FEATURE                Location/Qualifiers
REGION                 1..596
                       note = CT 539: pLenti 1 CEA TCR TRAV8-1*01 S112T TRBV26*01
                        L117T withregular murine constant region
source                 1..596
                       mol_type = protein
                       organism = synthetic construct
SEQUENCE: 43
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTTGGNYK  120
FGKGTSLVVH PDIQNPEPAV YQLKDPRSQD STLCLFTDFD SQINVPKTME SGTFITDKTV  180
LDMKAMDSKS NGAIAWSNQT SFTCQDIFKE TNATYPSSDV PCDATLTEKS FETDMNLNFQ  240
NLSVMGLRIL LLKVAGFNLL MTLRLWSSGS GATNFSLLKQ AGDVEENPGP MATRLLCYTV  300
LCLLGARILN SKVIQTPRYL VKGQGQKAKM RCIPEKGHPV VFWYQQNKNN EFKFLINFQN  360
QEVLQQIDMT EKRFSAECPS NSPCSLEIQS SEAGDSALYL CASSLGTGDY EQYFGPGTRL  420
TVLEDLRNVT PPKVSLFEPS KAEIANKQKA TLVCLARGFF PDHVELSWWV NGKEVHSGVS  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 44          moltype = AA  length = 596
FEATURE                Location/Qualifiers
REGION                 1..596
                       note = CT 540: pLenti 1 CEA TCR TRAV8-1*01 L110F & S112T
                        TRBV26*01 L117Twith regular murine constant region
source                 1..596
                       mol_type = protein
                       organism = synthetic construct
SEQUENCE: 44
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDFTTGGNYK  120
FGKGTSLVVH PDIQNPEPAV YQLKDPRSQD STLCLFTDFD SQINVPKTME SGTFITDKTV  180
LDMKAMDSKS NGAIAWSNQT SFTCQDIFKE TNATYPSSDV PCDATLTEKS FETDMNLNFQ  240
```

```
NLSVMGLRIL LLKVAGFNLL MTLRLWSSGS GATNFSLLKQ AGDVEENPGP MATRLLCYTV  300
LCLLGARILN SKVIQTPRYL VKGQGQKAKM RCIPEKGHPV VFWYQQNKNN EFKFLINFQN  360
QEVLQQIDMT EKRFSAECPS NSPCSLEIQS SEAGDSALYL CASSLGTGDY EQYFGPGTRL  420
TVLEDLRNVT PPKVSLFEPS KAEIANKQKA TLVCLARGFF PDHVELSWWV NGKEVHSGVS  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 45           moltype = AA  length = 596
FEATURE                 Location/Qualifiers
REGION                  1..596
                        note = CT 541: pLenti 1 CEA TCR TRAV8-1*01 L110F TRBV26*01
                         with murineconstant region
source                  1..596
                        mol_type = protein
                        organism = synthetic construct
SEQUENCE: 45
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDFTSGGNYK  120
FGKGTSLVVH PNIQNPEPAV YQLKDPRSQD STLCLFTDFD SQINVPKTME SGTFITDKCV  180
LDMKAMDSKS NGAIAWSNQT SFTCQDIFKE TNATYPSSDV PCDATLTEKS FETDMNLNFQ  240
NLLVIVLRIL LLKVAGFNLL MTLRLWSSGS GATNFSLLKQ AGDVEENPGP MATRLLCYTV  300
LCLLGARILN SKVIQTPRYL VKGQGQKAKM RCIPEKGHPV VFWYQQNKNN EFKFLINFQN  360
QEVLQQIDMT EKRFSAECPS NSPCSLEIQS SEAGDSALYL CASSLGLGDY EQYFGPGTRL  420
TVLEDLRNVT PPKVSLFEPS KAEIANKQKA TLVCLARGFF PDHVELSWWV NGKEVHSGVC  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 46           moltype = AA  length = 596
FEATURE                 Location/Qualifiers
REGION                  1..596
                        note = CT 542:pLenti 1 CEA TCR TRAV8-1*01 S112T TRBV26*01
                         with murineconstant region
source                  1..596
                        mol_type = protein
                        organism = synthetic construct
SEQUENCE: 46
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTTGGNYK  120
FGKGTSLVVH PNIQNPEPAV YQLKDPRSQD STLCLFTDFD SQINVPKTME SGTFITDKCV  180
LDMKAMDSKS NGAIAWSNQT SFTCQDIFKE TNATYPSSDV PCDATLTEKS FETDMNLNFQ  240
NLLVIVLRIL LLKVAGFNLL MTLRLWSSGS GATNFSLLKQ AGDVEENPGP MATRLLCYTV  300
LCLLGARILN SKVIQTPRYL VKGQGQKAKM RCIPEKGHPV VFWYQQNKNN EFKFLINFQN  360
QEVLQQIDMT EKRFSAECPS NSPCSLEIQS SEAGDSALYL CASSLGLGDY EQYFGPGTRL  420
TVLEDLRNVT PPKVSLFEPS KAEIANKQKA TLVCLARGFF PDHVELSWWV NGKEVHSGVC  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 47           moltype = AA  length = 596
FEATURE                 Location/Qualifiers
REGION                  1..596
                        note = CT 543: pLenti 1 CEA TCR TRAV8-1*01 L110F & S112T
                         TRBV26*01 withmurine constant region
source                  1..596
                        mol_type = protein
                        organism = synthetic construct
SEQUENCE: 47
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDFTTGGNYK  120
FGKGTSLVVH PNIQNPEPAV YQLKDPRSQD STLCLFTDFD SQINVPKTME SGTFITDKCV  180
LDMKAMDSKS NGAIAWSNQT SFTCQDIFKE TNATYPSSDV PCDATLTEKS FETDMNLNFQ  240
NLLVIVLRIL LLKVAGFNLL MTLRLWSSGS GATNFSLLKQ AGDVEENPGP MATRLLCYTV  300
LCLLGARILN SKVIQTPRYL VKGQGQKAKM RCIPEKGHPV VFWYQQNKNN EFKFLINFQN  360
QEVLQQIDMT EKRFSAECPS NSPCSLEIQS SEAGDSALYL CASSLGLGDY EQYFGPGTRL  420
TVLEDLRNVT PPKVSLFEPS KAEIANKQKA TLVCLARGFF PDHVELSWWV NGKEVHSGVC  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 48           moltype = AA  length = 596
FEATURE                 Location/Qualifiers
REGION                  1..596
                        note = CT 544: pLenti 1 CEA TCRTRAV8-1*01 TRBV26*01 L117T
                         with murineconstant region
source                  1..596
                        mol_type = protein
                        organism = synthetic construct
SEQUENCE: 48
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTSGGNYK  120
FGKGTSLVVH PNIQNPEPAV YQLKDPRSQD STLCLFTDFD SQINVPKTME SGTFITDKCV  180
```

```
LDMKAMDSKS NGAIAWSNQT SFTCQDIFKE TNATYPSSDV PCDATLTEKS FETDMNLNFQ  240
NLLVIVLRIL LLKVAGFNLL MTLRLWSSGS GATNFSLLKQ AGDVEENPGP MATRLLCYTV  300
LCLLGARILN SKVIQTPRYL VKGQGQKAKM RCIPEKGHPV VFWYQQNKNN EFKFLINFQN  360
QEVLQQIDMT EKRFSAECPS NSPCSLEIQS SEAGDSALYL CASSLGTGDY EQYFGPGTRL  420
TVLEDLRNVT PPKVSLFEPS KAEIANKQKA TLVCLARGFF PDHVELSWWV NGKEVHSGVC  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 49          moltype = AA  length = 596
FEATURE                Location/Qualifiers
REGION                 1..596
                       note = CT 545: pLenti 1 CEA TCR TRAV8-1*01 L110F TRBV26*01
                        L117T withmurine constant region
source                 1..596
                       mol_type = protein
                       organism = synthetic construct
SEQUENCE: 49
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDFTSGGNYK  120
FGKGTSLVVH PNIQNPEPAV YQLKDPRSQD STLCLFTDFD SQINVPKTME SGTFITDKCV  180
LDMKAMDSKS NGAIAWSNQT SFTCQDIFKE TNATYPSSDV PCDATLTEKS FETDMNLNFQ  240
NLLVIVLRIL LLKVAGFNLL MTLRLWSSGS GATNFSLLKQ AGDVEENPGP MATRLLCYTV  300
LCLLGARILN SKVIQTPRYL VKGQGQKAKM RCIPEKGHPV VFWYQQNKNN EFKFLINFQN  360
QEVLQQIDMT EKRFSAECPS NSPCSLEIQS SEAGDSALYL CASSLGTGDY EQYFGPGTRL  420
TVLEDLRNVT PPKVSLFEPS KAEIANKQKA TLVCLARGFF PDHVELSWWV NGKEVHSGVC  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 50          moltype = AA  length = 596
FEATURE                Location/Qualifiers
REGION                 1..596
                       note = CT 546: pLenti 1 CEA TCR TRAV8-1*01 S112T TRBV26*01
                        L117T withmurine constant region
source                 1..596
                       mol_type = protein
                       organism = synthetic construct
SEQUENCE: 50
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDLTTGGNYK  120
FGKGTSLVVH PNIQNPEPAV YQLKDPRSQD STLCLFTDFD SQINVPKTME SGTFITDKCV  180
LDMKAMDSKS NGAIAWSNQT SFTCQDIFKE TNATYPSSDV PCDATLTEKS FETDMNLNFQ  240
NLLVIVLRIL LLKVAGFNLL MTLRLWSSGS GATNFSLLKQ AGDVEENPGP MATRLLCYTV  300
LCLLGARILN SKVIQTPRYL VKGQGQKAKM RCIPEKGHPV VFWYQQNKNN EFKFLINFQN  360
QEVLQQIDMT EKRFSAECPS NSPCSLEIQS SEAGDSALYL CASSLGTGDY EQYFGPGTRL  420
TVLEDLRNVT PPKVSLFEPS KAEIANKQKA TLVCLARGFF PDHVELSWWV NGKEVHSGVC  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 51          moltype = AA  length = 596
FEATURE                Location/Qualifiers
REGION                 1..596
                       note = CT 547: pLenti 1 CEA TCR TRAV8-1*01 L110F & S112T
                        TRBV26*01 L117Twith murine constant region
source                 1..596
                       mol_type = protein
                       organism = synthetic construct
SEQUENCE: 51
MHSLLGLLMV SLWLQLTRVN SQLAEENPWA LSVHEGESVT VNCSYKTSIT ALQWYRQKSG  60
EGPAQLILIR SNEREKRNGR LRATLDTSSQ SSSLSITATR CEDTAVYFCA TDFTTGGNYK  120
FGKGTSLVVH PNIQNPEPAV YQLKDPRSQD STLCLFTDFD SQINVPKTME SGTFITDKCV  180
LDMKAMDSKS NGAIAWSNQT SFTCQDIFKE TNATYPSSDV PCDATLTEKS FETDMNLNFQ  240
NLLVIVLRIL LLKVAGFNLL MTLRLWSSGS GATNFSLLKQ AGDVEENPGP MATRLLCYTV  300
LCLLGARILN SKVIQTPRYL VKGQGQKAKM RCIPEKGHPV VFWYQQNKNN EFKFLINFQN  360
QEVLQQIDMT EKRFSAECPS NSPCSLEIQS SEAGDSALYL CASSLGTGDY EQYFGPGTRL  420
TVLEDLRNVT PPKVSLFEPS KAEIANKQKA TLVCLARGFF PDHVELSWWV NGKEVHSGVC  480
TDPQAYKESN YSYCLSSRLR VSATFWHNPR NHFRCQVQFH GLSEEDKWPE GSPKPVTQNI  540
SAEAWGRADC GITSASYQQG VLSATILYEI LLGKATLYAV LVSTLVVMAM VKRKNS      596

SEQ ID NO: 52          moltype = AA  length = 535
FEATURE                Location/Qualifiers
REGION                 1..535
                       note = CT618: CAR with scFv that targetCEA
source                 1..535
                       mol_type = protein
                       organism = synthetic construct
SEQUENCE: 52
MDMRVPAQLL GLLLLWLRGA RCQVQLVQSG SELKKPGASV KVSCKASGYT FTEFGMNWVR  60
QAPGQGLEWM GWINTKTGEA TYVEEFKGRF VFSLDTSVST AYLQISSLKA EDTAVYYCAR  120
WDFAYYVEAM DYWGQGTTVT VSSGGGGSGG GGSGGGGSGG DIQMTQSPSS LSASVGDRVT  180
```

```
ITCKASQNVG TNVAWYQQKP GKAPKLLIYS ASYRYSGVPS RFSGSGSGTD FTLTISSLQP  240
EDFATYYCHQ YYTYPLFTFG QGTKLEIKTT TPAPRPPTPA PTIASQPLSL RPEACRPAAG  300
GAVHTRGLDF ACDFWVLVVV GGVLACYSLL VTVAFIIFWV RSKRSRLLHS DYMNMTPRRP  360
GPTRKHYQPY APPRDFAAYR SKRGRKKLLY IFKQPFMRPV QTTQEEDGCS CRFPEEEEGG  420
CELRVKFSRS ADAPAYKQGQ NQLYNELNLG RREEYDVLDK RRGRDPEMGG KPRRKNPQEG  480
LYNELQKDKM AEAYSEIGMK GERRRGKGHD GLYQGLSTAT KDTYDALHMQ ALPPR       535

SEQ ID NO: 53           moltype = AA  length = 537
FEATURE                 Location/Qualifiers
REGION                  1..537
                        note = CT619: CAR with scFv that targetCEA
source                  1..537
                        mol_type = protein
                        organism = synthetic construct
SEQUENCE: 53
MDMRVPAQLL GLLLLWLRGA RCQVQLVQSG AEVKKPGASV KVSCKASGYT FTEFGMNWVR  60
QAPGQGLEWM GWINTKTGEA TYVEEFKGRV TFTTDTSTST AYMELRSLRS DDTAVYYCAR  120
WDFAYYVEAM DYWGQGTTVT VSSGGGGSGG GGSGGGGSGG DIQMTQSPSS LSASVGDRVT  180
ITCKASAAVG TYVAWYQQKP GKAPKLLIYS ASYRKRGVPS RFSGSGSGTD FTLTISSLQP  240
EDFATYYCHQ YYTYPLFTFG QGTKLEIKRT TTTPAPRPPT PAPTIASQPL SLRPEACRPA  300
AGGAVHTRGL DFACDFWVLV VVGGVLACYS LLVTVAFIIF WVRSKRSRLL HSDYMNMTPR  360
RPGPTRKHYQ PYAPPRDFAA YRSKRGRKKL LYIFKQPFMR PVQTTQEEDG CSCRFPEEEE  420
GGCELRVKFS RSADAPAYKQ GQNQLYNELN LGRREEYDVL DKRRGRDPEM GGKPRRKNPQ  480
EGLYNELQKD KMAEAYSEIG MKGERRRGKG HDGLYQGLST ATKDTYDALH MQALPPR     537

SEQ ID NO: 54           moltype = AA  length = 536
FEATURE                 Location/Qualifiers
REGION                  1..536
                        note = CT620: CAR with scFv that targetCEA
source                  1..536
                        mol_type = protein
                        organism = synthetic construct
SEQUENCE: 54
MDMRVPAQLL GLLLLWLRGA RCQVQLVQSG SELKKPGASV KVSCKASGYT FTEFGMNWVR  60
QAPGQGLEWM GWINTKTGEA TYVEEFKGRF VFSLDTSVST AYLQISSLKA EDTAVYYCAR  120
WDFAHYFQTM DYWGQGTTVT VSSGGGGSGG GGSGGGGSGG DIQMTQSPSS LSASVGDRVT  180
ITCKASAAVG TYVAWYQQKP GKAPKLLIYS ASYRKRGVPS RFSGSGSGTD FTLTISSLQP  240
EDFATYYCHQ YYTYPLFTFG QGTKLEIKRT TTPAPRPPTP APTIASQPLS LRPEACRPAA  300
GGAVHTRGLD FACDFWVLVV VGGVLACYSL LVTVAFIIFW VRSKRSRLLH SDYMNMTPRR  360
PGPTRKHYQP YAPPRDFAAY RSKRGRKKLL YIFKQPFMRP VQTTQEEDGC SCRFPEEEEG  420
GCELRVKFSR SADAPAYKQG QNQLYNELNL GRREEYDVLD KRRGRDPEMG GKPRRKNPQE  480
GLYNELQKDK MAEAYSEIGM KGERRRGKGH DGLYQGLSTA TKDTYDALHM QALPPR      536

SEQ ID NO: 55           moltype = AA  length = 5
FEATURE                 Location/Qualifiers
REGION                  1..5
                        note = CEA scFv CDR-H1
source                  1..5
                        mol_type = protein
                        organism = synthetic construct
SEQUENCE: 55
EFGMN                                                              5

SEQ ID NO: 56           moltype = AA  length = 17
FEATURE                 Location/Qualifiers
REGION                  1..17
                        note = CEA scFv CDR-H2
source                  1..17
                        mol_type = protein
                        organism = synthetic construct
SEQUENCE: 56
WINTKTGEAT YVEEFKG                                                 17

SEQ ID NO: 57           moltype = AA  length = 12
FEATURE                 Location/Qualifiers
REGION                  1..12
                        note = CEA scFv CDR-H3
source                  1..12
                        mol_type = protein
                        organism = synthetic construct
SEQUENCE: 57
WDFAYYVEAM DY                                                      12

SEQ ID NO: 58           moltype = AA  length = 12
FEATURE                 Location/Qualifiers
REGION                  1..12
                        note = CEA scFv CDR-H3
source                  1..12
                        mol_type = protein
```

```
                        organism = synthetic construct
SEQUENCE: 58
WDFAHYFQTM DY                                                         12

SEQ ID NO: 59           moltype = AA  length = 11
FEATURE                 Location/Qualifiers
REGION                  1..11
                        note = CEA scFv CDR-L1
source                  1..11
                        mol_type = protein
                        organism = synthetic construct
SEQUENCE: 59
KASQNVGTNV A                                                          11

SEQ ID NO: 60           moltype = AA  length = 11
FEATURE                 Location/Qualifiers
REGION                  1..11
                        note = CEA scFv CDR-L1
source                  1..11
                        mol_type = protein
                        organism = synthetic construct
SEQUENCE: 60
KASAAVGTYV A                                                          11

SEQ ID NO: 61           moltype = AA  length = 7
FEATURE                 Location/Qualifiers
REGION                  1..7
                        note = CEA scFv CDR-L2
source                  1..7
                        mol_type = protein
                        organism = synthetic construct
SEQUENCE: 61
SASYRYS                                                               7

SEQ ID NO: 62           moltype = AA  length = 7
FEATURE                 Location/Qualifiers
REGION                  1..7
                        note = CEA scFv CDR-L2
source                  1..7
                        mol_type = protein
                        organism = synthetic construct
SEQUENCE: 62
SASYRYS                                                               7

SEQ ID NO: 63           moltype = AA  length = 10
FEATURE                 Location/Qualifiers
REGION                  1..10
                        note = CEA scFv CDR-L3
source                  1..10
                        mol_type = protein
                        organism = synthetic construct
SEQUENCE: 63
HQYYTYPLFT                                                            10

SEQ ID NO: 64           moltype = AA  length = 243
FEATURE                 Location/Qualifiers
REGION                  1..243
                        note = scFv that targets CEA
source                  1..243
                        mol_type = protein
                        organism = synthetic construct
SEQUENCE: 64
QVQLQQSGAE LVRSGTSVKL SCTASGFNIK DSYMHWLRQG PEQGLEWIGW IDPENGDTEY  60
APKFQGKATF TTDTSSNTAY LQLSSLTSED TAVYYCNEGT PTGPYYFDYW GQGTTVTVSS  120
GGGGSGGGGS GGGGSGGENV LTQSPAIMSA SPGEKVTITC SASSSVSYMH WFQQKPGTSP  180
KLWIYSTSNL ASGVPARFSG SGSGTSYSLT ISRMEAEDAA TYYCQQRSSY PLTFGAGTKL  240
ELK                                                                243

SEQ ID NO: 65           moltype = AA  length = 243
FEATURE                 Location/Qualifiers
REGION                  1..243
                        note = scFv that targets CEA
source                  1..243
                        mol_type = protein
                        organism = synthetic construct
SEQUENCE: 65
QVQLVQSGAE VKKPGASVKV SCKASGFNIK DSYMHWVRQA PGQGLEWMGW IDPENGDTEY  60
APKFQGRVTM TTDTSTSTAY MELRSLRSDD TAVYYCNEGT PTGPYYFDYW GQGTTVTVSS  120
GGGGSGGGGS GGGGSGGEIV LTQSPATLSL SPGERATLSC SASSSVSYMH WYQQKPGLAP  180
```

```
RLLIYSTSNL ASGIPDRFSG SGSGTDFTLT ISRLEPEDFA VYYCQQRSSY PLTFGQGTKL  240
EIK                                                               243

SEQ ID NO: 66          moltype = AA  length = 243
FEATURE                Location/Qualifiers
REGION                 1..243
                       note = scFv that targets CEA
source                 1..243
                       mol_type = protein
                       organism = synthetic construct
SEQUENCE: 66
EVQLAESGGG LVQPGGSLRL SCAASGFTFS SDAMSWVRQA PGKGLEWVSA ISGSGGSTYY  60
ADSVKGRFTI SRDNSKNTLY LQMNSLRAED TAVYYCAKSN EFLFDYWGQG TLVTVSSGGG  120
GSGGGGSGGG GSGGSSELTQ DPAVSVALGQ TVRITCQGDS LRSSYASWYR QRPGQAPVLV  180
IYGKNNRPSG IPDRFSGSSS GNTASLTITG AQAEDEADYY WNSSYAWLPY VVFGGGTKLT  240
VLG                                                               243

SEQ ID NO: 67          moltype = AA  length = 243
FEATURE                Location/Qualifiers
REGION                 1..243
                       note = scFv that targets CEA
source                 1..243
                       mol_type = protein
                       organism = synthetic construct
SEQUENCE: 67
QVQLEQSGAG VVKPGASVKL SCKASGFNIK DSYMHWLRQG PGQRLEWIGW IDPENGDTEY  60
APKFQGKATF TTDTSANTAY LGLSSLRPED TAVYYCNEGT PTGPYYFDYW GQGTLVTVSS  120
GGGGSGGGGS GGGGSGGENV LTQSPSSMSV SVGDRVNIAC SASSSVPYMH WLQQKPGKSP  180
KLLIYLTSNL ASGVPSRFSG SGSGTDYSLT ISSVQPEDAA TYYCQQRSSY PLTFGGGTKL  240
EIK                                                               243

SEQ ID NO: 68          moltype = AA  length = 246
FEATURE                Location/Qualifiers
REGION                 1..246
                       note = scFv that targets CEA
source                 1..246
                       mol_type = protein
                       organism = synthetic construct
SEQUENCE: 68
QVQLVQSGSE LKKPGASVKV SCKASGYTFT EFGMNWVRQA PGQGLEWMGW INTKTGEATY  60
VEEFKGRFVF SLDTSVSTAY LQISSLKAED TAVYYCARWD FAYYVEAMDY WGQGTTVTVS  120
SGGGGSGGGG SGGGGSGGDI QMTQSPSSLS ASVGDRVTIT CKASQNVGTN VAWYQQKPGK  180
APKLLIYSAS YRYSGVPSRF SGSGSGTDFT LTISSLQPED FATYYCHQYY TYPLFTFGQG  240
TKLEIK                                                            246

SEQ ID NO: 69          moltype = AA  length = 246
FEATURE                Location/Qualifiers
REGION                 1..246
                       note = scFv that targets CEA
source                 1..246
                       mol_type = protein
                       organism = synthetic construct
SEQUENCE: 69
QVQLVQSGAE VKKPGASVKV SCKASGYTFT EFGMNWVRQA PGQGLEWMGW INTKTGEATY  60
VEEFKGRVTF TTDTSTSTAY MELRSLRSDD TAVYYCARWD FAYYVEAMDY WGQGTTVTVS  120
SGGGGSGGGG SGGGGSGGDI QMTQSPSSLS ASVGDRVTIT CKASAAVGTY VAWYQQKPGK  180
APKLLIYSAS YRKRGVPSRF SGSGSGTDFT LTISSLQPED FATYYCHQYY TYPLFTFGQG  240
TKLEIK                                                            246

SEQ ID NO: 70          moltype = AA  length = 246
FEATURE                Location/Qualifiers
REGION                 1..246
                       note = scFv that targets CEA
source                 1..246
                       mol_type = protein
                       organism = synthetic construct
SEQUENCE: 70
QVQLVQSGSE LKKPGASVKV SCKASGYTFT EFGMNWVRQA PGQGLEWMGW INTKTGEATY  60
VEEFKGRFVF SLDTSVSTAY LQISSLKAED TAVYYCARWD FAHYFQTMDY WGQGTTVTVS  120
SGGGGSGGGG SGGGGSGGDI QMTQSPSSLS ASVGDRVTIT CKASAAVGTY VAWYQQKPGK  180
APKLLIYSAS YRKRGVPSRF SGSGSGTDFT LTISSLQPED FATYYCHQYY TYPLFTFGQG  240
TKLEIK                                                            246

SEQ ID NO: 71          moltype = AA  length = 45
FEATURE                Location/Qualifiers
REGION                 1..45
                       note = CD8alpha hinge
source                 1..45
                       mol_type = protein
```

```
                          organism = unidentified
SEQUENCE: 71
TTTPAPRPPT PAPTIASQPL SLRPEACRPA AGGAVHTRGL DFACD                 45

SEQ ID NO: 72             moltype = DNA  length = 135
FEATURE                   Location/Qualifiers
misc_feature              1..135
                          note = CD8alpha hinge
source                    1..135
                          mol_type = unassigned DNA
                          organism = unidentified
SEQUENCE: 72
accacgacgc cagcgccgcg accaccaaca ccggcgccca ccatcgcgtc gcagcccctg  60
tccctgcgcc cagaggcgtg ccggccagcg gcggggggcg cagtgcacac gagggggctg  120
gacttcgcct gtgat                                                  135

SEQ ID NO: 73             moltype = AA  length = 41
FEATURE                   Location/Qualifiers
REGION                    1..41
                          note = CD28 hinge
source                    1..41
                          mol_type = protein
                          organism = unidentified
SEQUENCE: 73
CTIEVMYPPP YLDNEKSNGT IIHVKGKHLC PSPLFPGPSK P                     41

SEQ ID NO: 74             moltype = DNA  length = 123
FEATURE                   Location/Qualifiers
misc_feature              1..123
                          note = CD28 hinge
source                    1..123
                          mol_type = unassigned DNA
                          organism = unidentified
SEQUENCE: 74
tgtaccattg aagttatgta tcctcctcct tacctagaca atgagaagag caatggaacc  60
attatccatg tgaaagggaa acacctttgt ccaagtcccc tatttcccgg accttctaag  120
ccc                                                               123

SEQ ID NO: 75             moltype = AA  length = 27
FEATURE                   Location/Qualifiers
REGION                    1..27
                          note = CD28 transmembrane domain
source                    1..27
                          mol_type = protein
                          organism = unidentified
SEQUENCE: 75
FWVLVVVGGV LACYSLLVTV AFIIFWV                                     27

SEQ ID NO: 76             moltype = DNA  length = 81
FEATURE                   Location/Qualifiers
misc_feature              1..81
                          note = CD28 transmembrane domain
source                    1..81
                          mol_type = unassigned DNA
                          organism = unidentified
SEQUENCE: 76
ttctgggtgc tggtcgttgt gggcggcgtg ctggcctgct acagcctgct ggtgacagtg  60
gccttcatca tcttttgggt g                                           81

SEQ ID NO: 77             moltype = AA  length = 25
FEATURE                   Location/Qualifiers
REGION                    1..25
                          note = IL-2Rbeta transmembrane domain
source                    1..25
                          mol_type = protein
                          organism = unidentified
SEQUENCE: 77
IPWLGHLLVG LSGAFGFIIL VYLLI                                       25

SEQ ID NO: 78             moltype = DNA  length = 75
FEATURE                   Location/Qualifiers
misc_feature              1..75
                          note = IL-2Rbeta transmembrane domain
source                    1..75
                          mol_type = unassigned DNA
                          organism = unidentified
SEQUENCE: 78
attccgtggc tcggccacct cctcgtgggc ctcagcgggg cttttggctt catcatctta  60
gtgtacttgc tgatc                                                  75
```

```
SEQ ID NO: 79          moltype = AA  length = 112
FEATURE                Location/Qualifiers
REGION                 1..112
                       note = CD3zeta activation domain
source                 1..112
                       mol_type = protein
                       organism = unidentified
SEQUENCE: 79
RVKFSRSADA PAYKQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 80          moltype = DNA  length = 336
FEATURE                Location/Qualifiers
misc_feature           1..336
                       note = CD3zeta activation domain
source                 1..336
                       mol_type = unassigned DNA
                       organism = unidentified
SEQUENCE: 80
agagtgaagt tcagcaggag cgcagacgcc cccgcgtaca agcagggcca gaaccagctc  60
tataacgagc tcaatctagg acgaagagag gagtacgatg ttttggacaa gcgtagaggc  120
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggactca gtacagccac caaggacacc  300
tacgacgccc ttcacatgca ggccctgccc cctcgc                            336

SEQ ID NO: 81          moltype = AA  length = 43
FEATURE                Location/Qualifiers
REGION                 1..43
                       note = CD3zeta activation domain
source                 1..43
                       mol_type = protein
                       organism = unidentified
SEQUENCE: 81
RVKFSRSADA PAYQQGQNQL YNELNLGRRE EYDVLHMQAL PPR                    43

SEQ ID NO: 82          moltype = DNA  length = 129
FEATURE                Location/Qualifiers
misc_feature           1..129
                       note = CD3zeta activation domain
source                 1..129
                       mol_type = unassigned DNA
                       organism = unidentified
SEQUENCE: 82
agagtgaagt tcagcaggag cgcagacgcc cccgcgtacc agcagggcca gaaccagctc  60
tataacgagc tcaatctagg acgaagagag gagtacgatg ttttgcacat gcaggccctg  120
ccccctcgc                                                          129

SEQ ID NO: 83          moltype = AA  length = 41
FEATURE                Location/Qualifiers
REGION                 1..41
                       note = CD28 co-stimulatory domain
source                 1..41
                       mol_type = protein
                       organism = unidentified
SEQUENCE: 83
RSKRSRLLHS DYMNMTPRRP GPTRKHYQPY APPRDFAAYR S                      41

SEQ ID NO: 84          moltype = DNA  length = 123
FEATURE                Location/Qualifiers
misc_feature           1..123
                       note = CD28 co-stimulatory domain
source                 1..123
                       mol_type = unassigned DNA
                       organism = unidentified
SEQUENCE: 84
aggagcaagc ggagcagact gctgcacagc gactacatga acatgacccc ccggaggcct  60
ggccccaccc ggaagcacta ccagccctac gcccctccca gggatttcgc cgcctaccgg  120
agc                                                                123

SEQ ID NO: 85          moltype = AA  length = 23
FEATURE                Location/Qualifiers
REGION                 1..23
                       note = TCR alpha transmembrane domain
source                 1..23
                       mol_type = protein
                       organism = unidentified
SEQUENCE: 85
```

```
VIGFRILLLK VAGFNLLMTL RLW                                        23

SEQ ID NO: 86          moltype = DNA  length = 69
FEATURE                Location/Qualifiers
misc_feature           1..69
                       note = TCR alpha transmembrane domain
source                 1..69
                       mol_type = unassigned DNA
                       organism = unidentified
SEQUENCE: 86
gtgattgggt tccgaatcct cctcctgaaa gtggccgggt ttaatctgct catgacgctg  60
cggctgtgg                                                         69

SEQ ID NO: 87          moltype = AA  length = 23
FEATURE                Location/Qualifiers
REGION                 1..23
                       note = TCR beta transmembrane domain
source                 1..23
                       mol_type = protein
                       organism = unidentified
SEQUENCE: 87
TILYEILLGK ATLYAVLVSA LVL                                        23

SEQ ID NO: 88          moltype = DNA  length = 69
FEATURE                Location/Qualifiers
misc_feature           1..69
                       note = TCR beta transmembrane domain
source                 1..69
                       mol_type = unassigned DNA
                       organism = unidentified
SEQUENCE: 88
accatcctct atgagatctt gctagggaag gccaccttgt atgccgtgct ggtcagtgcc  60
ctcgtgctg                                                         69

SEQ ID NO: 89          moltype = AA  length = 10
FEATURE                Location/Qualifiers
REGION                 1..10
                       note = TCR beta intracellular domain
source                 1..10
                       mol_type = protein
                       organism = unidentified
SEQUENCE: 89
MAMVKRKDSR                                                       10

SEQ ID NO: 90          moltype = DNA  length = 30
FEATURE                Location/Qualifiers
misc_feature           1..30
                       note = TCR beta intracellular domain
source                 1..30
                       mol_type = unassigned DNA
                       organism = unidentified
SEQUENCE: 90
atggccatgg tcaagagaaa ggattccaga                                 30

SEQ ID NO: 91          moltype = AA  length = 247
FEATURE                Location/Qualifiers
source                 1..247
                       mol_type = protein
                       organism = Mus musculus
SEQUENCE: 91
DVLMTQTPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSHVP RTSGGGTKLE IKGGGGSGGG  120
GSGGGGSGGQ VQLQQSGPEL VKPGASVRIS CKASGYTFTS YHIHWVKQRP GQGLEWIGWI  180
YPGNVNTEYN EKFKGKATLT ADKSSSTAYM HLSSLTSEDS AVYFCAREEI TYAMDYWGQG  240
TSVTVSS                                                           247

SEQ ID NO: 92          moltype = AA  length = 247
FEATURE                Location/Qualifiers
REGION                 1..247
                       note = humanized HLA-A*02 antigen binding domain
source                 1..247
                       mol_type = protein
                       organism = synthetic construct
SEQUENCE: 92
QVQLVQSGAE VKKPGSSVKV SCKASGYTFT SYHIHWVRQA PGQGLEWMGW IYPGNVNTEY  60
NEKFKGKATI TADKSTSTAY MELSSLRSED TAVYYCAREE ITYAMDYWGQ GTTVTVSSGG  120
GGSGGGGSGG GGSGGEIVLT QSPGTLSLSP GERATLSCRS SQSIVHSNGN TYLEWYQQKP  180
GQAPRLLIYK VSNRFSGIPD RFSGSGSGTD FTLTISRLEP EDFAVYYCFQ GSHVPRTFGG  240
GTKVEIK                                                           247
```

```
SEQ ID NO: 93           moltype = AA  length = 247
FEATURE                 Location/Qualifiers
REGION                  1..247
                        note = humanized HLA-A*02 antigen binding domain
source                  1..247
                        mol_type = protein
                        organism = synthetic construct
SEQUENCE: 93
QVQLVQSGAE VKKPGSSVKV SCKASGYTFT SYHIHWVRQA PGQGLEWMGW IYPGNVNTEY  60
NEKFKGKATI TADKSTSTAY MELSSLRSED TAVYYCAREE ITYAMDYWGQ GTTVTVSSGG  120
GGSGGGGSGG GGSGGDIVMT QTPLSLPVTP GEPASISCRS SQSIVHSNGN TYLEWYLQKP  180
GQSPQLLIYK VSNRFSGVPD RFSGSGSGTD FTLKISRVEA EDVGVYYCFQ GSHVPRTFGG  240
GTKVEIK                                                            247

SEQ ID NO: 94           moltype = AA  length = 247
FEATURE                 Location/Qualifiers
REGION                  1..247
                        note = humanized HLA-A*02 antigen binding domain
source                  1..247
                        mol_type = protein
                        organism = synthetic construct
SEQUENCE: 94
EVQLVESGGG LVKPGGSLRL SCAASGYTFT SYHIHWVRQA PGKGLEWVGW IYPGNVNTEY  60
NEKFKGRFTI SRDDSKNTLY LQMNSLKTED TAVYYCAREE ITYAMDYWGQ GTTVTVSSGG  120
GGSGGGGSGG GGSGGDIQMT QSPSSLSASV GDRVTITCRS SQSIVHSNGN TYLEWYQQKP  180
GKAPKLLIYK VSNRFSGVPS RFSGSGSGTD FTLTISSLQP EDFATYYCFQ GSHVPRTFGG  240
GTKVEIK                                                            247

SEQ ID NO: 95           moltype = AA  length = 247
FEATURE                 Location/Qualifiers
REGION                  1..247
                        note = humanized HLA-A*02 antigen binding domain
source                  1..247
                        mol_type = protein
                        organism = synthetic construct
SEQUENCE: 95
QVQLVQSGAE VKKPGSSVKV SCKASGYTFT SYHIHWVRQA PGQGLEWIGW IYPGNVNTEY  60
NEKFKGKATI TADESTNTAY MELSSLRSED TAVYYCAREE ITYAMDYWGQ GTLVTVSSGG  120
GGSGGGGSGG GGSGGDIQMT QSPSTLSASV GDRVTITCRS SQSIVHSNGN TYLEWYQQKP  180
GKAPKLLIYK VSNRFSGVPA RFSGSGSGTE FTLTISSLQP DDFATYYCFQ GSHVPRTFGQ  240
GTKVEVK                                                            247

SEQ ID NO: 96           moltype = AA  length = 247
FEATURE                 Location/Qualifiers
REGION                  1..247
                        note = humanized HLA-A*02 antigen binding domain
source                  1..247
                        mol_type = protein
                        organism = synthetic construct
SEQUENCE: 96
QVQLVQSGAE VKKPGSSVKV SCKASGYTFT SYHMHWVRQA PGQGLEWIGY IYPGNVNTEY  60
NEKFKGKATL TADKSTNTAY MELSSLRSED TAVYFCAREE ITYAMDYWGQ GTLVTVSSGG  120
GGSGGGGSGG GGSGGDVQMT QSPSTLSASV GDRVTITCSS SQSIVHSNGN TYMEWYQQKP  180
GKAPKLLIYK VSNRFSGVPD RFSGSGSGTE FTLTISSLQP DDFATYYCHQ GSHVPRTFGQ  240
GTKVEVK                                                            247

SEQ ID NO: 97           moltype = AA  length = 247
FEATURE                 Location/Qualifiers
source                  1..247
                        mol_type = protein
                        organism = Mus musculus
SEQUENCE: 97
QVQLQQSGPE LVKPGASVKM SCKASGYTFT SYHIQWVKQR PGQGLEWIGW IYPGDGSTQY  60
NEKFKGKTTL TADKSSSTAY MLLSSLTSED SAIYFCAREG TYYAMDYWGQ GTSVTVSSGG  120
GGSGGGGSGG GGSGGDVLMT QTPLSLPVSL GDQVSISCRS SQSIVHSNGN TYLEWYLQKP  180
GQSPKLLIYK VSNRFSGVPD RFSGSGSGTD FTLKISRVEA EDLGVYYCFQ GSHVPRTFGG  240
GTKLEIK                                                            247

SEQ ID NO: 98           moltype = AA  length = 247
FEATURE                 Location/Qualifiers
REGION                  1..247
                        note = humanized HLA-A*02 antigen binding domain
source                  1..247
                        mol_type = protein
                        organism = synthetic construct
SEQUENCE: 98
QLQLQESGPG LVKPSETLSL TCTVSGYTFT SYHIQWIRQP PGKGLEWIGW IYPGDGSTQY  60
NEKFKGRATI SVDTSKNQFS LNLDSVSAAD TAIYYCAREG TYYAMDYWGK GSTVTVSSGG  120
```

```
GGSGGGGSGG GGSGGDIQMT QSPSSLSASV GDRVTITCRS SQSIVHSNGN TYLEWYQQKP  180
GKAPKLLIYK VSNRFSGVPS RFSGSGSGTD FTFTISSLQP EDIATYYCFQ GSHVPRTFGP  240
GTKVDIK                                                            247

SEQ ID NO: 99          moltype = AA  length = 247
FEATURE                Location/Qualifiers
REGION                 1..247
                       note = humanized HLA-A*02 antigen binding domain
source                 1..247
                       mol_type = protein
                       organism = synthetic construct
SEQUENCE: 99
EVQLVQSGAE LKKPGSSVKV SCKASGYTFT SYHIQWVKQA PGQGLEWIGW IYPGDGSTQY  60
NEKFKGKATL TVDKSTNTAY MELSSLRSED TAVYYCAREG TYYAMDYWGQ GTLVTVSSGG  120
GGSGGGGSGG GGSGGDIQMT QSPSTLSASV GDRVTITCRS SQSIVHSNGN TYLEWYQQKP  180
GKAPKLLIYK VSNRFSGVPS RFSGSGSGTD FTLTISSLQP DDFATYYCFQ GSHVPRTFGQ  240
GTKVEVK                                                            247

SEQ ID NO: 100         moltype = AA  length = 247
FEATURE                Location/Qualifiers
REGION                 1..247
                       note = humanized HLA-A*02 antigen binding domain
source                 1..247
                       mol_type = protein
                       organism = synthetic construct
SEQUENCE: 100
QVQLVQSGAE VKKPGSSVKV SCKASGYTFT SYHIQWVRQA PGQGLEWMGW IYPGDGSTQY  60
NEKFKGRVTI TADKSTSTAY MELSSLRSED TAVYYCAREG TYYAMDYWGQ GTTVTVSSGG  120
GGSGGGGSGG GGSGGEIVLT QSPGTLSLSP GERATLSCRS SQSIVHSNGN TYLEWYQQKP  180
GQAPRLLIYK VSNRFSGIPD RFSGSGSGTD FTLTISRLEP EDFAVYYCFQ GSHVPRTFGG  240
GTKVEIK                                                            247

SEQ ID NO: 101         moltype = AA  length = 247
FEATURE                Location/Qualifiers
REGION                 1..247
                       note = humanized HLA-A*02 antigen binding domain
source                 1..247
                       mol_type = protein
                       organism = synthetic construct
SEQUENCE: 101
QVTLKQSGAE VKKPGSSVKV SCTASGYTFT SYHVSWVRQA PGQGLEWLGR IYPGDGSTQY  60
NEKFKGKVTI TADKSMDTSF MELTSLTSED TAVYYCAREG TYYAMDLWGQ GTLVTVSSGG  120
GGSGGGGSGG GGSGGEIVLT QSPGTLSLSP GERATLSCRS SQSIVHSNGN TYLAWYQQKP  180
GQAPRLLISK VSNRFSGVPD RFSGSGSGTD FTLTISRLEP EDFAVYYCQQ GSHVPRTFGG  240
GTKVEIK                                                            247

SEQ ID NO: 102         moltype = AA  length = 247
FEATURE                Location/Qualifiers
REGION                 1..247
                       note = humanized HLA-A*02 antigen binding domain
source                 1..247
                       mol_type = protein
                       organism = synthetic construct
SEQUENCE: 102
QVQLVQSGAE VKKPGASVKV SCKASGYTFT SYHMHWVRQA PGQRLEWMGW IYPGDGSTQY  60
NEKFKGKVTI TRDTSASTAY MELSSLRSED TAVYYCAREG TYYAMDYWGQ GTLVTVSSGG  120
GGSGGGGSGG GGSGGDIVMT QTPLSLPVTP GEPASISCRS SQSIVHSNGN TYLDWYLQKP  180
GQSPQLLIYK VSNRFSGVPD RFSGSGSGTD FTLKISRVEA EDVGVYYCMQ GSHVPRTFGG  240
GTKVEIK                                                            247

SEQ ID NO: 103         moltype = AA  length = 16
FEATURE                Location/Qualifiers
REGION                 1..16
                       note = HLA antigen binding domain CDR-L1
source                 1..16
                       mol_type = protein
                       organism = synthetic construct
SEQUENCE: 103
RSSQSIVHSN GNTYLE                                                  16

SEQ ID NO: 104         moltype = AA  length = 12
FEATURE                Location/Qualifiers
REGION                 1..12
                       note = HLA antigen binding domain CDR-L2
source                 1..12
                       mol_type = protein
                       organism = synthetic construct
SEQUENCE: 104
KVSNRFSGVP DR                                                      12
```

```
SEQ ID NO: 105          moltype = AA  length = 9
FEATURE                 Location/Qualifiers
REGION                  1..9
                        note = HLA antigen binding domain CDR-L3
source                  1..9
                        mol_type = protein
                        organism = synthetic construct
SEQUENCE: 105
FQGSHVPRT                                                         9

SEQ ID NO: 106          moltype = AA  length = 12
FEATURE                 Location/Qualifiers
REGION                  1..12
                        note = HLA antigen binding domain CDR-H1
source                  1..12
                        mol_type = protein
                        organism = synthetic construct
SEQUENCE: 106
ASGYTFTSYH IH                                                     12

SEQ ID NO: 107          moltype = AA  length = 18
FEATURE                 Location/Qualifiers
REGION                  1..18
                        note = HLA antigen binding domain CDR-H2
source                  1..18
                        mol_type = protein
                        organism = synthetic construct
SEQUENCE: 107
WIYPGNVNTE YNEKFKGK                                               18

SEQ ID NO: 108          moltype = AA  length = 9
FEATURE                 Location/Qualifiers
REGION                  1..9
                        note = HLA antigen binding domain CDR-H3
source                  1..9
                        mol_type = protein
                        organism = synthetic construct
SEQUENCE: 108
EEITYAMDY                                                         9

SEQ ID NO: 109          moltype = AA  length = 16
FEATURE                 Location/Qualifiers
REGION                  1..16
                        note = HLA antigen binding domain CDR-L1
source                  1..16
                        mol_type = protein
                        organism = synthetic construct
SEQUENCE: 109
RSSQSIVHSN GNTYLD                                                 16

SEQ ID NO: 110          moltype = AA  length = 12
FEATURE                 Location/Qualifiers
REGION                  1..12
                        note = HLA antigen binding domain CDR-L2
source                  1..12
                        mol_type = protein
                        organism = synthetic construct
SEQUENCE: 110
KVSNRFSGVP DR                                                     12

SEQ ID NO: 111          moltype = AA  length = 9
FEATURE                 Location/Qualifiers
REGION                  1..9
                        note = HLA antigen binding domain CDR-L3
source                  1..9
                        mol_type = protein
                        organism = synthetic construct
SEQUENCE: 111
MQGSHVPRT                                                         9

SEQ ID NO: 112          moltype = AA  length = 11
FEATURE                 Location/Qualifiers
REGION                  1..11
                        note = HLA antigen binding domain CDR-H1
source                  1..11
                        mol_type = protein
                        organism = synthetic construct
SEQUENCE: 112
```

```
SGYTFTSYHM H                                                      11

SEQ ID NO: 113          moltype = AA  length = 17
FEATURE                 Location/Qualifiers
REGION                  1..17
                        note = HLA antigen binding domain CDR-H2
source                  1..17
                        mol_type = protein
                        organism = synthetic construct
SEQUENCE: 113
WIYPGDGSTQ YNEKFKG                                                17

SEQ ID NO: 114          moltype = AA  length = 9
FEATURE                 Location/Qualifiers
REGION                  1..9
                        note = HLA antigen binding domain CDR-H3
source                  1..9
                        mol_type = protein
                        organism = synthetic construct
SEQUENCE: 114
EGTYYAMDY                                                         9

SEQ ID NO: 115          moltype = AA  length = 670
FEATURE                 Location/Qualifiers
REGION                  1..670
                        note = LILRB1
source                  1..670
                        mol_type = protein
                        organism = unidentified
SEQUENCE: 115
MTPILTVLIC LGLSLGPRTH VQAGHLPKPT LWAEPGSVIT QGSPVTLRCQ GGQETQEYRL  60
YREKKTALWI TRIPQELVKK GQFPIPSITW EHAGRYRCYY GSDTAGRSES SDPLELVVTG  120
AYIKPTLSAQ PSPVVNSGGN VILQCDSQVA FDGFSLCKEG EDEHPQCLNS QPHARGSSRA  180
IFSVGPVSPS RRWWYRCYAY DSNSPYEWSL PSDLLELLVL GVSKKPSLSV QPGPIVAPEE  240
TLTLQCGSDA GYNRFVLYKD GERDFLQLAG AQPQAGLSQA NFTLGPVSRS YGGQYRCYGA  300
HNLSSEWSAP SDPLDILIAG QFYDRVSLSV QPGPTVASGE NVTLLCQSQG WMQTFLLTKE  360
GAADDPWRLR STYQSQKYQA EFPMGPVTSA HAGTYRCYGS QSSKPYLLTH PSDPLELVVS  420
GPSGGPSSPT TGPTSTSGPE DQPLTPTGSD PQSGLGRHLG VVIGILVAVI LLLLLLLLLF  480
LILRHRRQGK HWTSTQRKAD FQHPAGAVGP EPTDRGLQWR SSPAADAQEE NLYAAVKHTQ  540
PEDGVEMDTR SPHDEDPQAV TYAEVKHSRP RREMASPPSP LSGEFLDTKD RQAEEDRQMD  600
TEAAASEAPQ DVTYAQLHSL TLRREATEPP PSQEGPSPAV PSIYATLAIH PSQEGPSPAV  660
PSIYATLAIH                                                        670

SEQ ID NO: 116          moltype = DNA  length = 3229
FEATURE                 Location/Qualifiers
misc_feature            1..3229
                        note = LILRB1
source                  1..3229
                        mol_type = unassigned DNA
                        organism = unidentified
SEQUENCE: 116
aaatgagttt taaaaaggct tgtccaggaa gcacatatgg gagctggtca ctctgcattt  60
tgggccctcc tggaggtgtt tagaccttcc gagagagaaa ctgagacaca tgagagggaa  120
gaaatgactc agtggtgaga ccctgtggag tcccacccac aaccagcaca ctgtgaccca  180
ctgcacaaac ctctagccca cagctcactt cctcctttaa gaagagaaga gaaaagagga  240
gaggagagga ggaacagaaa agaaaagaaa agaaaaagtg ggaaacaaat aatctaagaa  300
tgaggagaaa gcaagaagag tgaccccctt gtgggcactc cattggtttt atggcgcctc  360
tactttctgg agtttgtgta aaacaaaaat attatggtct ttgtgcacat ttacatcaag  420
ctcagcctgg gcggcacagc cagatgcgag atgcgtctct gctgatctga gtctgcctgc  480
agcatggacc tgggtcttcc ctgaagcatc tccagggctg gagggacgac tgccatgcac  540
cgagggctca tccatccaca gagcagggca gtgggaggag acgccatgac ccccatcctc  600
acggtcctga tctgtctcgg gctgagtctg ggcccccgga cccacgtgca ggcagggcac  660
ctccccaagc ccaccctctg ggctgaacca ggctctgtga tcacccaggg gagtcctgtg  720
accctcaggt gtcagggggg ccaggagacc caggagtacc gtctatatag agaaaagaaa  780
acagcaccct ggattacacg gatcccacag gagcttgtga agaagggcca gttccccatc  840
ccatccatca cctgggaaca cacagggcgg tatcgctgtt actatggtag cgacactgca  900
ggccgctcag agagcagtga ccccctggag ctggtggtga caggagccta catcaaaccc  960
accctctcag cccagcccag ccccgtggtg aactcaggag ggaatgtaac cctccagtgt  1020
gactcacagg tggcatttga tggcttcatt ctgtgtaagg aaggagaaga tgaacaccca  1080
caatgcctga actcccagcc ccatgcccgt gggtcgtccc gcgccatctt ctccgtgggc  1140
cccgtgagcc cgagtcgcag gtggtggtac aggtgctatg cttatgactc gaactctccc  1200
tatgagtggt ctctacccag tgatctcctg gagctcctgg tcctaggtgt ttctaagaag  1260
ccatcactct cagtgcagcc aggtcctatc gtggcccctg aggagaccct gactctgcag  1320
tgtggctctg atgctggcta caacagattt gttctgtata aggacgggga acgtgacttc  1380
cttcagctcg ctggcgcaca gccccaggct gggctctccc aggccaactt caccctgggc  1440
cctgtgagcc gctcctacgg gggccagtac agatgctacg gtgcacacaa cctctcctcc  1500
gagtggtcgg cccccagcga ccccctggac atcctgatcg caggacagtt ctatgacaga  1560
gtctccctct cggtgcagcc gggccccacg gtggcctcag gagagaacgt gaccctgctg  1620
tgtcagtcac agggatggat gcaaactttc cttctgacca aggagggggc agctgatgac  1680
```

```
ccatggcgtc taagatcaac gtaccaatct caaaaatacc aggctgaatt ccccatgggt  1740
cctgtgacct cagcccatgc ggggacctac aggtgctacg gctcacagag ctccaaaccc  1800
tacctgctga ctcaccccag tgaccccctg gagctcgtgg tctcaggacc gtctgggggc  1860
cccagctccc cgacaacagg ccccacctcc acatctggcc ctgaggacca gcccctcacc  1920
cccaccgggt cggatcccca gagtggtctg ggaaggcacc tgggggttgt gatcggcatc  1980
ttggtggccg tcatcctact gctcctcctc ctcctcctcc tcttcctcat cctccgacat  2040
cgacgtcagg gcaaacactg gacatcgacc cagagaaagg ctgatttcca acatcctgca  2100
ggggctgtgg ggccagagcc cacagacaga ggcctgcagt ggaggtccag cccagctgcc  2160
gatgcccagg aagaaaacct ctatgctgcc gtgaagcaca cacagcctga ggatggggtg  2220
gagatggaca ctcggagccc acacgatgaa gacccccagg cagtgacgta tgccgaggtg  2280
aaacactcca gacctaggag agaaatggcc tctcctcctt ccccactgtc tggggaattc  2340
ctggacacaa aggacagaca ggcggaagag gacaggcaga tggacactga ggctgctgca  2400
tctgaagccc cccaggatgt gacctacgcc cagctgcaca gcttgaccct cagacgggag  2460
gcaactgagc ctcctccatc ccaggaaggg ccctctccag ctgtgcccag catctacgcc  2520
actctggcca tccactagcc caggggggga cgcagacccc acactccatg gagtctggaa  2580
tgcatgggag ctgcccccc agtggacacc attggacccc acccagcctg gatctacccc  2640
aggagactct gggaactttt aggggtcact caattctgca gtataaataa ctaatgtctc  2700
tacaattttg aaataaagca acagacttct caataatcaa tgaagtagct gagaaaacta  2760
agtcagaaag tgcattaaac tgaatcacaa tgtaaatatt acacatcaag cgatgaaact  2820
ggaaaactac aagccacgaa tgaatgaatt aggaaagaaa aaaagtagga aatgaatgat  2880
cttggctttc ctataagaaa tttagggcag ggcacggtgg ctcacgcctg taattccagc  2940
actttgggag gccgaggcgg gcagatcacg agttcaggag atcgagacca tcttggccaa  3000
catggtgaaa ccctgtctct cctaaaaata caaaaattag ctggatgtgg tggcagtgcc  3060
tgtaatccca gctatttggg aggctgaggc aggagaatcg cttgaaccag ggagtcagag  3120
gtttcagtga gccaagatcg caccactgct ctccagcctg gcgacagagg gagactccat  3180
ctcaaattaa aaaaaaaaaa aaaaaagaaa gaaaaaaaaa aaaaaaaaa             3229
```

```
SEQ ID NO: 117          moltype = AA  length = 6
FEATURE                 Location/Qualifiers
REGION                  1..6
                        note = immunoreceptor tyrosine-based inhibitory motif
source                  1..6
                        mol_type = protein
                        organism = unidentified
SEQUENCE: 117
NLYAAV                                                        6

SEQ ID NO: 118          moltype = AA  length = 6
FEATURE                 Location/Qualifiers
REGION                  1..6
                        note = immunoreceptor tyrosine-based inhibitory motif
source                  1..6
                        mol_type = protein
                        organism = unidentified
SEQUENCE: 118
VTYAEV                                                        6

SEQ ID NO: 119          moltype = AA  length = 6
FEATURE                 Location/Qualifiers
REGION                  1..6
                        note = immunoreceptor tyrosine-based inhibitory motif
source                  1..6
                        mol_type = protein
                        organism = unidentified
SEQUENCE: 119
VTYAQL                                                        6

SEQ ID NO: 120          moltype = AA  length = 6
FEATURE                 Location/Qualifiers
REGION                  1..6
                        note = immunoreceptor tyrosine-based inhibitory motif
source                  1..6
                        mol_type = protein
                        organism = unidentified
SEQUENCE: 120
SIYATL                                                        6

SEQ ID NO: 121          moltype = AA  length = 35
FEATURE                 Location/Qualifiers
REGION                  1..35
                        note = ITIM1-2
source                  1..35
                        mol_type = protein
                        organism = unidentified
SEQUENCE: 121
NLYAAVKHTQ PEDGVEMDTR SPHDEDPQAV TYAEV                        35

SEQ ID NO: 122          moltype = AA  length = 58
FEATURE                 Location/Qualifiers
```

```
REGION               1..58
                     note = ITIM2-3
source               1..58
                     mol_type = protein
                     organism = unidentified
SEQUENCE: 122
VTYAEVKHSR PRREMASPPS PLSGEFLDTK DRQAEEDRQM DTEAAASEAP QDVTYAQL    58

SEQ ID NO: 123       moltype = AA  length = 36
FEATURE              Location/Qualifiers
REGION               1..36
                     note = ITIM3-4
source               1..36
                     mol_type = protein
                     organism = unidentified
SEQUENCE: 123
VTYAQLHSLT LRREATEPPP SQEGPSPAVP SIYATL                            36

SEQ ID NO: 124       moltype = AA  length = 87
FEATURE              Location/Qualifiers
REGION               1..87
                     note = ITIM1-3
source               1..87
                     mol_type = protein
                     organism = unidentified
SEQUENCE: 124
NLYAAVKHTQ PEDGVEMDTR SPHDEDPQAV TYAEVKHSRP RREMASPPSP LSGEFLDTKD  60
RQAEEDRQMD TEAAASEAPQ DVTYAQL                                      87

SEQ ID NO: 125       moltype = AA  length = 88
FEATURE              Location/Qualifiers
REGION               1..88
                     note = ITIM2-4
source               1..88
                     mol_type = protein
                     organism = unidentified
SEQUENCE: 125
VTYAEVKHSR PRREMASPPS PLSGEFLDTK DRQAEEDRQM DTEAAASEAP QDVTYAQLHS  60
LTLRREATEP PPSQEGPSPA VPSIYATL                                     88

SEQ ID NO: 126       moltype = AA  length = 117
FEATURE              Location/Qualifiers
REGION               1..117
                     note = ITIM1-4
source               1..117
                     mol_type = protein
                     organism = unidentified
SEQUENCE: 126
NLYAAVKHTQ PEDGVEMDTR SPHDEDPQAV TYAEVKHSRP RREMASPPSP LSGEFLDTKD  60
RQAEEDRQMD TEAAASEAPQ DVTYAQLHSL TLRREATEPP PSQEGPSPAV PSIYATL     117

SEQ ID NO: 127       moltype = AA  length = 20
FEATURE              Location/Qualifiers
REGION               1..20
                     note = D3D4 domain
source               1..20
                     mol_type = protein
                     organism = unidentified
SEQUENCE: 127
YGSQSSKPYL LTHPSDPLEL                                              20

SEQ ID NO: 128       moltype = AA  length = 43
FEATURE              Location/Qualifiers
REGION               1..43
                     note = Short hinge
source               1..43
                     mol_type = protein
                     organism = unidentified
SEQUENCE: 128
VVSGPSGGPS SPTTGPTSTS GPEDQPLTPT GSDPQSGLGR HLG                    43

SEQ ID NO: 129       moltype = AA  length = 86
FEATURE              Location/Qualifiers
REGION               1..86
                     note = Hinge-transmembrane
source               1..86
                     mol_type = protein
                     organism = unidentified
SEQUENCE: 129
```

```
YGSQSSKPYL LTHPSDPLEL VVSGPSGGPS SPTTGPTSTS GPEDQPLTPT GSDPQSGLGR  60
HLGVVIGILV AVILLLLLLL LLFLIL                                       86

SEQ ID NO: 130         moltype = AA  length = 190
FEATURE                Location/Qualifiers
REGION                 1..190
                       note = Transmembrane-intracellular domain
source                 1..190
                       mol_type = protein
                       organism = unidentified
SEQUENCE: 130
VVIGILVAVI LLLLLLLLLF LILRHRRQGK HWTSTQRKAD FQHPAGAVGP EPTDRGLQWR  60
SSPAADAQEE NLYAAVKHTQ PEDGVEMDTR SPHDEDPQAV TYAEVKHSRP RREMASPPSP  120
LSGEFLDTKD RQAEEDRQMD TEAAASEAPQ DVTYAQLHSL TLRREATEPP PSQEGPSPAV  180
PSIYATLAIH                                                         190

SEQ ID NO: 131         moltype = AA  length = 167
FEATURE                Location/Qualifiers
REGION                 1..167
                       note = LILRB1 intracellular domain
source                 1..167
                       mol_type = protein
                       organism = unidentified
SEQUENCE: 131
RHRRQGKHWT STQRKADFQH PAGAVGPEPT DRGLQWRSSP AADAQEENLY AAVKHTQPED  60
GVEMDTRSPH DEDPQAVTYA EVKHSRPRRE MASPPSPLSG EFLDTKDRQA EEDRQMDTEA  120
AASEAPQDVT YAQLHSLTLR REATEPPPSQ EGPSPAVPSI YATLAIH                167

SEQ ID NO: 132         moltype = AA  length = 253
FEATURE                Location/Qualifiers
REGION                 1..253
                       note = LILRB1 hinge-transmembrane-intracellular domain
source                 1..253
                       mol_type = protein
                       organism = unidentified
SEQUENCE: 132
YGSQSSKPYL LTHPSDPLEL VVSGPSGGPS SPTTGPTSTS GPEDQPLTPT GSDPQSGLGR  60
HLGVVIGILV AVILLLLLLL LLFLILRHRR QGKHWTSTQR KADFQHPAGA VGPEPTDRGL  120
QWRSSPAADA QEENLYAAVK HTQPEDGVEM DTRSPHDEDP QAVTYAEVKH SRPRREMASP  180
PSPLSGEFLD TKDRQAEEDR QMDTEAAASE APQDVTYAQL HSLTLRREAT EPPPSQEGPS  240
PAVPSIYATL AIH                                                     253

SEQ ID NO: 133         moltype = AA  length = 233
FEATURE                Location/Qualifiers
REGION                 1..233
                       note = LILRB1 hinge-transmembrane-intracellular domain
source                 1..233
                       mol_type = protein
                       organism = unidentified
SEQUENCE: 133
VVSGPSGGPS SPTTGPTSTS GPEDQPLTPT GSDPQSGLGR HLGVVIGILV AVILLLLLLL  60
LLFLILRHRR QGKHWTSTQR KADFQHPAGA VGPEPTDRGL QWRSSPAADA QEENLYAAVK  120
HTQPEDGVEM DTRSPHDEDP QAVTYAEVKH SRPRREMASP PSPLSGEFLD TKDRQAEEDR  180
QMDTEAAASE APQDVTYAQL HSLTLRREAT EPPPSQEGPS PAVPSIYATL AIH         233

SEQ ID NO: 134         moltype = AA  length = 63
FEATURE                Location/Qualifiers
REGION                 1..63
                       note = LILRB1 hinge domain
source                 1..63
                       mol_type = protein
                       organism = unidentified
SEQUENCE: 134
YGSQSSKPYL LTHPSDPLEL VVSGPSGGPS SPTTGPTSTS GPEDQPLTPT GSDPQSGLGR  60
HLG                                                                63

SEQ ID NO: 135         moltype = AA  length = 23
FEATURE                Location/Qualifiers
REGION                 1..23
                       note = LILRB1 transmembrane domain
source                 1..23
                       mol_type = protein
                       organism = unidentified
SEQUENCE: 135
VVIGILVAVI LLLLLLLLLF LIL                                          23

SEQ ID NO: 136         moltype = AA  length = 273
FEATURE                Location/Qualifiers
source                 1..273
```

```
                        mol_type = protein
                        organism = Homo sapiens
SEQUENCE: 136
MSGSQSEVAP SPQSPRSPEM GRDLRPGSRV LLLLLLLLLV YLTQPGNGNE GSVTGSCYCG  60
KRISSDSPPS VQFMNRLRKH LRAYHRCLYY TRFQLLSWSV CGGNKDPWVQ ELMSCLDLKE  120
CGHAYSGIVA HQKHLLPTSP PISQASEGAS SDIHTPAQML LSTLQSTQRP TLPVGSLSSD  180
KELTRPNETT IHTAGHSLAA GPEAGENQKQ PEKNAGPTAR TSATVPVLCL LAIIFILTAA  240
LSYVLCKRRR GQSPQSSPDL PVHYIPVAPD SNT                               273

SEQ ID NO: 137          moltype = AA  length = 742
FEATURE                 Location/Qualifiers
source                  1..742
                        mol_type = protein
                        organism = Homo sapiens
SEQUENCE: 137
MKDDFAEEEE VQSFGYKRFG IQEGTQCTKC KNNWALKFSI ILLYILCALL TITVAILGYK  60
VVEKMDNVTG GMETSRQTYD DKLTAVESDL KKLGDQTGKK AISTNSELST FRSDILDLRQ  120
QLREITEKTS KNKDTLEKLQ ASGDALVDRQ SQLKETLENN SFLITTVNKT LQAYNGYVTN  180
LQQDTSVLQG NLQNQMYSHN VVIMNLNNLN LTQVQQRNLI TNLQRSVDDT SQAIQRIKND  240
FQNLQQVFLQ AKKDTDWLKE KVQSLQTLAA NNSALAKANN DTLEDMNSQL NSFTGQMENI  300
TTISQANEQN LKDLQDLHKD AENRTAIKFN QLEERFQLFE TDIVNIISNI SYTAHHLRTL  360
TSNLNEVRTT CTDTLTKHTD DLTSLNNTLA NIRLDSVSLR MQQDLMRSRL DTEVANLSVI  420
MEEMKLVDSK HGQLIKNFTI LQGPPGPRGP RGDRGSQGPP GPTGNKGQKG EKGEPGPPGP  480
AGERGPIGPA GPPGERGGKG SKGSQGPKGS RGSPGKPGPQ GSSGDPGPPG PPGKEGLPGP  540
QGPPGFQGLQ GTVGEPGVPG PRGLPGLPGV PGMPGPKGPP GPPGPSGAVV PLALQNEPTP  600
APEDNGCPPH WKNFTDKCYY FSVEKEIFED AKLFCEDKSS HLVFINTREE QQWIKKQMVG  660
RESHWIGLTD SERENEWKWL DGTSPDYKNW KAGQPDNWGH GHGPGEDCAG LIYAGQWNDF  720
QCEDVNNFIC EKDRETVLSS AL                                           742

SEQ ID NO: 138          moltype = AA  length = 514
FEATURE                 Location/Qualifiers
source                  1..514
                        mol_type = protein
                        organism = Homo sapiens
SEQUENCE: 138
MSWPRRLLLR YLFPALLLHG LGEGSALLHP DSRSHPRSLE KSAWRAFKES QCHHMLKHLH  60
NGARITVQMP PTIEGHWVST GCEVRSGPEF ITRSYRFYHN NTFKAYQFYY GSNRCTNPTY  120
TLIIRGKIRL RQASWIIRGG TEADYQLHNV QVICHTEAVA EKLGQQVNRT CPGFLADGGP  180
WVQDVAYDLW REENGCECTK AVNFAMHELQ LIRVEKQYLH HNLDHLVEEL FLGDIHTDAT  240
QRMFYRPSSY QPPLQNAKNH DHACIACRII YRSDEHHPPI LPPKADLTIG LHGEWVSQRC  300
EVRPEVLFLT RHFIFHDNNN TWEGHYYHYS DPVCKHPTFS IYARGRYSRG VLSSRVMGGT  360
EFVFKVNHMK VTPMDAATAS LLNVFNGNEC GAEGSWQVGI QQDVTHTNGC VALGIKLPHT  420
EYEIFKMEQD ARGRYLLFNG QRPSDGSSPD RPEKRATSYQ MPLVQCASSS PRAEDLAEDS  480
GSSLYGRAPG RHTWSLLLAA LACLVPLLHW NIRR                              514

SEQ ID NO: 139          moltype = AA  length = 227
FEATURE                 Location/Qualifiers
SITE                    1
                        note = Xaa is any amino acid
source                  1..227
                        mol_type = protein
                        organism = Homo sapiens
SEQUENCE: 139
XDVAYDLWRE ENGCECTKAV NFAMHELQLI RVEKQYLHHN LDHLVEELFL GDIHTDATQR  60
MFYRPSSYQP PLQNAKCAAE SSGSFQILPQ DSSEKEQNGL SHWCLSRPGH QKDWALCAHA  120
GPATAGCPSC LWPPAETGRK AGRTSSKTVH ACPGEAGTSS FELFYFPNCW SIETKLKISL  180
NAKLSFKPRA SAPLETGHRV KIETLSQLVF LSFIQLCCEV QSPLANK                227

SEQ ID NO: 140          moltype = AA  length = 93
FEATURE                 Location/Qualifiers
source                  1..93
                        mol_type = protein
                        organism = Homo sapiens
SEQUENCE: 140
EDVLPALQLP APSAECQVEM GFHHVGQDGL QLPTSSDPPA LASQSAGITG VSHRPPGRHL  60
SNDLRTTTMP ASPVGSSIGQ TSTTLPSCPQ RQT                               93

SEQ ID NO: 141          moltype = AA  length = 1078
FEATURE                 Location/Qualifiers
REGION                  1..1078
                        note = CEA CAR-T2A-HLA-A*02 inhibitory Receptor
source                  1..1078
                        mol_type = protein
                        organism = synthetic construct
SEQUENCE: 141
MDMRVPAQLL GLLLLWLRGA RCDVLMTQTP LSLPVSLGDQ ASISCRSSQS IVHSNGNTYL  60
EWYLQKPGQS PKLLIYKVSN RFSGVPDRFS GSGSGTDFTL KISRVEAEDL GVYYCFQGSH  120
VPRTSGGGTK LEIKGGGGSG GGGSGGGGSG GQVQLQQSGP ELVKPGASVR ISCKASGYTF  180
TSYHIHWVKQ RPGQGLEWIG WIYPGNVNTE YNEKFKGKAT LTADKSSSTA YMHLSSLTSE  240
```

-continued

```
DSAVYFCARE EITYAMDYWG QGTSVTVSSY GSQSSKPYLL THPSDPLELV VSGPSGGPSS  300
PTTGPTSTSG PEDQPLTPTG SDPQSGLGRH LGVVIGILVA VILLLLLLLL LFLILRHRRQ  360
GKHWTSTQRK ADFQHPAGAV GPEPTDRGLQ WRSSPAADAQ EENLYAAVKH TQPEDGVEMD  420
TRSPHDEDPQ AVTYAEVKHS RPRREMASPP SPLSGEFLDT KDRQAEEDRQ MDTEAAASEA  480
PQDVTYAQLH SLTLRREATE PPPSQEGPSP AVPSIYATLA IHGSGEGRGS LLTCGDVEEN  540
PGPMDMRVPA QLLGLLLLWL RGARCQVQLV QSGSELKKPG ASVKVSCKAS GYTFTEFGMN  600
WVRQAPGQGL EWMGWINTKT GEATYVEEFK GRFVFSLDTS VSTAYLQISS LKAEDTAVYY  660
CARWDFAYYV EAMDYWGQGT TVTVSSGGGG SGGGGSGGGG SGGDIQMTQS PSSLSASVGD  720
RVTITCKASQ NVGTNVAWYQ QKPGKAPKLL IYSASYRYSG VPSRFSGSGS GTDFTLTISS  780
LQPEDFATYY CHQYYTYPLF TFGQGTKLEI KTTTPAPRPP TPAPTIASQP LSLRPEACRP  840
AAGGAVHTRG LDFACDFWVL VVVGGVLACY SLLVTVAFII FWVRSKRSRL LHSDYMNMTP  900
RRPGPTRKHY QPYAPPRDFA AYRSKRGRKK LLYIFKQPFM RPVQTTQEED GCSCRFPEEE  960
EGGCELRVKF SRSADAPAYK QGQNQLYNEL NLGRREEYDV LDKRRGRDPE MGGKPRRKNP  1020
QEGLYNELQK DKMAEAYSEI GMKGERRRGK GHDGLYQGLS TATKDTYDAL HMQALPPR    1078

SEQ ID NO: 142         moltype = DNA  length = 3237
FEATURE                Location/Qualifiers
misc_feature           1..3237
                       note = CEA CAR-T2A-HLA-A*02 inhibitory Receptor
source                 1..3237
                       mol_type = other DNA
                       organism = synthetic construct
SEQUENCE: 142
atggatatga gagtgcctgc ccagctgctc ggactgctcc ttctgtggtt gagaggagct  60
cggtgcgatg ttctgatgac ccaaactcca ctctccctgc ctgtcagtct tggagatcaa  120
gcctccatct cttgcagatc tagtcagagc attgtacata gtaatggaaa cacctattta  180
gaatggtacc tgcagaagcc aggccagtct ccaaagctgc tcatctacaa agtttccaac  240
cgattttctg gggtcccaga cagatttagc ggatctggct ctgggaccga tttcacactc  300
aagatcagta gagtggaggc tgaggatctg ggagtttatt actgctttca aggttcacat  360
gttcctcgga cgtccggtgg aggcacaaag ctggaaatca agggaggtgg cggctctgga  420
ggcggaggta gcggaggtgg aggctctggt ggccaggtcc agctgcagca gtctggacct  480
gagctggtga agccaggggc ttcagtgagg atatcctgta aggcctctgg ctacaccttt  540
acaagttacc atatacattg ggtgaagcag aggcctggac agggactcga atggattgga  600
tggatttatc ctggaaatgt taatactgag tacaatgaga agttcaaggg caaggccaca  660
ctgactgcag acaaatcgtc cagcacagcc tacatgcacc tcagcagcct gacctctgag  720
gactctgcgg tctatttctg tgccagagag gagattacct atgctatgga ttattggggt  780
caaggaacct cagtcaccgt gtcctcatac ggctcacaga gctccaaacc ctacctgctg  840
actcacccta gtgatcctct ggagctcgtg gtctcaggac cgtctggagg cccaagctct  900
ccgacaacag gccccacctc cacatctggc cctgaggacc agcccctcac acccaccggg  960
tcggatcctc agagtggtct gggaagacac ctgggagttg tgatcggcat cttggtggcc  1020
gtcatcctac tgctcctcct cctgctcctg ctcttcctca tcctccgaca tcgacgtcag  1080
ggcaaacact ggacatcgac ccagagaaag gctgatttcc aacatcctgc aggggctgtg  1140
gggccagagc ccacagacag aggcctgcag tggaggtcca gcccagctgc cgatgcccag  1200
gaagaaaacc tctatgctgc cgtgaagcac acacagcctg aggatggggt ggagatggat  1260
actcggagcc cacacgatga agatccacag gcagtgacgt atgccgaggt gaaacactcc  1320
agacctagaa gggaaatggc ctctcctcct tccccactgt ctggagagtt cctggacaca  1380
aaggacagac aggcggaaga ggacaggcag atggacactg aggctgctgc atctgaagct  1440
cctcaggatg tgacctacgc ccagctgcac agcttgaccc tcagacggga ggcaactgag  1500
cctcctccat cccaggaagg gccctctcca gctgtgccca gcatctacgc cactctggcc  1560
atccacggat ccggagaggg cagaggcagc ctgctgacat gtggcgacgt ggaagagaac  1620
cctggcccca tggacatgag ggtccccgct cagctcctgg ggctcctgct actctggctc  1680
cgaggtgcca gatgtcaggt gcagctggtg caatctgggt ctgagttgaa gaagcctggg  1740
gcctcagtga aggtttcctg caaggcttct ggatacacct tcactgagtt tggaatgaac  1800
tgggtgcgac aggcccctgg acaagggctt gagtggatgg gatggataaa caccaaaact  1860
ggagaggcaa catatgttga agagtttaag ggacggtttg tcttctcctt ggacacctct  1920
gtcagcacgg catatctgca gatcagcagc ctaaaggctg aagacactgc cgtgtattac  1980
tgtgcgagat gggacttcgc ttattacgtg gaggctatgg actactgggg ccaagggacc  2040
acggtgaccg tgtcatccgg cggaggtgga agcggagggg gaggatctgg cggcggagga  2100
agcggaggcg atatccagat gacccagtct ccatcctccc tgtctgcatc tgtgggagac  2160
agagtcacca tcacttgcaa ggccagtcag aatgtgggta ctaatgttgc ctggtatcag  2220
cagaaaccag ggaaagcacc taagctcctg atctattcgg catcctaccg ctacagtgga  2280
gtcccatcaa ggttcagtgg cagtggatct gggacagatt tcactctcac catcagcagt  2340
ctgcaacctg aagatttcgc aacttactac tgtcaccaat attacaccta tcctctattc  2400
acgtttggcc agggcaccaa gctcgagatc aagacaacga cgccagctcc ccgcccgcca  2460
acccctgcac ctacgattgc atcacaaccg ctgtccctgc ggcctgaagc ttgtcgccca  2520
gccgcaggtg gcgccgtaca tacacggggg ctggattttg cctgtgattt ctgggtgctg  2580
gtcgttgtgg gcggcgtgct ggcctgctac agcctgctgg tgacagtggc cttcatcatc  2640
ttttgggtga ggagcaagcg gagtcgactg ctgcacagcg actacatgaa catgaccccc  2700
cggaggcctg gcccacccg gaagcactac cagccctacg cccctcccag ggatttcgcc  2760
gcctaccgga gcaaacgggg cagaaagaaa ctcctgtata tattcaaaca accatttatg  2820
aggccagtac aaactactca agaggaagat ggctgtagct gccgatttcc agaagaagaa  2880
gaaggaggat gtgaactgag agtgaagttc agcaggagcg cagacgcccc cgcgtacaag  2940
cagggccaga accagctcta taacgagctc aatctaggac gaagagagga gtacgatgtt  3000
ttggacaagc gtagaggccg ggaccctgag atgggggaa agccgagaag gaagaaccct  3060
caggaaggcc tgtacaatga actgcagaaa gataagatgg cggaggccta cagtgagatt  3120
gggatgaaag gcgagcgccg gaggggcaag gggcacgatg gcctttacca gggactcagt  3180
acagccacca aggacaccta cgacgccctt cacatgcagg ccctgccccc tcgctaa     3237

SEQ ID NO: 143         moltype = DNA  length = 1605
```

```
FEATURE                Location/Qualifiers
misc_feature           1..1605
                       note = CEA CAR
source                 1..1605
                       mol_type = other DNA
                       organism = synthetic construct
SEQUENCE: 143
atggacatga gggtccccgc tcagctcctg gggctcctgc tactctggct ccgaggtgcc  60
agatgtcagg tgcagctggt gcaatctggg tctgagttga agaagcctgg ggcctcagtg  120
aaggtttcct gcaaggcttc tggatacacc ttcactgagt ttggaatgaa ctgggtgcga  180
caggcccctg gacaagggct tgagtggatg ggatggataa acaccaaaac tggagaggca  240
acatatgttg aagagtttaa gggacggttt gtcttctcct tggacacctc tgtcagcacg  300
gcatatctgc agatcagcag cctaaaggct gaagacactg ccgtgtatta ctgtgcgaga  360
tgggacttcg cttattacgt ggaggctatg gactactggg gccaagggac cacggtgacc  420
gtgtcatccg gcggaggtgg aagcggaggg ggaggatctg gcggcggagg aagcggaggc  480
gatatccaga tgacccagtc tccatcctcc ctgtctgcat ctgtgggaga cagagtcacc  540
atcacttgca aggccagtca gaatgtgggt actaatgttg cctggtatca gcagaaacca  600
gggaaagcac ctaagctcct gatctattcg gcatcctacc gctacagtgg agtcccatca  660
aggttcagtg gcagtggatc tgggacagat ttcactctca ccatcagcag tctgcaacct  720
gaagatttcg caacttacta ctgtcaccaa tattacacct atcctctatt cacgtttggc  780
cagggcacca agctcgagat caagacaacg acgccagctc cccgcccgcc aacccctgca  840
cctacgattg catcacaacc gctgtccctg cggcctgaag cttgtcgccc agccgcaggt  900
ggcgccgtac atacacgggg gctggatttt gcctgtgatt tctgggtgct ggtcgttgtg  960
ggcggcgtgc tggcctgcta cagcctgctg gtgacagtgg ccttcatcat cttttgggtg  1020
aggagcaagc ggagtcgact gctgcacagc gactacatga acatgacccc ccggaggcct  1080
ggccccaccc ggaagcacta ccagccctac gcccctccca gggatttcgc cgcctaccgg  1140
agcaaacggg gcagaaagaa actcctgtat atattcaaac aaccatttat gaggccagta  1200
caaactactc aagaggaaga tggctgtagc tgccgatttc cagaagaaga agaaggagga  1260
tgtgaactga gagtgaagtt cagcaggagc gcagacgccc ccgcgtacaa gcagggccag  1320
aaccagctct ataacgagct caatctagga cgaagagagg agtacgatgt tttggacaag  1380
cgtagaggcc gggaccctga gatgggggga aagccgagaa ggaagaaccc tcaggaaggc  1440
ctgtacaatg aactgcagaa agataagatg gcggaggcct acagtgagat tgggatgaaa  1500
ggcgagcgcc ggaggggcaa ggggcacgat ggcctttacc agggactcag tacagccacc  1560
aaggacacct acgacgccct tcacatgcag gccctgcccc ctcgc                  1605

SEQ ID NO: 144         moltype = AA  length = 121
FEATURE                Location/Qualifiers
REGION                 1..121
                       note = CEA VH region
source                 1..121
                       mol_type = protein
                       organism = synthetic construct
SEQUENCE: 144
QVQLVQSGSE LKKPGASVKV SCKASGYTFT EFGMNWVRQA PGQGLEWMGW INTKTGEATY  60
VEEFKGRFVF SLDTSVSTAY LQISSLKAED TAVYYCARWD FAYYVEAMDY WGQGTTVTVS  120
S                                                                 121

SEQ ID NO: 145         moltype = DNA  length = 363
FEATURE                Location/Qualifiers
misc_feature           1..363
                       note = CEA VH region
source                 1..363
                       mol_type = other DNA
                       organism = synthetic construct
SEQUENCE: 145
caggtgcagc tggtgcaatc tgggtctgag ttgaagaagc ctggggcctc agtgaaggtt  60
tcctgcaagg cttctggata caccttcact gagtttggaa tgaactgggt gcgacaggcc  120
cctggacaag ggcttgagtg gatgggatgg ataaacacca aaactggaga ggcaacatat  180
gttgaagagt ttaagggacg gtttgtcttc tccttggaca cctctgtcag cacggcatat  240
ctgcagatca gcagcctaaa ggctgaagac actgccgtgt attactgtgc gagatgggac  300
ttcgcttatt acgtggaggc tatggactac tggggccaag ggaccacggt gaccgtgtca  360
tcc                                                               363

SEQ ID NO: 146         moltype = AA  length = 17
FEATURE                Location/Qualifiers
REGION                 1..17
                       note = Linker
source                 1..17
                       mol_type = protein
                       organism = synthetic construct
SEQUENCE: 146
GGGGSGGGGS GGGGSGG                                                17

SEQ ID NO: 147         moltype = DNA  length = 51
FEATURE                Location/Qualifiers
misc_feature           1..51
                       note = Linker
source                 1..51
                       mol_type = other DNA
```

```
                      organism = synthetic construct
SEQUENCE: 147
ggcggaggtg gaagcggagg gggaggatct ggcggcggag gaagcggagg c          51

SEQ ID NO: 148        moltype = AA  length = 108
FEATURE               Location/Qualifiers
REGION                1..108
                      note = CEA VL region
source                1..108
                      mol_type = protein
                      organism = synthetic construct
SEQUENCE: 148
DIQMTQSPSS LSASVGDRVT ITCKASQNVG TNVAWYQQKP GKAPKLLIYS ASYRYSGVPS  60
RFSGSGSGTD FTLTISSLQP EDFATYYCHQ YYTYPLFTFG QGTKLEIK              108

SEQ ID NO: 149        moltype = DNA  length = 324
FEATURE               Location/Qualifiers
misc_feature          1..324
                      note = CEA VL region
source                1..324
                      mol_type = other DNA
                      organism = synthetic construct
SEQUENCE: 149
gatatccaga tgacccagtc tccatcctcc ctgtctgcat ctgtgggaga cagagtcacc  60
atcacttgca aggccagtca gaatgtgggt actaatgttg cctggtatca gcagaaacca  120
gggaaagcac ctaagctcct gatctattcg gcatcctacc gctacagtgg agtcccatca  180
aggttcagtg gcagtggatc tgggacagat ttcactctca ccatcagcag tctgcaacct  240
gaagatttcg caacttacta ctgtcaccaa tattacacct atcctctatt cacgtttggc  300
cagggcacca agctcgagat caag                                        324

SEQ ID NO: 150        moltype = DNA  length = 15
FEATURE               Location/Qualifiers
misc_feature          1..15
                      note = CDR-H1
source                1..15
                      mol_type = other DNA
                      organism = synthetic construct
SEQUENCE: 150
gagtttggaa tgaac                                                  15

SEQ ID NO: 151        moltype = DNA  length = 51
FEATURE               Location/Qualifiers
misc_feature          1..51
                      note = CDR-H2
source                1..51
                      mol_type = other DNA
                      organism = synthetic construct
SEQUENCE: 151
tggataaaca ccaaaactgg agaggcaaca tatgttgaag agtttaaggg a          51

SEQ ID NO: 152        moltype = DNA  length = 36
FEATURE               Location/Qualifiers
misc_feature          1..36
                      note = CDR-H3
source                1..36
                      mol_type = other DNA
                      organism = synthetic construct
SEQUENCE: 152
tgggacttcg cttattacgt ggaggctatg gactac                           36

SEQ ID NO: 153        moltype = DNA  length = 33
FEATURE               Location/Qualifiers
misc_feature          1..33
                      note = CDR-L1
source                1..33
                      mol_type = other DNA
                      organism = synthetic construct
SEQUENCE: 153
aaggccagtc agaatgtggg tactaatgtt gcc                              33

SEQ ID NO: 154        moltype = DNA  length = 21
FEATURE               Location/Qualifiers
misc_feature          1..21
                      note = CDR-L2
source                1..21
                      mol_type = other DNA
                      organism = synthetic construct
SEQUENCE: 154
tcggcatcct accgctacag t                                           21
```

```
SEQ ID NO: 155          moltype = DNA  length = 30
FEATURE                 Location/Qualifiers
misc_feature            1..30
                        note = CDR-L3
source                  1..30
                        mol_type = other DNA
                        organism = synthetic construct
SEQUENCE: 155
caccaatatt acacctatcc tctattcacg                                   30

SEQ ID NO: 156          moltype = DNA  length = 135
FEATURE                 Location/Qualifiers
misc_feature            1..135
                        note = CD8alpha hinge
source                  1..135
                        mol_type = other DNA
                        organism = synthetic construct
SEQUENCE: 156
acaacgacgc cagctccccg cccgccaacc cctgcaccta cgattgcatc acaaccgctg  60
tccctgcggc ctgaagcttg tcgcccagcc gcaggtggcg ccgtacatac acgggggctg  120
gattttgcct gtgat                                                   135

SEQ ID NO: 157          moltype = DNA  length = 81
FEATURE                 Location/Qualifiers
misc_feature            1..81
                        note = CD28 transmembrane domain
source                  1..81
                        mol_type = other DNA
                        organism = synthetic construct
SEQUENCE: 157
ttctgggtgc tggtcgttgt gggcggcgtg ctggcctgct acagcctgct ggtgacagtg  60
gccttcatca tcttttgggt g                                            81

SEQ ID NO: 158          moltype = AA  length = 195
FEATURE                 Location/Qualifiers
REGION                  1..195
                        note = CD28-41BB-CD3zeta intracellular domain
source                  1..195
                        mol_type = protein
                        organism = synthetic construct
SEQUENCE: 158
RSKRSRLLHS DYMNMTPRRP GPTRKHYQPY APPRDFAAYR SKRGRKKLLY IFKQPFMRPV  60
QTTQEEDGCS CRFPEEEEGG CELRVKFSRS ADAPAYKQGQ NQLYNELNLG RREEYDVLDK  120
RRGRDPEMGG KPRRKNPQEG LYNELQKDKM AEAYSEIGMK GERRRGKGHD GLYQGLSTAT  180
KDTYDALHMQ ALPPR                                                   195

SEQ ID NO: 159          moltype = DNA  length = 585
FEATURE                 Location/Qualifiers
misc_feature            1..585
                        note = CD28-41BB-CD3zeta intracellular domain
source                  1..585
                        mol_type = other DNA
                        organism = synthetic construct
SEQUENCE: 159
aggagcaagc ggagtcgact gctgcacagc gactacatga acatgacccc ccggaggcct  60
ggccccaccc ggaagcacta ccagccctac gcccctccca gggatttcgc cgcctaccgg  120
agcaaacggg gcagaaagaa actcctgtat atattcaaac aaccatttat gaggccagta  180
caaactactc aagaggaaga tggctgtagc tgccgatttc cagaagaaga agaaggagga  240
tgtgaactga gagtgaagtt cagcaggagc gcagacgccc ccgcgtacaa gcagggccag  300
aaccagctct ataacgagct caatctagga cgaagagagg agtacgatgt tttggacaag  360
cgtagaggcc gggaccctga gatgggggga aagccgagaa ggaagaaccc tcaggaaggc  420
ctgtacaatg aactgcagaa agataagatg gcggaggcct acagtgagat tgggatgaaa  480
ggcgagcgcc ggaggggcaa ggggcacgat ggcctttacc agggactcag tacagccacc  540
aaggacacct acgacgccct tcacatgcag gccctgcccc ctcgc                  585

SEQ ID NO: 160          moltype = DNA  length = 123
FEATURE                 Location/Qualifiers
misc_feature            1..123
                        note = CD28 co-stimulatory domain
source                  1..123
                        mol_type = unassigned DNA
                        organism = unidentified
SEQUENCE: 160
aggagcaagc ggagtcgact gctgcacagc gactacatga acatgacccc ccggaggcct  60
ggccccaccc ggaagcacta ccagccctac gcccctccca gggatttcgc cgcctaccgg  120
agc                                                                123

SEQ ID NO: 161          moltype = AA  length = 42
```

```
FEATURE                 Location/Qualifiers
REGION                  1..42
                        note = 4-1BB
source                  1..42
                        mol_type = protein
                        organism = unidentified
SEQUENCE: 161
KRGRKKLLYI FKQPFMRPVQ TTQEEDGCSC RFPEEEEGGC EL                    42

SEQ ID NO: 162          moltype = DNA  length = 126
FEATURE                 Location/Qualifiers
misc_feature            1..126
                        note = 4-1BB
source                  1..126
                        mol_type = unassigned DNA
                        organism = unidentified
SEQUENCE: 162
aaacggggca gaaagaaact cctgtatata ttcaaacaac catttatgag gccagtacaa  60
actactcaag aggaagatgg ctgtagctgc cgatttccag aagaagaaga aggaggatgt  120
gaactg                                                            126

SEQ ID NO: 163          moltype = DNA  length = 336
FEATURE                 Location/Qualifiers
misc_feature            1..336
                        note = CD3zeta
source                  1..336
                        mol_type = unassigned DNA
                        organism = unidentified
SEQUENCE: 163
agagtgaagt tcagcaggag cgcagacgcc cccgcgtaca agcagggcca gaaccagctc  60
tataacgagc tcaatctagg acgaagagag gagtacgatg ttttggacaa gcgtagaggc  120
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggactca gtacagccac caaggacacc  300
tacgacgccc ttcacatgca ggccctgccc cctcgc                           336

SEQ ID NO: 164          moltype = AA  length = 522
FEATURE                 Location/Qualifiers
REGION                  1..522
                        note = Inhibitory Receptor anti-HLA-A*02 scFv - LILRB1
                         hinge, TM and ICD
source                  1..522
                        mol_type = protein
                        organism = synthetic construct
SEQUENCE: 164
MDMRVPAQLL GLLLLWLRGA RCDVLMTQTP LSLPVSLGDQ ASISCRSSQS IVHSNGNTYL  60
EWYLQKPGQS PKLLIYKVSN RFSGVPDRFS GSGSGTDFTL KISRVEAEDL GVYYCFQGSH  120
VPRTSGGGTK LEIKGGGGSG GGGSGGGGSG GQVQLQQSGP ELVKPGASVR ISCKASGYTF  180
TSYHIHWVKQ RPGQGLEWIG WIYPGNVNTE YNEKFKGKAT LTADKSSSTA YMHLSSLTSE  240
DSAVYFCARE EITYAMDYWG QGTSVTVSSY GSQSSKPYLL THPSDPLELV VSGPSGGPSS  300
PTTGPTSTSG PEDQPLTPTG SDPQSGLGRH LGVVIGILVA VILLLLLLLL LFLILRHRRQ  360
GKHWTSTQRK ADFQHPAGAV GPEPTDRGLQ WRSSPAADAQ EENLYAAVKH TQPEDGVEMD  420
TRSPHDEDPQ AVTYAEVKHS RPRREMASPP SPLSGEFLDT KDRQAEEDRQ MDTEAAASEA  480
PQDVTYAQLH SLTLRREATE PPPSQEGPSP AVPSIYATLA IH                    522

SEQ ID NO: 165          moltype = DNA  length = 1566
FEATURE                 Location/Qualifiers
misc_feature            1..1566
                        note = Inhibitory Receptor anti-HLA-A*02 scFv - LILRB1
                         hinge, TM and ICD
source                  1..1566
                        mol_type = other DNA
                        organism = synthetic construct
SEQUENCE: 165
atggatatga gagtgcctgc ccagctgctc ggactgctcc ttctgtggtt gagaggagct  60
cggtgcgatg ttctgatgac ccaaactcca ctctccctgc ctgtcagtct tggagatcaa  120
gcctccatct cttgcagatc tagtcagagc attgtacata gtaatggaaa cacctattta  180
gaatggtacc tgcagaagcc aggccagtct ccaaagctgc tcatctacaa agtttccaac  240
cgattttctg gggtcccaga cagatttagc ggatctggct ctggaccga tttcacactc  300
aagatcagta gagtggaggc tgaggatctg ggagtttatt actgctttca aggttcacat  360
gttcctcgga cgtccggtgg aggcacaaag ctggaaatca agggaggtgg cggctctgga  420
ggcggaggta gcggaggtgg aggctctggt ggccaggtcc agctgcagca gtctggacct  480
gagctggtga agccaggggc ttcagtgagg atatcctgta aggcctctgg ctacaccttt  540
acaagttacc atatacattg ggtgaagcag aggcctggac agggactcga atggattgga  600
tggatttatc ctggaaatgt taatactgag tacaatgaga agttcaaggg caaggccaca  660
ctgactgcag acaaatcgtc cagcacagcc tacatgcacc tcagcagcct gacctctgag  720
gactctgcgg tctatttctg tgccagagag gagattacct atgctatgga ttattggggt  780
caaggaacct cagtcaccgt gtcctcatac ggctcacaga gctccaaacc ctacctgctg  840
actcacccta gtgatcctct ggagctcgtg gtctcaggac cgtctggagg cccaagctct  900
```

```
ccgacaacag gccccacctc cacatctggc cctgaggacc agcccctcac acccaccggg  960
tcggatcctc agagtggtct gggaagacac ctgggagttg tgatcggcat cttggtggcc  1020
gtcatcctac tgctcctcct cctgctcctg ctcttcctca tcctccgaca tcgacgtcag  1080
ggcaaacact ggacatcgac ccagagaaag gctgatttcc aacatcctgc aggggctgtg  1140
gggccagagc ccacagacag aggcctgcag tggaggtcca gcccagctgc cgatgcccag  1200
gaagaaaacc tctatgctgc cgtgaagcac acacagcctg aggatggggt ggagatggat  1260
actcggagcc cacacgatga agatccacag gcagtgacgt atgccgaggt gaaacactcc  1320
agacctagaa gggaaatggc ctctcctcct tccccactgt ctggagagtt cctggacaca  1380
aaggacagac aggcggaaga ggacaggcag atggacactg aggctgctgc atctgaagct  1440
cctcaggatg tgacctacgc ccagctgcac agcttgaccc tcagacggga ggcaactgag  1500
cctcctccat cccaggaagg gccctctcca gctgtgccca gcatctacgc cactctggcc  1560
atccac                                                             1566

SEQ ID NO: 166         moltype = AA  length = 112
FEATURE                Location/Qualifiers
REGION                 1..112
                       note = Inhibitory Receptor VL
source                 1..112
                       mol_type = protein
                       organism = synthetic construct
SEQUENCE: 166
DVLMTQTPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSHVP RTSGGGTKLE IK          112

SEQ ID NO: 167         moltype = DNA  length = 336
FEATURE                Location/Qualifiers
misc_feature           1..336
                       note = Inhibitory Receptor VL
source                 1..336
                       mol_type = other DNA
                       organism = synthetic construct
SEQUENCE: 167
gatgttctga tgacccaaac tccactctcc ctgcctgtca gtcttggaga tcaagcctcc  60
atctcttgca gatctagtca gagcattgta catagtaatg gaaacaccta tttagaatgg  120
tacctgcaga agccaggcca gtctccaaag ctgctcatct acaaagtttc caaccgattt  180
tctggggtcc cagacagatt tagcggatct ggctctggga ccgatttcac actcaagatc  240
agtagagtgg aggctgagga tctgggagtt tattactgct ttcaaggttc acatgttcct  300
cggacgtccg gtggaggcac aaagctggaa atcaag                            336

SEQ ID NO: 168         moltype = DNA  length = 51
FEATURE                Location/Qualifiers
misc_feature           1..51
                       note = linker
source                 1..51
                       mol_type = other DNA
                       organism = synthetic construct
SEQUENCE: 168
ggaggtggcg gctctggagg cggaggtagc ggaggtggag gctctggtgg c           51

SEQ ID NO: 169         moltype = DNA  length = 48
FEATURE                Location/Qualifiers
misc_feature           1..48
                       note = Inhibitory Receptor CDR-L1
source                 1..48
                       mol_type = other DNA
                       organism = synthetic construct
SEQUENCE: 169
agatctagtc agagcattgt acatagtaat ggaaacacct atttagaa               48

SEQ ID NO: 170         moltype = DNA  length = 36
FEATURE                Location/Qualifiers
misc_feature           1..36
                       note = Inhibitory Receptor CDR-L2
source                 1..36
                       mol_type = other DNA
                       organism = synthetic construct
SEQUENCE: 170
aaagtttcca accgattttc tggggtccca gacaga                            36

SEQ ID NO: 171         moltype = DNA  length = 27
FEATURE                Location/Qualifiers
misc_feature           1..27
                       note = Inhibitory Receptor CDR-L3
source                 1..27
                       mol_type = other DNA
                       organism = synthetic construct
SEQUENCE: 171
tttcaaggtt cacatgttcc tcggacg                                      27
```

```
SEQ ID NO: 172          moltype = DNA  length = 36
FEATURE                 Location/Qualifiers
misc_feature            1..36
                        note = Inhibitory Receptor CDR-H1
source                  1..36
                        mol_type = other DNA
                        organism = synthetic construct
SEQUENCE: 172
gcctctggct acacctttac aagttaccat atacat                            36

SEQ ID NO: 173          moltype = DNA  length = 54
FEATURE                 Location/Qualifiers
misc_feature            1..54
                        note = Inhibitory Receptor CDR-H2
source                  1..54
                        mol_type = other DNA
                        organism = synthetic construct
SEQUENCE: 173
tggatttatc ctggaaatgt taatactgag tacaatgaga agttcaaggg caag        54

SEQ ID NO: 174          moltype = DNA  length = 27
FEATURE                 Location/Qualifiers
misc_feature            1..27
                        note = Inhibitory Receptor CDR-H3
source                  1..27
                        mol_type = other DNA
                        organism = synthetic construct
SEQUENCE: 174
gaggagatta cctatgctat ggattat                                      27

SEQ ID NO: 175          moltype = DNA  length = 759
FEATURE                 Location/Qualifiers
misc_feature            1..759
                        note = LILR1B hinge, TM and ICD
source                  1..759
                        mol_type = other DNA
                        organism = synthetic construct
SEQUENCE: 175
tacggctcac agagctccaa accctacctg ctgactcacc ctagtgatcc tctggagctc  60
gtggtctcag gaccgtctgg aggcccaagc tctccgacaa caggccccac ctccacatct  120
ggccctgagg accagcccct cacacccacc gggtcggatc ctcagagtgg tctgggaaga  180
cacctgggag ttgtgatcgg catcttggtg gccgtcatcc tactgctcct cctcctgctc  240
ctgctcttcc tcatcctccg acatcgacgt cagggcaaac actggacatc gacccagaga  300
aaggctgatt tccaacatcc tgcaggggct gtggggccag agcccacaga cagaggcctg  360
cagtggaggt ccagcccagc tgccgatgcc caggaagaaa acctctatgc tgccgtgaag  420
cacacacagc ctgaggatgg ggtggagatg gatactcgga gcccacacga tgaagatcca  480
caggcagtga cgtatgccga ggtgaaacac tccagaccta gaagggaaat ggcctctcct  540
ccttccccac tgtctggaga gttcctggac acaaaggaca gacaggcgga agaggacagg  600
cagatggaca ctgaggctgc tgcatctgaa gctcctcagg atgtgaccta cgcccagctg  660
cacagcttga ccctcagacg ggaggcaact gagcctcctc catcccagga agggccctct  720
ccagctgtgc ccagcatcta cgccactctg gccatccac                         759

SEQ ID NO: 176          moltype = DNA  length = 189
FEATURE                 Location/Qualifiers
misc_feature            1..189
                        note = LILRB1 hinge
source                  1..189
                        mol_type = other DNA
                        organism = synthetic construct
SEQUENCE: 176
tacggctcac agagctccaa accctacctg ctgactcacc ctagtgatcc tctggagctc  60
gtggtctcag gaccgtctgg aggcccaagc tctccgacaa caggccccac ctccacatct  120
ggccctgagg accagcccct cacacccacc gggtcggatc ctcagagtgg tctgggaaga  180
cacctggga                                                          189

SEQ ID NO: 177          moltype = DNA  length = 69
FEATURE                 Location/Qualifiers
misc_feature            1..69
                        note = LILRB1 TM
source                  1..69
                        mol_type = other DNA
                        organism = synthetic construct
SEQUENCE: 177
gttgtgatcg gcatcttggt ggccgtcatc ctactgctcc tcctcctgct cctgctcttc  60
ctcatcctc                                                          69

SEQ ID NO: 178          moltype = DNA  length = 501
FEATURE                 Location/Qualifiers
misc_feature            1..501
```

```
                        note = LILRB1 ICD
source                  1..501
                        mol_type = other DNA
                        organism = synthetic construct
SEQUENCE: 178
cgacatcgac gtcagggcaa acactggaca tcgacccaga gaaaggctga tttccaacat  60
cctgcagggg ctgtggggcc agagcccaca gacagaggcc tgcagtggag gtccagccca  120
gctgccgatg cccaggaaga aaacctctat gctgccgtga agcacacaca gcctgaggat  180
ggggtggaga tggatactcg gagcccacac gatgaagatc cacaggcagt gacgtatgcc  240
gaggtgaaac actccagacc tagaagggaa atggcctctc ctccttcccc actgtctgga  300
gagttcctgg acacaaagga cagacaggcg gaagaggaca ggcagatgga cactgaggct  360
gctgcatctg aagctcctca ggatgtgacc tacgcccagc tgcacagctt gaccctcaga  420
cgggaggcaa ctgagcctcc tccatcccag gaagggccct ctccagctgt gcccagcatc  480
tacgccactc tggccatcca c                                            501

SEQ ID NO: 179          moltype = DNA  length = 46
FEATURE                 Location/Qualifiers
misc_feature            1..46
                        note = B2M shRNA
source                  1..46
                        mol_type = unassigned DNA
                        organism = unidentified
SEQUENCE: 179
gcactcaaag cttgttaaga tcgaaatctt aacaagcttt gagtgc                 46

SEQ ID NO: 180          moltype = DNA  length = 46
FEATURE                 Location/Qualifiers
misc_feature            1..46
                        note = B2M shRNA
source                  1..46
                        mol_type = unassigned DNA
                        organism = unidentified
SEQUENCE: 180
gttaacttcc aatttacata ccgaagtatg taaattggaa gttaac                 46

SEQ ID NO: 181          moltype = AA  length = 21
FEATURE                 Location/Qualifiers
REGION                  1..21
                        note = T2A self-cleaving polypeptide
source                  1..21
                        mol_type = protein
                        organism = unidentified
SEQUENCE: 181
GSGEGRGSLL TCGDVEENPG P                                            21

SEQ ID NO: 182          moltype = AA  length = 1179
FEATURE                 Location/Qualifiers
source                  1..1179
                        mol_type = protein
                        organism = Homo sapiens
SEQUENCE: 182
MWLFHTLLCI ASLALLAAFN VDVARPWLTP KGGAPFVLSS LLHQDPSTNQ TWLLVTSPRT  60
KRTPGPLHRC SLVQDEILCH PVEHVPIPKG RHRGVTVVRS HHGVLICIQV LVRRPHSLSS  120
ELTGTCSLLG PDLRPQAQAN FFDLENLLDP DARVDTGDCY SNKEGGGEDD VNTARQRRAL  180
EKEEEEDKEE EEDEEEEEAG TEIAIILDGS GSIDPPDFQR AKDFISNMMR NFYEKCFECN  240
FALVQYGGVI QTEFDLRDSQ DVMASLARVQ NITQVGSVTK TASAMQHVLD SIFTSSHGSR  300
RKASKVMVVL TDGGIFEDPL NLTTVINSPK MQGVERFAIG VGEEFKSART ARELNLIASD  360
PDETHAFKVT NYMALDGLLS KLRYNIISME GTVGDALHYQ LAQIGFSAQI LDERQVLLGA  420
VGAFDWSGGA LLYDTRSRRG RFLNQTAAAA ADAEAAQYSY LGYAVAVLHK TCSLSYIAGA  480
PRYKHHGAVF ELQKEGREAS FLPVLEGEQM GSYFGSELCP VDIDMDGSTD FLLVAAPFYH  540
VHGEEGRVYV YRLSEQDGSF SLARILSGHP GFTNARFGFA MAAMGDLSQD KLTDVAIGAP  600
LEGFGADDGA SFGSVYIYNG HWDGLSASPS QRIRASTVAP GLQYFGMSMA GGFDISGDGL  660
ADITVGTLGQ AVVFRSRPVV RLKVSMAFTP SALPIGFNGV VNVRLCFEIS SVTTASESGL  720
REALLNFTLD VDVGKQRRRL QCSDVRSCLG CLREWSSGSQ LCEDLLLMPT EGELCEEDCF  780
SNASVKVSYQ LQTPEGQTDH PQPILDRYTE PFAIFQLPYE KACKNKLFCV AELQLATTVS  840
QQELVVGLTK ELTLNINLTN SGEDSYMTSM ALNYPRNLQL KRMQKPPSPN IQCDDPQPVA  900
SVLIMNCRIG HPVLKRSSAH VSVVWQLEEN AFPNRTADIT VTVTNSNERR SLANETHTLQ  960
FRHGFVAVLS KPSIMYVNTG QGLSHHKEFL FHVHGENLFG AEYQLQICVP TKLRGLQVVA  1020
VKKLTRTQAS TVCTWSQERA CAYSSVQHVE EWHSVSCVIA SDKENVTVAA EISWDHSEEL  1080
LKDVTELQIL GEISFNKSLY EGLNAENHRT KITVVFLKDE KYHSLPIIIK GSVGGLLVLI  1140
VILVILFKCG FFKRKYQQLN LESIRKAQLK SENLLEEEN                          1179

SEQ ID NO: 183          moltype = AA  length = 1163
FEATURE                 Location/Qualifiers
source                  1..1163
                        mol_type = protein
                        organism = Homo sapiens
SEQUENCE: 183
MTRTRAALLL FTALATSLGF NLDTEELTAF RVDSAGFGDS VVQYANSWVV VGAPQKITAA  60
```

```
NQTGGLYQCG YSTGACEPIG LQVPPEAVNM SLGLSLASTT SPSQLLACGP TVHHECGRNM  120
YLTGLCFLLG PTQLTQRLPV SRQECPRQEQ DIVFLIDGSG SISSRNFATM MNFVRAVISQ  180
FQRPSTQFSL MQFSNKFQTH FTFEEFRRSS NPLSLLASVH QLQGFTYTAT AIQNVVHRLF  240
HASYGARRDA AKILIVITDG KKEGDSLDYK DVIPMADAAG IIRYAIGVGL AFQNRNSWKE  300
LNDIASKPSQ EHIFKVEDFD ALKDIQNQLK EKIFAIEGTE TTSSSSFELE MAQEGFSAVF  360
TPDGPVLGAV GSFTWSGGAF LYPPNMSPTF INMSQENVDM RDSYLGYSTE LALWKGVQSL  420
VLGAPRYQHT GKAVIFTQVS RQWRMKAEVT GTQIGSYFGA SLCSVDVDSD GSTDLVLIGA  480
PHYYEQTRGG QVSVCPLPRG WRRWWCDAVL YGEQGHPWGR FGAALTVLGD VNGDKLTDVV  540
IGAPGEEENR GAVYLFHGVL GPSISPSHSQ RIAGSQLSSR LQYFGQALSG GQDLTQDGLV  600
DLAVGARGQV LLLRTRPVLW VGVSMQFIPA EIPRSAFECR EQVVSEQTLV QSNICLYIDK  660
RSKNLLGSRD LQSSVTLDLA LDPGRLSPRA TFQETKNRSL SRVRVLGLKA HCENFNLLLP  720
SCVEDSVTPI TLRLNFTLVG KPLLAFRNLR PMLAADAQRY FTASLPFEKN CGADHICQDN  780
LGISFSFPGL KSLLVGSNLE LNAEVMVWND GEDSYGTTIT FSHPAGLSYR YVAEGQKQGQ  840
LRSLHLTCDS APVGSQGTWS TSCRINHLIF RGGAQITFLA TFDVSPKAVL GDRLLLTANV  900
SSENNTPRTS KTTFQLELPV KYAVYTVVSS HEQFTKYLNF SESEEKESHV AMHRYQVNNL  960
GQRDLPVSIN FWVPVELNQE AVWMDVEVSH PQNPSLRCSS EKIAPPASDF LAHIQKNPVL  1020
DCSIAGCLRF RCDVPSFSVQ EELDFTLKGN LSFGWVRQIL QKKVSVVSVA EITFDTSVYS  1080
QLPGQEAFMR AQTTTVLEKY KVHNPTPLIV GSSIGGLLLL ALITAVLYKV GFFKRQYKEM  1140
MEEANGQIAP ENGTQTPSPP SEK                                          1163

SEQ ID NO: 184          moltype = AA  length = 22
FEATURE                 Location/Qualifiers
REGION                  1..22
                        note = signal sequence
source                  1..22
                        mol_type = protein
                        organism = unidentified
SEQUENCE: 184
MDMRVPAQLL GLLLLWLRGA RC                                           22

SEQ ID NO: 185          moltype = DNA  length = 66
FEATURE                 Location/Qualifiers
misc_feature            1..66
                        note = signal sequence
source                  1..66
                        mol_type = unassigned DNA
                        organism = unidentified
SEQUENCE: 185
atggacatga gggtccccgc tcagctcctg gggctcctgc tactctggct ccgaggtgcc  60
agatgt                                                             66

SEQ ID NO: 186          moltype = AA  length = 19
FEATURE                 Location/Qualifiers
REGION                  1..19
                        note = P2A self-cleaving peptide
source                  1..19
                        mol_type = protein
                        organism = unidentified
SEQUENCE: 186
ATNFSLLKQA GDVEENPGP                                               19

SEQ ID NO: 187          moltype = DNA  length = 1800
FEATURE                 Location/Qualifiers
misc_feature            1..1800
                        note = CT 548: pLenti 1 CEA TCR TRAV8-1*01 118P & 119T with
                         murineconstant region
source                  1..1800
                        mol_type = other DNA
                        organism = synthetic construct
SEQUENCE: 187
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatctaa cctcaggagg aaactacaaa  360
cctacgtttg ggaaagggac cagcctcgtg gttcatccag acattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
acggttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
ttccagaatc tgtcagtgat gggtctgcgg atcctgcttc tgaaggttgc aggattcaat  780
cttcttatga ctctccggct ctggtcttca ggttctggcg cgacgaattt tagtttgctt  840
aagcaagccg gagatgtgga ggaaaatcct ggaccgatgg ctacaaggct cctctgttac  900
acagtacttt gtctcctggg tgcaagaatt ttgaactcaa aagtcattca gactccaaga  960
tatctggtga aagggcaagg acaaaaagca aagatgaggt gtatccctga aaagggacat  1020
ccagttgtat tctggtatca acaaaataag aacaatgagt ttaaattttt gattaacttt  1080
cagaatcaag aagttcttca gcaaatagac atgactgaaa aacgattctc tgctgagtgt  1140
```

```
ccttcaaact caccttgcag cctagaaatt cagtcctctg aggcaggaga ctcagcactg  1200
tacctctgtg ccagcagtct gggactgggg gactatgaac agtacttcgg tcccggcacc  1260
aggctcacgg ttttagagga tctccggaac gtcaccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtccactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg ggtagagcc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800

SEQ ID NO: 188          moltype = DNA  length = 1800
FEATURE                 Location/Qualifiers
misc_feature            1..1800
                        note = CT 549: pLenti 1 CEA TCR TRAV8-1*01 118P & 119T
                         TRBV26*01 L117Twith murine constant region
source                  1..1800
                        mol_type = other DNA
                        organism = synthetic construct
SEQUENCE: 188
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatctaa cctcaggagg aaactacaaa  360
cctacgtttg ggaaagggac cagcctcgtg gttcatccag acattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
acggttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
ttccagaatc tgtcagtgat gggtctgcgg atcctgcttc tgaaggttgc aggattcaat  780
cttcttatga ctctccggct ctggtcttca ggttctggcg cgacgaattt tagtttgctt  840
aagcaagccg gagatgtgga ggaaaatcct ggaccgatgg ctacaaggct cctctgttac  900
acagtacttt gtctcctggg tgcaagaatt ttgaactcaa aagtcattca gactccaaga  960
tatctggtga aagggcaagg acaaaaagca aagatgaggt gtatccctga aaagggacat  1020
ccagttgtat tctggtatca acaaaataag aacaatgagt ttaaattttt gattaacttt  1080
cagaatcaag aagttcttca gcaaatagac atgactgaaa aacgattctc tgctgagtgt  1140
ccttcaaact caccttgcag cctagaaatt cagtcctctg aggcaggaga ctcagcactg  1200
tacctctgtg ccagcagtct ggggacaggg gactatgaac agtacttcgg tcccggcacc  1260
aggctcacgg ttttagagga tctccggaac gtcaccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtccactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg ggtagagcc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800

SEQ ID NO: 189          moltype = DNA  length = 1800
FEATURE                 Location/Qualifiers
misc_feature            1..1800
                        note = CT 550: pLenti 1 CEA TCR TRAV8-1*01 118P & 119T with
                         murineconstant region
source                  1..1800
                        mol_type = other DNA
                        organism = synthetic construct
SEQUENCE: 189
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatctaa cctcaggagg aaactacaaa  360
cctacgtttg ggaaagggac cagcctcgtg gttcatccaa atattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
tgcgttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
ttccagaatc tgctggtgat cgttctgcgg atcctgcttc tgaaggttgc aggattcaat  780
cttcttatga ctctccggct ctggtcttca ggttctggcg cgacgaattt tagtttgctt  840
aagcaagccg gagatgtgga ggaaaatcct ggaccgatgg ctacaaggct cctctgttac  900
acagtacttt gtctcctggg tgcaagaatt ttgaactcaa aagtcattca gactccaaga  960
tatctggtga aagggcaagg acaaaaagca aagatgaggt gtatccctga aaagggacat  1020
ccagttgtat tctggtatca acaaaataag aacaatgagt ttaaattttt gattaacttt  1080
```

```
cagaatcaag aagttcttca gcaaatagac atgactgaaa aacgattctc tgctgagtgt  1140
ccttcaaact caccttgcag cctagaaatt cagtcctctg aggcaggaga ctcagcactg  1200
tacctctgtg ccagcagtct gggactgggg gactatgaac agtacttcgg tcccggcacc  1260
aggctcacgg ttttagagga cctgcgcaac gtcacccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtgcactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg ggtagagcc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800
```

```
SEQ ID NO: 190          moltype = DNA  length = 1800
FEATURE                 Location/Qualifiers
misc_feature            1..1800
                        note = CT 551: pLenti 1 CEA TCR TRAV8-1*01 L110F 118P &
                         119T with murineconstant region
source                  1..1800
                        mol_type = other DNA
                        organism = synthetic construct
SEQUENCE: 190
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca cctcaggagg aaactacaaa  360
cctacgtttg ggaaagggac cagcctcgtg gttcatccag acattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
acggttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
ttccagaatc tgtcagtgat gggtctgcgg atcctgcttc tgaaggttgc aggattcaat  780
cttcttatga ctctccggct ctggtcttca ggttctggcg cgacgaattt tagtttgctt  840
aagcaagccg gagatgtgga ggaaaatcct ggaccgatgg ctacaaggct cctctgttac  900
acagtacttt gtctcctggg tgcaagaatt ttgaactcaa aagtcattca gactccaaga  960
tatctggtga aagggcaagg acaaaaagca aagatgaggt gtatccctga aaagggacat  1020
ccagttgtat tctggtatca acaaaataag aacaatgagt ttaaattttt gattaacttt  1080
cagaatcaag aagttcttca gcaaatagac atgactgaaa aacgattctc tgctgagtgt  1140
ccttcaaact caccttgcag cctagaaatt cagtcctctg aggcaggaga ctcagcactg  1200
tacctctgtg ccagcagtct gggactgggg gactatgaac agtacttcgg tcccggcacc  1260
aggctcacgg ttttagagga tctccggaac gtcacccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtccactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg ggtagagcc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800
```

```
SEQ ID NO: 191          moltype = DNA  length = 1800
FEATURE                 Location/Qualifiers
misc_feature            1..1800
                        note = CT 552: pLenti 1 CEA TCR TRAV8-1*01 S112T 118P &
                         119T with murineconstant region
source                  1..1800
                        mol_type = other DNA
                        organism = synthetic construct
SEQUENCE: 191
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatctaa ccaccggagg aaactacaaa  360
cctacgtttg ggaaagggac cagcctcgtg gttcatccag acattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
acggttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
ttccagaatc tgtcagtgat gggtctgcgg atcctgcttc tgaaggttgc aggattcaat  780
cttcttatga ctctccggct ctggtcttca ggttctggcg cgacgaattt tagtttgctt  840
aagcaagccg gagatgtgga ggaaaatcct ggaccgatgg ctacaaggct cctctgttac  900
acagtacttt gtctcctggg tgcaagaatt ttgaactcaa aagtcattca gactccaaga  960
tatctggtga aagggcaagg acaaaaagca aagatgaggt gtatccctga aaagggacat  1020
```

```
ccagttgtat tctggtatca acaaaataag aacaatgagt ttaaattttt gattaacttt  1080
cagaatcaag aagttcttca gcaaatagac atgactgaaa aacgattctc tgctgagtgt  1140
ccttcaaact caccttgcag cctagaaatt cagtcctctg aggcaggaga ctcagcactg  1200
tacctctgtg ccagcagtct gggactgggg gactatgaac agtacttcgg tcccggcacc  1260
aggctcacgg ttttagagga tctccggaac gtcaccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtccactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg ggtagagcc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800

SEQ ID NO: 192          moltype = DNA  length = 1800
FEATURE                 Location/Qualifiers
misc_feature            1..1800
                        note = CT 553: pLenti 1 CEA TCR TRAV8-1*01 L110F S112T 118P
                         & 119T withmurine constant region
source                  1..1800
                        mol_type = other DNA
                        organism = synthetic construct
SEQUENCE: 192
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca ccaccggagg aaactacaaa  360
cctacgtttg ggaaagggac cagcctcgtg gttcatccag acattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
acggttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
ttccagaatc tgtcagtgat gggtctgcgg atcctgcttc tgaaggttgc aggattcaat  780
cttcttatga ctctccggct ctggtcttca ggttctggcg cgacgaattt tagtttgctt  840
aagcaagccg gagatgtgga ggaaaatcct ggaccgatgg ctacaaggct cctctgttac  900
acagtacttt gtctcctggg tgcaagaatt ttgaactcaa aagtcattca gactccaaga  960
tatctggtga aagggcaagg acaaaaagca aagatgaggt gtatccctga aaagggacat  1020
ccagttgtat tctggtatca acaaaataag aacaatgagt ttaaattttt gattaacttt  1080
cagaatcaag aagttcttca gcaaatagac atgactgaaa aacgattctc tgctgagtgt  1140
ccttcaaact caccttgcag cctagaaatt cagtcctctg aggcaggaga ctcagcactg  1200
tacctctgtg ccagcagtct gggactgggg gactatgaac agtacttcgg tcccggcacc  1260
aggctcacgg ttttagagga tctccggaac gtcaccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtccactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg ggtagagcc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800

SEQ ID NO: 193          moltype = DNA  length = 1800
FEATURE                 Location/Qualifiers
misc_feature            1..1800
                        note = CT 554: pLenti 1 CEA TCR TRAV8-1*01 L110F 118P &
                         119T TRBV26*01L117T with murine constant region
source                  1..1800
                        mol_type = other DNA
                        organism = synthetic construct
SEQUENCE: 193
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca cctcaggagg aaactacaaa  360
cctacgtttg ggaaagggac cagcctcgtg gttcatccag acattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
acggttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
ttccagaatc tgtcagtgat gggtctgcgg atcctgcttc tgaaggttgc aggattcaat  780
cttcttatga ctctccggct ctggtcttca ggttctggcg cgacgaattt tagtttgctt  840
aagcaagccg gagatgtgga ggaaaatcct ggaccgatgg ctacaaggct cctctgttac  900
acagtacttt gtctcctggg tgcaagaatt ttgaactcaa aagtcattca gactccaaga  960
```

```
tatctggtga aagggcaagg acaaaaagca aagatgaggt gtatccctga aaagggacat  1020
ccagttgtat tctggtatca acaaaataag aacaatgagt ttaaattttt gattaacttt  1080
cagaatcaag aagttcttca gcaaatagac atgactgaaa aacgattctc tgctgagtgt  1140
ccttcaaact caccttgcag cctagaaatt cagtcctctg aggcaggaga ctcagcactg  1200
tacctctgtg ccagcagtct ggggacaggg gactatgaac agtacttcgg tcccggcacc  1260
aggctcacgg ttttagagga tctccggaac gtcaccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtccactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg ggtagagcc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800

SEQ ID NO: 194          moltype = DNA  length = 1800
FEATURE                 Location/Qualifiers
misc_feature            1..1800
                        note = CT 555: pLenti 1 CEA TCR TRAV8-1*01 S112T 118P &
                         119T TRBV26*01L117T with murine constant region
source                  1..1800
                        mol_type = other DNA
                        organism = synthetic construct
SEQUENCE: 194
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatctaa ccaccggagg aaactacaaa  360
cctacgtttg ggaaagggac cagcctcgtg gttcatccag acattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
acggttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
ttccagaatc tgtcagtgat gggtctgcgg atcctgcttc tgaaggttgc aggattcaat  780
cttcttatga ctctccggct ctggtcttca ggttctggcg cgacgaattt tagtttgctt  840
aagcaagccg gagatgtgga ggaaaatcct ggaccgatgg ctacaaggct cctctgttac  900
acagtacttt gtctcctggg tgcaagaatt ttgaactcaa aagtcattca gactccaaga  960
tatctggtga aagggcaagg acaaaaagca aagatgaggt gtatccctga aaagggacat  1020
ccagttgtat tctggtatca acaaaataag aacaatgagt ttaaattttt gattaacttt  1080
cagaatcaag aagttcttca gcaaatagac atgactgaaa aacgattctc tgctgagtgt  1140
ccttcaaact caccttgcag cctagaaatt cagtcctctg aggcaggaga ctcagcactg  1200
tacctctgtg ccagcagtct ggggacaggg gactatgaac agtacttcgg tcccggcacc  1260
aggctcacgg ttttagagga tctccggaac gtcaccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtccactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg ggtagagcc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800

SEQ ID NO: 195          moltype = DNA  length = 1800
FEATURE                 Location/Qualifiers
misc_feature            1..1800
                        note = CT 556: pLenti 1 CEA TCR TRAV8-1*01 L110F S112T 118P
                         & 119TTRBV26*01 L117T with murine constant region
source                  1..1800
                        mol_type = other DNA
                        organism = synthetic construct
SEQUENCE: 195
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca ccaccggagg aaactacaaa  360
cctacgtttg ggaaagggac cagcctcgtg gttcatccag acattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
acggttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
ttccagaatc tgtcagtgat gggtctgcgg atcctgcttc tgaaggttgc aggattcaat  780
cttcttatga ctctccggct ctggtcttca ggttctggcg cgacgaattt tagtttgctt  840
aagcaagccg gagatgtgga ggaaaatcct ggaccgatgg ctacaaggct cctctgttac  900
```

```
acagtacttt gtctcctggg tgcaagaatt ttgaactcaa aagtcattca gactccaaga  960
tatctggtga aagggcaagg acaaaaagca aagatgaggt gtatccctga aaagggacat  1020
ccagttgtat tctggtatca acaaaataag aacaatgagt ttaaattttt gattaacttt  1080
cagaatcaag aagttcttca gcaaatagac atgactgaaa aacgattctc tgctgagtgt  1140
ccttcaaact caccttgcag cctagaaatt cagtcctctg aggcaggaga ctcagcactg  1200
tacctctgtg ccagcagtct ggggacaggg gactatgaac agtacttcgg tcccggcacc  1260
aggctcacgg ttttagagga tctccggaac gtcaccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtccactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg gggtagagcc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800
```

```
SEQ ID NO: 196          moltype = DNA  length = 1800
FEATURE                 Location/Qualifiers
misc_feature            1..1800
                        note = CT 557: pLenti 1 CEA TCR TRAV8-1*01 L110F 118P &
                         119T with murineconstant region
source                  1..1800
                        mol_type = other DNA
                        organism = synthetic construct
SEQUENCE: 196
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca cctcaggagg aaactacaaa  360
cctacgtttg ggaaagggac cagcctcgtg gttcatccaa atattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
tgcgttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
ttccagaatc tgctggtgat cgttctgcgg atcctgcttc tgaaggttgc aggattcaat  780
cttcttatga ctctccggct ctggtcttca ggttctggcg cgacgaattt tagtttgctt  840
aagcaagccg gagatgtgga ggaaaatcct ggaccgatgg ctacaaggct cctctgttac  900
acagtacttt gtctcctggg tgcaagaatt ttgaactcaa aagtcattca gactccaaga  960
tatctggtga aagggcaagg acaaaaagca aagatgaggt gtatccctga aaagggacat  1020
ccagttgtat tctggtatca acaaaataag aacaatgagt ttaaattttt gattaacttt  1080
cagaatcaag aagttcttca gcaaatagac atgactgaaa aacgattctc tgctgagtgt  1140
ccttcaaact caccttgcag cctagaaatt cagtcctctg aggcaggaga ctcagcactg  1200
tacctctgtg ccagcagtct gggactgggg gactatgaac agtacttcgg tcccggcacc  1260
aggctcacgg ttttagagga cctgcgcaac gtcaccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtgcactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg gggtagagcc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800
```

```
SEQ ID NO: 197          moltype = DNA  length = 1800
FEATURE                 Location/Qualifiers
misc_feature            1..1800
                        note = CT 558: pLenti 1 CEA TCR TRAV8-1*01 S112T 118P &
                         119T with murineconstant region
source                  1..1800
                        mol_type = other DNA
                        organism = synthetic construct
SEQUENCE: 197
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatctaa ccaccggagg aaactacaaa  360
cctacgtttg ggaaagggac cagcctcgtg gttcatccaa atattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
tgcgttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
ttccagaatc tgctggtgat cgttctgcgg atcctgcttc tgaaggttgc aggattcaat  780
cttcttatga ctctccggct ctggtcttca ggttctggcg cgacgaattt tagtttgctt  840
```

```
aagcaagccg gagatgtgga ggaaaatcct ggaccgatgg ctacaaggct cctctgttac  900
acagtacttt gtctcctggg tgcaagaatt ttgaactcaa aagtcattca gactccaaga  960
tatctggtga aagggcaagg acaaaaagca aagatgaggt gtatccctga aaagggacat  1020
ccagttgtat tctggtatca acaaaataag aacaatgagt ttaaattttt gattaacttt  1080
cagaatcaag aagttcttca gcaaatagac atgactgaaa aacgattctc tgctgagtgt  1140
ccttcaaact caccttgcag cctagaaatt cagtcctctg aggcaggaga ctcagcactg  1200
tacctctgtg ccagcagtct gggactgggg gactatgaac agtacttcgg tcccggcacc  1260
aggctcacgg ttttagagga cctgcgcaac gtcaccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtgcactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg ggtagagccc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800
```

```
SEQ ID NO: 198          moltype = DNA  length = 1800
FEATURE                 Location/Qualifiers
misc_feature            1..1800
                        note = CT 559: pLenti 1 CEA TCR TRAV8-1*01 L110F S112T 118P
                         & 119T withmurine constant region
source                  1..1800
                        mol_type = other DNA
                        organism = synthetic construct
SEQUENCE: 198
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca ccaccggagg aaactacaaa  360
cctacgtttg ggaaagggac cagcctcgtg gttcatccaa atattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
tgcgttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
ttccagaatc tgctggtgat cgttctgcgg atcctgcttc tgaaggttgc aggattcaat  780
cttcttatga ctctccggct ctggtcttca ggttctggcg cgacgaattt tagtttgctt  840
aagcaagccg gagatgtgga ggaaaatcct ggaccgatgg ctacaaggct cctctgttac  900
acagtacttt gtctcctggg tgcaagaatt ttgaactcaa aagtcattca gactccaaga  960
tatctggtga aagggcaagg acaaaaagca aagatgaggt gtatccctga aaagggacat  1020
ccagttgtat tctggtatca acaaaataag aacaatgagt ttaaattttt gattaacttt  1080
cagaatcaag aagttcttca gcaaatagac atgactgaaa aacgattctc tgctgagtgt  1140
ccttcaaact caccttgcag cctagaaatt cagtcctctg aggcaggaga ctcagcactg  1200
tacctctgtg ccagcagtct gggactgggg gactatgaac agtacttcgg tcccggcacc  1260
aggctcacgg ttttagagga cctgcgcaac gtcaccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtgcactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg ggtagagccc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800
```

```
SEQ ID NO: 199          moltype = DNA  length = 1800
FEATURE                 Location/Qualifiers
misc_feature            1..1800
                        note = CT 560: pLenti 1 CEA TCR TRAV8-1*01 118P & 119T
                         TRBV26*01 L117Twith murine constant region
source                  1..1800
                        mol_type = other DNA
                        organism = synthetic construct
SEQUENCE: 199
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatctaa cctcaggagg aaactacaaa  360
cctacgtttg ggaaagggac cagcctcgtg gttcatccaa atattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
tgcgttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
ttccagaatc tgctggtgat cgttctgcgg atcctgcttc tgaaggttgc aggattcaat  780
```

```
cttcttatga ctctccggct ctggtcttca ggttctggcg cgacgaattt tagtttgctt  840
aagcaagccg gagatgtgga ggaaaatcct ggaccgatgg ctacaaggct cctctgttac  900
acagtacttt gtctcctggg tgcaagaatt ttgaactcaa aagtcattca gactccaaga  960
tatctggtga aagggcaagg acaaaaagca aagatgaggt gtatccctga aaagggacat  1020
ccagttgtat tctggtatca acaaaataag aacaatgagt ttaaattttt gattaacttt  1080
cagaatcaag aagttcttca gcaaatagac atgactgaaa aacgattctc tgctgagtgt  1140
ccttcaaact caccttgcag cctagaaatt cagtcctctg aggcaggaga ctcagcactg  1200
tacctctgtg ccagcagtct ggggacaggg gactatgaac agtacttcgg tcccggcacc  1260
aggctcacgg ttttagagga cctgcgcaac gtcaccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtgcactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg ggtagagcc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800
```

```
SEQ ID NO: 200          moltype = DNA  length = 1800
FEATURE                 Location/Qualifiers
misc_feature            1..1800
                        note = CT 561: pLenti 1 CEA TCR TRAV8-1*01 L110F 118P &
                         119T TRBV26*01L117T with murine constant region
source                  1..1800
                        mol_type = other DNA
                        organism = synthetic construct
SEQUENCE: 200
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca cctcaggagg aaactacaaa  360
cctacgtttg ggaaagggac cagcctcgtg gttcatccaa atattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
tgcgttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
ttccagaatc tgctggtgat cgttctgcgg atcctgcttc tgaaggttgc aggattcaat  780
cttcttatga ctctccggct ctggtcttca ggttctggcg cgacgaattt tagtttgctt  840
aagcaagccg gagatgtgga ggaaaatcct ggaccgatgg ctacaaggct cctctgttac  900
acagtacttt gtctcctggg tgcaagaatt ttgaactcaa aagtcattca gactccaaga  960
tatctggtga aagggcaagg acaaaaagca aagatgaggt gtatccctga aaagggacat  1020
ccagttgtat tctggtatca acaaaataag aacaatgagt ttaaattttt gattaacttt  1080
cagaatcaag aagttcttca gcaaatagac atgactgaaa aacgattctc tgctgagtgt  1140
ccttcaaact caccttgcag cctagaaatt cagtcctctg aggcaggaga ctcagcactg  1200
tacctctgtg ccagcagtct ggggacaggg gactatgaac agtacttcgg tcccggcacc  1260
aggctcacgg ttttagagga cctgcgcaac gtcaccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtgcactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg ggtagagcc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800
```

```
SEQ ID NO: 201          moltype = DNA  length = 1800
FEATURE                 Location/Qualifiers
misc_feature            1..1800
                        note = CT 562: pLenti 1 CEA TCR TRAV8-1*01 S112T 118P &
                         119T TRBV26*01L117T with murine constant region
source                  1..1800
                        mol_type = other DNA
                        organism = synthetic construct
SEQUENCE: 201
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatctaa ccaccggagg aaactacaaa  360
cctacgtttg ggaaagggac cagcctcgtg gttcatccaa atattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
tgcgttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
```

```
ttccagaatc tgctggtgat cgttctgcgg atcctgcttc tgaaggttgc aggattcaat  780
cttcttatga ctctccggct ctggtcttca ggttctggcg cgacgaattt tagtttgctt  840
aagcaagccg gagatgtgga ggaaaatcct ggaccgatgg ctacaaggct cctctgttac  900
acagtacttt gtctcctggg tgcaagaatt ttgaactcaa aagtcattca gactccaaga  960
tatctggtga aagggcaagg acaaaaagca aagatgaggt gtatccctga aaagggacat  1020
ccagttgtat tctggtatca acaaaataag aacaatgagt ttaaattttt gattaacttt  1080
cagaatcaag aagttcttca gcaaatagac atgactgaaa aacgattctc tgctgagtgt  1140
ccttcaaact caccttgcag cctagaaatt cagtcctctg aggcaggaga ctcagcactg  1200
tacctctgtg ccagcagtct ggggacaggg gactatgaac agtacttcgg tcccggcacc  1260
aggctcacgg ttttagagga cctgcgcaac gtcaccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtgcactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg ggtagagccc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800
```

```
SEQ ID NO: 202          moltype = DNA  length = 1800
FEATURE                 Location/Qualifiers
misc_feature            1..1800
                        note = CT 563: pLenti 1 CEA TCR TRAV8-1*01 L110F S112T 118P
                         & 119TTRBV26*01 L117T with murine constant region
source                  1..1800
                        mol_type = other DNA
                        organism = synthetic construct
SEQUENCE: 202
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca ccaccggagg aaactacaaa  360
cctacgtttg ggaaagggac cagcctcgtg gttcatccaa atattcagaa ccccgaacca  420
gccgtatatc agttgaagga cccaagatct caggatagta cactctgttt gtttacggac  480
tttgactcac aaatcaacgt cccgaagact atggaaagtg gtacgttcat cacagataag  540
tgcgttctgg acatgaaggc tatggactca aagagcaacg gggcaattgc ttggtccaac  600
cagacaagct ttacctgtca ggacattttt aaggagacta atgctactta tccctccagc  660
gacgttccgt gtgatgcgac tcttaccgag aagtcttttg agaccgatat gaatctcaac  720
ttccagaatc tgctggtgat cgttctgcgg atcctgcttc tgaaggttgc aggattcaat  780
cttcttatga ctctccggct ctggtcttca ggttctggcg cgacgaattt tagtttgctt  840
aagcaagccg gagatgtgga ggaaaatcct ggaccgatgg ctacaaggct cctctgttac  900
acagtacttt gtctcctggg tgcaagaatt ttgaactcaa aagtcattca gactccaaga  960
tatctggtga aagggcaagg acaaaaagca aagatgaggt gtatccctga aaagggacat  1020
ccagttgtat tctggtatca acaaaataag aacaatgagt ttaaattttt gattaacttt  1080
cagaatcaag aagttcttca gcaaatagac atgactgaaa aacgattctc tgctgagtgt  1140
ccttcaaact caccttgcag cctagaaatt cagtcctctg aggcaggaga ctcagcactg  1200
tacctctgtg ccagcagtct ggggacaggg gactatgaac agtacttcgg tcccggcacc  1260
aggctcacgg ttttagagga cctgcgcaac gtcaccccac caaaggtcag tttgtttgag  1320
ccatcaaagg cggagatcgc caacaaacag aaagctacgc tcgtgtgttt ggctcggggc  1380
ttcttcccag accacgtaga actttcctgg tgggtcaatg gaaaggaggt tcattccgga  1440
gtgtgcactg atccccaagc gtacaaggaa tccaactata gctactgtct ctcatctcgg  1500
ctccgggtga gtgcgacatt ctggcataat cctcggaacc actttcgatg ccaagtgcag  1560
tttcatgggt tgagcgagga agacaagtgg cccgagggca gtcctaaacc agtcactcaa  1620
aacataagcg ccgaggcatg ggtagagccc gattgtggga ttactagcgc ttcataccaa  1680
caaggggtat tgagcgctac aattctttac gaaattctcc tcggcaaggc gacgctctac  1740
gccgtactgg tgtctactct cgtggttatg gcaatggtga aacggaaaaa cagctaatag  1800
```

```
SEQ ID NO: 203          moltype = DNA  length = 1794
FEATURE                 Location/Qualifiers
misc_feature            1..1794
                        note = CT 532: pLenti 1 CEA TCR TRAV8-1*01 TRBV26*01 with
                         regular murineconstant region
source                  1..1794
                        mol_type = other DNA
                        organism = synthetic construct
SEQUENCE: 203
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatctaa cctcaggagg aaactacaaa  360
tttgggaaag ggaccagcct cgtggttcat ccagacattc agaaccccga accagccgta  420
tatcagttga aggacccaag atctcaggat agtacactct gtttgtttac ggactttgac  480
tcacaaatca acgtcccgaa gactatggaa agtggtacgt tcatcacaga taagacggtt  540
ctggacatga aggctatgga ctcaaagagc aacggggcaa ttgcttggtc caaccagaca  600
agctttacct gtcaggacat ttttaaggag actaatgcta cttatccctc cagcgacgtt  660
```

```
ccgtgtgatg cgactcttac cgagaagtct tttgagaccg atatgaatct caacttccag  720
aatctgtcag tgatgggtct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat ttttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctgggact gggggactat gaacagtact tcggtcccgg caccaggctc  1260
acggttttag aggatctccg gaacgtcacc ccaccaaagg tcagtttgtt tgagccatca  1320
aaggcggaga tcgccaacaa acagaaagct acgctcgtgt gtttggctcg gggcttcttc  1380
ccagaccacg tagaactttc ctggtgggtc aatggaaagg aggttcattc cggagtgtcc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794

SEQ ID NO: 204          moltype = DNA  length = 1794
FEATURE                 Location/Qualifiers
misc_feature            1..1794
                        note = CT 533: pLenti 1 CEA TCR TRAV8-1*01 TRBV26*01 L117T
                         with regularmurine constant region
source                  1..1794
                        mol_type = other DNA
                        organism = synthetic construct
SEQUENCE: 204
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatctaa cctcaggagg aaactacaaa  360
tttgggaaag ggaccagcct cgtggttcat ccagacattc agaaccccga accagccgta  420
tatcagttga aggacccaag atctcaggat agtacactct gtttgtttac ggactttgac  480
tcacaaatca acgtcccgaa gactatggaa agtggtacgt tcatcacaga taagacggtt  540
ctggacatga aggctatgga ctcaaagagc aacggggcaa ttgcttggtc caaccagaca  600
agctttacct gtcaggacat ttttaaggag actaatgcta cttatccctc cagcgacgtt  660
ccgtgtgatg cgactcttac cgagaagtct tttgagaccg atatgaatct caacttccag  720
aatctgtcag tgatgggtct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat ttttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctggggac aggggactat gaacagtact tcggtcccgg caccaggctc  1260
acggttttag aggatctccg gaacgtcacc ccaccaaagg tcagtttgtt tgagccatca  1320
aaggcggaga tcgccaacaa acagaaagct acgctcgtgt gtttggctcg gggcttcttc  1380
ccagaccacg tagaactttc ctggtgggtc aatggaaagg aggttcattc cggagtgtcc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794

SEQ ID NO: 205          moltype = DNA  length = 1794
FEATURE                 Location/Qualifiers
misc_feature            1..1794
                        note = CT 534: pLenti 1 CEA TCR TRAV8-1*01 TRBV26*01 murine
                         constantregion (no PT)
source                  1..1794
                        mol_type = other DNA
                        organism = synthetic construct
SEQUENCE: 205
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatctaa cctcaggagg aaactacaaa  360
tttgggaaag ggaccagcct cgtggttcat ccaaatattc agaaccccga accagccgta  420
tatcagttga aggacccaag atctcaggat agtacactct gtttgtttac ggactttgac  480
tcacaaatca acgtcccgaa gactatggaa agtggtacgt tcatcacaga taagtgcgtt  540
ctggacatga aggctatgga ctcaaagagc aacggggcaa ttgcttggtc caaccagaca  600
```

```
agctttacct gtcaggacat ttttaaggag actaatgcta cttatccctc cagcgacgtt  660
ccgtgtgatg cgactcttac cgagaagtct tttgagaccg atatgaatct caacttccag  720
aatctgctgg tgatcgttct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat tttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctgggact gggggactat gaacagtact tcggtcccgg caccaggctc  1260
acggttttag aggacctgcg caacgtcacc ccaccaaagg tcagtttgtt tgagccatca  1320
aaggcggaga tcgccaacaa acagaaagct acgctcgtgt gtttggctcg ggcttcttc  1380
ccagaccacg tagaactttc ctggtgggtc aatggaaagg aggttcattc cggagtgtgc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794

SEQ ID NO: 206          moltype = DNA  length = 1794
FEATURE                 Location/Qualifiers
misc_feature            1..1794
                        note = CT 535: pLenti 1 CEA TCR TRAV8-1*01 L110F TRBV26*01
                         with regularmurine constant region
source                  1..1794
                        mol_type = other DNA
                        organism = synthetic construct
SEQUENCE: 206
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca cctcaggagg aaactacaaa  360
tttgggaaag ggaccagcct cgtggttcat ccagacattc agaaccccga accagccgta  420
tatcagttga aggacccaag atctcaggat agtacactct gtttgtttac ggactttgac  480
tcacaaatca acgtcccgaa gactatggaa agtggtacgt tcatcacaga taagacggtt  540
ctggacatga aggctatgga ctcaaagagc aacggggcaa ttgcttggtc caaccagaca  600
agctttacct gtcaggacat ttttaaggag actaatgcta cttatccctc cagcgacgtt  660
ccgtgtgatg cgactcttac cgagaagtct tttgagaccg atatgaatct caacttccag  720
aatctgtcag tgatgggtct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat tttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctgggact gggggactat gaacagtact tcggtcccgg caccaggctc  1260
acggttttag aggatctccg gaacgtcacc ccaccaaagg tcagtttgtt tgagccatca  1320
aaggcggaga tcgccaacaa acagaaagct acgctcgtgt gtttggctcg ggcttcttc  1380
ccagaccacg tagaactttc ctggtgggtc aatggaaagg aggttcattc cggagtgtcc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794

SEQ ID NO: 207          moltype = DNA  length = 1794
FEATURE                 Location/Qualifiers
misc_feature            1..1794
                        note = CT 536: pLenti 1 CEA TCR TRAV8-1*01 S112TTRBV26*01
                         with regularmurine constant region
source                  1..1794
                        mol_type = other DNA
                        organism = synthetic construct
SEQUENCE: 207
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatctaa ccaccggagg aaactacaaa  360
tttgggaaag ggaccagcct cgtggttcat ccagacattc agaaccccga accagccgta  420
tatcagttga aggacccaag atctcaggat agtacactct gtttgtttac ggactttgac  480
tcacaaatca acgtcccgaa gactatggaa agtggtacgt tcatcacaga taagacggtt  540
```

```
ctggacatga aggctatgga ctcaaagagc aacggggcaa ttgcttggtc caaccagaca  600
agctttacct gtcaggacat ttttaaggag actaatgcta cttatccctc cagcgacgtt  660
ccgtgtgatg cgactcttac cgagaagtct tttgagaccg atatgaatct caacttccag  720
aatctgtcag tgatgggtct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat ttttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctgggact gggggactat gaacagtact tcggtcccgg caccaggctc  1260
acggttttag aggatctccg gaacgtcacc ccaccaaagg tcagtttgtt tgagccatca  1320
aaggcggaga tcgccaacaa acagaaagct acgctcgtgt gtttggctcg gggcttcttc  1380
ccagaccacg tagaactttc ctggtgggtc aatggaaagg aggttcattc cggagtgtcc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794

SEQ ID NO: 208         moltype = DNA  length = 1794
FEATURE                Location/Qualifiers
misc_feature           1..1794
                       note = CT 537: pLenti 1 CEA TCR TRAV8-1*01 L110F & S112T
                        TRBV26*01 withregular murine constant region
source                 1..1794
                       mol_type = other DNA
                       organism = synthetic construct
SEQUENCE: 208
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca ccaccggagg aaactacaaa  360
tttgggaaag ggaccagcct cgtggttcat ccagacattc agaaccccga accagccgta  420
tatcagttga aggacccaag atctcaggat agtacactct gtttgtttac ggactttgac  480
tcacaaatca acgtcccgaa gactatggaa agtggtacgt tcatcacaga taagacggtt  540
ctggacatga aggctatgga ctcaaagagc aacggggcaa ttgcttggtc caaccagaca  600
agctttacct gtcaggacat ttttaaggag actaatgcta cttatccctc cagcgacgtt  660
ccgtgtgatg cgactcttac cgagaagtct tttgagaccg atatgaatct caacttccag  720
aatctgtcag tgatgggtct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat ttttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctgggact gggggactat gaacagtact tcggtcccgg caccaggctc  1260
acggttttag aggatctccg gaacgtcacc ccaccaaagg tcagtttgtt tgagccatca  1320
aaggcggaga tcgccaacaa acagaaagct acgctcgtgt gtttggctcg gggcttcttc  1380
ccagaccacg tagaactttc ctggtgggtc aatggaaagg aggttcattc cggagtgtcc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794

SEQ ID NO: 209         moltype = DNA  length = 1794
FEATURE                Location/Qualifiers
misc_feature           1..1794
                       note = CT 538: pLenti 1 CEA TCR TRAV8-1*01 L110F TRBV26*01
                        L117T withregular murine constant region
source                 1..1794
                       mol_type = other DNA
                       organism = synthetic construct
SEQUENCE: 209
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca cctcaggagg aaactacaaa  360
tttgggaaag ggaccagcct cgtggttcat ccagacattc agaaccccga accagccgta  420
tatcagttga aggacccaag atctcaggat agtacactct gtttgtttac ggactttgac  480
```

```
tcacaaatca acgtcccgaa gactatggaa agtggtacgt tcatcacaga taagacggtt  540
ctggacatga aggctatgga ctcaaagagc aacggggcaa ttgcttggtc caaccagaca  600
agctttacct gtcaggacat ttttaaggag actaatgcta cttatccctc cagcgacgtt  660
ccgtgtgatg cgactcttac cgagaagtct tttgagaccg atatgaatct caacttccag  720
aatctgtcag tgatgggtct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat ttttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctggggac aggggactat gaacagtact tcggtcccgg caccaggctc  1260
acggttttag aggatctccg gaacgtcacc ccaccaaagg tcagtttgtt tgagccatca  1320
aaggcggaga tcgccaacaa acagaaagct acgctcgtgt gtttggctcg ggcttcttc   1380
ccagaccacg tagaactttc ctggtgggtc aatggaaagg aggttcattc cggagtgtcc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794
```

```
SEQ ID NO: 210         moltype = DNA  length = 1794
FEATURE                Location/Qualifiers
misc_feature           1..1794
                       note = CT 539: pLenti 1 CEA TCR TRAV8-1*01 S112T TRBV26*01
                        L117T withregular murine constant region
source                 1..1794
                       mol_type = other DNA
                       organism = synthetic construct
SEQUENCE: 210
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatctaa ccaccggagg aaactacaaa  360
tttgggaaag ggaccagcct cgtggttcat ccagacattc agaaccccga accagccgta  420
tatcagttga aggacccaag atctcaggat agtacactct gtttgtttac ggactttgac  480
tcacaaatca acgtcccgaa gactatggaa agtggtacgt tcatcacaga taagacggtt  540
ctggacatga aggctatgga ctcaaagagc aacggggcaa ttgcttggtc caaccagaca  600
agctttacct gtcaggacat ttttaaggag actaatgcta cttatccctc cagcgacgtt  660
ccgtgtgatg cgactcttac cgagaagtct tttgagaccg atatgaatct caacttccag  720
aatctgtcag tgatgggtct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat ttttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctggggac aggggactat gaacagtact tcggtcccgg caccaggctc  1260
acggttttag aggatctccg gaacgtcacc ccaccaaagg tcagtttgtt tgagccatca  1320
aaggcggaga tcgccaacaa acagaaagct acgctcgtgt gtttggctcg ggcttcttc   1380
ccagaccacg tagaactttc ctggtgggtc aatggaaagg aggttcattc cggagtgtcc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794
```

```
SEQ ID NO: 211         moltype = DNA  length = 1794
FEATURE                Location/Qualifiers
misc_feature           1..1794
                       note = CT 540: pLenti 1 CEA TCR TRAV8-1*01 L110F & S112T
                        TRBV26*01 L117Twith regular murine constant region
source                 1..1794
                       mol_type = other DNA
                       organism = synthetic construct
SEQUENCE: 211
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca ccaccggagg aaactacaaa  360
tttgggaaag ggaccagcct cgtggttcat ccagacattc agaaccccga accagccgta  420
```

```
tatcagttga aggacccaag atctcaggat agtacactct gtttgtttac ggactttgac  480
tcacaaatca acgtcccgaa gactatggaa agtggtacgt tcatcacaga taagacggtt  540
ctggacatga aggctatgga ctcaaagagc aacggggcaa ttgcttggtc caaccagaca  600
agctttacct gtcaggacat ttttaaggag actaatgcta cttatccctc cagcgacgtt  660
ccgtgtgatg cgactcttac cgagaagtct tttgagaccg atatgaatct caacttccag  720
aatctgtcag tgatgggtct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat ttttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctggggac aggggactat gaacagtact tcggtcccgg caccaggctc  1260
acggttttag aggatctccg gaacgtcacc ccaccaaagg tcagtttgtt tgagccatca  1320
aaggcggaga tcgccaacaa acagaaagct acgctcgtgt gtttggctcg gggcttcttc  1380
ccagaccacg tagaactttc ctggtgggtc aatggaaagg aggttcattc cggagtgtcc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794

SEQ ID NO: 212          moltype = DNA  length = 1794
FEATURE                 Location/Qualifiers
misc_feature            1..1794
                        note = CT 541: pLenti 1 CEA TCR TRAV8-1*01 L110F TRBV26*01
                         with murineconstant region
source                  1..1794
                        mol_type = other DNA
                        organism = synthetic construct
SEQUENCE: 212
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca cctcaggagg aaactacaaa  360
tttgggaaag ggaccagcct cgtggttcat ccaaatattc agaaccccga accagccgta  420
tatcagttga aggacccaag atctcaggat agtacactct gtttgtttac ggactttgac  480
tcacaaatca acgtcccgaa gactatggaa agtggtacgt tcatcacaga taagtgcgtt  540
ctggacatga aggctatgga ctcaaagagc aacggggcaa ttgcttggtc caaccagaca  600
agctttacct gtcaggacat ttttaaggag actaatgcta cttatccctc cagcgacgtt  660
ccgtgtgatg cgactcttac cgagaagtct tttgagaccg atatgaatct caacttccag  720
aatctgctgg tgatcgttct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat ttttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctgggact ggggactat gaacagtact tcggtcccgg caccaggctc  1260
acggttttag aggacctgcg caacgtcacc ccaccaaagg tcagtttgtt tgagccatca  1320
aaggcggaga tcgccaacaa acagaaagct acgctcgtgt gtttggctcg gggcttcttc  1380
ccagaccacg tagaactttc ctggtgggtc aatggaaagg aggttcattc cggagtgtgc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794

SEQ ID NO: 213          moltype = DNA  length = 1794
FEATURE                 Location/Qualifiers
misc_feature            1..1794
                        note = CT 542:pLenti 1 CEA TCR TRAV8-1*01 S112T TRBV26*01
                         with murineconstant region
source                  1..1794
                        mol_type = other DNA
                        organism = synthetic construct
SEQUENCE: 213
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatctaa ccaccggagg aaactacaaa  360
```

```
tttgggaaag ggaccagcct cgtggttcat ccaaatattc agaaccccga accagccgta  420
tatcagttga aggacccaag atctcaggat agtacactct gtttgtttac ggactttgac  480
tcacaaatca acgtcccgaa gactatggaa agtggtacgt tcatcacaga taagtgcgtt  540
ctggacatga aggctatgga ctcaaagagc aacggggcaa ttgcttggtc caaccagaca  600
agctttacct gtcaggacat ttttaaggag actaatgcta cttatccctc cagcgacgtt  660
ccgtgtgatg cgactcttac cgagaagtct tttgagaccg atatgaatct caacttccag  720
aatctgctgg tgatcgttct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat ttttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctgggact gggggactat gaacagtact tcggtcccgg caccaggctc  1260
acggttttag aggacctgcg caacgtcacc ccaccaaagg tcagtttgtt tgagccatca  1320
aaggcggaga tcgccaacaa acagaaagct acgctcgtgt gtttggctcg gggcttcttc  1380
ccagaccacg tagaactttc ctggtgggtc aatggaaagg aggttcattc cggagtgtgc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794
```

```
SEQ ID NO: 214          moltype = DNA  length = 1794
FEATURE                 Location/Qualifiers
misc_feature            1..1794
                        note = CT 543: pLenti 1 CEA TCR TRAV8-1*01 L110F & S112T
                         TRBV26*01 withmurine constant region
source                  1..1794
                        mol_type = other DNA
                        organism = synthetic construct
SEQUENCE: 214
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca ccaccggagg aaactacaaa  360
tttgggaaag ggaccagcct cgtggttcat ccaaatattc agaaccccga accagccgta  420
tatcagttga aggacccaag atctcaggat agtacactct gtttgtttac ggactttgac  480
tcacaaatca acgtcccgaa gactatggaa agtggtacgt tcatcacaga taagtgcgtt  540
ctggacatga aggctatgga ctcaaagagc aacggggcaa ttgcttggtc caaccagaca  600
agctttacct gtcaggacat ttttaaggag actaatgcta cttatccctc cagcgacgtt  660
ccgtgtgatg cgactcttac cgagaagtct tttgagaccg atatgaatct caacttccag  720
aatctgctgg tgatcgttct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat ttttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctgggact gggggactat gaacagtact tcggtcccgg caccaggctc  1260
acggttttag aggacctgcg caacgtcacc ccaccaaagg tcagtttgtt tgagccatca  1320
aaggcggaga tcgccaacaa acagaaagct acgctcgtgt gtttggctcg gggcttcttc  1380
ccagaccacg tagaactttc ctggtgggtc aatggaaagg aggttcattc cggagtgtgc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794
```

```
SEQ ID NO: 215          moltype = DNA  length = 1794
FEATURE                 Location/Qualifiers
misc_feature            1..1794
                        note = CT 544: pLenti 1 CEA TCRTRAV8-1*01 TRBV26*01 L117T
                         with murineconstant region
source                  1..1794
                        mol_type = other DNA
                        organism = synthetic construct
SEQUENCE: 215
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
```

```
tgtgaagaca ccgctgtgta cttctgtgct actgatctaa cctcaggagg aaactacaaa  360
tttgggaaag ggaccagcct cgtggttcat ccaaatattc agaaccccga accagccgta  420
tatcagttga aggacccaag atctcaggat agtacactct gtttgtttac ggactttgac  480
tcacaaatca acgtcccgaa gactatggaa agtggtacgt tcatcacaga taagtgcgtt  540
ctggacatga aggctatgga ctcaaagagc aacggggcaa ttgcttggtc caaccagaca  600
agctttacct gtcaggacat ttttaaggag actaatgcta cttatccctc cagcgacgtt  660
ccgtgtgatg cgactcttac cgagaagtct tttgagaccg atatgaatct caacttccag  720
aatctgctgg tgatcgttct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat ttttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctggggac aggggactat gaacagtact tcggtcccgg caccaggctc  1260
acggttttag aggacctgcg caacgtcacc ccaccaaagg tcagtttgtt tgagccatca  1320
aaggcggaga tcgccaacaa acagaaagct acgctcgtgt gtttggctcg gggcttcttc  1380
ccagaccacg tagaactttc ctggtgggtc aatggaaagg aggttcattc cggagtgtgc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794

SEQ ID NO: 216          moltype = DNA  length = 1794
FEATURE                 Location/Qualifiers
misc_feature            1..1794
                        note = CT 545: pLenti 1 CEA TCR TRAV8-1*01 L110F TRBV26*01
                         L117T withmurine constant region
source                  1..1794
                        mol_type = other DNA
                        organism = synthetic construct
SEQUENCE: 216
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca cctcaggagg aaactacaaa  360
tttgggaaag ggaccagcct cgtggttcat ccaaatattc agaaccccga accagccgta  420
tatcagttga aggacccaag atctcaggat agtacactct gtttgtttac ggactttgac  480
tcacaaatca acgtcccgaa gactatggaa agtggtacgt tcatcacaga taagtgcgtt  540
ctggacatga aggctatgga ctcaaagagc aacggggcaa ttgcttggtc caaccagaca  600
agctttacct gtcaggacat ttttaaggag actaatgcta cttatccctc cagcgacgtt  660
ccgtgtgatg cgactcttac cgagaagtct tttgagaccg atatgaatct caacttccag  720
aatctgctgg tgatcgttct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat ttttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctggggac aggggactat gaacagtact tcggtcccgg caccaggctc  1260
acggttttag aggacctgcg caacgtcacc ccaccaaagg tcagtttgtt tgagccatca  1320
aaggcggaga tcgccaacaa acagaaagct acgctcgtgt gtttggctcg gggcttcttc  1380
ccagaccacg tagaactttc ctggtgggtc aatggaaagg aggttcattc cggagtgtgc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794

SEQ ID NO: 217          moltype = DNA  length = 1794
FEATURE                 Location/Qualifiers
misc_feature            1..1794
                        note = CT 546: pLenti 1 CEA TCR TRAV8-1*01 S112T TRBV26*01
                         L117T withmurine constant region
source                  1..1794
                        mol_type = other DNA
                        organism = synthetic construct
SEQUENCE: 217
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
```

```
ctcagagcca cccttgacac ctccagccag agcagctcct tgtccatcac tgctactcgg  300
tgtgaagaca ccgctgtgta cttctgtgct actgatctaa ccaccggagg aaactacaaa  360
tttgggaaag ggaccagcct cgtggttcat ccaaatattc agaaccccga accagccgta  420
tatcagttga aggacccaag atctcaggat agtacactct gtttgtttac ggactttgac  480
tcacaaatca acgtcccgaa gactatggaa agtggtacgt tcatcacaga taagtgcgtt  540
ctggacatga aggctatgga ctcaaagagc aacggggcaa ttgcttggtc caaccagaca  600
agctttacct gtcaggacat ttttaaggag actaatgcta cttatccctc cagcgacgtt  660
ccgtgtgatg cgactcttac cgagaagtct tttgagaccg atatgaatct caacttccag  720
aatctgctgg tgatcgttct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat ttttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctggggac aggggactat gaacagtact tcggtcccgg caccaggctc  1260
acggttttag aggacctgcg caacgtcacc ccaccaaagg tcagtttgtt tgagccatca  1320
aaggcggaga tcgccaacaa acagaaagct acgctcgtgt gtttggctcg gggcttcttc  1380
ccagaccacg tagaactttc ctggtgggtc aatggaaagg aggttcattc cggagtgtgc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794

SEQ ID NO: 218         moltype = DNA  length = 1794
FEATURE                Location/Qualifiers
misc_feature           1..1794
                       note = CT 547: pLenti 1 CEA TCR TRAV8-1*01 L110F & S112T
                        TRBV26*01 L117Twith murine constant region
source                 1..1794
                       mol_type = other DNA
                       organism = synthetic construct
SEQUENCE: 218
atgcacagcc tcctggggtt gttgatggtg tcactgtggc tgcaactgac aagggtgaat  60
agtcaactag cagaagagaa tccgtgggcc ctgagcgtcc acgagggtga aagtgtcacg  120
gtgaattgta gttacaagac atccataact gccctacagt ggtacagaca gaagtcaggc  180
gaaggccctg cccagctaat cttaatacgt tcaaatgaga gagagaagcg caatggaaga  240
ctcagagcca cccttgacac ctccagccag agcagctcct tgtccatcac tgctactcgg  300
tgtgaagaca ccgctgtgta cttctgtgct actgatttca ccaccggagg aaactacaaa  360
tttgggaaag ggaccagcct cgtggttcat ccaaatattc agaaccccga accagccgta  420
tatcagttga aggacccaag atctcaggat agtacactct gtttgtttac ggactttgac  480
tcacaaatca acgtcccgaa gactatggaa agtggtacgt tcatcacaga taagtgcgtt  540
ctggacatga aggctatgga ctcaaagagc aacggggcaa ttgcttggtc caaccagaca  600
agctttacct gtcaggacat ttttaaggag actaatgcta cttatccctc cagcgacgtt  660
ccgtgtgatg cgactcttac cgagaagtct tttgagaccg atatgaatct caacttccag  720
aatctgctgg tgatcgttct gcggatcctg cttctgaagg ttgcaggatt caatcttctt  780
atgactctcc ggctctggtc ttcaggttct ggcgcgacga attttagttt gcttaagcaa  840
gccggagatg tggaggaaaa tcctggaccg atggctacaa ggctcctctg ttacacagta  900
ctttgtctcc tgggtgcaag aattttgaac tcaaaagtca ttcagactcc aagatatctg  960
gtgaaagggc aaggacaaaa agcaaagatg aggtgtatcc ctgaaaaggg acatccagtt  1020
gtattctggt atcaacaaaa taagaacaat gagtttaaat ttttgattaa ctttcagaat  1080
caagaagttc ttcagcaaat agacatgact gaaaaacgat tctctgctga gtgtccttca  1140
aactcacctt gcagcctaga aattcagtcc tctgaggcag gagactcagc actgtacctc  1200
tgtgccagca gtctggggac aggggactat gaacagtact tcggtcccgg caccaggctc  1260
acggttttag aggacctgcg caacgtcacc ccaccaaagg tcagtttgtt tgagccatca  1320
aaggcggaga tcgccaacaa acagaaagct acgctcgtgt gtttggctcg gggcttcttc  1380
ccagaccacg tagaactttc ctggtgggtc aatggaaagg aggttcattc cggagtgtgc  1440
actgatcccc aagcgtacaa ggaatccaac tatagctact gtctctcatc tcggctccgg  1500
gtgagtgcga cattctggca taatcctcgg aaccactttc gatgccaagt gcagtttcat  1560
gggttgagcg aggaagacaa gtggcccgag ggcagtccta aaccagtcac tcaaaacata  1620
agcgccgagg catggggtag agccgattgt gggattacta gcgcttcata ccaacaaggg  1680
gtattgagcg ctacaattct ttacgaaatt ctcctcggca aggcgacgct ctacgccgta  1740
ctggtgtcta ctctcgtggt tatggcaatg gtgaaacgga aaaacagcta atag        1794

SEQ ID NO: 219         moltype = DNA  length = 1608
FEATURE                Location/Qualifiers
misc_feature           1..1608
                       note = CT618: CAR with scFv that targetCEA
source                 1..1608
                       mol_type = other DNA
                       organism = synthetic construct
SEQUENCE: 219
atggacatga gggtccccgc tcagctcctg gggctcctgc tactctggct ccgaggtgcc  60
agatgtcagg tgcagctggt gcaatctggg tctgagttga agaagcctgg ggcctcagtg  120
aaggtttcct gcaaggcttc tggatacacc ttcactgagt ttggaatgaa ctgggtgcga  180
caggcccctg gacaagggct tgagtggatg ggatggataa acaccaaaac tggagaggca  240
```

```
acatatgttg aagagtttaa gggacggttt gtcttctcct tggacacctc tgtcagcacg  300
gcatatctgc agatcagcag cctaaaggct gaagacactg ccgtgtatta ctgtgcgaga  360
tgggacttcg cttattacgt ggaggctatg gactactggg gccaagggac cacggtgacc  420
gtgtcatccg gcggaggtgg aagcggaggg ggaggatctg gcggcggagg aagcggaggc  480
gatatccaga tgacccagtc tccatcctcc ctgtctgcat ctgtgggaga cagagtcacc  540
atcacttgca aggccagtca gaatgtgggt actaatgttg cctggtatca gcagaaacca  600
gggaaagcac ctaagctcct gatctattcg gcatcctacc gctacagtgg agtcccatca  660
aggttcagtg gcagtggatc tgggacagat ttcactctca ccatcagcag tctgcaacct  720
gaagatttcg caacttacta ctgtcaccaa tattacacct atcctctatt cacgtttggc  780
cagggcacca agctcgagat caagacaacg acgccagctc cccgcccgcc aacccctgca  840
cctacgattg catcacaacc gctgtccctg cggcctgaag cttgtcgccc agccgcaggt  900
ggcgccgtac atacacgggg gctggatttt gcctgtgatt tctgggtgct ggtcgttgtg  960
ggcggcgtgc tggcctgcta cagcctgctg gtgacagtgg ccttcatcat cttttgggtg  1020
aggagcaagc ggagtcgact gctgcacagc gactacatga acatgacccc ccggaggcct  1080
ggccccaccc ggaagcacta ccagccctac gcccctccca gggatttcgc cgcctaccgg  1140
agcaaacggg gcagaaagaa actcctgtat atattcaaac aaccatttat gaggccagta  1200
caaactactc aagaggaaga tggctgtagc tgccgatttc cagaagaaga agaaggagga  1260
tgtgaactga gagtgaagtt cagcaggagc gcagacgccc ccgcgtacaa gcagggccag  1320
aaccagctct ataacgagct caatctagga cgaagagagg agtacgatgt tttggacaag  1380
cgtagaggcc gggaccctga gatgggggga aagccgagaa ggaagaaccc tcaggaaggc  1440
ctgtacaatg aactgcagaa agataagatg gcggaggcct acagtgagat tgggatgaaa  1500
ggcgagcgcc ggaggggcaa ggggcacgat ggcctttacc agggactcag tacagccacc  1560
aaggacacct acgacgccct tcacatgcag gccctgcccc ctcgctaa              1608
```

```
SEQ ID NO: 220          moltype = DNA  length = 1614
FEATURE                 Location/Qualifiers
misc_feature            1..1614
                        note = CT619: CAR with scFv that targetCEA
source                  1..1614
                        mol_type = other DNA
                        organism = synthetic construct
SEQUENCE: 220
atggacatga gggtccccgc tcagctcctg gggctcctgc tactctggct ccgaggtgcc  60
agatgtcagg tgcagctggt gcagtctggc gccgaagtga agaaacctgg agctagtgtg  120
aaggtgtcct gcaaggccag cggctacacc ttcaccgagt tcggcatgaa ctgggtccga  180
caggctccag gccagggcct cgaatggatg ggctggatca acaccaagac cggcgaggcc  240
acctacgtgg aagagttcaa gggcagagtg accttcacca cggacaccag caccagcacc  300
gcctacatgg aactgcggag cctgagaagc gacgacaccg ccgtgtacta ctgcgccaga  360
tgggacttcg cttattacgt ggaagccatg gactactggg gccagggcac caccgtgacc  420
gtgtctagcg gcggaggtgg aagcggaggg ggaggatctg gcggcggagg aagcggaggc  480
gatatccaga tgacccagtc tccatcctcc ctgtctgcat ctgtgggaga cagagtcacc  540
atcacttgca aggccagtgc ggctgtgggt acgtatgttg cgtggtatca gcagaaacca  600
gggaaagcac ctaagctcct gatctattcg gcatcctacc gcaaaagggg agtcccatca  660
aggttcagtg gcagtggatc tgggacagat ttcactctca ccatcagcag tctgcaacct  720
gaagatttcg caacttacta ctgtcaccaa tattacacct atcctctatt cacgtttggc  780
cagggcacca agctcgagat caagcgtacg acaacgacgc cagctccccg cccgccaacc  840
cctgcaccta cgattgcatc acaaccgctg tccctgcggc ctgaagcttg tcgcccagcc  900
gcaggtggcg ccgtacatac acgggggctg gattttgcct gtgatttctg ggtgctggtc  960
gttgtgggcg gcgtgctggc ctgctacagc ctgctggtga cagtggcctt catcatcttt  1020
tgggtgagga gcaagcggag tcgactgctg cacagcgact acatgaacat gaccccccgg  1080
aggcctggcc ccacccggaa gcactaccag ccctacgccc ctcccaggga tttcgccgcc  1140
taccggagca aacggggcag aaagaaactc ctgtatatat tcaaacaacc atttatgagg  1200
ccagtacaaa ctactcaaga ggaagatggc tgtagctgcc gatttccaga agaagaagaa  1260
ggaggatgtg aactgagagt gaagttcagc aggagcgcag acgcccccgc gtacaagcag  1320
ggccagaacc agctctataa cgagctcaat ctaggacgaa gagaggagta cgatgttttg  1380
gacaagcgta gaggccggga ccctgagatg gggggaaagc cgagaaggaa gaaccctcag  1440
gaaggcctgt acaatgaact gcagaaagat aagatggcgg aggcctacag tgagattggg  1500
atgaaaggcg agcgccggag gggcaagggg cacgatggcc tttaccaggg actcagtaca  1560
gccaccaagg acacctacga cgcccttcac atgcaggccc tgccccctcg ctag        1614
```

```
SEQ ID NO: 221          moltype = DNA  length = 1611
FEATURE                 Location/Qualifiers
misc_feature            1..1611
                        note = CT620: CAR with scFv that targetCEA
source                  1..1611
                        mol_type = other DNA
                        organism = synthetic construct
SEQUENCE: 221
atggacatga gggtccccgc tcagctcctg gggctcctgc tactctggct ccgaggtgcc  60
agatgtcagg tgcagctggt gcaatctggg tctgagttga agaagcctgg ggcctcagtg  120
aaggtttcct gcaaggcttc tggatacacc ttcactgagt ttggaatgaa ctgggtgcga  180
caggcccctg gacaagggct tgagtggatg ggatggataa acaccaaaac tggagaggca  240
acatatgttg aagagtttaa gggacggttt gtcttctcct tggacacctc tgtcagcacg  300
gcatatctgc agatcagcag cctaaaggct gaagacactg ccgtgtatta ctgtgcgaga  360
tgggactttg ctcattactt tcagactatg gactactggg gccaagggac cacggtcacc  420
gtctcctcag gcggaggtgg aagcggaggg ggaggatctg gcggcggagg aagcggaggc  480
gatatccaga tgacccagtc tccatcctcc ctgtctgcat ctgtgggaga cagagtcacc  540
atcacttgca aggccagtgc ggctgtgggt acgtatgttg cgtggtatca gcagaaacca  600
gggaaagcac ctaagctcct gatctattcg gcatcctacc gcaaaagggg agtcccatca  660
```

```
aggttcagtg gcagtggatc tgggacagat ttcactctca ccatcagcag tctgcaacct  720
gaagatttcg caacttacta ctgtcaccaa tattacacct atcctctatt cacgtttggc  780
cagggcacca agctcgagat caagcgtaca acgacgccag ctccccgccc gccaacccct  840
gcacctacga ttgcatcaca accgctgtcc ctgcggcctg aagcttgtcg cccagccgca  900
ggtggcgccg tacatacacg ggggctggat tttgcctgtg atttctgggt gctggtcgtt  960
gtgggcggcg tgctggcctg ctacagcctg ctggtgacag tggccttcat catcttttgg  1020
gtgaggagca agcggagtcg actgctgcac agcgactaca tgaacatgac cccccggagg  1080
cctggcccca cccggaagca ctaccagccc tacgcccctc ccagggattt cgccgcctac  1140
cggagcaaac ggggcagaaa gaaactcctg tatatattca aacaaccatt tatgaggcca  1200
gtacaaacta ctcaagagga agatggctgt agctgccgat ttccagaaga agaagaagga  1260
ggatgtgaac tgagagtgaa gttcagcagg agcgcagacg cccccgcgta caagcagggc  1320
cagaaccagc tctataacga gctcaatcta ggacgaagag aggagtacga tgttttggac  1380
aagcgtagag gccgggaccc tgagatgggg ggaaagccga gaaggaagaa ccctcaggaa  1440
ggcctgtaca atgaactgca gaaagataag atggcggagg cctacagtga gattgggatg  1500
aaaggcgagc gccggagggg caaggggcac gatggccttt accagggact cagtacagcc  1560
accaaggaca cctacgacgc ccttcacatg caggccctgc cccctcgcta g            1611

SEQ ID NO: 222          moltype = DNA  length = 729
FEATURE                 Location/Qualifiers
misc_feature            1..729
                        note = scFv that targets CEA
source                  1..729
                        mol_type = other DNA
                        organism = synthetic construct
SEQUENCE: 222
caggtccagc tgcagcagtc tggggcagag cttgtgaggt cagggacctc agtcaagttg  60
tcctgcacag cttctggctt caacattaaa gactcctata tgcactggtt gaggcagggg  120
cctgaacagg gcctggagtg gattggatgg attgatcctg agaatggtga tactgaatat  180
gccccgaagt tccagggcaa ggccactttt actacagaca catcctccaa cacagcctac  240
ctgcagctca gcagcctgac atctgaggac actgccgtct attactgtaa tgaagggaca  300
ccgacagggc catactattt tgactactgg ggtcaaggaa ccacagtcac cgtgtcctca  360
ggcggaggtg gaagcggagg gggaggatct ggcggcggag gaagcggagg cgagaacgtt  420
ctcacccagt ctccagcaat catgtctgca tctccagggg agaaggtcac cataacctgc  480
agtgccagct caagtgtaag ttacatgcac tggttccagc agaagccagg cacttctccc  540
aaactctgga tttatagcac atccaacctg gcttctggag tccctgctcg cttcagtggc  600
agtggatctg ggacctctta ctctctcaca atcagccgaa tggaggctga agatgctgcc  660
acttattact gccagcaaag gagtagttac ccgctcacgt tcggtgctgg gaccaagctg  720
gagctgaaa                                                         729

SEQ ID NO: 223          moltype = DNA  length = 729
FEATURE                 Location/Qualifiers
misc_feature            1..729
                        note = scFv that targets CEA
source                  1..729
                        mol_type = other DNA
                        organism = synthetic construct
SEQUENCE: 223
caggtccagc tggtgcagtc tggggcagag gtgaagaaac caggggcctc agtcaaggtg  60
tcctgcaaag cttctggctt caacattaaa gactcctata tgcactgggt gaggcaggcg  120
cctggacagg gcctggagtg gatgggatgg attgatcctg agaatggtga tactgaatat  180
gccccgaagt tccagggcag ggtcactatg actacagaca catccacctc cacagcctac  240
atggagctca ggagcctgag atctgacgac actgccgtct attactgtaa tgaagggaca  300
ccgacagggc catactattt tgactactgg ggtcaaggaa ccacagtcac cgtgtcctca  360
ggcggaggtg gaagcggagg gggaggatct ggcggcggag gaagcggagg cgagatcgtt  420
ctcacccagt ctccagcaac cttgtctctg tctccagggg agagggccac cctaagctgc  480
agtgccagct caagtgtaag ttacatgcac tggtaccagc agaagccagg ccttgctccc  540
agactcctga tttatagcac atccaacctg gcttctggaa tccctgatcg cttcagtggc  600
agtggatctg ggaccgattt cactctcaca atcagccgac tggagcctga agatttcgcc  660
gtttattact gccagcaaag gagtagttac ccgctcacgt tcggtcaggg gaccaagctg  720
gagatcaaa                                                         729

SEQ ID NO: 224          moltype = DNA  length = 729
FEATURE                 Location/Qualifiers
misc_feature            1..729
                        note = scFv that targets CEA
source                  1..729
                        mol_type = other DNA
                        organism = synthetic construct
SEQUENCE: 224
gaggtgcagc tggcggagtc tgggggaggc ttggtacagc ctggggggtc cctgagactc  60
tcctgtgcag cctctggatt cacctttagc agcgatgcca tgagctgggt ccgccaggct  120
ccagggaagg ggctggagtg ggtctcagct attagtggta gtggtggtag cacatactac  180
gcagactccg tgaagggccg gttcaccatc tccagagaca attccaagaa cacgctgtat  240
ctgcaaatga acagcctgag agccgaggac acggccgtgt attactgtgc aaagtctaat  300
gagtttcttt ttgactactg gggccaaggt accctggtca ccgtgtcgag tggcggaggt  360
ggaagcggag gggaggatc tggcggcgga ggaagcggag gctcttctga gctgactcag  420
gaccctgctg tgtctgtggc cttgggacag acagtcagga tcacatgcca aggagacagc  480
ctcagaagct cttatgcaag ctggtaccgg cagaggccag gacaggcccc tgtacttgtc  540
atctatggta aaaacaaccg gccctcaggg atcccagacc gattctctgg ctccagctca  600
```

```
ggaaacacag cttccttgac catcactggg gctcaggcgg aagatgaggc tgactattac  660
tggaactcca gctacgcttg gctgccctac gtggtattcg gcggagggac caagctgacc  720
gtcctaggt                                                          729

SEQ ID NO: 225         moltype = DNA  length = 729
FEATURE                Location/Qualifiers
misc_feature           1..729
                       note = scFv that targets CEA
source                 1..729
                       mol_type = other DNA
                       organism = synthetic construct
SEQUENCE: 225
caggtccagc tggagcagtc tggggcaggg gttgtgaagc caggggcctc agtcaagttg  60
tcctgcaaag cttctggctt caacattaaa gactcctata tgcactggtt gaggcagggg  120
cctggacagc gcctggagtg gattggatgg attgatcctg agaatggtga tactgaatat  180
gccccgaagt tccagggcaa ggccactttt actacagaca catccgccaa cacagcctac  240
ctggggctca gcagcctgag acctgaggac actgccgtct attactgtaa tgaagggaca  300
ccgacagggc catactattt tgactactgg ggtcaaggaa ccctagtcac cgtgtcctca  360
ggcggaggtg gaagcggagg gggaggatct ggcggcggag gaagcggagg cgagaacgtt  420
ctcacccagt ctccaagctc tatgtctgta tctgtcgggg acagggtcaa catcgcctgc  480
agtgccagct caagtgtacc ttacatgcac tggctccagc agaagccagg caaatctccc  540
aaactcctga tttatctcac atccaacctg gcttctggag tccctagccg cttcagtggc  600
agtggatctg ggaccgatta ctctctcaca atcagctcag tgcagcctga agatgctgcc  660
acttattact gccagcaaag gagtagttac ccgctcacgt tcggtggtgg gaccaagctg  720
gagatcaaa                                                          729

SEQ ID NO: 226         moltype = DNA  length = 738
FEATURE                Location/Qualifiers
misc_feature           1..738
                       note = scFv that targets CEA
source                 1..738
                       mol_type = other DNA
                       organism = synthetic construct
SEQUENCE: 226
caggtgcagc tggtgcaatc tgggtctgag ttgaagaagc ctggggcctc agtgaaggtt  60
tcctgcaagg cttctggata caccttcact gagtttggaa tgaactgggt gcgacaggcc  120
cctggacaag ggcttgagtg gatgggatgg ataaacacca aaactggaga ggcaacatat  180
gttgaagagt ttaagggacg gtttgtcttc tccttggaca cctctgtcag cacggcatat  240
ctgcagatca gcagcctaaa ggctgaagac actgccgtgt attactgtgc gagatgggac  300
ttcgcttatt acgtggaggc tatggactac tggggccaag ggaccacggt gaccgtgtca  360
tccggcggag gtggaagcgg agggggagga tctggcggcg gaggaagcgg aggcgatatc  420
cagatgaccc agtctccatc ctccctgtct gcatctgtgg gagacagagt caccatcact  480
tgcaaggcca gtcagaatgt gggtactaat gttgcctggt atcagcagaa accagggaaa  540
gcacctaagc tcctgatcta ttcggcatcc taccgctaca gtggagtccc atcaaggttc  600
agtggcagtg gatctgggac agatttcact ctcaccatca gcagtctgca acctgaagat  660
ttcgcaactt actactgtca ccaatattac acctatcctc tattcacgtt tggccagggc  720
accaagctcg agatcaag                                                738

SEQ ID NO: 227         moltype = DNA  length = 738
FEATURE                Location/Qualifiers
misc_feature           1..738
                       note = scFv that targets CEA
source                 1..738
                       mol_type = other DNA
                       organism = synthetic construct
SEQUENCE: 227
caggtgcagc tggtgcagtc tggcgccgaa gtgaagaaac ctggagctag tgtgaaggtg  60
tcctgcaagg ccagcggcta caccttcacc gagttcggca tgaactgggt ccgacaggct  120
ccaggccagg gcctcgaatg gatgggctgg atcaacacca agaccggcga ggccacctac  180
gtggaagagt tcaagggcag agtgaccttc accacggaca ccagcaccag caccgcctac  240
atggaactgc ggagcctgag aagcgacgac accgccgtgt actactgcgc cagatgggac  300
ttcgcttatt acgtggaagc catggactac tggggccagg gcaccaccgt gaccgtgtct  360
agcggcggag gtggaagcgg agggggagga tctggcggcg gaggaagcgg aggcgatatc  420
cagatgaccc agtctccatc ctccctgtct gcatctgtgg gagacagagt caccatcact  480
tgcaaggcca gtgcggctgt gggtacgtat gttgcgtggt atcagcagaa accagggaaa  540
gcacctaagc tcctgatcta ttcggcatcc taccgcaaaa ggggagtccc atcaaggttc  600
agtggcagtg gatctgggac agatttcact ctcaccatca gcagtctgca acctgaagat  660
ttcgcaactt actactgtca ccaatattac acctatcctc tattcacgtt tggccagggc  720
accaagctcg agatcaag                                                738

SEQ ID NO: 228         moltype = DNA  length = 738
FEATURE                Location/Qualifiers
misc_feature           1..738
                       note = scFv that targets CEA
source                 1..738
                       mol_type = other DNA
                       organism = synthetic construct
SEQUENCE: 228
caggtgcagc tggtgcaatc tgggtctgag ttgaagaagc ctggggcctc agtgaaggtt  60
```

```
tcctgcaagg cttctggata caccttcact gagtttggaa tgaactgggt gcgacaggcc  120
cctggacaag ggcttgagtg gatgggatgg ataaacacca aaactggaga ggcaacatat  180
gttgaagagt ttaagggacg gtttgtcttc tccttggaca cctctgtcag cacggcatat  240
ctgcagatca gcagcctaaa ggctgaagac actgccgtgt attactgtgc gagatgggac  300
tttgctcatt actttcagac tatggactac tggggccaag ggaccacggt caccgtctcc  360
tcaggcggag gtggaagcgg agggggagga tctggcggcg gaggaagcgg aggcgatatc  420
cagatgaccc agtctccatc ctccctgtct gcatctgtgg gagacagagt caccatcact  480
tgcaaggcca gtgcggctgt gggtacgtat gttgcgtggt atcagcagaa accagggaaa  540
gcacctaagc tcctgatcta ttcggcatcc taccgcaaaa ggggagtccc atcaaggttc  600
agtggcagtg gatctgggac agatttcact ctcaccatca gcagtctgca acctgaagat  660
ttcgcaactt actactgtca ccaatattac acctatcctc tattcacgtt tggccagggc  720
accaagctcg agatcaag                                                 738

SEQ ID NO: 229         moltype = AA  length = 616
FEATURE                Location/Qualifiers
REGION                 1..616
                       note = H141/A192V allele of TNFRSF11A
source                 1..616
                       mol_type = protein
                       organism = synthetic construct
SEQUENCE: 229
MAPRARRRRP LFALLLLCAL LARLQVALQI APPCTSEKHY EHLGRCCNKC EPGKYMSSKC  60
TTTSDSVCLP CGPDEYLDSW NEEDKCLLHK VCDTGKALVA VVAGNSTTPR RCACTAGYHW  120
SQDCECCRRN TECAPGLGAQ HPLQLNKDTV CKPCLAGYFS DAFSSTDKCR PWTNCTFLGK  180
RVEHHGTEKS DVVCSSSLPA RKPPNEPHVY LPGLIILLLF ASVALVAAII FGVCYRKKGK  240
ALTANLWHWI NEACGRLSGD KESSGDSCVS THTANFGQQG ACEGVLLLTL EEKTFPEDMC  300
YPDQGGVCQG TCVGGGPYAQ GEDARMLSLV SKTEIEEDSF RQMPTEDEYM DRPSQPTDQL  360
LFLTEPGSKS TPPFSEPLEV GENDSLSQCF TGTQSTVGSE SCNCTEPLCR TDWTPMSSEN  420
YLQKEVDSGH CPHWAASPSP NWADVCTGCR NPPGEDCEPL VGSPKRGPLP QCAYGMGLPP  480
EEEASRTEAR DQPEDGADGR LPSSARAGAG SGSSPGGQSP ASGNVTGNSN STFISSGQVM  540
NFKGDIIVVY VSQTSQEGAA AAAEPMGRPV QEETLARRDS FAGNGPRFPD PCGGPEGLRE  600
PEKASRPVQE QGGAKA                                                   616

SEQ ID NO: 230         moltype = AA  length = 616
FEATURE                Location/Qualifiers
REGION                 1..616
                       note = H141Y/A192 allele of TNFRSF11A
source                 1..616
                       mol_type = protein
                       organism = synthetic construct
SEQUENCE: 230
MAPRARRRRP LFALLLLCAL LARLQVALQI APPCTSEKHY EHLGRCCNKC EPGKYMSSKC  60
TTTSDSVCLP CGPDEYLDSW NEEDKCLLHK VCDTGKALVA VVAGNSTTPR RCACTAGYHW  120
SQDCECCRRN TECAPGLGAQ YPLQLNKDTV CKPCLAGYFS DAFSSTDKCR PWTNCTFLGK  180
RVEHHGTEKS DAVCSSSLPA RKPPNEPHVY LPGLIILLLF ASVALVAAII FGVCYRKKGK  240
ALTANLWHWI NEACGRLSGD KESSGDSCVS THTANFGQQG ACEGVLLLTL EEKTFPEDMC  300
YPDQGGVCQG TCVGGGPYAQ GEDARMLSLV SKTEIEEDSF RQMPTEDEYM DRPSQPTDQL  360
LFLTEPGSKS TPPFSEPLEV GENDSLSQCF TGTQSTVGSE SCNCTEPLCR TDWTPMSSEN  420
YLQKEVDSGH CPHWAASPSP NWADVCTGCR NPPGEDCEPL VGSPKRGPLP QCAYGMGLPP  480
EEEASRTEAR DQPEDGADGR LPSSARAGAG SGSSPGGQSP ASGNVTGNSN STFISSGQVM  540
NFKGDIIVVY VSQTSQEGAA AAAEPMGRPV QEETLARRDS FAGNGPRFPD PCGGPEGLRE  600
PEKASRPVQE QGGAKA                                                   616

SEQ ID NO: 231         moltype = AA  length = 616
FEATURE                Location/Qualifiers
REGION                 1..616
                       note = H141Y/A192V allele of TNFRSF11A
source                 1..616
                       mol_type = protein
                       organism = synthetic construct
SEQUENCE: 231
MAPRARRRRP LFALLLLCAL LARLQVALQI APPCTSEKHY EHLGRCCNKC EPGKYMSSKC  60
TTTSDSVCLP CGPDEYLDSW NEEDKCLLHK VCDTGKALVA VVAGNSTTPR RCACTAGYHW  120
SQDCECCRRN TECAPGLGAQ YPLQLNKDTV CKPCLAGYFS DAFSSTDKCR PWTNCTFLGK  180
RVEHHGTEKS DVVCSSSLPA RKPPNEPHVY LPGLIILLLF ASVALVAAII FGVCYRKKGK  240
ALTANLWHWI NEACGRLSGD KESSGDSCVS THTANFGQQG ACEGVLLLTL EEKTFPEDMC  300
YPDQGGVCQG TCVGGGPYAQ GEDARMLSLV SKTEIEEDSF RQMPTEDEYM DRPSQPTDQL  360
LFLTEPGSKS TPPFSEPLEV GENDSLSQCF TGTQSTVGSE SCNCTEPLCR TDWTPMSSEN  420
YLQKEVDSGH CPHWAASPSP NWADVCTGCR NPPGEDCEPL VGSPKRGPLP QCAYGMGLPP  480
EEEASRTEAR DQPEDGADGR LPSSARAGAG SGSSPGGQSP ASGNVTGNSN STFISSGQVM  540
NFKGDIIVVY VSQTSQEGAA AAAEPMGRPV QEETLARRDS FAGNGPRFPD PCGGPEGLRE  600
PEKASRPVQE QGGAKA                                                   616

SEQ ID NO: 232         moltype = AA  length = 1179
FEATURE                Location/Qualifiers
REGION                 1..1179
                       note = R950W/V1019 allele of ITGAE
source                 1..1179
                       mol_type = protein
```

```
                         organism = synthetic construct
SEQUENCE: 232
MWLFHTLLCI ASLALLAAFN VDVARPWLTP KGGAPFVLSS LLHQDPSTNQ TWLLVTSPRT  60
KRTPGPLHRC SLVQDEILCH PVEHVPIPKG RHRGVTVVRS HHGVLICIQV LVRRPHSLSS  120
ELTGTCSLLG PDLRPQAQAN FFDLENLLDP DARVDTGDCY SNKEGGGEDD VNTARQRRAL  180
EKEEEEDKEE EEDEEEEEAG TEIAIILDGS GSIDPPDFQR AKDFISNMMR NFYEKCFECN  240
FALVQYGGVI QTEFDLRDSQ DVMASLARVQ NITQVGSVTK TASAMQHVLD SIFTSSHGSR  300
RKASKVMVVL TDGGIFEDPL NLTTVINSPK MQGVERFAIG VGEEFKSART ARELNLIASD  360
PDETHAFKVT NYMALDGLLS KLRYNIISME GTVGDALHYQ LAQIGFSAQI LDERQVLLGA  420
VGAFDWSGGA LLYDTRSRRG RFLNQTAAAA ADAEAAQYSY LGYAVAVLHK TCSLSYIAGA  480
PRYKHHGAVF ELQKEGREAS FLPVLEGEQM GSYFGSELCP VDIDMDGSTD FLLVAAPFYH  540
VHGEEGRVYV YRLSEQDGSF SLARILSGHP GFTNARFGFA MAAMGDLSQD KLTDVAIGAP  600
LEGFGADDGA SFGSVYIYNG HWDGLSASPS QRIRASTVAP GLQYFGMSMA GGFDISGDGL  660
ADITVGTLGQ AVVFRSRPVV RLKVSMAFTP SALPIGFNGV VNVRLCFEIS SVTTASESGL  720
REALLNFTLD VDVGKQRRRL QCSDVRSCLG CLREWSSGSQ LCEDLLLMPT EGELCEEDCF  780
SNASVKVSYQ LQTPEGQTDH PQPILDRYTE PFAIFQLPYE KACKNKLFCV AELQLATTVS  840
QQELVVGLTK ELTLNINLTN SGEDSYMTSM ALNYPRNLQL KRMQKPPSPN IQCDDPQPVA  900
SVLIMNCRIG HPVLKRSSAH VSVVWQLEEN AFPNRTADIT VTVTNSNERW SLANETHTLQ  960
FRHGFVAVLS KPSIMYVNTG QGLSHHKEFL FHVHGENLFG AEYQLQICVP TKLRGLQVVA  1020
VKKLTRTQAS TVCTWSQERA CAYSSVQHVE EWHSVSCVIA SDKENVTVAA EISWDHSEEL  1080
LKDVTELQIL GEISFNKSLY EGLNAENHRT KITVVFLKDE KYHSLPIIIK GSVGGLLVLI  1140
VILVILFKCG FFKRKYQQLN LESIRKAQLK SENLLEEEN                        1179

SEQ ID NO: 233           moltype = AA  length = 1179
FEATURE                  Location/Qualifiers
REGION                   1..1179
                         note = R950/V1019A allele of ITGAE
source                   1..1179
                         mol_type = protein
                         organism = synthetic construct
SEQUENCE: 233
MWLFHTLLCI ASLALLAAFN VDVARPWLTP KGGAPFVLSS LLHQDPSTNQ TWLLVTSPRT  60
KRTPGPLHRC SLVQDEILCH PVEHVPIPKG RHRGVTVVRS HHGVLICIQV LVRRPHSLSS  120
ELTGTCSLLG PDLRPQAQAN FFDLENLLDP DARVDTGDCY SNKEGGGEDD VNTARQRRAL  180
EKEEEEDKEE EEDEEEEEAG TEIAIILDGS GSIDPPDFQR AKDFISNMMR NFYEKCFECN  240
FALVQYGGVI QTEFDLRDSQ DVMASLARVQ NITQVGSVTK TASAMQHVLD SIFTSSHGSR  300
RKASKVMVVL TDGGIFEDPL NLTTVINSPK MQGVERFAIG VGEEFKSART ARELNLIASD  360
PDETHAFKVT NYMALDGLLS KLRYNIISME GTVGDALHYQ LAQIGFSAQI LDERQVLLGA  420
VGAFDWSGGA LLYDTRSRRG RFLNQTAAAA ADAEAAQYSY LGYAVAVLHK TCSLSYIAGA  480
PRYKHHGAVF ELQKEGREAS FLPVLEGEQM GSYFGSELCP VDIDMDGSTD FLLVAAPFYH  540
VHGEEGRVYV YRLSEQDGSF SLARILSGHP GFTNARFGFA MAAMGDLSQD KLTDVAIGAP  600
LEGFGADDGA SFGSVYIYNG HWDGLSASPS QRIRASTVAP GLQYFGMSMA GGFDISGDGL  660
ADITVGTLGQ AVVFRSRPVV RLKVSMAFTP SALPIGFNGV VNVRLCFEIS SVTTASESGL  720
REALLNFTLD VDVGKQRRRL QCSDVRSCLG CLREWSSGSQ LCEDLLLMPT EGELCEEDCF  780
SNASVKVSYQ LQTPEGQTDH PQPILDRYTE PFAIFQLPYE KACKNKLFCV AELQLATTVS  840
QQELVVGLTK ELTLNINLTN SGEDSYMTSM ALNYPRNLQL KRMQKPPSPN IQCDDPQPVA  900
SVLIMNCRIG HPVLKRSSAH VSVVWQLEEN AFPNRTADIT VTVTNSNERR SLANETHTLQ  960
FRHGFVAVLS KPSIMYVNTG QGLSHHKEFL FHVHGENLFG AEYQLQICVP TKLRGLQVAA  1020
VKKLTRTQAS TVCTWSQERA CAYSSVQHVE EWHSVSCVIA SDKENVTVAA EISWDHSEEL  1080
LKDVTELQIL GEISFNKSLY EGLNAENHRT KITVVFLKDE KYHSLPIIIK GSVGGLLVLI  1140
VILVILFKCG FFKRKYQQLN LESIRKAQLK SENLLEEEN                        1179

SEQ ID NO: 234           moltype = AA  length = 1179
FEATURE                  Location/Qualifiers
REGION                   1..1179
                         note = R950/V1019G allele of ITGAE
source                   1..1179
                         mol_type = protein
                         organism = synthetic construct
SEQUENCE: 234
MWLFHTLLCI ASLALLAAFN VDVARPWLTP KGGAPFVLSS LLHQDPSTNQ TWLLVTSPRT  60
KRTPGPLHRC SLVQDEILCH PVEHVPIPKG RHRGVTVVRS HHGVLICIQV LVRRPHSLSS  120
ELTGTCSLLG PDLRPQAQAN FFDLENLLDP DARVDTGDCY SNKEGGGEDD VNTARQRRAL  180
EKEEEEDKEE EEDEEEEEAG TEIAIILDGS GSIDPPDFQR AKDFISNMMR NFYEKCFECN  240
FALVQYGGVI QTEFDLRDSQ DVMASLARVQ NITQVGSVTK TASAMQHVLD SIFTSSHGSR  300
RKASKVMVVL TDGGIFEDPL NLTTVINSPK MQGVERFAIG VGEEFKSART ARELNLIASD  360
PDETHAFKVT NYMALDGLLS KLRYNIISME GTVGDALHYQ LAQIGFSAQI LDERQVLLGA  420
VGAFDWSGGA LLYDTRSRRG RFLNQTAAAA ADAEAAQYSY LGYAVAVLHK TCSLSYIAGA  480
PRYKHHGAVF ELQKEGREAS FLPVLEGEQM GSYFGSELCP VDIDMDGSTD FLLVAAPFYH  540
VHGEEGRVYV YRLSEQDGSF SLARILSGHP GFTNARFGFA MAAMGDLSQD KLTDVAIGAP  600
LEGFGADDGA SFGSVYIYNG HWDGLSASPS QRIRASTVAP GLQYFGMSMA GGFDISGDGL  660
ADITVGTLGQ AVVFRSRPVV RLKVSMAFTP SALPIGFNGV VNVRLCFEIS SVTTASESGL  720
REALLNFTLD VDVGKQRRRL QCSDVRSCLG CLREWSSGSQ LCEDLLLMPT EGELCEEDCF  780
SNASVKVSYQ LQTPEGQTDH PQPILDRYTE PFAIFQLPYE KACKNKLFCV AELQLATTVS  840
QQELVVGLTK ELTLNINLTN SGEDSYMTSM ALNYPRNLQL KRMQKPPSPN IQCDDPQPVA  900
SVLIMNCRIG HPVLKRSSAH VSVVWQLEEN AFPNRTADIT VTVTNSNERR SLANETHTLQ  960
FRHGFVAVLS KPSIMYVNTG QGLSHHKEFL FHVHGENLFG AEYQLQICVP TKLRGLQVGA  1020
VKKLTRTQAS TVCTWSQERA CAYSSVQHVE EWHSVSCVIA SDKENVTVAA EISWDHSEEL  1080
LKDVTELQIL GEISFNKSLY EGLNAENHRT KITVVFLKDE KYHSLPIIIK GSVGGLLVLI  1140
```

```
VILVILFKCG FFKRKYQQLN LESIRKAQLK SENLLEEEN                     1179

SEQ ID NO: 235          moltype = AA  length = 1179
FEATURE                 Location/Qualifiers
REGION                  1..1179
                        note = R950W/V1019 allele of ITGAE
source                  1..1179
                        mol_type = protein
                        organism = synthetic construct
SEQUENCE: 235
MWLFHTLLCI ASLALLAAFN VDVARPWLTP KGGAPFVLSS LLHQDPSTNQ TWLLVTSPRT  60
KRTPGPLHRC SLVQDEILCH PVEHVPIPKG RHRGVTVVRS HHGVLICIQV LVRRPHSLSS  120
ELTGTCSLLG PDLRPQAQAN FFDLENLLDP DARVDTGDCY SNKEGGGEDD VNTARQRRAL  180
EKEEEEDKEE EEDEEEEEAG TEIAIILDGS GSIDPPDFQR AKDFISNMMR NFYEKCFECN  240
FALVQYGGVI QTEFDLRDSQ DVMASLARVQ NITQVGSVTK TASAMQHVLD SIFTSSHGSR  300
RKASKVMVVL TDGGIFEDPL NLTTVINSPK MQGVERFAIG VGEEFKSART ARELNLIASD  360
PDETHAFKVT NYMALDGLLS KLRYNIISME GTVGDALHYQ LAQIGFSAQI LDERQVLLGA  420
VGAFDWSGGA LLYDTRSRRG RFLNQTAAAA ADAEAAQYSY LGYAVAVLHK TCSLSYIAGA  480
PRYKHHGAVF ELQKEGREAS FLPVLEGEQM GSYFGSELCP VDIDMDGSTD FLLVAAPFYH  540
VHGEEGRVYV YRLSEQDGSF SLARILSGHP GFTNARFGFA MAAMGDLSQD KLTDVAIGAP  600
LEGFGADDGA SFGSVYIYNG HWDGLSASPS QRIRASTVAP GLQYFGMSMA GGFDISGDGL  660
ADITVGTLGQ AVVFRSRPVV RLKVSMAFTP SALPIGFNGV VNVRLCFEIS SVTTASESGL  720
REALLNFTLD VDVGKQRRRL QCSDVRSCLG CLREWSSGSQ LCEDLLLMPT EGELCEEDCF  780
SNASVKVSYQ LQTPEGQTDH PQPILDRYTE PFAIFQLPYE KACKNKLFCV AELQLATTVS  840
QQELVVGLTK ELTLNINLTN SGEDSYMTSM ALNYPRNLQL KRMQKPPSPN IQCDDPQPVA  900
SVLIMNCRIG HPVLKRSSAH VSVVWQLEEN AFPNRTADIT VTVTNSNERW SLANETHTLQ  960
FRHGFVAVLS KPSIMYVNTG QGLSHHKEFL FHVHGENLFG AEYQLQICVP TKLRGLQVVA  1020
VKKLTRTQAS TVCTWSQERA CAYSSVQHVE EWHSVSCVIA SDKENVTVAA EISWDHSEEL  1080
LKDVTELQIL GEISFNKSLY EGLNAENHRT KITVVFLKDE KYHSLPIIIK GSVGGLLVLI  1140
VILVILFKCG FFKRKYQQLN LESIRKAQLK SENLLEEEN                     1179

SEQ ID NO: 236          moltype = AA  length = 1179
FEATURE                 Location/Qualifiers
REGION                  1..1179
                        note = R950W/V1019A allele of ITGAE
source                  1..1179
                        mol_type = protein
                        organism = synthetic construct
SEQUENCE: 236
MWLFHTLLCI ASLALLAAFN VDVARPWLTP KGGAPFVLSS LLHQDPSTNQ TWLLVTSPRT  60
KRTPGPLHRC SLVQDEILCH PVEHVPIPKG RHRGVTVVRS HHGVLICIQV LVRRPHSLSS  120
ELTGTCSLLG PDLRPQAQAN FFDLENLLDP DARVDTGDCY SNKEGGGEDD VNTARQRRAL  180
EKEEEEDKEE EEDEEEEEAG TEIAIILDGS GSIDPPDFQR AKDFISNMMR NFYEKCFECN  240
FALVQYGGVI QTEFDLRDSQ DVMASLARVQ NITQVGSVTK TASAMQHVLD SIFTSSHGSR  300
RKASKVMVVL TDGGIFEDPL NLTTVINSPK MQGVERFAIG VGEEFKSART ARELNLIASD  360
PDETHAFKVT NYMALDGLLS KLRYNIISME GTVGDALHYQ LAQIGFSAQI LDERQVLLGA  420
VGAFDWSGGA LLYDTRSRRG RFLNQTAAAA ADAEAAQYSY LGYAVAVLHK TCSLSYIAGA  480
PRYKHHGAVF ELQKEGREAS FLPVLEGEQM GSYFGSELCP VDIDMDGSTD FLLVAAPFYH  540
VHGEEGRVYV YRLSEQDGSF SLARILSGHP GFTNARFGFA MAAMGDLSQD KLTDVAIGAP  600
LEGFGADDGA SFGSVYIYNG HWDGLSASPS QRIRASTVAP GLQYFGMSMA GGFDISGDGL  660
ADITVGTLGQ AVVFRSRPVV RLKVSMAFTP SALPIGFNGV VNVRLCFEIS SVTTASESGL  720
REALLNFTLD VDVGKQRRRL QCSDVRSCLG CLREWSSGSQ LCEDLLLMPT EGELCEEDCF  780
SNASVKVSYQ LQTPEGQTDH PQPILDRYTE PFAIFQLPYE KACKNKLFCV AELQLATTVS  840
QQELVVGLTK ELTLNINLTN SGEDSYMTSM ALNYPRNLQL KRMQKPPSPN IQCDDPQPVA  900
SVLIMNCRIG HPVLKRSSAH VSVVWQLEEN AFPNRTADIT VTVTNSNERW SLANETHTLQ  960
FRHGFVAVLS KPSIMYVNTG QGLSHHKEFL FHVHGENLFG AEYQLQICVP TKLRGLQVAA  1020
VKKLTRTQAS TVCTWSQERA CAYSSVQHVE EWHSVSCVIA SDKENVTVAA EISWDHSEEL  1080
LKDVTELQIL GEISFNKSLY EGLNAENHRT KITVVFLKDE KYHSLPIIIK GSVGGLLVLI  1140
VILVILFKCG FFKRKYQQLN LESIRKAQLK SENLLEEEN                     1179

SEQ ID NO: 237          moltype = AA  length = 1179
FEATURE                 Location/Qualifiers
REGION                  1..1179
                        note = R950W/V1019G allele of ITGAE
source                  1..1179
                        mol_type = protein
                        organism = synthetic construct
SEQUENCE: 237
MWLFHTLLCI ASLALLAAFN VDVARPWLTP KGGAPFVLSS LLHQDPSTNQ TWLLVTSPRT  60
KRTPGPLHRC SLVQDEILCH PVEHVPIPKG RHRGVTVVRS HHGVLICIQV LVRRPHSLSS  120
ELTGTCSLLG PDLRPQAQAN FFDLENLLDP DARVDTGDCY SNKEGGGEDD VNTARQRRAL  180
EKEEEEDKEE EEDEEEEEAG TEIAIILDGS GSIDPPDFQR AKDFISNMMR NFYEKCFECN  240
FALVQYGGVI QTEFDLRDSQ DVMASLARVQ NITQVGSVTK TASAMQHVLD SIFTSSHGSR  300
RKASKVMVVL TDGGIFEDPL NLTTVINSPK MQGVERFAIG VGEEFKSART ARELNLIASD  360
PDETHAFKVT NYMALDGLLS KLRYNIISME GTVGDALHYQ LAQIGFSAQI LDERQVLLGA  420
VGAFDWSGGA LLYDTRSRRG RFLNQTAAAA ADAEAAQYSY LGYAVAVLHK TCSLSYIAGA  480
PRYKHHGAVF ELQKEGREAS FLPVLEGEQM GSYFGSELCP VDIDMDGSTD FLLVAAPFYH  540
VHGEEGRVYV YRLSEQDGSF SLARILSGHP GFTNARFGFA MAAMGDLSQD KLTDVAIGAP  600
LEGFGADDGA SFGSVYIYNG HWDGLSASPS QRIRASTVAP GLQYFGMSMA GGFDISGDGL  660
```

```
ADITVGTLGQ AVVFRSRPVV RLKVSMAFTP SALPIGFNGV VNVRLCFEIS SVTTASESGL  720
REALLNFTLD VDVGKQRRRL QCSDVRSCLG CLREWSSGSQ LCEDLLLMPT EGELCEEDCF  780
SNASVKVSYQ LQTPEGQTDH PQPILDRYTE PFAIFQLPYE KACKNKLFCV AELQLATTVS  840
QQELVVGLTK ELTLNINLTN SGEDSYMTSM ALNYPRNLQL KRMQKPPSPN IQCDDPQPVA  900
SVLIMNCRIG HPVLKRSSAH VSVVWQLEEN AFPNRTADIT VTVTNSNERW SLANETHTLQ  960
FRHGFVAVLS KPSIMYVNTG QGLSHHKEFL FHVHGENLFG AEYQLQICVP TKLRGLQVGA  1020
VKKLTRTQAS TVCTWSQERA CAYSSVQHVE EWHSVSCVIA SDKENVTVAA EISWDHSEEL  1080
LKDVTELQIL GEISFNKSLY EGLNAENHRT KITVVFLKDE KYHSLPIIIK GSVGGLLVLI  1140
VILVILFKCG FFKRKYQQLN LESIRKAQLK SENLLEEEN                         1179

SEQ ID NO: 238          moltype = DNA  length = 741
FEATURE                 Location/Qualifiers
source                  1..741
                        mol_type = unassigned DNA
                        organism = Mus musculus
SEQUENCE: 238
gatgttctga tgacccaaac tccactctcc ctgcctgtca gtcttggaga tcaagcctcc  60
atctcttgca gatctagtca gagcattgta catagtaatg gaaacaccta tttagaatgg  120
tacctgcaga agccaggcca gtctccaaag ctgctcatct acaaagtttc caaccgattt  180
tctggggtcc cagacagatt tagcggatct ggctctggga ccgatttcac actcaagatc  240
agtagagtgg aggctgagga tctgggagtt tattactgct ttcaaggttc acatgttcct  300
cggacgtccg gtggaggcac aaagctggaa atcaagggag gtggcggctc tggaggcgga  360
ggtagcggag gtggaggctc tggtggccag gtccagctgc agcagtctgg acctgagctg  420
gtgaagccag gggcttcagt gaggatatcc tgtaaggcct ctggctacac ctttacaagt  480
taccatatac attgggtgaa gcagaggcct ggacagggac tcgaatggat tggatggatt  540
tatcctggaa atgttaatac tgagtacaat gagaagttca agggcaaggc cacactgact  600
gcagacaaat cgtccagcac agcctacatg cacctcagca gcctgacctc tgaggactct  660
gcggtctatt tctgtgccag agaggagatt acctatgcta tggattattg gggtcaagga  720
acctcagtca ccgtgtcctc a                                            741

SEQ ID NO: 239          moltype = DNA  length = 741
FEATURE                 Location/Qualifiers
misc_feature            1..741
                        note = humanized HLA-A*02 antigen binding domain
source                  1..741
                        mol_type = other DNA
                        organism = synthetic construct
SEQUENCE: 239
caggtgcagc tggtgcagtc tggggctgag gtgaagaagc ctgggtcctc agtgaaggtt  60
tcctgcaagg cttctggata caccttcact agctatcata tacattgggt gcgccaggcc  120
cccggacaag ggcttgagtg gatgggatgg atctaccctg gcaatgttaa cacagaatat  180
aatgagaagt tcaagggcaa agccaccatt accgcggaca aatccacgag cacagcctac  240
atggagctga gcagcctgag atctgaagac acggctgtgt attactgtgc gagggaggaa  300
attacctacg ctatggacta ctggggccag ggaaccacag tcaccgtgtc ctcaggcgga  360
ggtggaagcg gaggggggagg atctggcggc ggaggaagcg gaggcgagat tgtattgacc  420
cagagcccag gcaccctgag cctctctcca ggagagcggg ccaccctcag ttgtagatcc  480
agtcagagta ttgtacacag taatgggaac acctatttgg aatggtatca gcagaaacca  540
ggtcaagccc caagattgct catctacaaa gtctctaaca gatttagtgg tattccagac  600
aggttcagcg gttccggaag tggtactgat ttcaccctca cgatctccag gctcgagcca  660
gaagatttcg ccgtttatta ctgttttcaa ggttcacatg tgccgcgcac attcggtggg  720
ggtactaaag tagaaatcaa a                                            741

SEQ ID NO: 240          moltype = DNA  length = 741
FEATURE                 Location/Qualifiers
misc_feature            1..741
                        note = humanized HLA-A*02 antigen binding domain
source                  1..741
                        mol_type = other DNA
                        organism = synthetic construct
SEQUENCE: 240
caggtgcagc tggtgcagtc tggggctgag gtgaagaagc ctgggtcctc agtgaaggtt  60
tcctgcaagg cttctggata caccttcact agctatcata tacattgggt gcgccaggcc  120
cccggacaag ggcttgagtg gatgggatgg atctaccctg gcaatgttaa cacagaatat  180
aatgagaagt tcaagggcaa agccaccatt accgcggaca aatccacgag cacagcctac  240
atggagctga gcagcctgag atctgaagac acggctgtgt attactgtgc gagggaggaa  300
attacctacg ctatggacta ctggggccag ggaaccacag tcaccgtgtc ctcaggcgga  360
ggtggaagcg gaggggggagg atctggcggc ggaggaagcg gaggcgacat tgtaatgacc  420
cagaccccac tcagcctgcc cgtcactcca ggagagccgg ccagcatcag ttgtagatcc  480
agtcagagta ttgtacacag taatgggaac acctatttgg aatggtatct gcagaaacca  540
ggtcaatccc cacaattgct catctacaaa gtctctaaca gatttagtgg tgtaccagac  600
aggttcagcg gttccggaag tggtactgat ttcaccctca agatctccag ggtcgaggca  660
gaagatgtcg gcgtttatta ctgttttcaa ggttcacatg tgccgcgcac attcggtggg  720
ggtactaaag tagaaatcaa a                                            741

SEQ ID NO: 241          moltype = DNA  length = 741
FEATURE                 Location/Qualifiers
misc_feature            1..741
                        note = humanized HLA-A*02 antigen binding domain
source                  1..741
```

```
                        mol_type = other DNA
                        organism = synthetic construct
SEQUENCE: 241
gaggtgcagc tggtggagtc tgggggtggg ctggtgaagc ctgggggctc actgaggctt  60
tcctgcgcgg cttctggata caccttcact agctatcata tacattgggt gcgccaggcc  120
cccggaaaag ggcttgagtg ggtgggatgg atctaccctg gcaatgttaa cacagaatat  180
aatgagaagt tcaagggcag attcaccatt agcagggacg attccaagaa cacactctac  240
ctgcagatga acagcctgaa aactgaagac acggctgtgt attactgtgc gagggaggaa  300
attacctacg ctatggacta ctggggccag ggaaccacag tcaccgtgtc ctcaggcgga  360
ggtggaagcg gagggggagg atctggcggc ggaggaagcg gaggcgacat tcaaatgacc  420
cagagcccat ccagcctgag cgcatctgta ggtgaccggg tcaccatcac ttgtagatcc  480
agtcagagta ttgtacacag taatgggaac acctatttgg aatggtatca gcagaaacca  540
ggtaaagccc caaaattgct catctacaaa gtctctaaca gatttagtgg tgtaccaagc  600
aggttcagcg gttccggaag tggtactgat ttcaccctca cgatctcctc tctccagcca  660
gaagatttcg ccacttatta ctgttttcaa ggttcacatg tgccgcgcac attcggtggg  720
ggtactaaag tagaaatcaa a                                           741

SEQ ID NO: 242          moltype = DNA  length = 741
FEATURE                 Location/Qualifiers
misc_feature            1..741
                        note = humanized HLA-A*02 antigen binding domain
source                  1..741
                        mol_type = other DNA
                        organism = synthetic construct
SEQUENCE: 242
caggtgcagc tggtgcagtc tggggctgag gtgaagaagc ctgggtcctc agtgaaggtt  60
tcctgcaagg cttctggata caccttcact agctatcata tacattgggt gcgccaggcc  120
cccggacaag ggcttgagtg gatcggatgg atctaccctg gcaatgttaa cacagaatat  180
aatgagaagt tcaagggcaa agccaccatt accgcggacg aatccacgaa cacagcctac  240
atggagctga gcagcctgag atctgaagac acggctgtgt attactgtgc gagggaggaa  300
attacctacg ctatggacta ctggggccag ggaaccctgg tcaccgtgtc ctcaggcgga  360
ggtggaagcg gagggggagg atctggcggc ggaggaagcg gaggcgacat tcaaatgacc  420
cagagcccat ccaccctgag cgcatctgta ggtgaccggg tcaccatcac ttgtagatcc  480
agtcagagta ttgtacacag taatgggaac acctatttgg aatggtatca gcagaaacca  540
ggtaaagccc caaaattgct catctacaaa gtctctaaca gatttagtgg tgtaccagcc  600
aggttcagcg gttccggaag tggtactgaa ttcaccctca cgatctcctc tctccagcca  660
gatgatttcg ccacttatta ctgttttcaa ggttcacatg tgccgcgcac attcggtcag  720
ggtactaaag tagaagtcaa a                                           741

SEQ ID NO: 243          moltype = DNA  length = 741
FEATURE                 Location/Qualifiers
misc_feature            1..741
                        note = humanized HLA-A*02 antigen binding domain
source                  1..741
                        mol_type = other DNA
                        organism = synthetic construct
SEQUENCE: 243
caggtgcagc tggtgcagtc tggggctgag gtgaagaagc ctgggtcctc agtgaaggtt  60
tcctgcaagg cttctggata caccttcact agctatcata tgcattgggt gcgccaggcc  120
cccggacaag ggcttgagtg gatcggatac atctaccctg gcaatgttaa cacagaatat  180
aatgagaagt tcaagggcaa agccaccctt accgcggaca aatccacgaa cacagcctac  240
atggagctga gcagcctgag atctgaagac acggctgtgt atttctgtgc gagggaggaa  300
attacctacg ctatggacta ctggggccag ggaaccctgg tcaccgtgtc ctcaggcgga  360
ggtggaagcg gagggggagg atctggcggc ggaggaagcg gaggcgacgt tcaaatgacc  420
cagagcccat ccaccctgag cgcatctgta ggtgaccggg tcaccatcac ttgtagctcc  480
agtcagagta ttgtacacag taatgggaac acctatatgg aatggtatca gcagaaacca  540
ggtaaagccc caaaattgct catctacaaa gtctctaaca gatttagtgg tgtaccagac  600
aggttcagcg gttccggaag tggtactgaa ttcaccctca cgatctcctc tctccagcca  660
gatgatttcg ccacttatta ctgtcatcaa ggttcacatg tgccgcgcac attcggtcag  720
ggtactaaag tagaagtcaa a                                           741

SEQ ID NO: 244          moltype = DNA  length = 741
FEATURE                 Location/Qualifiers
source                  1..741
                        mol_type = unassigned DNA
                        organism = Mus musculus
SEQUENCE: 244
caggtgcagc tgcagcagtc tgggcctgag ctggtgaagc ctggggcctc agtgaagatg  60
tcctgcaagg cttctggata caccttcact agctatcata tccagtgggt gaagcagagg  120
cctggacaag ggcttgagtg gatcggatgg atctaccctg gcgatggtag tacacagtat  180
aatgagaagt tcaagggcaa aaccaccctt accgcggaca aatcctccag cacagcctac  240
atgttgctga gcagcctgac ctctgaagac tctgctatct atttctgtgc gagggagggg  300
acctactacg ctatggacta ctggggccag ggaacctcag tcaccgtgtc ctcaggcgga  360
ggtggaagcg gagggggagg atctggcggc ggaggaagcg gaggcgatgt tttgatgacc  420
cagactccac tctccctgcc tgtctctctt ggagaccaag tctccatctc ttgtagatcc  480
agtcagagta ttgtacacag taatgggaac acctatttag aatggtatct gcagaaacca  540
ggtcagtctc caaagttgct catctacaaa gtctctaaca gatttagtgg tgtaccagac  600
aggttcagcg gttccggaag tggtactgat ttcaccctca agatctcgag agtggaggct  660
gaggatctgg gagtttatta ctgttttcaa ggttcacatg tgccgcgcac attcggtgga  720
```

```
ggtactaaac tggaaatcaa a                                          741

SEQ ID NO: 245         moltype = DNA  length = 741
FEATURE                Location/Qualifiers
misc_feature           1..741
                       note = humanized HLA-A*02 antigen binding domain
source                 1..741
                       mol_type = other DNA
                       organism = synthetic construct
SEQUENCE: 245
cagctgcagc tgcaggagtc tgggcccggg ctggtgaagc cttcggaaac gctgagcctc  60
acctgcacgg tttctggata caccttcacc agctatcata tccagtggat ccgacagccc  120
cctggaaaag ggcttgagtg gatcggatgg atctaccctg gcgatggttc aacacagtac  180
aatgagaagt tcaagggcag agccacgatt agcgtggaca catccaagaa ccaattctcc  240
ctgaacctgg acagcgtgag tgctgcggac acggccattt attactgtgc gagagaggga  300
acttactacg ctatggacta ctggggcaaa gggagcacgg tcaccgtgtc ctcaggcgga  360
ggtggaagcg gagggggagg atctggcggc ggaggaagcg gaggcgacat ccagatgacc  420
cagagcccaa gctccctgag tgcgtccgtg ggcgaccgcg tgaccatcac ttgcagatcc  480
tctcagtcca tcgtgcactc caacggcaac acgtacctcg agtggtacca gcagaagccc  540
gggaaggccc cgaaactgct catctacaag gtgagcaacc ggttctccgg cgtccccagc  600
cgcttctcag ggtccggctc ggggacggat ttcaccttca cgattagcag cttgcagccc  660
gaagacatcg ccacgtacta ctgctttcag ggaagtcacg tgccgcgtac cttcgggccg  720
ggcacgaaag tggatattaa g                                          741

SEQ ID NO: 246         moltype = DNA  length = 741
FEATURE                Location/Qualifiers
misc_feature           1..741
                       note = humanized HLA-A*02 antigen binding domain
source                 1..741
                       mol_type = other DNA
                       organism = synthetic construct
SEQUENCE: 246
gaggtgcagc tggtgcagtc tggggccgag ctgaagaagc ctgggtcctc ggtgaaggtg  60
tcctgcaagg cttctggata caccttcacc agctatcata tccagtgggt aaaacaggcc  120
cctggacaag ggcttgagtg gatcggatgg atctaccctg gcgatggttc aacacagtac  180
aatgagaagt tcaagggcaa agccacgctt accgtggaca aatccacgaa cacagcctac  240
atggagctga gcagcctgag atctgaggac acggccgtat attactgtgc gagagaggga  300
acttactacg ctatggacta ctggggccaa gggaccctgg tcaccgtgtc ctcaggcgga  360
ggtggaagcg gagggggagg atctggcggc ggaggaagcg gaggcgacat ccagatgacc  420
cagagcccat ccaccctgag tgcgtccgtg ggcgaccgcg tgaccatcac ttgcagatcc  480
tctcagtcca tcgtgcactc caacggcaac acgtacctcg agtggtacca gcagaagccc  540
gggaaggccc cgaaactgct catctacaag gtgagcaacc ggttctccgg cgtccccagc  600
cgcttctcag ggtccggctc ggggacggat ttcaccctca cgattagcag cttgcagccc  660
gatgacttcg ccacgtacta ctgctttcag ggaagtcacg tgccgcgtac cttcgggcag  720
ggcacgaaag tggaagttaa g                                          741

SEQ ID NO: 247         moltype = DNA  length = 741
FEATURE                Location/Qualifiers
misc_feature           1..741
                       note = humanized HLA-A*02 antigen binding domain
source                 1..741
                       mol_type = other DNA
                       organism = synthetic construct
SEQUENCE: 247
caggtgcagc tggtgcagtc tggggccgag gtgaagaagc ctgggtcctc ggtgaaggtg  60
tcctgcaagg cttctggata caccttcacc agctatcata tccagtgggt acgacaggcc  120
cctggacaag ggcttgagtg gatgggatgg atctaccctg gcgatggttc aacacagtac  180
aatgagaagt tcaagggcag agtcacgatt accgcggaca aatccacgag cacagcctac  240
atggagctga gcagcctgag atctgaggac acggccgtat attactgtgc gagagaggga  300
acttactacg ctatggacta ctggggccaa gggaccacgg tcaccgtgtc ctcaggcgga  360
ggtggaagcg gagggggagg atctggcggc ggaggaagcg gaggcgagat cgtcctgacc  420
cagagcccag ggaccctgag tttgtccccg ggcgagcgcg cgaccctcag ttgcagatcc  480
tctcagtcca tcgtgcactc caacggcaac acgtacctcg agtggtacca gcagaagccc  540
gggcaggccc cgcgactgct catctacaag gtgagcaacc ggttctccgg catccccgac  600
cgcttctcag ggtccggctc ggggacggat ttcaccctca cgattagccg cttggagccc  660
gaagacttcg ccgtgtacta ctgctttcag ggaagtcacg tgccgcgtac cttcgggggg  720
ggcacgaaag tggaaattaa g                                          741

SEQ ID NO: 248         moltype = DNA  length = 741
FEATURE                Location/Qualifiers
misc_feature           1..741
                       note = humanized HLA-A*02 antigen binding domain
source                 1..741
                       mol_type = other DNA
                       organism = synthetic construct
SEQUENCE: 248
caggtgaccc tgaagcagtc tggggccgag gtgaagaagc ctgggtcctc ggtgaaggtg  60
tcctgcacgg cttctggata caccttcacc agctatcatg tcagctgggt acgacaggcc  120
cctggacaag ggcttgagtg gttgggaagg atctaccctg gcgatggttc aacacagtac  180
```

```
aatgagaagt tcaagggcaa agtcacgatt accgcggaca aatccatgga cacatccttc  240
atggagctga ccagcctgac atctgaggac acggccgtat attactgtgc gagagaggga  300
acttactacg ctatggacct ctggggccaa gggaccctgg tcaccgtgtc ctcaggcgga  360
ggtggaagcg gagggggagg atctggcggc ggaggaagcg gaggcgagat cgtcctgacc  420
cagagcccag ggaccctgag tttgtccccg ggcgagcgcg cgaccctcag ttgcagatcc  480
tctcagtcca tcgtgcactc caacggcaac acgtacctcg cgtggtacca gcagaagccc  540
gggcaggccc cgcgactgct catctccaag gtgagcaacc ggttctccgg cgtccccgac  600
cgcttctcag ggtccggctc ggggacggat ttcaccctca cgattagccg cttggagccc  660
gaagacttcg ccgtgtacta ctgccaacag ggaagtcacg tgccgcgtac cttcgggggg  720
ggcacgaaag tggaaattaa g                                            741
```

```
SEQ ID NO: 249         moltype = DNA  length = 741
FEATURE                Location/Qualifiers
misc_feature           1..741
                       note = humanized HLA-A*02 antigen binding domain
source                 1..741
                       mol_type = other DNA
                       organism = synthetic construct
SEQUENCE: 249
caggtgcagc tggtgcagtc tggggccgag gtgaagaagc ctggggcctc ggtgaaggtg  60
tcctgcaagg cttctggata caccttcacc agctatcata tgcactgggt acgacaggcc  120
cctggacaaa ggcttgagtg gatgggatgg atctaccctg gcgatggttc aacacagtac  180
aatgagaagt tcaagggcaa agtcacgatt acccgggaca catccgcgag cacagcctac  240
atggagctga gcagcctgag atctgaggac acggccgtat attactgtgc gagagaggga  300
acttactacg ctatggacta ctggggccaa gggaccctgg tcaccgtgtc ctcaggcgga  360
ggtggaagcg gagggggagg atctggcggc ggaggaagcg gaggcgacat cgtcatgacc  420
cagaccccac tgtccctgcc tgtgaccccg ggcgagcccg cgagcatcag ttgcagatcc  480
tctcagtcca tcgtgcactc caacggcaac acgtacctcg actggtacct gcagaagccc  540
gggcagtccc cgcaactgct catctacaag gtgagcaacc ggttctccgg cgtccccgac  600
cgcttctcag ggtccggctc ggggacggat ttcaccctca agattagccg cgtggaggcc  660
gaagacgtcg gcgtgtacta ctgcatgcag ggaagtcacg tgccgcgtac cttcgggggg  720
ggcacgaaag tggaaattaa g                                            741
```

```
SEQ ID NO: 250         moltype = AA  length = 244
FEATURE                Location/Qualifiers
REGION                 1..244
                       note = HLA-B*07 antigen binding domain 1.10_scFv
source                 1..244
                       mol_type = protein
                       organism = synthetic construct
SEQUENCE: 250
QVQLQESGPG LVKPSQTLSL TCTVSGYSIT SGYSWHWIRQ PPGKGLEWIG YIHFSGSTHY  60
HPSLKSRVTI SVDTSKNQFS LKLSSVTAAD TAVYYCARGG VVSHYAMDCW GQGTTVTVSS  120
GGGGSGGGGS GGGGSGGDIQ MTQSPSSLSA SVGDRVTITC RASENIYSNL AWYQQKPGKA  180
PKLLIYAATY LPDGVPSRFS GSGSGTDFTL TISSLQPEDF ATYYCQHFWV TPYTFGGGTK  240
VEIK                                                               244
```

```
SEQ ID NO: 251         moltype = AA  length = 244
FEATURE                Location/Qualifiers
REGION                 1..244
                       note = HLA-B*07 antigen binding domain 1.9_scFv
source                 1..244
                       mol_type = protein
                       organism = synthetic construct
SEQUENCE: 251
EVQLVESGGG LVKPGGSLRL SCAASGYSIT SGYSWHWVRQ APGKGLEWVS YIHFSGSTHY  60
HPSLKSRFTI SRDNAKNSLY LQMNSLRAED TAVYYCARGG VVSHYAMDCW GQGTTVTVSS  120
GGGGSGGGGS GGGGSGGDIQ MTQSPSSVSA SVGDRVTITC RASENIYSNL AWYQQKPGKA  180
PKLLIYAATY LPDGVPSRFS GSGSGTDFTL TISSLQPEDF ATYYCQHFWV TPYTFGGGTK  240
VEIK                                                               244
```

```
SEQ ID NO: 252         moltype = AA  length = 244
FEATURE                Location/Qualifiers
REGION                 1..244
                       note = HLA-B*07 antigen binding domain 1.8_scFv
source                 1..244
                       mol_type = protein
                       organism = synthetic construct
SEQUENCE: 252
EVQLVESGGG LVKPGGSLRL SCAASGYSIT SGYSWHWVRQ APGKGLEWVG YIHFSGSTHY  60
HPSLKSRFTI SRDDSKNTLY LQMNSLKTED TAVYYCARGG VVSHYAMDCW GQGTTVTVSS  120
GGGGSGGGGS GGGGSGGEIV LTQSPATLSL SPGERATLSC RASENIYSNL AWYQQKPGQA  180
PRLLIYAATY LPDGIPARFS GSGSGTDFTL TISSLEPEDF AVYYCQHFWV TPYTFGGGTK  240
VEIK                                                               244
```

```
SEQ ID NO: 253         moltype = AA  length = 244
FEATURE                Location/Qualifiers
REGION                 1..244
                       note = HLA-B*07 antigen binding domain 1.7_scFv
```

```
source                  1..244
                        mol_type = protein
                        organism = synthetic construct
SEQUENCE: 253
QVQLQQSGPG LVKPSQTLSL TCAISGYSIT SGYSWHWIRQ SPSRGLEWLG YIHFSGSTHY  60
HPSLKSRITI NPDTSKNQFS LQLNSVTPED TAVYYCARGG VVSHYAMDCW GQGTTVTVSS  120
GGGGSGGGGS GGGGSGGEIV LTQSPATLSL SPGERATLSC RASENIYSNL AWYQQKPGQA  180
PRLLIYAATY LPDGIPARFS GSGSGTDFTL TISRLEPEDF AVYYCQHFWV TPYTFGGGTK  240
VEIK                                                               244

SEQ ID NO: 254          moltype = AA  length = 244
FEATURE                 Location/Qualifiers
REGION                  1..244
                        note = HLA-B*07 antigen binding domain 1.6_scFv
source                  1..244
                        mol_type = protein
                        organism = synthetic construct
SEQUENCE: 254
EVQLVESGGG LVKPGGSLRL SCAASGYSIT SGYSWHWVRQ APGKGLEWVG YIHFSGSTHY  60
HPSLKSRFTI SRDDSKNTLY LQMNSLKTED TAVYYCARGG VVSHYAMDCW GQGTTVTVSS  120
GGGGSGGGGS GGGGSGGDIQ MTQSPSSVSA SVGDRVTITC RASENIYSNL AWYQQKPGKA  180
PKLLIYAATY LPDGVPSRFS GSGSGTDFTL TISSLQPEDF ATYYCQHFWV TPYTFGGGTK  240
VEIK                                                               244

SEQ ID NO: 255          moltype = AA  length = 244
FEATURE                 Location/Qualifiers
REGION                  1..244
                        note = HLA-B*07 antigen binding domain 1.5_scFv
source                  1..244
                        mol_type = protein
                        organism = synthetic construct
SEQUENCE: 255
EVQLVESGGG LVQPGGSLRL SCAASGYSIT SGYSWHWVRQ APGKGLEWVS YIHFSGSTHY  60
HPSLKSRFTI SRDNSKNTLY LQMNSLRAED TAVYYCARGG VVSHYAMDCW GQGTTVTVSS  120
GGGGSGGGGS GGGGSGGDIQ MTQSPSSLSA SVGDRVTITC RASENIYSNL AWYQQKPGKA  180
PKLLIYAATY LPDGVPSRFS GSGSGTDFTL TISSLQPEDF ATYYCQHFWV TPYTFGGGTK  240
VEIK                                                               244

SEQ ID NO: 256          moltype = AA  length = 244
FEATURE                 Location/Qualifiers
REGION                  1..244
                        note = HLA-B*07 antigen binding domain 1.4_scFv
source                  1..244
                        mol_type = protein
                        organism = synthetic construct
SEQUENCE: 256
EVQLVESGGG LVKPGGSLRL SCAASGYSIT SGYSWHWVRQ APGKGLEWVG YIHFSGSTHY  60
HPSLKSRFTI SRDDSKNTLY LQMNSLKTED TAVYYCARGG VVSHYAMDCW GQGTTVTVSS  120
GGGGSGGGGS GGGGSGGDIQ MTQSPSSLSA SVGDRVTITC RASENIYSNL AWYQQKPGKA  180
PKLLIYAATY LPDGVPSRFS GSGSGTDFTL TISSLQPEDF ATYYCQHFWV TPYTFGGGTK  240
VEIK                                                               244

SEQ ID NO: 257          moltype = AA  length = 244
FEATURE                 Location/Qualifiers
REGION                  1..244
                        note = HLA-B*07 antigen binding domain 1.3_scFv
source                  1..244
                        mol_type = protein
                        organism = synthetic construct
SEQUENCE: 257
QVQLQQWGAG LLKPSETLSL TCAVYGYSIT SGYSWHWIRQ PPGKGLEWIG YIHFSGSTHY  60
HPSLKSRVTI SVDTSKNQFS LKLSSVTAAD TAVYYCARGG VVSHYAMDCW GQGTTVTVSS  120
GGGGSGGGGS GGGGSGGDIQ MTQSPSSLSA SVGDRVTITC RASENIYSNL AWYQQKPGKA  180
PKLLIYAATY LPDGVPSRFS GSGSGTDFTL TISSLQPEDF ATYYCQHFWV TPYTFGGGTK  240
VEIK                                                               244

SEQ ID NO: 258          moltype = AA  length = 244
FEATURE                 Location/Qualifiers
REGION                  1..244
                        note = HLA-B*07 antigen binding domain 1.2_scFv
source                  1..244
                        mol_type = protein
                        organism = synthetic construct
SEQUENCE: 258
QVQLQESGPG LVKPSQTLSL TCTVSGYSIT SGYSWHWIRQ HPGKGLEWIG YIHFSGSTHY  60
HPSLKSRVTI SVDTSKNQFS LKLSSVTAAD TAVYYCARGG VVSHYAMDCW GQGTTVTVSS  120
GGGGSGGGGS GGGGSGGDIQ MTQSPSSLSA SVGDRVTITC RASENIYSNL AWYQQKPGKA  180
PKLLIYAATY LPDGVPSRFS GSGSGTDFTL TISSLQPEDF ATYYCQHFWV TPYTFGGGTK  240
VEIK                                                               244
```

```
SEQ ID NO: 259          moltype = AA  length = 244
FEATURE                 Location/Qualifiers
REGION                  1..244
                        note = HLA-B*07 antigen binding domain 1.1_scFv
source                  1..244
                        mol_type = protein
                        organism = synthetic construct
SEQUENCE: 259
QVQLQQSGPG LVKPSQTLSL TCAISGYSIT SGYSWHWIRQ SPSRGLEWLG YIHFSGSTHY  60
HPSLKSRITI NPDTSKNQFS LQLNSVTPED TAVYYCARGG VVSHYAMDCW GQGTTVTVSS  120
GGGGSGGGGS GGGGSGGDIQ MTQSPSSLSA SVGDRVTITC RASENIYSNL AWYQQKPGKA  180
PKLLIYAATY LPDGVPSRFS GSGSGTDFTL TISSLQPEDF ATYYCQHFWV TPYTFGGGTK  240
VEIK                                                               244

SEQ ID NO: 260          moltype = AA  length = 243
FEATURE                 Location/Qualifiers
REGION                  1..243
                        note = HLA-A*11 antigen binding domain
source                  1..243
                        mol_type = protein
                        organism = synthetic construct
SEQUENCE: 260
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARH YYYYSMDVWG KGTTVTVSSG  120
GGGSGGGGSG GGGSGGDIQM TQSPSSLSAS VGDRVTITCR ASQSISSYLN WYQQKPGKAP  180
KLLIYAASSL QSGVPSRFSG SGSGTDFTLT ISSLQPEDFA TYYCQQSYST PLTFGGGTKV  240
EIK                                                                243

SEQ ID NO: 261          moltype = DNA  length = 729
FEATURE                 Location/Qualifiers
misc_feature            1..729
                        note = HLA-A*11 antigen binding domain
source                  1..729
                        mol_type = other DNA
                        organism = synthetic construct
SEQUENCE: 261
caggtgcagc tgcaggaaag cggccctggc ctggtgaaac ccagccagac cctgagcctg  60
acctgcacag tgtccggcgg ctcgatcagc agcggcggct actactggtc ctggatcaga  120
cagccccctg gcaagggcct ggaatggatc ggctacatct actacagcgg cagcacctac  180
tacaacccca gcctgaagtc cagagtgacc atcagcgtgg acaccagcaa gaaccagttc  240
agcctgaagc tgagcagcgt gacagccgcc gacaccgctg tgtattactg tgcgagacac  300
tactactact actccatgga cgtctggggc aaagggacca cggtcaccgt gtcctcaggc  360
ggaggtggaa gcggaggggg aggatctggc ggcggaggaa gcggaggcga catccagatg  420
acccagtctc catcctccct gtctgcatct gtaggagaca gagtcaccat cacttgccgg  480
gcaagtcaga gcattagcag ctatttaaat tggtatcagc agaaaccagg gaaagcccct  540
aagctcctga tctatgctgc atccagtttg caaagtgggg tcccatcaag gttcagtggc  600
agtggatctg ggacagattt cactctcacc atcagcagtc tgcaacctga agattttgca  660
acttactact gtcaacagag ttacagtacc cctctcactt tcggcggcgg aacaaaggtg  720
gagatcaag                                                          729

SEQ ID NO: 262          moltype = AA  length = 244
FEATURE                 Location/Qualifiers
REGION                  1..244
                        note = HLA-A*11 antigen binding domain
source                  1..244
                        mol_type = protein
                        organism = synthetic construct
SEQUENCE: 262
QITLKESGPT LVKPTQTLTL TCTFSGFSLS TSGVGVGWIR QPPGKALEWL ALIYWNDDKR  60
YSPSLKSRLT ITKDTSKNQV VLTMTNMDPV DTATYYCAHR HMRLSCFDYW GQGTLVTVSS  120
GGGGSGGGGS GGGGSGGDIQ MTQSPSSLSA SVGDRVTITC RASQSISSYL NWYQQKPGKA  180
PKLLIYAASS LQSGVPSRFS GSGSGTDFTL TISSLQPEDF ATYYCQQSYS TPLTFGGGTK  240
VEIK                                                               244

SEQ ID NO: 263          moltype = DNA  length = 732
FEATURE                 Location/Qualifiers
misc_feature            1..732
                        note = HLA-A*11 antigen binding domain
source                  1..732
                        mol_type = other DNA
                        organism = synthetic construct
SEQUENCE: 263
cagatcaccc tgaaagagtc cggccccacc ctggtgaaac ccacccagac cctgaccctg  60
acatgcacct tcagcggctt cagcctgagc acctctggcg tgggcgtggg ctggatcaga  120
cagcctcccg gcaaggccct ggaatggctg gccctgatct actggaacga cgacaagcgg  180
tacagcccca gcctgaagtc ccggctgacc atcaccaagg acacctcgaa gaaccaggtg  240
gtgctgacca tgacaaacat ggaccccgtg gacaccgcca catattactg tgcacacaga  300
cacatgcgtt taagctgttt tgactactgg ggccagggaa ccctggtcac cgtgtcctca  360
```

```
ggcggaggtg gaagcggagg gggaggatct ggcggcggag gaagcggagg cgacatccag  420
atgacccagt ctccatcctc cctgtctgca tctgtaggag acagagtcac catcacttgc  480
cgggcaagtc agagcattag cagctattta aattggtatc agcagaaacc agggaaagcc  540
cctaagctcc tgatctatgc tgcatccagt ttgcaaagtg gggtcccatc aaggttcagt  600
ggcagtggat ctgggacaga tttcactctc accatcagca gtctgcaacc tgaagatttt  660
gcaacttact actgtcaaca gagttacagt acccctctca ctttcggcgg cggaacaaag  720
gtggagatca ag                                                       732

SEQ ID NO: 264         moltype = AA  length = 245
FEATURE                Location/Qualifiers
REGION                 1..245
                       note = HLA-A*11 antigen binding domain
source                 1..245
                       mol_type = protein
                       organism = synthetic construct
SEQUENCE: 264
QVQLVQSGAE VKKPGASVKV SCKASGYTFT SYAMHWVRQA PGQRLEWMGW INAGNGNTKY  60
SQKFQGRVTI TRDTSASTAY MELSSLRSED TAVYYCAREG NGANPDAFDI WGQGTMVTVS  120
SGGGGSGGGG SGGGGSGGDI QMTQSPSSLS ASVGDRVTIT CRASQSISSY LNWYQQKPGK  180
APKLLIYAAS SLQSGVPSRF SGSGSGTDFT LTISSLQPED FATYYCQQSY STPLTFGGGT  240
KVEIK                                                               245

SEQ ID NO: 265         moltype = DNA  length = 735
FEATURE                Location/Qualifiers
misc_feature           1..735
                       note = HLA-A*11 antigen binding domain
source                 1..735
                       mol_type = other DNA
                       organism = synthetic construct
SEQUENCE: 265
caggtgcagc tggtgcagtc tggcgccgaa gtgaagaaac ctggcgcctc cgtgaaggtg  60
tcctgcaagg ccagcggcta caccttcacc agctacgcca tgcactgggt tcgacaggcc  120
cctggccaga gactggaatg gatgggctgg atcaacgccg gcaacggcaa caccaagtac  180
agccagaaat tccagggcag agtgaccatc acccgggaca ccagcgccag caccgcctac  240
atggaactga gcagcctgcg gagcgaggac accgctgtgt attactgtgc gagagaagga  300
aatggtgcca accctgatgc ttttgatatc tggggccaag ggacaatggt caccgtgtcc  360
tcaggcggag gtggaagcgg agggggagga tctggcggcg gaggaagcgg aggcgacatc  420
cagatgaccc agtctccatc ctccctgtct gcatctgtag gagacagagt caccatcact  480
tgccgggcaa gtcagagcat tagcagctat ttaaattggt atcagcagaa accagggaaa  540
gcccctaagc tcctgatcta tgctgcatcc agtttgcaaa gtggggtccc atcaaggttc  600
agtggcagtg gatctgggac agatttcact ctcaccatca gcagtctgca acctgaagat  660
tttgcaactt actactgtca acagagttac agtacccctc tcactttcgg cggcggaaca  720
aaggtggaga tcaag                                                    735

SEQ ID NO: 266         moltype = AA  length = 243
FEATURE                Location/Qualifiers
REGION                 1..243
                       note = HLA-A*11 antigen binding domain
source                 1..243
                       mol_type = protein
                       organism = synthetic construct
SEQUENCE: 266
EVQLVESGGG LVQPGGSLRL SCAASGFTFS SYDMHWVRQA TGKGLEWVSA IGTAGDTYYP  60
GSVKGRFTIS RENAKNSLYL QMNSLRAGDT AVYYCARDLP GSYWYFDLWG RGTLVTVSSG  120
GGGSGGGGSG GGGSGGDIQM TQSPSSLSAS VGDRVTITCR ASQSISSYLN WYQQKPGKAP  180
KLLIYAASSL QSGVPSRFSG SGSGTDFTLT ISSLQPEDFA TYYCQQSYST PLTFGGGTKV  240
EIK                                                                 243

SEQ ID NO: 267         moltype = DNA  length = 729
FEATURE                Location/Qualifiers
misc_feature           1..729
                       note = HLA-A*11 antigen binding domain
source                 1..729
                       mol_type = other DNA
                       organism = synthetic construct
SEQUENCE: 267
gaagtgcagc tggtggaaag cggcggaggc ctggtgcagc ctggcggcag cctgagactg  60
tcttgcgccg ccagcggctt caccttcagc agctacgaca tgcactgggt ccgccaggcc  120
accggcaagg gactggaatg ggtgtccgcc atcggcacag ccggcgacac ttactacccc  180
ggcagcgtga agggccggtt caccatcagc agagagaacg ccaagaacag cctgtacctg  240
cagatgaaca gccttcgagc cggcgatacc gccgtgtatt actgtgcaag agatctccct  300
ggtagctact ggtacttcga tctctggggc cgtggcaccc tggtcactgt gtcctcaggc  360
ggaggtggaa gcggaggggg aggatctggc ggcggaggaa gcggaggcga catccagatg  420
acccagtctc catcctccct gtctgcatct gtaggagaca gagtcaccat cacttgccgg  480
gcaagtcaga gcattagcag ctatttaaat tggtatcagc agaaaccagg gaaagcccct  540
aagctcctga tctatgctgc atccagtttg caaagtgggg tcccatcaag gttcagtggc  600
agtggatctg ggacagattt cactctcacc atcagcagtc tgcaacctga agattttgca  660
acttactact gtcaacagag ttacagtacc cctctcactt tcggcggcgg aacaaaggtg  720
gagatcaag                                                           729
```

```
SEQ ID NO: 268          moltype = AA  length = 243
FEATURE                 Location/Qualifiers
REGION                  1..243
                        note = HLA-A*11 antigen binding domain
source                  1..243
                        mol_type = protein
                        organism = synthetic construct
SEQUENCE: 268
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARH YYYYYLDVWG KGTTVTVSSG  120
GGGSGGGGSG GGGSGGDIQM TQSPSSLSAS VGDRVTITCR ASQSISSYLN WYQQKPGKAP  180
KLLIYAASSL QSGVPSRFSG SGSGTDFTLT ISSLQPEDFA TYYCQQSYST PLTFGGGTKV  240
EIK                                                                243

SEQ ID NO: 269          moltype = DNA  length = 729
FEATURE                 Location/Qualifiers
misc_feature            1..729
                        note = HLA-A*11 antigen binding domain
source                  1..729
                        mol_type = other DNA
                        organism = synthetic construct
SEQUENCE: 269
caggtgcagc tgcaggaaag cggccctggc ctggtgaaac ccagccagac cctgagcctg  60
acctgcacag tgtccggcgg ctcgatcagc agcggcggct actactggtc ctggatcaga  120
cagccccctg gcaagggcct ggaatggatc ggctacatct actacagcgg cagcacctac  180
tacaacccca gcctgaagtc cagagtgacc atcagcgtgg acaccagcaa gaaccagttc  240
agcctgaagc tgagcagcgt gacagccgcc gacaccgctg tgtattactg tgcgagacac  300
tactactact actacctgga cgtctggggc aaagggacca cggtcaccgt gtcctcaggc  360
ggaggtggaa gcggaggggg aggatctggc ggcggaggaa gcggaggcga catccagatg  420
acccagtctc catcctccct gtctgcatct gtaggagaca gagtcaccat cacttgccgg  480
gcaagtcaga gcattagcag ctatttaaat tggtatcagc agaaaccagg gaaagcccct  540
aagctcctga tctatgctgc atccagtttg caaagtgggg tcccatcaag gttcagtggc  600
agtggatctg ggacagattt cactctcacc atcagcagtc tgcaacctga agattttgca  660
acttactact gtcaacagag ttacagtacc cctctcactt tcggcggcgg aacaaaggtg  720
gagatcaag                                                          729

SEQ ID NO: 270          moltype = AA  length = 243
FEATURE                 Location/Qualifiers
REGION                  1..243
                        note = HLA-A*11 antigen binding domain
source                  1..243
                        mol_type = protein
                        organism = synthetic construct
SEQUENCE: 270
EVQLVESGGG LVQPGGSLRL SCAASGFTFS SYWMHWVRQA PGKGLVWVSR INSDGSSTSY  60
ADSVKGRFTI SRDNAKNTLY LQMNSLRAED TAVYYCCLGV LLYNWFDPWG QGTLVTVSSG  120
GGGSGGGGSG GGGSGGDIQM TQSPSSLSAS VGDRVTITCR ASQSISSYLN WYQQKPGKAP  180
KLLIYAASSL QSGVPSRFSG SGSGTDFTLT ISSLQPEDFA TYYCQQSYST PLTFGGGTKV  240
EIK                                                                243

SEQ ID NO: 271          moltype = DNA  length = 729
FEATURE                 Location/Qualifiers
misc_feature            1..729
                        note = HLA-A*11 antigen binding domain
source                  1..729
                        mol_type = other DNA
                        organism = synthetic construct
SEQUENCE: 271
gaagtgcagc tggtggaaag cggcggaggc ctggtgcagc ctggcggcag cctgagactg  60
tcttgcgccg ccagcggctt caccttcagc agctactgga tgcactgggt ccgccaggcc  120
cctggcaagg gactggtctg ggtgtctcga atcaacagcg acggcagcag caccagctac  180
gccgacagcg tgaagggccg gttcaccatc agccgggaca acgccaagaa caccctgtac  240
ctgcagatga acagcctgcg ggccgaggac accgccgtgt attactgttg tttgggtgtt  300
ttattataca actggttcga cccctggggc cagggaaccc tggtcaccgt gtcctcaggc  360
ggaggtggaa gcggaggggg aggatctggc ggcggaggaa gcggaggcga catccagatg  420
acccagtctc catcctccct gtctgcatct gtaggagaca gagtcaccat cacttgccgg  480
gcaagtcaga gcattagcag ctatttaaat tggtatcagc agaaaccagg gaaagcccct  540
aagctcctga tctatgctgc atccagtttg caaagtgggg tcccatcaag gttcagtggc  600
agtggatctg ggacagattt cactctcacc atcagcagtc tgcaacctga agattttgca  660
acttactact gtcaacagag ttacagtacc cctctcactt tcggcggcgg aacaaaggtg  720
gagatcaag                                                          729

SEQ ID NO: 272          moltype = AA  length = 242
FEATURE                 Location/Qualifiers
REGION                  1..242
                        note = HLA-A*11 antigen binding domain
source                  1..242
                        mol_type = protein
```

```
                      organism = synthetic construct
SEQUENCE: 272
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARH YYYYMDVWGK GTTVTVSSGG  120
GGSGGGGSGG GGSGGDIQMT QSPSSLSASV GDRVTITCRA SQSISSYLNW YQQKPGKAPK  180
LLIYAASSLQ SGVPSRFSGS GSGTDFTLTI SSLQPEDFAT YYCQQSYSTP LTFGGGTKVE  240
IK                                                                242

SEQ ID NO: 273        moltype = DNA  length = 726
FEATURE               Location/Qualifiers
misc_feature          1..726
                      note = HLA-A*11 antigen binding domain
source                1..726
                      mol_type = other DNA
                      organism = synthetic construct
SEQUENCE: 273
caggtgcagc tgcaggaaag cggccctggc ctggtgaaac ccagccagac cctgagcctg  60
acctgcacag tgtccggcgg ctcgatcagc agcggcggct actactggtc ctggatcaga  120
cagcccccctg gcaagggcct ggaatggatc ggctacatct actacagcgg cagcacctac  180
tacaacccca gcctgaagtc cagagtgacc atcagcgtgg acaccagcaa gaaccagttc  240
agcctgaagc tgagcagcgt gacagccgcc gacaccgctg tgtattactg tgcgagacac  300
tactactact acatggacgt ctggggcaaa gggaccacgg tcaccgtgtc ctcaggcgga  360
ggtggaagcg gagggggagg atctggcggc ggaggaagcg gaggcgacat ccagatgacc  420
cagtctccat cctccctgtc tgcatctgta ggagacagag tcaccatcac ttgccgggca  480
agtcagagca ttagcagcta tttaaattgg tatcagcaga aaccagggaa agcccctaag  540
ctcctgatct atgctgcatc cagtttgcaa agtggggtcc catcaaggtt cagtggcagt  600
ggatctggga cagatttcac tctcaccatc agcagtctgc aacctgaaga ttttgcaact  660
tactactgtc aacagagtta cagtacccct ctcactttcg gcggcggaac aaaggtggag  720
atcaag                                                            726

SEQ ID NO: 274        moltype = AA  length = 243
FEATURE               Location/Qualifiers
REGION                1..243
                      note = HLA-A*11 antigen binding domain
source                1..243
                      mol_type = protein
                      organism = synthetic construct
SEQUENCE: 274
QITLKESGPT LVKPTQTLTL TCTFSGFSLS TSGVGVGWIR QPPGKALEWL ALIYWNDDKR  60
YSPSLKSRLT ITKDTSKNQV VLTMTNMDPV DTATYYCAHK TTSFYFDYWG QGTLVTVSSG  120
GGGSGGGGSG GGGSGGDIQM TQSPSSLSAS VGDRVTITCR ASQSISSYLN WYQQKPGKAP  180
KLLIYAASSL QSGVPSRFSG SGSGTDFTLT ISSLQPEDFA TYYCQQSYST PLTFGGGTKV  240
EIK                                                               243

SEQ ID NO: 275        moltype = DNA  length = 729
FEATURE               Location/Qualifiers
misc_feature          1..729
                      note = HLA-A*11 antigen binding domain
source                1..729
                      mol_type = other DNA
                      organism = synthetic construct
SEQUENCE: 275
cagatcaccc tgaaagagtc cggccccacc ctggtgaaac ccacccagac cctgaccctg  60
acatgcacct tcagcggctt cagcctgagc acctctggcg tgggcgtggg ctggatcaga  120
cagcctcccg gcaaggccct ggaatggctg gccctgatct actggaacga cgacaagcgg  180
tacagcccca gcctgaagtc ccggctgacc atcaccaagg acacctcgaa gaaccaggtg  240
gtgctgacca tgacaaacat ggaccccgtg gacaccgcca catattactg tgcacacaaa  300
acgacgtcgt tttactttga ctactggggc cagggaaccc tggtcaccgt gtcctcaggc  360
ggaggtggaa gcggaggggg aggatctggc ggcggaggaa gcggaggcga catccagatg  420
acccagtctc catcctccct gtctgcatct gtaggagaca gagtcaccat cacttgccgg  480
gcaagtcaga gcattagcag ctatttaaat tggtatcagc agaaaccagg gaaagcccct  540
aagctcctga tctatgctgc atccagtttg caaagtgggg tcccatcaag gttcagtggc  600
agtggatctg ggacagattt cactctcacc atcagcagtc tgcaacctga agattttgca  660
acttactact gtcaacagag ttacagtacc cctctcactt tcggcggcgg aacaaaggtg  720
gagatcaag                                                         729

SEQ ID NO: 276        moltype = AA  length = 243
FEATURE               Location/Qualifiers
REGION                1..243
                      note = HLA-A*11 antigen binding domain
source                1..243
                      mol_type = protein
                      organism = synthetic construct
SEQUENCE: 276
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARH YYYYYMDVWG KGTTVTVSSG  120
GGGSGGGGSG GGGSGGDIQM TQSPSSLSAS VGDRVTITCR ASQSISSYLN WYQQKPGKAP  180
KLLIYAASSL QSGVPSRFSG SGSGTDFTLT ISSLQPEDFA TYYCQQSYST PLTFGGGTKV  240
EIK                                                               243
```

```
SEQ ID NO: 277          moltype = DNA  length = 729
FEATURE                 Location/Qualifiers
misc_feature            1..729
                        note = HLA-A*11 antigen binding domain
source                  1..729
                        mol_type = other DNA
                        organism = synthetic construct
SEQUENCE: 277
caggtgcagc tgcaggaaag cggccctggc ctggtgaaac ccagccagac cctgagcctg  60
acctgcacag tgtccggcgg ctcgatcagc agcggcggct actactggtc ctggatcaga  120
cagcccccctg gcaagggcct ggaatggatc ggctacatct actacagcgg cagcacctac  180
tacaacccca gcctgaagtc cagagtgacc atcagcgtgg acaccagcaa gaaccagttc  240
agcctgaagc tgagcagcgt gacagccgcc gacaccgctg tgtattactg tgcgagacac  300
tactactact actacatgga cgtctggggc aaagggacca cggtcaccgt gtcctcaggc  360
ggaggtggaa gcggaggggg aggatctggc ggcggaggaa gcggaggcga catccagatg  420
acccagtctc catcctccct gtctgcatct gtaggagaca gagtcaccat cacttgccgg  480
gcaagtcaga gcattagcag ctatttaaat tggtatcagc agaaaccagg gaaagcccct  540
aagctcctga tctatgctgc atccagtttg caaagtgggg tcccatcaag gttcagtggc  600
agtggatctg ggacagattt cactctcacc atcagcagtc tgcaacctga agattttgca  660
acttactact gtcaacagag ttacagtacc cctctcactt tcggcggcgg aacaaaggtg  720
gagatcaag                                                          729

SEQ ID NO: 278          moltype = AA  length = 240
FEATURE                 Location/Qualifiers
REGION                  1..240
                        note = HLA-C*07 antigen binding domain C7-45
source                  1..240
                        mol_type = protein
                        organism = synthetic construct
SEQUENCE: 278
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAVSF DWFDPWGQGT LVTVSSGGGG  120
SGGGGSGGGG SGGDIQMTQS PSSLSASVGD RVTITCRASQ SISSYLNWYQ QKPGKAPKLL  180
IYAASSLQSG VPSRFSGSGS GTDFTLTISS LQPEDFATYY CQQSYSTPLT FGGGTKVEIK  240

SEQ ID NO: 279          moltype = AA  length = 248
FEATURE                 Location/Qualifiers
REGION                  1..248
                        note = HLA-C*07 antigen binding domain C7-44
source                  1..248
                        mol_type = protein
                        organism = synthetic construct
SEQUENCE: 279
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARE RSISPYYYYY MDVWGKGTTV  120
TVSSGGGGSG GGGSGGGGSG GDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPLTFG  240
GGTKVEIK                                                           248

SEQ ID NO: 280          moltype = AA  length = 247
FEATURE                 Location/Qualifiers
REGION                  1..247
                        note = HLA-C*07 antigen binding domain C7-43
source                  1..247
                        mol_type = protein
                        organism = synthetic construct
SEQUENCE: 280
QLQLQESGPG LVKPSETLSL TCTVSGGSIS SSSYYWGWIR QPPGKGLEWI GSIYYSGSTY  60
YNPSLKSRVT ISVDTSKNQF SLKLSSVTAA DTAVYYCARD SVIWYWFDPW GQGTLVTVSS  120
GGGGSGGGGS GGGGSGGQSV LTQPPSASGT PGQRVTISCS GSSSNIGSNT VNWYQQLPGT  180
APKLLIYSNN QRPSGVPDRF SGSKSGTSAS LAISGLQSED EADYYCAAWD DSLNGWVFGG  240
GTKLTVL                                                            247

SEQ ID NO: 281          moltype = AA  length = 249
FEATURE                 Location/Qualifiers
REGION                  1..249
                        note = HLA-C*07 antigen binding domain C7-42
source                  1..249
                        mol_type = protein
                        organism = synthetic construct
SEQUENCE: 281
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARE EILPRLSYYY YMDVWGKGTT  120
VTVSSGGGGS GGGGSGGGGS GGDIQMTQSP SSLSASVGDR VTITCRASQS ISSYLNWYQQ  180
KPGKAPKLLI YAASSLQSGV PSRFSGSGSG TDFTLTISSL QPEDFATYYC QQSYSTPLTF  240
GGGTKVEIK                                                          249

SEQ ID NO: 282          moltype = AA  length = 245
```

```
FEATURE                Location/Qualifiers
REGION                 1..245
                       note = HLA-C*07 antigen binding domain C7-41
source                 1..245
                       mol_type = protein
                       organism = synthetic construct
SEQUENCE: 282
QVQLVQSGSE LKKPGASVKV SCKASGYTFT SYAMNWVRQA PGQGLEWMGW INTNTGNPTY  60
AQGFTGRFVF SFDTSVSTAY LQICSLKAED TAVYYCARGG RAHSSWYFDL WGRGTLVTVS  120
SGGGGSGGGG SGGGGSGGDI QMTQSPSSLS ASVGDRVTIT CRASQSISSY LNWYQQKPGK  180
APKLLIYAAS SLQSGVPSRF SGSGSGTDFT LTISSLQPED FATYYCQQSY STPLTFGGGT  240
KVEIK                                                              245

SEQ ID NO: 283         moltype = AA  length = 251
FEATURE                Location/Qualifiers
REGION                 1..251
                       note = HLA-C*07 antigen binding domain C7-40
source                 1..251
                       mol_type = protein
                       organism = synthetic construct
SEQUENCE: 283
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD RIKILPRLGY YYYMDVWGKG  120
TTVTVSSGGG GSGGGGSGGG GSGGDIQMTQ SPSSLSASVG DRVTITCRAS QSISSYLNWY  180
QQKPGKAPKL LIYAASSLQS GVPSRFSGSG SGTDFTLTIS SLQPEDFATY YCQQSYSTPL  240
TFGGGTKVEI K                                                       251

SEQ ID NO: 284         moltype = AA  length = 246
FEATURE                Location/Qualifiers
REGION                 1..246
                       note = HLA-C*07 antigen binding domain C7-39
source                 1..246
                       mol_type = protein
                       organism = synthetic construct
SEQUENCE: 284
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD TVIHYYYYMD VWGKGTTVTV  120
SSGGGGSGGG GSGGGGSGGD IQMTQSPSSL SASVGDRVTI TCRASQSISS YLNWYQQKPG  180
KAPKLLIYAA SSLQSGVPSR FSGSGSGTDF TLTISSLQPE DFATYYCQQS YSTPLTFGGG  240
TKVEIK                                                             246

SEQ ID NO: 285         moltype = AA  length = 250
FEATURE                Location/Qualifiers
REGION                 1..250
                       note = HLA-C*07 antigen binding domain C7-38
source                 1..250
                       mol_type = protein
                       organism = synthetic construct
SEQUENCE: 285
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD VIVEVFLSYY YYMDVWGKGT  120
TVTVSSGGGG SGGGGSGGGG SGGDIQMTQS PSSLSASVGD RVTITCRASQ SISSYLNWYQ  180
QKPGKAPKLL IYAASSLQSG VPSRFSGSGS GTDFTLTISS LQPEDFATYY CQQSYSTPLT  240
FGGGTKVEIK                                                         250

SEQ ID NO: 286         moltype = AA  length = 246
FEATURE                Location/Qualifiers
REGION                 1..246
                       note = HLA-C*07 antigen binding domain C7-37
source                 1..246
                       mol_type = protein
                       organism = synthetic construct
SEQUENCE: 286
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD IFIHYYYYMD VWGKGTTVTV  120
SSGGGGSGGG GSGGGGSGGD IQMTQSPSSL SASVGDRVTI TCRASQSISS YLNWYQQKPG  180
KAPKLLIYAA SSLQSGVPSR FSGSGSGTDF TLTISSLQPE DFATYYCQQS YSTPLTFGGG  240
TKVEIK                                                             246

SEQ ID NO: 287         moltype = AA  length = 247
FEATURE                Location/Qualifiers
REGION                 1..247
                       note = HLA-C*07 antigen binding domain C7-36
source                 1..247
                       mol_type = protein
                       organism = synthetic construct
SEQUENCE: 287
EVQLVESGGG LVQPGGSLRL SCAASGFTFS SYSMNWVRQA PGKGLEWVSY ISSSSSTIYY  60
ADSVKGRFTI SRDNAKNSLY LQMNSLRAED TAVYYCARDG TFYSYSPYYF DYWGQGTLVT  120
```

```
VSSGGGGSGG GGSGGGGSGG DIQMTQSPSS LSASVGDRVT ITCRASQSIS SYLNWYQQKP  180
GKAPKLLIYA ASSLQSGVPS RFSGSGSGTD FTLTISSLQP EDFATYYCQQ SYSTPLTFGG  240
GTKVEIK                                                             247

SEQ ID NO: 288         moltype = AA  length = 251
FEATURE                Location/Qualifiers
REGION                 1..251
                       note = HLA-C*07 antigen binding domain C7-35
source                 1..251
                       mol_type = protein
                       organism = synthetic construct
SEQUENCE: 288
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARE WIKILPRLGY YYYMDVWGKG  120
TTVTVSSGGG GSGGGGSGGG GSGGDIQMTQ SPSSLSASVG DRVTITCRAS QSISSYLNWY  180
QQKPGKAPKL LIYAASSLQS GVPSRFSGSG SGTDFTLTIS SLQPEDFATY YCQQSYSTPL  240
TFGGGTKVEI K                                                        251

SEQ ID NO: 289         moltype = AA  length = 246
FEATURE                Location/Qualifiers
REGION                 1..246
                       note = HLA-C*07 antigen binding domain C7-34
source                 1..246
                       mol_type = protein
                       organism = synthetic construct
SEQUENCE: 289
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD RSLYYYYYMD VWGKGTTVTV  120
SSGGGGSGGG GSGGGGSGGD IQMTQSPSSL SASVGDRVTI TCRASQSISS YLNWYQQKPG  180
KAPKLLIYAA SSLQSGVPSR FSGSGSGTDF TLTISSLQPE DFATYYCQQS YSTPLTFGGG  240
TKVEIK                                                              246

SEQ ID NO: 290         moltype = AA  length = 248
FEATURE                Location/Qualifiers
REGION                 1..248
                       note = HLA-C*07 antigen binding domain C7-33
source                 1..248
                       mol_type = protein
                       organism = synthetic construct
SEQUENCE: 290
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD KILAPNYYYY MDVWGKGTTV  120
TVSSGGGGSG GGGSGGGGSG GDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPLTFG  240
GGTKVEIK                                                            248

SEQ ID NO: 291         moltype = AA  length = 250
FEATURE                Location/Qualifiers
REGION                 1..250
                       note = HLA-C*07 antigen binding domain C7-32
source                 1..250
                       mol_type = protein
                       organism = synthetic construct
SEQUENCE: 291
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARE KSWKYFYYYY YYMDVWGKGT  120
TVTVSSGGGG SGGGGSGGGG SGGDIQMTQS PSSLSASVGD RVTITCRASQ SISSYLNWYQ  180
QKPGKAPKLL IYAASSLQSG VPSRFSGSGS GTDFTLTISS LQPEDFATYY CQQSYSTPLT  240
FGGGTKVEIK                                                          250

SEQ ID NO: 292         moltype = AA  length = 249
FEATURE                Location/Qualifiers
REGION                 1..249
                       note = HLA-C*07 antigen binding domain C7-31
source                 1..249
                       mol_type = protein
                       organism = synthetic construct
SEQUENCE: 292
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARE NTSTIPYYYY YMDVWGKGTT  120
VTVSSGGGGS GGGGSGGGGS GGDIQMTQSP SSLSASVGDR VTITCRASQS ISSYLNWYQQ  180
KPGKAPKLLI YAASSLQSGV PSRFSGSGSG TDFTLTISSL QPEDFATYYC QQSYSTPLTF  240
GGGTKVEIK                                                           249

SEQ ID NO: 293         moltype = AA  length = 253
FEATURE                Location/Qualifiers
REGION                 1..253
                       note = HLA-C*07 antigen binding domain C7-30
source                 1..253
```

```
                         mol_type = protein
                         organism = synthetic construct
SEQUENCE: 293
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARE DVDKNTSTIY YYYYYMDVWG  120
KGTTVTVSSG GGGSGGGGSG GGGSGGDIQM TQSPSSLSAS VGDRVTITCR ASQSISSYLN  180
WYQQKPGKAP KLLIYAASSL QSGVPSRFSG SGSGTDFTLT ISSLQPEDFA TYYCQQSYST  240
PLTFGGGTKV EIK                                                     253

SEQ ID NO: 294           moltype = AA  length = 250
FEATURE                  Location/Qualifiers
REGION                   1..250
                         note = HLA-C*07 antigen binding domain C7-29
source                   1..250
                         mol_type = protein
                         organism = synthetic construct
SEQUENCE: 294
QVQLVESGGG LVKPGGSLRL SCAASGFTFS DYYMSWIRQA PGKGLEWVSY ISSSGSTIYY  60
ADSVKGRFTI SRDNAKNSLY LQMNSLRAED TAVYYCARDG GDIVSSSAIY WYFDLWGRGT  120
LVTVSSGGGG SGGGGSGGGG SGGAIQLTQS PSSLSASVGD RVTITCRASQ GISSALAWYQ  180
QKPGKAPKLL IYDASSLESG VPSRFSGSGS GTDFTLTISS LQPEDFATYY CQQFNSYPLT  240
FGGGTKVEIK                                                         250

SEQ ID NO: 295           moltype = AA  length = 248
FEATURE                  Location/Qualifiers
REGION                   1..248
                         note = HLA-C*07 antigen binding domain C7-28
source                   1..248
                         mol_type = protein
                         organism = synthetic construct
SEQUENCE: 295
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD LILPPYYYYY MDVWGKGTTV  120
TVSSGGGGSG GGGSGGGGSG GDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPLTFG  240
GGTKVEIK                                                           248

SEQ ID NO: 296           moltype = AA  length = 253
FEATURE                  Location/Qualifiers
REGION                   1..253
                         note = HLA-C*07 antigen binding domain C7-27
source                   1..253
                         mol_type = protein
                         organism = synthetic construct
SEQUENCE: 296
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARE TWIKILPRYY YYYYYMDVWG  120
KGTTVTVSSG GGGSGGGGSG GGGSGGDIQM TQSPSSLSAS VGDRVTITCR ASQSISSYLN  180
WYQQKPGKAP KLLIYAASSL QSGVPSRFSG SGSGTDFTLT ISSLQPEDFA TYYCQQSYST  240
PLTFGGGTKV EIK                                                     253

SEQ ID NO: 297           moltype = AA  length = 246
FEATURE                  Location/Qualifiers
REGION                   1..246
                         note = HLA-C*07 antigen binding domain C7-26
source                   1..246
                         mol_type = protein
                         organism = synthetic construct
SEQUENCE: 297
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD LSRYYYYYMD VWGKGTTVTV  120
SSGGGGSGGG GSGGGGSGGD IQMTQSPSSL SASVGDRVTI TCRASQSISS YLNWYQQKPG  180
KAPKLLIYAA SSLQSGVPSR FSGSGSGTDF TLTISSLQPE DFATYYCQQS YSTPLTFGGG  240
TKVEIK                                                             246

SEQ ID NO: 298           moltype = AA  length = 242
FEATURE                  Location/Qualifiers
REGION                   1..242
                         note = HLA-C*07 antigen binding domain C7-25
source                   1..242
                         mol_type = protein
                         organism = synthetic construct
SEQUENCE: 298
EVQLVESGGG LVQPGGSLRL SCAASGFTFS SYSMNWVRQA PGKGLEWVSY ISSSSSTIYY  60
ADSVKGRFTI SRDNAKNSLY LQMNSLRAED TAVYYCAREH IVLCFDYWGQ GTLVTVSSGG  120
GGSGGGGSGG GGSGGDIQMT QSPSSLSASV GDRVTITCRA SQGISSWLAW YQQKPEKAPK  180
SLIYAASSLQ SGVPSRFSGS GSGTDFTLTI SSLQPEDFAT YYCQQYNSYP LTFGGGTKVE  240
IK                                                                 242
```

```
SEQ ID NO: 299         moltype = AA  length = 249
FEATURE                Location/Qualifiers
REGION                 1..249
                       note = HLA-C*07 antigen binding domain C7-24
source                 1..249
                       mol_type = protein
                       organism = synthetic construct
SEQUENCE: 299
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD KILPRPYYYY YMDVWGKGTT  120
VTVSSGGGGS GGGGSGGGGS GGDIQMTQSP SSLSASVGDR VTITCRASQS ISSYLNWYQQ  180
KPGKAPKLLI YAASSLQSGV PSRFSGSGSG TDFTLTISSL QPEDFATYYC QQSYSTPLTF  240
GGGTKVEIK                                                          249

SEQ ID NO: 300         moltype = AA  length = 244
FEATURE                Location/Qualifiers
REGION                 1..244
                       note = HLA-C*07 antigen binding domain C7-23
source                 1..244
                       mol_type = protein
                       organism = synthetic construct
SEQUENCE: 300
QVQLVQSGAE VKKPGASVKV SCKASGYTFT SYGISWVRQA PGQGLEWMGW ISAYNGNTNY  60
AQKLQGRVTM TTDTSTSTAY MELRSLRSDD TAVYYCARGS NEYFQHWGQG TLVTVSSGGG  120
GSGGGGSGGG GSGGQSALTQ PPSASGSPGQ SVTISCTGTS SDVGGYNYVS WYQQHPGKAP  180
KLMIYEVSKR PSGVPDRFSG SKSGNTASLT VSGLQAEDEA DYYCSSYAGS NNWVFGGGTK  240
LTVL                                                               244

SEQ ID NO: 301         moltype = AA  length = 242
FEATURE                Location/Qualifiers
REGION                 1..242
                       note = HLA-C*07 antigen binding domain C7-22
source                 1..242
                       mol_type = protein
                       organism = synthetic construct
SEQUENCE: 301
QVQLVQSGSE LKKPGASVKV SCKASGYTFT SYAMNWVRQA PGQGLEWMGW INTNTGNPTY  60
AQGFTGRFVF SFDTSVSTAY LQICSLKAED TAVYYCARGT SYWYFDLWGR GTLVTVSSGG  120
GGSGGGGSGG GGSGGDIQMT QSPSSLSASV GDRVTITCRA SQSISSYLNW YQQKPGKAPK  180
LLIYAASSLQ SGVPSRFSGS GSGTDFTLTI SSLQPEDFAT YYCQQSYSTP LTFGGGTKVE  240
IK                                                                 242

SEQ ID NO: 302         moltype = AA  length = 248
FEATURE                Location/Qualifiers
REGION                 1..248
                       note = HLA-C*07 antigen binding domain C7-21
source                 1..248
                       mol_type = protein
                       organism = synthetic construct
SEQUENCE: 302
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARE EIVEVFYYYY MDVWGKGTTV  120
TVSSGGGGSG GGGSGGGGSG GDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPLTFG  240
GGTKVEIK                                                           248

SEQ ID NO: 303         moltype = AA  length = 241
FEATURE                Location/Qualifiers
REGION                 1..241
                       note = HLA-C*07 antigen binding domain C7-20
source                 1..241
                       mol_type = protein
                       organism = synthetic construct
SEQUENCE: 303
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKVD DYYFDYWGQG TLVTVSSGGG  120
GSGGGGSGGG GSGGDIQMTQ SPSSLSASVG DRVTITCRAS QSISSYLNWY QQKPGKAPKL  180
LIYAASSLQS GVPSRFSGSG SGTDFTLTIS SLQPEDFATY YCQQSYSTPL TFGGGTKVEI  240
K                                                                  241

SEQ ID NO: 304         moltype = AA  length = 247
FEATURE                Location/Qualifiers
REGION                 1..247
                       note = HLA-C*07 antigen binding domain C7-19
source                 1..247
                       mol_type = protein
                       organism = synthetic construct
SEQUENCE: 304
EVQLVESGGG LVQPGGSLRL SCAASGFTFS SYWMHWVRQA PGKGLVWVSR INSDGSSTSY  60
```

```
ADSVKGRFTI SRDNAKNTLY LQMNSLRAED TAVYYCAWST NILLSYTKAF DIWGQGTMVT  120
VSSGGGGSGG GGSGGGGSGG DIQMTQSPSS LSASVGDRVT ITCRASQSIS SYLNWYQQKP  180
GKAPKLLIYA ASSLQSGVPS RFSGSGSGTD FTLTISSLQP EDFATYYCQQ SYSTPLTFGG  240
GTKVEIK                                                           247

SEQ ID NO: 305          moltype = AA  length = 246
FEATURE                 Location/Qualifiers
REGION                  1..246
                        note = HLA-C*07 antigen binding domain C7-18
source                  1..246
                        mol_type = protein
                        organism = synthetic construct
SEQUENCE: 305
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD KTYYYYYYMD VWGKGTTVTV  120
SSGGGGSGGG GSGGGGSGGD IQMTQSPSSL SASVGDRVTI TCRASQSISS YLNWYQQKPG  180
KAPKLLIYAA SSLQSGVPSR FSGSGSGTDF TLTISSLQPE DFATYYCQQS YSTPLTFGGG  240
TKVEIK                                                            246

SEQ ID NO: 306          moltype = AA  length = 253
FEATURE                 Location/Qualifiers
REGION                  1..253
                        note = HLA-C*07 antigen binding domain C7-17
source                  1..253
                        mol_type = protein
                        organism = synthetic construct
SEQUENCE: 306
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARE KYFHDKYFHD YYYYYMDVWG  120
KGTTVTVSSG GGGSGGGGSG GGGSGGDIQM TQSPSSLSAS VGDRVTITCR ASQSISSYLN  180
WYQQKPGKAP KLLIYAASSL QSGVPSRFSG SGSGTDFTLT ISSLQPEDFA TYYCQQSYST  240
PLTFGGGTKV EIK                                                    253

SEQ ID NO: 307          moltype = AA  length = 246
FEATURE                 Location/Qualifiers
REGION                  1..246
                        note = HLA-C*07 antigen binding domain C7-16
source                  1..246
                        mol_type = protein
                        organism = synthetic construct
SEQUENCE: 307
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD TSVYYYYYMD VWGKGTTVTV  120
SSGGGGSGGG GSGGGGSGGD IQMTQSPSSL SASVGDRVTI TCRASQSISS YLNWYQQKPG  180
KAPKLLIYAA SSLQSGVPSR FSGSGSGTDF TLTISSLQPE DFATYYCQQS YSTPLTFGGG  240
TKVEIK                                                            246

SEQ ID NO: 308          moltype = AA  length = 248
FEATURE                 Location/Qualifiers
REGION                  1..248
                        note = HLA-C*07 antigen binding domain C7-15
source                  1..248
                        mol_type = protein
                        organism = synthetic construct
SEQUENCE: 308
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARE KILPYYYYYY MDVWGKGTTV  120
TVSSGGGGSG GGGSGGGGSG GDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPLTFG  240
GGTKVEIK                                                          248

SEQ ID NO: 309          moltype = AA  length = 257
FEATURE                 Location/Qualifiers
REGION                  1..257
                        note = HLA-C*07 antigen binding domain C7-14
source                  1..257
                        mol_type = protein
                        organism = synthetic construct
SEQUENCE: 309
EVQLVESGGG LVQPGGSLRL SCAASGFTFS SYSMNWVRQA PGKGLEWVSY ISSSSSTIYY  60
ADSVKGRFTI SRDNAKNSLY LQMNSLRAED TAVYYCAIQW IYIYINPRGF IFLHDAFDIW  120
GQGTMVTVSS GGGGSGGGGS GGGGSGGQSV LTQPPSASGT PGQRVTISCS GSSSNIGSNT  180
VNWYQQLPGT APKLLIYSNN QRPSGVPDRF SGSKSGTSAS LAISGLQSED EADYYCAAWD  240
DSLNGWVFGG GTKLTVL                                                257

SEQ ID NO: 310          moltype = AA  length = 248
FEATURE                 Location/Qualifiers
REGION                  1..248
                        note = HLA-C*07 antigen binding domain C7-13
```

```
source                  1..248
                        mol_type = protein
                        organism = synthetic construct
SEQUENCE: 310
QVQLQQSGPG LVKPSQTLSL TCAISGDSVS SNSAAWNWIR QSPSRGLEWL GRTYYRSKWY  60
NDYAVSVKSR ITINPDTSKN QFSLQLNSVT PEDTAVYYCA KEDVDFHHDA FDIWGQGTMV  120
TVSSGGGGSG GGGSGGGGSG GDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPLTFG  240
GGTKVEIK                                                           248

SEQ ID NO: 311          moltype = AA  length = 253
FEATURE                 Location/Qualifiers
REGION                  1..253
                        note = HLA-C*07 antigen binding domain C7-12
source                  1..253
                        mol_type = protein
                        organism = synthetic construct
SEQUENCE: 311
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARE GVDKNTSTIY YYYYYMDVWG  120
KGTTVTVSSG GGGSGGGGSG GGGSGGDIQM TQSPSSLSAS VGDRVTITCR ASQSISSYLN  180
WYQQKPGKAP KLLIYAASSL QSGVPSRFSG SGSGTDFTLT ISSLQPEDFA TYYCQQSYST  240
PLTFGGGTKV EIK                                                     253

SEQ ID NO: 312          moltype = AA  length = 241
FEATURE                 Location/Qualifiers
REGION                  1..241
                        note = HLA-C*07 antigen binding domain C7-11
source                  1..241
                        mol_type = protein
                        organism = synthetic construct
SEQUENCE: 312
EVQLVESGGG LVQPGGSLRL SCAASGFTFS SYSMNWVRQA PGKGLEWVSY ISSSSSTIYY  60
ADSVKGRFTI SRDNAKNSLY LQMNSLRAED TAVYYCARDR RGYFDLWGRG TLVTVSSGGG  120
GSGGGGSGGG GSGGDIQMTQ SPSSLSASVG DRVTITCRAS QGISSWLAWY QQKPEKAPKS  180
LIYAASSLQS GVPSRFSGSG SGTDFTLTIS SLQPEDFATY YCQQYNSYPL TFGGGTKVEI  240
K                                                                  241

SEQ ID NO: 313          moltype = AA  length = 248
FEATURE                 Location/Qualifiers
REGION                  1..248
                        note = HLA-C*07 antigen binding domain C7-10
source                  1..248
                        mol_type = protein
                        organism = synthetic construct
SEQUENCE: 313
EVQLVQSGAE VKKPGATVKI SCKVSGYTFT DYYMHWVQQA PGKGLEWMGL VDPEDGETIY  60
AEKFQGRVTI TADTSTDTAY MELSSLRSED TAVYYCATGI HVDIRSMEDW FDPWGQGTLV  120
TVSSGGGGSG GGGSGGGGSG GDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPLTFG  240
GGTKVEIK                                                           248

SEQ ID NO: 314          moltype = AA  length = 246
FEATURE                 Location/Qualifiers
REGION                  1..246
                        note = HLA-C*07 antigen binding domain C7-9
source                  1..246
                        mol_type = protein
                        organism = synthetic construct
SEQUENCE: 314
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD IGTSYYYYMD VWGKGTTVTV  120
SSGGGGSGGG GSGGGGSGGD IQMTQSPSSL SASVGDRVTI TCRASQSISS YLNWYQQKPG  180
KAPKLLIYAA SSLQSGVPSR FSGSGSGTDF TLTISSLQPE DFATYYCQQS YSTPLTFGGG  240
TKVEIK                                                             246

SEQ ID NO: 315          moltype = AA  length = 249
FEATURE                 Location/Qualifiers
REGION                  1..249
                        note = HLA-C*07 antigen binding domain C7-8
source                  1..249
                        mol_type = protein
                        organism = synthetic construct
SEQUENCE: 315
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARE VVEVFLYYYY YMDVWGKGTT  120
VTVSSGGGGS GGGGSGGGGS GGDIQMTQSP SSLSASVGDR VTITCRASQS ISSYLNWYQQ  180
KPGKAPKLLI YAASSLQSGV PSRFSGSGSG TDFTLTISSL QPEDFATYYC QQSYSTPLTF  240
GGGTKVEIK                                                          249
```

```
SEQ ID NO: 316         moltype = AA  length = 246
FEATURE                Location/Qualifiers
REGION                 1..246
                       note = HLA-C*07 antigen binding domain C7-7
source                 1..246
                       mol_type = protein
                       organism = synthetic construct
SEQUENCE: 316
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD LYYYYYYYMD VWGKGTTVTV  120
SSGGGGSGGG GSGGGGSGGD IQMTQSPSSL SASVGDRVTI TCRASQSISS YLNWYQQKPG  180
KAPKLLIYAA SSLQSGVPSR FSGSGSGTDF TLTISSLQPE DFATYYCQQS YSTPLTFGGG  240
TKVEIK                                                            246

SEQ ID NO: 317         moltype = AA  length = 256
FEATURE                Location/Qualifiers
REGION                 1..256
                       note = HLA-C*07 antigen binding domain C7-6
source                 1..256
                       mol_type = protein
                       organism = synthetic construct
SEQUENCE: 317
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARE SWKYFYPRGS IFIHYYYYMD  120
VWGKGTTVTV SSGGGGSGGG GSGGGGSGGD IQMTQSPSSL SASVGDRVTI TCRASQSISS  180
YLNWYQQKPG KAPKLLIYAA SSLQSGVPSR FSGSGSGTDF TLTISSLQPE DFATYYCQQS  240
YSTPLTFGGG TKVEIK                                                 256

SEQ ID NO: 318         moltype = AA  length = 248
FEATURE                Location/Qualifiers
REGION                 1..248
                       note = HLA-C*07 antigen binding domain C7-5
source                 1..248
                       mol_type = protein
                       organism = synthetic construct
SEQUENCE: 318
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD RIVEVFYYYY MDVWGKGTTV  120
TVSSGGGGSG GGGSGGGGSG GDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPLTFG  240
GGTKVEIK                                                          248

SEQ ID NO: 319         moltype = AA  length = 250
FEATURE                Location/Qualifiers
REGION                 1..250
                       note = HLA-C*07 antigen binding domain C7-4
source                 1..250
                       mol_type = protein
                       organism = synthetic construct
SEQUENCE: 319
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARE KYFHDWLYYY YYMDVWGKGT  120
TVTVSSGGGG SGGGGSGGGG SGGDIQMTQS PSSLSASVGD RVTITCRASQ SISSYLNWYQ  180
QKPGKAPKLL IYAASSLQSG VPSRFSGSGS GTDFTLTISS LQPEDFATYY CQQSYSTPLT  240
FGGGTKVEIK                                                        250

SEQ ID NO: 320         moltype = AA  length = 250
FEATURE                Location/Qualifiers
REGION                 1..250
                       note = HLA-C*07 antigen binding domain C7-3
source                 1..250
                       mol_type = protein
                       organism = synthetic construct
SEQUENCE: 320
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD LVDKNTSYYY YYMDVWGKGT  120
TVTVSSGGGG SGGGGSGGGG SGGDIQMTQS PSSLSASVGD RVTITCRASQ SISSYLNWYQ  180
QKPGKAPKLL IYAASSLQSG VPSRFSGSGS GTDFTLTISS LQPEDFATYY CQQSYSTPLT  240
FGGGTKVEIK                                                        250

SEQ ID NO: 321         moltype = AA  length = 244
FEATURE                Location/Qualifiers
REGION                 1..244
                       note = HLA-C*07 antigen binding domain C7-2
source                 1..244
                       mol_type = protein
                       organism = synthetic construct
SEQUENCE: 321
```

-continued

```
QVQLVQSGAE VKKPGASVKV SCKASGYTFT SYGISWVRQA PGQGLEWMGW ISAYNGNTNY  60
AQKLQGRVTM TTDTSTSTAY MELRSLRSDD TAVYYCARVQ NEYFQHWGQG TLVTVSSGGG  120
GSGGGGSGGG GSGGQSALTQ PPSASGSPGQ SVTISCTGTS SDVGGYNYVS WYQQHPGKAP  180
KLMIYEVSKR PSGVPDRFSG SKSGNTASLT VSGLQAEDEA DYYCSSYAGS NNWVFGGGTK  240
LTVL                                                              244

SEQ ID NO: 322          moltype = AA  length = 239
FEATURE                 Location/Qualifiers
REGION                  1..239
                        note = HLA-C*07 antigen binding domain C7-1
source                  1..239
                        mol_type = protein
                        organism = synthetic construct
SEQUENCE: 322
QVQLVESGGG LVKPGGSLRL SCAASGFTFS DYYMSWIRQA PGKGLEWVSY ISSSGSTIYY  60
ADSVKGRFTI SRDNAKNSLY LQMNSLRAED TAVYYCATAN WFDPWGQGTL VTVSSGGGGS  120
GGGGSGGGGS GGDIQMTQSP SSVSASVGDR VTITCRASQG ISSWLAWYQQ KPGKAPKLLI  180
YAASSLQSGV PSRFSGSGSG TDFTLTISSL QPEDFATYYC QQANSFPLTF GGGTKVEIK   239

SEQ ID NO: 323          moltype = AA  length = 244
FEATURE                 Location/Qualifiers
REGION                  1..244
                        note = HLA-A*03 scFv Sequence 15
source                  1..244
                        mol_type = protein
                        organism = synthetic construct
SEQUENCE: 323
QVQLVQSGAE VKKPGASVKV SCKASGYTFT SYGISWVRQA PGQGLEWMGW ISAYNGNTNY  60
AQKLQGRVTM TTDTSTSTAY MELRSLRSDD TAVYYCARER VSQRGAFDIW GQGTMVTVSS  120
GGGGSGGGGS GGGGSGGDIQ MTQSPSSLSA SVGDRVTITC RASQSISSYL NWYQQKPGKA  180
PKLLIYAASS LQSGVPSRFS GSGSGTDFTL TISSLQPEDF ATYYCQQSYS TPLTFGGGTK  240
VEIK                                                              244

SEQ ID NO: 324          moltype = AA  length = 243
FEATURE                 Location/Qualifiers
REGION                  1..243
                        note = HLA-A*03 scFv Sequence 16
source                  1..243
                        mol_type = protein
                        organism = synthetic construct
SEQUENCE: 324
EVQLVESGGG LVQPGGSLRL SCAASGFTFS SYSMNWVRQA PGKGLEWVSY ISSSSSTIYY  60
ADSVKGRFTI SRDNAKNSLY LQMNSLRAED TAVYYCARGN PDKDPFDYWG QGTLVTVSSG  120
GGGSGGGGSG GGGSGGDIQM TQSPSSLSAS VGDRVTITCR ASQSISSYLN WYQQKPGKAP  180
KLLIYAASSL QSGVPSRFSG SGSGTDFTLT ISSLQPEDFA TYYCQQSYST PLTFGGGTKV  240
EIK                                                               243

SEQ ID NO: 325          moltype = AA  length = 245
FEATURE                 Location/Qualifiers
REGION                  1..245
                        note = HLA-A*03 scFv Sequence 17
source                  1..245
                        mol_type = protein
                        organism = synthetic construct
SEQUENCE: 325
QVQLQESGPG LVKPSETLSL TCTVSGGSVS SGSYYWSWIR QPPGKGLEWI GYIYYSGSTN  60
YNPSLKSRVT ISVDTSKNQF SLKLSSVTAA DTAVYYCARD FYCTNWYFDL WGRGTLVTVS  120
SGGGGSGGGG SGGGGSGGDI QMTQSPSSLS ASVGDRVTIT CRASQSISSY LNWYQQKPGK  180
APKLLIYAAS SLQSGVPSRF SGSGSGTDFT LTISSLQPED FATYYCQQSY STPLTFGGGT  240
KVEIK                                                             245

SEQ ID NO: 326          moltype = AA  length = 244
FEATURE                 Location/Qualifiers
REGION                  1..244
                        note = HLA-A*03 scFv Sequence 18
source                  1..244
                        mol_type = protein
                        organism = synthetic construct
SEQUENCE: 326
QVQLQESGPG LVKPSETLSL TCTVSGGSIS SYYWSWIRQP PGKGLEWIGY IYYSGSTNYN  60
PSLKSRVTIS VDTSKNQFSL KLSSVTAADT AVYYCARESS SGSYWYFDLW GRGTLVTVSS  120
GGGGSGGGGS GGGGSGGDIQ MTQSPSSLSA SVGDRVTITC RASQSISSYL NWYQQKPGKA  180
PKLLIYAASS LQSGVPSRFS GSGSGTDFTL TISSLQPEDF ATYYCQQSYS TPLTFGGGTK  240
VEIK                                                              244

SEQ ID NO: 327          moltype = AA  length = 250
FEATURE                 Location/Qualifiers
REGION                  1..250
                        note = HLA-A*03 scFv Sequence 19
```

```
source                  1..250
                        mol_type = protein
                        organism = synthetic construct
SEQUENCE: 327
EVQLVQSGAE VKKPGESLKI SCKGSGYSFT SYWIGWVRQM PGKGLEWMGI IYPGDSDTRY  60
SPSFQGQVTI SADKSISTAY LQWSSLKASD TAMYYCARDS GYKYNLYYYY YYMDVWGKGT  120
TVTVSSGGGG SGGGGSGGGG SGGDIQMTQS PSSLSASVGD RVTITCRASQ SISSYLNWYQ  180
QKPGKAPKLL IYAASSLQSG VPSRFSGSGS GTDFTLTISS LQPEDFATYY CQQSYSTPLT  240
FGGGTKVEIK                                                         250

SEQ ID NO: 328          moltype = AA  length = 249
FEATURE                 Location/Qualifiers
REGION                  1..249
                        note = HLA-A*03 scFv Sequence 20
source                  1..249
                        mol_type = protein
                        organism = synthetic construct
SEQUENCE: 328
QVQLVQSGAE VKKPGASVKV SCKASGYTFT SYGISWVRQA PGQGLEWMGW ISAYNGNTNY  60
AQKLQGRVTM TTDTSTSTAY MELRSLRSDD TAVYYCARGG DLSHYYYYMD VWGKGTTVTV  120
SSGGGGSGGG GSGGGGSGGQ TVVTQEPSLT VSPGGTVTLT CASSTGAVTS GYYPNWFQQK  180
PGQAPRALIY STSNKHSWTP ARFSGSLLGG KAALTLSGVQ PEDEAEYYCL LYYGGAQWVF  240
GGGTKLTVL                                                          249

SEQ ID NO: 329          moltype = AA  length = 246
FEATURE                 Location/Qualifiers
REGION                  1..246
                        note = HLA-A*03 scFv Sequence 21
source                  1..246
                        mol_type = protein
                        organism = synthetic construct
SEQUENCE: 329
QVQLVQSGAE VKKPGASVKV SCKASGYTFT SYGISWVRQA PGQGLEWMGW ISAYNGNTNY  60
AQKLQGRVTM TTDTSTSTAY MELRSLRSDD TAVYYCAREN RRYNSCYYFD YWGQGTLVTV  120
SSGGGGSGGG GSGGGGSGGD IQMTQSPSSL SASVGDRVTI TCRASQSISS YLNWYQQKPG  180
KAPKLLIYAA SSLQSGVPSR FSGSGSGTDF TLTISSLQPE DFATYYCQQS YSTPLTFGGG  240
TKVEIK                                                             246

SEQ ID NO: 330          moltype = AA  length = 249
FEATURE                 Location/Qualifiers
REGION                  1..249
                        note = HLA-A*03 scFv Sequence 22
source                  1..249
                        mol_type = protein
                        organism = synthetic construct
SEQUENCE: 330
QVQLVQSGAE VKKPGASVKV SCKASGYTFT SYGISWVRQA PGQGLEWMGW ISAYNGNTNY  60
AQKLQGRVTM TTDTSTSTAY MELRSLRSDD TAVYYCARGG DLSHYYYYLD VWGKGTTVTV  120
SSGGGGSGGG GSGGGGSGGQ TVVTQEPSLT VSPGGTVTLT CASSTGAVTS GYYPNWFQQK  180
PGQAPRALIY STSNKHSWTP ARFSGSLLGG KAALTLSGVQ PEDEAEYYCL LYYGGAQWVF  240
GGGTKLTVL                                                          249

SEQ ID NO: 331          moltype = AA  length = 245
FEATURE                 Location/Qualifiers
REGION                  1..245
                        note = HLA-A*03 scFv Sequence 23
source                  1..245
                        mol_type = protein
                        organism = synthetic construct
SEQUENCE: 331
EVQLVESGGG LVQPGGSLRL SCAASGFTVS SNYMSWVRQA PGKGLEWVSV IYSGGSTYYA  60
DSVKGRFTIS RDNSKNTLYL QMNSLRAEDT AVYYCARATL LSLSYDAFDI WGQGTMVTVS  120
SGGGGSGGGG SGGGGSGGDI QMTQSPSSLS ASVGDRVTIT CRASQSISSY LNWYQQKPGK  180
APKLLIYAAS SLQSGVPSRF SGSGSGTDFT LTISSLQPED FATYYCQQSY STPLTFGGGT  240
KVEIK                                                              245

SEQ ID NO: 332          moltype = AA  length = 248
FEATURE                 Location/Qualifiers
REGION                  1..248
                        note = HLA-A*03 scFv Sequence 24
source                  1..248
                        mol_type = protein
                        organism = synthetic construct
SEQUENCE: 332
QVQLVQSGAE VKKPGASVKV SCKASGYTFT SYGISWVRQA PGQGLEWMGW ISAYNGNTNY  60
AQKLQGRVTM TTDTSTSTAY MELRSLRSDD TAVYYCARGG DLSHYYYMDV WGKGTTVTVS  120
SGGGGSGGGG SGGGGSGGQT VVTQEPSLTV SPGGTVTLTC ASSTGAVTSG YYPNWFQQKP  180
GQAPRALIYS TSNKHSWTPA RFSGSLLGGK AALTLSGVQP EDEAEYYCLL YYGGAQWVFG  240
GGTKLTVL                                                           248
```

```
SEQ ID NO: 333          moltype = AA  length = 241
FEATURE                 Location/Qualifiers
REGION                  1..241
                        note = HLA-A*03 scFv Sequence 25
source                  1..241
                        mol_type = protein
                        organism = synthetic construct
SEQUENCE: 333
EVQLVQSGAE VKKPGESLKI SCKGSGYSFT SYWIGWVRQM PGKGLEWMGI IYPGDSDTRY  60
SPSFQGQVTI SADKSISTAY LQWSSLKASD TAMYYCARER DRWFDPWGQG TLVTVSSGGG  120
GSGGGGSGGG GSGGDIQMTQ SPSSLSASVG DRVTITCRAS QSISSYLNWY QQKPGKAPKL  180
LIYAASSLQS GVPSRFSGSG SGTDFTLTIS SLQPEDFATY YCQQSYSTPL TFGGGTKVEI  240
K                                                                  241

SEQ ID NO: 334          moltype = AA  length = 247
FEATURE                 Location/Qualifiers
REGION                  1..247
                        note = HLA-A*03 scFv Sequence 26
source                  1..247
                        mol_type = protein
                        organism = synthetic construct
SEQUENCE: 334
QVQLVQSGAE VKKPGASVKV SCKASGYTFT SYGISWVRQA PGQGLEWMGW ISAYNGNTNY  60
AQKLQGRVTM TTDTSTSTAY MELRSLRSDD TAVYYCARET PPSLGAFDIW GQGTMVTVSS  120
GGGGSGGGGS GGGGSGGQSA LTQPPSASGS PGQSVTISCT GTSSDVGGYN YVSWYQQHPG  180
KAPKLMIYEV SKRPSGVPDR FSGSKSGNTA SLTVSGLQAE DEADYYCSSY AGSNNWVFGG  240
GTKLTVL                                                            247

SEQ ID NO: 335          moltype = AA  length = 251
FEATURE                 Location/Qualifiers
REGION                  1..251
                        note = HLA-A*03 scFv Sequence 27
source                  1..251
                        mol_type = protein
                        organism = synthetic construct
SEQUENCE: 335
QLQLQESGPG LVKPSETLSL TCTVSGGSIS SSSYYWGWIR QPPGKGLEWI GSIYYSGSTY  60
YNPSLKSRVT ISVDTSKNQF SLKLSSVTAA DTAVYYCARE AYCLSDSYWY FDLWGRGTLV  120
TVSSGGGGSG GGGSGGGGSG GQSVLTQPPS ASGTPGQRVT ISCSGSSSNI GSNTVNWYQQ  180
LPGTAPKLLI YSNNQRPSGV PDRFSGSKSG TSASLAISGL QSEDEADYYC AAWDDSLNGW  240
VFGGGTKLTV L                                                       251

SEQ ID NO: 336          moltype = AA  length = 248
FEATURE                 Location/Qualifiers
REGION                  1..248
                        note = HLA-A*03 scFv Sequence 28
source                  1..248
                        mol_type = protein
                        organism = synthetic construct
SEQUENCE: 336
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARE SWKYFYPRGY MDVWGKGTTV  120
TVSSGGGGSG GGGSGGGGSG GDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPLTFG  240
GGTKVEIK                                                           248

SEQ ID NO: 337          moltype = AA  length = 248
FEATURE                 Location/Qualifiers
REGION                  1..248
                        note = A1-9
source                  1..248
                        mol_type = protein
                        organism = synthetic construct
SEQUENCE: 337
QVQLVQSGAE VKKPGASVKV SCKASGYTFT SYGISWVRQA PGQGLEWMGW ISAYNGNTNY  60
AQKLQGRVTM TTDTSTSTAY MELRSLRSDD TAVYYCARGG WTAWYYYMDV WGKGTTVTVS  120
SGGGGSGGGG SGGGGSGGQT VVTQEPSLTV SPGGTVTLTC ASSTGAVTSG YYPNWFQQKP  180
GQAPRALIYS TSNKHSWTPA RFSGSLLGGK AALTLSGVQP EDEAEYYCLL YYGGAQWVFG  240
GGTKLTVL                                                           248

SEQ ID NO: 338          moltype = AA  length = 244
FEATURE                 Location/Qualifiers
REGION                  1..244
                        note = A1-8
source                  1..244
                        mol_type = protein
                        organism = synthetic construct
SEQUENCE: 338
```

```
EVQLVESGGG LVQPGGSLRL SCAASGFTFS SYSMNWVRQA PGKGLEWVSY ISSSSSTIYY  60
ADSVKGRFTI SRDNAKNSLY LQMNSLRAED TAVYYCARAK YYYMDVWGKG TTVTVSSGGG  120
GSGGGGSGGG GSGGQSVLTQ PPSASGTPGQ RVTISCSGSS SNIGSNTVNW YQQLPGTAPK  180
LLIYSNNQRP SGVPDRFSGS KSGTSASLAI SGLQSEDEAD YYCAAWDDSL NGWVFGGGTK  240
LTVL                                                               244

SEQ ID NO: 339          moltype = AA  length = 248
FEATURE                 Location/Qualifiers
REGION                  1..248
                        note = A1-7
source                  1..248
                        mol_type = protein
                        organism = synthetic construct
SEQUENCE: 339
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD QVDKNTYYYY MDVWGKGTTV  120
TVSSGGGGSG GGGSGGGGSG GDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPLTFG  240
GGTKVEIK                                                           248

SEQ ID NO: 340          moltype = AA  length = 243
FEATURE                 Location/Qualifiers
REGION                  1..243
                        note = A1-6
source                  1..243
                        mol_type = protein
                        organism = synthetic construct
SEQUENCE: 340
QVQLVESGGG LVKPGGSLRL SCAASGFTFS DYYMSWIRQA PGKGLEWVSY ISSSGSTIYY  60
ADSVKGRFTI SRDNAKNSLY LQMNSLRAED TAVYYCARAC QLAEYFQHWG QGTLVTVSSG  120
GGGSGGGGSG GGGSGGDIQM TQSPSSVSAS VGDRVTITCR ASQGISSWLA WYQQKPGKAP  180
KLLIYAASSL QSGVPSRFSG SGSGTDFTLT ISSLQPEDFA TYYCQQANSF PLTFGGGTKV  240
EIK                                                                243

SEQ ID NO: 341          moltype = AA  length = 248
FEATURE                 Location/Qualifiers
REGION                  1..248
                        note = A1-5
source                  1..248
                        mol_type = protein
                        organism = synthetic construct
SEQUENCE: 341
QVQLQESGPG LVKPSQTLSL TCTVSGGSIS SGGYYWSWIR QPPGKGLEWI GYIYYSGSTY  60
YNPSLKSRVT ISVDTSKNQF SLKLSSVTAA DTAVYYCARD RVDKNTSYYY MDVWGKGTTV  120
TVSSGGGGSG GGGSGGGGSG GDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPLTFG  240
GGTKVEIK                                                           248

SEQ ID NO: 342          moltype = AA  length = 245
FEATURE                 Location/Qualifiers
REGION                  1..245
                        note = A1-4
source                  1..245
                        mol_type = protein
                        organism = synthetic construct
SEQUENCE: 342
QVQLQESGPG LVKPSDTLSL TCAVSGYSIS SSNWWGWIRQ PPGKGLEWIG YIYYSGSTYY  60
NPSLKSRVTM SVDTSKNQFS LKLSSVTAVD TAVYYCARRV QLKLVHWFDP WGQGTLVTVS  120
SGGGGSGGGG SGGGGSGGDI QMTQSPSSLS ASVGDRVTIT CRASQSISSY LNWYQQKPGK  180
APKLLIYAAS SLQSGVPSRF SGSGSGTDFT LTISSLQPED FATYYCQQSY STPLTFGGGT  240
KVEIK                                                              245

SEQ ID NO: 343          moltype = AA  length = 245
FEATURE                 Location/Qualifiers
REGION                  1..245
                        note = A1-3
source                  1..245
                        mol_type = protein
                        organism = synthetic construct
SEQUENCE: 343
QVQLVQSGAE VKKPGASVKV SCKASGYTFT SYDINWVRQA TGQGLEWMGW MNPNSGNTGY  60
AQKFQGRVTM TRNTSISTAY MELSSLRSED TAVYYCATYY DYVTVFYFQH WGQGTLVTVS  120
SGGGGSGGGG SGGGGSGGDI QMTQSPSSLS ASVGDRVTIT CRASQSISSY LNWYQQKPGK  180
APKLLIYAAS SLQSGVPSRF SGSGSGTDFT LTISSLQPED FATYYCQQSY STPLTFGGGT  240
KVEIK                                                              245

SEQ ID NO: 344          moltype = AA  length = 245
FEATURE                 Location/Qualifiers
REGION                  1..245
```

```
                         note = A1-2
source                   1..245
                         mol_type = protein
                         organism = synthetic construct
SEQUENCE: 344
QLQLQESGSG LVKPSQTLSL TCAVSGGSIS SGGYSWSWIR QPPGKGLEWI GYIYHSGSTY  60
YNPSLKSRVT ISVDRSKNQF SLKLSSVTAA DTAVYYCARE SYPSFYAFDI WGQGTMVTVS  120
SGGGGSGGGG SGGGGSGGDI QMTQSPSSLS ASVGDRVTIT CRASQSISSY LNWYQQKPGK  180
APKLLIYAAS SLQSGVPSRF SGSGSGTDFT LTISSLQPED FATYYCQQSY STPLTFGGGT  240
KVEIK                                                              245

SEQ ID NO: 345           moltype = AA  length = 249
FEATURE                  Location/Qualifiers
REGION                   1..249
                         note = A1-1
source                   1..249
                         mol_type = protein
                         organism = synthetic construct
SEQUENCE: 345
QITLKESGPT LVKPTQTLTL TCTFSGFSLS TSGVGVGWIR QPPGKALEWL ALIYWNDDKR  60
YSPSLKSRLT ITKDTSKNQV VLTMTNMDPV DTATYYCAHS NMWSYSLNDY YFDYWGQGTL  120
VTVSSGGGGS GGGGSGGGGS GGDIQMTQSP SSLSASVGDR VTITCRASQS ISSYLNWYQQ  180
KPGKAPKLLI YAASSLQSGV PSRFSGSGSG TDFTLTISSL QPEDFATYYC QQSYSTPLTF  240
GGGTKVEIK                                                          249

SEQ ID NO: 346           moltype = AA  length = 11
FEATURE                  Location/Qualifiers
REGION                   1..11
                         note = CDR-L1
source                   1..11
                         mol_type = protein
                         organism = synthetic construct
SEQUENCE: 346
RASQSISSYL N                                                       11

SEQ ID NO: 347           moltype = AA  length = 14
FEATURE                  Location/Qualifiers
REGION                   1..14
                         note = CDR-L1
source                   1..14
                         mol_type = protein
                         organism = synthetic construct
SEQUENCE: 347
ASSTGAVTSG YYPN                                                    14

SEQ ID NO: 348           moltype = AA  length = 14
FEATURE                  Location/Qualifiers
REGION                   1..14
                         note = CDR-L1
source                   1..14
                         mol_type = protein
                         organism = synthetic construct
SEQUENCE: 348
TGTSSDVGGY NYVS                                                    14

SEQ ID NO: 349           moltype = AA  length = 13
FEATURE                  Location/Qualifiers
REGION                   1..13
                         note = CDR-L1
source                   1..13
                         mol_type = protein
                         organism = synthetic construct
SEQUENCE: 349
SGSSSNIGSN TVN                                                     13

SEQ ID NO: 350           moltype = AA  length = 11
FEATURE                  Location/Qualifiers
REGION                   1..11
                         note = CDR-L1
source                   1..11
                         mol_type = protein
                         organism = synthetic construct
SEQUENCE: 350
RASENIYSNL A                                                       11

SEQ ID NO: 351           moltype = AA  length = 11
FEATURE                  Location/Qualifiers
REGION                   1..11
                         note = CDR-L1
```

```
source                  1..11
                        mol_type = protein
                        organism = synthetic construct
SEQUENCE: 351
RASQGISSAL A                                                     11

SEQ ID NO: 352          moltype = AA  length = 11
FEATURE                 Location/Qualifiers
REGION                  1..11
                        note = CDR-L1
source                  1..11
                        mol_type = protein
                        organism = synthetic construct
SEQUENCE: 352
RASQGISSWL A                                                     11

SEQ ID NO: 353          moltype = AA  length = 7
FEATURE                 Location/Qualifiers
REGION                  1..7
                        note = CDR-L2
source                  1..7
                        mol_type = protein
                        organism = synthetic construct
SEQUENCE: 353
AASSLQS                                                          7

SEQ ID NO: 354          moltype = AA  length = 7
FEATURE                 Location/Qualifiers
REGION                  1..7
                        note = CDR-L2
source                  1..7
                        mol_type = protein
                        organism = synthetic construct
SEQUENCE: 354
STSNKHS                                                          7

SEQ ID NO: 355          moltype = AA  length = 7
FEATURE                 Location/Qualifiers
REGION                  1..7
                        note = CDR-L2
source                  1..7
                        mol_type = protein
                        organism = synthetic construct
SEQUENCE: 355
EVSKRPS                                                          7

SEQ ID NO: 356          moltype = AA  length = 7
FEATURE                 Location/Qualifiers
REGION                  1..7
                        note = CDR-L2
source                  1..7
                        mol_type = protein
                        organism = synthetic construct
SEQUENCE: 356
SNNQRPS                                                          7

SEQ ID NO: 357          moltype = AA  length = 7
FEATURE                 Location/Qualifiers
REGION                  1..7
                        note = CDR-L2
source                  1..7
                        mol_type = protein
                        organism = synthetic construct
SEQUENCE: 357
AATYLPD                                                          7

SEQ ID NO: 358          moltype = AA  length = 9
FEATURE                 Location/Qualifiers
REGION                  1..9
                        note = CDR-L3
source                  1..9
                        mol_type = protein
                        organism = synthetic construct
SEQUENCE: 358
QQSYSTPLT                                                        9

SEQ ID NO: 359          moltype = AA  length = 10
FEATURE                 Location/Qualifiers
REGION                  1..10
```

```
                          note = CDR-L3
source                    1..10
                          mol_type = protein
                          organism = synthetic construct
SEQUENCE: 359
LLYYGGAQWV                                                        10

SEQ ID NO: 360            moltype = AA  length = 10
FEATURE                   Location/Qualifiers
REGION                    1..10
                          note = CDR-L3
source                    1..10
                          mol_type = protein
                          organism = synthetic construct
SEQUENCE: 360
SSYAGSNNWV                                                        10

SEQ ID NO: 361            moltype = AA  length = 11
FEATURE                   Location/Qualifiers
REGION                    1..11
                          note = CDR-L3
source                    1..11
                          mol_type = protein
                          organism = synthetic construct
SEQUENCE: 361
AAWDDSLNGW V                                                      11

SEQ ID NO: 362            moltype = AA  length = 9
FEATURE                   Location/Qualifiers
REGION                    1..9
                          note = CDR-L3
source                    1..9
                          mol_type = protein
                          organism = synthetic construct
SEQUENCE: 362
QHFWVTPYT                                                         9

SEQ ID NO: 363            moltype = AA  length = 9
FEATURE                   Location/Qualifiers
REGION                    1..9
                          note = CDR-L3
source                    1..9
                          mol_type = protein
                          organism = synthetic construct
SEQUENCE: 363
QQYNSYPLT                                                         9

SEQ ID NO: 364            moltype = AA  length = 9
FEATURE                   Location/Qualifiers
REGION                    1..9
                          note = CDR-L3
source                    1..9
                          mol_type = protein
                          organism = synthetic construct
SEQUENCE: 364
QQANSFPLT                                                         9

SEQ ID NO: 365            moltype = AA  length = 5
FEATURE                   Location/Qualifiers
REGION                    1..5
                          note = CDR-H1
source                    1..5
                          mol_type = protein
                          organism = synthetic construct
SEQUENCE: 365
SYGIS                                                             5

SEQ ID NO: 366            moltype = AA  length = 5
FEATURE                   Location/Qualifiers
REGION                    1..5
                          note = CDR-H1
source                    1..5
                          mol_type = protein
                          organism = synthetic construct
SEQUENCE: 366
SYSMN                                                             5

SEQ ID NO: 367            moltype = AA  length = 7
FEATURE                   Location/Qualifiers
```

```
REGION                  1..7
                        note = CDR-H1
source                  1..7
                        mol_type = protein
                        organism = synthetic construct
SEQUENCE: 367
SGSYYWS                                                                 7

SEQ ID NO: 368          moltype = AA  length = 5
FEATURE                 Location/Qualifiers
REGION                  1..5
                        note = CDR-H1
source                  1..5
                        mol_type = protein
                        organism = synthetic construct
SEQUENCE: 368
SYYWS                                                                   5

SEQ ID NO: 369          moltype = AA  length = 5
FEATURE                 Location/Qualifiers
REGION                  1..5
                        note = CDR-H1
source                  1..5
                        mol_type = protein
                        organism = synthetic construct
SEQUENCE: 369
SYWIG                                                                   5

SEQ ID NO: 370          moltype = AA  length = 5
FEATURE                 Location/Qualifiers
REGION                  1..5
                        note = CDR-H1
source                  1..5
                        mol_type = protein
                        organism = synthetic construct
SEQUENCE: 370
SNYMS                                                                   5

SEQ ID NO: 371          moltype = AA  length = 7
FEATURE                 Location/Qualifiers
REGION                  1..7
                        note = CDR-H1
source                  1..7
                        mol_type = protein
                        organism = synthetic construct
SEQUENCE: 371
SSSYYWG                                                                 7

SEQ ID NO: 372          moltype = AA  length = 7
FEATURE                 Location/Qualifiers
REGION                  1..7
                        note = CDR-H1
source                  1..7
                        mol_type = protein
                        organism = synthetic construct
SEQUENCE: 372
SGGYYWS                                                                 7

SEQ ID NO: 373          moltype = AA  length = 6
FEATURE                 Location/Qualifiers
REGION                  1..6
                        note = CDR-H1
source                  1..6
                        mol_type = protein
                        organism = synthetic construct
SEQUENCE: 373
SGYSWH                                                                  6

SEQ ID NO: 374          moltype = AA  length = 7
FEATURE                 Location/Qualifiers
REGION                  1..7
                        note = CDR-H1
source                  1..7
                        mol_type = protein
                        organism = synthetic construct
SEQUENCE: 374
TSGVGVG                                                                 7

SEQ ID NO: 375          moltype = AA  length = 5
```

```
FEATURE                 Location/Qualifiers
REGION                  1..5
                        note = CDR-H1
source                  1..5
                        mol_type = protein
                        organism = synthetic construct
SEQUENCE: 375
SYWMH                                                                        5

SEQ ID NO: 376          moltype = AA  length = 5
FEATURE                 Location/Qualifiers
REGION                  1..5
                        note = CDR-H1
source                  1..5
                        mol_type = protein
                        organism = synthetic construct
SEQUENCE: 376
SYDMH                                                                        5

SEQ ID NO: 377          moltype = AA  length = 5
FEATURE                 Location/Qualifiers
REGION                  1..5
                        note = CDR-H1
source                  1..5
                        mol_type = protein
                        organism = synthetic construct
SEQUENCE: 377
SYAMH                                                                        5

SEQ ID NO: 378          moltype = AA  length = 5
FEATURE                 Location/Qualifiers
REGION                  1..5
                        note = CDR-H1
source                  1..5
                        mol_type = protein
                        organism = synthetic construct
SEQUENCE: 378
SYAMS                                                                        5

SEQ ID NO: 379          moltype = AA  length = 5
FEATURE                 Location/Qualifiers
REGION                  1..5
                        note = CDR-H1
source                  1..5
                        mol_type = protein
                        organism = synthetic construct
SEQUENCE: 379
SYAMN                                                                        5

SEQ ID NO: 380          moltype = AA  length = 5
FEATURE                 Location/Qualifiers
REGION                  1..5
                        note = CDR-H1
source                  1..5
                        mol_type = protein
                        organism = synthetic construct
SEQUENCE: 380
DYYMS                                                                        5

SEQ ID NO: 381          moltype = AA  length = 7
FEATURE                 Location/Qualifiers
REGION                  1..7
                        note = CDR-H1
source                  1..7
                        mol_type = protein
                        organism = synthetic construct
SEQUENCE: 381
SNSAAWN                                                                      7

SEQ ID NO: 382          moltype = AA  length = 5
FEATURE                 Location/Qualifiers
REGION                  1..5
                        note = CDR-H1
source                  1..5
                        mol_type = protein
                        organism = synthetic construct
SEQUENCE: 382
DYYMH                                                                        5
```

```
SEQ ID NO: 383          moltype = AA  length = 6
FEATURE                 Location/Qualifiers
REGION                  1..6
                        note = CDR-H1
source                  1..6
                        mol_type = protein
                        organism = synthetic construct
SEQUENCE: 383
SSNWWG                                                                6

SEQ ID NO: 384          moltype = AA  length = 5
FEATURE                 Location/Qualifiers
REGION                  1..5
                        note = CDR-H1
source                  1..5
                        mol_type = protein
                        organism = synthetic construct
SEQUENCE: 384
SYDIN                                                                 5

SEQ ID NO: 385          moltype = AA  length = 7
FEATURE                 Location/Qualifiers
REGION                  1..7
                        note = CDR-H1
source                  1..7
                        mol_type = protein
                        organism = synthetic construct
SEQUENCE: 385
SGGYSWS                                                               7

SEQ ID NO: 386          moltype = AA  length = 17
FEATURE                 Location/Qualifiers
REGION                  1..17
                        note = CDR-H2
source                  1..17
                        mol_type = protein
                        organism = synthetic construct
SEQUENCE: 386
WISAYNGNTN YAQKLQG                                                    17

SEQ ID NO: 387          moltype = AA  length = 17
FEATURE                 Location/Qualifiers
REGION                  1..17
                        note = CDR-H2
source                  1..17
                        mol_type = protein
                        organism = synthetic construct
SEQUENCE: 387
YISSSSSTIY YADSVKG                                                    17

SEQ ID NO: 388          moltype = AA  length = 16
FEATURE                 Location/Qualifiers
REGION                  1..16
                        note = CDR-H2
source                  1..16
                        mol_type = protein
                        organism = synthetic construct
SEQUENCE: 388
YIYYSGSTNY NPSLKS                                                     16

SEQ ID NO: 389          moltype = AA  length = 17
FEATURE                 Location/Qualifiers
REGION                  1..17
                        note = CDR-H2
source                  1..17
                        mol_type = protein
                        organism = synthetic construct
SEQUENCE: 389
IIYPGDSDTR YSPSFQG                                                    17

SEQ ID NO: 390          moltype = AA  length = 16
FEATURE                 Location/Qualifiers
REGION                  1..16
                        note = CDR-H2
source                  1..16
                        mol_type = protein
                        organism = synthetic construct
SEQUENCE: 390
VIYSGGSTYY ADSVKG                                                     16
```

```
SEQ ID NO: 391          moltype = AA  length = 16
FEATURE                 Location/Qualifiers
REGION                  1..16
                        note = CDR-H2
source                  1..16
                        mol_type = protein
                        organism = synthetic construct
SEQUENCE: 391
SIYYSGSTYY NPSLKS                                                  16

SEQ ID NO: 392          moltype = AA  length = 16
FEATURE                 Location/Qualifiers
REGION                  1..16
                        note = CDR-H2
source                  1..16
                        mol_type = protein
                        organism = synthetic construct
SEQUENCE: 392
YIYYSGSTYY NPSLKS                                                  16

SEQ ID NO: 393          moltype = AA  length = 16
FEATURE                 Location/Qualifiers
REGION                  1..16
                        note = CDR-H2
source                  1..16
                        mol_type = protein
                        organism = synthetic construct
SEQUENCE: 393
YIHFSGSTHY HPSLKS                                                  16

SEQ ID NO: 394          moltype = AA  length = 16
FEATURE                 Location/Qualifiers
REGION                  1..16
                        note = CDR-H2
source                  1..16
                        mol_type = protein
                        organism = synthetic construct
SEQUENCE: 394
LIYWNDDKRY SPSLKS                                                  16

SEQ ID NO: 395          moltype = AA  length = 17
FEATURE                 Location/Qualifiers
REGION                  1..17
                        note = CDR-H2
source                  1..17
                        mol_type = protein
                        organism = synthetic construct
SEQUENCE: 395
RINSDGSSTS YADSVKG                                                 17

SEQ ID NO: 396          moltype = AA  length = 16
FEATURE                 Location/Qualifiers
REGION                  1..16
                        note = CDR-H2
source                  1..16
                        mol_type = protein
                        organism = synthetic construct
SEQUENCE: 396
AIGTAGDTYY PGSVKG                                                  16

SEQ ID NO: 397          moltype = AA  length = 17
FEATURE                 Location/Qualifiers
REGION                  1..17
                        note = CDR-H2
source                  1..17
                        mol_type = protein
                        organism = synthetic construct
SEQUENCE: 397
WINAGNGNTK YSQKFQG                                                 17

SEQ ID NO: 398          moltype = AA  length = 17
FEATURE                 Location/Qualifiers
REGION                  1..17
                        note = CDR-H2
source                  1..17
                        mol_type = protein
                        organism = synthetic construct
SEQUENCE: 398
```

```
AISGSGGSTY YADSVKG                                                    17

SEQ ID NO: 399          moltype = AA  length = 17
FEATURE                 Location/Qualifiers
REGION                  1..17
                        note = CDR-H2
source                  1..17
                        mol_type = protein
                        organism = synthetic construct
SEQUENCE: 399
WINTNTGNPT YAQGFTG                                                    17

SEQ ID NO: 400          moltype = AA  length = 17
FEATURE                 Location/Qualifiers
REGION                  1..17
                        note = CDR-H2
source                  1..17
                        mol_type = protein
                        organism = synthetic construct
SEQUENCE: 400
YISSSGSTIY YADSVKG                                                    17

SEQ ID NO: 401          moltype = AA  length = 18
FEATURE                 Location/Qualifiers
REGION                  1..18
                        note = CDR-H2
source                  1..18
                        mol_type = protein
                        organism = synthetic construct
SEQUENCE: 401
RTYYRSKWYN DYAVSVKS                                                   18

SEQ ID NO: 402          moltype = AA  length = 17
FEATURE                 Location/Qualifiers
REGION                  1..17
                        note = CDR-H2
source                  1..17
                        mol_type = protein
                        organism = synthetic construct
SEQUENCE: 402
LVDPEDGETI YAEKFQG                                                    17

SEQ ID NO: 403          moltype = AA  length = 17
FEATURE                 Location/Qualifiers
REGION                  1..17
                        note = CDR-H2
source                  1..17
                        mol_type = protein
                        organism = synthetic construct
SEQUENCE: 403
WMNPNSGNTG YAQKFQG                                                    17

SEQ ID NO: 404          moltype = AA  length = 16
FEATURE                 Location/Qualifiers
REGION                  1..16
                        note = CDR-H2
source                  1..16
                        mol_type = protein
                        organism = synthetic construct
SEQUENCE: 404
YIYHSGSTYY NPSLKS                                                     16

SEQ ID NO: 405          moltype = AA  length = 11
FEATURE                 Location/Qualifiers
REGION                  1..11
                        note = CDR-H2
source                  1..11
                        mol_type = protein
                        organism = synthetic construct
SEQUENCE: 405
ERVSQRGAFD I                                                          11

SEQ ID NO: 406          moltype = AA  length = 10
FEATURE                 Location/Qualifiers
REGION                  1..10
                        note = CDR-H2
source                  1..10
                        mol_type = protein
                        organism = synthetic construct
```

```
SEQUENCE: 406
GNPDKDPFDY                                                          10

SEQ ID NO: 407          moltype = AA  length = 11
FEATURE                 Location/Qualifiers
REGION                  1..11
                        note = CDR-H2
source                  1..11
                        mol_type = protein
                        organism = synthetic construct
SEQUENCE: 407
DFYCTNWYFD L                                                        11

SEQ ID NO: 408          moltype = AA  length = 12
FEATURE                 Location/Qualifiers
REGION                  1..12
                        note = CDR-H2
source                  1..12
                        mol_type = protein
                        organism = synthetic construct
SEQUENCE: 408
ESSSGSYWYF DL                                                       12

SEQ ID NO: 409          moltype = AA  length = 17
FEATURE                 Location/Qualifiers
REGION                  1..17
                        note = CDR-H2
source                  1..17
                        mol_type = protein
                        organism = synthetic construct
SEQUENCE: 409
DSGYKYNLYY YYYYMDV                                                  17

SEQ ID NO: 410          moltype = AA  length = 13
FEATURE                 Location/Qualifiers
REGION                  1..13
                        note = CDR-H2
source                  1..13
                        mol_type = protein
                        organism = synthetic construct
SEQUENCE: 410
GGDLSHYYYY MDV                                                      13

SEQ ID NO: 411          moltype = AA  length = 13
FEATURE                 Location/Qualifiers
REGION                  1..13
                        note = CDR-H2
source                  1..13
                        mol_type = protein
                        organism = synthetic construct
SEQUENCE: 411
ENRRYNSCYY FDY                                                      13

SEQ ID NO: 412          moltype = AA  length = 13
FEATURE                 Location/Qualifiers
REGION                  1..13
                        note = CDR-H2
source                  1..13
                        mol_type = protein
                        organism = synthetic construct
SEQUENCE: 412
GGDLSHYYYY LDV                                                      13

SEQ ID NO: 413          moltype = AA  length = 13
FEATURE                 Location/Qualifiers
REGION                  1..13
                        note = CDR-H2
source                  1..13
                        mol_type = protein
                        organism = synthetic construct
SEQUENCE: 413
ATLLSLSYDA FDI                                                      13

SEQ ID NO: 414          moltype = AA  length = 12
FEATURE                 Location/Qualifiers
REGION                  1..12
                        note = CDR-H2
source                  1..12
                        mol_type = protein
```

```
                        organism = synthetic construct
SEQUENCE: 414
GGDLSHYYYM DV                                                       12

SEQ ID NO: 415          moltype = AA  length = 8
FEATURE                 Location/Qualifiers
REGION                  1..8
                        note = CDR-H2
source                  1..8
                        mol_type = protein
                        organism = synthetic construct
SEQUENCE: 415
ERDRWFDP                                                            8

SEQ ID NO: 416          moltype = AA  length = 11
FEATURE                 Location/Qualifiers
REGION                  1..11
                        note = CDR-H2
source                  1..11
                        mol_type = protein
                        organism = synthetic construct
SEQUENCE: 416
ETPPSLGAFD I                                                        11

SEQ ID NO: 417          moltype = AA  length = 14
FEATURE                 Location/Qualifiers
REGION                  1..14
                        note = CDR-H2
source                  1..14
                        mol_type = protein
                        organism = synthetic construct
SEQUENCE: 417
EAYCLSDSYW YFDL                                                     14

SEQ ID NO: 418          moltype = AA  length = 14
FEATURE                 Location/Qualifiers
REGION                  1..14
                        note = CDR-H2
source                  1..14
                        mol_type = protein
                        organism = synthetic construct
SEQUENCE: 418
ESWKYFYPRG YMDV                                                     14

SEQ ID NO: 419          moltype = AA  length = 11
FEATURE                 Location/Qualifiers
REGION                  1..11
                        note = CDR-H2
source                  1..11
                        mol_type = protein
                        organism = synthetic construct
SEQUENCE: 419
GGVVSHYAMD C                                                        11

SEQ ID NO: 420          moltype = AA  length = 9
FEATURE                 Location/Qualifiers
REGION                  1..9
                        note = CDR-H2
source                  1..9
                        mol_type = protein
                        organism = synthetic construct
SEQUENCE: 420
HYYYYYMDV                                                           9

SEQ ID NO: 421          moltype = AA  length = 9
FEATURE                 Location/Qualifiers
REGION                  1..9
                        note = CDR-H2
source                  1..9
                        mol_type = protein
                        organism = synthetic construct
SEQUENCE: 421
KTTSFYFDY                                                           9

SEQ ID NO: 422          moltype = AA  length = 8
FEATURE                 Location/Qualifiers
REGION                  1..8
                        note = CDR-H2
source                  1..8
```

```
                        mol_type = protein
                        organism = synthetic construct
SEQUENCE: 422
HYYYYMDV                                                        8

SEQ ID NO: 423          moltype = AA  length = 10
FEATURE                 Location/Qualifiers
REGION                  1..10
                        note = CDR-H2
source                  1..10
                        mol_type = protein
                        organism = synthetic construct
SEQUENCE: 423
GVLLYNWFDP                                                      10

SEQ ID NO: 424          moltype = AA  length = 9
FEATURE                 Location/Qualifiers
REGION                  1..9
                        note = CDR-H2
source                  1..9
                        mol_type = protein
                        organism = synthetic construct
SEQUENCE: 424
HYYYYYLDV                                                       9

SEQ ID NO: 425          moltype = AA  length = 11
FEATURE                 Location/Qualifiers
REGION                  1..11
                        note = CDR-H2
source                  1..11
                        mol_type = protein
                        organism = synthetic construct
SEQUENCE: 425
DLPGSYWYFD L                                                    11

SEQ ID NO: 426          moltype = AA  length = 12
FEATURE                 Location/Qualifiers
REGION                  1..12
                        note = CDR-H2
source                  1..12
                        mol_type = protein
                        organism = synthetic construct
SEQUENCE: 426
EGNGANPDAF DI                                                   12

SEQ ID NO: 427          moltype = AA  length = 10
FEATURE                 Location/Qualifiers
REGION                  1..10
                        note = CDR-H2
source                  1..10
                        mol_type = protein
                        organism = synthetic construct
SEQUENCE: 427
RHMRLSCFDY                                                      10

SEQ ID NO: 428          moltype = AA  length = 9
FEATURE                 Location/Qualifiers
REGION                  1..9
                        note = CDR-H2
source                  1..9
                        mol_type = protein
                        organism = synthetic construct
SEQUENCE: 428
HYYYYSMDV                                                       9

SEQ ID NO: 429          moltype = AA  length = 7
FEATURE                 Location/Qualifiers
REGION                  1..7
                        note = CDR-H2
source                  1..7
                        mol_type = protein
                        organism = synthetic construct
SEQUENCE: 429
SFDWFDP                                                         7

SEQ ID NO: 430          moltype = AA  length = 14
FEATURE                 Location/Qualifiers
REGION                  1..14
                        note = CDR-H2
```

```
source                 1..14
                       mol_type = protein
                       organism = synthetic construct
SEQUENCE: 430
ERSISPYYYY YMDV                                                   14

SEQ ID NO: 431         moltype = AA  length = 10
FEATURE                Location/Qualifiers
REGION                 1..10
                       note = CDR-H2
source                 1..10
                       mol_type = protein
                       organism = synthetic construct
SEQUENCE: 431
DSVIWYWFDP                                                        10

SEQ ID NO: 432         moltype = AA  length = 15
FEATURE                Location/Qualifiers
REGION                 1..15
                       note = CDR-H2
source                 1..15
                       mol_type = protein
                       organism = synthetic construct
SEQUENCE: 432
EEILPRLSYY YYMDV                                                  15

SEQ ID NO: 433         moltype = AA  length = 12
FEATURE                Location/Qualifiers
REGION                 1..12
                       note = CDR-H2
source                 1..12
                       mol_type = protein
                       organism = synthetic construct
SEQUENCE: 433
GGRAHSSWYF DL                                                     12

SEQ ID NO: 434         moltype = AA  length = 17
FEATURE                Location/Qualifiers
REGION                 1..17
                       note = CDR-H3
source                 1..17
                       mol_type = protein
                       organism = synthetic construct
SEQUENCE: 434
DRIKILPRLG YYYYMDV                                                17

SEQ ID NO: 435         moltype = AA  length = 12
FEATURE                Location/Qualifiers
REGION                 1..12
                       note = CDR-H3
source                 1..12
                       mol_type = protein
                       organism = synthetic construct
SEQUENCE: 435
DTVIHYYYYM DV                                                     12

SEQ ID NO: 436         moltype = AA  length = 16
FEATURE                Location/Qualifiers
REGION                 1..16
                       note = CDR-H3
source                 1..16
                       mol_type = protein
                       organism = synthetic construct
SEQUENCE: 436
DVIVEVFLSY YYYMDV                                                 16

SEQ ID NO: 437         moltype = AA  length = 12
FEATURE                Location/Qualifiers
REGION                 1..12
                       note = CDR-H3
source                 1..12
                       mol_type = protein
                       organism = synthetic construct
SEQUENCE: 437
DIFIHYYYYM DV                                                     12

SEQ ID NO: 438         moltype = AA  length = 14
FEATURE                Location/Qualifiers
REGION                 1..14
```

```
                        note = CDR-H3
source                  1..14
                        mol_type = protein
                        organism = synthetic construct
SEQUENCE: 438
DGTFYSYSPY YFDY                                                     14

SEQ ID NO: 439          moltype = AA  length = 17
FEATURE                 Location/Qualifiers
REGION                  1..17
                        note = CDR-H3
source                  1..17
                        mol_type = protein
                        organism = synthetic construct
SEQUENCE: 439
EWIKILPRLG YYYYMDV                                                  17

SEQ ID NO: 440          moltype = AA  length = 12
FEATURE                 Location/Qualifiers
REGION                  1..12
                        note = CDR-H3
source                  1..12
                        mol_type = protein
                        organism = synthetic construct
SEQUENCE: 440
DRSLYYYYYM DV                                                       12

SEQ ID NO: 441          moltype = AA  length = 14
FEATURE                 Location/Qualifiers
REGION                  1..14
                        note = CDR-H3
source                  1..14
                        mol_type = protein
                        organism = synthetic construct
SEQUENCE: 441
DKILAPNYYY YMDV                                                     14

SEQ ID NO: 442          moltype = AA  length = 16
FEATURE                 Location/Qualifiers
REGION                  1..16
                        note = CDR-H3
source                  1..16
                        mol_type = protein
                        organism = synthetic construct
SEQUENCE: 442
EKSWKYFYYY YYYMDV                                                   16

SEQ ID NO: 443          moltype = AA  length = 15
FEATURE                 Location/Qualifiers
REGION                  1..15
                        note = CDR-H3
source                  1..15
                        mol_type = protein
                        organism = synthetic construct
SEQUENCE: 443
ENTSTIPYYY YYMDV                                                    15

SEQ ID NO: 444          moltype = AA  length = 19
FEATURE                 Location/Qualifiers
REGION                  1..19
                        note = CDR-H3
source                  1..19
                        mol_type = protein
                        organism = synthetic construct
SEQUENCE: 444
EDVDKNTSTI YYYYYYMDV                                                19

SEQ ID NO: 445          moltype = AA  length = 17
FEATURE                 Location/Qualifiers
REGION                  1..17
                        note = CDR-H3
source                  1..17
                        mol_type = protein
                        organism = synthetic construct
SEQUENCE: 445
DGGDIVSSSA IYWYFDL                                                  17

SEQ ID NO: 446          moltype = AA  length = 14
FEATURE                 Location/Qualifiers
```

```
REGION                  1..14
                        note = CDR-H3
source                  1..14
                        mol_type = protein
                        organism = synthetic construct
SEQUENCE: 446
DLILPPYYYY YMDV                                                     14

SEQ ID NO: 447          moltype = AA  length = 19
FEATURE                 Location/Qualifiers
REGION                  1..19
                        note = CDR-H3
source                  1..19
                        mol_type = protein
                        organism = synthetic construct
SEQUENCE: 447
ETWIKILPRY YYYYYMDV                                                 19

SEQ ID NO: 448          moltype = AA  length = 12
FEATURE                 Location/Qualifiers
REGION                  1..12
                        note = CDR-H3
source                  1..12
                        mol_type = protein
                        organism = synthetic construct
SEQUENCE: 448
DLSRYYYYYM DV                                                       12

SEQ ID NO: 449          moltype = AA  length = 9
FEATURE                 Location/Qualifiers
REGION                  1..9
                        note = CDR-H3
source                  1..9
                        mol_type = protein
                        organism = synthetic construct
SEQUENCE: 449
EHIVLCFDY                                                           9

SEQ ID NO: 450          moltype = AA  length = 15
FEATURE                 Location/Qualifiers
REGION                  1..15
                        note = CDR-H3
source                  1..15
                        mol_type = protein
                        organism = synthetic construct
SEQUENCE: 450
DKILPRPYYY YYMDV                                                    15

SEQ ID NO: 451          moltype = AA  length = 8
FEATURE                 Location/Qualifiers
REGION                  1..8
                        note = CDR-H3
source                  1..8
                        mol_type = protein
                        organism = synthetic construct
SEQUENCE: 451
GSNEYFQH                                                            8

SEQ ID NO: 452          moltype = AA  length = 9
FEATURE                 Location/Qualifiers
REGION                  1..9
                        note = CDR-H3
source                  1..9
                        mol_type = protein
                        organism = synthetic construct
SEQUENCE: 452
GTSYWYFDL                                                           9

SEQ ID NO: 453          moltype = AA  length = 14
FEATURE                 Location/Qualifiers
REGION                  1..14
                        note = CDR-H3
source                  1..14
                        mol_type = protein
                        organism = synthetic construct
SEQUENCE: 453
EEIVEVFYYY YMDV                                                     14

SEQ ID NO: 454          moltype = AA  length = 8
```

```
FEATURE                 Location/Qualifiers
REGION                  1..8
                        note = CDR-H3
source                  1..8
                        mol_type = protein
                        organism = synthetic construct
SEQUENCE: 454
VDDYYFDY                                                                    8

SEQ ID NO: 455          moltype = AA  length = 14
FEATURE                 Location/Qualifiers
REGION                  1..14
                        note = CDR-H3
source                  1..14
                        mol_type = protein
                        organism = synthetic construct
SEQUENCE: 455
STNILLSYTK AFDI                                                             14

SEQ ID NO: 456          moltype = AA  length = 12
FEATURE                 Location/Qualifiers
REGION                  1..12
                        note = CDR-H3
source                  1..12
                        mol_type = protein
                        organism = synthetic construct
SEQUENCE: 456
DKTYYYYYYM DV                                                               12

SEQ ID NO: 457          moltype = AA  length = 19
FEATURE                 Location/Qualifiers
REGION                  1..19
                        note = CDR-H3
source                  1..19
                        mol_type = protein
                        organism = synthetic construct
SEQUENCE: 457
EKYFHDKYFH DYYYYYMDV                                                        19

SEQ ID NO: 458          moltype = AA  length = 12
FEATURE                 Location/Qualifiers
REGION                  1..12
                        note = CDR-H3
source                  1..12
                        mol_type = protein
                        organism = synthetic construct
SEQUENCE: 458
DTSVYYYYYM DV                                                               12

SEQ ID NO: 459          moltype = AA  length = 14
FEATURE                 Location/Qualifiers
REGION                  1..14
                        note = CDR-H3
source                  1..14
                        mol_type = protein
                        organism = synthetic construct
SEQUENCE: 459
EKILPYYYYY YMDV                                                             14

SEQ ID NO: 460          moltype = AA  length = 21
FEATURE                 Location/Qualifiers
REGION                  1..21
                        note = CDR-H3
source                  1..21
                        mol_type = protein
                        organism = synthetic construct
SEQUENCE: 460
QWIYIYINPR GFIFLHDAFD I                                                     21

SEQ ID NO: 461          moltype = AA  length = 12
FEATURE                 Location/Qualifiers
REGION                  1..12
                        note = CDR-H3
source                  1..12
                        mol_type = protein
                        organism = synthetic construct
SEQUENCE: 461
EDVDFHHDAF DI                                                               12
```

```
SEQ ID NO: 462          moltype = AA  length = 19
FEATURE                 Location/Qualifiers
REGION                  1..19
                        note = CDR-H3
source                  1..19
                        mol_type = protein
                        organism = synthetic construct
SEQUENCE: 462
EGVDKNTSTI YYYYYYMDV                                             19

SEQ ID NO: 463          moltype = AA  length = 8
FEATURE                 Location/Qualifiers
REGION                  1..8
                        note = CDR-H3
source                  1..8
                        mol_type = protein
                        organism = synthetic construct
SEQUENCE: 463
DRRGYFDL                                                         8

SEQ ID NO: 464          moltype = AA  length = 15
FEATURE                 Location/Qualifiers
REGION                  1..15
                        note = CDR-H3
source                  1..15
                        mol_type = protein
                        organism = synthetic construct
SEQUENCE: 464
GIHVDIRSME DWFDP                                                 15

SEQ ID NO: 465          moltype = AA  length = 12
FEATURE                 Location/Qualifiers
REGION                  1..12
                        note = CDR-H3
source                  1..12
                        mol_type = protein
                        organism = synthetic construct
SEQUENCE: 465
DIGTSYYYYM DV                                                    12

SEQ ID NO: 466          moltype = AA  length = 15
FEATURE                 Location/Qualifiers
REGION                  1..15
                        note = CDR-H3
source                  1..15
                        mol_type = protein
                        organism = synthetic construct
SEQUENCE: 466
EVVEVFLYYY YYMDV                                                 15

SEQ ID NO: 467          moltype = AA  length = 12
FEATURE                 Location/Qualifiers
REGION                  1..12
                        note = CDR-H3
source                  1..12
                        mol_type = protein
                        organism = synthetic construct
SEQUENCE: 467
DLYYYYYYYM DV                                                    12

SEQ ID NO: 468          moltype = AA  length = 22
FEATURE                 Location/Qualifiers
REGION                  1..22
                        note = CDR-H3
source                  1..22
                        mol_type = protein
                        organism = synthetic construct
SEQUENCE: 468
ESWKYFYPRG SIFIHYYYYM DV                                         22

SEQ ID NO: 469          moltype = AA  length = 14
FEATURE                 Location/Qualifiers
REGION                  1..14
                        note = CDR-H3
source                  1..14
                        mol_type = protein
                        organism = synthetic construct
SEQUENCE: 469
DRIVEVFYYY YMDV                                                  14
```

```
SEQ ID NO: 470          moltype = AA  length = 16
FEATURE                 Location/Qualifiers
REGION                  1..16
                        note = CDR-H3
source                  1..16
                        mol_type = protein
                        organism = synthetic construct
SEQUENCE: 470
EKYFHDWLYY YYYMDV                                                   16

SEQ ID NO: 471          moltype = AA  length = 16
FEATURE                 Location/Qualifiers
REGION                  1..16
                        note = CDR-H3
source                  1..16
                        mol_type = protein
                        organism = synthetic construct
SEQUENCE: 471
DLVDKNTSYY YYYMDV                                                   16

SEQ ID NO: 472          moltype = AA  length = 8
FEATURE                 Location/Qualifiers
REGION                  1..8
                        note = CDR-H3
source                  1..8
                        mol_type = protein
                        organism = synthetic construct
SEQUENCE: 472
VQNEYFQH                                                            8

SEQ ID NO: 473          moltype = AA  length = 6
FEATURE                 Location/Qualifiers
REGION                  1..6
                        note = CDR-H3
source                  1..6
                        mol_type = protein
                        organism = synthetic construct
SEQUENCE: 473
ANWFDP                                                              6

SEQ ID NO: 474          moltype = AA  length = 12
FEATURE                 Location/Qualifiers
REGION                  1..12
                        note = CDR-H3
source                  1..12
                        mol_type = protein
                        organism = synthetic construct
SEQUENCE: 474
GGWTAWYYYM DV                                                       12

SEQ ID NO: 475          moltype = AA  length = 8
FEATURE                 Location/Qualifiers
REGION                  1..8
                        note = CDR-H3
source                  1..8
                        mol_type = protein
                        organism = synthetic construct
SEQUENCE: 475
AKYYYMDV                                                            8

SEQ ID NO: 476          moltype = AA  length = 14
FEATURE                 Location/Qualifiers
REGION                  1..14
                        note = CDR-H3
source                  1..14
                        mol_type = protein
                        organism = synthetic construct
SEQUENCE: 476
DQVDKNTYYY YMDV                                                     14

SEQ ID NO: 477          moltype = AA  length = 10
FEATURE                 Location/Qualifiers
REGION                  1..10
                        note = CDR-H3
source                  1..10
                        mol_type = protein
                        organism = synthetic construct
SEQUENCE: 477
```

```
ACQLAEYFQH                                                    10

SEQ ID NO: 478         moltype = AA  length = 14
FEATURE                Location/Qualifiers
REGION                 1..14
                       note = CDR-H3
source                 1..14
                       mol_type = protein
                       organism = synthetic construct
SEQUENCE: 478
DRVDKNTSYY YMDV                                               14

SEQ ID NO: 479         moltype = AA  length = 12
FEATURE                Location/Qualifiers
REGION                 1..12
                       note = CDR-H3
source                 1..12
                       mol_type = protein
                       organism = synthetic construct
SEQUENCE: 479
RVQLKLVHWF DP                                                 12

SEQ ID NO: 480         moltype = AA  length = 12
FEATURE                Location/Qualifiers
REGION                 1..12
                       note = CDR-H3
source                 1..12
                       mol_type = protein
                       organism = synthetic construct
SEQUENCE: 480
YYDYVTVFYF QH                                                 12

SEQ ID NO: 481         moltype = AA  length = 11
FEATURE                Location/Qualifiers
REGION                 1..11
                       note = CDR-H3
source                 1..11
                       mol_type = protein
                       organism = synthetic construct
SEQUENCE: 481
ESYPSFYAFD I                                                  11

SEQ ID NO: 482         moltype = AA  length = 15
FEATURE                Location/Qualifiers
REGION                 1..15
                       note = CDR-H3
source                 1..15
                       mol_type = protein
                       organism = synthetic construct
SEQUENCE: 482
SNMWSYSLND YYFDY                                              15

SEQ ID NO: 483         moltype = AA  length = 64
FEATURE                Location/Qualifiers
REGION                 1..64
                       note = Hinge (iTIM hinge)
source                 1..64
                       mol_type = protein
                       organism = synthetic construct
SEQUENCE: 483
YGSQSSKPYL LTHPSDPLEL VVSGPSGGPS SPTTGPTSTS GPEDQPLTPT GSDPQSGLGR  60
HLGV                                                          64

SEQ ID NO: 484         moltype = AA  length = 44
FEATURE                Location/Qualifiers
REGION                 1..44
                       note = Short hinge 2
source                 1..44
                       mol_type = protein
                       organism = synthetic construct
SEQUENCE: 484
VVSGPSGGPS SPTTGPTSTS GPEDQPLTPT GSDPQSGLGR HLGV              44

SEQ ID NO: 485         moltype = AA  length = 67
FEATURE                Location/Qualifiers
REGION                 1..67
                       note = Long hinge 1
source                 1..67
                       mol_type = protein
```

```
                         organism = synthetic construct
SEQUENCE: 485
AGSGGSGGSG GSPVPSTPPT PSPSTPPTPS PSGGSGNSSG SGGSPVPSTP PTPSPSTPPT  60
PSPSASV                                                            67

SEQ ID NO: 486           moltype = AA  length = 75
FEATURE                  Location/Qualifiers
REGION                   1..75
                         note = Long hinge 2
source                   1..75
                         mol_type = protein
                         organism = synthetic construct
SEQUENCE: 486
AGSGGSGGSG GSPVPSTPPT NSSSTPPTPS PSPVPSTPPT NSSSTPPTPS PSPVPSTPPT  60
NSSSTPPTPS PSASV                                                   75

SEQ ID NO: 487           moltype = AA  length = 85
FEATURE                  Location/Qualifiers
REGION                   1..85
                         note = 2x short hinge
source                   1..85
                         mol_type = protein
                         organism = synthetic construct
SEQUENCE: 487
VVSGPSGGPS SPTTGPTSTS GPEDQPLTPT GSDPQSGLGR HVVSGPSGGP SSPTTGPTST  60
SGPEDQPLTP TGSDPQSGLG RHLGV                                        85

SEQ ID NO: 488           moltype = AA  length = 32
FEATURE                  Location/Qualifiers
REGION                   1..32
                         note = Hinge (truncated)
source                   1..32
                         mol_type = protein
                         organism = synthetic construct
SEQUENCE: 488
TTGPTSTSGP EDQPLTPTGS DPQSGLGRHL GV                                32

SEQ ID NO: 489           moltype = AA  length = 18
FEATURE                  Location/Qualifiers
REGION                   1..18
                         note = T2A self-cleaving peptide
source                   1..18
                         mol_type = protein
                         organism = unidentified
SEQUENCE: 489
EGRGSLLTCG DVEENPGP                                                18

SEQ ID NO: 490           moltype = AA  length = 20
FEATURE                  Location/Qualifiers
REGION                   1..20
                         note = E2A self-cleaving peptide
source                   1..20
                         mol_type = protein
                         organism = unidentified
SEQUENCE: 490
QCTNYALLKL AGDVESNPGP                                              20

SEQ ID NO: 491           moltype = AA  length = 22
FEATURE                  Location/Qualifiers
REGION                   1..22
                         note = F2A self-cleaving peptide
source                   1..22
                         mol_type = protein
                         organism = unidentified
SEQUENCE: 491
VKQTLNFDLL KLAGDVESNP GP                                           22

SEQ ID NO: 492           moltype = DNA  length = 63
FEATURE                  Location/Qualifiers
misc_feature             1..63
                         note = encodes T2A self-cleaving peptide
source                   1..63
                         mol_type = unassigned DNA
                         organism = unidentified
SEQUENCE: 492
ggatccggag agggcagagg cagcctgctg acatgtggcg acgtggaaga gaaccctggc  60
ccc                                                                63

SEQ ID NO: 493           moltype = RNA  length = 943
```

```
FEATURE                Location/Qualifiers
source                 1..943
                       mol_type = unassigned RNA
                       organism = Homo sapiens
SEQUENCE: 493
attcctgaag ctgacagcat tcgggccgag atgtctcgct ccgtggcctt agctgtgctc  60
gcgctactct ctctttctgg cctggaggct atccagcgta ctccaaagat tcaggtttac  120
tcacgtcatc cagcagagaa tggaaagtca aatttcctga attgctatgt gtctgggttt  180
catccatccg acattgaagt tgacttactg aagaatggag agagaattga aaaagtggag  240
cattcagact tgtctttcag caaggactgg tctttctatc tcttgtacta cactgaattc  300
acccccactg aaaaagatga gtatgcctgc cgtgtgaacc atgtgacttt gtcacagccc  360
aagatagtta agtgggatcg agacatgtaa gcagcatcat ggaggtttga agatgccgca  420
tttggattgg atgaattcca aattctgctt gcttgctttt taatattgat atgcttatac  480
acttacactt tatgcacaaa atgtagggtt ataataatgt taacatggac atgatcttct  540
ttataattct actttgagtg ctgtctccat gtttgatgta tctgagcagg ttgctccaca  600
ggtagctcta ggagggctgg caacttagag gtggggagca gagaattctc ttatccaaca  660
tcaacatctt ggtcagattt gaactcttca atctcttgca ctcaaagctt gttaagatag  720
ttaagcgtgc ataagttaac ttccaattta catactctgc ttagaatttg gggaaaatt  780
tagaaatata attgacagga ttattggaaa tttgttataa tgaatgaaac attttgtcat  840
ataagattca tatttacttc ttatacattt gataaagtaa ggcatggttg tggttaatct  900
ggtttatttt tgttccacaa gttaaataaa tcataaaact tga                    943

SEQ ID NO: 494         moltype = DNA  length = 6654
FEATURE                Location/Qualifiers
source                 1..6654
                       mol_type = unassigned DNA
                       organism = Homo sapiens
SEQUENCE: 494
aagtggaggc gtcgcgctgg cgggcattcc tgaagctgac agcattcggg ccgagatgtc  60
tcgctccgtg gccttagctg tgctcgcgct actctctctt tctggcctgg aggctatcca  120
gcgtgagtct ctcctaccct cccgctctgg tccttcctct cccgctctgc accctctgtg  180
gccctcgctg tgctctctcg ctccgtgact tcccttctcc aagttctcct tggtggcccg  240
ccgtggggct agtccagggc tggatctcgg ggaagcggcg gggtggcctg ggagtgggga  300
agggggtgcg cacccgggac gcgcgctact tgcccctttc ggcggggagc aggggagacc  360
tttggcctac ggcgacggga gggtcgggac aaagtttagg gcgtcgataa gcgtcagagc  420
gccgaggttg ggggagggtt tctcttccgc tctttcgcgg ggcctctggc tcccccagcg  480
cagctggagt gggggacggg taggctcgtc ccaaaggcgc ggcgctgagg tttgtgaacg  540
cgtggagggg cgcttggggt ctgggggagg cgtcgcccgg gtaagcctgt ctgctgcggc  600
tctgcttccc ttagactgga gagctgtgga cttcgtctag gcgcccgcta agttcgcatg  660
tcctagcacc tctgggtcta tgtggggcca caccgtgggg aggaaacagc acgcgacgtt  720
tgtagaatgc ttggctgtga tacaaagcgg tttcgaataa ttaacttatt tgttcccatc  780
acatgtcact tttaaaaaat tataagaact acccgttatt gacatctttc tgtgtgccaa  840
ggactttatg tgctttgcgt catttaattt tgaaaacagt tatcttccgc catagataac  900
tactatggtt atcttctgcc tctcacagat gaagaaacta aggcaccgag attttaagaa  960
acttaattac acaggggata aatggcagca atcgagattg aagtcaagcc taaccagggc  1020
ttttgcggga gcgcatgcct tttggctgta attcgtgcat ttttttttaa gaaaaacgcc  1080
tgccttctgc gtgagattct ccagagcaaa ctgggcggca tgggccctgt ggtcttttcg  1140
tacagagggc ttcctctttg gctctttgcc tggttgtttc caagatgtac tgtgcctctt  1200
actttcggtt ttgaaaacat gagggggttg ggcgtggtag cttacgcctg taatcccagc  1260
acttagggag gccgaggcgg gaggatggct tgaggtccgt agttgagacc agcctggcca  1320
acatggtgaa gcctggtctc tacaaaaaat aataacaaaa attagccggg tgtggtggct  1380
cgtgcctgtg gtcccagctg ctccggtggc tgaggcggga ggatctcttg agcttaggct  1440
tttgagctat catggcgcca gtgcactcca gcgtgggcaa cagagcgaga ccctgtctct  1500
caaaaaagaa aaaaaaaaaa aaagaaagag aaaagaaaag aaagaaagaa gtgaaggttt  1560
gtcagtcagg ggagctgtaa aaccattaat aaagataatc caagatggtt accaagactg  1620
ttgaggacgc cagagatctt gagcactttc taagtacctg gcaatacact aagcgcgctc  1680
accttttcct ctggcaaaac atgatcgaaa gcagaatgtt ttgatcatga gaaaattgca  1740
tttaatttga atacaattta tttacaacat aaaggataat gtatatatca ccaccattac  1800
tggtatttgc tggttatgtt agatgtcatt ttaaaaaata acaatctgat atttaaaaaa  1860
aaatcttatt ttgaaaattt ccaaagtaat acatgccatg catagaccat ttctggaaga  1920
taccacaaga aacatgtaat gatgattgcc tctgaaggtc tattttcctc ctctgacctg  1980
tgtgtgggtt ttgtttttgt tttactgtgg gcataaatta atttttcagt taagttttgg  2040
aagcttaaat aactctccaa aagtcataaa gccagtaact ggttgagccc aaattcaaac  2100
ccagcctgtc tgatacttgt cctcttctta gaaaagatta cagtgatgct ctcacaaaat  2160
cttgccgcct tccctcaaac agagagttcc aggcaggatg aatctgtgct ctgatccctg  2220
aggcatttaa tatgttctta ttattagaag ctcagatgca aagagctctc ttagctttta  2280
atgttatgaa aaaaatcagg tcttcattag attccccaat ccacctcttg atggggctag  2340
tagcctttcc ttaatgatag ggtgtttcta gagagatata tctggtcaag gtggcctggt  2400
actcctcctt ctccccacag cctcccagac aaggaggagt agctgccttt tagtgatcat  2460
gtaccctgaa tataagtgta tttaaaagaa ttttatacac atatatttag tgtcaatctg  2520
tatatttagt agcactaaca cttctcttca ttttcaatga aaaatataga gtttataata  2580
ttttcttccc acttccccat ggatggtcta gtcatgcctc tcattttgga aagtactgtt  2640
tctgaaacat taggcaatat attcccaacc tggctagttt acagcaatca cctgtggatg  2700
ctaattaaaa cgcaaatccc actgtcacat gcattactcc atttgatcat aatggaaagt  2760
atgttctgtc ccatttgcca tagtcctcac ctatccctgt tgtattttat cgggtccaac  2820
tcaaccattt aaggtatttg ccagctcttg tatgcattta ggttttgttt ctttgttttt  2880
tagctcatga aattaggtac aaagtcagag aggggtctgg catataaaac ctcagcagaa  2940
ataaagaggt tttgttgttt ggtaagaaca taccttgggt tggttgggca cggtggctcg  3000
tgcctgtaat cccaacactt tgggaggcca aggcaggctg atcacttgaa gttgggagtt  3060
```

```
caagaccagc ctggccaaca tggtgaaatc ccgtctctac tgaaaataca aaaattaacc  3120
aggcatggtg gtgtgtgcct gtagtcccag gaatcacttg aacccaggag gcggaggttg  3180
cagtgagctg agatctcacc actgcacact gcactccagc ctgggcaatg gaatgagatt  3240
ccatcccaaa aaataaaaaa ataaaaaaat aaagaacata ccttgggttg atccacttag  3300
gaacctcaga taataacatc tgccacgtat agagcaattg ctatgtccca ggcactctac  3360
tagacacttc atacagttta gaaaatcaga tgggtgtaga tcaaggcagg agcaggaacc  3420
aaaaagaaag gcataaacat aagaaaaaaa atggaagggg tggaaacaga gtacaataac  3480
atgagtaatt tgatgggggc tattatgaac tgagaaatga actttgaaaa gtatcttggg  3540
gccaaatcat gtagactctt gagtgatgtg ttaaggaatg ctatgagtgc tgagagggca  3600
tcagaagtcc ttgagagcct ccagagaaag gctcttaaaa atgcagcgca atctccagtg  3660
acagaagata ctgctagaaa tctgctagaa aaaaaacaaa aaaggcatgt atagaggaat  3720
tatgagggaa agataccaag tcacggttta ttcttcaaaa tggaggtggc ttgttgggaa  3780
ggtggaagct catttggcca gagtggaaat ggaattggga gaaatcgatg accaaatgta  3840
aacacttggt gcctgatata gcttgacacc aagttagccc caagtgaaat accctggcaa  3900
tattaatgtg tcttttcccg atattcctca ggtactccaa agattcaggt ttactcacgt  3960
catccagcag agaatggaaa gtcaaatttc ctgaattgct atgtgtctgg gtttcatcca  4020
tccgacattg aagttgactt actgaagaat ggagagagaa ttgaaaaagt ggagcattca  4080
gacttgtctt tcagcaagga ctggtctttc tatctcttgt actacactga attcaccccc  4140
actgaaaaag atgagtatgc ctgccgtgtg aaccatgtga ctttgtcaca gcccaagata  4200
gttaagtggg gtaagtctta cattcttttg taagctgctg aaagttgtgt atgagtagtc  4260
atatcataaa gctgctttga tataaaaaag gtctatggcc atactaccct gaatgagtcc  4320
catcccatct gatataaaca atctgcatat tgggattgtc agggaatgtt cttaaagatc  4380
agattagtgg cacctgctga gatactgatg cacagcatgg tttctgaacc agtagtttcc  4440
ctgcagttga gcagggagca gcagcagcac ttgcacaaat acatatacac tcttaacact  4500
tcttacctac tggcttcctc tagcttttgt ggcagcttca ggtatattta gcactgaacg  4560
aacatctcaa gaaggtatag gcctttgttt gtaagtcctg ctgtcctagc atcctataat  4620
cctggacttc tccagtactt tctggctgga ttggtatctg aggctagtag gaagggcttg  4680
ttcctgctgg gtagctctaa acaatgtatt catgggtagg aacagcagcc tattctgcca  4740
gccttatttc taaccatttt agacatttgt tagtacatgg tattttaaaa gtaaaactta  4800
atgtcttcct tttttttctc cactgtcttt ttcatagatc gagacatgta agcagcatca  4860
tggaggtaag tttttgacct tgagaaaatg tttttgtttc actgtcctga ggactattta  4920
tagacagctc taacatgata accctcacta tgtggagaac attgacagag taacatttta  4980
gcagggaaag aagaatccta cagggtcatg ttcccttctc ctgtggagtg gcatgaagaa  5040
ggtgtatggc cccaggtatg gccatattac tgaccctcta cagagagggc aaaggaactg  5100
ccagtatggt attgcaggat aaaggcaggt ggttacccac attacctgca aggctttgat  5160
ctttcttctg ccatttccac attggacatc tctgctgagg agagaaaatg aaccactctt  5220
ttcctttgta taatgttgtt ttattcttca gacagaagag aggagttata cagctctgca  5280
gacatcccat tcctgtatgg ggactgtgtt tgcctcttag aggttcccag gccactagag  5340
gagataaagg gaaacagatt gttataactt gatataatga tactataata gatgtaacta  5400
caaggagctc cagaagcaag agagagggag gaacttggac ttctctgcat ctttagttgg  5460
agtccaaagg cttttcaatg aaattctact gcccagggta cattgatgct gaaaccccat  5520
tcaaatctcc tgttatattc tagaacaggg aattgatttg ggagagcatc aggaaggtgg  5580
atgatctgcc cagtcacact gttagtaaat tgtagagcca ggacctgaac tctaatatag  5640
tcatgtgtta cttaatgacg gggacatgtt ctgagaaatg cttacacaaa cctaggtgtt  5700
gtagcctact acacgcatag gctacatggt atagcctatt gctcctagac tacaaacctg  5760
tacagcctgt tactgtactg aatactgtgg gcagttgtaa cacaatggta agtatttgtg  5820
tatctaaaca tagaagttgc agtaaaaata tgctatttta atcttatgag accactgtca  5880
tatatacagt ccatcattga ccaaaacatc atatcagcat tttttcttct aagattttgg  5940
gagcaccaaa gggatacact aacaggatat actctttata atgggtttgg agaactgtct  6000
gcagctactt cttttaaaaa ggtgatctac acagtagaaa ttagacaagt ttggtaatga  6060
gatctgcaat ccaaataaaa taaattcatt gctaaccttt ttcttttctt ttcaggtttg  6120
aagatgccgc atttggattg gatgaattcc aaattctgct tgcttgcttt ttaatattga  6180
tatgcttata cacttacact ttatgcacaa aatgtagggt tataataatg ttaacatgga  6240
catgatcttc tttataattc tactttgagt gctgtctcca tgtttgatgt atctgagcag  6300
gttgctccac aggtagctct aggagggctg gcaacttaga ggtggggagc agagaattct  6360
cttatccaac atcaacatct tggtcagatt tgaactcttc aatctcttgc actcaaagct  6420
tgttaagata gttaagcgtg cataagttaa cttccaattt acatactctg cttagaattt  6480
gggggaaaat ttagaaatat aattgacagg attattggaa atttgttata atgaatgaaa  6540
cattttgtca tataagattc atatttactt cttatacatt tgataaagta aggcatggtt  6600
gtggttaatc tggtttattt ttgttccaca agttaaataa atcataaaac ttga        6654
```

```
SEQ ID NO: 495          moltype = DNA  length = 1698
FEATURE                 Location/Qualifiers
misc_feature            1..1698
                        note = HLA-A*02:01:01:01 sequence encoding mRNA
source                  1..1698
                        mol_type = other DNA
                        organism = synthetic construct
SEQUENCE: 495
cagaagcaga ggggtcaggg cgaagtccca gggccccagg cgtggctctc agggtctcag  60
gccccgaagg cggtgtatgg attggggagt cccagccttg gggattcccc aactccgcag  120
tttcttttct ccctctccca acctatgtag ggtccttctt cctggatact cacgacgcgg  180
acccagttct cactcccatt gggtgtcggg tttccagaga agccaatcag tgtcgtcgcg  240
gtcgcggttc taaagtccgc acgcacccac cgggactcag attctcccca gacgccgagg  300
atggccgtca tggcgccccg aaccctcgtc ctgctactct cgggggctct ggccctgacc  360
cagacctggg cgggctctca ctccatgagg tatttcttca catccgtgtc ccggcccggc  420
cgcggggagc cccgcttcat cgcagtgggc tacgtggacg acacgcagtt cgtgcggttc  480
gacagcgacg ccgcgagcca gaggatggag ccgcgggcgc cgtggataga gcaggagggt  540
ccggagtatt gggacgggga gacacggaaa gtgaaggccc actcacagac tcaccgagtg  600
```

```
gacctgggga ccctgcgcgg ctactacaac cagagcgagg ccggttctca caccgtccag  660
aggatgtatg gctgcgacgt ggggtcggac tggcgcttcc tccgcgggta ccaccagtac  720
gcctacgacg gcaaggatta catcgccctg aaagaggacc tgcgctcttg gaccgcggcg  780
gacatggcag ctcagaccac caagcacaag tgggaggcgg cccatgtggc ggagcagttg  840
agagcctacc tggagggcac gtgcgtggag tggctccgca gatacctgga gaacgggaag  900
gagacgctgc agcgcacgga cgcccccaaa acgcatatga ctcaccacgc tgtctctgac  960
catgaagcca ccctgaggtg ctgggccctg agcttctacc ctgcggagat cacactgacc  1020
tggcagcggg atggggagga ccagacccag gacacggagc tcgtggagac caggcctgca  1080
ggggatggaa ccttccagaa gtgggcggct gtggtggtgc cttctggaca ggagcagaga  1140
tacacctgcc atgtgcagca tgagggtttg cccaagcccc tcaccctgag atgggagccg  1200
tcttcccagc ccaccatccc catcgtgggc atcattgctg gcctggttct ctttggagct  1260
gtgatcactg gagctgtggt cgctgctgtg atgtggagga ggaagagctc agatagaaaa  1320
ggagggagct actctcaggc tgcaagcagt gacagtgccc agggctctga tgtgtctctc  1380
acagcttgta aagtgtgaga cagctgcctt gtgtgggact gagaggcaag agttgttcct  1440
gcccttccct ttgtgacttg aagaaccctg actttgtttc tgcaaaggca cctgcatgtg  1500
tctgtgttcg tgtaggcata atgtgaggag gtggggagac caccccaccc ccatgtccac  1560
catgaccctc ttcccacgct gacctgtgct ccctccccaa tcatctttcc tgttccagag  1620
aggtggggct gaggtgtctc catctctgtc tcaacttcat ggtgcactga gctgtaactt  1680
cttccttccc tattaaaa                                                1698

SEQ ID NO: 496         moltype = DNA  length = 3217
FEATURE                Location/Qualifiers
source                 1..3217
                       mol_type = unassigned DNA
                       organism = Homo sapiens
SEQUENCE: 496
atggccgtca tggcgccccg aaccctcgtc ctgctactct cggggggctct ggccctgacc  60
```

```
atggccgtca tggcgccccg aaccctcgtc ctgctactct cgggggctct ggccctgacc  60
cagacctggg cgggtgagtg cggggtcggg agggaaacgg cctctgtggg gagaagcaac  120
gggcccgcct ggcgggggcg caggacccgg gaagccgcgc cgggaggagg gtcgggcggg  180
tctcagccac tcctcgtccc caggctctca ctccatgagg tatttcttca catccgtgtc  240
ccggcccggc cgcggggagc cccgcttcat cgcagtgggc tacgtggacg acacgcagtt  300
cgtgcggttc gacagcgacg ccgcgagcca gaggatggag ccgcgggcgc cgtggataga  360
gcaggagggt ccggagtatt gggacgggga gacacggaaa gtgaaggccc actcacagac  420
tcaccgagtg gacctgggga ccctgcgcgg ctactacaac cagagcgagg ccggtgagtg  480
accccggccc ggggcgcagg tcacgacctc tcatccccca cggacgggcc aggtcgccca  540
cagtctccgg gtccgagatc cgccccgaag ccgcgggacc ccgagaccct tgccccggga  600
gaggcccagg cgcctttacc cggtttcatt ttcagtttag gccaaaaatc cccccaggtt  660
ggtcggggcg gggcggggct cggggggaccg ggctgaccgc ggggtccggg ccaggttctc  720
acaccgtcca gaggatgtat ggctgcgacg tggggtcgga ctggcgcttc ctccgcgggt  780
accaccagta cgcctacgac ggcaaggatt acatcgccct gaaagaggac ctgcgctctt  840
tgaccgcggc ggacatggca gctcagacca ccaagcacaa gtgggaggcg gcccatgtgg  900
cggagcagtt gagagcctac ctggagggca cgtgcgtgga gtggctccgc agatacctgg  960
agaacgggaa ggagacgctg cagcgcacgg gtaccagggg ccacggggcg cctccctgat  1020
cgcctgtaga tctcccgggc tggcctccca caaggagggg agacaattgg gaccaacact  1080
agaatatcgc cctccctctg gtcctgaggg agaggaatcc tcctgggttt ccagatcctg  1140
taccagagag tgactctgag gttccgccct gctctctgac acaattaagg gataaaatct  1200
ctgaaggaat gacgggaaga cgatccctcg aatactgatg agtggttccc tttgacacac  1260
acaggcagca gccttgggcc cgtgactttt cctctcaggc cttgttctct gcttcacact  1320
caatgtgtgt gggggtctga gtccagcact tctgagtcct tcagcctcca ctcaggtcag  1380
gaccagaagt cgctgttccc tcttcaggga ctagaatttt ccacggaata ggagattatc  1440
ccaggtgcct gtgtccaggc tggtgtctgg gttctgtgct cccttcccca tcccaggtgt  1500
cctgtccatt ctcaagatag ccacatgtgt gctggaggag tgtcccatga cagatgcaaa  1560
atgcctgaat gatctgactc ttcctgacag acgcccccaa aacgcatatg actcaccacg  1620
ctgtctctga ccatgaagcc accctgaggt gctgggccct gagcttctac cctgcggaga  1680
tcacactgac ctggcagcgg gatggggagg accagaccca ggacacggag ctcgtggaga  1740
ccaggcctgc aggggatgga accttccaga agtgggcggc tgtggtggtg ccttctggac  1800
aggagcagag atacacctgc catgtgcagc atgagggttt gcccaagccc ctcaccctga  1860
gatggggtaa ggagggagac gggggtgtca tgtcttttag ggaaagcagg agcctctctg  1920
acctttagca gggtcagggc ccctcacctt cccctctttt cccagagccg tcttcccagc  1980
ccaccatccc catcgtgggc atcattgctg gcctggttct ctttggagct gtgatcactg  2040
gagctgtggt cgctgctgtg atgtggagga ggaagagctc aggtggggaa ggggtgaagg  2100
gtgggtctga gatttcttgt ctcactgagg gttccaagac ccaggtagaa gtgtgccctg  2160
cctcgttact gggaagcacc acccacaatt atgggcctac ccagcctggg ccctgtgtgc  2220
cagcacttac tcttttgtaa agcacctgtt aaaatgaagg acagatttat caccttgatt  2280
acagcggtga tgggacctga tcccagcagt cacaagtcac aggggaaggt ccctgaggac  2340
cttcaggagg gcggttggtc caggacccac acctgctttc ttcatgtttc ctgatcccgc  2400
cctgggtctg cagtcacaca tttctggaaa cttctctgag gtccaagact tggaggttcc  2460
tctaggacct taaggccctg actcctttct ggtatctcac aggacatttt cttcccacag  2520
atagaaaagg agggagctac tctcaggctg caagtaagta tgaaggaggc tgatgcctga  2580
ggtccttggg atattgtgtt tgggagccca tgggggagct cacccacccc acaattcctc  2640
ctctagccac atcttctgtg ggatctgacc aggttctgtt tttgttctac cccaggcagt  2700
gacagtgccc agggctctga tgtgtctctc acagcttgta aaggtgagag cctggagggc  2760
ctgatgtgtg ttgggtgttg ggcggaacag tggacacagc tgtgctatgg ggtttctttc  2820
cattggatgt attgagcatg cgatgggctg tttaaagtgt gacccctcac tgtgacagat  2880
acgaatttgt tcatgaatat ttttttctat agtgtgagac agctgccttg tgtgggactg  2940
agaggcaaga gttgttcctg cccttccctt tgtgacttga agaaccctga ctttgtttct  3000
gcaaaggcac ctgcatgtgt ctgtgttcgt gtaggcataa tgtgaggagg tggggagacc  3060
accccacccc catgtccacc atgaccctct tcccacgctg acctgtgctc cctccccaat  3120
catctttcct gttccagaga ggtggggctg aggtgtctcc atctctgtct caacttcatg  3180
```

```
gtgcactgag ctgtaacttc ttccttccct attaaaa                         3217

SEQ ID NO: 497         moltype = DNA  length = 83
FEATURE                Location/Qualifiers
misc_feature           1..83
                       note = encodes scaffold sequence
source                 1..83
                       mol_type = unassigned DNA
                       organism = unidentified
SEQUENCE: 497
gttttagagc tagaaatagc aagttaaaat aaggctagtc cgttatcaac ttgaaaaagt  60
ggcaccgagt cggtgctttt ttt                                         83

SEQ ID NO: 498         moltype = DNA  length = 20
FEATURE                Location/Qualifiers
misc_feature           1..20
                       note = Guide Nucleic Acid Targeting Sequence
source                 1..20
                       mol_type = other DNA
                       organism = synthetic construct
SEQUENCE: 498
tggacgacac gcagttcgtg                                             20

SEQ ID NO: 499         moltype = DNA  length = 20
FEATURE                Location/Qualifiers
misc_feature           1..20
                       note = Guide Nucleic Acid Targeting Sequence
source                 1..20
                       mol_type = other DNA
                       organism = synthetic construct
SEQUENCE: 499
cagatacctg gagaacggga                                             20

SEQ ID NO: 500         moltype = DNA  length = 20
FEATURE                Location/Qualifiers
misc_feature           1..20
                       note = Guide Nucleic Acid Targeting Sequence
source                 1..20
                       mol_type = other DNA
                       organism = synthetic construct
SEQUENCE: 500
tcccgttctc caggtatctg                                             20

SEQ ID NO: 501         moltype = DNA  length = 20
FEATURE                Location/Qualifiers
misc_feature           1..20
                       note = Guide Nucleic Acid Targeting Sequence
source                 1..20
                       mol_type = other DNA
                       organism = synthetic construct
SEQUENCE: 501
ccgccgcggt ccaagagcgc                                             20

SEQ ID NO: 502         moltype = DNA  length = 20
FEATURE                Location/Qualifiers
misc_feature           1..20
                       note = Guide Nucleic Acid Targeting Sequence
source                 1..20
                       mol_type = other DNA
                       organism = synthetic construct
SEQUENCE: 502
cctgcgctct tggaccgcgg                                             20

SEQ ID NO: 503         moltype = DNA  length = 21
FEATURE                Location/Qualifiers
misc_feature           1..21
                       note = Guide Nucleic Acid Targeting Sequence
source                 1..21
                       mol_type = other DNA
                       organism = synthetic construct
SEQUENCE: 503
ggacctgcgc tcttggaccg c                                           21

SEQ ID NO: 504         moltype = DNA  length = 23
FEATURE                Location/Qualifiers
misc_feature           1..23
                       note = Guide Nucleic Acid Targeting Sequence
source                 1..23
                       mol_type = other DNA
```

```
                        organism = synthetic construct
SEQUENCE: 504
aaggagacgc tgcagcgcac ggg                                              23

SEQ ID NO: 505          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 505
gaaggagacg ctgcagcgca cgg                                              23

SEQ ID NO: 506          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 506
gcgggcgccg tggatagagc agg                                              23

SEQ ID NO: 507          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 507
tgctctatcc acggcgcccg cgg                                              23

SEQ ID NO: 508          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 508
cgatgaagcg gggctccccg cgg                                              23

SEQ ID NO: 509          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 509
cgtgtcccgg cccggccgcg ggg                                              23

SEQ ID NO: 510          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 510
cggctccatc ctctggctcg cgg                                              23

SEQ ID NO: 511          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 511
gatgtaatcc ttgccgtcgt agg                                              23

SEQ ID NO: 512          moltype = DNA  length = 23
FEATURE                 Location/Qualifiers
misc_feature            1..23
                        note = Guide Nucleic Acid Targeting Sequence
source                  1..23
```

```
                         mol_type = other DNA
                         organism = synthetic construct
SEQUENCE: 512
acagcgacgc cgcgagccag agg                                              23

SEQ ID NO: 513           moltype = DNA  length = 23
FEATURE                  Location/Qualifiers
misc_feature             1..23
                         note = Guide Nucleic Acid Targeting Sequence
source                   1..23
                         mol_type = other DNA
                         organism = synthetic construct
SEQUENCE: 513
ggatggagcc gcgggcgccg tgg                                              23

SEQ ID NO: 514           moltype = DNA  length = 23
FEATURE                  Location/Qualifiers
misc_feature             1..23
                         note = Guide Nucleic Acid Targeting Sequence
source                   1..23
                         mol_type = other DNA
                         organism = synthetic construct
SEQUENCE: 514
ggcgccgtgg atagagcagg agg                                              23

SEQ ID NO: 515           moltype = DNA  length = 23
FEATURE                  Location/Qualifiers
misc_feature             1..23
                         note = Guide Nucleic Acid Targeting Sequence
source                   1..23
                         mol_type = other DNA
                         organism = synthetic construct
SEQUENCE: 515
gcgccgtgga tagagcagga ggg                                              23

SEQ ID NO: 516           moltype = DNA  length = 23
FEATURE                  Location/Qualifiers
misc_feature             1..23
                         note = Guide Nucleic Acid Targeting Sequence
source                   1..23
                         mol_type = other DNA
                         organism = synthetic construct
SEQUENCE: 516
cggctactac aaccagagcg agg                                              23

SEQ ID NO: 517           moltype = DNA  length = 23
FEATURE                  Location/Qualifiers
misc_feature             1..23
                         note = Guide Nucleic Acid Targeting Sequence
source                   1..23
                         mol_type = other DNA
                         organism = synthetic construct
SEQUENCE: 517
ctggttgtag tagccgcgca ggg                                              23

SEQ ID NO: 518           moltype = DNA  length = 23
FEATURE                  Location/Qualifiers
misc_feature             1..23
                         note = Guide Nucleic Acid Targeting Sequence
source                   1..23
                         mol_type = other DNA
                         organism = synthetic construct
SEQUENCE: 518
tactacaacc agagcgaggc cgg                                              23

SEQ ID NO: 519           moltype = DNA  length = 23
FEATURE                  Location/Qualifiers
misc_feature             1..23
                         note = Guide Nucleic Acid Targeting Sequence
source                   1..23
                         mol_type = other DNA
                         organism = synthetic construct
SEQUENCE: 519
ctacctggag ggcacgtgcg tgg                                              23

SEQ ID NO: 520           moltype = DNA  length = 23
FEATURE                  Location/Qualifiers
misc_feature             1..23
                         note = Guide Nucleic Acid Targeting Sequence
```

```
source                  1..23
                        mol_type = other DNA
                        organism = synthetic construct
SEQUENCE: 520
cacgcacgtg ccctccaggt agg                                          23

SEQ ID NO: 521          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 521
gcagggtccc caggtccact cgg                                          23

SEQ ID NO: 522          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 522
gtggacctgg ggaccctgcg cgg                                          23

SEQ ID NO: 523          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 523
tggagggcac gtgcgtggag tgg                                          23

SEQ ID NO: 524          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 524
gtatggctgc gacgtggggt cgg                                          23

SEQ ID NO: 525          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 525
ctgagctgcc atgtccgccg cgg                                          23

SEQ ID NO: 526          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 526
ggattacatc gccctgaaag agg                                          23

SEQ ID NO: 527          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 527
caagtgggag gcggcccatg tgg                                          23

SEQ ID NO: 528          moltype = DNA  length = 23
FEATURE                 Location/Qualifiers
misc_feature            1..23
```

```
                         note = Guide Nucleic Acid Targeting Sequence
source                   1..23
                         mol_type = other DNA
                         organism = synthetic construct
SEQUENCE: 528
gtgggaggcg gcccatgtgg cgg                                          23

SEQ ID NO: 529           moltype = DNA  length = 23
FEATURE                  Location/Qualifiers
misc_feature             1..23
                         note = Guide Nucleic Acid Targeting Sequence
source                   1..23
                         mol_type = other DNA
                         organism = synthetic construct
SEQUENCE: 529
cagttgagag cctacctgga ggg                                          23

SEQ ID NO: 530           moltype = DNA  length = 23
FEATURE                  Location/Qualifiers
misc_feature             1..23
                         note = Guide Nucleic Acid Targeting Sequence
source                   1..23
                         mol_type = other DNA
                         organism = synthetic construct
SEQUENCE: 530
gcagttgaga gcctacctgg agg                                          23

SEQ ID NO: 531           moltype = DNA  length = 23
FEATURE                  Location/Qualifiers
misc_feature             1..23
                         note = Guide Nucleic Acid Targeting Sequence
source                   1..23
                         mol_type = other DNA
                         organism = synthetic construct
SEQUENCE: 531
taccaccagt acgcctacga cgg                                          23

SEQ ID NO: 532           moltype = DNA  length = 23
FEATURE                  Location/Qualifiers
misc_feature             1..23
                         note = Guide Nucleic Acid Targeting Sequence
source                   1..23
                         mol_type = other DNA
                         organism = synthetic construct
SEQUENCE: 532
tgccgtcgta ggcgtactgg tgg                                          23

SEQ ID NO: 533           moltype = DNA  length = 23
FEATURE                  Location/Qualifiers
misc_feature             1..23
                         note = Guide Nucleic Acid Targeting Sequence
source                   1..23
                         mol_type = other DNA
                         organism = synthetic construct
SEQUENCE: 533
ccagtacgcc tacgacggca agg                                          23

SEQ ID NO: 534           moltype = DNA  length = 23
FEATURE                  Location/Qualifiers
misc_feature             1..23
                         note = Guide Nucleic Acid Targeting Sequence
source                   1..23
                         mol_type = other DNA
                         organism = synthetic construct
SEQUENCE: 534
ggatgtgaag aaatacctca tgg                                          23

SEQ ID NO: 535           moltype = DNA  length = 23
FEATURE                  Location/Qualifiers
misc_feature             1..23
                         note = Guide Nucleic Acid Targeting Sequence
source                   1..23
                         mol_type = other DNA
                         organism = synthetic construct
SEQUENCE: 535
atttcttcac atccgtgtcc cgg                                          23

SEQ ID NO: 536           moltype = DNA  length = 23
FEATURE                  Location/Qualifiers
```

```
misc_feature          1..23
                      note = Guide Nucleic Acid Targeting Sequence
source                1..23
                      mol_type = other DNA
                      organism = synthetic construct
SEQUENCE: 536
aggcgtactg gtggtacccg cgg                                          23

SEQ ID NO: 537        moltype = DNA  length = 23
FEATURE               Location/Qualifiers
misc_feature          1..23
                      note = Guide Nucleic Acid Targeting Sequence
source                1..23
                      mol_type = other DNA
                      organism = synthetic construct
SEQUENCE: 537
cgtactggtg gtacccgcgg agg                                          23

SEQ ID NO: 538        moltype = DNA  length = 23
FEATURE               Location/Qualifiers
misc_feature          1..23
                      note = Guide Nucleic Acid Targeting Sequence
source                1..23
                      mol_type = other DNA
                      organism = synthetic construct
SEQUENCE: 538
gaggatgtat ggctgcgacg tgg                                          23

SEQ ID NO: 539        moltype = DNA  length = 23
FEATURE               Location/Qualifiers
misc_feature          1..23
                      note = Guide Nucleic Acid Targeting Sequence
source                1..23
                      mol_type = other DNA
                      organism = synthetic construct
SEQUENCE: 539
ggatgtatgg ctgcgacgtg ggg                                          23

SEQ ID NO: 540        moltype = DNA  length = 23
FEATURE               Location/Qualifiers
misc_feature          1..23
                      note = Guide Nucleic Acid Targeting Sequence
source                1..23
                      mol_type = other DNA
                      organism = synthetic construct
SEQUENCE: 540
ctcagaccac caagcacaag tgg                                          23

SEQ ID NO: 541        moltype = DNA  length = 23
FEATURE               Location/Qualifiers
misc_feature          1..23
                      note = Guide Nucleic Acid Targeting Sequence
source                1..23
                      mol_type = other DNA
                      organism = synthetic construct
SEQUENCE: 541
tcagaccacc aagcacaagt ggg                                          23

SEQ ID NO: 542        moltype = DNA  length = 23
FEATURE               Location/Qualifiers
misc_feature          1..23
                      note = Guide Nucleic Acid Targeting Sequence
source                1..23
                      mol_type = other DNA
                      organism = synthetic construct
SEQUENCE: 542
caccaagcac aagtgggagg cgg                                          23

SEQ ID NO: 543        moltype = DNA  length = 23
FEATURE               Location/Qualifiers
misc_feature          1..23
                      note = Guide Nucleic Acid Targeting Sequence
source                1..23
                      mol_type = other DNA
                      organism = synthetic construct
SEQUENCE: 543
gaccaccaag cacaagtggg agg                                          23

SEQ ID NO: 544        moltype = DNA  length = 23
```

```
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 544
gagccccgct tcatcgcagt ggg                                          23

SEQ ID NO: 545         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 545
gtagcccact gcgatgaagc ggg                                          23

SEQ ID NO: 546         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 546
tagcccactg cgatgaagcg ggg                                          23

SEQ ID NO: 547         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 547
cgtagcccac tgcgatgaag cgg                                          23

SEQ ID NO: 548         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 548
cttcatcgca gtgggctacg tgg                                          23

SEQ ID NO: 549         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 549
ggagccccgc ttcatcgcag tgg                                          23

SEQ ID NO: 550         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 550
cggggagaca cggaaagtga agg                                          23

SEQ ID NO: 551         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 551
agtattggga cggggagaca cgg                                          23
```

```
SEQ ID NO: 552         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 552
agggtccgga gtattgggac ggg                                          23

SEQ ID NO: 553         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 553
gagggtccgg agtattggga cgg                                          23

SEQ ID NO: 554         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 554
ggaccctcct gctctatcca cgg                                          23

SEQ ID NO: 555         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 555
gtggatagag caggagggtc cgg                                          23

SEQ ID NO: 556         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 556
agactcaccg agtggacctg ggg                                          23

SEQ ID NO: 557         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 557
cactcggtga gtctgtgagt ggg                                          23

SEQ ID NO: 558         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 558
cagactcacc gagtggacct ggg                                          23

SEQ ID NO: 559         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 559
ccactcacag actcaccgag tgg                                          23
```

```
SEQ ID NO: 560          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 560
ccactcggtg agtctgtgag tgg                                          23

SEQ ID NO: 561          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 561
tcggactggc gcttcctccg cgg                                          23

SEQ ID NO: 562          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 562
gcagccatac atcctctgga cgg                                          23

SEQ ID NO: 563          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 563
tctcaactgc tccgccacat ggg                                          23

SEQ ID NO: 564          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 564
accctcatgc tgcacatggc agg                                          23

SEQ ID NO: 565          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 565
acctgccatg tgcagcatga ggg                                          23

SEQ ID NO: 566          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 566
cacctgccat gtgcagcatg agg                                          23

SEQ ID NO: 567          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 567
```

```
ggaggaccag acccaggaca cgg                                          23

SEQ ID NO: 568         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 568
ggatggggag gaccagaccc agg                                          23

SEQ ID NO: 569         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 569
gacctggcag cgggatgggg agg                                          23

SEQ ID NO: 570         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 570
agatcacact gacctggcag cgg                                          23

SEQ ID NO: 571         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 571
gatcacactg acctggcagc ggg                                          23

SEQ ID NO: 572         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 572
aggtcagtgt gatctccgca ggg                                          23

SEQ ID NO: 573         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 573
aagcccctca ccctgagatg ggg                                          23

SEQ ID NO: 574         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 574
ctgcggagat cacactgacc tgg                                          23

SEQ ID NO: 575         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
```

```
SEQUENCE: 575
cagcaatgat gcccacgatg ggg                                          23

SEQ ID NO: 576         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 576
ccagcaatga tgcccacgat ggg                                          23

SEQ ID NO: 577         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 577
gccagcaatg atgcccacga tgg                                          23

SEQ ID NO: 578         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 578
ggatggaacc ttccagaagt ggg                                          23

SEQ ID NO: 579         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 579
gggatggaac cttccagaag tgg                                          23

SEQ ID NO: 580         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 580
atgcccacga tggggatggt ggg                                          23

SEQ ID NO: 581         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 581
cagcccacca tccccatcgt ggg                                          23

SEQ ID NO: 582         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 582
ccagcccacc atccccatcg tgg                                          23

SEQ ID NO: 583         moltype = DNA  length = 23
FEATURE                Location/Qualifiers
misc_feature           1..23
                       note = Guide Nucleic Acid Targeting Sequence
source                 1..23
                       mol_type = other DNA
```

```
                       organism = synthetic construct
SEQUENCE: 583
gatgcccacg atggggatgg tgg                                          23

SEQ ID NO: 584         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 584
cagggcccag cacctcaggg tgg                                          23

SEQ ID NO: 585         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 585
aatgatgccc acgatgggga tgg                                          23

SEQ ID NO: 586         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 586
ggccctgacc cagacctggg cgg                                          23

SEQ ID NO: 587         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 587
gacccaggac acggagctcg tgg                                          23

SEQ ID NO: 588         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 588
acacggagct cgtggagacc agg                                          23

SEQ ID NO: 589         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 589
cgtggagacc aggcctgcag ggg                                          23

SEQ ID NO: 590         moltype = DNA  length = 23
FEATURE                Location/Qualifiers
misc_feature           1..23
                       note = Guide Nucleic Acid Targeting Sequence
source                 1..23
                       mol_type = other DNA
                       organism = synthetic construct
SEQUENCE: 590
tcgtggagac caggcctgca ggg                                          23

SEQ ID NO: 591         moltype = DNA  length = 23
FEATURE                Location/Qualifiers
misc_feature           1..23
                       note = Guide Nucleic Acid Targeting Sequence
source                 1..23
```

```
                        mol_type = other DNA
                        organism = synthetic construct
SEQUENCE: 591
agctgtgatc actggagctg tgg                                            23

SEQ ID NO: 592          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 592
aaaaggaggg agctactctc agg                                            23

SEQ ID NO: 593          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 593
atgtggagga ggaagagctc agg                                            23

SEQ ID NO: 594          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 594
gtgtctctca cagcttgtaa agg                                            23

SEQ ID NO: 595          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 595
gagagacaca tcagagccct ggg                                            23

SEQ ID NO: 596          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 596
ctccgcaggg tagaagctca ggg                                            23

SEQ ID NO: 597          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 597
ggccctgagc ttctaccctg cgg                                            23

SEQ ID NO: 598          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 598
gctcagggcc cagcacctca ggg                                            23

SEQ ID NO: 599          moltype = DNA  length = 23
FEATURE                 Location/Qualifiers
misc_feature            1..23
                        note = Guide Nucleic Acid Targeting Sequence
```

```
source                  1..23
                        mol_type = other DNA
                        organism = synthetic construct
SEQUENCE: 599
tatctctgct cctgtccaga agg                                          23

SEQ ID NO: 600          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 600
agtagcagga cgagggttcg ggg                                          23

SEQ ID NO: 601          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 601
ccccgagagt agcaggacga ggg                                          23

SEQ ID NO: 602          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 602
ccctcgtcct gctactctcg ggg                                          23

SEQ ID NO: 603          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 603
cctcgtcctg ctactctcgg ggg                                          23

SEQ ID NO: 604          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 604
ctgtggtcgc tgctgtgatg tgg                                          23

SEQ ID NO: 605          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 605
tcgctgctgt gatgtggagg agg                                          23

SEQ ID NO: 606          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 606
tggtcgctgc tgtgatgtgg agg                                          23

SEQ ID NO: 607          moltype = DNA  length = 23
FEATURE                 Location/Qualifiers
misc_feature            1..23
```

```
                        note = Guide Nucleic Acid Targeting Sequence
source                  1..23
                        mol_type = other DNA
                        organism = synthetic construct
SEQUENCE: 607
cacagccgcc cacttctgga agg                                            23

SEQ ID NO: 608          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 608
ccagaagtgg gcggctgtgg tgg                                            23

SEQ ID NO: 609          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 609
tggaaccttc cagaagtggg cgg                                            23

SEQ ID NO: 610          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 610
tcacagctcc aaagagaacc agg                                            23

SEQ ID NO: 611          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 611
ctgaccatga agccaccctg agg                                            23

SEQ ID NO: 612          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 612
gcaaaccctc atgctgcaca tgg                                            23

SEQ ID NO: 613          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 613
tgaagccacc ctgaggtgct ggg                                            23

SEQ ID NO: 614          moltype = DNA  length = 23
FEATURE                 Location/Qualifiers
misc_feature            1..23
                        note = Guide Nucleic Acid Targeting Sequence
source                  1..23
                        mol_type = other DNA
                        organism = synthetic construct
SEQUENCE: 614
ggtgagtcat atgcgttttg ggg                                            23

SEQ ID NO: 615          moltype = DNA  length = 23
FEATURE                 Location/Qualifiers
```

```
misc_feature          1..23
                      note = Guide Nucleic Acid Targeting Sequence
source                1..23
                      mol_type = other DNA
                      organism = synthetic construct
SEQUENCE: 615
gtgagtcata tgcgttttgg ggg                                          23

SEQ ID NO: 616        moltype = DNA  length = 23
FEATURE               Location/Qualifiers
misc_feature          1..23
                      note = Guide Nucleic Acid Targeting Sequence
source                1..23
                      mol_type = other DNA
                      organism = synthetic construct
SEQUENCE: 616
cttcatggtc agagacagcg tgg                                          23

SEQ ID NO: 617        moltype = DNA  length = 23
FEATURE               Location/Qualifiers
misc_feature          1..23
                      note = Guide Nucleic Acid Targeting Sequence
source                1..23
                      mol_type = other DNA
                      organism = synthetic construct
SEQUENCE: 617
tctggccctg acccagacct ggg                                          23

SEQ ID NO: 618        moltype = DNA  length = 20
FEATURE               Location/Qualifiers
misc_feature          1..20
                      note = sequence targeting B2M
source                1..20
                      mol_type = other DNA
                      organism = synthetic construct
SEQUENCE: 618
cgcgagcaca gctaaggcca                                              20

SEQ ID NO: 619        moltype = DNA  length = 20
FEATURE               Location/Qualifiers
misc_feature          1..20
                      note = sequence targeting B2M
source                1..20
                      mol_type = other DNA
                      organism = synthetic construct
SEQUENCE: 619
gagtagcgcg agcacagcta                                              20

SEQ ID NO: 620        moltype = DNA  length = 20
FEATURE               Location/Qualifiers
misc_feature          1..20
                      note = sequence targeting B2M
source                1..20
                      mol_type = other DNA
                      organism = synthetic construct
SEQUENCE: 620
agggtaggag agactcacgc                                              20

SEQ ID NO: 621        moltype = DNA  length = 20
FEATURE               Location/Qualifiers
misc_feature          1..20
                      note = sequence targeting B2M
source                1..20
                      mol_type = other DNA
                      organism = synthetic construct
SEQUENCE: 621
ctgaatcttt ggagtacctg                                              20

SEQ ID NO: 622        moltype = DNA  length = 20
FEATURE               Location/Qualifiers
misc_feature          1..20
                      note = sequence targeting B2M
source                1..20
                      mol_type = other DNA
                      organism = synthetic construct
SEQUENCE: 622
tcacgtcatc cagcagagaa                                              20

SEQ ID NO: 623        moltype = DNA  length = 20
```

```
FEATURE                Location/Qualifiers
misc_feature           1..20
                       note = sequence targeting B2M
source                 1..20
                       mol_type = other DNA
                       organism = synthetic construct
SEQUENCE: 623
tcctgaattg ctatgtgtct                                              20

SEQ ID NO: 624         moltype = DNA  length = 20
FEATURE                Location/Qualifiers
misc_feature           1..20
                       note = sequence targeting B2M
source                 1..20
                       mol_type = other DNA
                       organism = synthetic construct
SEQUENCE: 624
aagtcaactt caatgtcgga                                              20

SEQ ID NO: 625         moltype = DNA  length = 20
FEATURE                Location/Qualifiers
misc_feature           1..20
                       note = sequence targeting B2M
source                 1..20
                       mol_type = other DNA
                       organism = synthetic construct
SEQUENCE: 625
gtcttttccc gatattcctc                                              20

SEQ ID NO: 626         moltype = DNA  length = 20
FEATURE                Location/Qualifiers
misc_feature           1..20
                       note = sequence targeting B2M
source                 1..20
                       mol_type = other DNA
                       organism = synthetic construct
SEQUENCE: 626
tggagtacct gaggaatatc                                              20

SEQ ID NO: 627         moltype = DNA  length = 20
FEATURE                Location/Qualifiers
misc_feature           1..20
                       note = sequence targeting B2M
source                 1..20
                       mol_type = other DNA
                       organism = synthetic construct
SEQUENCE: 627
cagcccaaga tagttaagtg                                              20

SEQ ID NO: 628         moltype = DNA  length = 20
FEATURE                Location/Qualifiers
misc_feature           1..20
                       note = sequence targeting B2M
source                 1..20
                       mol_type = other DNA
                       organism = synthetic construct
SEQUENCE: 628
acaaagtcac atggttcaca                                              20

SEQ ID NO: 629         moltype = DNA  length = 20
FEATURE                Location/Qualifiers
misc_feature           1..20
                       note = sequence targeting B2M
source                 1..20
                       mol_type = other DNA
                       organism = synthetic construct
SEQUENCE: 629
actctctctt tctggcctgg                                              20

SEQ ID NO: 630         moltype = DNA  length = 20
FEATURE                Location/Qualifiers
misc_feature           1..20
                       note = sequence targeting B2M
source                 1..20
                       mol_type = other DNA
                       organism = synthetic construct
SEQUENCE: 630
tgggctgtga caaagtcaca                                              20
```

```
SEQ ID NO: 631          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 631
ggccgagatg tctcgctccg                                                   20

SEQ ID NO: 632          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 632
cagtaagtca acttcaatgt                                                   20

SEQ ID NO: 633          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 633
actcacgctg gatagcctcc                                                   20

SEQ ID NO: 634          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 634
catactcatc tttttcagtg                                                   20

SEQ ID NO: 635          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 635
cacagcccaa gatagttaag                                                   20

SEQ ID NO: 636          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 636
ttcagacttg tctttcagca                                                   20

SEQ ID NO: 637          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 637
agtcacatgg ttcacacggc                                                   20

SEQ ID NO: 638          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 638
atactcatct ttttcagtgg                                                   20
```

```
SEQ ID NO: 639          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 639
ggcatactca tctttttcag                                              20

SEQ ID NO: 640          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 640
acagcccaag atagttaagt                                              20

SEQ ID NO: 641          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 641
gctactctct ctttctggcc                                              20

SEQ ID NO: 642          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 642
tggagagaga attgaaaaag                                              20

SEQ ID NO: 643          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 643
acttgtcttt cagcaaggac                                              20

SEQ ID NO: 644          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 644
gaagttgact tactgaagaa                                              20

SEQ ID NO: 645          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 645
ggccacggag cgagacatct                                              20

SEQ ID NO: 646          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 646
```

```
gcatactcat ctttttcagt                                              20

SEQ ID NO: 647          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 647
cgtgagtaaa cctgaatctt                                              20

SEQ ID NO: 648          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 648
ttaccccact taactatctt                                              20

SEQ ID NO: 649          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 649
ttggagtacc tgaggaatat                                              20

SEQ ID NO: 650          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 650
acccagacac atagcaattc                                              20

SEQ ID NO: 651          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 651
tttgactttc cattctctgc                                              20

SEQ ID NO: 652          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 652
ttcctgaatt gctatgtgtc                                              20

SEQ ID NO: 653          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 653
ctcaggtact ccaaagattc                                              20

SEQ ID NO: 654          moltype = DNA  length = 20
FEATURE                 Location/Qualifiers
misc_feature            1..20
                        note = sequence targeting B2M
source                  1..20
                        mol_type = other DNA
                        organism = synthetic construct
```

```
SEQUENCE: 654
cttaccccac ttaactatct                                              20

SEQ ID NO: 655          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 655
ctcgcgctac tctctctttc                                              20

SEQ ID NO: 656          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 656
tcgatctatg aaaaagacag                                              20

SEQ ID NO: 657          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 657
gagacatgta agcagcatca                                              20

SEQ ID NO: 658          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 658
acatgtaagc agcatcatgg                                              20

SEQ ID NO: 659          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 659
gaagtcctag aatgagcgcc                                              20

SEQ ID NO: 660          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 660
gagcgcccgg tgtcccaagc                                              20

SEQ ID NO: 661          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 661
agcgcccggt gtcccaagct                                              20

SEQ ID NO: 662          moltype = DNA  length = 20
FEATURE                 Location/Qualifiers
misc_feature            1..20
                        note = sequence targeting B2M
source                  1..20
                        mol_type = other DNA
```

```
                        organism = synthetic construct
SEQUENCE: 662
gcgcccggtg tcccaagctg                                                 20

SEQ ID NO: 663          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 663
ctggggcgcg caccccagat                                                 20

SEQ ID NO: 664          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 664
gggcgcgcac cccagatcgg                                                 20

SEQ ID NO: 665          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 665
ggcgcgcacc ccagatcgga                                                 20

SEQ ID NO: 666          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 666
catcacgaga ctctaagaaa                                                 20

SEQ ID NO: 667          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 667
taagaaaagg aaactgaaaa                                                 20

SEQ ID NO: 668          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 668
aagaaaagga aactgaaaac                                                 20

SEQ ID NO: 669          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 669
gaaagtccct ctctctaacc                                                 20

SEQ ID NO: 670          moltype = DNA  length = 20
FEATURE                 Location/Qualifiers
misc_feature            1..20
                        note = sequence targeting B2M
source                  1..20
```

```
                         mol_type = other DNA
                         organism = synthetic construct
SEQUENCE: 670
ctaacctggc actgcgtcgc                                               20

SEQ ID NO: 671           moltype = DNA  length = 20
FEATURE                  Location/Qualifiers
misc_feature             1..20
                         note = sequence targeting B2M
source                   1..20
                         mol_type = other DNA
                         organism = synthetic construct
SEQUENCE: 671
ctggcactgc gtcgctggct                                               20

SEQ ID NO: 672           moltype = DNA  length = 20
FEATURE                  Location/Qualifiers
misc_feature             1..20
                         note = sequence targeting B2M
source                   1..20
                         mol_type = other DNA
                         organism = synthetic construct
SEQUENCE: 672
tgcgtcgctg gcttggagac                                               20

SEQ ID NO: 673           moltype = DNA  length = 20
FEATURE                  Location/Qualifiers
misc_feature             1..20
                         note = sequence targeting B2M
source                   1..20
                         mol_type = other DNA
                         organism = synthetic construct
SEQUENCE: 673
gctggcttgg agacaggtga                                               20

SEQ ID NO: 674           moltype = DNA  length = 20
FEATURE                  Location/Qualifiers
misc_feature             1..20
                         note = sequence targeting B2M
source                   1..20
                         mol_type = other DNA
                         organism = synthetic construct
SEQUENCE: 674
gagacaggtg acggtccctg                                               20

SEQ ID NO: 675           moltype = DNA  length = 20
FEATURE                  Location/Qualifiers
misc_feature             1..20
                         note = sequence targeting B2M
source                   1..20
                         mol_type = other DNA
                         organism = synthetic construct
SEQUENCE: 675
agacaggtga cggtccctgc                                               20

SEQ ID NO: 676           moltype = DNA  length = 20
FEATURE                  Location/Qualifiers
misc_feature             1..20
                         note = sequence targeting B2M
source                   1..20
                         mol_type = other DNA
                         organism = synthetic construct
SEQUENCE: 676
cctgcgggcc ttgtcctgat                                               20

SEQ ID NO: 677           moltype = DNA  length = 20
FEATURE                  Location/Qualifiers
misc_feature             1..20
                         note = sequence targeting B2M
source                   1..20
                         mol_type = other DNA
                         organism = synthetic construct
SEQUENCE: 677
cgggccttgt cctgattggc                                               20

SEQ ID NO: 678           moltype = DNA  length = 20
FEATURE                  Location/Qualifiers
misc_feature             1..20
                         note = sequence targeting B2M
```

```
source                  1..20
                        mol_type = other DNA
                        organism = synthetic construct
SEQUENCE: 678
gggccttgtc ctgattggct                                              20

SEQ ID NO: 679          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 679
gggcacgcgt ttaatataag                                              20

SEQ ID NO: 680          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 680
cacgcgttta atataagtgg                                              20

SEQ ID NO: 681          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 681
tataagtgga ggcgtcgcgc                                              20

SEQ ID NO: 682          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 682
aagtggaggc gtcgcgctgg                                              20

SEQ ID NO: 683          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 683
agtggaggcg tcgcgctggc                                              20

SEQ ID NO: 684          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 684
ttcctgaagc tgacagcatt                                              20

SEQ ID NO: 685          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 685
tcctgaagct gacagcattc                                              20

SEQ ID NO: 686          moltype = DNA  length = 20
FEATURE                 Location/Qualifiers
misc_feature            1..20
```

```
                        note = sequence targeting B2M
source                  1..20
                        mol_type = other DNA
                        organism = synthetic construct
SEQUENCE: 686
gcccgaatgc tgtcagcttc                                              20

SEQ ID NO: 687          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 687
aaacgcgtgc ccagccaatc                                              20

SEQ ID NO: 688          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 688
gtgcccagcc aatcaggaca                                              20

SEQ ID NO: 689          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 689
ccaatcagga caaggcccgc                                              20

SEQ ID NO: 690          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 690
caatcaggac aaggcccgca                                              20

SEQ ID NO: 691          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 691
caagccagcg acgcagtgcc                                              20

SEQ ID NO: 692          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 692
cgcagtgcca ggttagagag                                              20

SEQ ID NO: 693          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 693
gcagtgccag gttagagaga                                              20

SEQ ID NO: 694          moltype = DNA  length = 20
FEATURE                 Location/Qualifiers
```

```
misc_feature            1..20
                        note = sequence targeting B2M
source                  1..20
                        mol_type = other DNA
                        organism = synthetic construct
SEQUENCE: 694
gagtctcgtg atgtttaaga                                              20

SEQ ID NO: 695          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 695
taagaaggca tgcactagac                                              20

SEQ ID NO: 696          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 696
aagaaggcat gcactagact                                              20

SEQ ID NO: 697          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 697
tgagtttgct gtctgtacat                                              20

SEQ ID NO: 698          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 698
tacatcggcg ccctccgatc                                              20

SEQ ID NO: 699          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 699
acatcggcgc cctccgatct                                              20

SEQ ID NO: 700          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 700
catcggcgcc ctccgatctg                                              20

SEQ ID NO: 701          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 701
ctggggtgcg cgccccagct                                              20

SEQ ID NO: 702          moltype = DNA  length = 20
```

```
FEATURE                 Location/Qualifiers
misc_feature            1..20
                        note = sequence targeting B2M
source                  1..20
                        mol_type = other DNA
                        organism = synthetic construct
SEQUENCE: 702
tggggtgcgc gccccagctt                                              20

SEQ ID NO: 703          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 703
cgcgccccag cttgggacac                                              20

SEQ ID NO: 704          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 704
gcgccccagc ttgggacacc                                              20

SEQ ID NO: 705          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 705
caagtcactt agcatctctg                                              20

SEQ ID NO: 706          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 706
acagaagttc tccttctgct                                              20

SEQ ID NO: 707          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 707
attcaaagat cttaatcttc                                              20

SEQ ID NO: 708          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 708
ttcaaagatc ttaatcttct                                              20

SEQ ID NO: 709          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 709
ttttctcgaa tgaaaaatgc                                              20
```

```
SEQ ID NO: 710          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 710
tgcaggtccg agcagttaac                                              20

SEQ ID NO: 711          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 711
ggtccgagca gttaactggc                                              20

SEQ ID NO: 712          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 712
gtccgagcag ttaactggct                                              20

SEQ ID NO: 713          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 713
tccgagcagt taactggctg                                              20

SEQ ID NO: 714          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 714
agcaagtcac ttagcatctc                                              20

SEQ ID NO: 715          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 715
gcaagtcact tagcatctct                                              20

SEQ ID NO: 716          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 716
tggggccagt ctgcaaagcg                                              20

SEQ ID NO: 717          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 717
ggggccagtc tgcaaagcga                                              20
```

```
SEQ ID NO: 718          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 718
gggccagtct gcaaagcgag                                              20

SEQ ID NO: 719          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 719
ggccagtctg caaagcgagg                                              20

SEQ ID NO: 720          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 720
ggacaccggg cgctcattct                                              20

SEQ ID NO: 721          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 721
ggcgctcatt ctaggacttc                                              20

SEQ ID NO: 722          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 722
ctcattctag gacttcaggc                                              20

SEQ ID NO: 723          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 723
attctaggac ttcaggctgg                                              20

SEQ ID NO: 724          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 724
ttcaggctgg aggcacatta                                              20

SEQ ID NO: 725          moltype = DNA  length = 20
FEATURE                 Location/Qualifiers
misc_feature            1..20
                        note = sequence targeting B2M
source                  1..20
                        mol_type = other DNA
                        organism = synthetic construct
SEQUENCE: 725
```

```
tgccccctcg ctttgcagac                                              20

SEQ ID NO: 726         moltype = DNA  length = 20
FEATURE                Location/Qualifiers
misc_feature           1..20
                       note = sequence targeting B2M
source                 1..20
                       mol_type = other DNA
                       organism = synthetic construct
SEQUENCE: 726
gatgctaagt gacttgctaa                                              20

SEQ ID NO: 727         moltype = DNA  length = 20
FEATURE                Location/Qualifiers
misc_feature           1..20
                       note = sequence targeting B2M
source                 1..20
                       mol_type = other DNA
                       organism = synthetic construct
SEQUENCE: 727
gccccagcca gttaactgct                                              20

SEQ ID NO: 728         moltype = DNA  length = 20
FEATURE                Location/Qualifiers
misc_feature           1..20
                       note = sequence targeting B2M
source                 1..20
                       mol_type = other DNA
                       organism = synthetic construct
SEQUENCE: 728
gcatttttca ttcgagaaaa                                              20

SEQ ID NO: 729         moltype = DNA  length = 20
FEATURE                Location/Qualifiers
misc_feature           1..20
                       note = sequence targeting B2M
source                 1..20
                       mol_type = other DNA
                       organism = synthetic construct
SEQUENCE: 729
tttgaatgct acctagcaga                                              20

SEQ ID NO: 730         moltype = DNA  length = 20
FEATURE                Location/Qualifiers
misc_feature           1..20
                       note = sequence targeting B2M
source                 1..20
                       mol_type = other DNA
                       organism = synthetic construct
SEQUENCE: 730
ttctgtttat aactacagct                                              20

SEQ ID NO: 731         moltype = DNA  length = 20
FEATURE                Location/Qualifiers
misc_feature           1..20
                       note = sequence targeting B2M
source                 1..20
                       mol_type = other DNA
                       organism = synthetic construct
SEQUENCE: 731
tctgtttata actacagctt                                              20

SEQ ID NO: 732         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 732
agagaatgga aagtcaaatt t                                            21

SEQ ID NO: 733         moltype = DNA  length = 21
FEATURE                Location/Qualifiers
misc_feature           1..21
                       note = target B2M sequence complement
source                 1..21
                       mol_type = other DNA
                       organism = synthetic construct
```

```
SEQUENCE: 733
atggacatga tcttctttat a                                             21

SEQ ID NO: 734         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 734
tggacatgat cttctttata a                                             21

SEQ ID NO: 735         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 735
ggacatgatc ttctttataa t                                             21

SEQ ID NO: 736         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 736
tgacaggatt attggaaatt t                                             21

SEQ ID NO: 737         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 737
ttgtggttaa tctggtttat t                                             21

SEQ ID NO: 738         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 738
tgtggttaat ctggtttatt t                                             21

SEQ ID NO: 739         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 739
gcagagaatg gaaagtcaaa t                                             21

SEQ ID NO: 740         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 740
cagagaatgg aaagtcaaat t                                             21

SEQ ID NO: 741         moltype = DNA  length = 21
FEATURE                Location/Qualifiers
misc_feature           1..21
                       note = target B2M sequence complement
source                 1..21
                       mol_type = other DNA
```

```
                         organism = synthetic construct
SEQUENCE: 741
gagaatggaa agtcaaattt c                                              21

SEQ ID NO: 742           moltype = DNA  length = 21
FEATURE                  Location/Qualifiers
misc_feature             1..21
                         note = target B2M sequence complement
source                   1..21
                         mol_type = other DNA
                         organism = synthetic construct
SEQUENCE: 742
gtcacagccc aagatagtta a                                              21

SEQ ID NO: 743           moltype = DNA  length = 21
FEATURE                  Location/Qualifiers
misc_feature             1..21
                         note = target B2M sequence complement
source                   1..21
                         mol_type = other DNA
                         organism = synthetic construct
SEQUENCE: 743
tgcttataca cttacacttt a                                              21

SEQ ID NO: 744           moltype = DNA  length = 21
FEATURE                  Location/Qualifiers
misc_feature             1..21
                         note = target B2M sequence complement
source                   1..21
                         mol_type = other DNA
                         organism = synthetic construct
SEQUENCE: 744
gcttatacac ttacacttta t                                              21

SEQ ID NO: 745           moltype = DNA  length = 21
FEATURE                  Location/Qualifiers
misc_feature             1..21
                         note = target B2M sequence complement
source                   1..21
                         mol_type = other DNA
                         organism = synthetic construct
SEQUENCE: 745
cttatacact tacactttat g                                              21

SEQ ID NO: 746           moltype = DNA  length = 21
FEATURE                  Location/Qualifiers
misc_feature             1..21
                         note = target B2M sequence complement
source                   1..21
                         mol_type = other DNA
                         organism = synthetic construct
SEQUENCE: 746
acatggacat gatcttcttt a                                              21

SEQ ID NO: 747           moltype = DNA  length = 21
FEATURE                  Location/Qualifiers
misc_feature             1..21
                         note = target B2M sequence complement
source                   1..21
                         mol_type = other DNA
                         organism = synthetic construct
SEQUENCE: 747
catggacatg atcttcttta t                                              21

SEQ ID NO: 748           moltype = DNA  length = 21
FEATURE                  Location/Qualifiers
misc_feature             1..21
                         note = target B2M sequence complement
source                   1..21
                         mol_type = other DNA
                         organism = synthetic construct
SEQUENCE: 748
atcaacatct tggtcagatt t                                              21

SEQ ID NO: 749           moltype = DNA  length = 21
FEATURE                  Location/Qualifiers
misc_feature             1..21
                         note = target B2M sequence complement
source                   1..21
```

```
                        mol_type = other DNA
                        organism = synthetic construct
SEQUENCE: 749
cttgcactca aagcttgtta a                                               21

SEQ ID NO: 750          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 750
agttaagcgt gcataagtta a                                               21

SEQ ID NO: 751          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 751
gcataagtta acttccaatt t                                               21

SEQ ID NO: 752          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 752
tacatactct gcttagaatt t                                               21

SEQ ID NO: 753          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 753
acatactctg cttagaattt g                                               21

SEQ ID NO: 754          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 754
ttgacaggat tattggaaat t                                               21

SEQ ID NO: 755          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 755
gacaggatta ttggaaattt g                                               21

SEQ ID NO: 756          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 756
taaggcatgg ttgtggttaa t                                               21

SEQ ID NO: 757          moltype = DNA  length = 21
FEATURE                 Location/Qualifiers
misc_feature            1..21
                        note = target B2M sequence complement
```

```
source                  1..21
                        mol_type = other DNA
                        organism = synthetic construct
SEQUENCE: 757
gttgtggtta atctggttta t                                             21

SEQ ID NO: 758          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 758
gttccacaag ttaaataaat c                                             21

SEQ ID NO: 759          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 759
tccagcgtac tccaaagatt c                                             21

SEQ ID NO: 760          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 760
tactccaaag attcaggttt a                                             21

SEQ ID NO: 761          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 761
actccaaaga ttcaggttta c                                             21

SEQ ID NO: 762          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 762
cacgtcatcc agcagagaat g                                             21

SEQ ID NO: 763          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 763
ggtttcatcc atccgacatt g                                             21

SEQ ID NO: 764          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 764
ccgacattga agttgactta c                                             21

SEQ ID NO: 765          moltype = DNA  length = 21
FEATURE                 Location/Qualifiers
misc_feature            1..21
```

```
                        note = target B2M sequence complement
source                  1..21
                        mol_type = other DNA
                        organism = synthetic construct
SEQUENCE: 765
tgaagaatgg agagagaatt g                                              21

SEQ ID NO: 766          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 766
gagcattcag acttgtcttt c                                              21

SEQ ID NO: 767          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 767
ttcagcaagg actggtcttt c                                              21

SEQ ID NO: 768          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 768
gcaaggactg gtctttctat c                                              21

SEQ ID NO: 769          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 769
cgtgtgaacc atgtgacttt g                                              21

SEQ ID NO: 770          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 770
ctttgtcaca gcccaagata g                                              21

SEQ ID NO: 771          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 771
tcacagccca agatagttaa g                                              21

SEQ ID NO: 772          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 772
agtgggatcg agacatgtaa g                                              21

SEQ ID NO: 773          moltype = DNA  length = 21
FEATURE                 Location/Qualifiers
```

```
misc_feature          1..21
                      note = target B2M sequence complement
source                1..21
                      mol_type = other DNA
                      organism = synthetic construct
SEQUENCE: 773
aggtttgaag atgccgcatt t                                           21

SEQ ID NO: 774        moltype = DNA  length = 21
FEATURE               Location/Qualifiers
misc_feature          1..21
                      note = target B2M sequence complement
source                1..21
                      mol_type = other DNA
                      organism = synthetic construct
SEQUENCE: 774
ggtttgaaga tgccgcattt g                                           21

SEQ ID NO: 775        moltype = DNA  length = 21
FEATURE               Location/Qualifiers
misc_feature          1..21
                      note = target B2M sequence complement
source                1..21
                      mol_type = other DNA
                      organism = synthetic construct
SEQUENCE: 775
ttgatatgct tatacactta c                                           21

SEQ ID NO: 776        moltype = DNA  length = 21
FEATURE               Location/Qualifiers
misc_feature          1..21
                      note = target B2M sequence complement
source                1..21
                      mol_type = other DNA
                      organism = synthetic construct
SEQUENCE: 776
tgagtgctgt ctccatgttt g                                           21

SEQ ID NO: 777        moltype = DNA  length = 21
FEATURE               Location/Qualifiers
misc_feature          1..21
                      note = target B2M sequence complement
source                1..21
                      mol_type = other DNA
                      organism = synthetic construct
SEQUENCE: 777
tgtctccatg tttgatgtat c                                           21

SEQ ID NO: 778        moltype = DNA  length = 21
FEATURE               Location/Qualifiers
misc_feature          1..21
                      note = target B2M sequence complement
source                1..21
                      mol_type = other DNA
                      organism = synthetic construct
SEQUENCE: 778
tcaacatctt ggtcagattt g                                           21

SEQ ID NO: 779        moltype = DNA  length = 21
FEATURE               Location/Qualifiers
misc_feature          1..21
                      note = target B2M sequence complement
source                1..21
                      mol_type = other DNA
                      organism = synthetic construct
SEQUENCE: 779
tcagatttga actcttcaat c                                           21

SEQ ID NO: 780        moltype = DNA  length = 21
FEATURE               Location/Qualifiers
misc_feature          1..21
                      note = target B2M sequence complement
source                1..21
                      mol_type = other DNA
                      organism = synthetic construct
SEQUENCE: 780
ttcaatctct tgcactcaaa g                                           21

SEQ ID NO: 781        moltype = DNA  length = 21
```

```
FEATURE                Location/Qualifiers
misc_feature           1..21
                       note = target B2M sequence complement
source                 1..21
                       mol_type = other DNA
                       organism = synthetic construct
SEQUENCE: 781
ttgcactcaa agcttgttaa g                                            21

SEQ ID NO: 782         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 782
actcaaagct tgttaagata g                                            21

SEQ ID NO: 783         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 783
agatagttaa gcgtgcataa g                                            21

SEQ ID NO: 784         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 784
tgcataagtt aacttccaat t                                            21

SEQ ID NO: 785         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 785
gttaacttcc aatttacata c                                            21

SEQ ID NO: 786         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 786
attgacagga ttattggaaa t                                            21

SEQ ID NO: 787         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 787
gtaaggcatg gttgtggtta a                                            21

SEQ ID NO: 788         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 788
ggttgtggtt aatctggttt a                                            21
```

```
SEQ ID NO: 789          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 789
ttcctgaagc tgacagcatt c                                            21

SEQ ID NO: 790          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 790
gctatccagc gtactccaaa g                                            21

SEQ ID NO: 791          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 791
catccagcag agaatggaaa g                                            21

SEQ ID NO: 792          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 792
caaatttcct gaattgctat g                                            21

SEQ ID NO: 793          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 793
attgctatgt gtctgggttt c                                            21

SEQ ID NO: 794          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 794
gaagatgccg catttggatt g                                            21

SEQ ID NO: 795          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 795
caatttacat actctgctta g                                            21

SEQ ID NO: 796          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 796
tatccagcgt actccaaaga t                                            21
```

```
SEQ ID NO: 797         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 797
atccagcgta ctccaaagat t                                            21

SEQ ID NO: 798         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 798
ctccaaagat tcaggtttac t                                            21

SEQ ID NO: 799         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 799
tgctatgtgt ctgggtttca t                                            21

SEQ ID NO: 800         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 800
tttcatccat ccgacattga a                                            21

SEQ ID NO: 801         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 801
gaagttgact tactgaagaa t                                            21

SEQ ID NO: 802         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 802
gaagaatgga gagagaattg a                                            21

SEQ ID NO: 803         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 803
agaatggaga gagaattgaa a                                            21

SEQ ID NO: 804         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 804
```

```
cagcaaggac tggtctttct a                                            21

SEQ ID NO: 805         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 805
agcaaggact ggtctttcta t                                            21

SEQ ID NO: 806         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 806
actttgtcac agcccaagat a                                            21

SEQ ID NO: 807         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 807
ttgtcacagc ccaagatagt t                                            21

SEQ ID NO: 808         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 808
tgtcacagcc caagatagtt a                                            21

SEQ ID NO: 809         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 809
cacagcccaa gatagttaag t                                            21

SEQ ID NO: 810         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 810
gcagcatcat ggaggtttga a                                            21

SEQ ID NO: 811         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 811
ccgcatttgg attggatgaa t                                            21

SEQ ID NO: 812         moltype = DNA  length = 21
FEATURE                Location/Qualifiers
misc_feature           1..21
                       note = target B2M sequence complement
source                 1..21
                       mol_type = other DNA
                       organism = synthetic construct
```

```
SEQUENCE: 812
ttgagtgctg tctccatgtt t                                      21

SEQ ID NO: 813         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 813
agtgctgtct ccatgtttga t                                      21

SEQ ID NO: 814         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 814
ctgtctccat gtttgatgta t                                      21

SEQ ID NO: 815         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 815
tctaggaggg ctggcaactt a                                      21

SEQ ID NO: 816         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 816
caacatcttg gtcagatttg a                                      21

SEQ ID NO: 817         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 817
gtcagatttg aactcttcaa t                                      21

SEQ ID NO: 818         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 818
tcttgcactc aaagcttgtt a                                      21

SEQ ID NO: 819         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 819
tgcactcaaa gcttgttaag a                                      21

SEQ ID NO: 820         moltype = DNA  length = 21
FEATURE                Location/Qualifiers
misc_feature           1..21
                       note = target B2M sequence complement
source                 1..21
                       mol_type = other DNA
```

```
                         organism = synthetic construct
SEQUENCE: 820
gcactcaaag cttgttaaga t                                            21

SEQ ID NO: 821           moltype = DNA  length = 21
FEATURE                  Location/Qualifiers
misc_feature             1..21
                         note = target B2M sequence complement
source                   1..21
                         mol_type = other DNA
                         organism = synthetic construct
SEQUENCE: 821
cactcaaagc ttgttaagat a                                            21

SEQ ID NO: 822           moltype = DNA  length = 21
FEATURE                  Location/Qualifiers
misc_feature             1..21
                         note = target B2M sequence complement
source                   1..21
                         mol_type = other DNA
                         organism = synthetic construct
SEQUENCE: 822
tcaaagcttg ttaagatagt t                                            21

SEQ ID NO: 823           moltype = DNA  length = 21
FEATURE                  Location/Qualifiers
misc_feature             1..21
                         note = target B2M sequence complement
source                   1..21
                         mol_type = other DNA
                         organism = synthetic construct
SEQUENCE: 823
caaagcttgt taagatagtt a                                            21

SEQ ID NO: 824           moltype = DNA  length = 21
FEATURE                  Location/Qualifiers
misc_feature             1..21
                         note = target B2M sequence complement
source                   1..21
                         mol_type = other DNA
                         organism = synthetic construct
SEQUENCE: 824
gatagttaag cgtgcataag t                                            21

SEQ ID NO: 825           moltype = DNA  length = 21
FEATURE                  Location/Qualifiers
misc_feature             1..21
                         note = target B2M sequence complement
source                   1..21
                         mol_type = other DNA
                         organism = synthetic construct
SEQUENCE: 825
atagttaagc gtgcataagt t                                            21

SEQ ID NO: 826           moltype = DNA  length = 21
FEATURE                  Location/Qualifiers
misc_feature             1..21
                         note = target B2M sequence complement
source                   1..21
                         mol_type = other DNA
                         organism = synthetic construct
SEQUENCE: 826
tagttaagcg tgcataagtt a                                            21

SEQ ID NO: 827           moltype = DNA  length = 21
FEATURE                  Location/Qualifiers
misc_feature             1..21
                         note = target B2M sequence complement
source                   1..21
                         mol_type = other DNA
                         organism = synthetic construct
SEQUENCE: 827
ttaagcgtgc ataagttaac t                                            21

SEQ ID NO: 828           moltype = DNA  length = 21
FEATURE                  Location/Qualifiers
misc_feature             1..21
                         note = target B2M sequence complement
source                   1..21
```

```
                        mol_type = other DNA
                        organism = synthetic construct
SEQUENCE: 828
taagcgtgca taagttaact t                                              21

SEQ ID NO: 829          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 829
atttacatac tctgcttaga a                                              21

SEQ ID NO: 830          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 830
tttacatact ctgcttagaa t                                              21

SEQ ID NO: 831          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 831
acaggattat tggaaatttg t                                              21

SEQ ID NO: 832          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 832
caggattatt ggaaatttgt t                                              21

SEQ ID NO: 833          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 833
aggcatggtt gtggttaatc t                                              21

SEQ ID NO: 834          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 834
cagcagagaa tggaaagtca a                                              21

SEQ ID NO: 835          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 835
tccgacattg aagttgactt a                                              21

SEQ ID NO: 836          moltype = DNA  length = 21
FEATURE                 Location/Qualifiers
misc_feature            1..21
                        note = target B2M sequence complement
```

```
source                  1..21
                        mol_type = other DNA
                        organism = synthetic construct
SEQUENCE: 836
ctggtctttc tatctcttgt a                                            21

SEQ ID NO: 837          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 837
ccgtgtgaac catgtgactt t                                            21

SEQ ID NO: 838          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 838
cccaagatag ttaagtggga t                                            21

SEQ ID NO: 839          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 839
ggttgctcca caggtagctc t                                            21

SEQ ID NO: 840          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 840
gctccacagg tagctctagg a                                            21

SEQ ID NO: 841          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 841
gggagcagag aattctctta t                                            21

SEQ ID NO: 842          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 842
ggagcagaga attctcttat c                                            21

SEQ ID NO: 843          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 843
gagcagagaa ttctcttatc c                                            21

SEQ ID NO: 844          moltype = DNA  length = 21
FEATURE                 Location/Qualifiers
misc_feature            1..21
```

```
                        note = target B2M sequence complement
source                  1..21
                        mol_type = other DNA
                        organism = synthetic construct
SEQUENCE: 844
gagaattctc ttatccaaca t                                             21

SEQ ID NO: 845          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 845
gaattctctt atccaacatc a                                             21

SEQ ID NO: 846          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 846
aagtggagca ttcagacttg t                                             21

SEQ ID NO: 847          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 847
aaggactggt ctttctatct c                                             21

SEQ ID NO: 848          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 848
aagcttgtta agatagttaa g                                             21

SEQ ID NO: 849          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 849
aagcgtgcat aagttaactt c                                             21

SEQ ID NO: 850          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 850
aagatgccgc atttggattg g                                             21

SEQ ID NO: 851          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 851
aagaatggag agagaattga a                                             21

SEQ ID NO: 852          moltype = DNA  length = 21
FEATURE                 Location/Qualifiers
```

```
misc_feature          1..21
                      note = target B2M sequence complement
source                1..21
                      mol_type = other DNA
                      organism = synthetic construct
SEQUENCE: 852
aacatcaaca tcttggtcag a                                            21

SEQ ID NO: 853        moltype = DNA  length = 21
FEATURE               Location/Qualifiers
misc_feature          1..21
                      note = target B2M sequence complement
source                1..21
                      mol_type = other DNA
                      organism = synthetic construct
SEQUENCE: 853
aaggcatggt tgtggttaat c                                            21

SEQ ID NO: 854        moltype = DNA  length = 21
FEATURE               Location/Qualifiers
misc_feature          1..21
                      note = target B2M sequence complement
source                1..21
                      mol_type = other DNA
                      organism = synthetic construct
SEQUENCE: 854
aagcagcatc atggaggttt g                                            21

SEQ ID NO: 855        moltype = DNA  length = 21
FEATURE               Location/Qualifiers
misc_feature          1..21
                      note = target B2M sequence complement
source                1..21
                      mol_type = other DNA
                      organism = synthetic construct
SEQUENCE: 855
aagatgagta tgcctgccgt g                                            21

SEQ ID NO: 856        moltype = DNA  length = 21
FEATURE               Location/Qualifiers
misc_feature          1..21
                      note = target B2M sequence complement
source                1..21
                      mol_type = other DNA
                      organism = synthetic construct
SEQUENCE: 856
aagttgactt actgaagaat g                                            21

SEQ ID NO: 857        moltype = DNA  length = 21
FEATURE               Location/Qualifiers
misc_feature          1..21
                      note = target B2M sequence complement
source                1..21
                      mol_type = other DNA
                      organism = synthetic construct
SEQUENCE: 857
aagatagtta agcgtgcata a                                            21

SEQ ID NO: 858        moltype = DNA  length = 21
FEATURE               Location/Qualifiers
misc_feature          1..21
                      note = target B2M sequence complement
source                1..21
                      mol_type = other DNA
                      organism = synthetic construct
SEQUENCE: 858
aacttccaat ttacatactc t                                            21

SEQ ID NO: 859        moltype = DNA  length = 21
FEATURE               Location/Qualifiers
misc_feature          1..21
                      note = target B2M sequence complement
source                1..21
                      mol_type = other DNA
                      organism = synthetic construct
SEQUENCE: 859
aacatcttgg tcagatttga a                                            21

SEQ ID NO: 860        moltype = DNA  length = 21
```

```
FEATURE                Location/Qualifiers
misc_feature           1..21
                       note = target B2M sequence complement
source                 1..21
                       mol_type = other DNA
                       organism = synthetic construct
SEQUENCE: 860
aactcttcaa tctcttgcac t                                       21

SEQ ID NO: 861         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 861
aatttcctga attgctatgt g                                       21

SEQ ID NO: 862         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 862
aatggaaagt caaatttcct g                                       21

SEQ ID NO: 863         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 863
aaccatgtga ctttgtcaca g                                       21

SEQ ID NO: 864         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 864
aattgacagg attattggaa a                                       21

SEQ ID NO: 865         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 865
aattctctta tccaacatca a                                       21

SEQ ID NO: 866         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 866
aaagtggagc attcagactt g                                       21

SEQ ID NO: 867         moltype = DNA  length = 21
FEATURE                Location/Qualifiers
misc_feature           1..21
                       note = target B2M sequence complement
source                 1..21
                       mol_type = other DNA
                       organism = synthetic construct
SEQUENCE: 867
aaagtcaaat ttcctgaatt g                                       21
```

```
SEQ ID NO: 868          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 868
gttgctccac aggtagctct a                                            21

SEQ ID NO: 869          moltype = DNA  length = 21
FEATURE                 Location/Qualifiers
misc_feature            1..21
                        note = target B2M sequence complement
source                  1..21
                        mol_type = other DNA
                        organism = synthetic construct
SEQUENCE: 869
aatttacata ctctgcttag a                                            21

SEQ ID NO: 870          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 870
cttcttcctt ccctattaaa a                                            21

SEQ ID NO: 871          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 871
tctcactcca tgaggtattt c                                            21

SEQ ID NO: 872          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 872
ctctcactcc atgaggtatt t                                            21

SEQ ID NO: 873          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 873
gaggaggaag agctcagata g                                            21

SEQ ID NO: 874          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 874
gctctcactc catgaggtat t                                            21

SEQ ID NO: 875          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 875
aggattacat cgccctgaaa g                                            21
```

```
SEQ ID NO: 876          moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 876
acaccgtcca gaggatgtat g                                              21

SEQ ID NO: 877         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 877
agggtccttc ttcctggata c                                              21

SEQ ID NO: 878         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 878
cctacgacgg caaggattac a                                              21

SEQ ID NO: 879         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 879
tcactccatg aggtatttct t                                              21

SEQ ID NO: 880         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 880
ctacgacggc aaggattaca t                                              21

SEQ ID NO: 881         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 881
ctcactccat gaggtatttc t                                              21

SEQ ID NO: 882         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 882
ggaggaagag ctcagataga a                                              21

SEQ ID NO: 883         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 883
```

```
cacaccgtcc agaggatgta t                                           21

SEQ ID NO: 884          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 884
cacgctgtct ctgaccatga a                                           21

SEQ ID NO: 885          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 885
ctggacagga gcagagatac a                                           21

SEQ ID NO: 886          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 886
tggaggagga agagctcaga t                                           21

SEQ ID NO: 887          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 887
ggctctcact ccatgaggta t                                           21

SEQ ID NO: 888          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 888
catctctgtc tcaacttcat g                                           21

SEQ ID NO: 889          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 889
tacgacggca aggattacat c                                           21

SEQ ID NO: 890          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 890
ggattacatc gccctgaaag a                                           21

SEQ ID NO: 891          moltype = DNA  length = 21
FEATURE                 Location/Qualifiers
misc_feature            1..21
                        note = target HLA sequence complement
source                  1..21
                        mol_type = other DNA
                        organism = synthetic construct
```

```
SEQUENCE: 891
gattacatcg ccctgaaaga g                                          21

SEQ ID NO: 892          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 892
ctcagaccac caagcacaag t                                          21

SEQ ID NO: 893          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 893
tcacaccgtc cagaggatgt a                                          21

SEQ ID NO: 894          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 894
actccatgag gtatttcttc a                                          21

SEQ ID NO: 895          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 895
cactccatga ggtatttctt c                                          21

SEQ ID NO: 896          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 896
ccatgaggta tttcttcaca t                                          21

SEQ ID NO: 897          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 897
acttcttcct tccctattaa a                                          21

SEQ ID NO: 898          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 898
gtgtctctca cagcttgtaa a                                          21

SEQ ID NO: 899          moltype = DNA  length = 21
FEATURE                 Location/Qualifiers
misc_feature            1..21
                        note = target HLA sequence complement
source                  1..21
                        mol_type = other DNA
```

```
                         organism = synthetic construct
SEQUENCE: 899
ctgtgttcgt gtaggcataa t                                             21

SEQ ID NO: 900           moltype = DNA  length = 21
FEATURE                  Location/Qualifiers
misc_feature             1..21
                         note = target HLA sequence complement
source                   1..21
                         mol_type = other DNA
                         organism = synthetic construct
SEQUENCE: 900
tgtgttcgtg taggcataat g                                             21

SEQ ID NO: 901           moltype = DNA  length = 21
FEATURE                  Location/Qualifiers
misc_feature             1..21
                         note = target HLA sequence complement
source                   1..21
                         mol_type = other DNA
                         organism = synthetic construct
SEQUENCE: 901
taacttcttc cttccctatt a                                             21

SEQ ID NO: 902           moltype = DNA  length = 21
FEATURE                  Location/Qualifiers
misc_feature             1..21
                         note = target HLA sequence complement
source                   1..21
                         mol_type = other DNA
                         organism = synthetic construct
SEQUENCE: 902
tctggacagg agcagagata c                                             21

SEQ ID NO: 903           moltype = DNA  length = 21
FEATURE                  Location/Qualifiers
misc_feature             1..21
                         note = target HLA sequence complement
source                   1..21
                         mol_type = other DNA
                         organism = synthetic construct
SEQUENCE: 903
ttgctggcct ggttctcttt g                                             21

SEQ ID NO: 904           moltype = DNA  length = 21
FEATURE                  Location/Qualifiers
misc_feature             1..21
                         note = target HLA sequence complement
source                   1..21
                         mol_type = other DNA
                         organism = synthetic construct
SEQUENCE: 904
tgtctctcac agcttgtaaa g                                             21

SEQ ID NO: 905           moltype = DNA  length = 21
FEATURE                  Location/Qualifiers
misc_feature             1..21
                         note = target HLA sequence complement
source                   1..21
                         mol_type = other DNA
                         organism = synthetic construct
SEQUENCE: 905
acttgaagaa ccctgacttt g                                             21

SEQ ID NO: 906           moltype = DNA  length = 21
FEATURE                  Location/Qualifiers
misc_feature             1..21
                         note = target HLA sequence complement
source                   1..21
                         mol_type = other DNA
                         organism = synthetic construct
SEQUENCE: 906
gaagaaccct gactttgttt c                                             21

SEQ ID NO: 907           moltype = DNA  length = 21
FEATURE                  Location/Qualifiers
misc_feature             1..21
                         note = target HLA sequence complement
source                   1..21
```

```
                        mol_type = other DNA
                        organism = synthetic construct
SEQUENCE: 907
tctgtgttcg tgtaggcata a                                              21

SEQ ID NO: 908          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 908
catggtgcac tgagctgtaa c                                              21

SEQ ID NO: 909          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 909
gtaacttctt ccttccctat t                                              21

SEQ ID NO: 910          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 910
catgtgcagc atgagggttt g                                              21

SEQ ID NO: 911          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 911
ttgttcctgc ccttcccttt g                                              21

SEQ ID NO: 912          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 912
acccagttct cactcccatt g                                              21

SEQ ID NO: 913          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 913
gggtttccag agaagccaat c                                              21

SEQ ID NO: 914          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 914
ttctccctct cccaacctat g                                              21

SEQ ID NO: 915          moltype = DNA  length = 21
FEATURE                 Location/Qualifiers
misc_feature            1..21
                        note = target HLA sequence complement
```

```
source                 1..21
                       mol_type = other DNA
                       organism = synthetic construct
SEQUENCE: 915
gtctctcaca gcttgtaaag t                                               21

SEQ ID NO: 916         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 916
tgtgtctctc acagcttgta a                                               21

SEQ ID NO: 917         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 917
gaggaagagc tcagatagaa a                                               21

SEQ ID NO: 918         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 918
tgaagaaccc tgactttgtt t                                               21

SEQ ID NO: 919         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 919
ttgaagaacc ctgactttgt t                                               21

SEQ ID NO: 920         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 920
gtgttcgtgt aggcataatg t                                               21

SEQ ID NO: 921         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 921
tggtgcactg agctgtaact t                                               21

SEQ ID NO: 922         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 922
ctccctctcc caacctatgt a                                               21

SEQ ID NO: 923         moltype = DNA  length = 21
FEATURE                Location/Qualifiers
misc_feature           1..21
```

```
                        note = target HLA sequence complement
source                  1..21
                        mol_type = other DNA
                        organism = synthetic construct
SEQUENCE: 923
aggaggaaga gctcagatag a                                              21

SEQ ID NO: 924          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 924
acctatgtag ggtccttctt c                                              21

SEQ ID NO: 925          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 925
gggtccttct tcctggatac t                                              21

SEQ ID NO: 926          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 926
ggtccttctt cctggatact c                                              21

SEQ ID NO: 927          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 927
gtccttcttc ctggatactc a                                              21

SEQ ID NO: 928          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 928
aagccaatca gtgtcgtcgc g                                              21

SEQ ID NO: 929          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 929
aagaggacct gcgctcttgg a                                              21

SEQ ID NO: 930          moltype = DNA  length = 21
FEATURE                 Location/Qualifiers
misc_feature            1..21
                        note = target HLA sequence complement
source                  1..21
                        mol_type = other DNA
                        organism = synthetic construct
SEQUENCE: 930
aagtgtgaga cagctgcctt g                                              21

SEQ ID NO: 931          moltype = DNA  length = 21
FEATURE                 Location/Qualifiers
```

```
misc_feature           1..21
                       note = target HLA sequence complement
source                 1..21
                       mol_type = other DNA
                       organism = synthetic construct
SEQUENCE: 931
aaggcacctg catgtgtctg t                                            21

SEQ ID NO: 932         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 932
aatcatcttt cctgttccag a                                            21

SEQ ID NO: 933         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 933
aaaggcacct gcatgtgtct g                                            21

SEQ ID NO: 934         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 934
aaagaggacc tgcgctcttg g                                            21

SEQ ID NO: 935         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 935
aaacgcatat gactcaccac g                                            21

SEQ ID NO: 936         moltype = DNA  length = 19
FEATURE                Location/Qualifiers
misc_feature           1..19
                       note = target HLA sequence complement
source                 1..19
                       mol_type = other DNA
                       organism = synthetic construct
SEQUENCE: 936
ggaagagctc agatagaaa                                               19

SEQ ID NO: 937         moltype = DNA  length = 19
FEATURE                Location/Qualifiers
misc_feature           1..19
                       note = target HLA sequence complement
source                 1..19
                       mol_type = other DNA
                       organism = synthetic construct
SEQUENCE: 937
gggagacacg gaaagtgaa                                               19

SEQ ID NO: 938         moltype = DNA  length = 21
FEATURE                Location/Qualifiers
misc_feature           1..21
                       note = target HLA sequence complement
source                 1..21
                       mol_type = other DNA
                       organism = synthetic construct
SEQUENCE: 938
cacctgccat gtgcagcatg a                                            21

SEQ ID NO: 939         moltype = DNA  length = 21
```

```
FEATURE                Location/Qualifiers
misc_feature           1..21
                       note = target HLA sequence complement
source                 1..21
                       mol_type = other DNA
                       organism = synthetic construct
SEQUENCE: 939
ggagatcaca ctgacctggc a                                             21

SEQ ID NO: 940         moltype = DNA  length = 20
FEATURE                Location/Qualifiers
misc_feature           1..20
                       note = target HLA sequence complement
source                 1..20
                       mol_type = other DNA
                       organism = synthetic construct
SEQUENCE: 940
ggattacatc gccctgaaag                                               20

SEQ ID NO: 941         moltype = DNA  length = 20
FEATURE                Location/Qualifiers
misc_feature           1..20
                       note = target HLA sequence complement
source                 1..20
                       mol_type = other DNA
                       organism = synthetic construct
SEQUENCE: 941
gcaggagggt ccggagtatt                                               20

SEQ ID NO: 942         moltype = DNA  length = 20
FEATURE                Location/Qualifiers
misc_feature           1..20
                       note = target HLA sequence complement
source                 1..20
                       mol_type = other DNA
                       organism = synthetic construct
SEQUENCE: 942
ggacggggag acacggaaag                                               20

SEQ ID NO: 943         moltype = DNA  length = 19
FEATURE                Location/Qualifiers
misc_feature           1..19
                       note = target HLA sequence complement
source                 1..19
                       mol_type = other DNA
                       organism = synthetic construct
SEQUENCE: 943
gaaagtgaag gcccactca                                                19

SEQ ID NO: 944         moltype = DNA  length = 20
FEATURE                Location/Qualifiers
misc_feature           1..20
                       note = target HLA sequence complement
source                 1..20
                       mol_type = other DNA
                       organism = synthetic construct
SEQUENCE: 944
gatacctgga gaacgggaag                                               20

SEQ ID NO: 945         moltype = DNA  length = 20
FEATURE                Location/Qualifiers
misc_feature           1..20
                       note = target HLA sequence complement
source                 1..20
                       mol_type = other DNA
                       organism = synthetic construct
SEQUENCE: 945
gctgtggtgg tgccttctgg                                               20

SEQ ID NO: 946         moltype = DNA  length = 20
FEATURE                Location/Qualifiers
misc_feature           1..20
                       note = target HLA sequence complement
source                 1..20
                       mol_type = other DNA
                       organism = synthetic construct
SEQUENCE: 946
gctactacaa ccagagcgag                                               20
```

```
SEQ ID NO: 947          moltype = DNA  length = 19
FEATURE                 Location/Qualifiers
misc_feature            1..19
                        note = target HLA sequence complement
source                  1..19
                        mol_type = other DNA
                        organism = synthetic construct
SEQUENCE: 947
gtggctccgc agatacctg                                               19

SEQ ID NO: 948          moltype = DNA  length = 19
FEATURE                 Location/Qualifiers
misc_feature            1..19
                        note = target HLA sequence complement
source                  1..19
                        mol_type = other DNA
                        organism = synthetic construct
SEQUENCE: 948
gccaatcagt gtcgtcgcg                                               19

SEQ ID NO: 949          moltype = DNA  length = 19
FEATURE                 Location/Qualifiers
misc_feature            1..19
                        note = target HLA sequence complement
source                  1..19
                        mol_type = other DNA
                        organism = synthetic construct
SEQUENCE: 949
gaggacctgc gctcttgga                                               19

SEQ ID NO: 950          moltype = DNA  length = 19
FEATURE                 Location/Qualifiers
misc_feature            1..19
                        note = target HLA sequence complement
source                  1..19
                        mol_type = other DNA
                        organism = synthetic construct
SEQUENCE: 950
gtgtgagaca gctgccttg                                               19

SEQ ID NO: 951          moltype = DNA  length = 19
FEATURE                 Location/Qualifiers
misc_feature            1..19
                        note = target HLA sequence complement
source                  1..19
                        mol_type = other DNA
                        organism = synthetic construct
SEQUENCE: 951
ggcacctgca tgtgtctgt                                               19

SEQ ID NO: 952          moltype = DNA  length = 19
FEATURE                 Location/Qualifiers
misc_feature            1..19
                        note = target HLA sequence complement
source                  1..19
                        mol_type = other DNA
                        organism = synthetic construct
SEQUENCE: 952
tcatctttcc tgttccaga                                               19

SEQ ID NO: 953          moltype = DNA  length = 19
FEATURE                 Location/Qualifiers
misc_feature            1..19
                        note = target HLA sequence complement
source                  1..19
                        mol_type = other DNA
                        organism = synthetic construct
SEQUENCE: 953
aggcacctgc atgtgtctg                                               19

SEQ ID NO: 954          moltype = DNA  length = 19
FEATURE                 Location/Qualifiers
misc_feature            1..19
                        note = target HLA sequence complement
source                  1..19
                        mol_type = other DNA
                        organism = synthetic construct
SEQUENCE: 954
agaggacctg cgctcttgg                                               19
```

```
SEQ ID NO: 955          moltype = DNA  length = 19
FEATURE                 Location/Qualifiers
misc_feature            1..19
                        note = target HLA sequence complement
source                  1..19
                        mol_type = other DNA
                        organism = synthetic construct
SEQUENCE: 955
acgcatatga ctcaccacg                                               19

SEQ ID NO: 956          moltype =   length =
SEQUENCE: 956
000

SEQ ID NO: 957          moltype = RNA  length = 23
FEATURE                 Location/Qualifiers
misc_feature            1..23
                        note = 5' Flank Sequence
source                  1..23
                        mol_type = other RNA
                        organism = synthetic construct
SEQUENCE: 957
acaccatgtt gccagtctct agg                                          23

SEQ ID NO: 958          moltype = RNA  length = 23
FEATURE                 Location/Qualifiers
misc_feature            1..23
                        note = 5' Flank Sequence
source                  1..23
                        mol_type = other RNA
                        organism = synthetic construct
SEQUENCE: 958
tgatagcaat gtcagcagtg cct                                          23

SEQ ID NO: 959          moltype = RNA  length = 23
FEATURE                 Location/Qualifiers
misc_feature            1..23
                        note = 5' Flank Sequence
source                  1..23
                        mol_type = other RNA
                        organism = synthetic construct
SEQUENCE: 959
tattgctgtt gacagtgagc gac                                          23

SEQ ID NO: 960          moltype = RNA  length = 21
FEATURE                 Location/Qualifiers
misc_feature            1..21
                        note = 3' Flank Sequence
source                  1..21
                        mol_type = other RNA
                        organism = synthetic construct
SEQUENCE: 960
tggcgtctgg cccaaccaca c                                            21

SEQ ID NO: 961          moltype = RNA  length = 21
FEATURE                 Location/Qualifiers
misc_feature            1..21
                        note = 3' Flank Sequence
source                  1..21
                        mol_type = other RNA
                        organism = synthetic construct
SEQUENCE: 961
gtaaggttga ccatactcta c                                            21

SEQ ID NO: 962          moltype =   length =
SEQUENCE: 962
000

SEQ ID NO: 963          moltype =   length =
SEQUENCE: 963
000

SEQ ID NO: 964          moltype =   length =
SEQUENCE: 964
000

SEQ ID NO: 965          moltype =   length =
SEQUENCE: 965
```

000

SEQ ID NO: 966 moltype = length =
SEQUENCE: 966
000

SEQ ID NO: 967 moltype = RNA length = 12
FEATURE Location/Qualifiers
misc_feature 1..12
note = Loop Region Sequence
source 1..12
mol_type = other RNA
organism = synthetic construct
SEQUENCE: 967
cttcctgtca ga 12

SEQ ID NO: 968 moltype = RNA length = 15
FEATURE Location/Qualifiers
misc_feature 1..15
note = Loop Region Sequence
source 1..15
mol_type = other RNA
organism = synthetic construct
SEQUENCE: 968
cttccctttg tcaga 15

SEQ ID NO: 969 moltype = RNA length = 12
FEATURE Location/Qualifiers
misc_feature 1..12
note = Loop Region Sequence
source 1..12
mol_type = other RNA
organism = synthetic construct
SEQUENCE: 969
gtgttattct tg 12

SEQ ID NO: 970 moltype = RNA length = 12
FEATURE Location/Qualifiers
misc_feature 1..12
note = Loop Region Sequence
source 1..12
mol_type = other RNA
organism = synthetic construct
SEQUENCE: 970
gtgtcttaat tg 12

SEQ ID NO: 971 moltype = RNA length = 12
FEATURE Location/Qualifiers
misc_feature 1..12
note = Loop Region Sequence
source 1..12
mol_type = other RNA
organism = synthetic construct
SEQUENCE: 971
gtgttagtct tg 12

SEQ ID NO: 972 moltype = length =
SEQUENCE: 972
000

SEQ ID NO: 973 moltype = RNA length = 12
FEATURE Location/Qualifiers
misc_feature 1..12
note = Loop Region Sequence
source 1..12
mol_type = other RNA
organism = synthetic construct
SEQUENCE: 973
ggacatccag gg 12

SEQ ID NO: 974 moltype = RNA length = 15
FEATURE Location/Qualifiers
misc_feature 1..15
note = Loop Region Sequence
source 1..15
mol_type = other RNA
organism = synthetic construct
SEQUENCE: 974
gtgaagccac agatg 15

```
SEQ ID NO: 975          moltype = RNA  length = 10
FEATURE                 Location/Qualifiers
misc_feature            1..10
                        note = Loop Region Sequence
source                  1..10
                        mol_type = other RNA
                        organism = synthetic construct
SEQUENCE: 975
gattctaaaa                                                         10

SEQ ID NO: 976          moltype = DNA  length = 20
FEATURE                 Location/Qualifiers
misc_feature            1..20
                        note = gRNA targeting sequence
source                  1..20
                        mol_type = other DNA
                        organism = synthetic construct
SEQUENCE: 976
gatctgactt tatgacgtgt                                              20

SEQ ID NO: 977          moltype = DNA  length = 20
FEATURE                 Location/Qualifiers
misc_feature            1..20
                        note = gRNA targeting sequence
source                  1..20
                        mol_type = other DNA
                        organism = synthetic construct
SEQUENCE: 977
ccttcacatt ccgtgtctcc                                              20

SEQ ID NO: 978          moltype = DNA  length = 20
FEATURE                 Location/Qualifiers
misc_feature            1..20
                        note = gRNA targeting sequence
source                  1..20
                        mol_type = other DNA
                        organism = synthetic construct
SEQUENCE: 978
acagcgacgc cgcgagccag                                              20

SEQ ID NO: 979          moltype = DNA  length = 20
FEATURE                 Location/Qualifiers
misc_feature            1..20
                        note = gRNA targeting sequence
source                  1..20
                        mol_type = other DNA
                        organism = synthetic construct
SEQUENCE: 979
ttcacatccg tgtcccggcc                                              20

SEQ ID NO: 980          moltype = DNA  length = 51
FEATURE                 Location/Qualifiers
misc_feature            1..51
                        note = linker
source                  1..51
                        mol_type = other DNA
                        organism = synthetic construct
SEQUENCE: 980
ggaggtggcg gctctggagg cggaggtagc ggaggtggag gctctggtgg c           51

SEQ ID NO: 981          moltype = AA  length = 118
FEATURE                 Location/Qualifiers
REGION                  1..118
                        note = anti-HLA-A*02 scFv - LILRB1 VH
source                  1..118
                        mol_type = protein
                        organism = synthetic construct
SEQUENCE: 981
QVQLQQSGPE LVKPGASVRI SCKASGYTFT SYHIHWVKQR PGQGLEWIGW IYPGNVNTEY  60
NEKFKGKATL TADKSSSTAY MHLSSLTSED SAVYFCAREE ITYAMDYWGQ GTSVTVSS    118

SEQ ID NO: 982          moltype = DNA  length = 354
FEATURE                 Location/Qualifiers
misc_feature            1..354
                        note = anti-HLA-A*02 scFv - LILRB1 VH
source                  1..354
                        mol_type = other DNA
                        organism = synthetic construct
```

-continued

```
SEQUENCE: 982
caggtccagc tgcagcagtc tggacctgag ctggtgaagc caggggcttc agtgaggata  60
tcctgtaagg cctctggcta caccttaca agttaccata tacattgggt gaagcagagg  120
cctggacagg gactcgaatg gattggatgg atttatcctg gaaatgttaa tactgagtac  180
aatgagaagt tcaagggcaa ggccacactg actgcagaca aatcgtccag cacagcctac  240
atgcacctca gcagcctgac ctctgaggac tctgcggtct atttctgtgc cagagaggag  300
attacctatg ctatggatta ttggggtcaa ggaacctcag tcaccgtgtc ctca        354

SEQ ID NO: 983         moltype =   length =
SEQUENCE: 983
000

SEQ ID NO: 984         moltype =   length =
SEQUENCE: 984
000
```